US008188085B2

(12) United States Patent
Greenlee et al.

(10) Patent No.: US 8,188,085 B2
(45) Date of Patent: May 29, 2012

(54) ANTIFUNGAL AGENTS

(75) Inventors: Mark L. Greenlee, Plainfield, NJ (US);
Robert Wilkening, Maplewood, NJ (US); James Apgar, Edison, NJ (US);
Donald Sperbeck, East Hanover, NJ (US); Kenneth J. Wildonger,
Bridgewater, NJ (US); Dongfang Meng, Westfield, NJ (US); Dann L. Parker, Jr.,
Cranford, NJ (US); Gregory J. Pacofsky, Raleigh, NC (US); Brian H. Heasley, Wake Forest, NC (US); Ahmed Mamai, Raleigh, NC (US); Kingsley Nelson, Mebane, NC (US)

(73) Assignees: Merck Sharp & Dohme Corp.,
Rahway, NC (US); Seynexis, Inc.,
Research Triangle Park, NC (US)

( * ) Notice: Subject to any disclaimer, the term of this patent is extended or adjusted under 35 U.S.C. 154(b) by 411 days.

(21) Appl. No.: 12/461,318

(22) Filed: Aug. 7, 2009

(65) Prior Publication Data

US 2010/0113439 A1    May 6, 2010

Related U.S. Application Data

(60) Provisional application No. 61/136,101, filed on Aug. 12, 2008.

(51) Int. Cl.
*A61K 31/41* (2006.01)
*A61K 31/445* (2006.01)
*A61K 31/501* (2006.01)
*C07D 231/02* (2006.01)
*C07D 249/08* (2006.01)
*C07D 401/00* (2006.01)
*C07D 401/02* (2006.01)
*C07D 405/02* (2006.01)
*C07D 405/14* (2006.01)

(52) U.S. Cl. .................. 514/252.05; 514/320; 514/337; 514/359; 514/383; 514/406; 546/210; 546/272.4; 548/256; 548/264.8; 548/266.2; 548/267.6; 548/364.4

(58) Field of Classification Search ............. 514/252.05, 514/320, 337, 359, 383, 406; 546/210, 272.4; 548/256, 264.8, 266.2, 267.6, 364.4
See application file for complete search history.

(56) References Cited

U.S. PATENT DOCUMENTS

| | | | |
|---|---|---|---|
| 5,756,472 | A | 5/1998 | Liesch et al. |
| 6,960,600 | B2 | 11/2005 | Babin et al. |
| 7,230,023 | B2 | 6/2007 | Mori et al. |
| 2008/0009504 | A1 | 1/2008 | Balkovec et al. |

FOREIGN PATENT DOCUMENTS

| | | |
|---|---|---|
| WO | WO-97/27860 A1 | 8/1997 |
| WO | WO-03/086271 A2 | 10/2003 |
| WO | WO-2007/126900 A2 | 11/2007 |
| WO | WO-2007/127012 A1 | 11/2007 |

OTHER PUBLICATIONS

Bundgaard, H. (ed.), *Design of Prodrugs*, Elsevier (1985).
Chezal, J., et al., "Heterocyclization of Functionalized Vinylic Derivatives of Imidazo[1,2-a]pyridines," *The Journal of Organic Chemistry*, vol. 66, No. 20, pp. 6576-6584 (2001).
Chezal, J., et al., "Aminoimidazo[1,2-a]pyridines: regioselective synthesis of substituted imidazonaphthridines, azacarbolines and cyclazines," *Tetrahedron*, vol. 58, No. 2, pp. 295-307 (2002).
Curtis, A.D.M., "Product Class 14: 1,2,4-Triazoles," *Science of Synthesis*, vol. 13, pp. 603-639 (2004).
Davies, H., et al., "Recent Advances in Catalytic Intramolecular C—H Aminations," *Angewandte Chemie International Edition*, vol. 44, No. 23, pp. 3518-3520 (2005).
Dineen, T., et al., "Efficient Transamidation of Primary Carboxamides by in Situ Activation with N,N-Dialkylformamide Dimethyl Acetals," *Journal of the American Chemical Society*, vol. 128, No. 50, pp. 16406-16409 (2006).
Ellman, J., et al., "N-tert-Butanesulfinyl Imines: Versatile Intermediates for the Asymmetric Synthesis of Amines," *Accounts of Chemical Research*, vol. 35, No. 11, pp. 984-995 (2002).
Gennaro, A. (ed.), *Remington: The Science and Practice of Pharmacy*, 20th edition (2000).
Gontcharov, A., et al., "tert-Butylsulfonamide. A New Nitrogen Source for Catalytic Aminohydroxylation and Aziridination of Olefins," *Organic Letters*, vol. 1, No. 5, pp. 783-786 (1999).
Hanna, N., et al., "Synthesis and Single-Crystal X-ray Diffraction Studies of 1-β-D-Ribofuranosyl-1,2,4-triazole-3-sulfonamide and Certain Related Nucleosides," *Journal of Heterocyclic Chemistry*, vol. 25, No. 4-6, pp. 1857-1868 (1988).
Hu, X., "Nucleophilic ring opening of aziridines," *Tetrahedron*, vol. 60, Report No. 673, pp. 2701-2743 (2004).
Jeong, J., et al., "Bromine-Catalyzed Aziridination of Olefins. A Rare Example of Atom-Transfer Redox Catalysis by a Main Group Element," *Journal of the American Chemical Society*, vol. 120, No. 26-30, pp. 6844-6845 (1998).
Kawabata, T., et al., "Asymmetric Cyclization via Memory of Chirality: A Concise Access to Cyclic Amino Acids with a Quaternary Stereocenter," *Journal of the American Chemical Society*, vol. 125, No. 43, pp. 13012-13013 (2003).
Kuethe, J., et al., "A Concise Synthesis of (S)-N-Ethoxycarbonyl-α-methylvaline," *The Journal of Organic Chemistry*, vol. 72, No. 19, pp. 7469-7472 (2007).
Liang, J., et al., "Intramolecular C—N Bond Formation Reactions Catalyzed by Ruthenium Porphyrins: Amidation of Sulfamate Esters and Aziridination of Unsaturated Sulfonamides," *The Journal of Organic Chemistry*, vol. 69, No. 11, pp. 3610-3619 (2004).

(Continued)

*Primary Examiner* — Barbara P Badio
(74) *Attorney, Agent, or Firm* — Covington & Burling LLP; Paul J. Berman; Melody Wu

(57) ABSTRACT

Novel derivatives of enfumafungin are disclosed herein, along with their pharmaceutically acceptable salts, hydrates and prodrugs. Also disclosed are compositions comprising such compounds, methods of preparing such compounds and methods of using such compounds as antifungal agents and/or inhibitors of (1,3)-β-D-glucan synthase. The disclosed compounds, their pharmaceutically acceptable salts, hydrates and prodrugs, as well as compositions comprising such compounds, salts, hydrates and prodrugs, are useful for treating and/or preventing fungal infections and associated diseases and conditions.

51 Claims, No Drawings

OTHER PUBLICATIONS

Lin, Y., at al., "New Synthesis of 1,2,4-Triazoles and 1,2,4-Oxadiazoles," *The Journal of Organic Chemistry*, vol. 44, No. 21, pp. 4160-4164 (1979).

Lin, Y., et al., "Novel Two Step Synthesis of Pyrazoles and Isoxazoles from Aryl Methyl Ketones," *Journal of Heterocyclic Chemistry*, vol. 14, No. 1. pp. 345-347 (1977).

McCoull, W., et al., "Recent Synthetic Applications of Chiral Aziridines," *Synthesis*, pp. 1347-1365 (2000).

Melendez, R., et al., "Synthesis and reactivity of cyclic sulfamidites and sulfamidates," *Tetrahedron*, vol. 59, Report No. 636, pp. 2581-2616 (2003).

Morton, D., et al., "Direct synthesis of chiral aziridines from *N-tert*-butyl-sulfinylketimines," *Chem. Commun.*, pp. 1833-1835 (2006).

Onishi, J., et al., "Discovery of Novel Antifungal (1,3)-β-D-Glucan Synthase Inhibitors," *Antimicrobial Agents and Chemotherapy*, vol. 44, No. 2, pp. 368-377 (2000).

Osborn, H., et al., "The asymmetric synthesis of aziridines," *Tetrahedron: Asymmetry*, vol. 8, Nos. 7-12, pp. 1693-1715 (1997).

Pelaez, F., et al., "The Discovery of Enfumafungin, a Novel Antifungal Compound Produced by an Endophytic *Hormonema* Species—Biological Activity and Taxonomy of the Producing Organisms," *Systematic and Applied Microbiology*, vol. 23, No. 3, pp. 333-343 (2000).

Ruge, E., et al., "Current state of three-dimensional characterisation of antifungal targets and its use for molecular modelling in drug design," International Journal of Antimicrobial Agents 26, pp. 427-441 (2005).

Schwartz, R. et al., "Isolation and Structural Determination of Enfumafungin, a Triterpene Glycoside Antifungal Agent That Is a Specific Inhibitor of Glucan Synthesis," *Journal of the American Chemical Society*, vol. 122, No. 16-20, pp. 4882-4886 (2000).

Schwartz, R., "Cell wall active antifungal agents," *Expert Opinion on Therapeutic Patents*, vol. 11(11), pp. 1761-1772 (2001).

Shafiee, A., et al., "Enzymatic deglycosylation of enfumafungin, a triterpene glycoside natural product, and its chemically synthesized analogues," *Journal of Molecular Catalysis B: Enzymatic*, vol. 16, No. 1, pp. 27-32 (2001).

Speake, J., et al., "2-(Anilinomethyl)imidazolines as $\alpha_1$ Adrenergic Receptor Agonists: $\alpha_{1a}$ Subtype Selective 2'-Heteroaryl Compounds," *Bioorganic & Medicinal Chemistry Letters*, vol. 13, pp. 1183-1186 (2003).

Sweeney, J.B., "Aziridines: epoxides' ugly cousins?" *Chemical Society Reviews*, vol. 31, pp. 247-258 (2002).

Vicario, J., et al., "An improved procedure for the preparation of chiral nonracemic *N*-tosyl-2-alkylaziridines and *N,2*-dialkylaziridines on multigram-scale," *ARKIVOC*, vol. iv, pp. 304-311 (2007).

Watson, I., et al., "Advances in Nitrogen Transfer Reactions Involving Aziridines," *Accounts of Chemical Research*, vol. 39, No. 3, pp. 194-206 (2006).

Balkovec, J. M. et al., "Derivatives of the β-1,3-Glucan Synthase (GS) Inhibitor Enfumafungin—Initial Studies," presented at Interscience Conference on Antimicrobial Agents and Chemotherapy 49th Annual Meeting (ICAAC), San Francisco, California: Sep. 12-15, 2009.

Liberator, P.A. et al., "Semi-Synthetic Analogs of Enfumafungin: Novel Inhibitors of beta-1,3-Glucan Synthase (GS) With Potent In Vitro Anti-Fungal Activity," presented at Interscience Conference on Antimicrobial Agents and Chemotherapy 49th Annual Meeting (ICAAC), San Francisco, California: Sep. 12-15, 2009.

Peel, M., "New beta-1,3-Glucan Synthase (GS) Inhibitors With Potent Antifungal Activity," presented at Interscience Conference on Antimicrobial Agents and Chemotherapy 49th Annual Meeting (ICAAC), San Francisco, California: Sep. 12-15, 2009.

ANTIFUNGAL AGENTS

JOINT RESEARCH AGREEMENT

The claimed subject matter was made as a result of activities undertaken within the scope of a joint research agreement between Merck & Co., Inc. and Scynexis, Inc.

FIELD OF THE INVENTION

The claimed subject matter relates to novel compounds and pharmaceutically acceptable salts, hydrates and prodrugs thereof, compositions containing such compounds, synthesis of such compounds, and use of such compounds as antifungal agents and/or inhibitors of (1,3)-β-D-glucan synthesis. The compounds described herein are derivatives of enfumafungin. The novel compounds of this disclosure, their pharmaceutically acceptable salts, hydrates and prodrugs, and compositions comprising such compounds, salts, hydrates and/or prodrugs, are useful for treating and/or preventing antifungal infections and associated diseases and conditions.

BACKGROUND OF THE INVENTION

Fungal infection is a major healthcare problem, and the incidence of hospital-acquired fungal diseases continues to rise. Severe systemic fungal infection in hospitals (such as candidiasis, aspergillosis, histoplasmosis, blastomycosis and coccidioidomycosis) is commonly seen in neutropaenic patients following chemotherapy and in other oncology patients with immune suppression, in patients who are immune-compromised due to Acquired Immune Deficiency Syndrome (AIDS) caused by HIV infection, and in patients in intensive care. Systemic fungal infections cause ~25% of infection-related deaths in leukaemics. Infections due to *Candida* species are the fourth most important cause of nosocomial bloodstream infection. Serious fungal infections may cause 5-10% of deaths in patients undergoing lung, pancreas or liver transplantation. Treatment failures are still very common with all systemic mycoses. Secondary resistance also arises. Thus, there remains an increasing need for effective new therapy against mycotic infections.

Enfumafungin is a hemiacetal triterpene glycoside that is produced in fermentations of a *Hormonema* spp. associated with living leaves of *Juniperus communis* (U.S. Pat. No. 5,756,472; Pelaez et al., *Systematic and Applied Microbiology*, 23:333-343, 2000; Schwartz et al., *JACS*, 122:4882-4886, 2000; Schwartz, R. E., *Expert Opinion on Therapeutic Patents*, 11(11):1761-1772, 2001). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., *Antimicrobial Agents and Chemotherapy*, 44:368-377, 2000; Pelaez et al., *Systematic and Applied Microbiology*, 23:333-343, 2000). 1,3-β-D-Glucan synthase remains an attractive target for antifungal drug action because it is present in many pathogenic fungi which affords broad antifungal spectrum and there is no mammalian counterpart and as such, compounds inhibiting 1,3-β-D-Glucan synthase have little or no mechanism-based toxicity.

Various enfumafungin derivatives have been disclosed, e.g., in International Patent Publication Nos. WO 2007/126900 and WO 2007/127012.

SUMMARY OF THE INVENTION

The present invention relates to enfumafungin derivatives. These compounds, or pharmaceutically acceptable salts thereof, are useful in the inhibition of (1,3)-β-D-glucan synthase and are useful in the prevention or treatment of mycotic infections caused by one or more of various pathogens including, but are not limited to, *Aspergillus, Cryptococcus, Candida, Mucor, Actinomyces, Histoplasma*, Dermatophyte, *Malassezia, Fusarium*, and *Pneumocystis carinii*. In particular, the present invention includes a compound of Formula I:

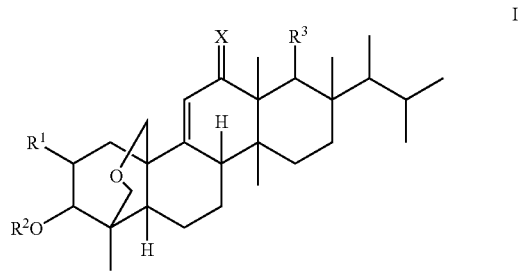

or a pharmaceutically acceptable salt thereof, wherein:
R¹ is a group of the following structure:

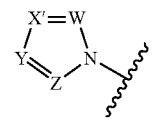

wherein W, X', Y, and Z are independently selected from N and CR^e provided that two or three of W, X', Y and Z are CR^e;
R^e is independently selected from
a) H;
b) Halogen;
c) NR^fR^g;
d) NHC(O)R°;
e) NHC(O)NR^fR^g;
f) NHC(O)OR°;
g) NO₂;
h) OR°;
i) SR°;
j) SO₂R°;
k) SO₂N(R°)₂;
l) CN;
m) C(O)R°;
n) C(O)OR°;
o) C(O)NR^fR^g;
p) C(=NR°)N(R°)₂;
q) C₁-C₆-alkyl optionally substituted with 1 to 3 substituents independently selected from phenyl, pyridyl, OR°, N(R°)₂, CO₂R°, C(O)N(R°)₂ or halogen;
r) C₂-C₆-alkenyl optionally substituted with 1 to 3 substituents independently selected from phenyl, OR°, N(R°)₂, CO₂R°, C(O)N(R°)₂ or halogen;
s) C₃-C₆-cycloalkyl, optionally substituted with oxo, OR°, N(R°)₂, CO₂R° or C(O)N(R°)₂;
t) heterocyclyl, wherein the heterocyclyl is a 4- to 6-membered saturated or unsaturated non-aromatic ring having 1, 2 or 3 heteroatoms selected from N, O or S, attached through a carbon or nitrogen on the ring, and optionally substituted on a ring carbon with 1 to 2 substituents independently selected from N(R°)₂, imino, oxo, OR°, CO₂R°, C(O)N(R°)₂ and C₁-C₆-alkyl unsubstituted or substituted with 1 to 3 substituents independently selected from N(R°)₂, OR°, CO₂R°, C(O)N(R°)₂ and halogen; the heterocyclyl may also be optionally substituted on a ring nitrogen atom that is not the point of attachment with $C(O)R^o$, $CO_2R^o$, $C(O)N(R^o)_2$, $SO_2R^o$ or $C_1$-$C_6$ alkyl substituted or substituted with 1 to 3 substituents independently selected from $N(R^o)_2$, $OR^o$, $CO_2R^o$, $C(O)N(R^o)_2$ and halogen; the heterocyclyl may also be optionally substituted on a sulfur atom with 1 or 2 oxo groups;

u) aryl, wherein aryl is phenyl or napthyl and aryl is unsubstituted or substituted with 1 or 2 substituents independently selected from halogen, $N(R^o)_2$, $OR^o$, $CO_2R^o$, CN, $C(O)N(R^o)_2$, $C(=NR^o)N(R^o)_2$, heterocyclyl as defined above, phenyl, pyridyl, and $C_1$-$C_6$-alkyl wherein said alkyl is optionally substituted with 1 to 3 substituents independently selected from $N(R^o)_2$, $OR^o$, or halogen;

v) heteroaryl, wherein heteroaryl is a 5- or 6-membered monocyclic aromatic ring or 9- or 10-membered bicyclic aromatic ring having 1, 2 or 3 heteroatoms selected from N, O or S, attached through a ring carbon or nitrogen, and optionally substituted on a ring carbon that is not the point of attachment, with 1 or 2 substituents independently selected from halogen, $CF_3$, $NR^fR^g$, $NHC(O)R^o$, $OR^o$, $CO_2R^o$, $C(O)N(R^o)_2$, $C(=NR^o)N(R^o)_2$, CN, heterocyclyl as defined above, phenyl, pyridyl, and $C_1$-$C_6$ alkyl unsubstituted or substituted with 1 or 2 substituents independently selected from $N(R^o)_2$ and $OR^o$; the heteroaryl may also be optionally substituted on a ring nitrogen atom that is not the point of attachment with O or $C_1$-$C_6$ alkyl;

$R^f$ is H, $C_1$-$C_6$-alkyl, $C_3$-$C_6$-cycloalkyl or phenyl;

$R^g$ is H or $C_1$-$C_6$-alkyl optionally substituted with 1 to 3 substituents independently selected from phenyl, $OR^o$, $N(R^o)_2$ or halogen;

$R^f$ and $R^g$ are optionally taken together with the attached nitrogen atom to form a 3- to 7-membered ring having 0-1 additional heteroatoms independently selected from N, O and S wherein said ring may be optionally substituted on a ring nitrogen atom that is not the point of attachment with $C(O)R^o$, $CO_2R^o$, $C(O)N(R^o)_2$, $SO_2R^o$, or $C_1$-$C_6$ alkyl unsubstituted or substituted with 1 or 2 substituents independently selected from $N(R^o)_2$, $OR^o$, $CO_2R^o$, $C(O)N(R^o)_2$ or halogen; said ring may also be optionally substituted on a sulfur atom with 1 or 2 oxo groups;

$R^2$ is a group of the following structure:

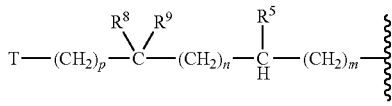

m is 0 or 1;
n is 0 or 1;
p is 0 or 1;
T is $NR^6R^7$ or $OR^{10}$;
$R^5$ is H or $C_1$-$C_6$-alkyl, unsubstituted or substituted with 1 or 2 substituents independently selected from $N(R^o)_2$ and $OR^o$;
$R^6$ is H, $C_1$-$C_6$-alkyl or $C_3$-$C_6$ cycloalkyl;
$R^7$ is selected from the group consisting of:
a) H;
b) $C_1$-$C_6$-alkyl, unsubstituted or substituted with 1 or 2 substituents independently selected from $N(R^o)_2$, $OR^o$, $CO_2R^o$, $OC(O)R^o$, $NHC(O)R^o$, $C(O)N(R^o)_2$, phenyl, heteroaryl, and heterocyclyl, wherein heteroaryl and heterocyclyl are as defined above in the definition of $R^e$;
c) $C_3$-$C_6$-cycloalkyl;
d) $C(O)R^o$;
e) $C(O)OC_1$-$C_6$-alkyl;
f) $C(O)NHR^o$;
g) $C(=NH)R^o$;
h) $C(=NR^o)NHR^o$;

$R^6$ and $R^7$ are optionally taken together with the attached nitrogen atom to form a 4- to 7-membered saturated, unsaturated or aromatic ring having 0 or 1 additional heteroatoms independently selected from N, O and S, wherein said ring is optionally substituted on a ring carbon with 1 to 2 substituents independently selected from halogen, $CF_3$, $N(R^o)_2$, $OR^o$, $CO_2R^o$, $C(O)N(R^o)_2$, and $C_1$-$C_6$ alkyl unsubstituted or substituted with 1 or 2 substituents independently selected from $OR^o$ and $N(R^o)_2$; said ring may also be optionally substituted on a ring nitrogen atom that is not the point of attachment with $C(O)R^o$, $CO_2R_o$, $C(O)N(R^o)_2$, $SO_2R^o$ or $C_1$-$C_6$ alkyl unsubstituted or substituted with 1 to 3 substituents independently selected from $N(R^o)_2$, $OR^o$, $CO_2R_o$, $C(O)N(R^o)_2$ and halogen; said ring may also be optionally substituted on a sulfur atom with 1 or 2 oxo groups;

$R^6$ and $R^8$ are optionally taken together to form, with the intervening atoms, a 4- to 7-membered saturated ring having 0 or 1 additional heteroatoms independently selected from N, O and S wherein said ring is optionally substituted as defined above for $R^6$ and $R^7$ when joined together to form a ring;

$R^6$ and $R^5$ are optionally taken together to form, with the intervening atoms, a 4- to 7-membered saturated ring having 0 or 1 additional heteroatoms independently selected from N, O and S wherein said ring is optionally substituted as defined above for $R^6$ and $R^7$ when joined together to form a ring;

$R^8$ is selected from the group consisting of
a) hydrogen,
b) $C_1$-$C_6$-alkyl, unsubstituted or substituted with F, $OR^o$, $N(R^o)_2$ or $SO_2R^o$,
c) $C_3$-$C_6$-cycloalkyl,
d) $C_4$-$C_7$-cycloalkyl-alkyl,
e) aryl, wherein aryl is phenyl or naphthyl and said aryl is unsubstituted or substituted with 1 to 3 substituents selected from $C_1$-$C_6$-alkyl, halogen, $OCF_3$, $CF_3$, $N(R^o)_2$ and $OR^o$, and
f) heteroaryl, wherein heteroaryl is as defined above in the definition of $R^e$;

$R^9$ is $C_1$-$C_6$-alkyl, unsubstituted or substituted with $OR^o$ or $SO_2R^o$;

$R^8$ and $R^9$ are optionally taken together to form a 3- to 7-membered saturated ring having 0 or 1 additional heteroatoms independently selected from N, O, and S, wherein said ring is optionally substituted as defined above for $R^6$ and $R^7$ when joined to form a ring;

$R^{10}$ is selected from the group consisting of
a) H,
b) $C_1$-$C_6$-alkyl, unsubstituted or substituted with 1 or 2 substituents selected from $N(R^o)_2$, $OR^o$, $CO_2R^o$, $OC(O)R^o$, $NHC(O)R^o$, $C(O)N(R^o)_2$, phenyl, heteroaryl, and heterocyclyl, wherein heteroaryl and heterocyclyl are as defined above in the definition of $R^e$,
c) $C_3$-$C_6$-cycloalkyl,
d) $C(O)R^o$,
e) $C(O)NHR^o$,
$R^3$ is $C(O)R^{14}$;
$R^{14}$ is OH, $OR^{15}$ or $N(R^o)_2$;
$R^{15}$ is $C_1$-$C_6$-alkyl, unsubstituted or substituted with 1 or 2 substituents independently selected from phenyl and $OC(O)R^o$, wherein said phenyl is optionally substituted with 1 to 3 $OR^o$ groups;
X is O or H, H;
each $R^o$ is independently H, $C_1$-$C_6$ alkyl, $C_3$-$C_6$ cycloalkyl or benzyl.

These compounds are potent antifungal agents useful against pathogens associated with human and agricultural fungal infections.

Additional aspects of the invention relate to compositions comprising the compounds of the invention, optionally in the presence of a second therapeutic agent. In addition, aspects of the invention relate to methods of preparing a compound of the invention, to methods of preparing compositions of the invention, to methods of treating or preventing fungal infection in patients using a compound of the invention, and to methods of controlling fungal infection in patients using a compound of the invention.

Other embodiments, aspects and features of the present invention are either further described in or will be apparent from the ensuing description, examples and appended claims.

DETAILED DESCRIPTION OF THE INVENTION

The present invention relates to compounds of Formula (I) and pharmaceutically acceptable salts thereof. Different embodiments further describing Formula (I) variables are described below.

In a first embodiment of the invention, $R^3$ is $C(O)R^{14}$, wherein $R^{14}$ is OH, and the other variables are as provided for in Formula (I) above.

In a first aspect of this embodiment, the compound is of Formula (Ia) wherein all variables are as provided for in Formula (I) above:

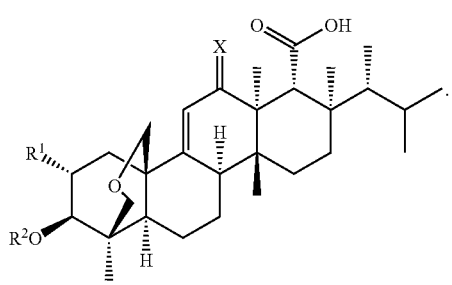

Ia

In a second embodiment of the invention, X is H, H, and the other variables are as provided for in Formula (I) above or in the first embodiment.

In a third embodiment of the invention, X is O, and the other variables are as provided for in Formula (I) above or in the first embodiment.

In a fourth embodiment of the invention, $R^2$ is a group of the following structure:

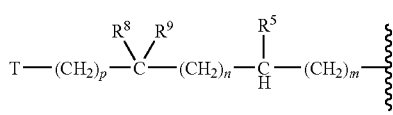

wherein T is $OR^{10}$ and the other variables are as provided for in Formula (I) above or in any of the first through third embodiments.

In a fifth embodiment of the invention, $R^2$ is a group of the following structure:

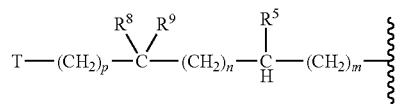

wherein T is $NR^6R^7$ and the other variables are as provided for in Formula (I) above or in any of the first through third embodiments.

In a first aspect of this embodiment, $R^2$ is a group of the following structure:

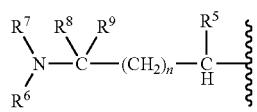

and the other variables are as provided for in Formula (I) above, or in any of the first through third embodiments.

In a second aspect of this embodiment, $R^2$ is a group of the following structure:

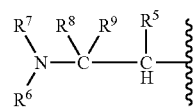

and the other variables are as provided for in Formula (I) above, or in any of the first through third embodiments.

In a further aspect, $R^5$ and $R^6$ may be joined together to form a ring providing $R^2$ of the following structure:

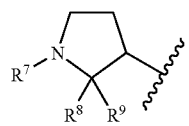

and the other variables are as provided for in Formula (I) above, or in any of the first through third embodiments.

In a third aspect of this embodiment, $R^2$ is a group of the following structure:

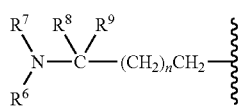

and the other variables are as provided for in Formula (I) above, or in any of the first through third embodiments.

In a fourth aspect of this embodiment, $R^2$ is a group of the following structure:

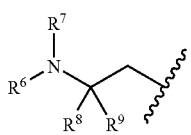

and the other variables are as provided for in Formula (I) above, or in an of the first through third embodiments.

In a further aspect, $R^6$ and $R^8$ may be joined together to form a ring providing $R^2$ of the following structure:

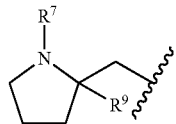

and the other variables are as provided for in Formula (I) above, or in any of the first through third embodiments.

In a fifth aspect of this embodiment, $R^2$ is a group of the following structure:

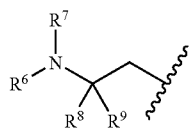

wherein
$R^6$ is H or $C_1$-$C_3$-alkyl;
$R^7$ is H or methyl;
$R^8$ is $C_1$-$C_5$-alkyl, $C_3$-$C_5$ cycloalkyl or $C_4$-$C_6$ cycloalkyl-alkyl;
$R^9$ is H or $C_1$-$C_3$-alkyl;
or $R^8$ and $R^9$ are optionally taken together to form a 5- to 6-membered saturated ring having 0-1 heteroatom selected from O or S; and the other variables are as provided for in Formula (I) above or in any of the first through third embodiments.

In a sixth aspect of this embodiment, $R^2$ is a group of the following structure:

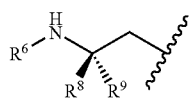

wherein
$R^6$ is H, methyl, ethyl or n-propyl;
$R^8$ is ethyl, i-propyl, t-butyl or 1-methylcyclopropyl;
$R^9$ is methyl or ethyl;
or $R^8$ and $R^9$ are optionally taken together to form a 6-membered saturated ring containing 0 or 1 oxygen atoms; and the other variables are as provided for in Formula (I) above or in any of the first through third embodiments.

In a seventh aspect of the embodiment, $R^2$ is selected from the group consisting of:

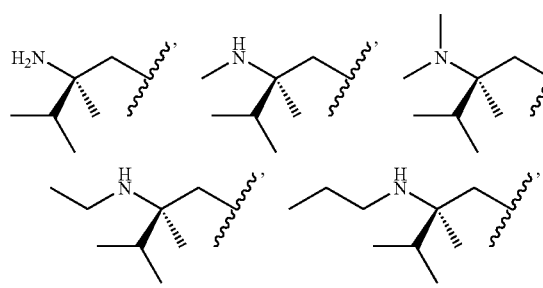

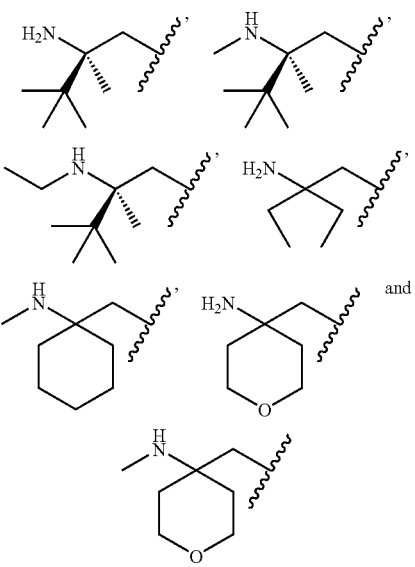

and the other variables are as provided for in Formula (I) above or in any of the first through third embodiments.

In a sixth embodiment of the invention, $R^1$ is a group of the following structure:

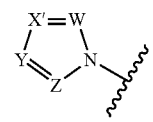

wherein W, X', Y, and Z are independently selected from N and $CR^e$ provided that two of W, X', Y and Z are $CR^e$, and the other variables are as provided for in Formula (I) above or in any of the first through fifth embodiments.

In a first aspect of this embodiment, $R^1$ is a group of the following structure:

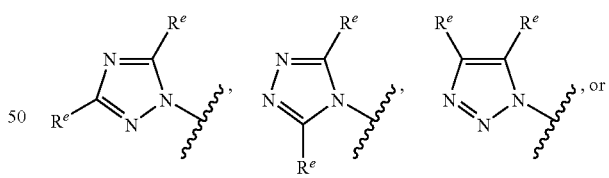

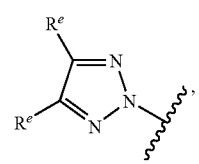

wherein each $R^e$ is independently selected as defined above, and the other variables are as provided for in Formula (I) above or in any of the first through fifth embodiments.

In a second aspect of this embodiment, $R^1$ is a group of the following structure:

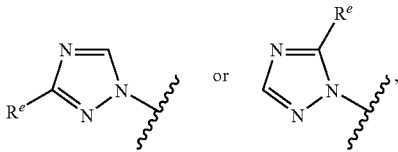

wherein $R^e$ is as defined above, and the other variables are as provided for in Formula (I) above or in any of the first through fifth embodiments.

In a third aspect of this embodiment, $R^1$ is a group of the following structure:

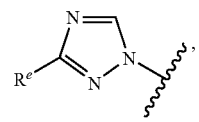

wherein $R^e$ is $NR^fR^g$, and $R^f$ and $R^g$ and the other variables are as provided for in Formula (I) above or in any of the first through fifth embodiments;

In a fourth aspect of this embodiment, $R^1$ is a group of the following structure:

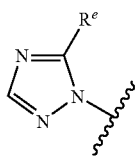

wherein $R^e$ is selected from the following and the other variables are as provided for in Formula (I) above or in any of the first through fifth embodiments:
  a) H,
  b) Halogen,
  c) $C(O)NR^fR^g$,
  d) heterocyclyl, wherein the heterocyclyl is a 4- to 6-membered saturated or unsaturated non-aromatic ring having 1 or 2 heteroatoms selected from N, O or S, attached through a carbon or nitrogen on the ring and optionally substituted on a ring carbon with $N(R^o)_2$, $OR^o$, imino or oxo; the heterocyclyl may also be optionally substituted on a ring nitrogen atom that is not the point of attachment with $C(O)R^o$, $CO_2R^o$, $C(O)N(R^o)_2$ or $C_1$-$C_4$ alkyl,
  e) aryl, wherein aryl is phenyl or napthyl and aryl is unsubstituted or substituted with 1 or 2 substituents independently selected from halogen, $CF_3$, $N(R^o)_2$, $OR^o$, $CO_2R^o$, $CN$, $C(O)N(R^o)_2$, $C(=NR^o)N(R^o)_2$, and $C_1$-$C_3$-alkyl wherein said alkyl is optionally substituted with $N(R^o)_2$ or $OR^o$; and
  f) heteroaryl, wherein heteroaryl is a 5- or 6-membered aromatic ring having 1, 2 or 3 heteroatoms selected from N, O or S, attached through a ring carbon or nitrogen, and optionally substituted on a ring carbon that is not the point of attachment, with 1 or 2 substituents independently selected from halogen, $CF_3$, $NR^fR^g$, $NHC(O)R^o$, $OR^o$, $CO_2R^o$, $C(O)N(R^o)_2$, $C(=NR^o)N(R^o)_2$, $CN$ and $C_1$-$C_3$ alkyl, wherein said alkyl is optionally substituted with $N(R^o)_2$ or $OR^o$; the heteroaryl may also be optionally substituted on a nitrogen atom that is not the point of attachment with O or $C_1$-$C_3$ alkyl.

In a fifth aspect of this embodiment, $R^1$ is a group of the following structure:

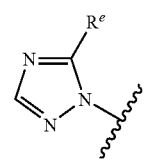

wherein $R^e$ is $C(O)NR^fR^g$ and the other variables are as provided for in Formula (I) above or in any of the first through fifth embodiments.

Exemplary $R^1$ groups of this aspect of the invention include but are not limited to the following:

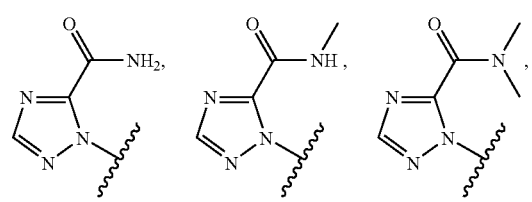

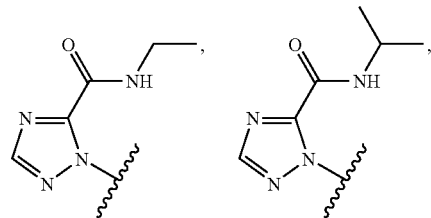

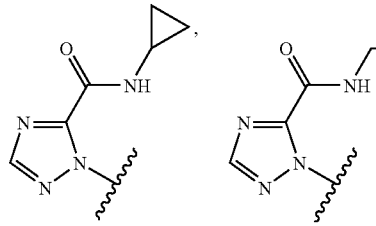 and

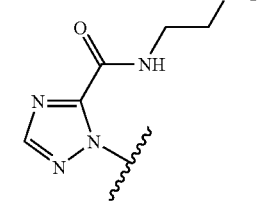

In a sixth aspect of this embodiment, $R^1$ is a group of the following structure:

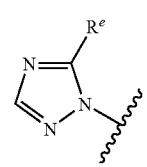

wherein $R^e$ is heterocyclyl, wherein the heterocyclyl is a 4- to 6-membered saturated or unsaturated non-aromatic ring having 1 or 2 heteroatoms selected from N, O or S, attached through a carbon or nitrogen on the ring and optionally substituted on a ring carbon with $N(R^o)_2$, $OR^o$, imino or oxo; the heterocyclyl may also be optionally substituted on a ring nitrogen atom that is not the point of attachment with $C(O)R^o$, $CO_2R^o$, $C(O)N(R^o)_2$ or $C_1$-$C_4$ alkyl; and the other variables are as provided for in Formula (I) above or in any of the first through fifth embodiments.

Exemplary $R^1$ groups of this aspect of the invention include but are not limited to the following:

In a seventh aspect of this embodiment, $R^1$ is a group of the following structure:

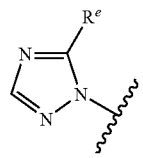

wherein $R^e$ is aryl, wherein aryl is phenyl or napthyl and aryl is unsubstituted or substituted with 1 or 2 substituents independently selected from halogen, $CF_3$, $N(R^o)_2$, $OR^o$, $CO_2R^o$, CN, $C(O)N(R^o)_2$, $C(=NR^o)N(R^o)_2$, and $C_1$-$C_3$-alkyl wherein said alkyl is optionally substituted with $N(R^o)_2$ or $OR^o$; and the other variables are as provided for in Formula (I) above or in any of the first through fifth embodiments.

Exemplary $R^1$ groups of this aspect of the invention include but are not limited to the following:

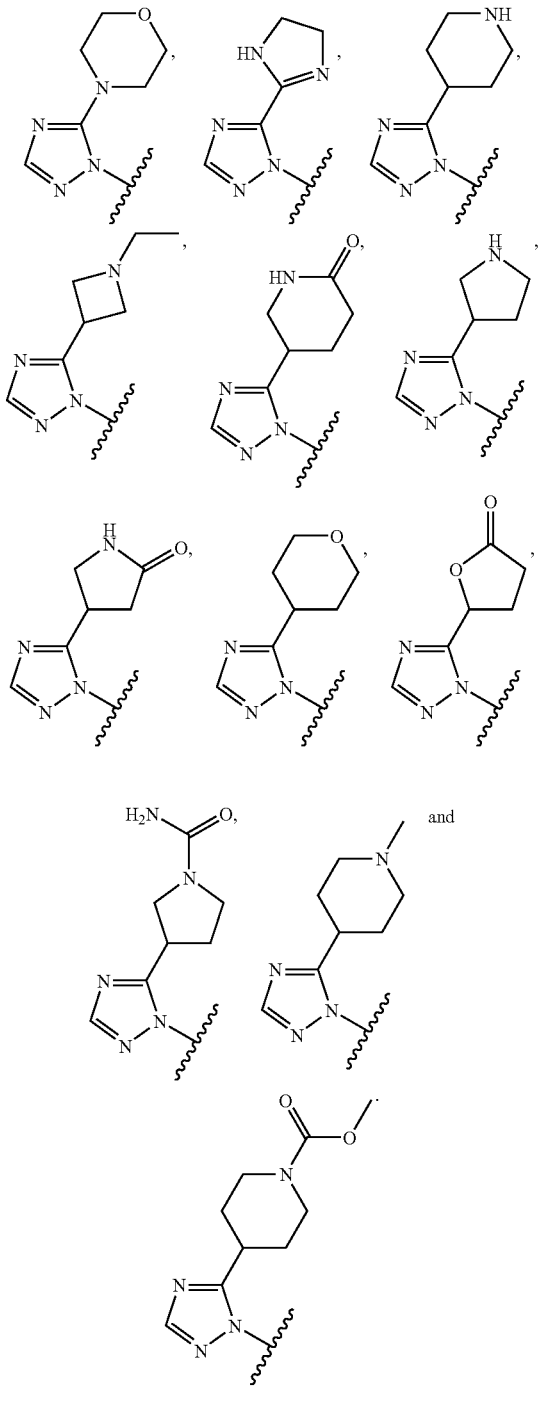

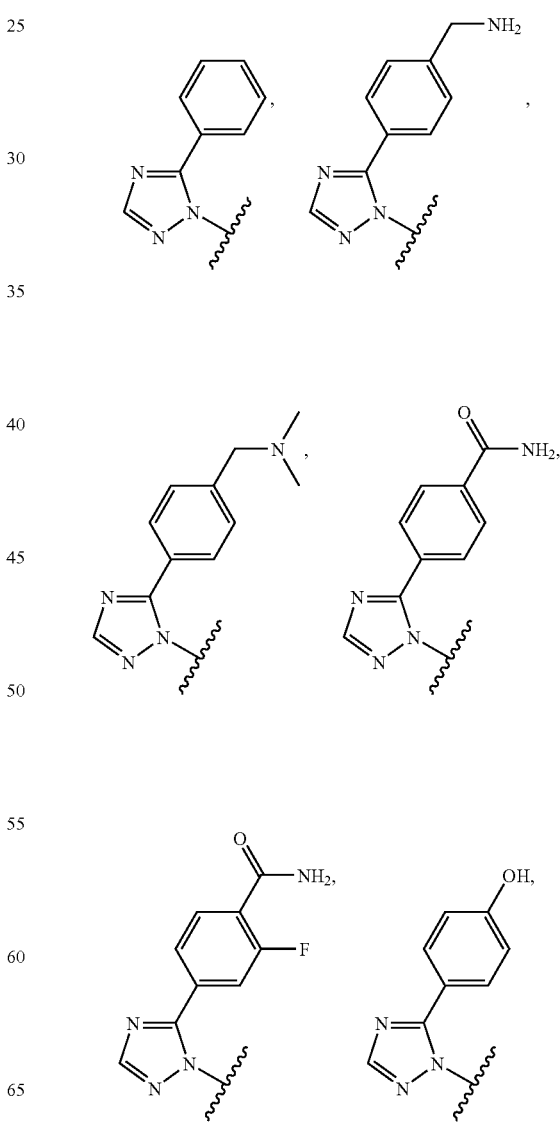

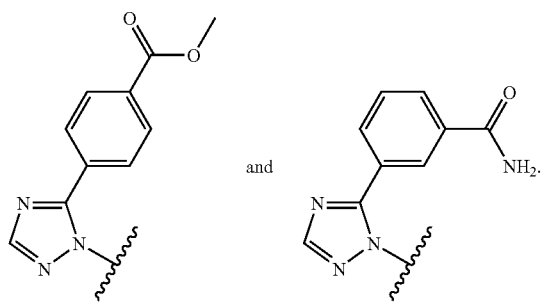

In an eighth aspect of this embodiment, $R^1$ is a group of the following structure:

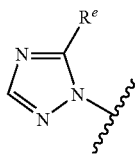

wherein $R^e$ is heteroaryl, wherein heteroaryl is a 5- or 6-membered aromatic ring having 1, 2 or 3 heteroatoms selected from N, O or S, attached through a ring carbon or nitrogen, and optionally substituted on a ring carbon that is not the point of attachment, with halogen, $NR^fR^g$, $NHC(O)R^o$, $OR^o$, $CO_2R^o$, $C(O)N(R^o)_2$, $C(=NR^o)N(R^o)_2$, CN or $C_1$-$C_3$ alkyl, wherein said alkyl is optionally substituted with $N(R^o)_2$ or $OR^o$; the heteroaryl may also be optionally substituted on a nitrogen atom that is not the point of attachment with O or $C_1$-$C_3$ alkyl; and the other variables are as provided for in Formula (I) above or in any of the first through fifth embodiments.

Exemplary $R^1$ groups of this aspect of the invention include but are not limited to the following:

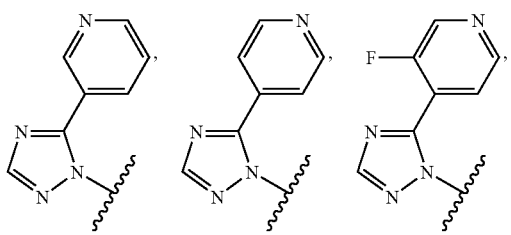

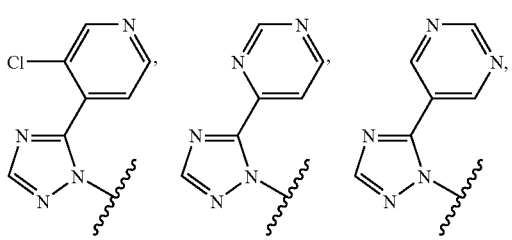

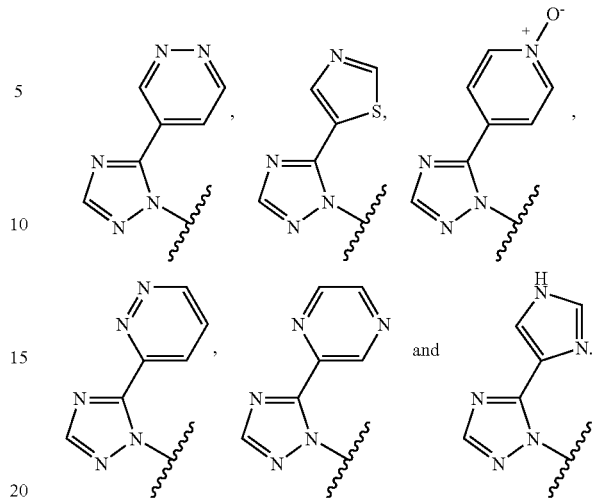

In a seventh embodiment of the invention, $R^1$ is a group of the following structure:

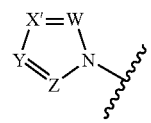

wherein W, X', Y, and Z are independently selected from N and $CR^e$ provided that three of W, X', Y and Z are $CR^e$, and the other variables are as provided for in Formula (I) above or in any of the first through fifth embodiments.

In a first aspect of this embodiment, $R^1$ is a group of the following structure:

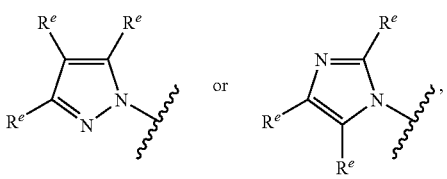

wherein each $R^e$ is independently selected as defined above, and the other variables are as provided for in Formula (I) above or in any of the first through fifth embodiments.

In a second aspect of this embodiment, $R^1$ is a group of the following structure:

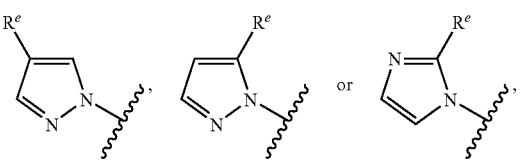

wherein $R^e$ is as defined above, and the other variables are as provided for in Formula (I) above or in any of the first through fifth embodiments.

In a third aspect of this embodiment, $R^1$ is a group of the following structure:

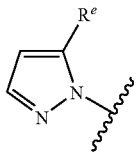

wherein $R^e$ is selected from the following and the other variables are as provided for in Formula (I) above or in any of the first through fifth embodiments:

a) H;

b) $C(O)NR^fR^g$;

c) aryl, wherein aryl is phenyl or napthyl and aryl is unsubstituted or substituted with 1 or 2 substituents independently selected from halogen, $CF_3$, $N(R^0)_2$, $OR^0$, $CO_2R^0$, CN, $C(O)N(R^0)_2$, $C(=NR^0)N(R^0)_2$, and $C_1$-$C_3$-alkyl wherein said alkyl is optionally substituted with $N(R^0)_2$ or $OR^0$; and d) heteroaryl, wherein heteroaryl is a 5- or 6-membered aromatic ring having 1, 2 or 3 heteroatoms selected from N, O or S, attached through a ring carbon or nitrogen, and optionally substituted on a ring carbon that is not the point of attachment, with halogen, $NR^fR^g$, $NHC(O)R^0$, $OR^0$, $CO_2R^0$, $C(O)N(R^0)_2$, $C(=NR^0)N(R^0)_2$, CN or $C_1$-$C_3$ alkyl, wherein said alkyl is optionally substituted with $N(R^0)_2$ or $OR^0$; the heteroaryl may also be optionally substituted on a nitrogen atom that is not the point of attachment with O or $C_1$-$C_3$ alkyl.

In one embodiment of the invention, a compound of Formula II, or a pharmaceutically acceptable salt thereof, is provided.

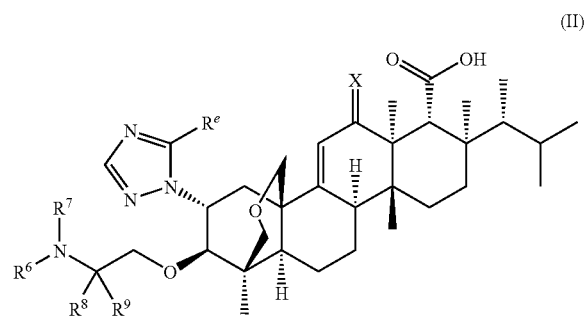

(II)

wherein:

X is O or H, H;

$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;

$R^f$, $R^g$, $R^6$ and $R^7$ are each independently hydrogen or $C_1$-$C_3$ alkyl;

$R^8$ is $C_1$-$C_4$ alkyl, $C_3$-$C_4$ cycloalkyl or $C_4$-$C_5$ cycloalkylalkyl;

$R^9$ is methyl or ethyl;

$R^8$ and $R^9$ are optionally taken together to form a 6-membered saturated ring containing 1 oxygen atom.

In another embodiment of the invention, a compound of Formula IIa, or a pharmaceutically acceptable salt thereof, is provided.

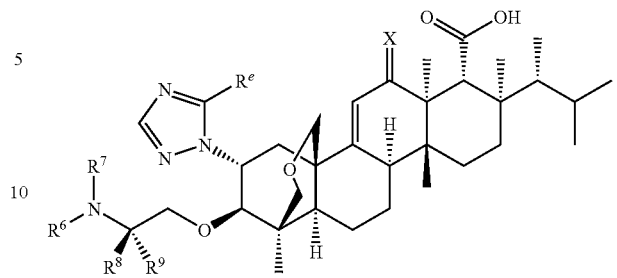

(IIa)

wherein each of the substituents is as provided for the general formula II.

In a first aspect of these embodiments (for formulas II and IIa), X is H, H, and the other substituents are as provided for the general formula II.

In a second aspect of these embodiments, $R^e$ is either pyridyl or pyrimidinyl optionally mono-substituted on a ring carbon with fluoro or chloro or on a ring nitrogen with oxygen, and the other substituents are as provided in the first aspect or the general formula II.

In a third aspect of these embodiments, $R^e$ is 4-pyridyl and the other substituents are as provided in the first aspect or the general formula II.

In a fourth aspect of these embodiments, $R^e$ is $C(O)NH_2$ or $C(O)NH(C_1$-$C_3$ alkyl) and the other substituents are as provided in the first aspect or the general formula II.

In a fifth aspect of these embodiments, $R^8$ is $C_1$-$C_4$ alkyl and $R^9$ is methyl; and the other substituents are as provided in the first to fourth aspects or the general formula II.

In a sixth aspect of these embodiments, $R^8$ is t-butyl, $R^9$ is methyl; and the other substituents are as provided in the first to fourth aspects or the general formula I.

In a seventh aspect of these embodiments, $R^6$ and $R^7$ are independently selected from hydrogen and methyl and the other substituents are as provided in the first to sixth aspects or the general formula II.

In another embodiment of the invention, the compound of the invention is selected from the exemplary species depicted in Examples 1 through 318 shown below (as the free base or a pharmaceutically acceptable salt thereof).

Other embodiments of the present invention include the following (where reference to a compound of formula (I) encompasses the various embodiments and aspects described above, as well as their pharmaceutically acceptable salts):

(a) A composition comprising a compound of Formula (I) and a carrier, adjuvant, or vehicle;

(b) A pharmaceutical composition comprising a compound of Formula (I) and a pharmaceutically acceptable carrier, adjuvant, or vehicle;

(c) The pharmaceutical composition of (b), further comprising a second therapeutic agent;

(d) The pharmaceutical composition of (c), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(e) The pharmaceutical composition of (d), wherein the second therapeutic agent is itraconazole, ketoconazole, miconazole, fluconazole, voriconazole, posaconazole, amphotericin B, flucytosine, anidulafungin, micafungin, or caspofungin;

(f) A pharmaceutical combination which is (1) a compound of Formula (I) and (2) a second therapeutic agent, wherein the compound of Formula (I) and the second therapeutic agent are each employed in an amount that renders the combination effective for treating or preventing fungal/bacterial infections;

(g) The combination of (f), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(h) The combination of (g), wherein the second therapeutic agent is itraconazole, ketoconazole, miconazole, fluconazole, voriconazole, posaconazole, amphotericin B, flucytosine, anidulafungin, micafungin, or caspofungin;

(i) A method of inhibiting (1,3)-β-D-glucan synthase in a subject in need thereof comprising administering to the subject an effective amount of a compound of Formula (I);

(j) A method of treating or preventing mycotic infections in a subject in need thereof comprising administering to the subject an effective amount of a compound of Formula (I);

(k) The method of (j), wherein the compound of Formula (I), is administered in combination, either sequentially or concurrently, with a second therapeutic agent effective against fungal/bacterial infections;

(l) The method of (k), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(m) The method of (l), wherein the second therapeutic agent is itraconazole, ketoconazole, miconazole, fluconazole, voriconazole, posaconazole, amphotericin B, flucytosine, anidulafungin, micafungin, or caspofungin;

(n) A method of inhibiting (1,3)-β-D-glucan synthase in a subject in need thereof comprising administering to the subject a pharmaceutical composition of (b), (c), (d), or (e) or the combination of (f), (g) or (h); and (o) A method of treating or preventing mycotic infections in a subject in need thereof comprising administering to the subject a pharmaceutical composition of (b), (c), (d), or (e) or the combination of (f), (g) or (h).

The present invention also includes a compound of the present invention (i) for use in, (ii) for use as a medicament for, or (iii) for use in the preparation of a medicament for: (a) inhibiting (1,3)-β-D-glucan synthase in a subject in need thereof, or (b) treating or preventing mycotic infections. In these uses, the compounds of the present invention can optionally be employed in combination, either sequentially or concurrently, with one or more therapeutic agents effective against fungal and/or bacterial infections.

In the embodiments of the compound as provided above, it is to be understood that each embodiment may be combined with one or more other embodiments, to the extent that such a combination provides a stable compound and is consistent with the description of the embodiments. It is further to be understood that the embodiments of compositions and methods provided as (a) through (o) above are understood to include all embodiments of the compounds, including such embodiments as result from combinations of embodiments of the compound.

In addition, it is understood that, in the description of embodiments of the compounds as set forth above, indicated substitutions are included only to the extent that the substitutents provide stable compounds consistent with the definition.

Additional embodiments of the invention include the pharmaceutical compositions, combinations and methods set forth in (a)-(o) above and the uses set forth in the preceding paragraph, wherein the compound of the present invention employed therein is a compound of one of the embodiments or aspects of the compounds described above. In all of these embodiments or aspects as well as those described hereinbelow, the compound may optionally be used in the form of a pharmaceutically acceptable salt or hydrate when appropriate.

The present compounds (including pharmaceutical acceptable salt and/or hydrate forms) have antimicrobial (e.g., antifungal) activities against yeasts and fungi, including one or more of the following: *Acremonium, Absidia* (e.g., *Absidia corymbifera*), *Alternaria, Aspergillus* (e.g., *Aspergillus clavatus, Aspergilius flavus, Aspergillus fumigatus, Aspergillus nidulans, Aspergillus niger, Aspergillus terreus,* and *Aspergillus versicolor*), *Bipolaris, Blastomyces* (e.g., *Blastomyces dermatitidis*), *Blastoschizomyces* (e.g., *Blastoschizomyces capitatus*), *Candida* (e.g., *Candida albicans, Candida glabrata* (*Torulopsis glabrata*), *Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cladosporium* (e.g., *Cladosporium carrionii* and *Cladosporium trichloides*), *Coccidioides* (e.g., *Coccidioides immitis*), *Cryptococcus* (e.g., *Cryptococcus neoformans*), *Curvularia, Cunninghamella* (e.g., *Cunninghamella elegans*), Dermatophyte, *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Histoplasma* (e.g., *Histoplasma capsulatum* var. *capsulatum*), *Malassezia* (e.g., *Malassezia furfur*), *Microsporum* (e.g., *Microsporum canis* and *Microsporum gypseum*), *Mucor, Paracoccidioides* (e.g., *Paracoccidioides brasiliensis*), *Penicillium* (e.g., *Penicillium marneffei*), *Phialophora, Pityrosporum ovale, Pneumocystis* (e.g., *Pneumocystis carinii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedosporium* (e.g., *Scedosporium apiosperum*), *Scopulariopsis, Sporothrix* (e.g., *Sporothrix schenckii*), *Trichoderma, Trichophyton* (e.g., *Trichophyton mentagrophytes* and *Trichophyton rubrum*), and *Trichosporon* (e.g., *Trichosporon asahii, Trichosporon beigelii* and *Trichosporon cutaneum*). The present compounds are not only useful against organisms causing systemic human pathogenic mycotic infections, but also useful against organisms causing superficial fungal infections such as *Trichoderma* sp. and other *Candida* spp. The compounds of the present invention are particularly effective against *Aspergilius flavus, Aspergillus fumigatus, Candida albicans, Candida parapsilosis, Cryptococcus neoformans, Saccharomyces cerevisiae,* and *Trichophyton mentagrophytes.*

In view of their antifungal activity, compounds of Formula (I) are useful for the treatment and/or prevention of one or more of a variety of superficial, cutaneous, subcutaneous and systemic mycotic infections in skin, eye, hair, nail, oral mucosa, gastrointestinal tract, bronchus, lung, endocardium, brain, meninges, urinary organ, vaginal portion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, blood, and so on.

Therefore, compounds of the present invention are useful for preventing and treating one or more of various infectious diseases, such as dermatophytosis (e.g., trichophytosis, ringworm or tinea infections), athletes foot, paronychia, pityriasis versicolor, erythrasma, intertrigo, fungal diaper rash, candida vulvitis, candida balanitis, otitis externa, candidiasis (cutaneous and mucocutaneous), chronic mucocandidiasis (e.g. thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia. The present compounds may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

Examples of azoles that may be used in combination with the present compounds include, but are not limited to, fluconazole, voriconazole, itraconazole, ketoconazole, miconazole, ravuconazole, detoconazole, clotrimazole, and posaconazole. Examples of polyenes that may be used in combination with the present compounds include, but are not limited to, amphotericin B, nystatin, liposamal and lipid forms thereof such as ABELCET, AMBISOME, and AMPHOCIL. Examples of purine or pyrimidine nucleotide inhibitors that may be used in combination with the present compounds include, but are not limited to, flucytosine or polyxins such as nikkomycines, in particular nikkomycine Z or nikkomycine X. Another class of therapeutic agents that may be used in combination with the present compounds includes chitin inhibitors. Examples of elongation factor inhibitors that may be used in combination with the present compounds include, but are not limited to, sordarin and analogs thereof. Examples of pneumocandin or echinocandin derivatives that may be used in combination with the present compounds include, but are not limited to, cilofungin, anidulafungin, micafungin, and caspofungin. Examples of mannan inhibitors that may be used in combination with the present compounds include but are not limited to predamycin. Examples of bactericidal/permeability-inducing (BPI) protein products that may be used in combination with the present compounds include but are not limited to XMP.97 and XMP.127. Examples of immunomodulators that may be used in combination with the present compounds include, but are not limited to, an interferon, (e.g., IL-1, IL-2, IL-3 and IL-8), defensines, tacrolimus and G-CSF (Granulocyte-colony stimulating factor).

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "cycloalkyl" refers to any cyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl.

The term "cycloalkyl-alkyl" (or equivalently "alkyl-cycloalkyl") as used herein, refers to a system that includes an alkyl portion as described above and also includes a cycloalkyl portion as described above. Attachment to a "cycloalkyl-alkyl" (or "alkyl-cycloalkyl") may be through either the cycloalkyl or the alkyl portion. The specified number of carbon atoms in "cycloalkyl-alkyl" systems refers to the total number of carbon atoms in both the alkyl and the cycloalkyl parts. Examples of $C_4$-$C_7$ cycloalkyl-alkyl include but are not limited to methylcyclopropyl, dimethylcyclopropyl, methylcyclobutyl, trimethylcyclobutyl, ethylcyclopentyl, methylcyclohexyl, cyclopropylmethyl, cyclopropylethyl, cyclobutylmethyl, cyclobutylpropyl, cyclopentylethyl and cyclohexylmethyl.

The term "alkenyl" refers to a straight or branched-chain acyclic unsaturated hydrocarbon having a number of carbon atoms in the specified range and containing at least one double bond. Thus, for example, "$C_2$-$C_3$ alkenyl" refers to vinyl, (1Z)-1-propenyl, (1E)-1-propenyl, 2-propenyl, or isopropenyl.

The term "halogen" (or "halo") refers to fluorine, chlorine, bromine and iodine (alternatively referred to as fluoro, chloro, bromo, and iodo).

The term "oxo" means =O and as used herein, the term "imino" means =$NR^o$, wherein $R^o$ is as previously defined.

As used herein, the term "or," as used herein, denotes alternatives that may, where appropriate, be combined.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results. Suitable 5- or 6-membered heteroaromatic rings include, but are not limited to, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable 9- or 10-membered heteroaryl rings include, but are not limited to, quinolinyl, isoquinolinyl, indolyl, indazolyl, benzimidazolyl, benztriazoyl, imidazopyridinyl, triazolopyridinyl, and imidazopyrimidinyl. Suitable 4- to 6-membered heterocyclyls include, but are not limited to, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiadiazinanyl, tetrahydropyranyl, tetrahydrothiopyranyl, and dioxanyl.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). Reference to a compound also includes stable complexes of the compound such as a stable hydrate.

As a result of the selection of substituents and substituent patterns, certain of the compounds of the present invention can have asymmetric centers and can occur as mixtures of stereoisomers, or as individual diastereomers, or enantiomers. Unless otherwise indicated, all isomeric forms of these compounds, whether isolated or in mixtures, are within the scope of the present invention. Also included within the scope of the present invention are tautomeric forms of the present compounds as depicted.

When any variable occurs more than one time in any constituent or in Formula (I) or in any other formula depicting and describing compounds of the invention, its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

A bond terminated by a wavy line is used herein to signify the point of attachment of a substituent group or partial structure. This usage is illustrated by the following example:

be accomplished by standard methods known in the art (e.g. neutralization with an appropriate inorganic base such as NaHCO$_3$). Other desired amine salts may then be prepared in a conventional manner by reacting the free base with a suitable organic or inorganic acid. Representative pharmaceutically acceptable quaternary ammonium salts include the following: hydrochloride, sulfate, phosphate, carbonate, acetate, tartrate, citrate, malate, succinate, lactate, stearate, fumarate, hippurate, maleate, gluconate, ascorbate, adipate, gluceptate, glutamate, glucoronate, propionate, benzoate, mesylate, tosylate, oleate, lactobionate, laurylsulfate, besylate, caprylate, isetionate, gentisate, malonate, napsylate, edisylate, pamoate, xinafoate, napadisylate, hydrobromide, nitrate, oxalate, cinnamate, mandelate, undecylenate, and camsylate. Many of the compounds of the invention carry an acidic carboxylic acid moiety, in which case suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the

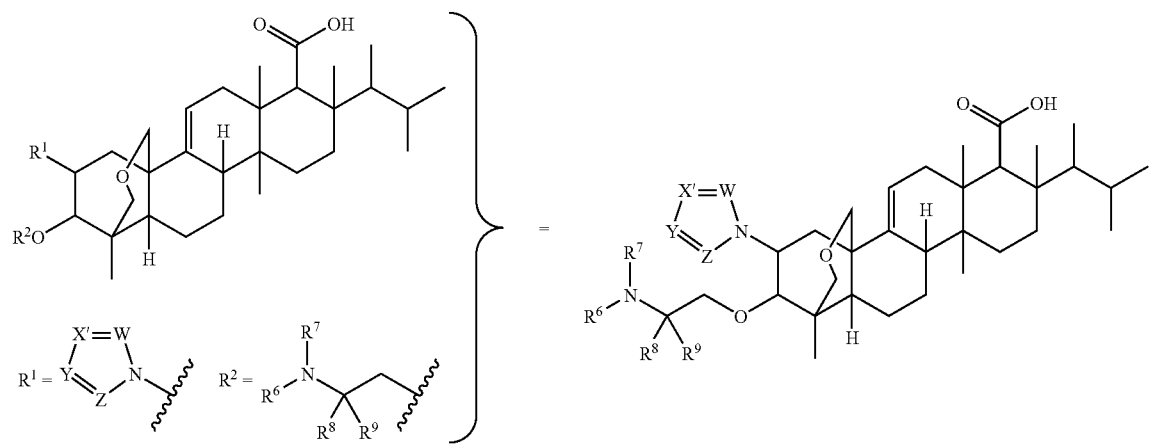

The compounds of this invention are also useful in the preparation and execution of screening assays for antifungal compounds. For example, the compounds of this invention are useful for isolating mutants, which are excellent screening tools for more powerful antifungal compounds.

All compounds of the present invention may be administered in the form of "pharmaceutically acceptable salts" or hydrates as appropriate. Other salts may, however, be useful in the preparation of the compounds according to the invention or of their pharmaceutically acceptable salts. For example, when the compounds of the present invention contain a basic amine group, they may be conveniently isolated as trifluoroacetic acid salts (e.g. following HPLC purification). Conversion of the trifluoroacetic acid salts to other salts, including pharmaceutically acceptable salts, may be accomplished by a number of standard methods known in the art. For example, an appropriate ion exchange resin may be employed to generate the desired salt. Alternatively, conversion of a trifluoroacetic acid salt to the parent free amine may treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "administration" and variants thereof (e.g., "administering" a compound) in reference to a compound of the invention mean providing the compound or a prodrug of the compound to the subject in need of treatment. When a compound of the invention or a prodrug thereof is provided in combination with one or more other active agents (e.g., other antifungal/antibacterial agents useful for treating fungal/bacterial infections), "administration" and its variants are each understood to include concurrent and sequential provision of the compound or prodrug and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented or for reducing the likelihood of occurrence. The term also includes herein the amount of active compound sufficient to inhibit (1,3)-β-D-glucan synthase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting (1,3)-β-D-glucan synthase or preventing or treating fungal infection, the compounds of the present invention, optionally in the form of a salt or a hydrate, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 20<sup>th</sup> edition, edited by A. R. Gennaro, Mack Publishing Co., 2000.

The compounds of this invention can be administered, e.g., orally or intravenously, in a dosage range of, for example, 0.001 to 1000 mg/kg of mammal (e.g., human) body weight per day in a single dose or in divided doses. An example of a dosage range is 0.01 to 500 mg/kg body weight per day orally or intravenously in a single dose or in divided doses. Another example of a dosage range is 0.1 to 100 mg/kg body weight per day orally or intravenously in single or divided doses. For oral administration, the compositions can be provided in the form of tablets or capsules containing, for example, 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention also includes processes for making compounds of Formula (I). The compounds of the present invention may be prepared according to the following reaction schemes and examples, or modifications thereof, from starting material enfumafungin. Enfumafungin is a natural product produced from a fungus strain of *Hormonema* sp. (deposited under the Budapest Treaty in the culture collection of the American Type Culture Collection and assigned accession number ATCC 74360) that was isolated from living leaves of an unidentified shrub collected in Navalquejigo, province of Madrid, Spain, as described in U.S. Pat. No. 5,756,472, the contents of which are hereby incorporated by reference in its entirety.

The following two examples illustrate the systematic name and numbering conventions employed for the compounds of the present invention.

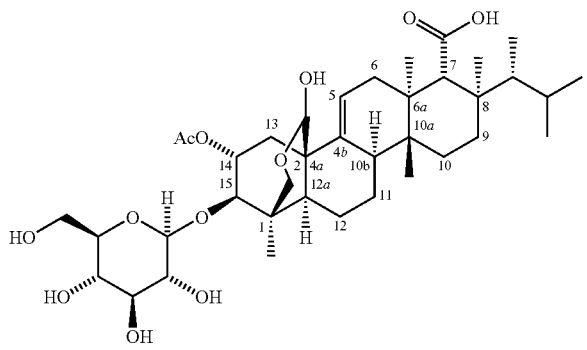

(1S,4aR,6aS,7R,8R,10aR,10bR,12aR,14R,15R)-14-(acetyloxy)-8-[(1R)-1,2-dimethylpropyl]-15-(β-D-glucopyranosyloxy)-1,6,6a,7,8,9,10,10a,10b,11,12,12a-dodecahydro-4-hydroxy-1,6a,8,10a-tetramethyl-4H-1,4a-propano-2H-phenanthro[1,2-c]pyran-7-carboxylic acid (common name: enfumafungin)
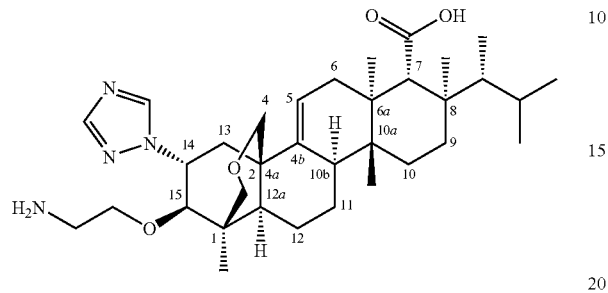
(1S,4aR,6aS,7R,8R,10aR,10bR,12aR,14R,15R)-15-(aminoethoxy)-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid
Scheme A
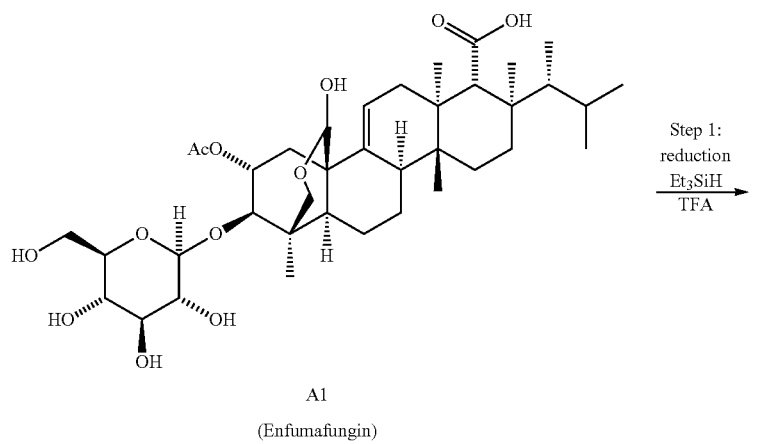
A1
(Enfumafungin)
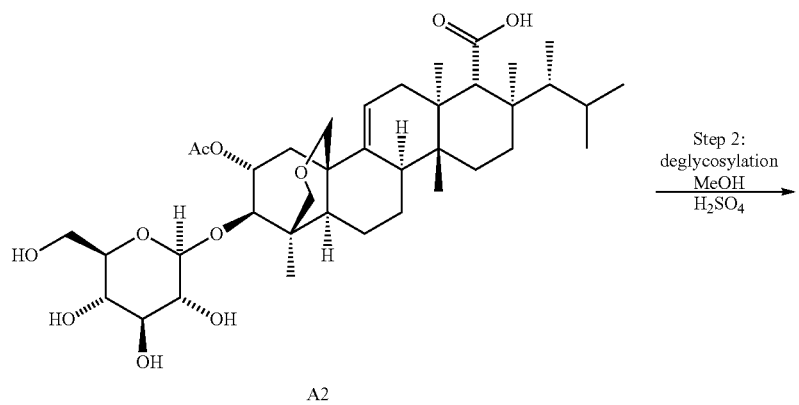
A2

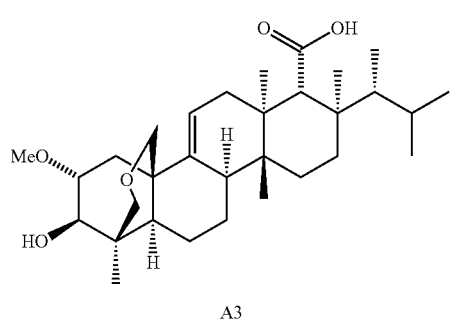

A3

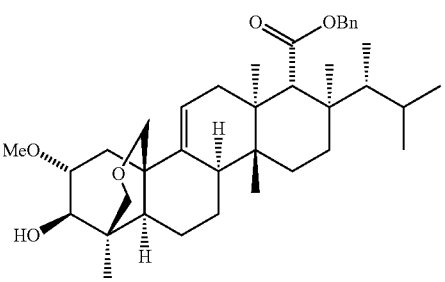

A4

Scheme A illustrates a method for deglycosylation of the natural product enfumafungin and additional modification to prepare the molecule for further elaboration. In a first step, the lactol group of enfumafungin is reduced by treatment with a suitable reducing agent such as triethylsilane under acidic conditions (e.g. trifluoroacetic acid) to give compound A2. Removal of the glucose moiety may be accomplished by heating A2 in methanol in the presence of a strong acid such as sulfuric acid. Under these conditions, the acetoxy group at C14 is also replaced by methoxy to produce the methyl ether compound A3. Other methods for deglycosylation of A2 and related compounds are also known (See e.g., International Patent Publication No. WO 2007/127012; and Shafiee et al., *J. Molecular Catalysis B: Enzymatic,* 2001(16), pp. 27-32). Next, selective protection of the carboxylic acid of A3 may by accomplished by treatment with benzyl bromide in the presence of a suitable base such as sodium bicarbonate or potassium carbonate to give A4. Other suitable protecting groups known in the art may also be employed.

Schemes B to E illustrate methods of introducing the $R^2$ substituent on the C15 hydroxy group. Additional methods are also described in International Patent Publication No. WO 2007/127012, herein incorporated by reference in its entirety. In the Schemes the variables $R^6$, $R^7$, $R^8$ and $R^9$ are as previously defined or are precursor groups thereto. Additional variables are as defined in the individual schemes.

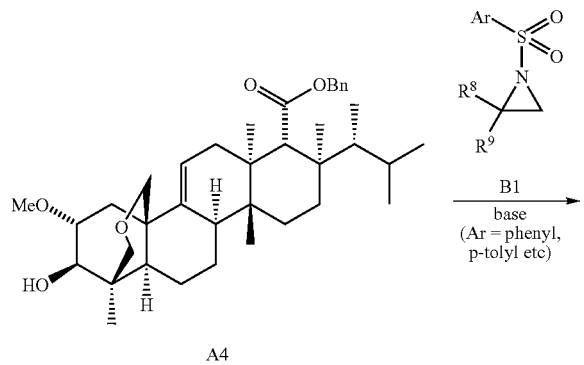

Scheme B

A4

As shown in Scheme B, reaction of A4 with an N-sulfonyl aziridine (B1) in the presence of a suitable base such as potassium hydride, sodium hydride or potassium tert-pentylate and optionally in the presence of an appropriate cation complexing agent such as 18-Crown-6 or 15-Crown-5, gives intermediate B2. Aziridines B1 are prepared by methods known in the art (see e.g. *Acc. Chem. Res.* 2006, 39, 194-206; *Tetrahedron* 2004, 60, 2701-2743; *J. Am. Chem. Soc.* 1998, 120, 6844; *Org. Lett.* 1999, 5, 783-786; *Chem. Soc. Rev.* 2002, 31, 247; *Synthesis* 2000, 1347; *ARKIVOC* 2007, 4, 304-311; *Tetrahedron: Asymmetry* 1997, 8, 1693; *Chem. Commun.* 2006, 1833-1835) and as exemplified further below. Removal of the N-sulfonyl group of B2 is accomplished by dissolving metal reduction with sodium or lithium in liquid ammonia employing a suitable co-solvent such as dimethoxyethane or tetrahydrofuran. This step also conveniently deprotects the carboxylic acid when it is protected as a benzyl ester, giving intermediate B3. It will be appreciated by one skilled in the art that other protecting group strategies may also be employed. Further substitution of the amino group of B3 may be carried-out at this point by standard methods known in the art such as alkylation or reductive amination to give compound B4.

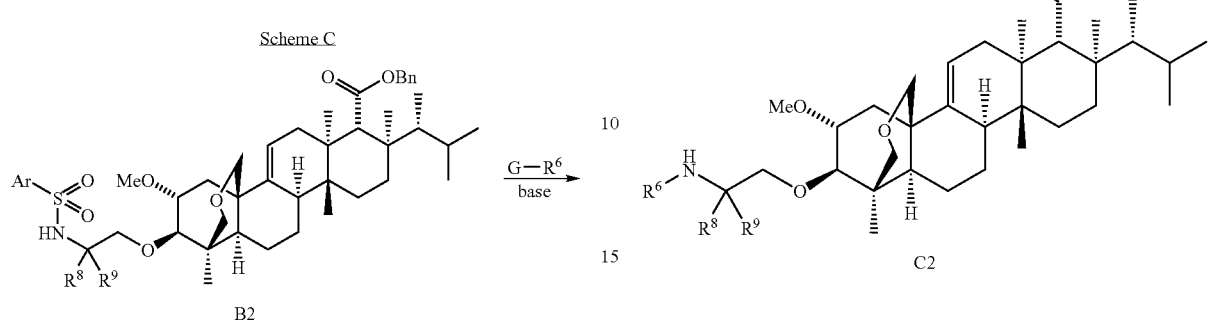

G = halogen, mesylate, triflate or other suitable leaving group

Scheme C illustrates an alternative method of substituting the amino group by alkylating the N-sulfonyl intermediate B2 with an appropriate alkylating agent such as methyl iodide, ethyl iodide or allyl bromide in the presence of a suitable base such as sodium hydride to give C1. Dissolving metal reduction as described previously for B2 then gives C2. The synthesis of Scheme C is particularly useful for introducing a single substitution on the aminoether nitrogen. In Scheme C introduction of an $R^6$ group is illustrated, but it will be apparent to one skilled in the art that the synthesis would work equally well for introduction of an $R^7$ group.

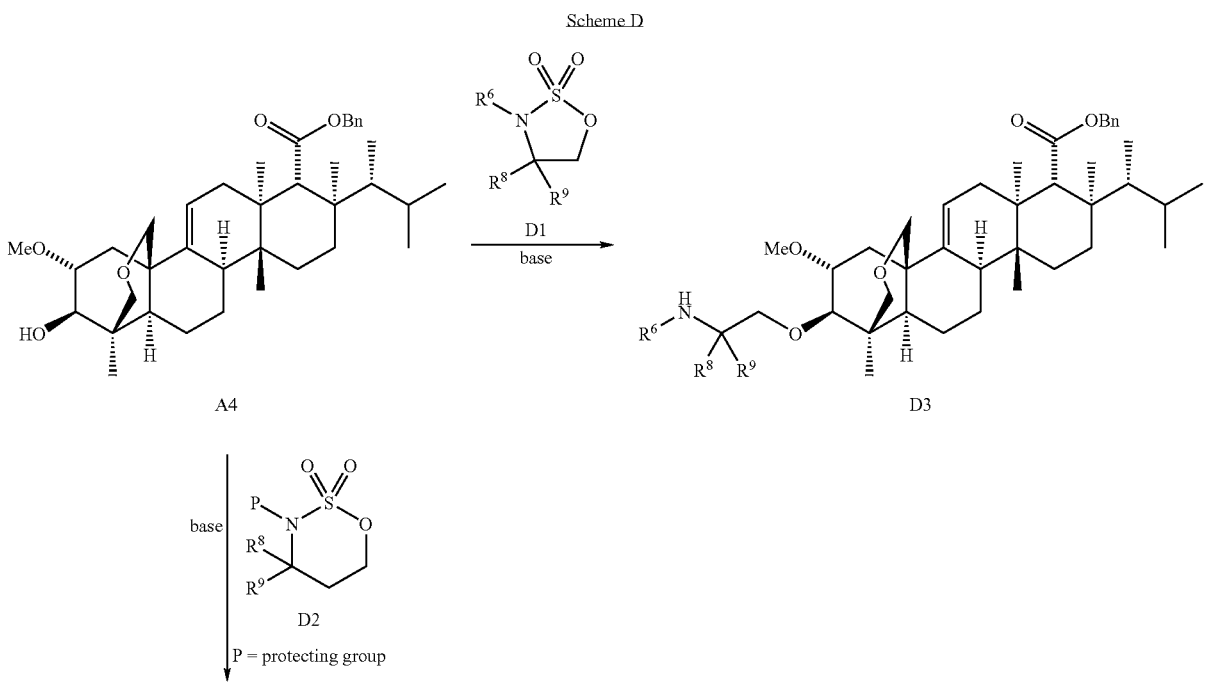

P = protecting group

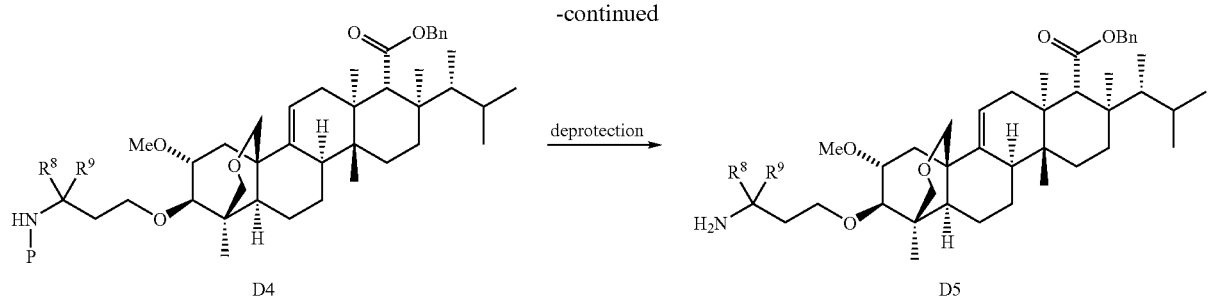

Scheme D describes additional methods for introducing the $R^2$ group. Reaction of A4 with the 5-membered cyclic sulfamidate reagent D1 gives intermediate D3. This reaction is carried-out under conditions analogous to those described in Scheme B for coupling with aziridine B1. An acidic aqueous work-up is carried-out which cleaves the initial N-sulfated product to give the amine D3. Similarly, reaction of A4 with the 6-membered cyclic sulfamidate reagent D2 gives D4 and after removal of the amine protecting group the aminopropyl ether intermediate D5 is obtained. Suitable protecting groups for D2 and D4 include t-butyloxycarbonyl (Boc) and benzyloxycarbonyl (Cbz). The cyclic sulfamidate reagents D1 and D2 are prepared by methods known in the art (e.g. Tetrahedron 2003, 59, 2581-2616; J. Org. Chem. 2004, 69, 3610-3619; Angew. Chem. Int. Ed. 2005, 44, 3518-3520) and as exemplified further below. While in Scheme D the synthesis of D3 with $R^6$ substitution on the nitrogen of the aminoether is illustrated, it will be apparent to one skilled in the art that the method would work equally well for the synthesis of a D3 compound with $R^7$ substitution on the nitrogen of the aminoether by employing the appropriately substituted D1 compound.

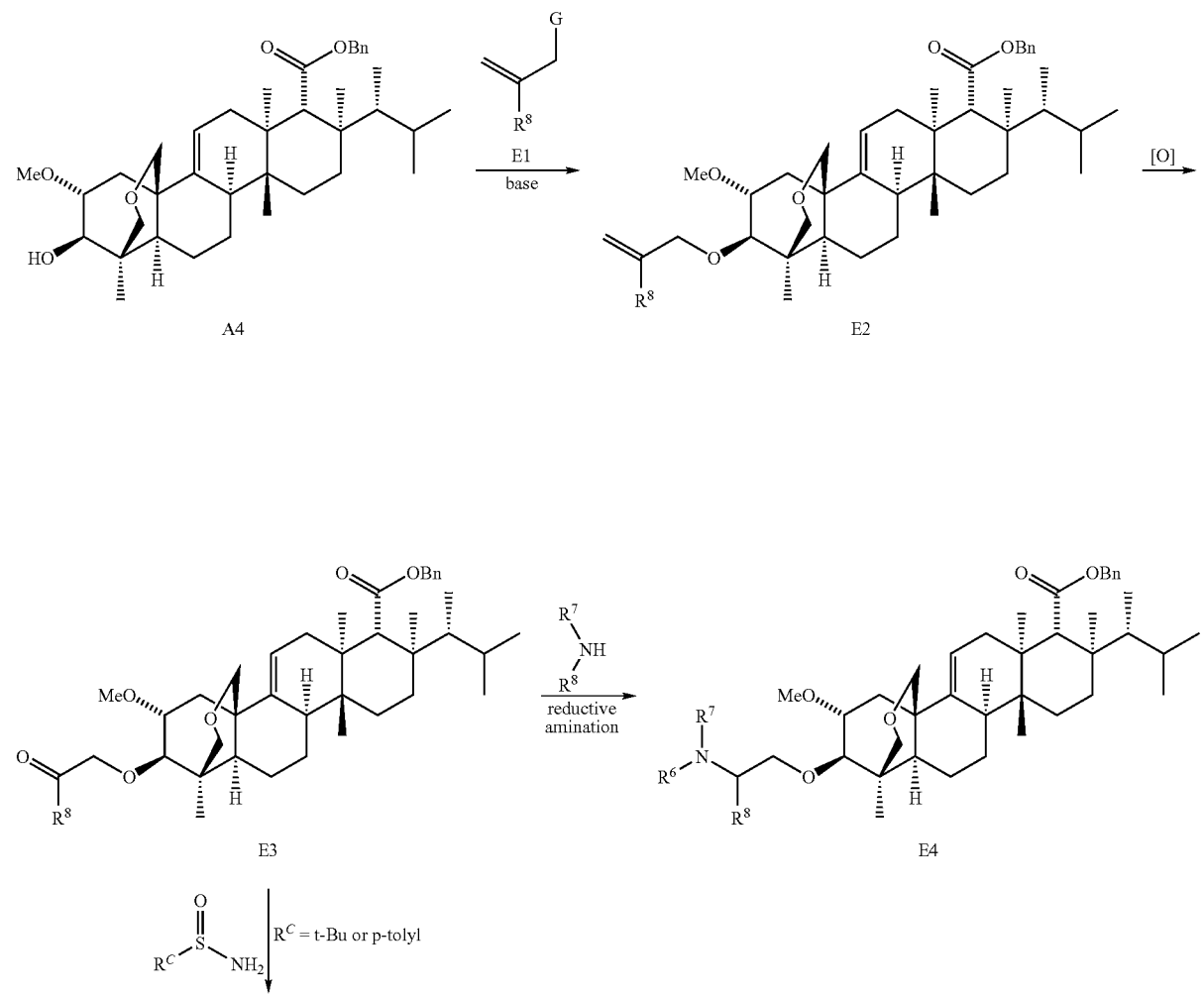

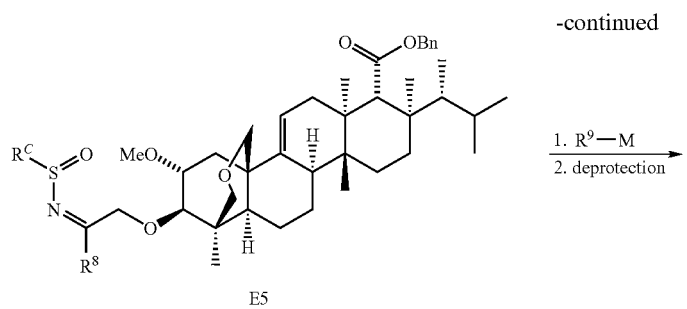

E5

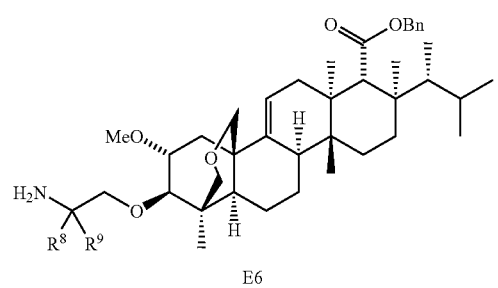

E6

Scheme E illustrates additional methods for introduction of the $R^2$ substitution on the C15 hydroxy group. Alkylation of A4 with an allylic halide or other suitably activated allylic species (E1) gives the allylic ether E2. Suitable bases for this reaction are sodium hydride or potassium hydride and the like. Oxidative cleavage of the alkenyl group under standard conditions (e.g. $OsO_4/NaIO_4$) gives the corresponding ketone (or aldehyde) E3. Reductive amination of E3 by standard methods (e.g. $R^6R^7NH$, $NaBH_3CN$, AcOH, MeOH, THF) then gives the aminoether E4. Alternatively, E3 can be converted to the sulfinylimine E5 by reaction with an alkyl- or arylsulfinylamide in the presence of a dehydrating agent such as copper sulfate or titanium ethoxide. Reaction of E5 with an alkyllithium reagent (e.g. $R^9Li/Me_3Al$), alkyl Grignard reagent (e.g. $R^9MgBr$) or (for $R^9$=H) a metal hydride reducing agent (e.g. lithium triethylborohydride) followed by acid treatment (e.g. HCl/MeOH) to cleave the N-sulfinyl group gives E6. In one useful variation of this synthesis Scheme, use of an enantiomerically pure alkyl- or arylsulfinylamide reagent for this sequence allows for control of the stereochemistry of the substitution adjacent to the amine in E6 (see e.g. *Acc. Chem. Res.* 2002, 35, 984-995). In another useful variation of this Scheme, the roles of $R^8$ and $R^9$ as illustrated in Scheme E may be reversed. In another useful variation of Scheme E, it will be appreciated by one skilled in the art that at the stage of intermediate E3, an $R^5$ substituent may be introduced by alkylation at the position adjacent to the carbonyl group using conventional conditions and reagents [e.g. $R^5I$, $LiN(i-Pr)_2$].

Schemes G-N illustrate methods for introducing $R^1$ heterocyclic groups. In the Schemes the various methods are exemplified by starting with intermediate B4, but it is understood that the same methods work equally well starting with many other intermediates including but not limited to B3, C2, D3, D5, E4, and E6. In addition, many of the intermediates and final compounds described in International Patent Publication No. WO 2007/127012 may also serve as starting materials for introduction of $R^1$ heterocyclic groups as described in Schemes G-N. In the Schemes the variables $R^e$, $R^6$, $R^7$, $R^8$ and $R^9$ are as previously defined or are precursor groups thereto.

Scheme G

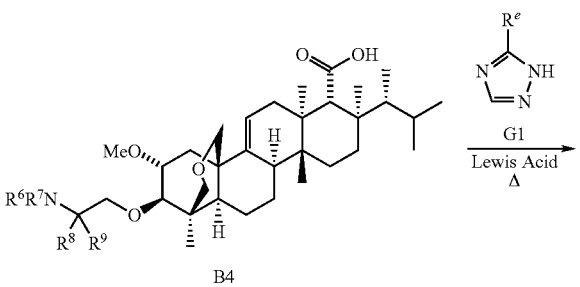

B4

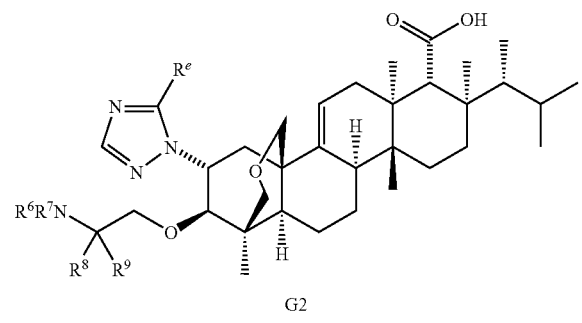

G2

+

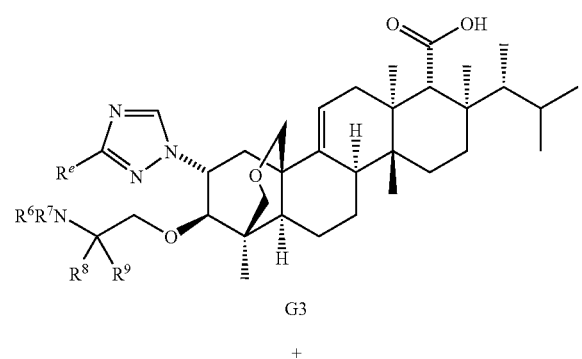

G3

+

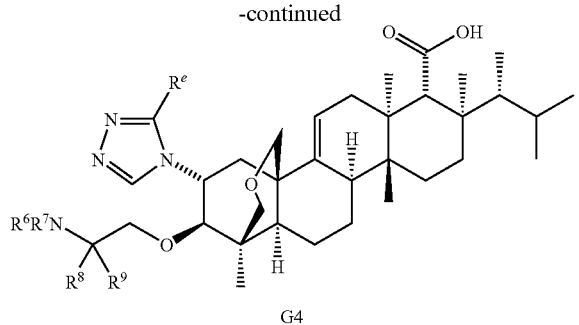

G4

Scheme G illustrates the introduction of a 1,2,4-triazole heterocycle at the C14 position. The displacement reaction between B4 and the triazole derivative G1 is promoted by a Lewis acid reagent. Suitable Lewis acid reagents include boron trifluoride diethyl etherate, copper trifluoromethansulfonate, zinc trifluoromethanesulfonate and the like. The reaction is conducted in a non-coordinating aprotic solvent such as 1,2-dichloroethane at a temperature of between about 20° C. and about 100° C. This displacement reaction generally occurs with retention of configuration at C14, possibly due to participation by the proximal bridging ether oxygen. When the triazole starting material G1 is unsymmetrically substituted (i.e. $R^e$ is not hydrogen) then three regioisomeric products may be formed in this displacement reaction, G2, G3 and G4. When two or three isomers are formed, it is often possible and desirable to separate them chromatographically or by other means. The ratio of the isomers may vary depending on the substituent group $R^e$. Depending on the desired $R^e$ substituent, the starting triazole compounds G1 are generally readily available either from commercial sources or through preparation by known literature methods. In the example illustrated in Scheme G, a mono-substituted triazole is employed. A disubstituted triazole heterocycle may also be introduced in an analogous manner.

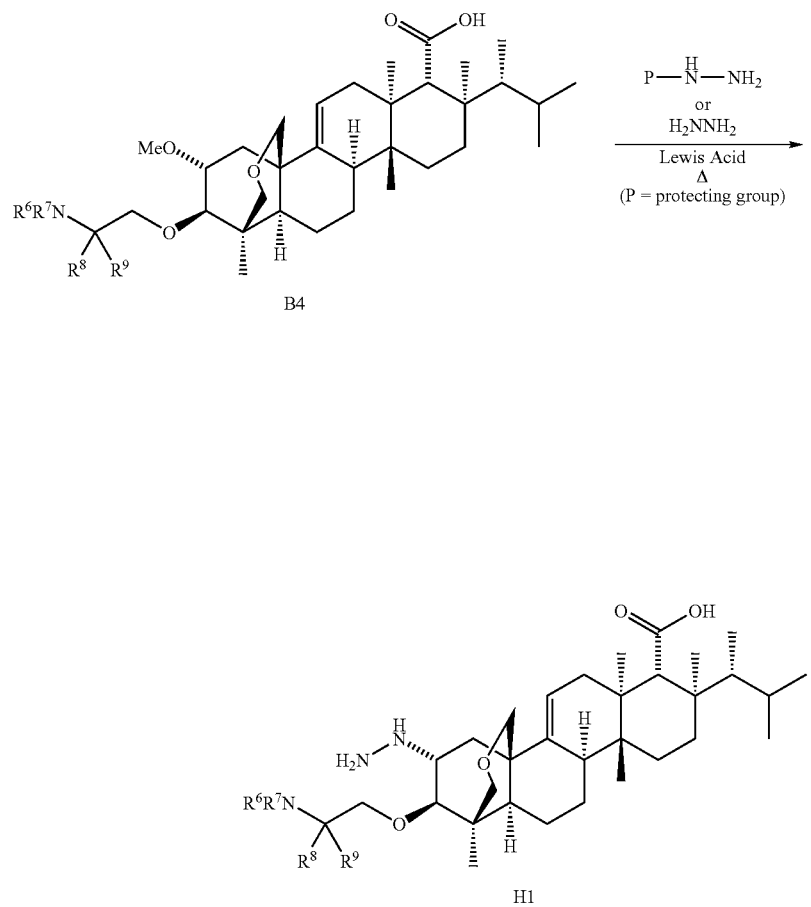

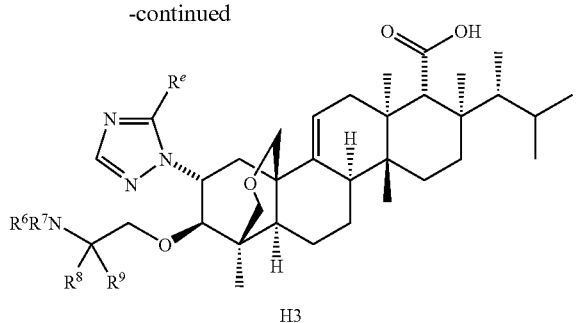

H3

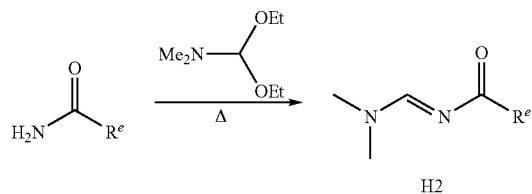

H2

Scheme H illustrates an alternative method for installing a substituted 1,2,4-triazole group. Reaction of intermediate B4 with anhydrous hydrazine promoted by a Lewis acid such as boron trifluoride diethyl etherate yields the hydrazine intermediate H1. The reaction is conducted in a non-coordinating aprotic solvent such as 1,2-dichloroethane at a temperature of between about 20° C. and 100° C. Alternatively, a protected hydrazine such as benzyl carbazate (P=benzyloxycarbonyl) or t-butyl carbazate (P=t-butyloxycarbonyl) can be employed in this reaction. With these protecting groups, deprotection occurs under the conditions of the displacement reaction to give H1 directly with no separate deprotection step being required. Other suitable protecting groups may also be employed which require a separate deprotection step (e.g. phthalimido). Cyclocondensation reaction of H1 with an acyl amidine derivative H2 by heating in acetic acid or another suitable solvent at a temperature between about 20° C. and about 120° C. yields the triazole product H3. This method of triazole synthesis is well known in the art (e.g. *J. Org. Chem.* 1979, 44, 4160-4164; *Science of Synthesis,* 2004, 13, 603-639). By this method a single triazole regioisomer H3 is produced. While this method of synthesis is not appropriate for all desired R$^e$ groups, it is especially useful for compounds in which R$^e$ is aryl, heteroaryl, heterocyclyl and certain alkyl groups. Acyl amidine compounds H2 are conveniently synthesized as shown in Scheme H by treating the requisite primary amide compound with dimethylformamide diethyl acetal or an equivalent reagent at a temperature between about 20° C. and about 120° C. (cf. *J. Org. Chem.* 1979, 44, 4160-4164; *J. Am. Chem. Soc.* 2006, 128, 16406-16409).

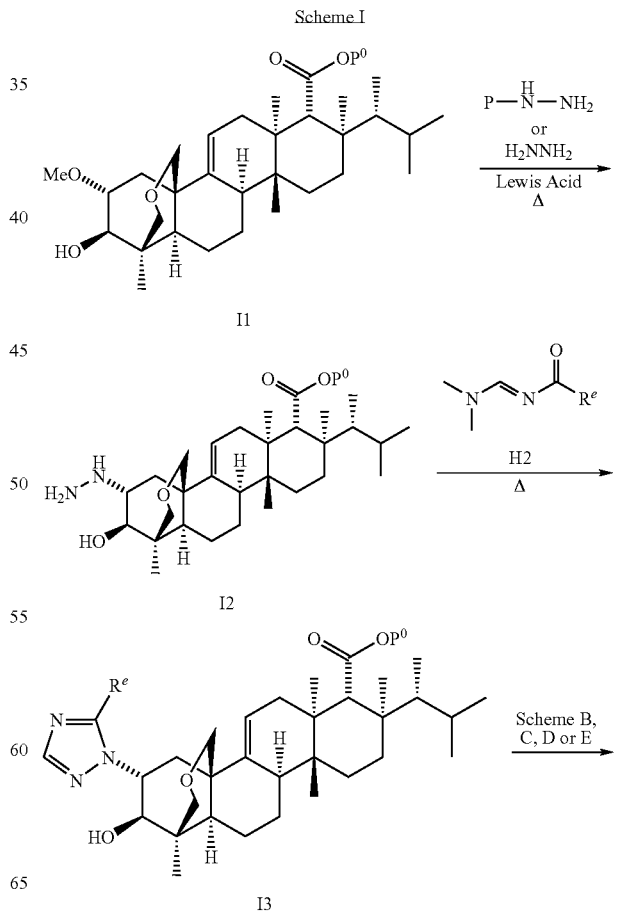

Scheme I

-continued

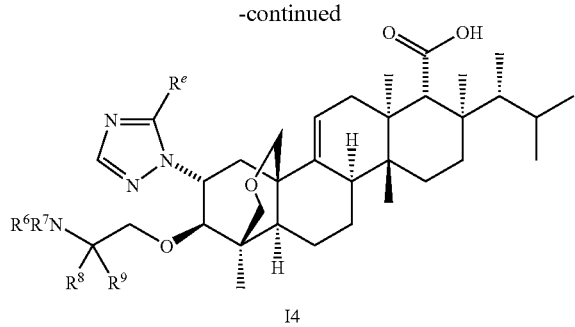

P = protecting group
P⁰ = hydrogen or protecting group

Scheme I describes a variation of the synthesis method of Scheme H which is useful in certain instances. In this case the $R^1$ heterocyclic group is introduced prior to installation of the $R^2$ ether substituent. The starting point for this mode of synthesis is intermediate I1 which may be synthesized according to Scheme A. Steps 1 and 2 in Scheme I are analogous to Steps 1 and 2 in Scheme H. Thus, reaction of I1 with hydrazine or a protected form of hydrazine promoted by a Lewis acid such as boron trifluoride diethyl etherate gives the hydrazino intermediate I2. As described previously, with certain hydrazine protecting groups (e.g. phthalimido) a deprotection step may be required at this stage in the synthetic Scheme. Reaction of I2 with an acyl amidine derivative H2 as described for step 2 in Scheme H yields the triazole intermediate I3. Further elaboration of I3 to a final compound such as I4 may then proceed according to the methods described in Schemes B, C, D and E. In Scheme I, protection of the carboxylic acid group may be necessary. The protection step can be conveniently carried-out at the stage of I1 or I3. Various carboxy protecting groups known in the art may be suitable, including benzyl, 4-methoxybenzyl, allyl and the like. Depending on the exact details of the synthesis, a final deprotection step may be required to give compound I4.

Additional compounds of the present invention may be prepared by further elaboration of a $R^1$ heterocyclic group once introduced at C14. Examples of this method of synthesis are illustrated in Schemes J and K.

Scheme J

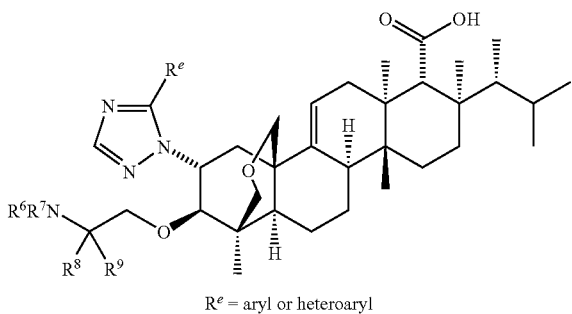
$R^e$ = aryl or heteroaryl
J2

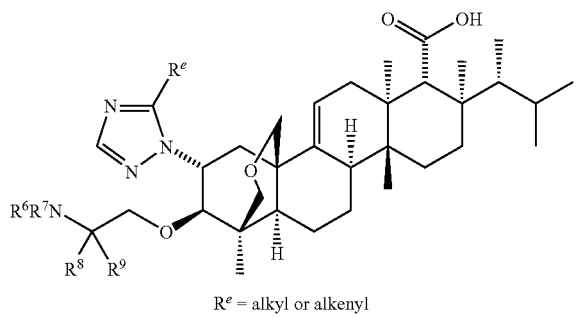
$R^e$ = alkyl or alkenyl
J3

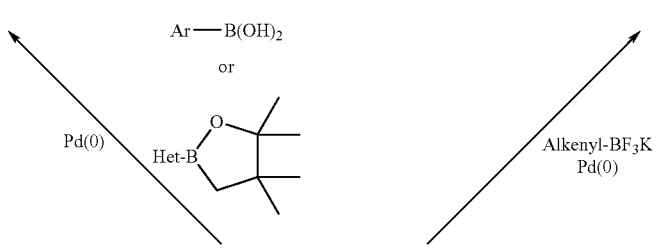

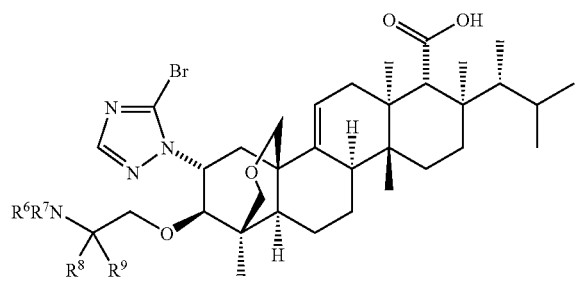
J1

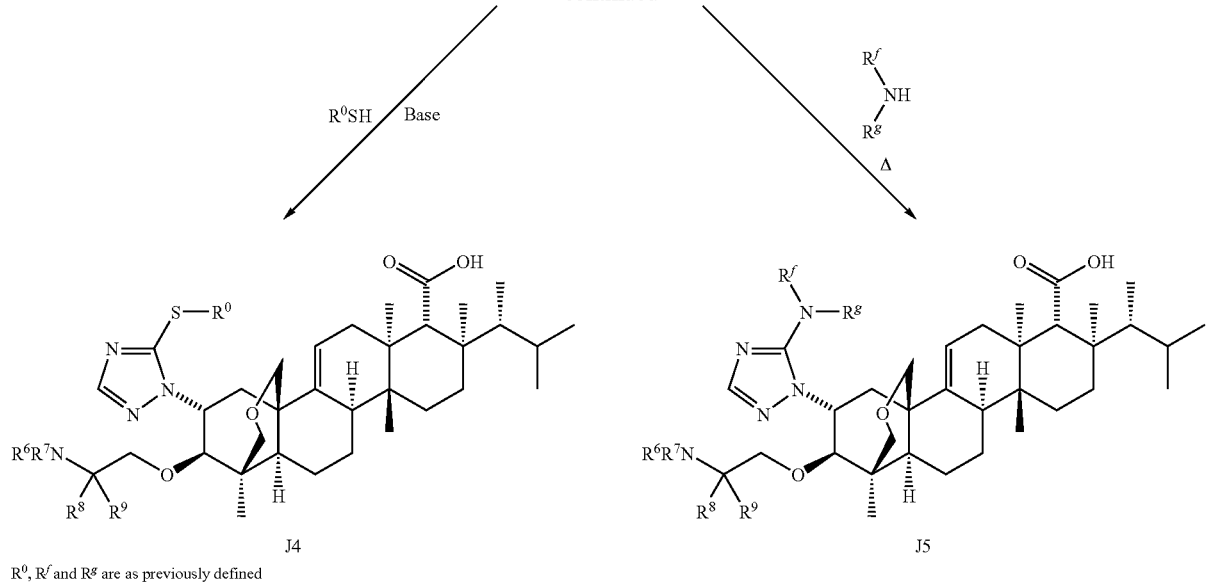

$R^0$, $R^f$ and $R^g$ are as previously defined

In Scheme J, a bromotriazole compound J1 is employed as a versatile intermediate. Compound J1 may be synthesized according to the method of Scheme G. Palladium catalyzed cross-coupling reactions between J1 and a variety of aryl- and heteroaryl-boronic acid and boronate ester derivatives are possible to give product compounds J2. These reactions are generally carried-out in the presence of a base (e.g. cesium carbonate) a palladium catalyst (e.g. palladium (II) acetate) and a phosphine ligand (e.g. 2-dicyclohexylphosphino-2',4',6'-triisopropylbiphenyl) at an elevated temperature (e.g. 50° C. to 120° C.). Such cross-coupling reactions are well-known in the art and are generically referred to as Suzuki couplings. Many suitable aryl- and heteroaryl boronic acid and boronate ester derivatives are readily available from commercial sources or are readily prepared by known methods. Other related cross-coupling reactions to give product compounds J2 are also possible, such as a Stille cross-coupling reaction between J1 and an aryl or heteroaryl stannane derivative. Introduction of alkenyl groups to give J3 may be accomplished by reaction of J1 with alkenyl trifluoroborate salts (e.g. potassium vinyltrifluoroborate) in the presence of a palladium catalyst. Further reaction of the alkenyl products J3 may also be carried-out (e.g. hydrogenation to give alkyl substitution). Direct reaction of J1 with alkyl trifluoroborate salts is also possible. Other transformations of J1 that may be carried-out include reaction with a thiol derivative in the presence of a base to give products J4 or reaction with an amino derivative under the influence of heat and optionally an additional base to give aminotriazole derivatives J5. Product compounds J4 may also be further derivatized (e.g. oxidation to a sulfone).

Scheme K

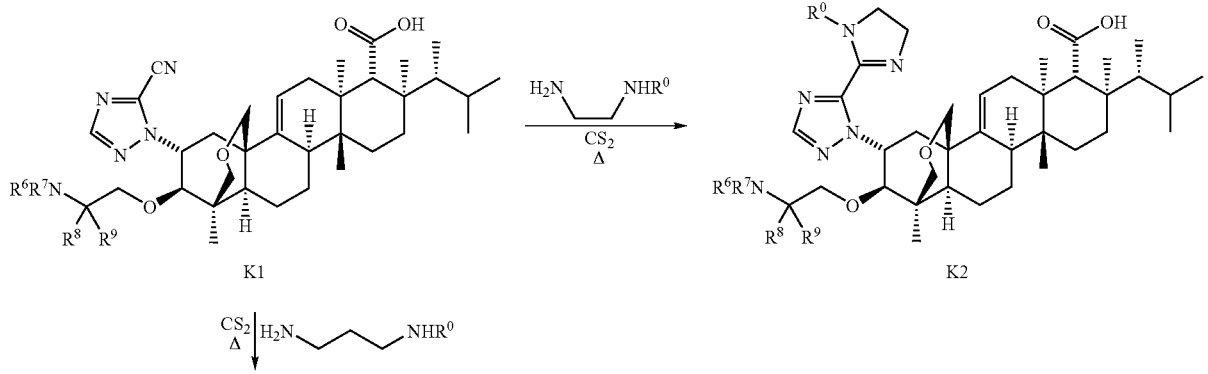

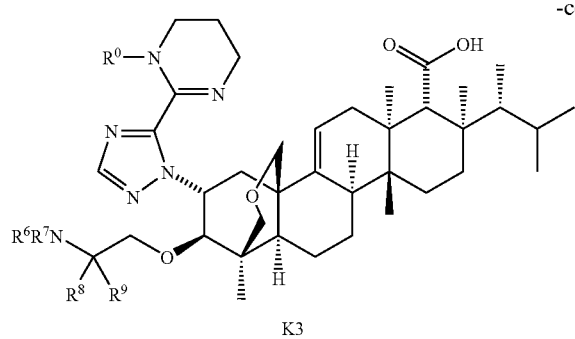

K3

$R^0$ is as previously defined

Scheme K illustrates the synthesis of another subclass of compounds of the invention. The starting cyanotriazole compound K1 may be synthesized by the method of Scheme G. Reaction of K1 with ethylenediamine or a substituted ethylenediamine derivative in the presence of carbon disulfide gives a cyclic amidine derivative K2. This reaction is generally carried-out at a temperature between about 20° C. and 100° C. Similarly, reaction of 1 with propylenediamine or a substituted propylenediamine derivative gives a 6-membered ring cyclic amidine derivative K3.

Scheme L

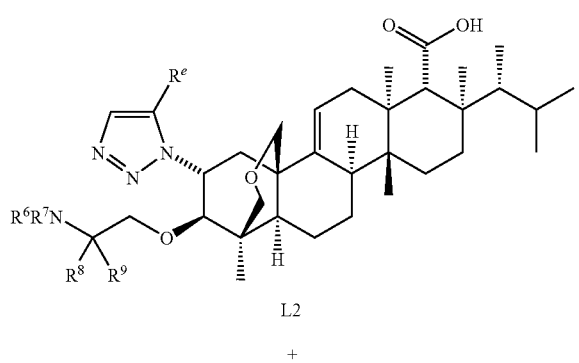

B4

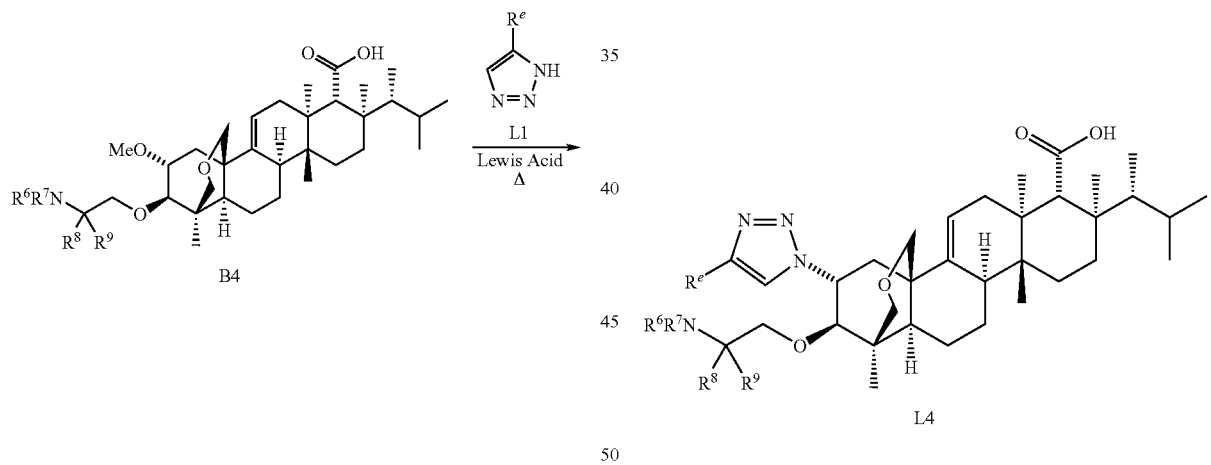

Schemes L to N illustrate the introduction of additional heterocyclic groups. Scheme L describes introduction of a mono substituted 1,2,3-triazole heterocycle. This synthesis is analogous to that described in Scheme G for a 1,2,4-triazole. When the triazole starting material L1 is unsymmetrically substituted (i.e. $R^e$ is not hydrogen) then three regioisomeric products may be formed in this displacement reaction, L2, L3 and L4. When two or three isomers are formed, it is often possible and desirable to separate them chromatographically or by other means. The ratio of the isomers may vary depending on the substituent group $R^e$. Depending on the desired $R^e$ substituent, the starting triazole compounds L1 are generally readily available either from commercial sources or through preparation by known literature methods. In the example illustrated in Scheme L, a mono-substituted triazole is employed. A disubstituted triazole may also be introduced in an analogous manner.

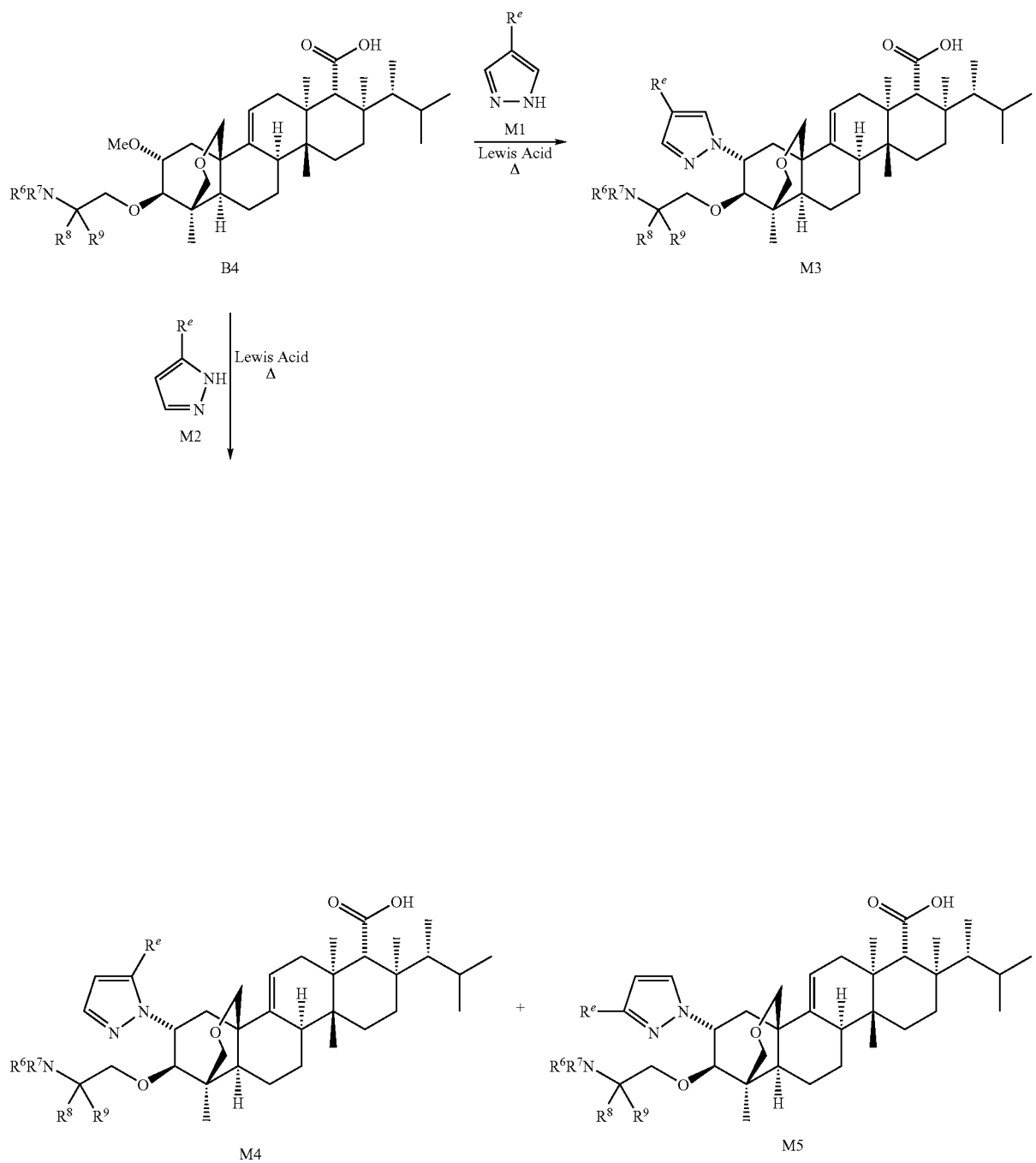

Scheme M

Scheme M illustrates the introduction of a mono-substituted pyrazole heterocycle. This synthesis is analogous to that described in Scheme G for a 1,2,4-triazole. When the pyrazole starting material is symmetrically substituted as is the case for M1, then a single product M3 is obtained. When the pyrazole starting material is unsymmetrically substituted (e.g. M2 where $R^e$ is not hydrogen) then two regioisomeric products may be formed in this displacement reaction, M4 and M5. When two isomers are formed, it is often possible and desirable to separate them chromatographically or by other means. The ratio of the isomers may vary depending on the substituent group $R^e$. Depending on the desired $R^e$ substituent, the starting pyrazole compounds M1 and M2 are generally readily available either from commercial sources or through preparation by known literature methods. While in the examples illustrated in Scheme M, mono-substituted pyrazoles are employed, di- and trisubstituted pyrazoles may also be introduced in an analogous manner. When regioisomer M4 is specifically desired, a synthesis analogous to that described in Scheme H or I may also be employed (see e.g. *J. Heterocyclic Chem.* 1977, 14, 345-347; *Bioorg. Med. Chem. Lett.* 2003, 13, 1183-1186).

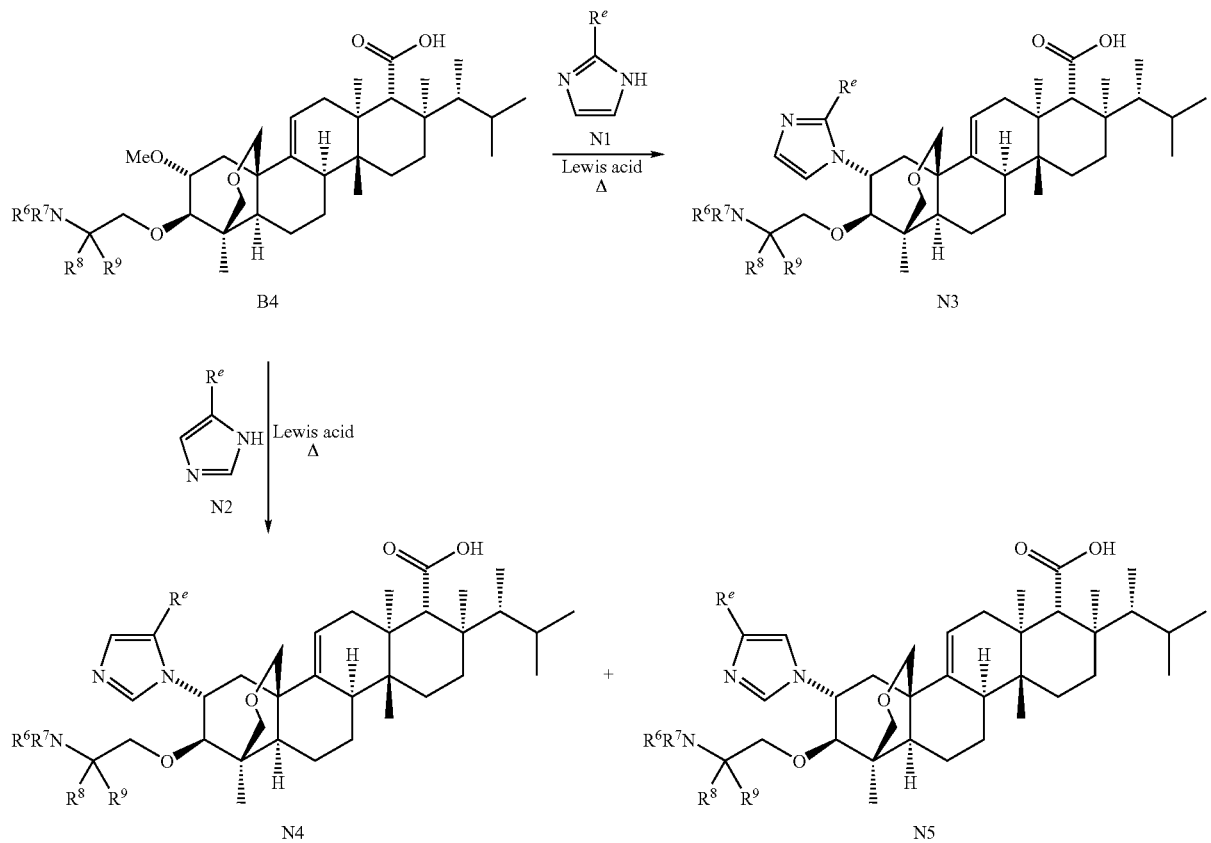

Scheme N illustrates the introduction of a mono-substituted imidazole heterocycle. This synthesis is analogous to that described in Scheme M for a mono-substituted pyrazole. When the imidazole starting material is symmetrically substituted as is the case for N1, then a single product N3 is obtained. When the imidazole starting material is unsymmetrically substituted (e.g. N2 where $R^e$ is not hydrogen) then two regioisomeric products may be formed in this displacement reaction, N4 and N5. When two isomers are formed, it is often possible and desirable to separate them chromatographically or by other means. The ratio of the isomers may vary depending on the substituent group $R^e$. Depending on the desired $R^e$ substituent, the starting imidazole compounds N1 and N2 are generally readily available either from commercial sources or through preparation by known literature methods. While in the examples illustrated in Scheme N, mono-substituted imidazoles are employed, di- and trisubstituted imidazole groups may also be introduced in an analogous manner.

The antifungal activity of the present compounds can be demonstrated by various assays known in the art, for example, by their glucan synthesis inhibitory activity ($IC_{50}$), minimum inhibitory concentration (MIC-100) or minimum prominent inhibition (MIC-50) against yeasts and minimum effective concentration (MEC) against filamentous moulds and dermatophytes in a broth microdilution assay, or in vivo anti-Candida activity in a mouse (TOKA). Compounds provided in the Examples were generally found to inhibit the growth of Candida spp. in the range of <0.03-32 μg/mL or to give an MEC against Aspergillus fumigatus in the range of <0.03-32 μg/mL.

Glucan Synthase Inhibition

The in vitro evaluation of glucan synthase inhibitory activity of compounds was measured in a polymerization assay in 96-well format. Each well contained 100 μL of $^3$H-UDPG at 0.5 mM (6000 to 8000 dpm/nmol), 50 mM HEPES pH 7.5 (Sigma), 10% w/v glycerol (Sigma), 1.5 mg/mL bovine serum albumin (Sigma A 9647. Lot 44H0190), 25 mM KF (Fisher), 1 mM EDTA (Gibco ULTRAPURE), 25 μM GTP-γ-S, enzyme sufficient to give 3 to 6 nmoles incorporation during the 60 min incubation at 22° C., and test compound added from wells in 3-fold serial dilutions in 100% DMSO (1 μL/well). The reaction was stopped by the addition of 100 μL of 20% trichloroacetic acid. Plates were chilled for a minimum of 10 min, and precipitated glucan collected by filtration on GF/C plates (Packard UNIFILTER®-96), washed with 5 cycles of water (about 1 mL/well each cycle) using a Packard FILTERMATE HARVESTER. 40 μL/well scintillation fluid (Packard ULTIMA GOLD TM-XR) was added and the sealed plates counted in a WALLAC BETA counter in top-counting mode at an efficiency of approximately 40%.

Stock solutions were stored at 10 mg/mL in DMSO at −20° C. For each new enzyme preparation, the initial titration performed started at 1 mg/mL, which was prepared by making a 10-fold dilution in DMSO (5 μL to 50 μL). 40 μL of this stock was placed in column 12 of a round-bottomed 96-well microtiter plate. 40 μL DMSO was added to columns 1 to 11 in the same row and ten 3-fold serial dilutions performed, by transferring 20 μL from column 12 to column 11 etc., with 4 mixings before each transfer. No test compound was transferred to from column 2 to column 1. Duplicate aliquots of 1

μL of all 12 dilutions were then transferred to the side walls of a 96-well Bioblock 1.1 mL plate (Fisher brand) to create two rows.

Graphs of the primary data were created in PRISM software (the average of two determinations) using PRISM's curve fitting program (sigmoidal dose response non-linear regression). The amount of compound required to inhibit glucan synthase activity by 50% in this assay ($IC_{50}$–ng/mL) was calculated.

Routine analysis was performed with glucan synthase (GS) prepared from *Candida albicans* MY1055 by the following procedure: MY1055 was grown in 10 liters YPD medium (10 g yeast extract, 20 g tryptone, 20 g glucose per liter) with vigorous shaking at 30° C., to early stationary phase. Cells were harvested by centrifugation, the pellet was washed and frozen at −70° C. until breakage. Thawed pellets were shaken with an equal volume of breakage buffer (50 mM HEPES pH 7.4, 10% glycerol, 1 mM EDTA, 1 mM PMSF, 1 mM DTT) and 4 times their weight of 0.5 mm acid washed glass beads for 2 hours at 4° C. Extent of breakage was assessed visually at 40× magnification. After low speed centrifugation to remove cell debris, the supernatant was centrifuged at 100,000×g for 60 min. to separate membranes plus ribosomes from cytoplasmic components. Membranes were further washed two additional times with breakage buffer using the same centrifugation conditions and finally suspended in breakage buffer at 25 to 30 mg/mL protein (Biorad) for storage at −70° C. Extraction of GS activity from membranes was performed at a protein concentration of 5 mg/mL in extraction buffer (50 mM $NaPO_4$ pH 7.5, 0.1 M KCl, 0.1M Na citrate, 20% glycerol, 5 μM GTP-γ-S, 1 mM DTT, 1 mM PMSF, 3 μg/mL pepstatin) plus 0.25% W1 by gentle mixing at 4° C. for 60 min, followed by centrifugation at 100,000×g for 60 min. After centrifugation, clear supernatant was removed from a pellet consisting of a hard layer usually with small amounts of gelatinous unextracted membranes above it.

Trapping was initiated immediately by 5-fold dilution in trapping buffer (50 mM HEPES pH 7.5, 10 mM KF, 1 mM EDTA, 2 mg/mL BSA) plus 2.5 mM UDPG and 10 μM GTP-γ-S. After incubation at 25° C. for 60 to 90 minutes, glucan was harvested by low speed centrifugation (3,000×g, 10 min). The soft pellet was washed 3 times with wash buffer (50 mM HEPES, 20% glycerol, 1 mM EDTA) plus 2.5 mM UDPG and 5 μM GTP-γ-S, once without UDPG, and suspended in about 5 volumes of PE extraction buffer (50 mM HEPES, 30% glycerol, 1 mM EDTA, 20 μM GTP-γ-S, 0.4% CHAPS, 0.08% cholesterol hemisuccinate) using a DOUNCE homogenizer. The suspension was frozen overnight at −70° C., and then centrifuged at 100,000×g for 10 min. The post-centrifugation supernatant was frozen as aliquots at −70° C. for subsequent assays.

Susceptibility Testing

To each well of a 96-well plate 100 μL of appropriate test medium (example: RPMI-1640 containing 0.165 M MOPS+3 g/L glutamine w/o sodium bicarbonate or RPMI-1640 containing 0.165 M MOPS+3 g/L glutamine w/o sodium bicarbonate with 3.2% DMSO or 2×RPMI-1640 containing 0.33 M MOPS+6 g/L glutamine w/o sodium bicarbonate with 6.4% DMSO for the plates with final concentration of 50% serum) was added.

The test compound was dissolved at concentration of 10 mg/mL in DMSO and diluted 1:78 into appropriate test medium with no DMSO or 1.92% DMSO or 5.12% DMSO. Example: added 25 μL of 10 mg/ml compound stock solution to 1925 μL of RPMI-1640 containing 0.165 M MOPS+3 g/L glutamine w/o sodium bicarbonate with 1.92% DMSO. The test compound concentration achieved was 128 μg/ml and DMSO concentration of 3.2%. To the first well of each row of appropriate test medium plate 100 μL of the compound stock solutions (128 μg/mL) were added. Compounds were serially diluted two-fold across the plate to column 11 (column 12 was the growth control well) and the last 100 μL was discarded yielding compound concentrations of 64 to 0.06 μg/mL. For plates with dermatophytes the last 100 μL were placed in the first row of a second plate and serial diluted two-fold and yielding compound concentrations of 64-0.00004 μg/mL. Amphotericin B and caspofungin, the control compounds, were prepared as a stock solution of 10 mg/mL in DMSO and prepared in micro-titer plate as stated above for test compounds.

Yeasts

In the microbroth dilution assay for yeasts, microorganisms *Candida* spp., *Cryptococcus neoformans* (MY2062) and *Saccharomyces cerevisiae* (MY2255) were selected by streaking a yeast culture on SABOURAUD Dextrose Agar (SDA) incubating for 24-48 hours at 35-37° C., thereafter selecting 1 characteristic colony and transferring to a fresh plate and incubating under same conditions. From the regrowth, 3 to 5 colonies were selected and suspended in 5 mL of sterile normal saline (BBL) and adjusted to match the turbidity of a 0.5 McFarland standard using DADE/BEHRING turbidity meter (preferred OD of 0.06 to 0.12). This resulted in a concentration of approximately $1\text{-}5\times10^6$ CFU/mL. The inocula were further diluted 1:1000 into RPMI-1640 containing 0.165 M MOPS+3 g/L glutamine w/o sodium bicarbonate with 3.2% DMSO. Assay plates previously titrated with test compound in RPMI-1640 containing 0.165 M MOPS+3 g/L glutamine w/o sodium bicarbonate with 3.2% DMSO were then inoculated with 100 μL/well of this dilution of culture. This resulted in a final organism concentration of $5\times10^2$ to $2.5\times10^3$ CFU/mL and final compound concentrations of 32 to 0.03 μg/mL. In addition *C. albicans* (MY1055) was also tested with heat inactivated (1 hour at 55° C.) mouse serum which was filtered twice using 0.22 micron GP EXPRESS PLUS MILLIPORE filtration system. This standardized suspension was diluted 1:1000 into mouse serum. Assay plates previously titrated with drug in 2×RPMI-1640 containing 0.33 M MOPS+6 g/l glutamine w/o sodium bicarbonate with 6.4% DMSO were then inoculated with 100 μl/well of this dilution of culture. This resulted in a final organism concentration of $5\times10^2$ to $2.5\times10^3$ CFU/mL and final compound concentration of 32 to 0.03 μg/ml and 50% mouse serum. Plates were incubated at 35-37° C. and MICs were read at 24 hours for *Candida* and 48 hours for *Cryptococcus neoformans*.

Filamentous Fungi

In the microbroth dilution assay for filamentous fungi *Aspergillus fumigatus* (MF5668) and dermatophyte *Trichophyton mentagrophytes* (MF7004) these microorganisms were grown on Sabouraud Dextrose Agar (SDA) slants at 35-37° C. for *Aspergillus fumigatus* and at 30° C. for *Trichophyton mentagrophytes* for 7 days prior to use. Inocula for filamentous fungi were prepared by adding 5 mL of sterile normal saline to slant followed by gently scraping the surface of stock slants growth with a sterile DACRON swab suspending the spores (conidia) in saline. Each spore suspension was then transferred to another tube and adjusted to match the turbidity of a 0.5 McFarland standard using the DADE/BEHRING turbidity meter (preferred OD of 0.06-0.09) for *A. fumigatus* and (preferred OD of 0.13-0.17) for dermatophyte *T. mentagrophytes*. This resulted in a concentration of approximately $1\text{-}5\times10^6$ CFU/mL. A spore count was performed on each culture suspension with a hemocytometer to insure the correct inoculum. This standardized suspension for A. fumigatus was diluted 1:500 in RPMI-1640 containing 0.165 M MOPS+3 g/L glutamine w/o sodium bicarbonate with 3.2% DMSO. This standardized suspension for T. mentagrophytes was diluted 1:500 in RPMI-1640 containing 0.165 M MOPS+3 g/L glutamine w/o sodium bicarbonate. Assay plates previously titrated with test compound in either RPMI-1640 containing 0.165 M MOPS+3 g/L glutamine w/o sodium bicarbonate with 3.2% DMSO or RPMI-1640 containing 0.165 M MOPS+3 g/L glutamine w/o sodium bicarbonate were then inoculated with 100 µL/well of this dilution. In addition A. fumigatus (MF5668) was also tested with heat inactivated human serum which was filtered once using 0.22 micron GP EXPRESS PLUS MILLIPORE filtration system. This standardized suspension was diluted 1:500 in human serum. Assay plates previously titrated with test compound in 2×RPMI-1640 containing 0.33 molar MOPS+6 g/L glutamine w/o sodium bicarbonate were then inoculated with 100 µl/well of this dilution of culture. Plates were incubated at 35° C. and MICs were read at 48 hours for Aspergillus fumigatus, and plates incubated at 30° C. and MICs were read at 96 hours for Dermatophyte T. mentagrophytes.

In the above testing, viable cell counts were performed on 0.5 McFarland samples to verify the CFU/mL. Serial dilutions (1:10) with the 0.5 McFarland were made in saline. One-hundred µl of each dilution ($10^4$, $10^5$, $10^6$) was spread onto a SABOURAUD Dextrose Agar (SDA) plates which were then incubated for 24 to 48 or 96 (dermatophytes) hours at 35° C. or 30° C. After incubation colonies were counted and recorded. Growth and sterility controls for each organism were also carried out. Column 12 was the growth control and contains no test compound. Row H was not inoculated with organism or test compound and was used as sterility control for each plate.

The minimum inhibitory concentration (MIC-100) for all test compounds is determined to be the lowest concentration of compound at which there was no visible growth as compared to growth control without test compound. The minimum prominent inhibition (MIC-80) in growth is indicated as 80% inhibition in growth compared to growth control without test compound. For Aspergillus and dermatophyte T. mentagrophytes minimum effective concentration (MEC) was determined as narly morphology of hyphae both macroscopic and microscopic.

In Vivo Anti-Candida Activity

A disseminated Candida infection is induced in DBA/2 mice by the I.V. inoculation of 0.2 mL of a yeast cell suspension containing $3.0\times10^4$ CFU of C. albicans MY1055 into the lateral tail vein. Therapy is initiated within 15 to 30 minutes after challenge. Mice are treated with test compound, either (1) I.P., b.i.d. for a total of 2 days, or (2) P.O., b.i.d. for a total of 2 days. For each route of administration and diluent, an appropriate sham-treated control group is included.

Kidneys from euthanized mice (4-5/group) are removed four days after challenge using aseptic techniques, weighed and placed in sterile WHIRL PAK bags containing 5 mL sterile saline. Kidneys are homogenized in the bags, serially diluted in saline and aliquots are plated on SD agar plates. Plates are incubated at 35° C. and enumerated after 30 to 48 hours for C. albicans colony forming units (CFUs). Means from CFU/g of paired kidneys of treated groups are compared to the means from sham-treated controls. Percent sterilization is indicated by the number of mice with no detectable yeast, where the limit of detection (because of the dilution scheme) is 50 yeast cells per pair of kidneys. For data from individual mice where no detectable yeast are recovered from paired kidneys, 9.8 is entered into the MICROSOFT EXCEL spread sheets formula [$\log_{10}$(5×raw count)/paired kidney weight)] so that the counts would be one less than the limit of detection (49 cells per pair of kidneys).

Mean $\log_{10}$ yeast CFU/g of paired kidneys are compared to the sham treated controls using Student's t-test (two tailed, unpaired) on MICROSOFT EXCEL. Comparisons are deemed significant at the p=0.05 level. Mean percent reduction in CFU/g of paired kidneys for treated groups at 4 days following challenge relative to control are computed. A linear trend is typically evident when dose and CFU are both expressed in $\log_{10}$ scale. Inverse regression (2) is subsequently used to estimate $ED_{90}$ and $ED_{99}$ values, defined as the doses (mg/kg) that reduced the number of CFU per organ by 90 and 99%, respectively.

Compounds provided in the Examples generally have GS $IC_{50}$ values less than 500 ng/mL and MIC-100 values against one or more organisms of <0.03-32 µg/mL; however, some compounds may have an $IC_{50}$ in the range of from about 500 to more than 10,000 ng/mL. Compounds provided in the Examples generally display prominent inhibition of growth in vitro (MIC-50) in the range of <0.03-32 µg/mL and MECs of <0.03-32 µg/mL. As for activity in the disseminated Candida infection, useful compounds will lower the number of fungal CFU/g kidney by greater than 1 $\log_{10}$ unit compared to sham treated controls and compounds that lower the CFU/g by 2 $\log_{10}$ units are especially useful.

Example Numbers correspond to the examples described in the Examples section.

| EXAMPLE NUMBER | Candida Albicans GS $IC_{50}$ (ng/mL) |
|---|---|
| 1B | 28 |
| 3 | 17 |
| 5 | 8 |
| 6C | 34 |
| 8A | 4 |
| 9B | 26 |
| 9C | 53 |
| 11 | 3 |
| 14 | 5 |
| 16 | 22 |
| 18 | 8 |
| 22 | 5 |
| 24 | 11 |
| 27 | 11 |
| 29B | 62 |
| 31 | 10 |
| 32A | 3 |
| 34 | 33 |
| 36 | 10 |
| 37B | 44 |
| 38 | 13 |
| 40 | 18 |
| 43 | 11 |
| 44 | 3 |
| 46 | 6 |
| 50 | 9 |
| 53 | 31 |
| 64 | 10 |
| 77 | 6 |
| 80 | 8 |
| 83 | 9 |
| 86 | 53 |
| 89 | 8 |
| 93 | 15 |
| 97 | 8 |
| 101 | 13 |
| 105 | 21 |
| 107 | 14 |
| 112 | 7 |
| 116 | 15 |
| 119 | 9 |

-continued

| EXAMPLE NUMBER | Candida Albicans GS IC$_{50}$ (ng/mL) |
|---|---|
| 123C | 4 |
| 126 | 26 |
| 128 | 6 |
| 136 | 9 |
| 138 | 6 |
| 140 | 5 |
| 144 | 6 |
| 148 | 13 |
| 150 | 2 |
| 158 | 16 |
| 163 | 5 |
| 168 | 3 |
| 169 | 3 |
| 173 | 0.6 |
| 174 | 2 |
| 178 | 0.8 |
| 181 | 8 |
| 182 | 4 |
| 190 | 3 |
| 193 | 3 |
| 199 | 0.4 |
| 200 | 6 |
| 202 | 0.2 |
| 208 | 0.7 |
| 214 | 1 |
| 218 | 0.8 |
| 221 | 3 |
| 228 | 6 |
| 231 | 10 |
| 235 | 5 |
| 239 | 0.1 |
| 241 | 1 |
| 245 | 6 |
| 256 | 5 |
| 261 | 2 |
| 264 | 0.3 |
| 268 | 0.3 |
| 272 | 8 |
| 276 | 2 |
| 285 | 3 |
| 288B | 11 |
| 289B | 88 |
| 291 | 35 |
| 293B | 3 |
| 295 | 41 |
| 298 | 27 |
| 300 | 479 |
| 303A | 22 |
| 307 | 4 |
| 312 | 13 |

The following examples serve only to illustrate the invention and its practice. The examples are not to be construed as limitations on the scope or spirit of the invention.

ABBREVIATIONS

Boc t-Butyloxycarbonyl
Cbz Benzyloxycarbonyl (also CBz)
CDCl$_3$ Deuterio-trichloromethane
CH$_3$CN Acetonitrile
DCE Dichloroethane
DCM Dichloromethane
DMAC Dimethylacetamide
DMAP 4-Dimethylaminopyridine
DMF Dimethylformamide
DMSO Dimethyl sulfoxide
Et Ethyl
EtOAc or EA Ethyl acetate
Et$_3$SiH Triethylsilane
H$_2$ Hydrogen or hydrogen atmosphere
H$_2$O Water
HOAc Acetic acid
H$_2$SO$_4$ Sulfuric acid
HCl Hydrochloric acid
K$_2$CO$_3$ Potassium carbonate
LAH LiAlH$_4$
MCPBA meta-Chloroperoxybenzoic acid
Me Methyl
MeOH Methanol
MOPS 3-(N-morpholino)propanesulfonic acid
NaCl Sodium chloride
NaHCO$_3$ Sodium bicarbonate
NH$_4$Cl Ammonium chloride
Na$_2$SO$_4$ Sodium sulfate
NMO 4-methylmorpholine N-oxide
PMSF Phenylmethanesulphonylfluoride
PTAB Phenyltrimethylammonium tribromide
RT or r.t. Room temperature, approximately 25° C.
SiO$_2$ Silica
TEA Triethanolamine
TFA Trifluoroacetic acid
THF Tetrahydrofuran
TLC Thin layer chromatography
UDGP Uridine-diphosphate glucose

Preparation 1

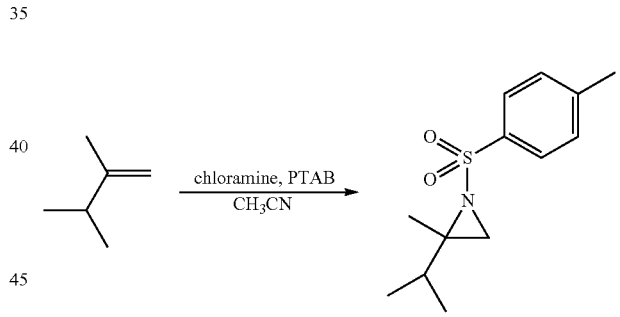

2-isopropyl-2-methyl-1-[(4-methylphenyl)sulfonyl]aziridine

To a solution of 2,3-dimethyl butene (300 ml, 2.42 mol) in 7.8 L of dry acetonitrile was added Chloramine-T (749.9 g, 1.1 eq) portionwise over 90 min. The temperature was maintained at approximately 20° C. To this reaction mixture was added phenyltrimethylammonium tribromide (91.4 g, 0.1 eq) in 10 g portions over 90 min. The temperature increased to 26° C. during the addition. The reaction mixture was stirred at room temperature for 2 days. The reaction mixture was concentrated down to approximately 15% of the initial volume and was them filtered, washing the solid with 1 L of acetonitrile. The organic liquid phase was concentrated and the residue dissolved in 2.5 L of EtOAc. The resulting solution was washed twice with water, dried over MgSO$_4$, and concentrated to give a solid. The crude was purified on a large plug of Celite using gradient elution 5% to 25% EtOAc/heptanes to afford 317 g of 2-isopropyl-2-methyl-1-[(4-methylphenyl)sulfonyl]aziridine as a solid.

Preparation 2

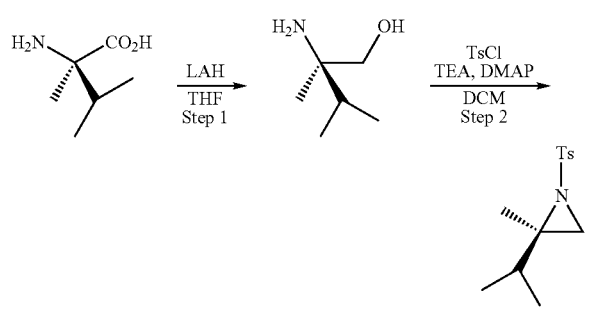

(2R)-2-isopropyl-2-methyl-1-[(4-methylphenyl)sulfonyl]aziridine

Step 1

(R)-α-methylvaline (8.05 g, 61.4 mmol) was added in small portions to a cold (0° C.) solution of LiAlH$_4$ in THF (1M, 123 mL, 123 mmol), maintaining the reaction temperature below 15° C. The reaction was stirred at 0° C. for a few minutes then heated at reflux for 4 h. The reaction mixture was cooled to RT and quenched by addition of sodium sulfate decahydrate/celite (1:1 by weight) until gas evolution ceased. The reaction mixture was filtered, washing with THF and methanol. The filtrate was concentrated under reduced pressure to provide 4.7 g of amino alcohol as a colorless oil.

Step 2

To a solution of the amino alcohol product from Step 1 (4.70 g, 40.1 mmol), Et$_3$N (22.36 mL, 160 mmol) and 4-dimethylaminopyridine (0.490 g, 4.01 mmol) in anhydrous CH$_2$Cl$_2$ (200 mL) at 0° C. was added p-toluenesulfonyl chloride (22.94 g, 120 mmol) in portions during 10 min. The reaction mixture was stirred at room temperature overnight. The volatiles were evaporated in vacuo by rotary evaporation and the residue was partitioned between CH$_2$Cl$_2$ and 1N HCl. The organic layer was washed with 1N HCl and dried over Na$_2$SO$_4$. The solvent was evaporated and the residue was chromatographed on silica gel using 1:1 CH$_2$Cl$_2$/hexane as eluant to remove excess TsCl and then 100% CH$_2$Cl$_2$ to elute the product. The title compound was obtained as an off-white solid (5.40 g).

$^1$H NMR (400 MHz, CDCl$_3$) δ 0.94 (d, J=6.88 Hz, 3H), 0.98 (d, J=6.88 Hz, 3H), 1.49 (quint, J=6.88 Hz, 1H), 1.59 (s, 3H), 2.20 (s, 1H), 2.43 (s, 3H), 2.60 (s, 1H), 7.31 (d, J=8.0 Hz, 2H), 7.83 (d, J=8.0 Hz, 2H).

Preparation 3

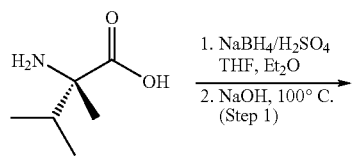

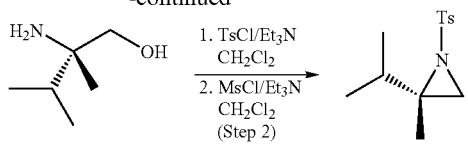

(2S)-2-isopropyl-2-methyl-1-[(4-methylphenyl)sulfonyl]aziridine

Step 1:

NaBH$_4$ (94.5 g, 2.498 mol) was charged into a 5 L three-necked flask containing 540 ml of dry THF. This solution was cooled with an ice bath. The (S)-α-methylvaline (75 g, 0.572 mol) was added to this solution. The mixture was stirred for 20 min under N$_2$ then a solution of H$_2$SO$_4$ (66.7 ml, 1.252 mol) in 160 ml of dry ether was added dropwise over a period of 3.5 h. The reaction mixture was stirred for one hour while in the ice bath then allowed to warm to RT overnight. TLC in CH$_2$Cl$_2$/MeOH (70/30) indicated the reaction was complete. The reaction was cooled with an ice bath and quenched by the slow addition of 250 ml of MeOH over 45 min. The mixture was then stirred at RT for 15 min then NaOH (5N, 700 ml) was added very slowly. The flask was equipped with a distillation head and heated to 100° C. with a heating mantle. The volatiles (bp<100° C.) were removed by distillation. The resulting mixture was heated to 100° C. (internal temp.) for 3 h then cooled to RT. Water (1 L) was added and the mixture was extracted with CH$_2$Cl$_2$ (6×500 ml). The combined organic layers were dried over Na$_2$SO$_4$, filtered and concentrated to afford the amino alcohol product as a yellow oil (64.2 g).

$^1$H NMR (400 MHz, CDCl$_3$) δ ppm 0.87 (d, J=6.93 Hz, 3H) 0.91 (d, J=6.93 Hz, 3H) 0.95 (s, 3H) 1.57-1.68 (m, 1H) 3.30 (d, J=10.30 Hz, 1H) 3.34 (d, J=10.30 Hz, 1H).

Step 2

A solution of amino alcohol from above (32 g, 273.5 mmol) in dry CH$_2$Cl$_2$ (1.7 L) was cooled with an ice bath and Et$_3$N (198 ml, 1422 mmol) was added. A solution p-toluenesulfonyl chloride (62.5 g, 328.2 mmol) in CH$_2$Cl$_2$ (250 ml) was added dropwise over a period of 3 h. The ice bath was removed and the solution was stirred at RT overnight. The mixture was cooled in an ice bath and Et$_3$N (61.6 ml, 442 mmol) was added followed by the dropwise addition of methanesulfonyl chloride (40 ml, 516.8 mmol). The reaction mixture was stirred for 4 h while keeping the temperature below 12° C. Water (600 ml) was added to the mixture followed by brine (sat. aqueous NaCl, 350 ml). The aqueous layer was extracted with CH$_2$Cl$_2$ (3×500 ml). The combined organic layers were dried over Na$_2$SO$_4$, filtered concentrated. The crude product was purified over a pad of silica gel (EtOAc/Heptanes: 5/95 then 10/90) to afford the title compound as a white solid (36 g).

¹H NMR (400 MHz, CDCl₃) δ ppm 0.94 (d, J=6.78 Hz, 3H) 0.98 (d, J=6.78 Hz, 3H) 1.44-1.53 (m, 1H) 1.59 (s, 3H) 2.20 (s, 1H) 2.42 (s, 3H) 2.60 (s, 1H) 7.30 (d, J=7.90 Hz, 2H) 7.83 (d, J=7.90 Hz, 2H).

Preparation 4

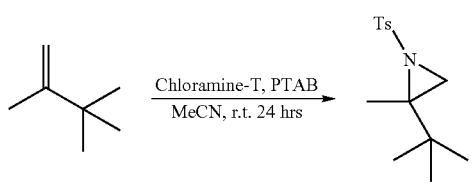

2-(1,1-dimethylethyl)-2-methyl-1-[(4-methylphenyl)sulfonyl]aziridine

Chloramine-T trihydrate (10.19 g, 36.2 mmol) was placed under high vacuum for hours and the remaining material (8.3 g) was suspended in acetonitrile (121 mL) at room temperature under nitrogen. To this suspension was added 2,2,3-trimethylbut-1-ene (50.6 mL, 362 mmol) followed by phenyltrimethylammonium tribromide (13.6 g, 36.2 mmol) in two roughly equal portions. After twenty hours the reaction mixture was concentrated to half volume and then filtered through a sintered glass funnel. The filtrate was concentrated to half volume again which caused further precipitation. This suspension was filtered washing with acetonitrile and the filtrate concentrated. The resulting material was dissolved/suspended in dichloromethane, filtered and the resulting filtrate was concentrated to an orange oil. This oil was diluted with ethyl acetate and washed with water. The organic phase was dried with MgSO₄, filtered and concentrated. The crude material was purified by column chromatography using a Biotage 65i column eluting with (0-100% EtOAc/hexane) to give 2-(1,1-dimethylethyl)-2-methyl-1-[(4-methylphenyl)sulfonyl]aziridine as a colorless solid (5.2 g).

¹H NMR (CDCl₃, 500 MHz, ppm) δ 0.92 (s, 9H), 1.72 (s, 3H), 2.33 (s, 1H), 2.43 (s, 3H), 2.51 (s, 1H), 7.30 (d, J=8.1 Hz, 2H), 7.83 (d, J=8.1 Hz, 2H).

Preparation 5A

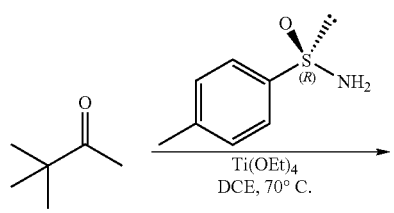

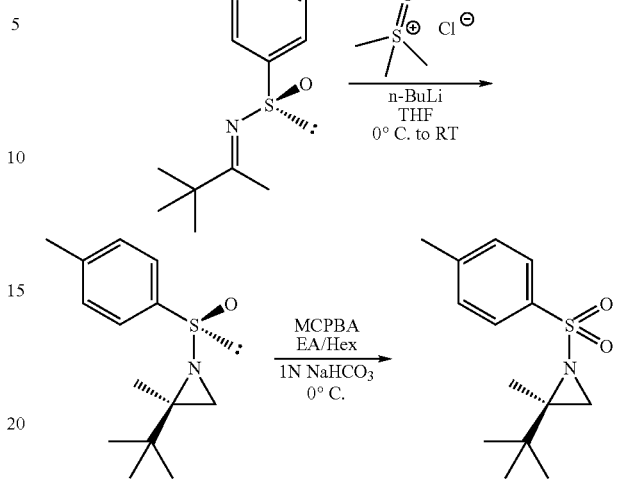

(2R)-2-(1,1-dimethylethyl)-2-methyl-1-[(4-methylphenyl)sulfonyl]aziridine

Step 1

To (R)-p-toluenesulfinamide (2.00 g, 12.89 mmol) in a 250 mL flask under argon were added dichloroethane (50 mL), t-butylmethylketone (8.1 mL, 64.4 mmol) and Ti(OEt)₄ (13.5 mL, 64.4 mmol). The stirred reaction solution was heated at 70° C. overnight. After 21 h, the yellow solution was cooled to RT and poured into a vigorously stirred suspension of 15 g of Celite in 100 mL of hexane, rinsing the flask with dichloromethane. To the stirred suspension was added 15 mL of H₂O dropwise. After several minutes, the mixture became very thick. Stirring was continued for 5 min. The resulting thick slurry was filtered through a 350 mL coarse sintered filter funnel. The solid was washed twice with 50 mL of 10% dichloromethane/hexane by resuspending the solid by stirring with a spatula and then filtering. The two-phase filtrate was transferred to a separatory funnel and the organic layer was washed with water and brine and dried over Na₂SO₄. Filtration and concentration by rotary evaporation gave 3.07 g of a yellow oil. Chromatography on an ISCO CombiFlash system (40 g silica gel column, 10:90 to 50:50 EA/hex, 20 min gradient, 40 mL/min, detection at 254 nM) gave 2.49 g of a pale yellow oil which solidified upon storage at −20° C.

¹H NMR (CD₂Cl₂, 500 MHz, ppm) δ 1.16 (s, 9H), 2.33 (s, 3H), 2.43 (s, 3H), 7.35 (d, J=8.1 Hz), 7.63, (d, J=8.1 Hz).

Step 2

A mixture of the trimethylsulfoxonium chloride (2.37 g, 18.6 mmol) in THF (35 mL) was sonicated briefly to break-up lumps and then cooled to 0° C. and BuLi/hex (2.5 M) was added dropwise. The stirred reaction mixture was heterogeneous. After 25 min., a solution of the ketimine product from Step 1 (1.45 g, 6.11 mmol) in THF (5+1 mL) was added dropwise to the stirred suspension during 15 min. The resulting white suspension stirred at 0° C. for 3 h and then allowed to warm to RT overnight. The reaction mixture was quenched with sat. NH₄Cl and partitioned between sat. NH₄Cl and ethyl acetate. The organic phase was washed with water and brine, dried over Na₂SO₄ and evaporated to give 1.539 g of a pale yellow oil.

¹H NMR (CD₂Cl₂, 500 MHz, ppm) δ 0.97 (s, 9H), 1.53 (s, 3H), 1.82 (s, 1H), 2.28 (s, 1H), 2.43 (s, 3H), 7.33 (d, J=8.1 Hz), 7.61, (d, J=8.1 Hz).

Step 3

The product from Step 2 (1.539 g, 6.2 mmol) was dissolved in EA (20 mL) and hexane (40 mL). After addition of 1 M NaHCO₃ solution (30 mL) the two phase reaction mixture was vigorously stirred and cooled to 0° C. Commercial grade MCPBA (2.11 g, ~9 mmol) was added in several portions during 5 min. The reaction was monitored by TLC (30:70 EA/hex). At T=45 min, the reaction was quenched by addition of 5% Na₂S₂O₃ (30 mL) and the mixture was stirred for several minutes until a negative starch-iodide test was obtained. The reaction mixture was diluted with ethyl acetate and the organic phase was washed with sat. NaHCO₃, H₂O and brine. Drying over Na₂SO₄ and evaporation gave 1.56 g of the title compound as an off-white crystalline solid.

¹H NMR (CD₂Cl₂, 500 MHz, ppm) δ 0.94 (s, 9H), 1.71 (s, 3H), 2.37 (s, 1H), 2.46 3H), 2.51 (s, 1H), 7.36 (d, J=8.1 Hz), 7.82, (d, J=8.1 Hz).

Preparation 5B

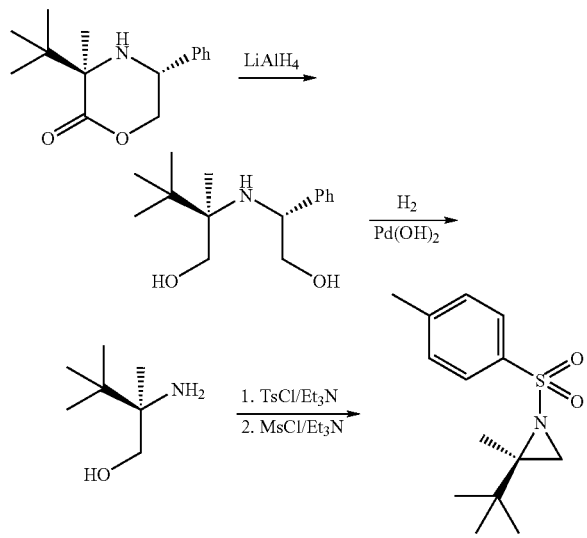

(2R)-2-(1,1-dimethylethyl)-2-methyl-1-[(4-methylphenyl)sulfonyl]aziridine

Step 1

To a solution of (3R,5R)-3-(1,1-dimethylethyl)-3-methyl-5-phenylmorpholin-2-one (Harwood, L. M. et al. *Synlett* 1996, 1051; 17.3 g, 70 mmol) in THF (1 L) at 0° C. was added LiAlH₄ (70 mL of a 2M solution in THF, 140 mmol) dropwise. The mixture was heated at 45° C. for 3 h. The reaction mixture was cooled to 0° C. and quenched carefully by sequential addition of 6 mL of water, 6 mL of 15% aqueous NaOH, and 18 mL of water. The slurry was stirred vigorously. The solid was removed by suction filtration, and the filter cake was thoroughly washed with ether and CH₂Cl₂. The filtrate was concentrated under reduced pressure to afford the product (17.0 g, 100%) as a viscous oil.

¹H NMR (400 MHz, CDCl₃) δ 0.96 (s, 3H) 1.02 (s, 9H) 3.09 (d, J=11.32 Hz, 1H) 3.39-3.46 (m, 1H) 3.46 (d, J=11.32 Hz, 1H) 3.62 (dd, J=10.52, 4.71 Hz, 1H) 4.02 (dd, J=9.22, 4.69 Hz, 1H) 7.08-7.44 (m, 5H).

Step 2:

To a solution of the product from Step 1 (17.0 g, 70 mmol) in MeOH was added HOAc (5 mL) and palladium hydroxide (5 g of 20 wt % on carbon). The flask was evacuated and filled with hydrogen several times. The suspension was stirred at room temperature under H₂ (balloon, 1 atm) for 3 h. The reaction mixture was filtered through a pad of Celite, the filter cake was washed with additional MeOH, and the filtrate was concentrated under reduced pressure. The residue was purified by flash chromatography, elution with 0-10% MeOH in CH₂Cl₂ with 1% HOAc followed by 100% MeOH with 1% HOAc, to provide 8.84 g of the product as an acetic acid salt. Anhydrous K₂CO₃ (50 g) was added to a solution of the acetate salt (7.03 g, 38.0 mmol) in CH₂Cl₂ (500 mL). The resulting suspension was stirred under nitrogen overnight after which the inorganic salts were removed by suction filtration. The filtrate was concentrated under reduced pressure and the residue was dried azeotropically using PhCH₃ until a constant weight was obtained to give the amino alcohol product (4.98 g, 66% overall).

¹H NMR (400 MHz, CDCl₃) δ 0.93 (s, 9H) 1.05 (s, 3H) 3.34 (d, J=10.05 Hz, 1H) 3.45 (d, J=10.05 Hz, 1H).

Step 3:

A solution of the amino alcohol from Step 2 (4.98 g, 38.0 mmol) in CH₂Cl₂ (200 mL) at 0° C. was treated with Et₃N (26 mL, 190 mmol) followed by a solution of p-toluenesulfonyl chloride (8.7 g, 45.6 mmol) in CH₂Cl₂ (50 mL) over 40 min. The reaction mixture was stirred at room temperature for 4 days. The mixture was cooled to 0° C. after which Et₃N (8.50 mL, 60.8 mmol) and methanesulfonyl chloride (5.88 mL, 76.0 mmol) were added. The mixture was stirred at 0° C. for 4 h. The reaction mixture was poured into a 1:1 mixture of saturated aqueous NaCl and water and was extracted with CH₂Cl₂. The organic layer was washed with saturated aqueous NaCl, dried with Na₂SO₄, filtered, and concentrated under reduced pressure. The residue was purified by flash chromatography, elution with 0-50% EtOAc in heptane, to provide the title compound (5.88 g, 58%) as a white solid.

¹H NMR (400 MHz, CDCl₃) δ 0.93 (s, 9H) 1.73 (s, 3H) 2.34 (s, 1H) 2.44 (s, 3H) 2.52 (s, 1H) 7.31 (d, J=7.96 Hz, 2H) 7.84 (d, J=8.35 Hz, 2H).

Preparation 6

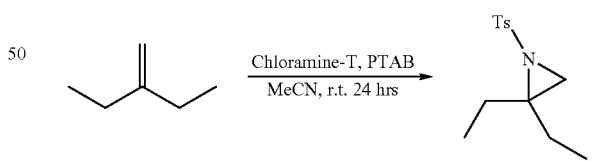

2,2-diethyl-1-[(4-methylphenyl)sulfonyl]-aziridine

Chloramine-T (10 g, 43.9 mmol) was suspended in acetonitrile (146 mL) at room temperature under nitrogen. To this suspension was added 2-ethylbut-1-ene (5.55 g, 65.9 mmol) followed by phenyltrimethylammonium tribromide (1.65 g, 4.39 mmol) in two roughly equal portions. After three days the reaction mixture was concentrated to half volume and then filtered through a sintered glass funnel. The filtrate was concentrated to half volume again which caused further precipitation. This mixture was filtered and the filtrate was partitioned between ethyl acetate and water. The organic phase was dried with MgSO₄, filtered and concentrated. The crude material was purified by column chromatography using a Biotage 65i column eluting with (0-100% EtOAc/hexane) to give 2,2-diethyl-1-[(4-methylphenyl)sulfonyl]-aziridine as a colorless solid (4.5 g).

¹H NMR (CDCl₃, 500 MHz, ppm) δ 1.00 (t, J=7.5 Hz, 6H), 1.75 (dddd, J=14.6 Hz, 7.5 Hz, 7.5 Hz, 7.5 Hz, 2H), 1.90 (dddd, J=14.6 Hz, 7.5 Hz, 7.5 Hz, 7.5 Hz, 2H), 2.41 (s, 2H), 2.43 (s, 3H), 7.38 (d, J=8.0 Hz, 2H), 7.78 (d, J=8.4 Hz, 2H).

Preparation 7

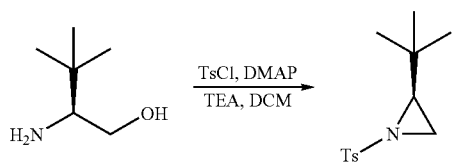

(2S)-2-(1,1-dimethylethyl)-1-[(4-methylphenyl)sulfonyl]-aziridine

To a solution of S-(+)-tert-leucinol (4.0 g, 34 mmol) in dichloromethane (170 mL) was added triethylamine (16.7 mL, 120 mmol), p-toluenesulfonyl chloride (26 g, 140 mmol, added in portions) and DMAP (420 mg, 3.4 mmol). The cooling bath was removed after 30 minutes and the reaction stirred at room temperature and additional reagents were added during the reaction: TsCl (at 16 hours: 5.3 g, at 40 hours: 3 g), triethylamine (at 24 hours: 3 mL) and DMAP (at 20 hours: 200 mg and at 40 hours: 150 mg). After 40 hours at room temperature the reaction was heated to 40° C. After a total of 44 hours the reaction was cooled to room temperature and filtered. The filtrate was concentrated in vacuo then partitioned between ethyl acetate and water. The organic phase was washed with brine, dried over MgSO₄ then filtered and concentrated. Column chromatography (Biotage 65i column, 10-100% EtOAc/hexane) afforded (2S)-2-(1,1-dimethylethyl)-1-[(4-methylphenyl)sulfonyl]-aziridine as an oil (6.3 g) which solidified upon storage at −20° C.

¹H NMR (CDCl₃, 500 MHz, ppm) δ 0.79 (s, 9H), 2.17 (d, J=4.6 Hz, 1H), 2.44 (s, 3H), 2.52 (d, J=7.1 Hz, 1H), 2.55 (d, J=4.6 Hz, 1H) 7.33 (d, J=8.0 Hz, 2H), 7.83 (d, J=8.2 Hz, 2H).

Preparation 8

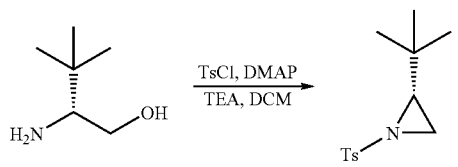

(2R)-2-(1,1-dimethylethyl)-1-[(4-methylphenyl)sulfonyl]-aziridine

A solution of R-(−)-tert-leucinol (4.0 g, 34 mmol) in dichloromethane (170 mL) was treated with triethylamine (19 mL, 140 mmol), p-toluenesulfonyl chloride (26 g, 140 mmol) and DMAP (834 mg, 6.83 mmol) and heated to 40° C. under nitrogen. After approximately 18 hours the reaction was cooled to room temperature and filtered. The filtrate was concentrated in vacuo then partitioned between ethyl acetate and water. The organic phase was washed with brine, dried over MgSO₄ then filtered and concentrated. Column chromatography (Biotage 65i column, 10-100% EtOAc/hexane) afforded (2R)-2-(1,1-dimethylethyl)-1-[(4-methylphenyl)sulfonyl]-aziridine as an oil (3.7 g) which solidified upon storage at −20° C.

¹H NMR (CDCl₃, 500 MHz, ppm) δ 0.78 (s, 9H), 2.17 (d, J=4.6 Hz, 1H), 2.44 (s, 3H), 2.52 (d, J=7.1 Hz, 1H), 2.55 (d, J=4.6 Hz, 1H) 7.33 (d, J=8.0 Hz, 2H), 7.83 (d, J=8.2 Hz, 2H).

Preparation 9

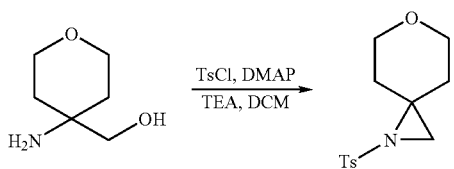

1-[(4-methylphenyl)sulfonyl]-6-oxa-1-azaspiro[2.5]octane

A solution of 4-aminotetrahydro-2H-pyran-4-methanol (16 g, 122 mmol) in dichloromethane (700 mL) was treated with triethylamine (85 mL, 610 mmol), p-toluenesulfonyl chloride (69.8 g, 366 mmol) and DMAP (1490 mg, 12.2 mmol) under nitrogen. After approximately 18 hours at room temperature, the reaction was filtered through a pad of silica gel. The filtrate was concentrated in vacuo then purified by chromatography on silica gel (5-20% EtOAc/hexane) to afford intermediate the title compound (12.5 g) as a white solid.

¹H NMR (CDCl₃, 500 MHz, ppm) δ 1.92 (m, 2H), 2.08 (m, 2H), 2.47 (s, 3H), 2.52 (s, 2H), 3.76 (m, 2H), 3.99 (m, 2H), 7.35 (d, J=8.0 Hz, 2H), 7.86 (d, J=8.5 Hz, 2H).

Preparation 10

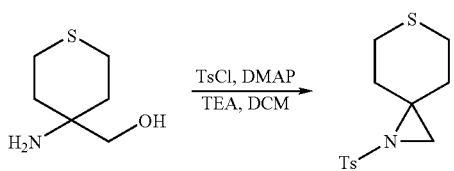

1-[(4-methylphenyl)sulfonyl]-6-thia-1-azaspiro[2.5]octane

The title compound was prepared analogously to the compound of Preparation 9, by starting with 4-aminotetrahydro-2H-thiopyran-4-methanol.

$^1$H NMR (CDCl$_3$, 500 MHz, ppm) δ 2.15 (m, 2H), 2.22 (m, 2H), 2.24 (s, 3H), 2.42 (s, 2H), 2.70 (m, 2H), 3.00 (m, 2H), 7.35 (d, J=8.0 Hz, 2H), 7.86 (d, J=8.3 Hz, 2H).

Preparation 11

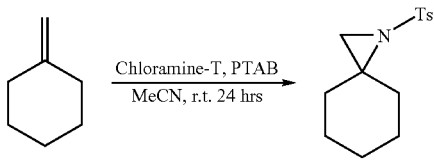

1-[(4-methylphenyl)sulfonyl]-1-azaspiro[2.5]octane

To a stirred suspension of dried Chloramine-T (5.10 g, 20.76 mmol) in CH$_3$CN (100 mL) under a nitrogen atmosphere was added methylenecyclohexane (9.98 g, 104 mmol). Phenyltrimethylammonium tribromide (7.80 g, 20.76 mmol) was added in three portions over 10 min. The mixture was stirred at room temperature for 16 hours. The solvent was evaporated and the residue was partitioned between dichloromethane and water. The organic layer was dried over Na$_2$SO$_4$ and the solvent was evaporated. The residue was chromatographed on silica gel with an ISCO Combiflash using EtOAc/hexanes (5-30% gradient) to afford the title compound as a white solid (2.66 g).

$^1$H NMR (CDCl$_3$, 500 MHz, ppm) δ 1.4-1.5 (m, 4H), 1.7-1.9 (m, 6H), 2.4 (s, 2H), 2.45 (s, 3H), 7.3 (d, 2H), 7.85 (d, 2H).

Preparation 12

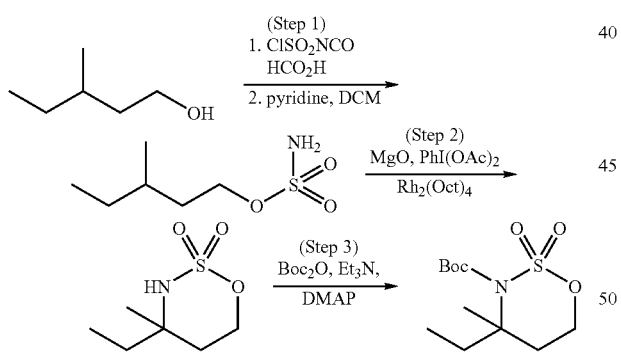

[cf. J. Du Bois, et. al., JACS, 2001, 123, 6935]

1,1-dimethylethyl 4-ethyl-4-methyldihydro-1,2,3-oxathiazine-3(4H)-carboxylate 2,2-dioxide Step 1:

Formic acid (65 mL, 17.2 mmol) was added dropwise to neat chlorosulfonyl isocyanate (1.5 mL, 17.2 mmol) at 0° C. with rapid stirring. Vigorous gas evolution was observed during the addition process. The resulting viscous suspension was stirred for 5 min at 0° C. during which time the mixture solidified. Dichloromethane (9 mL) was added and the solution was stirred for 1 h at 0° C. then 8 h at 25° C. The reaction mixture was cooled to 0° C. and a solution of 3-methylpentan-1-ol (11.5 mmol) and pyridine (1.4 mL, 17.2 mmol) in 8 mL of dichloromethane was added dropwise. The contents were warmed to 25° C. and stirred for 3 h. The reaction mixture was treated with EtOAc (80 mL) and water (50 mL), and the aqueous layer was extracted with EtOAc (2×20 mL). The combined organic phase was washed with brine, dried over MgSO$_4$, filtered and then concentrated. The crude product was purified by multiple flash chromatographies (7% ethyl acetate/dichloromethane) to give 3-methylpentyl sulfamate.

Step 2:

To a solution of 3-methylpentyl sulfamate from Step 1 (1.25 mmol) in 8 mL of dichloromethane was added sequentially MgO (116 mg, 30 mmol), PhI(OAc)$_2$ (443 mg 1.4 mmol), and Rh$_2$(oct)$_4$ (20 mg, 0.025 mmol). The suspension was stirred vigorously and heated at 40° C. for 3 h. The reaction mixture was cooled to room temperature, diluted with 20 mL of dichloromethane, and filtered through a pad of Celite then concentrated. The crude product was purified by multiple flash chromatographies (5% ethyl acetate/dichloromethane) to give 4-ethyl-4-methyltetrahydro-1,2,3-oxathiazine 2,2-dioxide.

Step 3:

To a solution of 4-ethyl-4-methyltetrahydro-1,2,3-oxathiazine 2,2-dioxide from Step 2 (5 g) in 100 mL of dichloromethane was added sequentially Et$_3$N (7.5 mL), DMAP (1 g), and Boc anhydride (8 g). The mixture was stirred vigorously for 5 minutes, and filtered through a pad of silica then concentrated. The crude product was purified by multiple flash chromatographies (30% ethyl acetate/hexane) to give the title compound (3 g).

$^1$H NMR (CDCl$_3$, 500 MHz, ppm) δ 0.96 (t, J=7.5 Hz, 3H), 1.55 (s, 9H), 1.64 (s, 3H), 1.86 (m, 1H), 2.00 (m, 1H), 2.28 (m, 1H), 2.62 (m, 1H), 4.64 (m, 2H).

Preparation 13

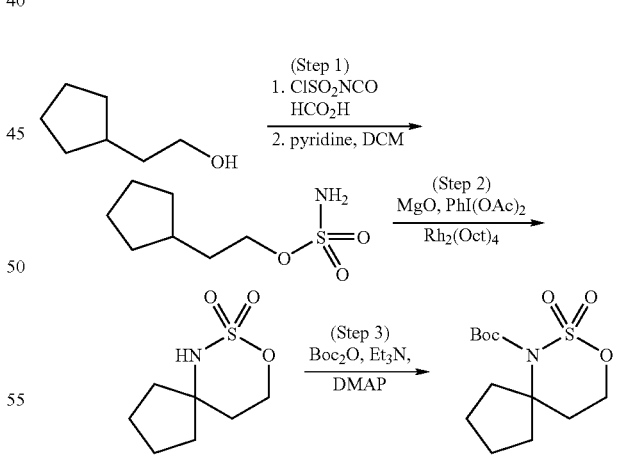

1,1-dimethylethyl 8-oxa-7-thia-6-azaspiro[4.5]decane-6-carboxylate 7,7-dioxide

In a manner analogous to that described for Preparation 11, the title compound was prepared starting with 2-cyclopentylethanol.

¹H NMR (CDCl₃, 500 MHz, ppm) δ 1.55 (s, 9H), 1.62 (m, 2H), 1.88-1.96 (m, 4H), 2.25 (t, J=6.4 Hz, 2H), 2.31 (m, 2H), 4.64 (t, J=6.4 Hz, 2H).

Preparation 14

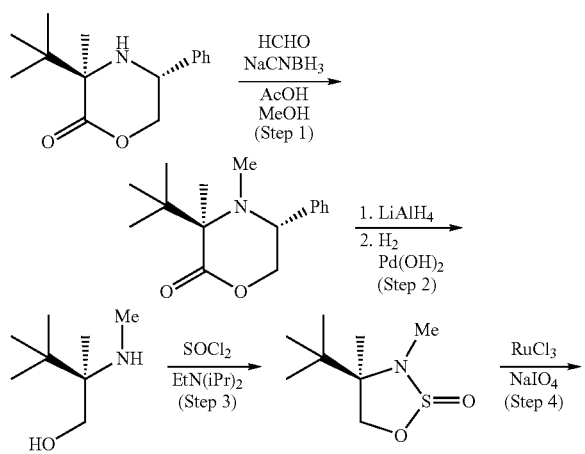

(4R)-4-(1,1-dimethylethyl)-3,4-dimethyl-1,2,3-oxathiazolidine 2,2-dioxide

Step 1:
To a solution of compound (3R,5R)-3-(1,1-dimethylethyl)-3-methyl-5-phenylmorpholin-2-one (100 mg, 0.40 mmol) in MeOH was added formaldehyde (1.40 mL, 37 wt % in water, 16.2 mmol), HOAc (0.14 mL, 2.4 mmol), and sodium cyanoborohydride (100 mg, 1.60 mmol). The reaction mixture was stirred at room temperature overnight, and the solvent was removed under reduced pressure. The residue was partitioned between EtOAc and saturated aqueous NaHCO₃, and the layers were separated. The organic layer was washed with saturated aqueous NaHCO₃, saturated aqueous NaCl, dried (Na₂SO₄), and concentrated under reduce pressure to provide the product (99.7 mg, 95%) as a viscous oil.

¹H NMR (400 MHz, CDCl₃) δ 1.08 (s, 9H) 1.30 (s, 3H) 2.28 (s, 3H) 3.97 (d, J=2.54 Hz, 1H) 4.45 (dd, J=10.91, 2.37 Hz, 1H) 4.89 (dd, J=10.88, 3.66 Hz, 1H) 7.13-7.41 (m, 5H).

Step 2:
Employing procedures analogous to those described for Steps 1 and 2 of Preparation 5B, the desired amino alcohol was prepared from the product of Step 1.

¹H NMR (400 MHz, CDCl₃) δ 1.08 (s, 9H) 1.17 (s, 3H) 1.99 (s, 3H) 2.63 (s, 3H) 3.53 (d, J=12.35 Hz, 1H) 3.84 (d, J=12.30 Hz, 1H) 5.32 (br. s., 4H).

Step 3:
To a solution of the amino alcohol product from Step 2 (59.4 mg, 0.29 mmol) in CH₂Cl₂ (3 mL) at 0° C. was added N,N-diisopropylethylamine (0.15 mL, 0.87 mmol) and thionyl chloride (21.0 µL, 0.29 mmol), and the resulting solution was stirred at 0° C. for 45 min. The reaction mixture was diluted with CH₂Cl₂ and washed with saturated aqueous NaCl, dried with Na₂SO₄, and concentrated under reduced pressure. The residue was purified by flash chromatography to provide two diastereoisomers (22.1 mg, 40%) as white solids.

ISOMER A: ¹H NMR (400 MHz, CDCl₃) δ ppm 1.05 (s, 9H) 1.24 (d, J=0.63 Hz, 3H) 2.87 (s, 3H) 4.12 (d, J=8.88 Hz, 1H) 4.87 (dd, J=8.88, 0.68 Hz, 1H);

ISOMER B: ¹H NMR (400 MHz, CDCl₃) δ ppm 0.92 (s, 9H) 1.38 (s, 3H) 2.72 (s, 3H) 4.42 (d, J=9.27 Hz, 1H) 4.59 (d, J=9.23 Hz, 1H).

Step 4:
A solution of the two diastereoisomers from Step 3 (15.2 mg, 0.08 mmol) in CH₃CN (0.5 mL) was added to a solution of ruthenium trichloride (1 mg, 0.0008 mmol) and sodium periodate (19 mg, 0.09 mmol) in water (1 mL) and CH₃CN (1 mL). The reaction mixture was stirred at room temperature for 1 h, diluted with EtOAc and washed with water. The aqueous layer was extracted with EtOAc. The combined organic layers were dried with Na₂SO₄, and concentrated under reduced pressure to provide the title compound (13.9 mg, 84%) directly as a white solid.

¹H NMR (400 MHz, CDCl₃) δ 1.00 (s, 9H) 1.31 (s, 3H) 2.81 (s, 3H) 4.03 (d, J=9.32 Hz, 1H) 4.55 (d, J=9.32 Hz, 1H).

Preparation 15

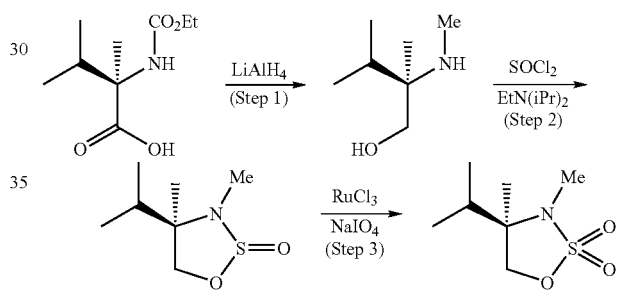

(4R)-3,4-dimethyl-4-(1-methylethyl)-1,2,3-oxathiazolidine 2,2-dioxide

Starting with (2R)-2-{[(ethyloxy)carbonyl]amino}-2,3-dimethylbutanoic acid (prepared as described in *J. Org. Chem.* 2007, 72, 7469-7472 but employing D-tartaric acid for the resolution step) and employing procedures analogous to those described for Preparation 5B Step 1 and Preparation 14 Steps 3 and 4, the title compound was prepared and isolated as a waxy solid.

¹H NMR (400 MHz, CDCl₃) δ: 4.38 (d, J=8.8 Hz, 1H), 4.06 (d, J=8.8 Hz, 1H), 2.65 (s, 3H), 1.85 (m, 1H), 1.32 (s, 3H), 0.94 (d, J=6.9 Hz, 3H), 0.89 (d, J=6.9 Hz, 3H) ppm.

Preparation 16

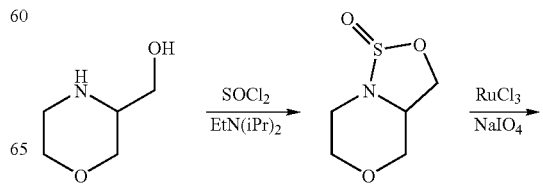

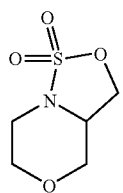

tetrahydro-3H-[1,2,3]oxathiazolo[4,3-c][1,4]ox-azine-1,1-dioxide

Following procedures analogous to those described for Steps 3 and 4 of Preparation 14, 3-hydroxymethylmorpholine was converted to the title compound.

$^1$H NMR (400 MHz, CDCl$_3$) δ 3.17 (ddd, J=12.10, 8.86, 3.34 Hz, 1H) 3.38 (dt, J=12.08, 3.60 Hz, 1H) 3.62 (dd, J=11.57, 7.76 Hz, 1H) 3.76 (ddd, J=11.87, 8.85, 3.15 Hz, 1H) 3.80-3.93 (m, J=15.62, 12.17, 3.36, 3.36 Hz, 2H) 4.03 (dd, J=11.59, 3.39 Hz, 1H) 4.32 (d, J=9.08 Hz, 1H) 4.59 (dd, J=8.00, 6.44 Hz, 1H).

Preparation 17

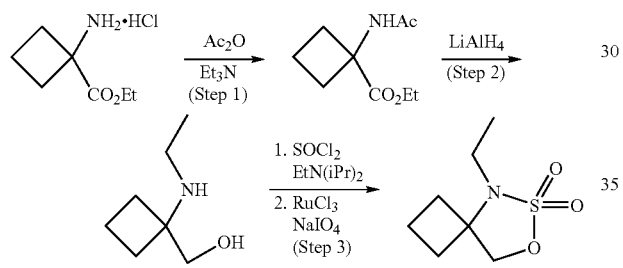

5-ethyl-7-oxa-6-thia-5-azaspiro[3,4]octane 6,6-dioxide

Step 1:

Et$_3$N (14.0 mL, 100 mmol) was added to a solution of 1-amino-cyclobutanecarboxylic acid ethyl ester hydrochloride (6.0 g, 33.4 mmol) in CH$_2$Cl$_2$ (40 mL) at 0° C. Acetic anhydride (3.8 mL, 40 mmol) was added, and the reaction mixture was stirred at 0° C. for 3 h. The reaction mixture was diluted with EtOAc (ca. 250 mL) and washed with water (ca. 100 mL). The aqueous layer was extracted with EtOAc. The combined organic layers were dried with Na$_2$SO$_4$, filtered and concentrated under reduced pressure to yield the product (7.0 g, 100%).

$^1$H NMR (400 MHz, CDCl$_3$) δ 1.30 (t, J=7.13 Hz, 3H) 2.01 (s, 3H) 2.02-2.13 (m, 2H) 2.33-2.52 (m, 2H) 2.52-2.74 (m, 2H) 4.24 (q, J=7.13 Hz, 2H) 6.15 (br s, 1H).

Step 2:

A solution of the product compound from Step 1 (7.0 g, 33.4 mmol) in THF (60 mL) was added dropwise to a solution of LiAlH$_4$ (50 mL of a 2.0 M solution in THF, 100 mmol) in THF (40 mL) at room temperature. The reaction was heated at 50° C. overnight. The reaction mixture was cooled to 0° C. and quenched by careful sequential addition of water (3.8 mL), 15% aqueous NaOH (3.8 mL), and water (12 mL). The mixture was stirred vigorously overnight and the salts were removed by suction filtration. The filter cake was washed with THF (2×200 mL), and the filtrate was concentrated under reduced pressure to give the desired amino alcohol (4.3 g, 100%).

$^1$H NMR (400 MHz, CDCl$_3$) δ 1.10 (t, J=7.13 Hz, 3H) 1.64-1.84 (m, 2H) 1.84-1.97 (m, 4H) 2.50 (q, J=7.14 Hz, 2H) 3.51 (s, 2H).

Step 3:

Following procedures analogous to those described for Steps 3 and 4 of Preparation 14, the amino alcohol product from Step 2 was converted to the title compound.

$^1$H NMR (400 MHz, CDCl$_3$) δ 1.38 (t, J=7.30 Hz, 3H) 1.63-1.94 (m, 2H) 2.09 (ddd, J=8.21, 5.50, 3.07 Hz, 2H) 2.50 (dd, J=10.35, 3.03 Hz, 2H) 3.26 (q, J=7.27 Hz, 2H) 4.53 (s, 2H)

Preparation 18

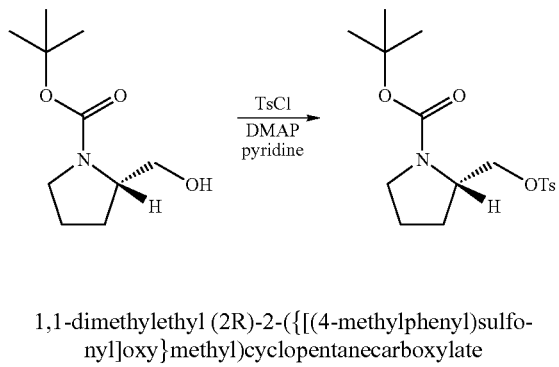

1,1-dimethylethyl (2R)-2-({[(4-methylphenyl)sulfonyl]oxy}methyl)cyclopentanecarboxylate To a solution of N-Boc-L-prolinol (520 mg, 2.6 mmol) and pyridine (0.63 mL, 7.8 mmol) in CH$_2$Cl$_2$ (40 mL) was added in one portion p-toluenesulfonyl chloride (542 mg, 2.86 mmol) followed by DMAP (130 mg, 1.1 mmol). The reaction was stirred for 24 h at which time saturated aqueous NH$_4$Cl was added and the mixture was extracted with CH$_2$Cl$_2$. The combined organic extracts were dried (Na$_2$SO$_4$), and concentrated under reduced pressure. The residue was purified by flash chromatography, elution with 0-100% EtOAc in heptane, to afford the title compound (720 mg, 78%) as a clear oil.

$^1$H NMR (400 MHz, DMSO-d$_6$) δ 1.12-1.43 (rotameric d, 9H) 1.54-1.83 (m, 3H) 1.90 (br s, 1H) 2.42 (s, 3H) 2.98-3.27 (m, 2H) 3.83 (br s, 1H) 3.90-4.21 (m, 2H) 7.48 (d, J=8.10 Hz, 2H) 7.77 (d, J=8.20 Hz, 2H).

Preparation 19

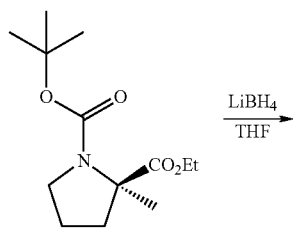

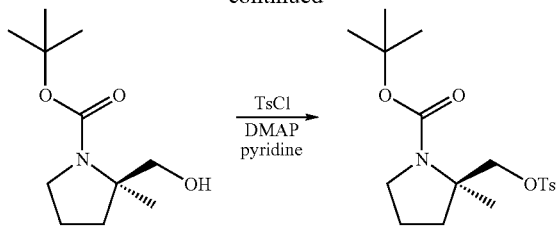

1,1-dimethylethyl (2R)-2-methyl-2-({[(4-methylphenyl)sulfonyl]oxy}methyl)pyrrolidine-1-carboxylate Step 1:
To a solution of 1-(1,1-dimethylethyl) 2-ethyl (2R)-2-methylpyrrolidine-1,2-dicarboxylate (Kawabata, T. et al. JACS 2003, 125, 13012; 2.33 g, 9.0 mmol) in THF (40 mL) maintained at 0° C. was added LiBH$_4$ (22.7 mL of a 2M solution in THF, 45 mmol) over 10 min. The reaction was stirred for 15 min at which time the ice bath was removed and stirring was continued for 48 h. The reaction was cooled to 0° C. and saturated aqueous NH$_4$Cl was added carefully. After gas evolution had ceased, the mixture was diluted with water and EtOAc and the layers were separated. The aqueous phase was extracted with EtOAc. The combined organic extracts were washed with half-saturated aqueous NaCl, dried with Na$_2$SO$_4$, and concentrated under reduced pressure. The residue was purified by flash chromatography, elution with 0-100% EtOAc in heptane, to afford the product (1.88 g, 96.5%) as a clear oil.
$^1$H NMR (400 MHz, CDCl$_3$) δ 1.36 (s, 3H) 1.46 (s, 9H) 1.55-2.02 (m, 4H) 3.21-3.76 (m, 4H) 5.28 (d, J=9.42 Hz, 1H).

Step 2:
Following a procedure analogous to that described for Preparation 18, the product from Step 1 was converted to the title compound.
$^1$H NMR (400 MHz, CDCl$_3$) δ 1.29 (d, J=9.81 Hz, 3H) 1.38 (d, J=15.42 Hz, 9H) 1.60-1.90 (m, 3H) 2.01-2.24 (m, 1H) 2.45 (d, J=2.83 Hz, 3H) 3.29-3.54 (m, 2H) 3.99-4.49 (m, 2H) 7.34 (dd, J=12.67, 8.03 Hz, 2H) 7.78 (t, J=7.32 Hz, 2H).

Preparation 20

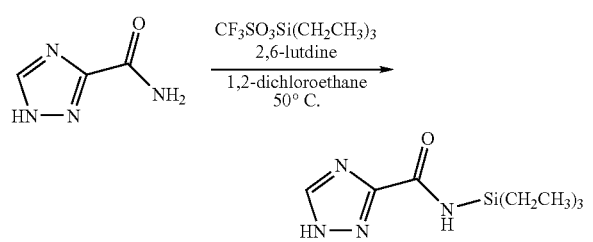

N-(triethylsilyl)-1H-1,2,4-triazole-3-carboxamide

A stirred mixture of 1H-1,2,4-triazole-3-carboxamide (500 mg, 4.46 mmol) in 1,2-dichloroethane (4.46 mL) treated at room temperature with 2,6-lutidine (2.08 mL, 17.84 mmol) and triethylsilyl trifluoromethanesulfonate (3.03 mL, 13.38 mmol) and heated under a nitrogen atmosphere at 50° C. After 4 hours of heating the reaction solution allowed to cool to room temperature and diluted with dichloromethane (25 mL), washed with water (25 mL), 0.5M hydrochloric acid (25 mL), water (25 mL), dried over MgSO$_4$, filtered, and evaporated to solid. The solid was flash chromatographed (silica gel, 10-65% ethyl acetate:hexane) to give the product as a white solid (683 mg).
$^1$H NMR (CDCl$_3$, 500 MHz, ppm) 0.89 (q, J=8 Hz, 6H, CH$_2$), 1.03 (t, J=8 Hz, 9H, CH$_3$), 6.77 (s, 1H, NH), 8.63 (s, 1H, triazole H-5).
LC/MS m/z (positive ion scan) M+1=227.20.

Preparation 21

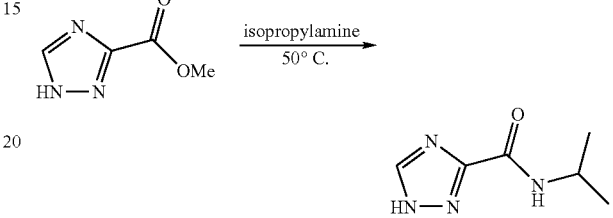

N-(1-methylethyl)-1H-1,2,4-triazole-3-carboxamide

Methyl 1H-1,2,4-triazole-3-carboxylate (3.53 g, 27.8 mmol) and isopropylamine (11 ml, 128 mmol) were combined in a 20 ml vial to give a white suspension. The vial was sealed and heated to 50° C. After 6 days the reaction mixture had become a translucent solid. The vial was cooled to room temperature and unsealed. The solid was dissolved in methanol and transferred to a 200 ml flask. The solvent was evaporated under reduced pressure and the resulting residue was stripped several times with ethanol to removed excess isopropylamine. The residue was stripped with toluene and placed under high vacuum overnight to give the title compound (4.07 g) as a white solid.
$^1$H NMR (CD$_3$OD, 600 MHz, ppm) δ 1.25 (d, 6H, 2Me), 4.15-4.22 (m, 1H, CONCH), 8.38 (s, 1H, triazole).
Mass Spectrum: (ESI) m/z=155.14 (M+H).

Preparation 22

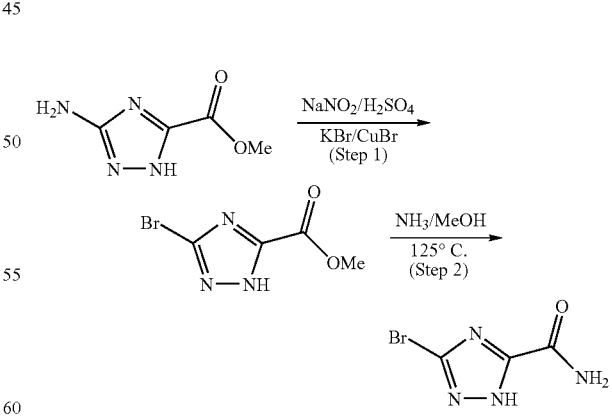

3-bromo-1H-1,2,4-triazole-5-carboxamide

Step 1:
A stirred mixture of methyl 3-amino-1H-1,2,4-triazole-5-carboxylate (2.00 g, 14.1 mmol) in 1M aqueous sulfuric acid (28.1 mL, 28.1 mmol) at ice bath temperature was treated with an aqueous solution of sodium nitrite (1.46 g, 21.1 mmol) in water (5 mL) and additional water was added (10 mL). After 25 minutes the reaction was treated with a solution of potassium bromide (3.35 g, 28.1 mmol) and copper(I) bromide (0.61 g, 4.22 mmol) in water (10 mL). This resulting mixture was stirred at room temperature. After 3 hours the reaction was extracted with ethyl acetate (3×25 mL) and the combined extracts washed with brine (20 mL), dried over magnesium sulfate, filtered and evaporated to a solid which was crystallized from ethyl acetate to give a white solid (592 mg). The mother liquors were purified by flash chromatography (silica gel, 0-14% ethyl acetate:hexane) to give additional product as a white solid (1.12 g).

LC/MS m/z (positive ion scan) M+1=206.07 (and 208.11).

Step 2:

A solution of methyl 3-bromo-1H-1,2,4-triazole-5-carboxylate from Step 1 (250 mg, 1.21 mmol) in 7M ammonia in methanol (4 mL, 28 mmol) was heated at 125° C. under microwave conditions for 40 minutes. The reaction solution was concentrated under vacuum to give the title compound as a solid.

LC/MS m/z (positive ion scan) M+1=191 (and 193.02).

Preparation 23

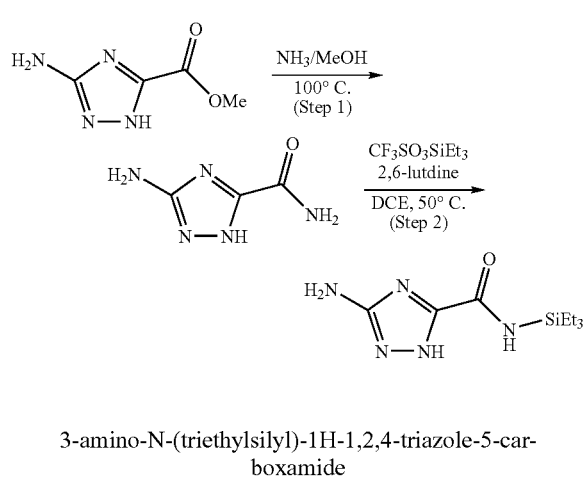

3-amino-N-(triethylsilyl)-1H-1,2,4-triazole-5-carboxamide

Step 1:

A stirred mixture of methyl 3-amino-1H-1,2,4-triazole-5-carboxylate (500 mg, 3.52 mmol) in 7M ammonia in methanol (5.0 mL, 35 mmol) was heated under microwave conditions at 100° C. for 30 minutes. The resulting mixture was filtered and washed with ethyl acetate to afford the desired product as a light gray solid (346 mg).

$^1$H NMR (DMSO-$d_6$, 500 MHz, ppm) 6.01 (br s), 7.34 (br s).

Step 2:

A stirred mixture of 3-amino-1H-1,2,4-triazole-5-carboxamide (103 mg, 0.810 mol) in 1,2-dichloroethane (1.62 mL) treated at room temperature with 2,6-lutidine (283 μL, 2.43 mmol) and triethylsilyl trifluoromethanesulfonate (458 μL, 2.03 mmol). After 22 hours the reaction was heated at 50° C. and after 1.5 hours of heating the reaction was allowed to cool to room temperature. The reaction mixture was diluted with ethyl acetate (20 mL) and washed with water (25 mL), dried over magnesium sulfate, filtered, and evaporated to an oil which was flash chromatographed (silica gel, 0-10% ethyl acetate:hexane) to give the title compound as a white solid (130 mg).

LC/MS m/z (positive ion scan) M+1=242.23.

Preparation 24

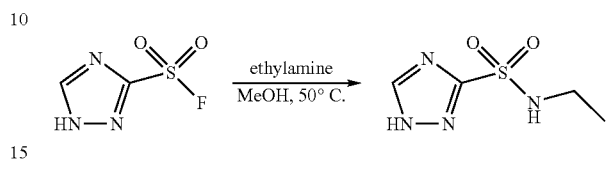

N-ethyl-1H-1,2,4-triazole-3-sulfonamide

To a solution of ethylamine in methanol (2 M, 2.4 mmol, 4.8 mmol) was added 1H-1,2,4-triazole-3-sulfonyl fluoride (200 mg, 1.18 mmol, *J. Heterocycl. Chem.* 1988, 25, 1857). After ten minutes the reaction was concentrated in vacuo to give a yellow oil. Ice-cold water (2-3 mL) was added and the resulting solution was sonicated for approximately one minute. Several drops of acetic acid were added which immediately caused precipitation of the title compound which was obtained as a white solid after filtration (57 mg).

$^1$H NMR (CD$_3$OD, 500 MHz, ppm) δ 1.11 (t, J=7.4 Hz, 3H), 3.12 (q, J=7.3 Hz, 2H), 8.58 (s, 1H).

Preparation 25

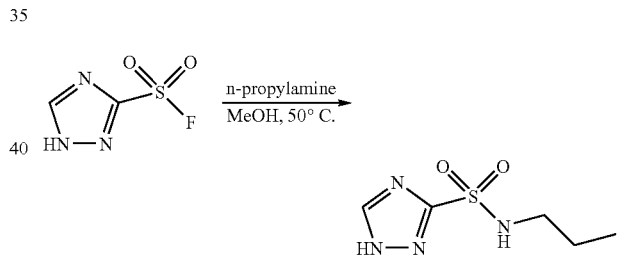

N-propyl-1H-1,2,4-triazole-3-sulfonamide

By a procedure analogous to that described for Preparation 24, the title compound was synthesized.

$^1$H NMR (CD$_3$OD, 500 MHz, ppm) δ 0.89 (t, J=7.4 Hz, 3H), 1.51 (tq, J=7.3 Hz, 7.1 Hz, 2H), 3.03 (t, J=7.1 Hz, 2H), 8.58 (s, 1H).

Preparation 26

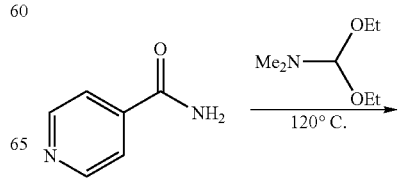

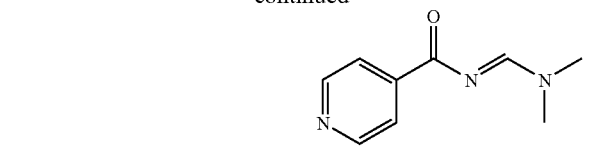

[cf. Y. Lin, et al. *J. Org. Chem.* 1979, 44, 4160]

N-[(1E)-(dimethylamino)methylidene]pyridine-4-carboxamide

Isonicotinamide (2.00 g, 16.38 mmol) and N,N-dimethylformamide diethyl acetal (2.8 ml, 16.38 mmol) were combined and heated to 120° C. A short path distillation apparatus was used to collect the ethanol that was liberated during the reaction. The reaction mixture was an orange solution. After 15 minutes, additional N,N-dimethylformamide diethyl acetal (1.0 ml, 5.83 mmol) was added to the reaction mixture. After 1.5 hours, the reaction mixture was cooled to room temperature. The reaction mixture solidified upon cooling and was placed under high vacuum overnight to give the title compound (2.92 g, 16.48 mmol) as a yellow solid.

$^1$H NMR (CD$_3$OD, 500 MHz, ppm) δ 3.28 (s, 3H, NMe), 3.29 (s, 3H, NMe), 8.10-8.12 (m, 2H, ArH), 8.66-8.68 (m, 2H, ArH), 8.70 (s, 1H).

Mass Spectrum: (ESI) m/z=178.19 (M+H).

Preparation 27

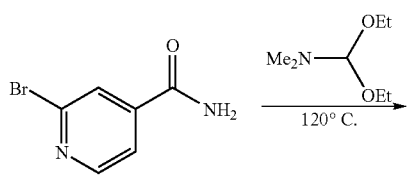

2-bromo-N-[(1E)-(dimethylamino)methylidene]pyridine-4-carboxamide 2-bromo-isonicotinamide (406.2 mg, 2.021 mmol) and N,N-dimethylformamide diethyl acetal (0.48 ml, 2.80 mmol) were combined and heated to 120° C. A short path distillation apparatus was used to collect the ethanol that was liberated during the reaction. The reaction mixture was a light orange solution that slowly turned darker until it had become a dark amber solution. After 1.5 hours, the reaction mixture was cooled to room temperature. The reaction mixture solidified upon cooling and was placed under high vacuum overnight to give the title compound (507.4 mg) as an off-white solid.

$^1$H NMR (CD$_3$OD, 500 MHz, ppm) δ 3.27 (s, 3H, NMe), 3.29 (s, 3H, NMe), 8.05 (dd, 1H, ArH), 8.23 (d, 1H, ArH), 8.46 (d, 1H, ArH), 8.69 (s, 1H)

Mass Spectrum: (ESI) m/z=256.01 (258.01) (M+H)..

Preparation 28

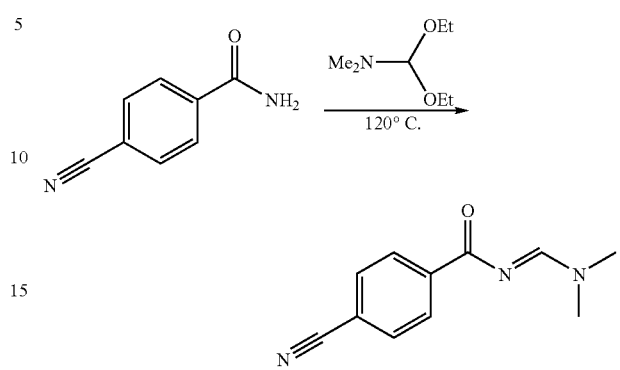

4-cyano-N-[(1E)-(dimethylamino)methylidene]benzamide 4-cyanobenzamide (327.0 mg, 2.237 mmol) and N,N-dimethylformamide diethyl acetal (0.53 ml, 3.09 mmol) were combined and heated to 120° C. A short path distillation apparatus was used to collect the ethanol that was liberated during the reaction. The reaction mixture was a dark purple solution that slowly turned lighter until it had become an amber solution. After 70 minutes, the reaction mixture solidified. The reaction mixture was cooled to room temperature and was placed under high vacuum overnight to give the title compound (432.7 mg, 2.150 mmol) as a yellow solid.

$^1$H NMR (CD$_3$OD, 600 MHz, ppm) δ 3.24 (s, 3H, NMe), 3.26 (s, 3H, NMe), 7.78 (d, 2H, ArH), 8.32 (d, 2H, ArH), 8.65 (s, 1H).

Mass Spectrum: (ESI) m/z=202.09 (M+H).

Preparation 29

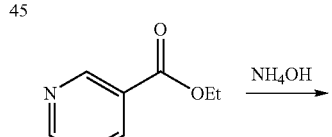

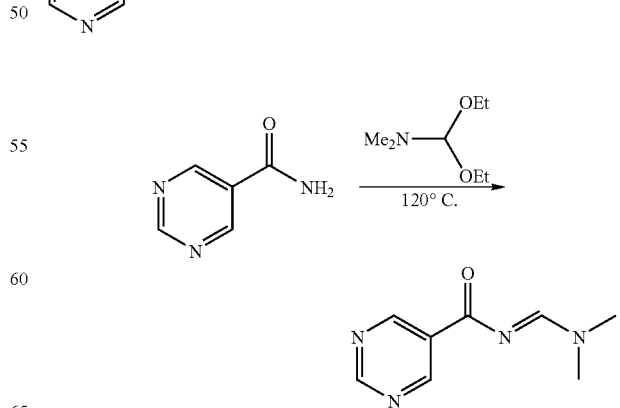

N-[(1E)-(dimethylamino)methylidene]pyrimidine-5-carboxamide

Step 1:

Ethyl 5-pyrimidine carboxylate (0.26 ml, 1.982 mmol) and ammonium hydroxide (2.8 ml, 20.13 mmol) were combined in a 25 ml flask to give a hazy solution. The reaction mixture was stirred at room temperature. After 15 minutes, a white precipitate formed, which turned the reaction mixture into a white suspension. After 2.5 hours, LMCS and $^1$H NMR showed complete conversion of starting material. The reaction mixture was filtered, rinsing over with water (3×1 ml). The filtered solid was air dried overnight to give the product (199.8 mg) as a white solid.

$^1$H NMR (CD$_3$OD, 500 MHz, ppm) δ 9.21 (s, 2H), 9.29 (s, 1H).

Mass Spectrum: (ESI) m/z=124.12 (M+H).

Step 2:

The product compound from Step 1 (199.8 mg, 1.623 mmol) and N,N-dimethylformamide diethyl acetal (0.39 ml, 2.276 mmol) were combined and heated to 120° C. A short path distillation apparatus was used to collect the ethanol that was liberated during the reaction. The reaction mixture slowly changed from a yellow suspension to an amber solution. A yellow precipitate formed. After 1.5 hours, the reaction mixture was cooled to room temperature. The reaction mixture solidified upon cooling and was placed under high vacuum for about an hour to give the title compound (284.9 mg) as a yellow solid.

$^1$H NMR (CD$_3$OD, 600 MHz, ppm) δ 3.26 (s, 3H, NMe), 3.27 (s, 3H, NMe), 8.70 (s, 1H), 9.23 (s, 1H, ArH), 9.41 (s, 2H, ArH).

Mass Spectrum: (ESI) m/z=179.20 (M+H).

Preparation 30

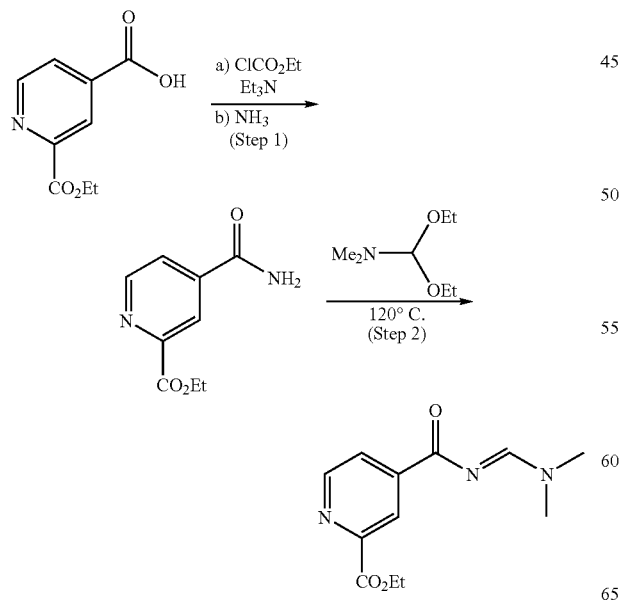

Ethyl 4-({[(1E)-(dimethylamino)methylidene]amino}carbonyl)pyridine-2-carboxylate Step 1:

A stirred solution of 2-(ethoxycarbonyl)isonicotinic acid (0.507 g, 2.60 mmol) and triethylamine (0.4 ml, 2.87 mmol) in 1,2-dimethoxyethane (5.2 ml) was cooled to 0° C. in an ice bath. Ethyl chloroformate (0.28 ml, 2.92 mmol) was added dropwise to the reaction mixture over a period of several minutes, resulting in a thick white suspension. The reaction mixture was stirred for an additional 40 minutes before ammonia was bubbled into the suspension over a period of 10 minutes. The reaction mixture was warmed to room temperature and evaporated under reduced pressure to give a light yellow solid. The solid was suspended in ice cold concentrated ammonium hydroxide (5 ml) and stirred in an ice bath for several minutes. The suspension was filtered, rinsing over with ice cold water (2×2 ml). The filtered solid was air dried overnight to give the amide product (313.1 mg) as a white solid.

$^1$H NMR (CD$_3$OD, 500 MHz, ppm) δ 1.45 (t, 3H), 4.48 (q, 2H, COOCH$_2$), 8.02 (dd, 1H, ArH), 8.54 (d, 1H, ArH), 8.83 (d, 1H, ArH).

Mass Spectrum: (ESI) m/z=195.42 (M+H).

Step 2:

The product compound from Step 1 (313.1 mg, 1.612 mmol) and N,N-dimethylformamide diethyl acetal (0.38 ml, 2.217 mmol) were combined and heated to 120° C. The reaction mixture was a light purple solution that slowly turned lighter until it had become an orange solution. After 25 minutes, the reaction mixture was slowly placed under vacuum. The reaction mixture was cooled to room temperature about five minutes after reaching full vacuum. The vacuum was released after the reaction mixture had cooled. The reaction mixture was placed under high vacuum and solidified after several hours to give the title compound (390.3 mg) as a tan solid.

$^1$H NMR (CD$_3$OD, 500 MHz, ppm) δ 1.45 (t, 3H), 3.30 (s, 3H, NMe), 3.31 (s, 3H, NMe), 4.48 (q, 2H, COOCH$_2$), 8.30 (dd, 1H, ArH), 8.72 (s, 1H), 8.77 (d, 1H, ArH), 8.80 (d, 1H, ArH).

Mass Spectrum: (ESI) m/z=250.40 (M+H).

Preparation 31

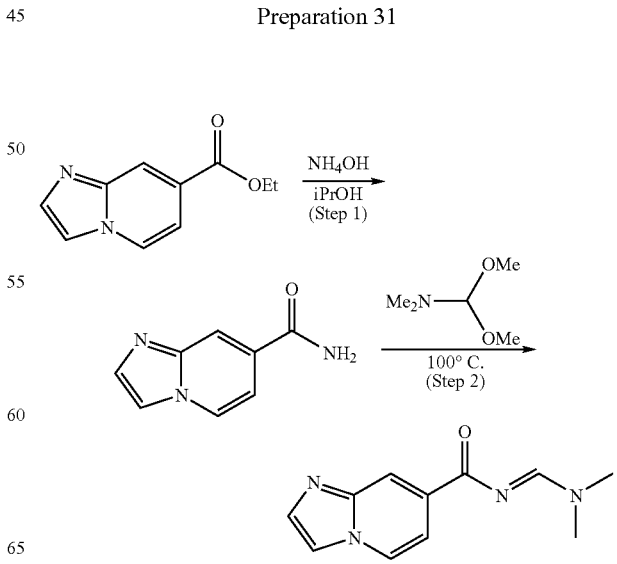

N-[(1E)-(dimethylamino)methylidene]imidazo[1,2-a]pyridine-7-carboxamide

Step 1:

To a solution of ethyl imidazo[1,2-a]pyridine-7-carboxylate (cf. Chezal, J. M. et al. *Tetrahedron* 2002, 58, 295-307; *J. Org. Chem.* 2001, 66, 6576-6584; 835 mg, 4.4 mmol) in i-PrOH (10 mL) was added 35% aqueous NH₄OH (90 mL) and the reaction was stirred at room temperature for 72 h. The reaction was concentrated under reduced pressure to provide the product as a solid.

$^1$H NMR (400 MHz, CDCl$_3$) δ 3.22 (s, 3H) 3.24 (s, 3H) 7.62 (dd, J=7.03, 1.42 Hz, 1H) 7.65 (s, 1H) 7.75 (d, J=0.88 Hz, 1H) 8.13 (dd, J=7.05, 0.85 Hz, 1H) 8.68 (d, J=14.15 Hz, 2H).

Intermediate 1

Benzyl (1S,4aR,6aS,7R,8R,10aR,10bR,12aR,14R,15R)-8-[(1R)-1,2-dimethylpropyl]-15-hydroxy-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

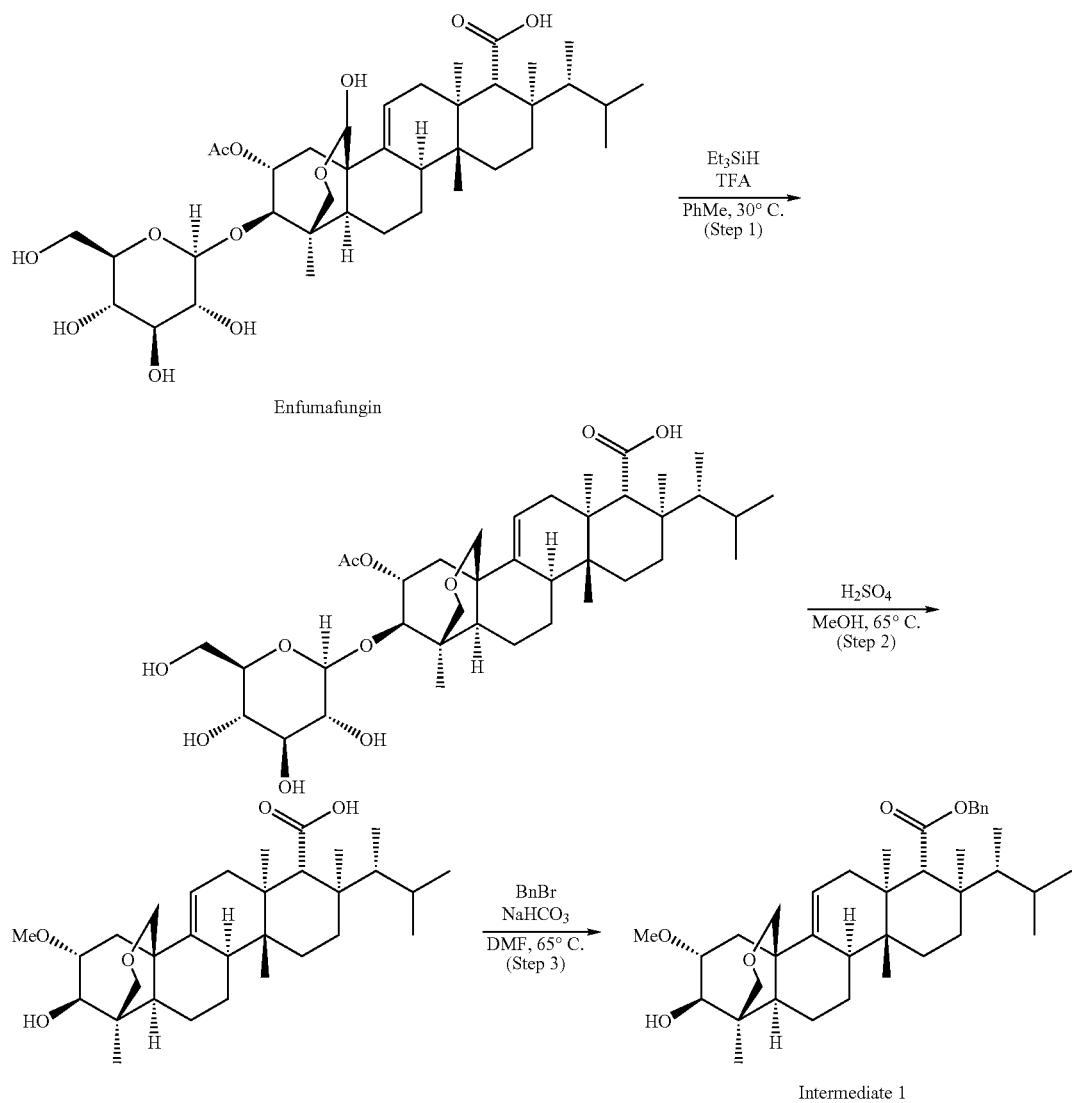

Step 2:

Compound the product from Step 1 was dissolved in DMF (25 mL). DMF dimethyl acetal (50 mL) was added and the mixture was heated at 100° C. for 4 h. The reaction mixture was cooled to room temperature and concentrated under reduced pressure. The residue was purified by flash chromatography, elution with 0-10% MeOH in CH₂Cl₂, to afford the title compound (680 mg, 72%) as an orange-brown solid.

Step 1:

To a slurry of enfumafungin (90.0 g, 126.9 mmol) in 846 ml of toluene with mechanical stirring at room temperature was added Et₃SiH (202.2 ml, 1269.5 mmol) in one portion. Trifluoroacetic acid (202.4 ml, 2627.8 mmol) was then added dropwise at a rapid rate. Once the trifluoroacetic acid addition was complete, the resulting amber colored solution was allowed to stir at room temperature for 2.5 hours. The TFA/toluene solution was then concentrated to dryness. Fresh toluene (300-500 ml) was added and the mixture was once again concentrated to dryness. The toluene stripping procedure was repeated two additional times. The crude solid was then dried overnight on a high vacuum line to yield 120 g of a purple brown solid. This material was carried on to the next step without additional purification.

Step 2:

To a solution of the solid from above (120 g crude material, ~126.9 mmol) in MeOH (1.27 L) with mechanical stirring, $H_2SO_4$ (31.2 ml, 585.3 mmol) was added dropwise at a fast rate. Once the addition was complete, the resulting solution was warmed to 65° C. and was allowed to stir for 4.5 hours. During the course of the reaction a white solid precipitated. The reaction was cooled to room temperature and the white solid was isolated by filtration. The solid was then washed with MeOH (2×200 ml) and $CH_3CN$ (2×200 ml). After drying, 47.91 g white solid was recovered.

Additional material was isolated from the initial filtrate and subsequent washings as follows. The total liquid volume was reduced to ⅓ by evaporation in vacuo. An excess of water was added and a purple white solid precipitated. The solid was filtered, washed with 3:7 MeOH:water (2×100 mL) and $CH_3CN$ (2×100 mL) and dried to give an additional 7.30 g of product as a brownish white solid. The combined yield of product was 55.21 g (86.5%).

Step 3:

The product from Step 2 (55.21 g, 109.8 mmol), $NaHCO_3$ (147.5 g, 1756.8 mmol) and benzyl bromide (65.29 ml, 549.0 mmol) were combined in 550 ml DMF with mechanical stirring. The mixture was warmed to 65° C. and was allowed to stir for 4.5 hours. The DMF was removed in vacuo and the resulting crude material was dissolved in 1 L of 3:2 water/MeOH. The mixture was vigorously stirred for 2-3 hours. During this time a brownish white solid formed. The precipitate was filtered and washed with additional 3:2 water/MeOH (2×250 mL). The solid was then rinsed with heptane and was allowed to air aspirate to initial dryness. The white solid recovered was then transferred to a recrystallizing dish and placed in a vacuum oven at 30° C. for four hours to give 52.2 g of white solid.

Additional material was isolated from the water:MeOH and heptane filtrates as follows. The combined solutions were extracted with EtOAc. The combined EtOAc washings were dried over $Na_2SO_4$ and concentrated to dryness. The resulting material was purified by $SiO_2$ chromatography (3:7 EtOAc:DCM) to yield an additional 5.42 g of product as a white solid. The total combined yield of Intermediate 1 was 57.6 g (88.5%).

$^1$H NMR (400 MHz, $CDCl_3$, ppm) δ 0.71-0.74 (m, 6H), 0.78 (d, J=6.83 Hz, 3H), 0.80-0.83 (m, 6H), 1.15 (s, 3H), 1.16-1.21 (m, 1H), 1.23 (s, 3H), 1.24-1.29 (m, 2H), 1.32-1.53 (m, 4H), 1.56-1.62 (m, 1H), 1.70-1.81 (m, 3H), 1.87-1.95 (m, 1H), 1.99-2.04 (m, 1H), 2.07-2.16 (m, 1H), 2.30 (d, J=2.25 Hz, 1H), 2.40-2.47 (m, 1H), 2.88 (s, 1H), 3.18 (d, J=8.88 Hz, 1H), 3.31 (d, J=11.76 Hz, 1H), 3.40-3.42 (m, 2H), 3.43 (s, 3H), 3.77 (d, J=11.81 Hz, 1H), 4.09-4.19 (m, 1H), 4.98 (d, 1H), 5.12 (d, 1H), 5.39-5.43 (m, 1H), and 7.32-7.39 (m, 5H).

Intermediate 2

(1S,4aR,6aS,7R,8R,10aR,10bR,12aR,14R,15R)-15-(2-aminoethoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

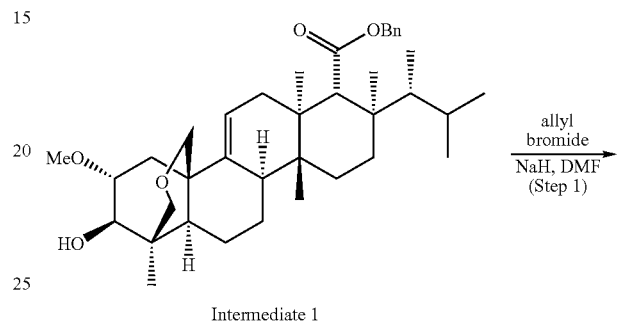

Intermediate 1

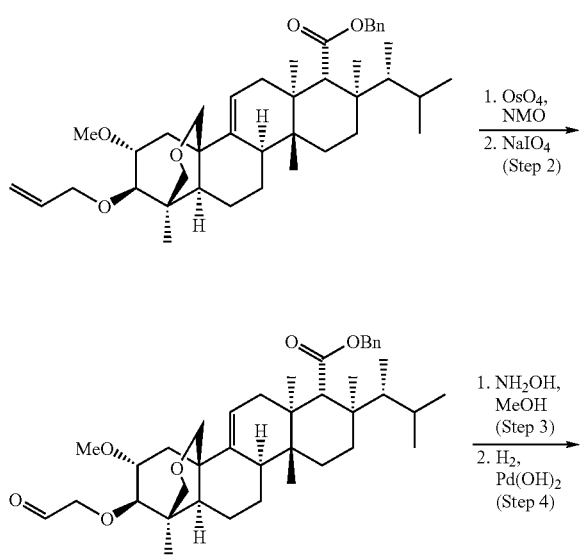

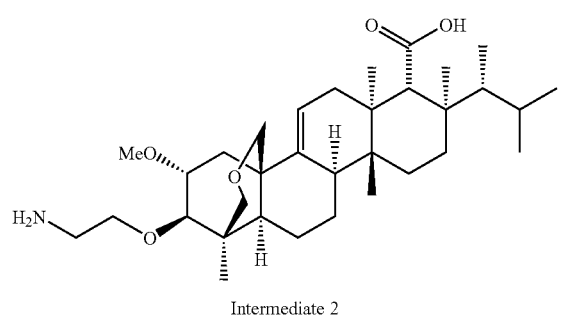

Intermediate 2

Step 1:

To a chilled solution of Intermediate 1 (611 mg; 1.025 mmol) in dimethylformamide (9 mL) was added sodium hydride (328 mg; 8.2 mmol) and allyl bromide (355 µL). The reaction was stirred at room temperature for 16 hours. The reaction was judged complete by TLC analysis. The reaction contents were concentrated and the residue was flash chromatographed (silica gel; 80:20 heptane:ethyl acetate) to yield 529 mg of purified material.

Step 2:

The material from above (529 mg) was dissolved in acetone (6.8 mL) and water (0.8 mL). Osmium tetroxide (4% solution; 531 µL; 0.08 mmol) and 4-methylmorpholine N-oxide (196 mg) were added and the reaction stirred at room temperature for 16 hours. The reaction was judged complete by TLC analysis. Florisil (550 mg) and sodium bisulfite (550 mg) were added and the reaction solution was stirred for 1 hour at room temperature. The reaction contents were filtered over a pad of Celite and concentrated. The residue was dissolved in tetrahydrofuran (12 mL) and water (3 mL) and sodium periodate (490 mg) was added. The reaction solution was stirred for 2 hours at room temperature and judged complete by TLC analysis. Water (5 mL) was added and the aqueous phase was thrice washed with ethyl acetate. The organic phase was dried over magnesium sulfate and concentrated. The residue was flash chromatographed (silica gel; 70:30 heptane:ethyl acetate) to yield the aldehyde intermediate (550 mg).

Step 3:

A mixture of aldehyde intermediate prepared as described in Step 2 (1 g, 1.58 mmol), hydroxylamine hydrochloride (1.1 g, 15.8 mmol) and sodium bicarbonate (5.3 g, 63.2 mmol) was suspended in methanol (50 mL) and stirred at room temperature for 1 hour. Ethyl acetate (200 mL) and water (200 mL) were added, the ethyl acetate layer was washed with brine (1×50 mL), dried with magnesium sulfate, filtered and evaporated to give the product as a foam 1.1 g). Examination of the solid by $^1$H NMR showed an approximately 1:1 mixture of E- and Z-oxime stereoisomers.

Step 4:

A mixture of the oxime from Step 3 (1.1 g, 1.58 mmol), TFA (608 µL, 7.9 mmol) and 20% Pd(OH)$_2$/C in methanol (50 mL) was stirred under a balloon of hydrogen for 3 hours at room temperature. The suspension was filtered, evaporated and freeze-dried from a mixture of ethanol and benzene to give Intermediate 2 as a white solid.

$^1$H NMR CD$_3$OD δ (PPM) 5.54 (dd, 1H, H5); 4.23 (m, 1H, H14); 3.87 (m, 1H); 3.68 (m); 3.62 (d, 1H); 3.40-3.43 (m); 3.39 (s, 3H, OMe); 3.32 (dd, 1H), 3.02-3.08 (m); 2.93 (d, 1H); 2.85 (s, 1H, H7), 2.54 (dd, 1H, H13); 2.19 (m, 1H); 2.08 (m, 1H); 1.96 (m, 1H); 1.70-1.84 (m); 1.46-1.64 (m); 1.22-1.28 (m); 1.21 (s, 3H, Me); 1.16 (s, 3H, Me); 0.90 (d, 3H, Me); 0.85 (s, 3H, Me); 0.78 (d, 3H, Me); 0.75 (d, 3H, Me) and 0.75 (s, 3H, Me).

LC/MS m/z (positive ion scan) M+1=546.98.

Intermediate 3

(1S,4aR,6aS,7R,8R,10aR,10bR,12aR,14R,15R)-15-(2-amino-2-methylpropoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

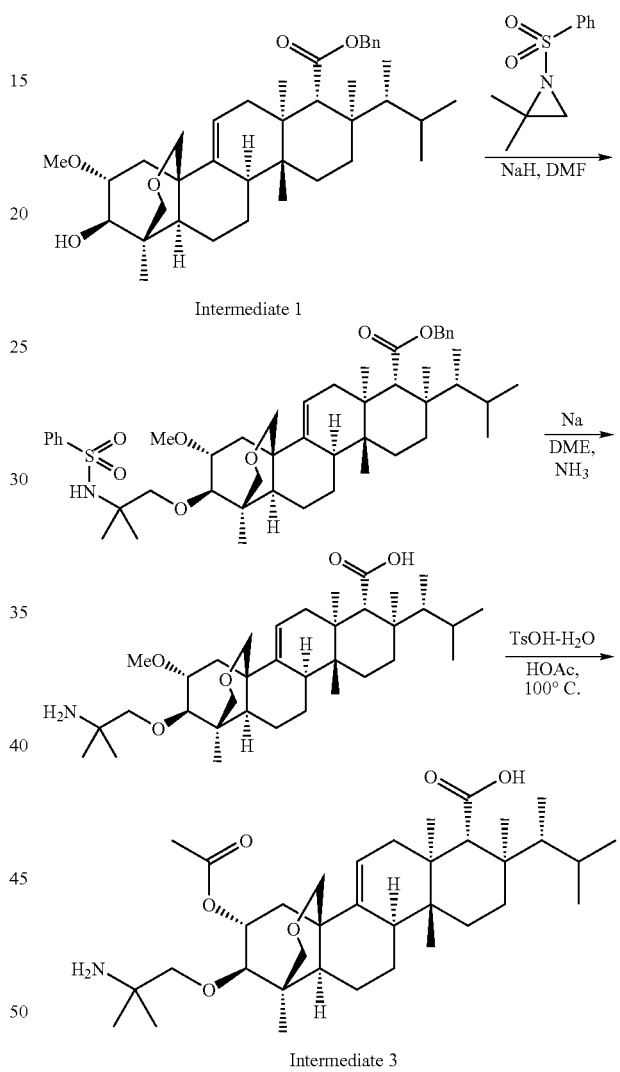

Step 1

To a solution of Intermediate 1 (1.5 g; 2.5 mmol) in dimethylformamide (30 mL) was added sodium hydride (1.0 g; 60% dispersion, 25.3 mmol) and 1-benzenesulfonyl-2,2-dimethyl-aziridine (2.67 g; 12.5 mmol). The reaction mixture was heated to 70° C. and stirred for 1 hour; the reaction was judged complete by TLC analysis. The reaction was cooled to room temperature and ethyl acetate (100 mL), methanol (10 mL) and water (50 mL) were added. The aqueous phase was twice washed with ethyl acetate. The organic phases were combined, dried over magnesium sulfate, and concentrated. The residue was flash chromatographed (silica gel; 90:10 heptane:ethyl acetate) to yield a white solid (1.75 g).

Step 2

A portion of the purified material from Step 1 (800 mg) was dissolved in dimethoxyethane (20 mL) and the solution was chilled to −70° C. Ammonia (20 g) was added to the reaction solution and sodium metal (enough to sustain a blue color) was added over the course of 1.5 hours. The reaction solution was stirred at −60° C. for 2 hours and then warmed to ammonia reflux for 30 minutes. The reaction was judged complete and methanol (15 mL) was slowly added. The reaction was then warmed to 0° C. and water (50 mL) was added. The aqueous phase was thrice washed with ethyl acetate (75 mL); the organic phases were combined, dried over magnesium sulfate, and concentrated to give the product as a white solid.

Step 3

To a stirred solution of the white solid from Step 2 in acetic acid (100 mL) was added p-TsOH—H$_2$O (0.93 g) and the reaction mixture was heated at 113° C. for 1.5 h. The reaction mixture was then allowed to cool to room temperature and the acetic acid was evaporated under reduced pressure. The residue was dissolved in EtOAc (200 mL) and washed with a saturated NaHCO$_3$ solution (100 mL) carefully. The aqueous phase was re-extracted with EtOAc (2×100 mL). The combined organic solutions were dried over anhydrous MgSO$_4$. After filtration and evaporation of the solvent Intermediate 3 was isolated as a white solid (0.87 g).

$^1$H NMR (CD$_3$OD, 600 MHz, ppm) δ 0.75 (s, 3H, Me), 0.77 (d, 3H, Me), 0.83 (s, 3H, Me), 0.85 (d, 3H, Me), 0.90 (d, 3H, Me), 1.16 (s, 3H, Me), 1.20 (s, 3H, Me), 1.30 (s, 3H, Me), 1.31 (s, 3H, Me), 1.22-1.44 (m), 1.45-1.52 (m), 1.53-1.69 (m), 1.72-1.87 (m), 1.92-1.97 (m), 2.04 (s, 3H, Me), 2.06-2.11 (m), 2.15-2.22 (m), 2.42 (dd, 1H, H1), 2.84 (s, 1H, H18), 3.22 (d, 1H), 3.38 (d, 1H), 3.43 (dd, 1H), 3.47 (d, 1H), 3.57 (d, 1H), 3.63 (d, 1H), 3.79 (d, 1H), 5.46 (dd, 1H, H11), 5.77-5.82 (m, 1H, H2).

Mass Spectrum: (ESI) m/z=603.02 (M+H).

Intermediates 4 & 5

Benzyl (1S,4aR,6aS,7R,8R,10aR,10bR,12aR,14R,15R)-15-[[(2R)-2,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (INTERMEDIATE 4) and Benzyl (1S,4aR,6aS,7R,8R,10aR,10bR,12aR,14R,15R)-15-[[(2S)-2,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate (INTERMEDIATE 5)

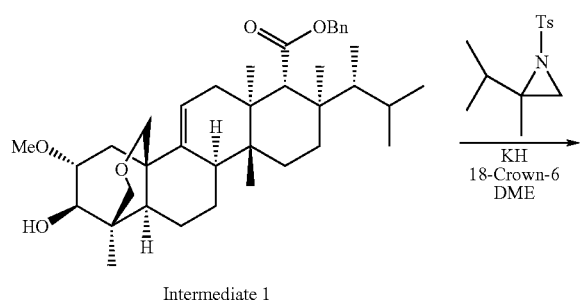

Intermediate 1

KH
18-Crown-6
DME

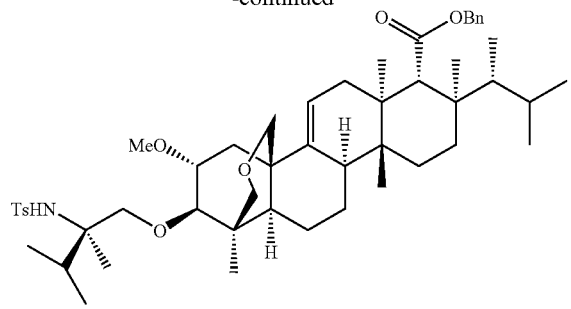

Intermediate 4

+

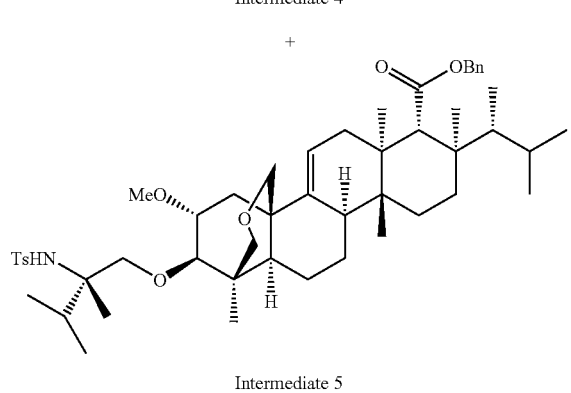

Intermediate 5

To a stirred solution of Intermediate 1 dissolved in anhydrous dimethoxyethane (400 mL) was added 18-crown-6 (33.7 g, 127.5 mmol) and 2-isopropyl-2-methyl-1-[(4-methylphenyl)sulfonyl]aziridine (21.4 g, 84.6 mmol, 1.66 equiv). The mixture was stirred under nitrogen for 10 min until all solids were dissolved. Potassium hydride (30% in oil, 17.0 g, 127.5 mmol, 2.5 equiv) was added portionwise (ca. 1 g portions) over a period of about 30 minutes. After the completion of the addition, the resulting suspension was stirred at room temperature for about 3 h. The reaction was carefully quenched by the dropwise addition of methanol (40 mL). The reaction mixture was then diluted with water (300 mL) and extracted with EtOAc (300 mL). The organic solution was washed with water (2×200 mL) and dried over anhydrous MgSO$_4$. The drying agent was removed by filtration and the organic solvent was removed under reduced pressure to afford the desired compound (67.4 g) as a mixture of diastereomers. Separation of the diastereomers was accomplished by chromatography on silica gel (0-15% EtOAc/heptanes) to give the faster eluting isomer, Intermediate 4, and the slower eluting isomer, Intermediate 5.

Intermediate 4

$^1$H NMR CDCl$_3$ δ (PPM) 7.81 (d, 1H, ArH); 7.38 (m, ArH); 7.34 (m, ArH); 7.26 (m, ArH); 6.65 (s, NH); 5.44 (m, 1H, H5); 5.12 (d, 2H, CH$_2$ Ar); 4.99 (d, 2H, CH$_2$ Ar); 4.23 (m, 1H, H14); 3.69 (d, 1H); 3.65 (d, 1H); 3.47 (s, 3H, OMe); 3.38 (m); 3.26 (d, 1H); 3.21 (d, 1H); 2.89 (s, 1H, H7), 2.83 (d, 1H); 2.49 (dd, 1H, H13); 2.42 (s, ArMe); 2.12 (m, 1H); 2.02-2.08 (m); 1.90-1.94 (m); 1.66-1.78 (m); 1.44-1.51 (m); 1.35-1.39 (m); 1.14-1.30 (m); 1.25 (s, 3H, Me); 1.18 (s, 3H, Me); 0.95 (d, 3H, Me); 0.93 (s, 3H, Me); 0.88 (d, 3H, Me); 0.82 (d, 3H, Me); 0.78 (d, 3H, Me); 0.73 (d, 3H, Me); 0.72 (s, 3H, Me) and 0.67 (s, 3H, Me).

Intermediate 5

$^1$H NMR CDCl$_3$ δ (PPM) 7.77 (d, 1H, ArH); 7.37 (m, ArH); 7.33 (m, ArH); 7.27 (s, ArH); 7.26 (d, ArH); 5.41 (m, 1H, H5);

5.19 (s, NH); 5.11 (d, 2H, CH₂ Ar); 4.98 (d, 2H, CH₂ Ar); 4.22 (m, 1H, H14); 3.72 (d, 1H); 3.68 (d, 1H); 3.50 (d, 1H); 3.39 (m); 3.37 (s, 3H, OMe); 3.30 (d, 1H); 2.89 (s, 1H, H7), 2.82 (d, 1H); 2.42-2.45 (m); 2.41 (s, ArMe); 2.11 (m, 1H); 2.00-2.04 (m); 1.89-1.94 (m); 1.70-1.79 (m); 1.44-1.58 (m); 1.35-1.39 (m); 1.14-1.27 (m); 1.23 (s, 3H, Me); 1.15 (s, 3H, Me); 1.00 (s, 3H, Me); 0.88 (d, 3H, Me); 0.86 (d, 3H, Me); 0.82 (s, 3H, Me); 0.81 (d, 3H, Me); 0.78 (d, 3H, Me); 0.73 (d, 3H, Me) and 0.72 (s, 3H, Me).

Intermediate 4

Alternative Synthesis

Benzyl (1S,4aR,6aS,7R,8R,10aR,10bR,12aR,14R, 15R)-15-[[(2R)-2,3-dimethyl-2-[[(4-methylphenyl) sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

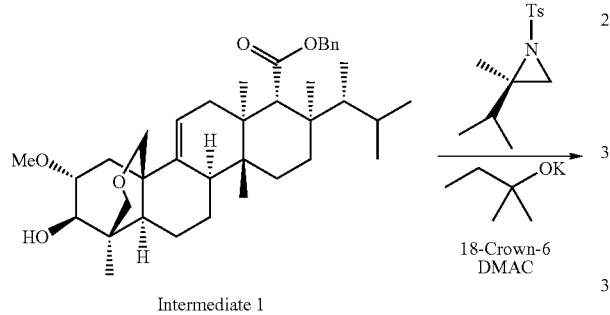

Intermediate 1

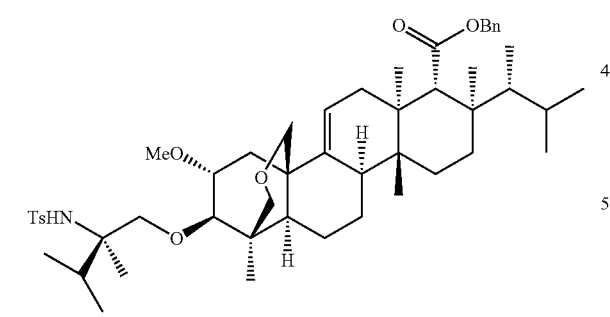

Intermediate 4

To a solution of Intermediate 1 (8.0 g, 13.49 mmol) in DMAC (50 mL) under a nitrogen atmosphere was added (2R)-2-isopropyl-2-methyl-1-[(4-methylphenyl)sulfonyl] aziridine (6.15 g, 24.29 mmol) and 18-crown-6 (3.57 g, 13.49 mmol). A solution of potassium tert pentoxide in toluene (~1.7 M, 9.53 mL, 16.19 mmol) was added in one portion. The mixture was stirred at room temperature for 16 hours and partitioned between EtOAc and 1N HCl. The organic layer was washed with brine and dried over Na₂SO₄. The solvent was evaporated and the residue was chromatographed with an ISCO Combiflash using 15-30% EtOAc/hexanes as gradient to afford Intermediate 4 as a pale yellow solid (7.50 g).

Intermediate 5

Alternative Synthesis

Benzyl (1S,4aR,6aS,7R,8R,10aR,10bR,12aR,14R, 15R)-15-[[(2S)-2,3-dimethyl-2-[[(4-methylphenyl) sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

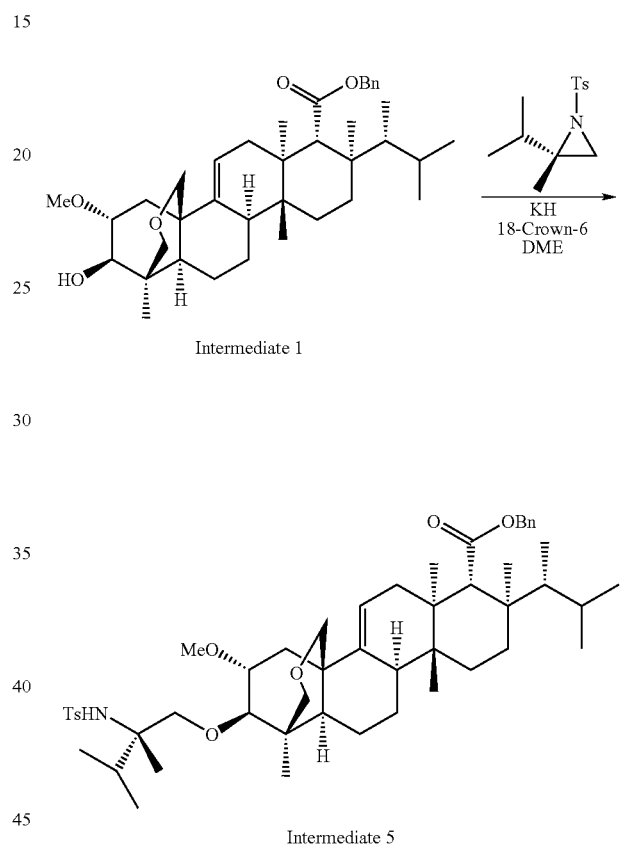

Intermediate 1

Intermediate 5

To a stirred solution of Intermediate 1 (60 g, 101 mmol) in anhydrous dimethoxyethane (800 mL) was added 18-crown-6 (67.4 g, 255 mmol) and (2S)-2-isopropyl-2-methyl-1-[(4-methylphenyl)sulfonyl]aziridine (42.8 g, 169.2 mmol). The mixture was stirred under nitrogen for 30 min until all solids were dissolved. Potassium hydride (30% in oil, 34.0 g, 255 mmol) was added portionwise (ca. 5 g portions) over a period of about 1 hour. The reaction temperature increased from 18° C. to 27° C. After the completion of the addition the resulting suspension was stirred at room temperature for about 3 h. The reaction was carefully quenched by the dropwise addition of methanol (80 mL). Following an initial period of bubbling, the rate of addition of methanol addition can be increased and a clear solution was obtained. The reaction mixture was then diluted with water (600 mL) and extracted with EtOAc (900 mL). The organic solution was diluted with CH₂Cl₂ (1 L) and dried over anhydrous MgSO₄. The drying agent was removed by filtration and the organic solvent was removed under reduced pressure to afford the crude compound (143.4 g). This material was purified on silica gel using ethyl acetate/heptanes to give the desired compound (75.4 g).

Intermediate 6

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-methoxy-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid

Intermediate 7

(1S,4aR,6aS,7R,8R,10aR,10bR,12aR,14R,15R)-15-
[[(2S)-2-amino-2,3-dimethylbutyl]oxy]-8-[(1R)-1,2-
dimethylpropyl]-14-methoxy-1,6,6a,7,8,9,10,10a,10
b,11,12,12a-dodecahydro-1,6a,8,10a-tetramethyl-
4H-1,4a-propano-2H-phenanthro[1,2-c]pyran-7-
carboxylic acid

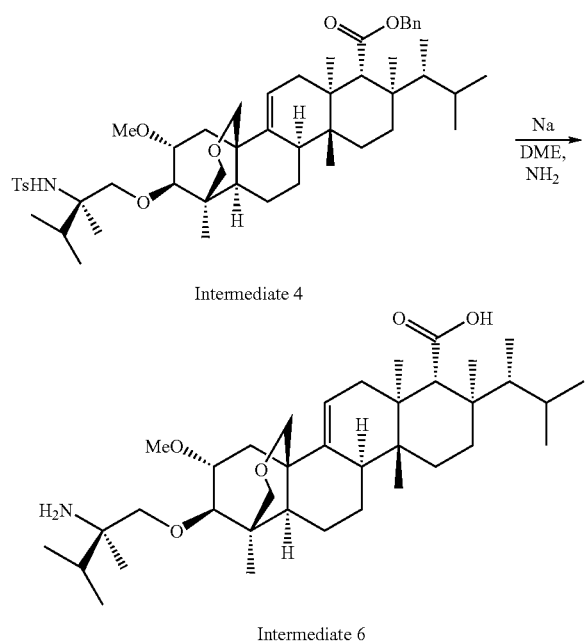

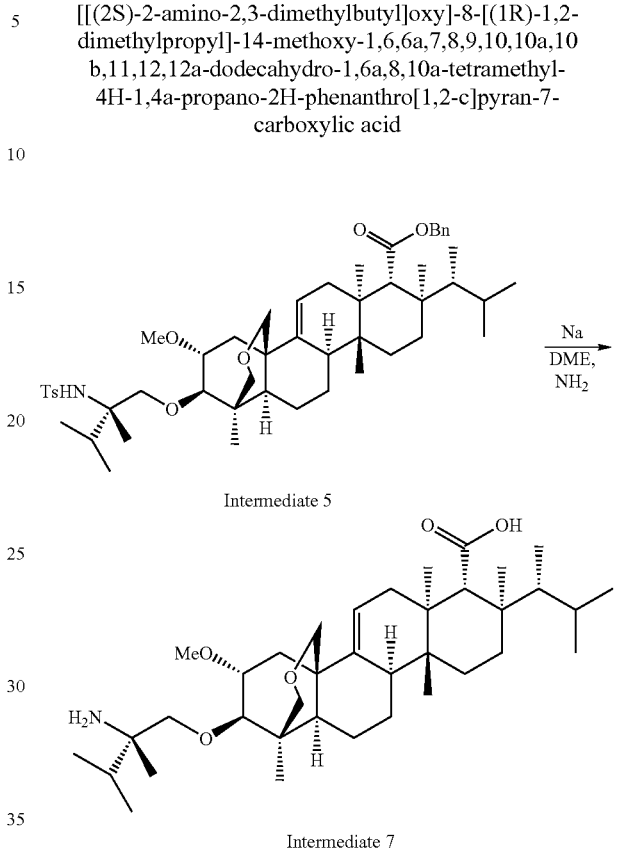

A 500 mL round bottom flask was cooled in a dry ice acetone bath and approximately 100 mL of ammonia was distilled into the flask. The flask was removed from the bath and allowed to warm to reflux. Sodium metal (5.7 g) was added to give a deep blue solution. DME (15 mL) was added followed by the dropwise addition of Intermediate 4 (5 grams) in DME (20 mL) over 6 minutes. The deep blue color persisted over the addition and the next 1.5 hours. At 1.5 hours, LC/MS analysis of an aliquot showed complete conversion to the product. Workup was as follows: The dropwise addition of methanol (130 mL) (with a stream of nitrogen blown over the surface) produced a heavy white suspension. The nitrogen stream was continued an additional 30 minutes. Ethyl acetate (800 mL) and water (400 mL) were added and the aqueous layer was re-extracted with more ethyl acetate (200 mL). The combined ethyl acetate was dried with magnesium sulfate, filtered and evaporated to give Intermediate 6 as a white solid (3.18 grams). No purification was necessary.

$^1$H NMR CD3OD δ (PPM) 5.52 (dd, 1H, H5); 4.23 (m, 1H, H14); 3.70 (m); 3.38 (s, 3H, OMe); 3.28-3.34 (m); 2.71 (s, 1H, H7), 2.54 (dd, 1H, H13), 2.29 (m); 1.98-2.08 (m); 1.54-1.84 (m); 1.44-1.50 (m); 1.34-1.41 (m); 1.27 (s, 3H, Me); 1.19 (s, 3H, Me); 1.15-1.24 (m); 1.10 (s, 3H, Me); 0.99 (d, 3H, Me); 0.96 (d, 3H, Me); 0.89 (d, 3H, Me); 0.83 (d, 3H, Me); 0.79 (s, 3H, Me); 0.77 (d, 3H, Me) and 0.76 (s, 3H, Me).

LC/MS m/z (positive ion scan) M+1=602.62.

A solution of Intermediate 5 (18.21 g, 21.60 mmol) in dimethoxyethane (300 mL) was added over about 20 minutes to liquid ammonia (approx. 400 mL) kept at −35 to −50° C. (bath temp). Sodium metal (4.0 g, in 0.2 g portions that were quickly washed with heptane prior to addition) was added to the ammonia solution over a period of 30 minutes ensuring that the reaction temperature was maintained at about −35° C. (bath temp). The deep blue reaction mixture was allowed to stir for 3 h. Analysis by TLC (50% EtOAc in Heptanes and 10% MeOH in DCM) indicated an incomplete reaction so additional sodium metal (1.0 g, divided into 0.5 g portions) was added over the course of about 10 minutes as described above. The reaction was stirred for an additional 2 h, whereupon the reaction was judged to be complete by TLC and LC-MS analysis. The reaction was quenched by the careful addition of isopropanol (10 mL, added dropwise over about 15 minutes), followed by 1:1 isopropanol-MeOH (80 mL over 30 minutes), and MeOH (40 mL over 30 minutes). The reaction mixture was stirred for 1 h and water (15 mL) was then added over 15 minutes. The ammonia was allowed to evaporate (several hours or overnight) and then water (300 mL) was added to the reaction. The mixture was extracted with EtOAc (3×350 mL). The organic solution was dried over anhydrous MgSO$_4$. Removal of the drying agent and evaporation of the solvent gave a white solid (7.96 g). The aqueous solution was treated with brine (400 mL) and re-extracted with dichloromethane (3×300 mL). The combined dichloromethane extracts were dried with MgSO$_4$, filtered and evaporated to afford additional white solid (4.53 g). The combined yield of Intermediate 7 was 12.49 g, which was used directly in the next step.

¹H NMR CD₃OD δ (PPM) 5.52 (dd, 1H, H5); 4.21 (m, 1H, H14); 3.83 (d, 1H)); 3.69 (d, 1H); 3.51 (d, 1H); 3.40 (s, 3H, OMe); 3.32 (d, 1H); 2.99 (d, 1H); 2.73 (s, 1H, H7); 2.53 (dd, 1H, H13), 2.30 (m); 1.98-2.078 (m); 1.94 (m); 1.66-1.84 (m); 1.54-1.61 (m); 1.44-1.49 (m); 1.40 (m); 1.33-1.37 (m); 1.26 (s, 3H, Me); 1.16-1.28 (m); 1.21 (s, 3H, Me); 1.10 (s, 3H, Me); 0.97 (d, 3H, Me); 0.96 (d, 3H, Me); 0.89 (d, 3H, Me); 0.84 (d, 3H, Me); 0.79 (s, 3H, Me); 0.76 (d, 3H, Me) and 0.75 (s, 3H, Me).

LC/MS m/z (positive ion scan) M+1=602.62.

Intermediate 8

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

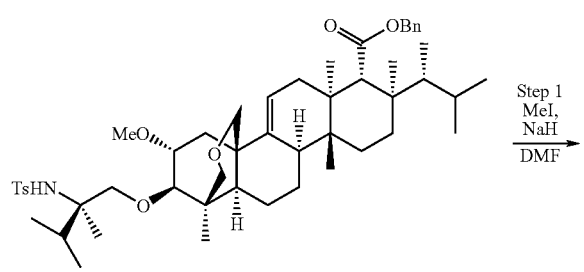

Intermediate 4

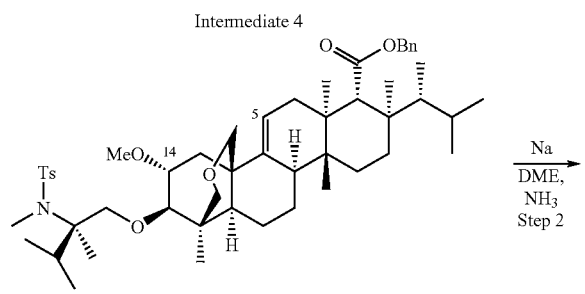

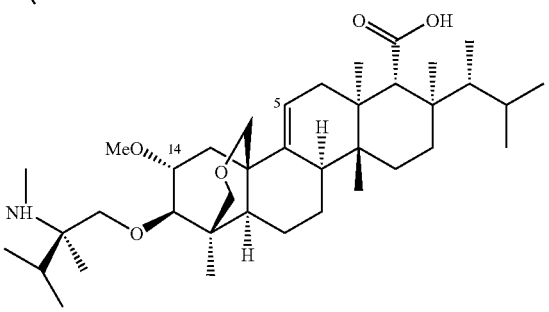

Intermediate 8

Step 1

Sodium hydride, a 60% dispersion in mineral oil (52 mg, 1.3 mmol), was added to a suspension of Intermediate 4 (1.1 g, 1.3 mmol) and methyl iodide (0.81 mL, 13 mmol) in anhydrous dimethylformamide (2.6 mL). The suspension was heated in a 50° C. oil bath for 1.5 hours, whereupon additional sodium hydride (47 mg, 1.2 mmol) was added. After an additional 1.5 hours, the mixture was cooled to room temperature, ethyl acetate (50 mL), water (50 mL) and 2N hydrochloric acid (7 mL) were added and the organic layer was washed with water (4×50 mL), brine (1×20 mL), dried with magnesium sulfate, filtered and evaporated to give a product as a foam (1.1 grams).

Selected ¹H NMR (CDCl₃, 600 MHz, ppm) 2.42 (s, 3H, PhMe), 3.06 (s, 3H, NMe); 3.28 (s, 3H, OMe); 4.14 (m, 1H, H14); 5.00 and 5.14 (2d, 2H, CH₂Ph); 5.22 (dd, 1H, H5), 7.25 (d, 2H, ArH), 7.75 (d, 2H, ArH).

Step 2

A solution of the product from Step 1 (1.1 g, 1.28 mmol) in anhydrous dimethoxyethane (6 mL) was added dropwise over 5 minutes to refluxing ammonia (ca. 20 mL) containing dimethoxyethane (4 mL) and sodium (1.68 g, 73.4 mmol). Additional ammonia (ca. 10 mL) was added and the deep blue colored mixture was stirred an additional 80 minutes. Dropwise addition of methanol (30 mL) produced a heavy white suspension over which a stream of nitrogen was passed for approximately 20 minutes. Ethyl acetate (200 mL) and water (100 mL) were added, the aqueous layer was re-extracted with more ethyl acetate (1×50 mL) and the combined ethyl acetate layers were dried with magnesium sulfate, filtered and evaporated to give Intermediate 8 as a foam (0.8 g).

Selected ¹H NMR (CDCl₃, 600 MHz, ppm) 2.64 (s, 3H, NMe); 3.32 (s, 3H, OMe); 4.22 (m, 1H, H14), 5.57 (dd, 1H, H5).

LC/MS m/z (positive ion scan) M+1=616.60.

Intermediate 9

(1S,4aR,6aS,7R,8R,10aR,10bR,12aR,14R,15R)-15-[[(2S)-2,3-dimethyl-2-(methylamino)butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

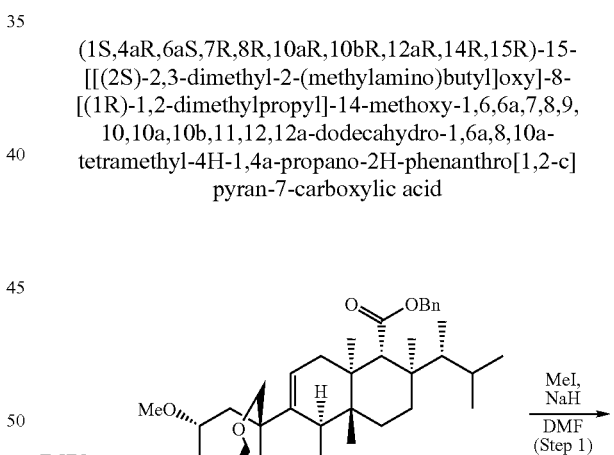

Intermediate 5

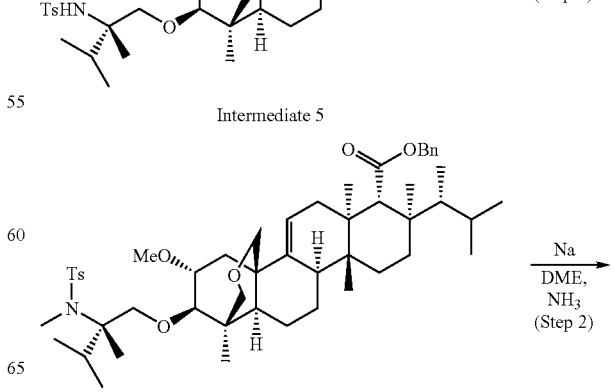

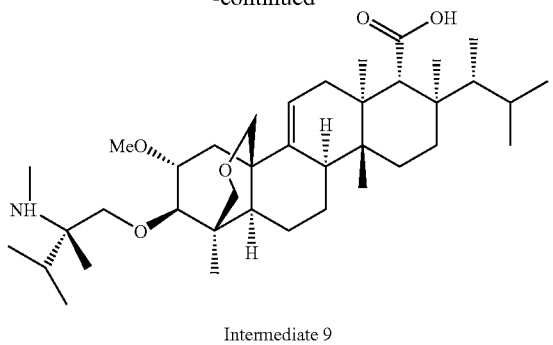

Intermediate 9

By a procedure analogous to that described for the synthesis of Intermediate 8, Intermediate 9 was synthesized starting with Intermediate 5.

¹H NMR CD₃OD δ (PPM) 5.54 (dd, 1H, H5); 4.24 (m, 1H, H14); 3.96 (d, 1H); 3.71 (d, 1H); 3.61 (m); 3.42 (s, 3H, OMe); 3.35 (m); 3.29 (m); 2.97 (d, 1H); 2.85 (s, 1H, H7), 2.66 (s, 3H, NMe); 2.57 (dd, 1H, H13), 2.19 (m); 2.14 (m); 2.06-2.11 (m); 1.94-1.98 (m); 1.70-1.96 (m); 1.58-1.65 (m); 1.46-1.52 (m); 1.38-1.42 (m); 1.22-1.30 (m); 1.22 (s, 3H, Me); 1.21 (s, 3H, Me); 1.17 (s, 3H, Me); 1.10 (d, 3H, Me); 0.99 (d, 3H, Me); 0.90 (d, 3H, Me); 0.85 (d, 3H, Me); 0.79 (s, 3H, Me); 0.77 (d, 3H, Me) and 0.76 (s, 3H, Me).

LC/MS m/z (positive ion scan) M+1=616.60.

Intermediate 10

(1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

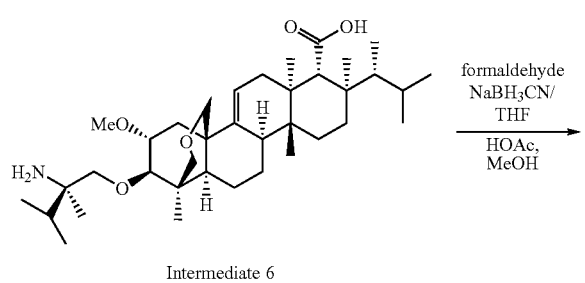

Intermediate 6

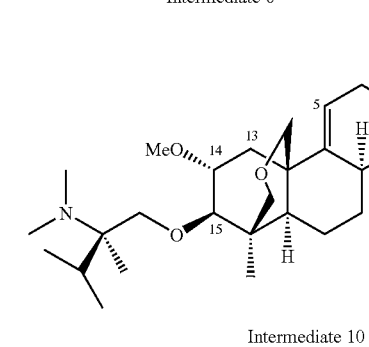

Intermediate 10

Acetic acid (0.25 ml, 4.37 mmol), formaldehyde 37% in water (0.66 ml, 8.86 mmol), and sodium cyanoborohydride 1.0 M in THF (8.8 ml, 8.80 mmol) were added to a stirred solution of Intermediate 6 (1.31 g, 2.18 mmol) in methanol (22.0 ml). The reaction mixture was a colorless solution. After about 16.5 hours, LCMS showed complete consumption of Intermediate 6. The reaction mixture was partitioned between ethyl acetate (200 ml) and water (200 ml). The aqueous layer was extracted with ethyl acetate (1×100 ml). The organic layers were combined, dried over magnesium sulfate, and filtered. The solvent was evaporated under reduced pressure. The residue was lyophilized from ethanol and benzene to give Intermediate 10 (1.29 g) as a white solid.

¹H NMR (CD₃OD, 500 MHz, ppm) δ 0.78 (s, 3H, Me), 0.79 (d, 3H, Me), 0.85 (s, 3H, Me), 0.88 (d, 3H, Me), 0.92 (d, 3H, Me), 1.10 (d, 3H, Me), 1.15 (d, 3H, Me), 1.18 (s, 3H, Me), 1.19 (s, 3H, Me), 1.23 (s, 3H, Me), 1.21-1.36 (m), 1.40-1.45 (m), 1.48-1.55 (m), 1.58-1.68 (m), 1.72-1.88 (m), 1.95-2.02 (m), 2.08-2.13 (m), 2.18-2.25 (m), 2.41-2.48 (m), 2.60 (dd, 1H, H13), 2.87 (s, 1H, H7), 2.98 (d, 1H), 2.99 (s, 6H, 2Me), 3.39 (d, 1H), 3.44 (s, 2H), 3.63 (d, 1H), 3.78 (d, 1H), 4.04 (d, 1H), 4.25-4.31 (m, 1H, H14), 5.57 (dd, 1H, H5).

Mass Spectrum: (ESI) m/z=630.62 (M+H).

Intermediate 11

(1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

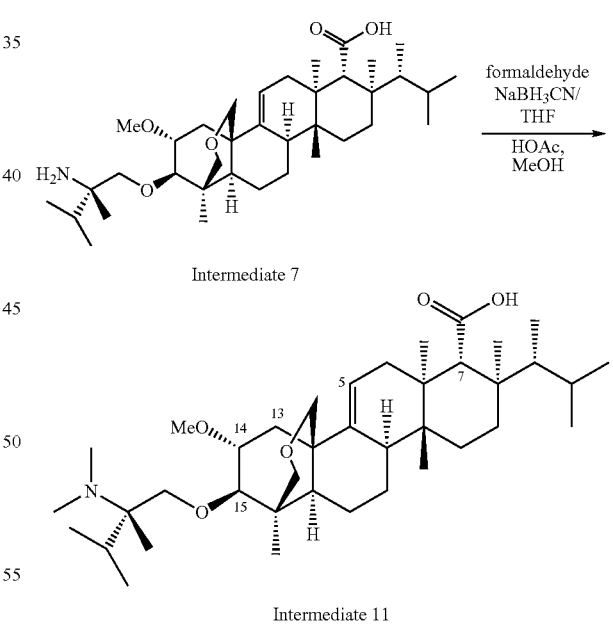

Intermediate 7

Intermediate 11

Intermediate 11 was prepared in a manner analogous to that described for Intermediate 10, but starting with Intermediate 7.

¹H NMR (CD₃OD, 600 MHz, ppm) δ 0.75 (s, 3H, Me), 0.76 (d, 3H, Me), 0.80 (s, 3H, Me), 0.84 (d, 3H, Me), 0.90 (d, 3H, Me), 1.05 (d, 3H, Me), 1.06 (d, 3H, Me), 1.18 (s, 3H, Me), 1.20 (s, 3H, Me), 1.22 (s, 3H, Me), 1.21-1.40 (m), 1.45-1.51 (m), 1.54-1.65 (m), 1.69-1.85 (m), 1.96-2.01 (m), 2.05-2.10 (m), 2.20-2.30 (m), 2.57 (dd, 1H, H13), 2.79 (s, 1H, H7), 2.84

(s, 6H, 2Me), 2.92 (d, 1H), 3.35 (d, 1H), 3.41 (s, 1H), 3.65 (d, 1H), 3.66 (d, 1H), 4.10 (d, 1H), 4.19-4.25 (m, 1H, H14), 5.53 (dd, 1H, H5).

Mass Spectrum: (ESI) m/z=630.62 (M+H).

Intermediates 12 & 13

Benzyl (1S,4aR,6aS,7R,8R,10aR,10bR,12aR,14R, 15R)-8-[(1R)-1,2-dimethylpropyl]-14-methoxy-15-[[(2R)-2,3,3-trimethyl-2-[[(4-methylphenyl)sulfonyl]amino]butyl]oxy]-1,6,6a,7,8,9,10,10a,10 b,11,12,12a-dodecahydro-1,6a,8,10a-tetramethyl-4H-1,4a-propano-2H-phenanthro[1,2-c]pyran-7-carboxylate (INTERMEDIATE 12) and Benzyl (1S,4aR,6aS,7R,8R,10aR,10bR,12aR,14R,15R)-8-[(1R)-1,2-dimethylpropyl]-14-methoxy-15-[[(2S)-2,3,3-trimethyl-2-[[(4-methylphenyl)sulfonyl]amino]butyl]oxy]-1,6,6a,7,8,9,10,10a,10 b,11,12,12a-dodecahydro-1,6a,8,10a-tetramethyl-4H-1,4a-propano-2H-phenanthro[1,2-c]pyran-7-carboxylate (INTERMEDIATE 13)

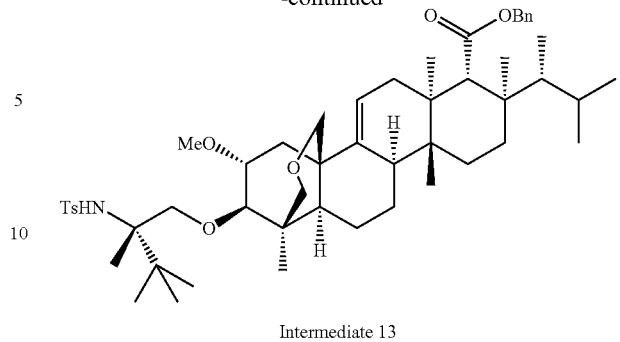

Intermediate 13

Intermediate 1 (5.00 g, 8.43 mmol), 18-crown-6 (11.15 g, 42.2 mmol), and 2-(1,1-dimethylethyl)-2-methyl-1-[(4-methylphenyl)sulfonyl]aziridine (4.51 g, 8.67 mmol) were dissolved in toluene and concentrated then placed under high vacuum for 1 hour. The resulting mixture was dissolved in dimethoxyethane (84 mL) placed under nitrogen atmosphere and cooled to 0° C. Potassium hydride (30% dispersion in mineral oil, 3.38 g, 25 mmol) was added and the reaction evacuated and charged with nitrogen (repeat evac./charge three times). The reaction was allowed to slowly warm to room temperature and after two hours additional 2-(1,1-dimethylethyl)-2-methyl-1-[(4-methylphenyl)sulfonyl]aziridine (0.43 g, 0.83 mmol) was added. After an additional hour the reaction was quenched by the addition of methanol followed by 1 N aq. HCl. The reaction mixture was partitioned between ethyl acetate and water and the aqueous extracted with ethyl acetate as necessary. The combined organic phase was dried over MgSO$_4$, filtered then concentrated. The crude product was purified by multiple flash chromatographies on Biotage 65i columns (0-100% ethyl acetate/hexane) which resolved the two diastereomeric products; the faster eluting Intermediate 12 (1.3 g) and the slower eluting Intermediate 13 (3.0 g).

Intermediate 12

$^1$H NMR (CDCl$_3$, 500 MHz, ppm) δ 0.63 (s, 3H), 0.71 (s, 3H) 0.72 (d, 3H, partially obscured), 0.78 (d, J=5.8 Hz, 3H), 0.81 (d, J=5.7 Hz, 3H), 0.96 (s, 3H), 1.02 (s, 9H), 1.14-1.3 (m), 1.2 (s, 3H), 1.25 (s, 3H), 1.32-1.8 (m), 1.92 (m, 1H), 2.04 (m, 1H), 2.12 (m, 1H), 2.41 (s, 3H), 2.52 (m, 1H), 2.72 (d, J=9.0 Hz, 1H), 2.88 (s, 1H), 2.98 (d, J=10.9 Hz, 1H), 3.25 (d, J=11.2 Hz, 1H), 3.35-3.4 (m, 2H), 3.49 (s, 3H), 3.63 (d, J=11.9 Hz, 1H), 3.85 (d, J=10.8 Hz, 1H), 4.25 (m, 1H), 4.98 (d, J=12.4 Hz, 1H), 5.12 (d, J=12.4 Hz, 1H), 5.44 (m, 1H), 6.89 (s, 1H), 7.25 (d, 2H, partially obscured), 7.32-7.4 (m, 5H), 7.84 (d, J=8.3 Hz, 2H).

Intermediate 13

$^1$H NMR (CDCl$_3$, 500 MHz, ppm) δ 0.71 (s, 3H), 0.72 (d, 3H, partially obscured), 0.77 (d, J=6.7 Hz, 3H), 0.81 (d, J=6.6 Hz, 3H), 0.83 (s, 3H), 0.97 (s, 9H), 1.02 (s, 3H), 1.12-1.28 (m), 1.14 (s, 3H), 1.24 (s, 3H), 1.34-1.6 (m), 1.68-1.8 (m), 1.92 (m, 1H), 2.02 (m, 1H), 2.11 (m, 1H), 2.40 (s, 3H), 2.45 (m, 1H, partially obscured), 2.77 (d, J=8.2 Hz, 1H), 2.87 (s, 1H), 2.96 (d, J=9.6 Hz, 1H), 3.29 (d, J=11.7 Hz, 1H), 3.34-3.41 (3d, 3H), 3.35 (s, 3H), 3.6 (d, J=11.6 Hz, 1H), 4.25 (m, 1H), 4.98 (d, J=12.3 Hz, 1H), 5.08 (s, 1H), 5.10 (d, J=12.4 Hz,

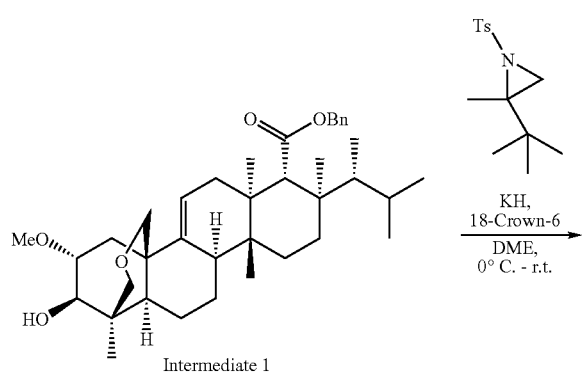

Intermediate 1

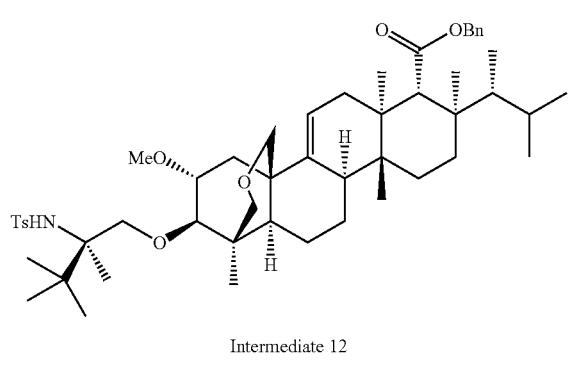

Intermediate 12

+

1H), 5.41 (m, 1H), 7.25 (d, 2H, partially obscured), 7.3-7.4 (m, 5H), 7.78 (d, J=5.8 Hz, 2H).

Intermediate 12

Alternative Synthesis

Benzyl (1S,4aR,6aS,7R,8R,10aR,10bR,12aR,14R,15R)-8-[(1R)-1,2-dimethylpropyl]-14-methoxy-15-[[(2R)-2,3,3-trimethyl-2-[[(4-methylphenyl)sulfonyl]amino]butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

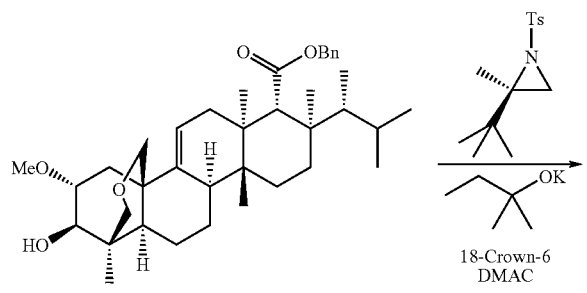

Intermediate 1

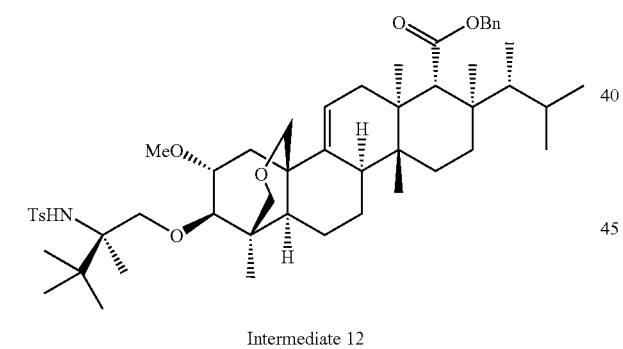

Intermediate 12

A solution of Intermediate 1 (21.26 g, 35.9 mmol), 18-crown-6 (11.37 g, 43.0 mmol), and (2R)-2-(1,1-dimethylethyl)-2-methyl-1-[(4-methylphenyl)sulfonyl]aziridine (9.59 g, 35.9 mmol), in toluene (25 mL) was evaporated under vacuum to azeotropically dry the reagents. The resulting oil was dissolved in N,N-dimethylacetamide (200 mL) and the solution was cooled under nitrogen in an ice bath. To the ice cold stirred solution was added over a 2 minute period a solution of potassium 2-methyl-2-butoxide in toluene (1.7 M, 25.3 mL, 43.0 mmol). The reaction was slowly allowed to warm to room temperature and monitored by TLC. After the reaction was judged complete, the reaction was quenched with 2N hydrochloric acid (22 mL), diluted with dichloromethane (500 mL), and the mixture was washed with water (3×300 mL). The organic phase was dried over magnesium sulfate, filtered, and evaporated to an oil which was flash chromatographed (silica gel, 5-60% ethyl acetate:hexane) to give Intermediate 12 as a white solid (24.04 g).

Intermediate 14

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

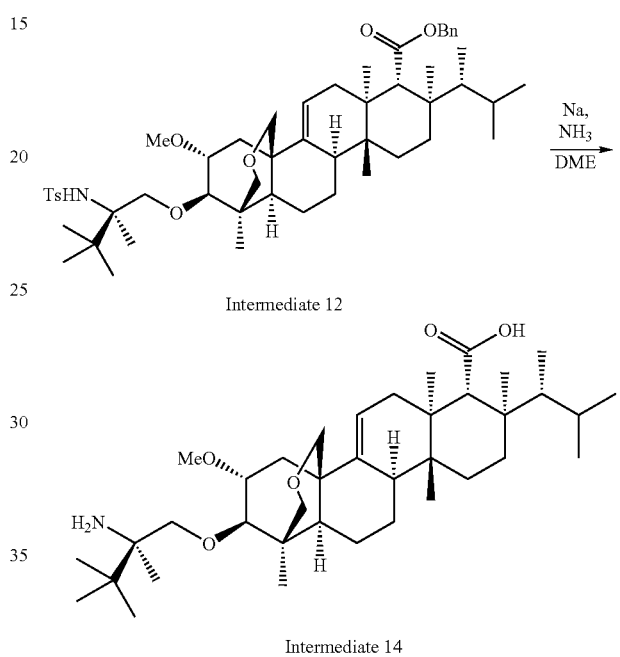

Ammonia (approx. 150 mL) was condensed into a 3-neck flask equipped with a cold-finger condenser and sodium (approx. 5 g, 220 mmol) was added to give a deep blue solution. To this solution was added a solution of Intermediate 12 (13.3 g, 15.5 mmol) in dimethoxymethane (130 mL) and the reaction was refluxed at −33° C. for 1.5 hours. The reaction was quenched by the careful addition of methanol followed by water until the reaction was a white slurry. The solvents were evaporated by a stream of nitrogen overnight. After approximately 18 hours methanol (approx. 50 mL) was added and the resulting white slurry/partial solution was stirred for about 10 minutes to ensure that all solids were in suspension (as opposed to fixed to the flask wall). This mixture was partitioned between ethyl acetate and water and the aqueous extracted twice with ethyl acetate. The combined organic phase was dried over MgSO$_4$, filtered then concentrated to give Intermediate 14 (9.8 g) as an off-white solid.

$^1$H NMR (CD$_3$OD, 500 MHz, ppm) δ 0.77 (s, 3H), 0.78 (d, J=7.4 Hz, 3H), 0.81 (s, 3H), 0.85 (d, J=6.9 Hz, 3H), 0.89 (d, J=6.8 Hz, 3H), 1.05 (s, 9H), 1.19 (s, 3H), 1.20 (s, 3H), 1.32 (s, 3H), 1.18-1.36 (m), 1.4 (m, 1H), 1.48 (m, 1H), 1.56-1.86 (m). 2.05 (m, 1H), 2.23 (m, 1H), 2.55 (dd, J=13.3 Hz, 6.7 Hz, 1H), 2.71 (s, 1H), 3.25 (m, 1H), 3.30 (m, 1H, partially obscured), 3.4 (AB, 2H, partially obscured), 3.4 (s, 3H), 3.67 (d, J=11.9 Hz, 1H), 3.74 (d, J=11.3 Hz, 1H), 3.92 (d, J=11.2 Hz, 1H), 4.24 (m, 1H), 5.54 (m, 1H)

m/z=616.34 (M+H).

Intermediate 15

(1S,4aR,6aS,7R,8R,10aR,10bR,12aR,14R,15R)-15-[[(2S)-2-amino-2,3,3-trimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

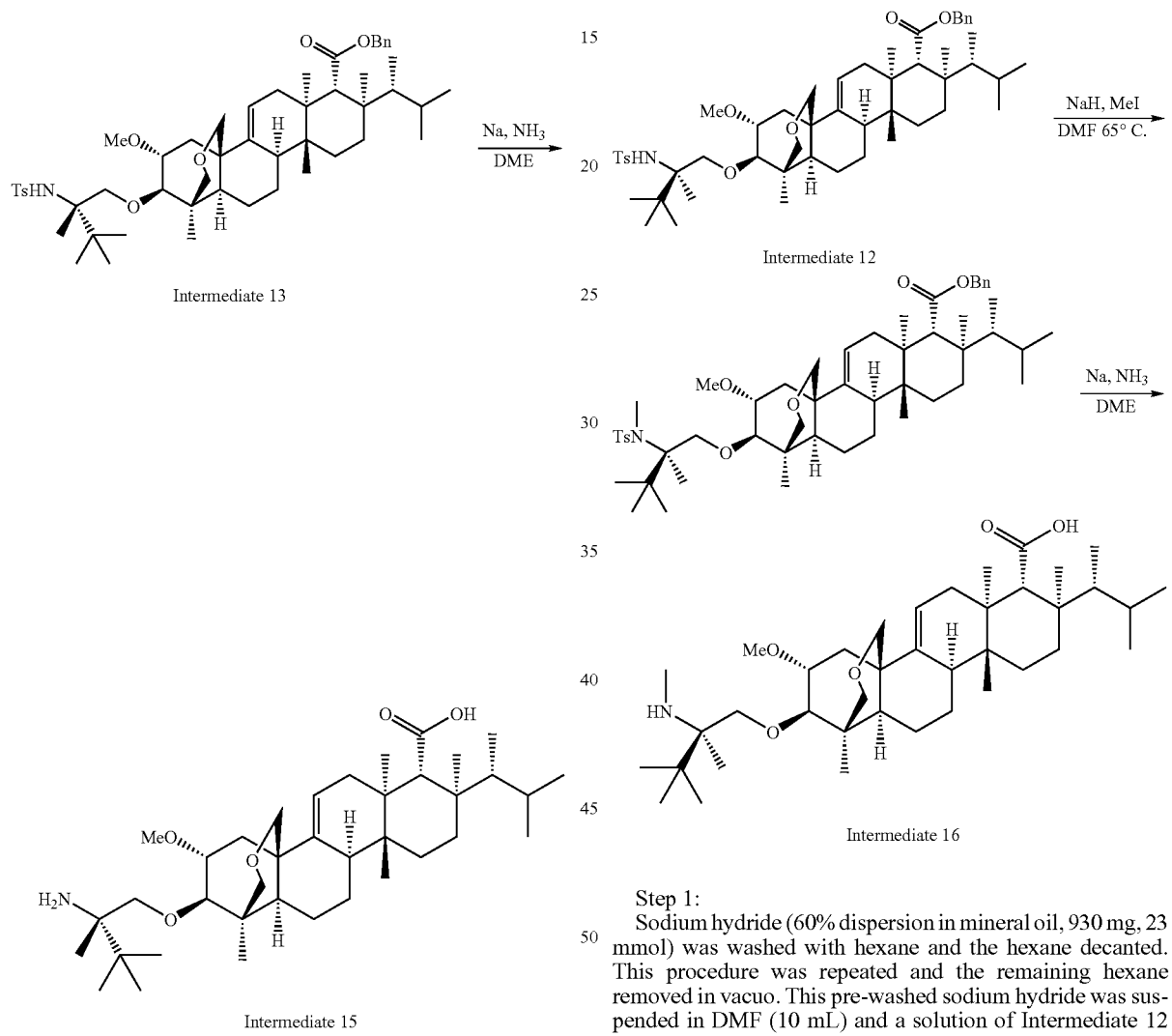

Intermediate 15 was prepared in a manner analogous to that described for Intermediate 14, but starting with Intermediate 13.

$^1$H NMR (CD$_3$OD, 500 MHz, ppm) δ 0.75 (d, 3H, partially obscured), 0.76 (s, 3H), 0.81 (s, 3H), 0.84 (d, J=6.4 Hz, 3H), 0.89 (d, J=6.4 Hz, 3H), 1.00 (s, 3H), 1.03 (s, 9H), 1.14-1.3 (m), 1.28 (s, 3H), 1.34-1.5 (m), 1.55-1.84 (m), 2.02 (m, 1H), 2.29 (m, 1H), 2.55 (dd, J=13.3 Hz, 6.9 Hz, 1H), 2.75 (s, 1H), 3.17 (d, J=8.7 Hz, 1H), 3.3 (m, obscured), 3.4 (m, obscured), 3.42 (s, 3H), 3.68 (d, J=11.9 Hz, 1H), 3.74 (d, J=11.2 Hz, 1H), 3.89 (d, J=11.2 Hz, 1H), 4.28 (m, 1H), 5.54 (m, 1H).

Intermediate 16

(1S,4aR,6aS,7R,8R,10aR,10bR,12aR,14R,15R)-8-[(1R)-1,2-dimethylpropyl]-14-methoxy-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid Step 1:
Sodium hydride (60% dispersion in mineral oil, 930 mg, 23 mmol) was washed with hexane and the hexane decanted. This procedure was repeated and the remaining hexane removed in vacuo. This pre-washed sodium hydride was suspended in DMF (10 mL) and a solution of Intermediate 12 (2.0 g, 2.3 mmol) in DMF (13 mL) was added. Methyl iodide (1.45 mL, 23 mmol) was added and the reaction mixture heat at 65° C. under nitrogen for 90 minutes. After cooling to room temperature the reaction was partitioned between ethyl acetate and saturated aqueous bicarbonate. The organic phase was washed with brine, dried under MgSO$_4$ filtered and concentrated in vacuo. Column chromatography (Biotage 40+M column, 5-100% EA/Hex) yielded the product (1.95 g).

Step 2:
The product from Step 1 was subjected to sodium/ammonia reduction by a procedure analogous to that described for the preparation of Intermediate 14. The product thus obtained was lyophilized from MeOH/benzene to give Intermediate 16 (1.4 g) as an off-white solid.

¹H NMR (CD₃OD, 500 MHz, ppm) δ 0.76 (s, 3H), 0.77 (d, 3H, partially obscured), 0.82 (s, 3H), 0.84 (d, J=6.8 Hz, 3H), 0.91 (d, J=6.7 Hz, 3H), 1.06 (s, 3H), 1.07 (s, 9H), 1.16-1.3 (m), 1.15 (s, 3H), 1.22 (s, 3H), 1.3-1.5 (m), 1.6 (m), 1.64-1.84 (m), 1.96-2.1 (m, 2H), 2.31 (m, 1H), 2.57 (m, 1H, partially obscured), 2.57 (s, 3H), 2.74 (s, 1H), 2.93 (d, J=8.5 Hz, 1H), 3.35 (m, 1H, partially obscured), 3.36 (s, 3H), 3.41 (br s, 2H), 3.62 (d, J=11.6 Hz, 1H), 3.8 (AB, 2H), 4.23 (m, 1H), 5.53 (m, 1H).

m/z=630.59 (M+H).

Intermediate 17

(1S,4aR,6aS,7R,8R,10aR,10bR,12aR,14R,15R)-8-[(1R)-1,2-dimethylpropyl]-15-[[(2R)-2-(ethylamino)-2,3,3-trimethylbutyl]oxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

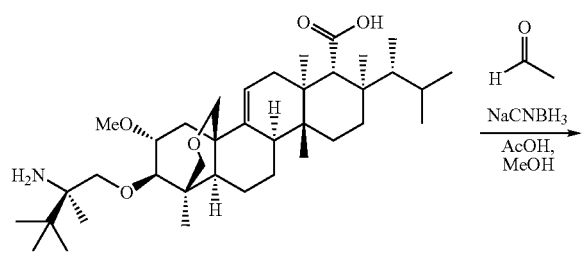

Intermediate 14

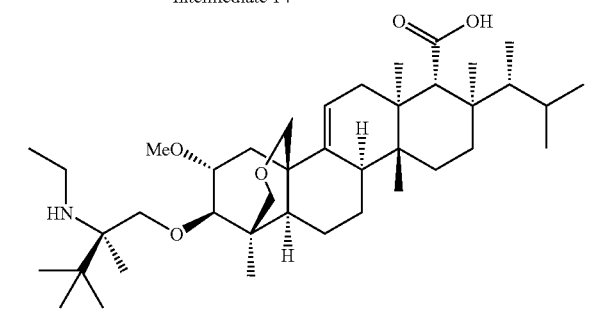

Intermediate 17

A solution of Intermediate 14 (140 mg, 0.23 mmol) in MeOH was treated with acetic acid (0.013 mL, 0.23 mmol) and acetaldehyde (0.32 mL, 5.7 mmol) at 0° C. After 20 minutes sodium cyanoborohydride (1 M in THF, 0.57 mL, 0.57 mmol) was added and the reaction allowed to slowly warm to room temperature. After 24 hours the reaction was partitioned between ethyl acetate and water and the aqueous phase extracted with ethyl acetate multiple times. The combined organic phase was dried under MgSO₄, filtered and concentrated to give Intermediate 17 (165 mg).

¹H NMR (CD₃OD, 500 MHz, ppm) δ 0.76 (s, 3H), 0.78 (d, J=6.6 Hz, 3H), 0.82 (s, 3H), 0.86 (d, J=6.6 Hz, 3H), 0.91 (d, J=6.8 Hz, 3H), 1.15 (s, 9H), 1.18 (s, 3H), 1.19 (s, 3H), 1.22 (s, 3H), 1.22-1.64 (m), 1.40 (t, J=7.3 Hz, 3H), 1.7-1.86 (m), 1.97 (m, 1H), 2.09 (m, 1H), 2.20 (m, 1H), 2.61 (dd, J=13.2 Hz, 6.6 Hz, 1H), 2.86 (s, 1H), 3.01 (d, J=8.7 Hz, 1H), 3.12 (m, 1H), 3.36 (m, partially obscured), 3.37 (s, 3H), 3.43 (br s, 2H), 3.61 (d, J=11.2 Hz, 1H), 3.81 (d, J=11.6 Hz, 1H), 3.99 (d, J=12.3 Hz, 1H), 4.29 (m, 1H), 5.56 (m, 1H).

m/z=644.27 (M+H).

Intermediate 18

Benzyl (1S,4aR,6aS,7R,8R,10aR,10bR,12aR,14R,15R)-8-[(1R)-1,2-dimethylpropyl]-15-[2-ethyl-2-[[(4-methylphenyl)sulfonyl]amino]butoxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

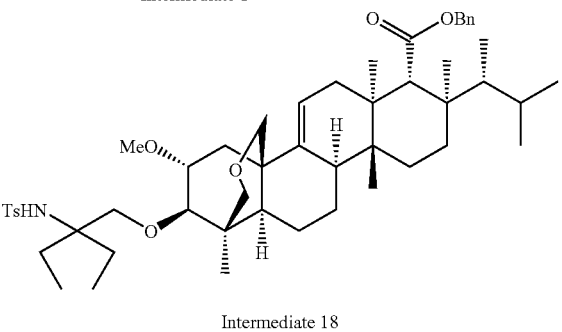

Intermediate 18

Intermediate 1 (5.00 g, 8.43 mmol), 18-crown-6 (11.15 g, 42.2 mmol), and 2,2-diethyl-1-[(4-methylphenyl)sulfonyl]-aziridine (4.27 g, 16.87 mmol) were dissolved in toluene and concentrated then placed under high vacuum for 1 hour. The resulting mixture was dissolved in dimethoxyethane (84 mL) placed under nitrogen atmosphere and cooled to 0° C. Potassium hydride (30% dispersion in mineral oil, 3.38 g, 25 mmol) was added and the reaction evacuated and charged with nitrogen (repeat three times). The reaction was allowed to slowly warm to room temperature over one hour. The reaction was quenched by the addition of water followed by 1 N aq. HCl. The reaction mixture was partitioned between ethyl acetate and water and the aqueous extracted with ethyl acetate. The combined organic phase was dried over MgSO₄, filtered then concentrated. The crude product was purified by flash chromatography on a Biotage 65i column (0-100% ethyl acetate/hexane) to give Intermediate 18 (6.9 g) as a colorless foam.

¹H NMR (CDCl₃, 500 MHz, ppm) δ 0.70-0.78 (m, 18H), 0.80 (d, J=6.6 Hz, 3H), 1.14-1.28 (m), 1.15 (s, 3H), 1.23 (s, 3H), 1.32-1.78 (m), 1.87-2.04 (m, 2H), 2.11 (m, 1H), 2.40 (s, 3H), 2.46 (dd, J=13.5 Hz, 6.8 Hz, 1H), 2.83 (d, J=8.5 Hz, 1H), 2.87 (s, 1H), 3.27 (d, J=11.4 Hz, 1H) 3.35-3.4 (m, 2H), 3.42 (s, 3H), 3.50 (d, J=9.9 Hz, 1H), 3.61 (d, J=9.6 Hz, 1H), 3.64 (d, J=11.7 Hz, 1H), 4.24 (m, 1H), 4.97 (d, J=12.4 Hz, 1H), 5.11 (d, J=12.4 Hz, 1H), 5.42 (m, 1H), 5.78 (s, 1H), 7.25 (d, 2H, partially obscured), 7.3-7.4 (m, 5H), 7.76 (d, J=8.5 Hz, 2H).

Intermediate 19

(1S,4aR,6aS,7R,8R,10aR,10bR,12aR,14R,15R)-15-(2-amino-2-ethylbutoxy)-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

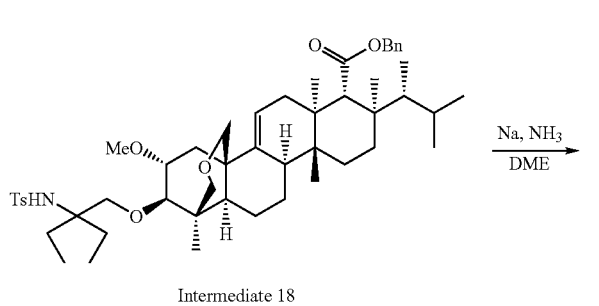

Intermediate 18

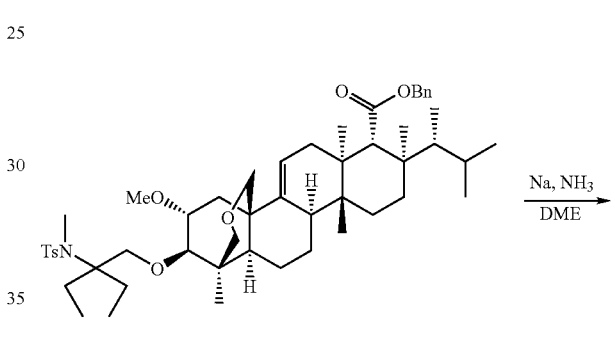

Intermediate 19

Ammonia (approx. 30 mL) was condensed into a 3-neck flask equipped with a cold-finger condenser and sodium (approx. 500 mg, 22 mmol) was added to give a deep blue solution. To this solution was added a solution of Intermediate 18 (2.0 g, 2.4 mmol) in dimethoxymethane (20 mL) and the reaction was refluxed at −33° C. for 1.5 hours. The reaction was quenched by the careful addition of methanol followed by water until the reaction was a white slurry. The solvents were evaporated by a stream of nitrogen overnight. At this point methanol (approx. 10 mL) was added and the resulting white slurry/partial solution was stirred for about 10 minutes to ensure that all solids were in suspension (as opposed to fixed to the flask wall). This mixture was partitioned between ethyl acetate and water and the aqueous extracted twice with ethyl acetate. The combined organic phase was dried over MgSO$_4$, filtered then concentrated then lyophilized from benzene to give Intermediate 19 as a colorless solid.

$^1$H NMR (CD$_3$OD, 500 MHz, ppm) δ 0.76 (s, 3H), 0.77 (d, J=3H, partially obscured), 0.80 (s, 3H), 0.84 (d, J=6.6 Hz, 1H), 0.90 (d, J=6.9 Hz, 3H), 0.91 (t, J=7.5 Hz, 3H), 0.93 (t, J=7.5 Hz, 3H), 1.17-1.84 (m), 1.21 (s, 3H), 1.27 (s, 3H), 1.98-2.08 (m), 2.31 (m, 1H), 2.54 (dd, J=13.3 Hz, 6.9 Hz, 1H), 2.72 (s, 1H), 3.03 (d, J=8.6 Hz, 1H), 3.34 (d, 1H, partially obscured), 3.39 (s, 3H), 3.40 (br s, 2H), 3.56 (d, J=10.3 Hz, 1H), 3.67 (d, J=11.7 Hz, 1H), 3.73 (d, H=10.2 Hz, 1H), 4.22 (m, 1H), 5.52 (m, 1H).

m/z=602.64 (M+H).

Intermediate 20

(1S,4aR,6aS,7R,8R,10aR,10bR,12aR,14R,15R)-8-[(1R)-1,2-dimethylpropyl]-15-[2-ethyl-2-(methylamino)butoxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

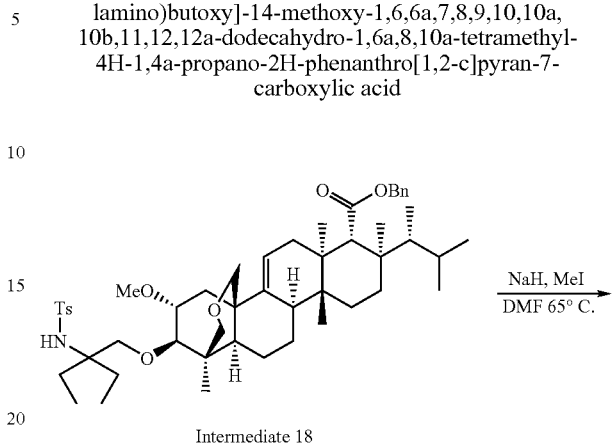

Intermediate 18

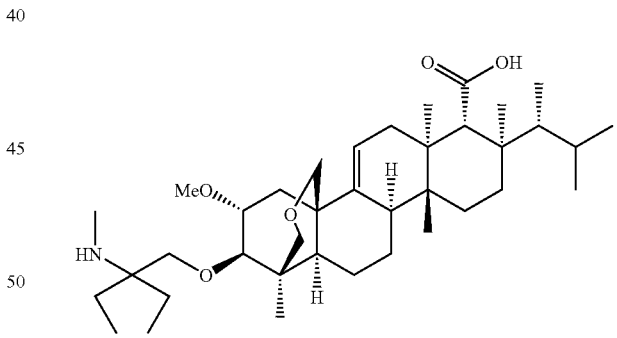

Intermediate 20

Starting with Intermediate 18, Intermediate 20 was prepared as an off-white solid in a manner analogous to that described for the preparation of Intermediate 16.

$^1$H NMR (CD$_3$OD, 500 MHz, ppm) δ 0.76 (s, 3H), 0.77 (d, 3H, partially obscured), 0.80 (s, 3H), 0.84 (d, J=6.7 Hz, 3H), 0.90 (d, J=7.0 Hz, 3H), 0.93 (t, J=7.6 Hz, 3H), 0.93 (t, J=7.6 Hz, 3H), 1.18-1.85 (m), 1.22 (s, 3H), 1.26 (s, 3H), 1.99-2.1 (m, 2H), 2.31 (m, 1H), 2.52 (s, 3H), 2.56 (dd, J=13.4 Hz, 6.9 Hz, 1H), 2.73 (s, 1H), 2.98 (d, J=8.5 Hz, 1H), 3.33 (d, J=11.9 Hz, 1H), 3.37 (s, 3H), 3.41 (br s, 2H), 3.54 (d, J=10.7 Hz, 1H), 3.68 (d, J=11.7 Hz, 1H), 3.82 (d, J=10.7 Hz, 1H), 4.22 (m, 1H), 5.53 (m, 1H).

m/z=616.55 (M+H).

Intermediate 21

Benzyl (1S,4aR,6aS,7R,8R,10aR,10bR,12aR,14R,15R)-15-[[(2S)-3,3-dimethyl-2-[[(4-methylphenyl)sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

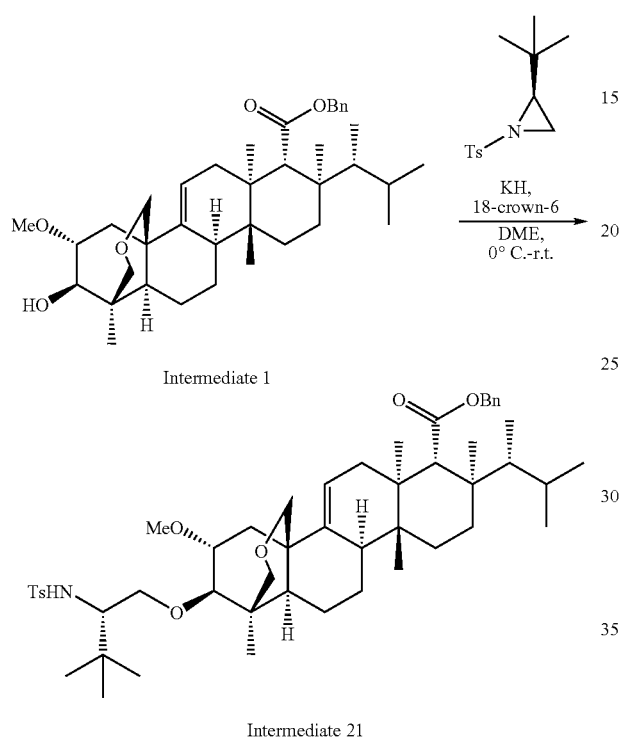

Intermediate 1

Intermediate 21

Intermediate 1 (7.5 g, 13 mmol), 18-crown-6 (16.7 g, 63.3 mmol), and (2S)-2-(1,1-dimethylethyl)-1-[(4-methylphenyl)sulfonyl]-aziridine (5.27 g, 20.8 mmol) were dissolved in toluene and concentrated then placed under high vacuum for 1 hour. The resulting mixture was dissolved in dimethoxyethane (63 mL) placed under nitrogen atmosphere and cooled to 0° C. Potassium hydride (30% dispersion in mineral oil, 3.7 g, 28 mmol) was added and then the reaction evacuated and charged with nitrogen (repeat three times). After 1 hour the reaction was quenched by the addition of methanol followed by 1 N aq. HCl. The reaction mixture was partitioned between ethyl acetate and water and the aqueous extracted with ethyl acetate. The combined organic phase was dried over MgSO$_4$, filtered then concentrated. Chromatography on Biotage 65i column (10-100% ethyl acetate/hexane) gave Intermediate 21 (7.4 g) as a colorless solid.

$^1$H NMR (CDCl$_3$, 500 MHz, ppm) δ 0.61 (s, 3H), 0.70 (s, 3H), 0.71 (d, J=7.3 Hz, 3H), 0.77 (d, J=6.8 Hz, 3H), 0.80 (d, J=8.0 Hz, 3H), 0.92 (s, 9H), 1.12 (s, 3H), 1.12-1.28 (m), 1.21 (s, 3H), 1.3-1.48 (m), 1.5-1.6 (m, 1H, partially obscured), 1.64-1.77 (m, 3H), 1.9 (m, 1H), 1.98 (m, 1H), 2.10 (m, 1H), 2.4 (m, 1H, partially obscured), 2.41 (s, 3H), 2.55 (d, J=8.5 Hz, 1H), 2.86 (s, 1H), 3.02 (m, 1H), 3.18 (dd, J=9.7 Hz, 4.0 Hz, 1H), 3.22 (d, J=12.5 Hz, 1H), 3.31 (s, 3H), 3.34 (AB, 2H, partially obscured), 3.50 (d, J=11.7 Hz, 1H), 4.01 (dd, J=9.9 Hz, 2.6 Hz, 1H), 4.08 (m, 1H), 4.96 (d, J=9.4 Hz, 1H), 4.97 (d, J=12.3 Hz, 1H), 5.09 (d, J=12.3 Hz, 1H), 5.38 (m, 1H), 7.25 (d, 2H, partially obscured), 7.3-7.38 (m, 5H), 7.73 (d, J=8.2 Hz, 2H).

Intermediate 22

(1S,4aR,6aS,7R,8R,10aR,10bR,12aR,14R,15R)-15-[[(2S)-2-amino-3,3-dimethylbutyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

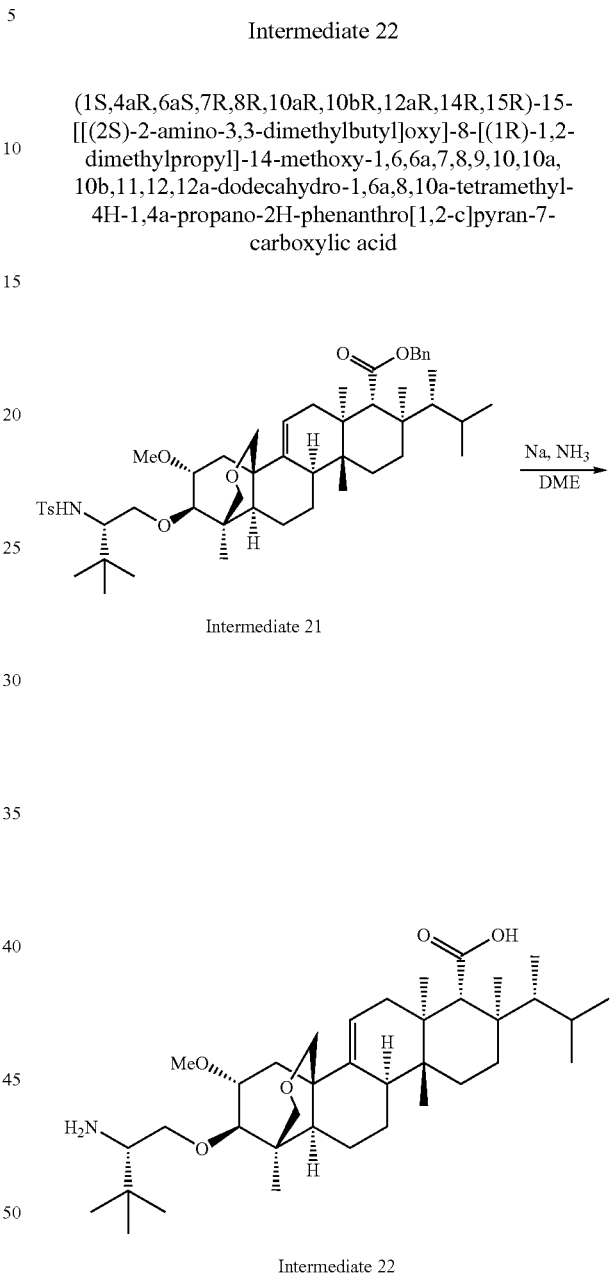

Intermediate 21

Intermediate 22

In a manner analogous to that described for Intermediate 14, Intermediate 22 was prepared starting with Intermediate 21.

$^1$H NMR (CD$_3$OD, 500 MHz, ppm) δ 0.75 (d, 3H, partially obscured), 0.76 (s, 3H), 0.81 (s, 3H), 0.84 (d, J=6.9 Hz, 3H), 0.88 (d, J=6.8 Hz, 3H), 1.02 (s, 9H), 1.18-1.24 (m) 1.19 (s, 3H), 1.30 (s, 3H), 1.36-1.85 (m), 2.0-2.06 (m), 2.29 (m, 1H), 2.54 (dd, J=13.1 Hz, 6.7 Hz, 1H), 2.78 (s, 1H), 2.94 (m, 1H), 3.25 (d, J=8.9 Hz, 1H), 3.34 (d, 1H, partially obscured), 3.4 (br s, 2H), 3.42 (s, 3H), 3.64 (d, J=11.7 Hz, 1H), 3.74 (m, 1H), 4.05 (m, 1H), 4.26 (m, 1H), 5.54 (m, 1H).

m/z=602.41 (M+H).

Intermediate 23

Benzyl (1S,4aR,6aS,7R,8R,10aR,10bR,12aR,14R, 15R)-15-[[(2R)-3,3-dimethyl-2-[[(4-methylphenyl) sulfonyl]amino]butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate

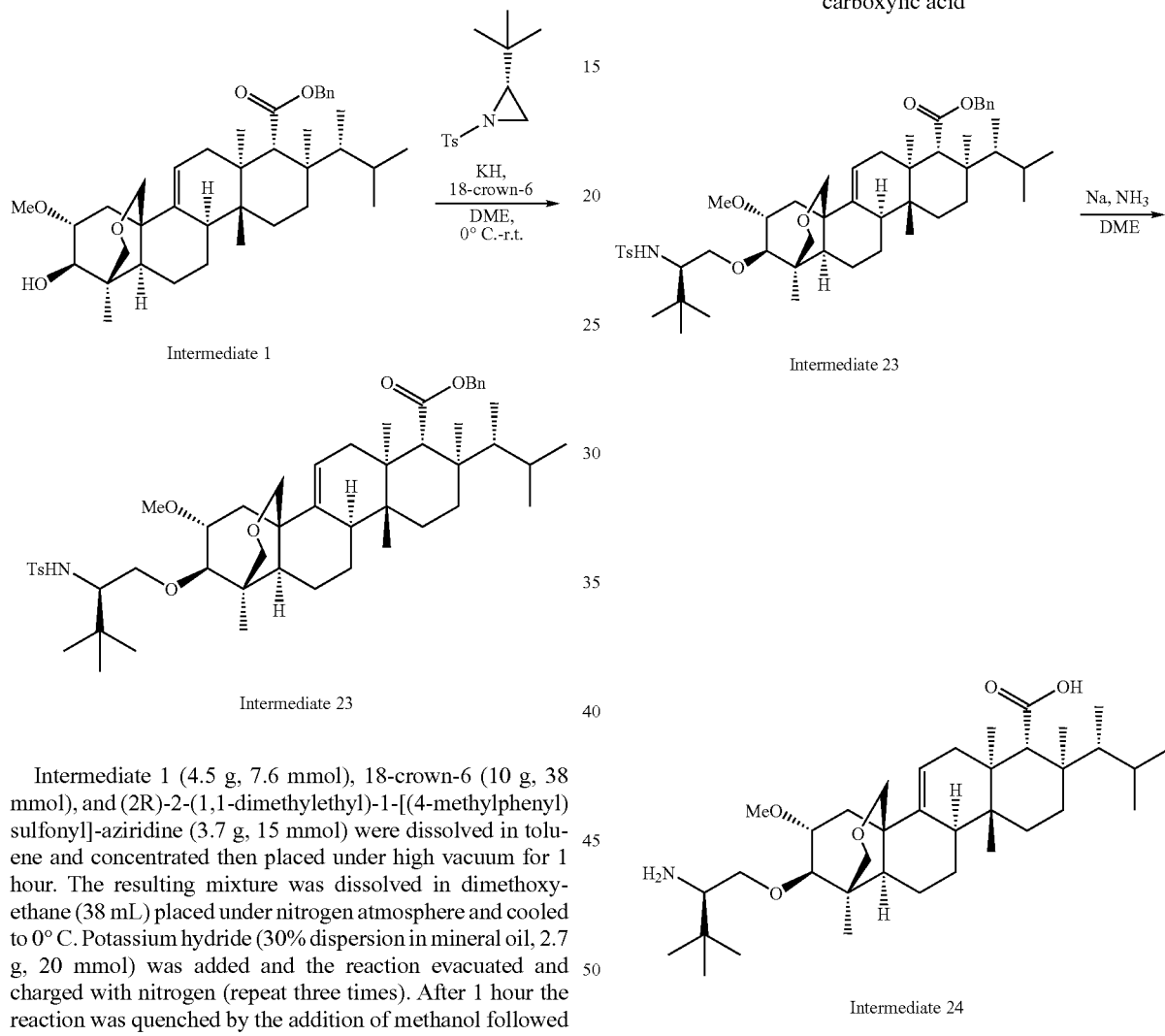

Intermediate 1 (4.5 g, 7.6 mmol), 18-crown-6 (10 g, 38 mmol), and (2R)-2-(1,1-dimethylethyl)-1-[(4-methylphenyl)sulfonyl]-aziridine (3.7 g, 15 mmol) were dissolved in toluene and concentrated then placed under high vacuum for 1 hour. The resulting mixture was dissolved in dimethoxyethane (38 mL) placed under nitrogen atmosphere and cooled to 0° C. Potassium hydride (30% dispersion in mineral oil, 2.7 g, 20 mmol) was added and the reaction evacuated and charged with nitrogen (repeat three times). After 1 hour the reaction was quenched by the addition of methanol followed by 1 N aq. HCl. The reaction mixture was partitioned between ethyl acetate and water and the aqueous extracted with ethyl acetate as necessary. The combined organic phase was dried over MgSO$_4$, filtered then concentrated. Chromatography on Biotage 65i column (0-100% ethyl acetate/hexane) gave Intermediate 23 (6.1 g) as a colorless foam.

$^1$H NMR (CDCl$_3$, 500 MHz, ppm) δ 0.49 (s, 3H), 0.71 (s, 3H), 0.73 (d, J=7.3 Hz, 3H), 0.78 (d, J=7.7 Hz, 3H), 0.79 (s, 3H), 0.81 (d, J=7.7 Hz, 3H), 0.95 (s, 9H), 1.1-1.3 (m), 1.22 (s, 3H), 1.25 (s, 3H), 1.34-1.77 (m), 1.82 (m, 1H), 2.02 (m, 1H), 2.11 (m, 1H), 2.29 (d, J=8.9 Hz, 1H), 2.44 (m, 1H, partially obscured), 2.43 (s, 3H), 2.84 (m, 2H), 2.88 (s, 1H), 3.18 (d, J=11.6 Hz, 1H), 3.33 (AB, 2H), 3.47 (s, 3H), 3.56 (d, J=11.6 Hz, 1H), 3.98 (d, J=9.8 Hz, 1H), 4.13 (m, 1H), 4.99 (d, J=12.1 Hz, 1H), 5.12 (d, J=12.1 Hz, 1H), 5.42 (m, 1H), 7.25 (d, 2H, partially obscured), 7.3-7.4 (m, 5H), 7.80 (d, J=8.0 Hz, 2H).

Intermediate 24

(1S,4aR,6aS,7R,8R,10aR,10bR,12aR,14R,15R)-15-[[(2R)-2-amino-3,3-dimethylbutyl]oxy]-8-[(1R)-1,2-dimethylpropyl]-14-methoxy-1,6,6a,7,8,9,10,10a, 10b,11,12,12a-dodecahydro-1,6a,8,10a-tetramethyl-4H-1,4a-propano-2H-phenanthro[1,2-c]pyran-7-carboxylic acid

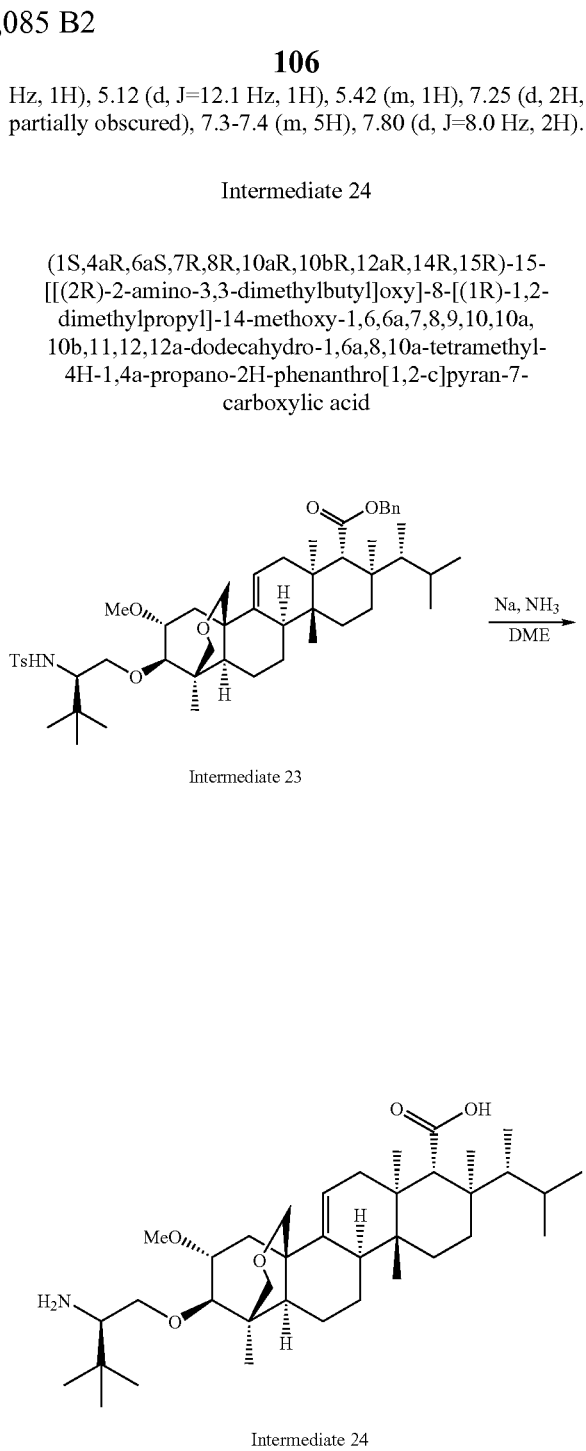

In a manner analogous to that described for Intermediate 14, Intermediate 24 was prepared starting with Intermediate 23.

$^1$H NMR (CDCl$_3$, 500 MHz, ppm) δ 0.76 (s, 3H) 0.77 (d, J=6.3 Hz, 3H), 0.81 (s, 3H), 0.86 (d, J=6.7 Hz, 3H), 0.91 (d, J=6.9 Hz, 3H), 1.05 (s, 9H), 1.18 (s, 3H), 1.2-1.32 (m) 1.22 (s, 3H), 1.38-1.66 (m), 1.69-1.87 (m), 1.98 (m, 1H), 2.09 (m, 1H), 2.21 (m, 1H), 2.56 (dd, J=13.2 Hz, 6.8 Hz, 1H), 2.84 (s, 1H), 2.86 (d, J=11.0 Hz, 1H), 3.18 (dd, J=8.2 Hz, 3.7 Hz, 1H), 3.34 (d, J=12.2 Hz, 1H), 3.41 (s, 3H), 3.42 (AB, 2H, partially obscured), 3.69 (d, J=12.3 Hz, 1H), 3.83 (m, 1H), 3.92 (m, 1H), 4.24 (m, 1H), 5.55 (m, 1H).

m/z=602.45 (M+H).

Intermediate 25

(1S,4aR,6aS,7R,8R,10aR,10bR,12aR,14R,15R)-15-[[(2R)-3,3-dimethyl-2-(methylamino)butyl]oxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

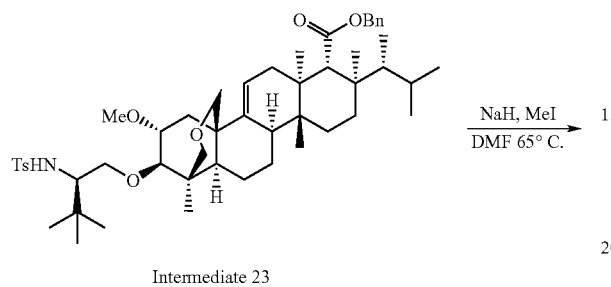

Intermediate 23

NaH, MeI
DMF 65° C.

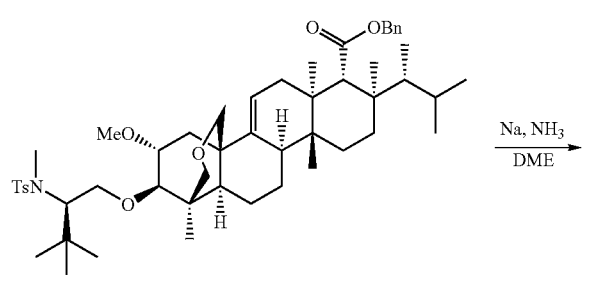

Na, NH₃
DME

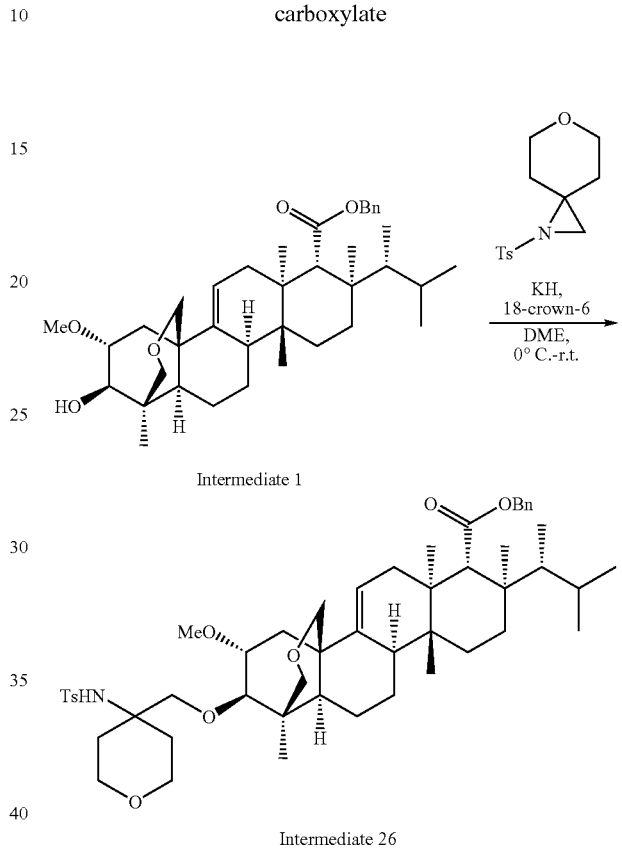

Intermediate 25

By a procedure analogous to that described for the preparation of Intermediate 16, Intermediate 25 was prepared starting with Intermediate 23.

m/z=616.54 (M+H).

Intermediate 26

Benzyl (1S,4aR,6aS,7R,8R,10aR,10bR,12aR,14R,15R)-8-[(1R)-1,2-dimethylpropyl]-14-methoxy-15-[[tetrahydro-4-[[(4-methylphenyl)sulfonyl]amino]-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylate Intermediate 1 (0.38 g, 0.641 mmol), 18-crown-6 (0.508 g, 1.92 mmol), and 1-[(4-methylphenyl)sulfonyl]-6-oxa-1-azaspiro[2.5]octane (0.257 g, 0.961 mmol) were dissolved in toluene and concentrated then placed under high vacuum for 1 hour. The resulting mixture was dissolved in dimethoxyethane (10 mL) placed under nitrogen atmosphere and cooled to 0° C. Potassium hydride (30% dispersion in mineral oil, 0.171 g, 1.28 mmol) was added and the reaction evacuated and charged with nitrogen (repeat three times). After an additional hour the reaction mixture was treated with aqueous ammonium chloride carefully, and the mixture was extracted with dichloromethane (2×20 mL). The combined organic phase was dried over MgSO₄, filtered then concentrated. The crude product was purified by flash chromatography (10-50% ethyl acetate/hexane) to yield Intermediate 26 (0.5 g) as a white foam.

¹H NMR (CDCl₃, 500 MHz, ppm) δ 0.74 (s, 3H), 0.75 (s, 3H) 0.80 (d, J=6.9 Hz, 3H), 0.84 (d, J=6.7 Hz, 3H), 1.14-1.3 (m), 1.19 (s, 3H), 1.26 (s, 3H), 1.32-1.8 (m), 1.84-1.98 (m), 2-2.18 (m), 2.45 (s, 3H), 2.47 (m, 1H), 2.89 (d, J=9.4 Hz, 1H), 2.90 (s, 1H), 3.29 (d, J=9.3 Hz, 1H), 3.35-3.45 (m, 5H=C2 MeO+2H?), 3.54 (m, 2H), 3.57 (m, 2H), 3.64-3.72 (m, 2H), 3.79 (d, J=10.1 Hz, 1H), 4.20 (m, 1H), 5.0 (d, J=12.1 Hz, 1H), 5.14 (d, J=12.1 Hz, 1H), 5.44 (m, 1H), 5.85 (s, 1H), 7.30 (d, J=9.2 Hz, 2H), 7.32-7.4 (m, 5H), 7.81 (d, J=8.2 Hz, 2H).

Intermediate 27

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

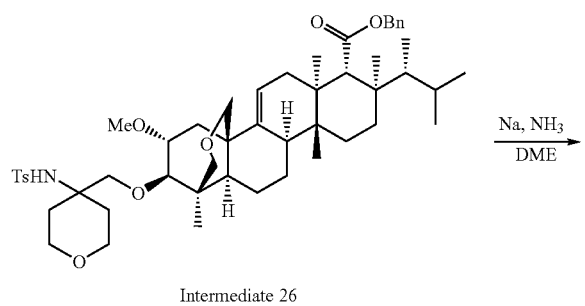

Intermediate 26

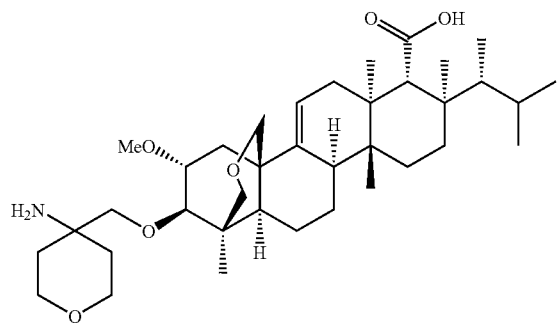

Intermediate 27

Ammonia (approx. 5 mL) was condensed into a 3-neck flask in a dry ice-acetone bath equipped with a cold-finger condenser and sodium (approx. 0.211 g, 9.11 mmol) was added to give a deep blue solution. To this solution was added a solution of Intermediate 26 (0.28 g, 0.326 mmol) in dimethoxymethane (8 mL) and the reaction was refluxed at −33° C. for 1.5 hours. The reaction was quenched by the careful addition of methanol followed by water until the reaction was a white slurry. The solvents were evaporated by a stream of nitrogen overnight. After approximately 18 hours methanol (approx 5 mL) was added and the resulting white slurry/partial solution was stirred for about 10 minutes to ensure that all solids were in suspension (as opposed to fixed to the flask wall). This mixture was partitioned between ethyl acetate and water and the aqueous extracted twice with ethyl acetate. The combined organic phase was dried over MgSO$_4$, filtered then concentrated to give Intermediate 27 (0.16 g) as an off-white solid.

$^1$H NMR (CD$_3$OD, 500 MHz, ppm) δ 0.77 (s, 3H), 0.78 (d, J=7.3 Hz, 3H), 0.81 (s, 3H), 0.86 (d, J=6.6 Hz, 3H), 0.91 (d, J=6.8 Hz, 3H), 1.21 (s, 3H), 1.26 (s, 3H), 1.18-1.42 (m), 1.46-1.88 (m). 1.98 (m, 1H), 2.02 (m, 1H), 2.06 (m, 1H), 2.08 (m, 1H), 2.26 (m, 1H), 2.55 (dd, J=13.5 Hz, 6.9 Hz, 1H), 2.78 (s, 1H), 3.03 (d, J=8.7 Hz, 1H), 3.3-3.36 (m, 3H), 3.42 (s, 3H), 3.6-3.84 (m, 3H), 3.90 (d, J=10.3 Hz, 1H), 4.22 (m, 1H), 5.54 (m, 1H).

Intermediate 28

(1S,4aR,6aS,7R,8R,10aR,10bR,12aR,14R,15R)-8-[(1R)-1,2-dimethylpropyl]-14-methoxy-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

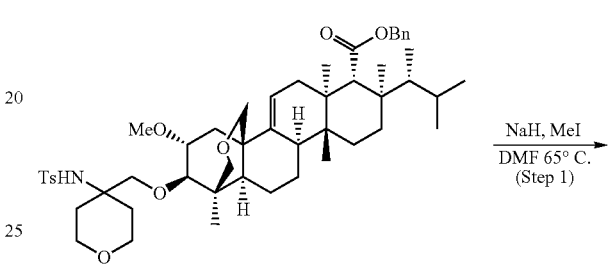

Intermediate 26

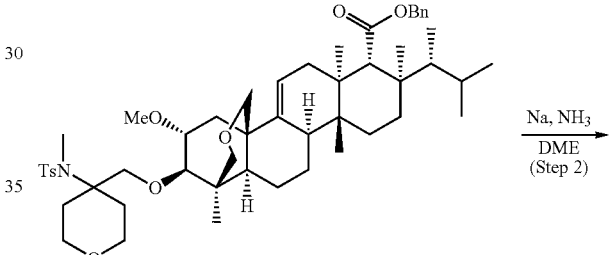

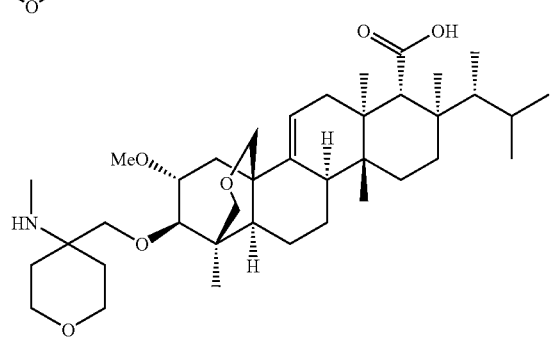

Intermediate 28

Step 1

Sodium hydride (60% dispersion in mineral oil, 84 mg, 2.1 mmol) was washed with hexane and the hexane decanted. This procedure was repeated and the remaining hexane removed in vacuo. This pre-washed sodium hydride was suspended in DMF (1 mL) and a solution of Intermediate 26 (0.18 g, 0.21 mmol) in DMF (1 mL) was added. Methyl iodide (0.131 mL, 2.1 mmol) was added and the reaction mixture heat at 60° C. under nitrogen for 60 minutes. After cooling to room temperature the reaction was partitioned between ethyl acetate and saturated aqueous bicarbonate. The organic phase was washed with brine, dried with MgSO$_4$ filtered and concentrated in vacuo to give the product (0.18 g, 98%).

Step 2

The product was subjected to the sodium/ammonia reduction by analogy to the preparation of Intermediate 27 then lyophilized from MeOH/Benzene to give intermediate 28 (0.16 g) as an off-white foam.

¹H NMR (CD₃OD, 500 MHz, ppm) δ 0.78 (s, 3H), 0.79 (d, 3H, partially obscured), 0.80 (s, 3H), 0.86 (d, J=6.6 Hz, 3H), 0.91 (d, J=6.6 Hz, 3H), 1.21 (s, 3H), 1.18-1.42 (m), 1.50 (m, 1H), 1.56-1.96 (m), 1.98 (m, 1H), 2.02 (m, 1H), 2.08 (m, 1H), 2.10 (m, 1H), 2.26 (m, 1H), 2.55 (s, 3H), 2.57 (m, 1H, partially obscured), 2.80 (s, 1H), 2.99 (d, J=8.7 Hz, 1H), 3.31 (s, 3H), 3.43 (s, 3H), 3.58 (m, 2H), 3.68 (d, J=11.7 Hz, 1H), 3.82 (d, J=10.5 Hz, 1H), 3.84-3.9 (m, 2H), 4.02 (d, J=10.7 Hz, 1H), 4.23 (m, 1H), 5.55 (m, 1H).

Intermediate 29

(1S,4aR,6aS,7R,8R,10aR,10bR,12aR,14R,15R)-8-[(1R)-1,2-dimethylpropyl]-15-[[4-(ethylamino)tetrahydro-2H-pyran-4-yl]methoxy]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

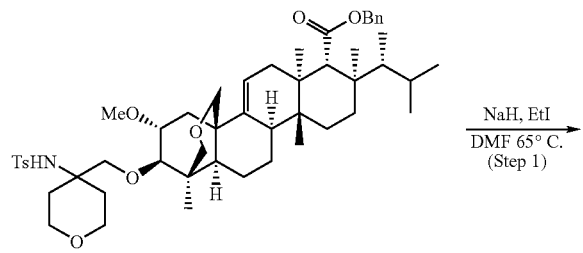

Intermediate 26

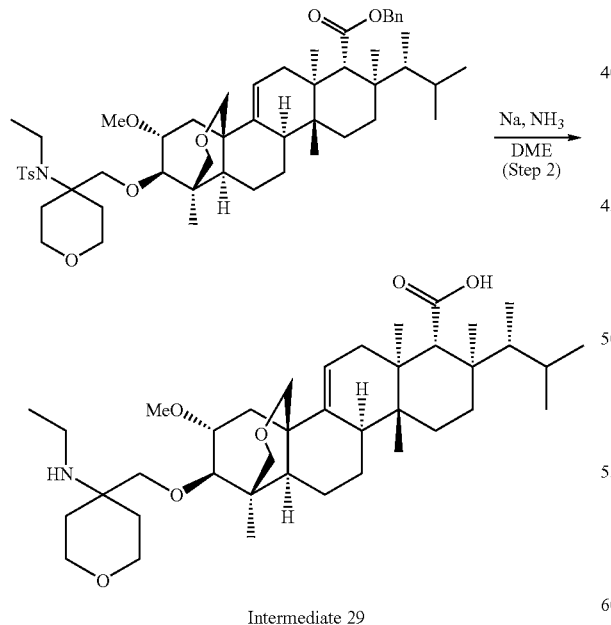

Intermediate 29

Step 1

Sodium hydride (60% dispersion in mineral oil, 84 mg, 2.1 mmol) was washed with hexane and the hexane decanted. This procedure was repeated and the remaining hexane removed in vacuo. This pre-washed sodium hydride was suspended in DMF (1 mL) and a solution of intermediate 26 (0.18 g, 0.21 mmol) in DMF (1 mL) was added. Ethyl iodide (0.169 mL, 2.1 mmol) was added and the reaction mixture heated at 60° C. under nitrogen for 60 minutes. After cooling to room temperature the reaction was partitioned between ethyl acetate and saturated aqueous bicarbonate. The organic phase was washed with brine, dried under MgSO₄ filtered and concentrated in vacuo to give the product (0.18 g).

Step 2

The product was subjected to sodium/ammonia reduction by analogy to the preparation of Intermediate 27 then lyophilized from MeOH/Benzene to give Intermediate 29 (0.16 g) as an off-white foam.

¹H NMR (CD₃OD, 500 MHz, ppm) δ 0.77 (s, 3H), 0.79 (d, 3H, partially obscured), 0.80 (s, 3H), 0.86 (d, J=6.7 Hz, 3H), 0.88 (d, J=5.3 Hz, 3H), 1.21 (s, 3H), 1.18-1.42 (m), 1.50 (m, 1H), 1.56-1.88 (m), 1.92 (m, 1H), 1.95 (m, 1H), 1.99 (m, 1H), 2.03 (m, 1H), 2.08 (m, 1H), 2.11 (m, 1H), 2.28 (m, 1H), 2.58 (m, 1H), 2.80 (s, 1H), 2.71 (m, 1H), 2.99 (d, J=8.7 Hz, 1H), 3.02 (m, 1H), 3.36 (s, 3H), 3.43 (s, 2H), 3.56 (m, 2H), 3.68 (d, J=11.7 Hz, 1H), 3.84-3.92 (m, 3H), 4.04 (d, J=10.8 Hz, 1H), 4.22 (m, 1H), 5.55 (m, 1H).

Intermediate 30

(1S,4aR,6aS,7R,8R,10aR,10bR,12aR,14R,15R)-15-[(1-aminocyclohexyl)methoxy]-8-[(1R)-1,2-dimethylpropyl]-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

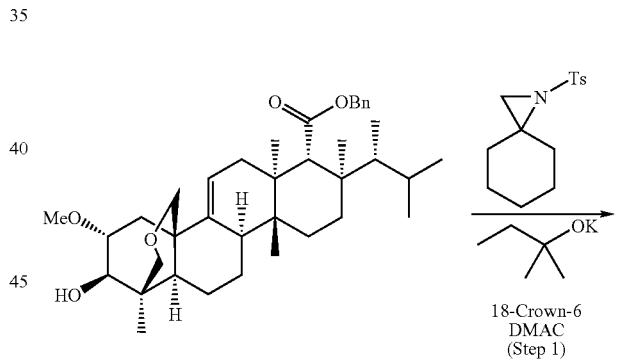

Intermediate 1

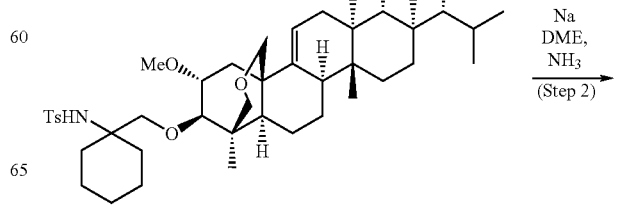

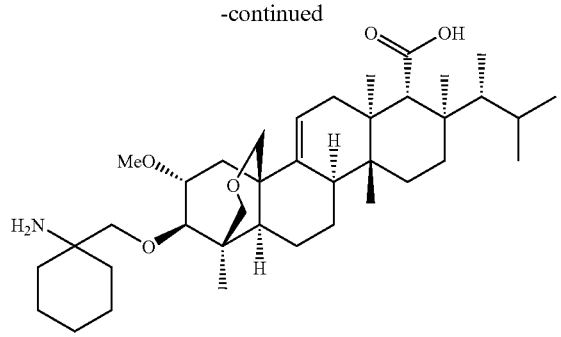

Intermediate 30

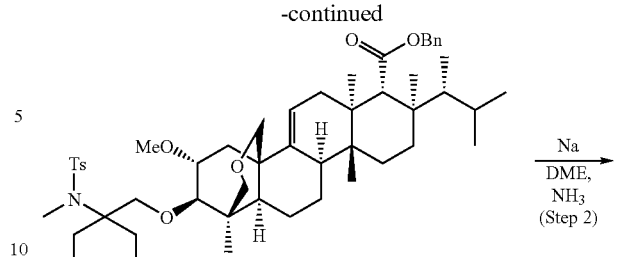

Step 1:

To a stirred solution of Intermediate 1 (5.0 g, 8.43 mmol), 1-[(4-methylphenyl)sulfonyl]-1-azaspiro[2.5]octane (4.03 g, 15.18 mmol) and 18-crown-6 (2.23 g, 8.43 mmol) in DMAC (16 mL) under a nitrogen atmosphere was added a solution of potassium tert-pentylate in toluene (~1.7 M, 5.95 mL, 10.12 mmol). The mixture was stirred at room temperature for 16 hours and partitioned between EtOAc and 1N HCl. The organic layer was dried over $Na_2SO_4$. The solvent was evaporated and the residue was chromatographed on silica gel with an ISCO Combiflash using EtOAc/hexanes 15-30% to afford a pale yellow solid (5.62 g).

MS ESI m/z=881 (M+Na).

Step 2:

Sodium metal (248 mg, 10.8 mmol) was added to a solution of liquid ammonia (20 mL) at −33° C. The mixture was diluted with dry DME (20 mL). A solution of the product compound from Step 1 (928 mg, 1.08 mmol) in DME (2 mL) was added dropwise over 5 min. The mixture was stirred at reflux for 2 hours and the reaction was quenched with careful addition of excess MeOH. The ammonia was allowed to evaporate and the mixture was partitioned between EtOAc and water. The organic layer was dried over $Na_2SO_4$ and the solvent was evaporated to give the title compound as a white solid (550 mg).

MS (ESI) m/z=614 (M+H).

Intermediate 31

(1S,4aR,6aS,7R,8R,10aR,10bR,12aR,14R,15R)-8-[(1R)-1,2-dimethylpropyl]-14-methoxy-15-[[1-(methylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

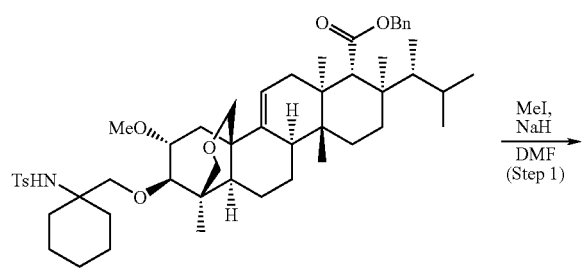

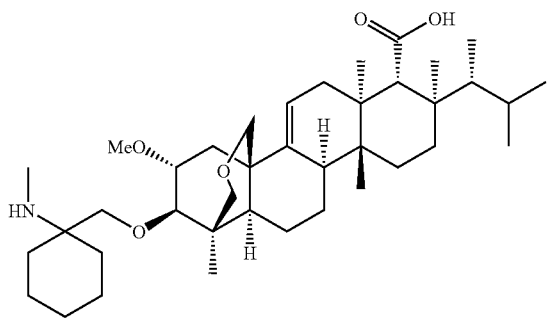

Intermediate 31

Step 1:

To a solution of the product compound of Step 1 in the synthesis of Intermediate (155 mg, 0.181 mmol) in DMF (3 mL) under a nitrogen atmosphere was added a suspension of 30% NaH (14 mg, 0.361 mmol). The mixture was stirred at room temperature for 5 minutes and iodomethane (64 mg, 0.451 mmol) was added. The mixture was stirred for 16 hours and partitioned between EtOAc and 1N HCl. The organic layer was dried over $Na_2SO_4$ and the solvent was evaporated to give an amber oil (158 mg).

Step 2:

Sodium metal (40 mg, 1.81 mmol) was added to a solution of liquid ammonia (10 mL) at −33° C. The mixture was diluted with dry DME (5 mL). A solution of product compound from Step 1 (158 mg, 0.181 mmol) in DME (2 mL) was added dropwise over 5 min. The mixture was stirred at reflux for 2 hours and the reaction was quenched by careful addition of excess MeOH. The ammonia was allowed to evaporate and the mixture was partitioned between EtOAc and water. The organic layer was dried over $Na_2SO_4$ and the solvent was evaporated to give the title compound as a white solid (100 mg).

MS (ESI) m/z=628 (M+H).

Intermediate 32

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-hydrazino-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

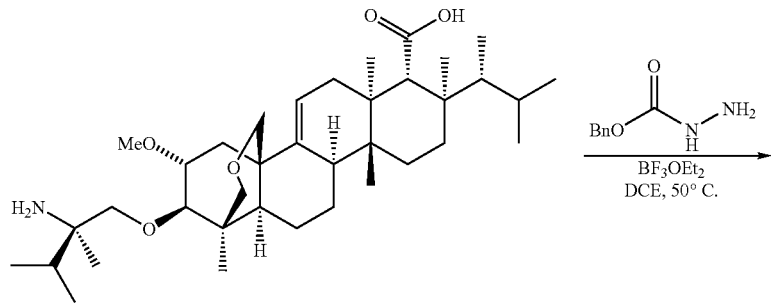

Intermediate 6

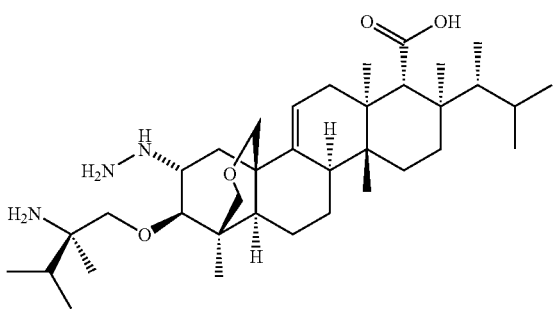

Intermediate 32

Benzyl carbazate (208.9 mg, 1.257 mmol) and BF₃O(CH₂CH₃)₂ (0.53 ml, 4.18 mmol) were added to a stirred hazy solution of Intermediate 6 (251.7 mg, 0.418 mmol) in 1,2-dichloroethane (4.2 ml). The reaction mixture was a hazy solution that was heated to 50° C. After 2.5 hours, LCMS and $^1$H NMR showed complete consumption of Intermediate 6. The reaction mixture was cooled to room temperature and partitioned between ethyl acetate (75 ml) and water (40 ml). The aqueous layer was extracted with ethyl acetate (2×40 ml). The organic layers were combined, dried over sodium sulfate, and filtered. The solvent was evaporated under reduced pressure to give a light yellow residue. The residue was dissolved in methanol and purified using four HPLC runs (~63 mg/run) on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give Intermediate 32 (146.4 mg) as a white solid (TFA salt).

$^1$H NMR (CD₃OD, 500 MHz, ppm) δ 0.78 (s, 3H, Me), 0.79 (d, 3H, Me), 0.85 (s, 3H, Me), 0.88 (d, 3H, Me), 0.92 (d, 3H, Me), 1.01 (d, 3H, Me), 1.04 (d, 3H, Me), 1.20 (s, 6H, 2Me), 1.23 (s, 3H, Me), 1.24-1.36 (m), 1.41-1.55 (m), 1.59-1.68 (m), 1.74-1.91 (m), 1.96-2.03 (m), 2.09-2.15 (m), 2.18-2.28 (m), 2.55 (dd, 1H, H13), 2.88 (s, 1H, H7), 3.17 (d, 1H), 3.42 (d, 1H), 3.49 (abq, 2H), 3.78 (d, 1H), 3.80 (d, 1H), 3.81 (dd, 1H), 4.17-4.25 (m, 1H, H14), 5.58 (dd, 1H, H5).

Mass Spectrum: (ESI) m/z=602.73 (M+H).

Intermediate 33

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-hydrazino-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

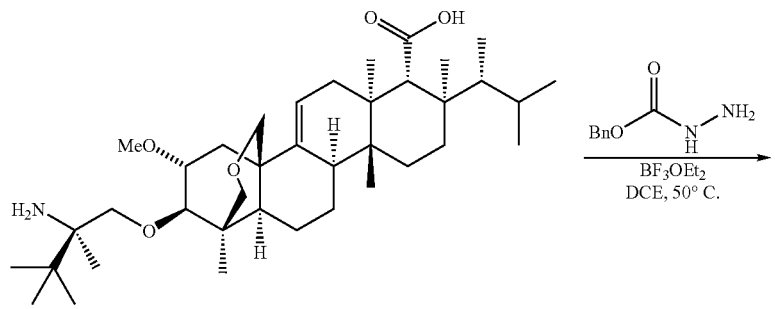

Intermediate 14

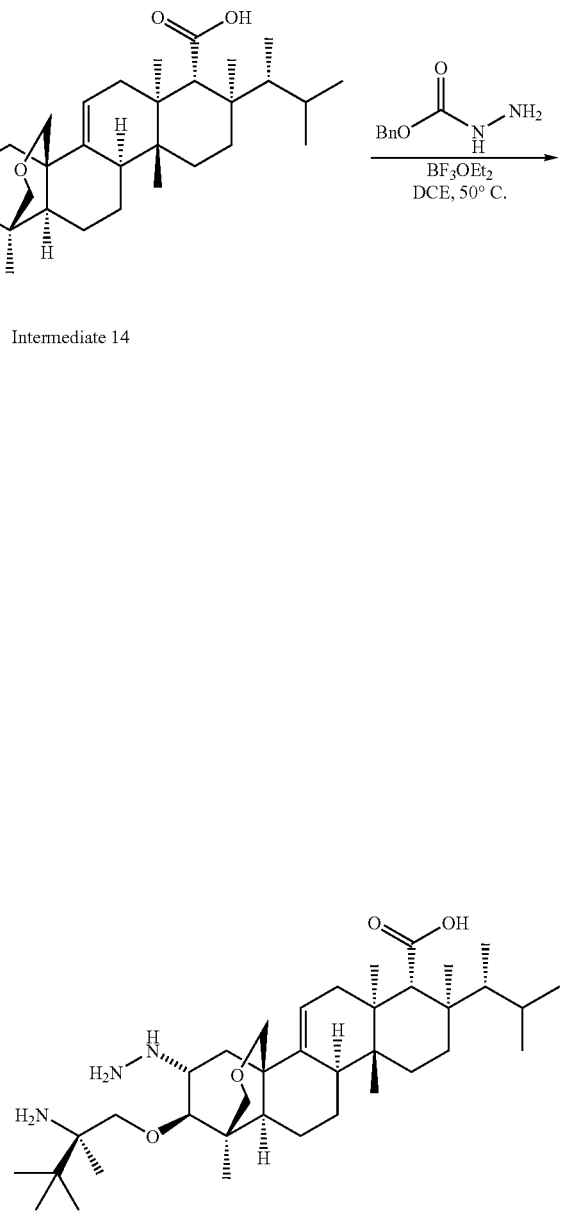

Intermediate 33

A suspension of Intermediate 14 (2.98 g, 0.048 mol), benzyl carbazate (2.55 g, 0.015 mol) and boron trifluoride etherate (6.15 mL, 0.048 mol) in 1,2-dichloroethane (50 mL) was blanketed with nitrogen and heated in a 50° C. oil bath for 4.5 hours. The mixture was cooled to room temperature, and partitioned between ethyl acetate (400 mL) and water (200 mL). The aqueous layer was extracted with more ethyl acetate (4×50 mL) and the combined ethyl acetate layers were dried with sodium sulfate, filtered and evaporated to a solid (6.0 g). The solid was purified by reverse phase HPLC using a 19×150 mm Sunfire Preparative C18 OBD column. Fractions containing the product were combined, evaporated and freeze-dried from a mixture of ethanol and benzene to give the title compound as a TFA salt (2.0 g).

Intermediate 33

Alternative Procedure (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-hydrazino-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

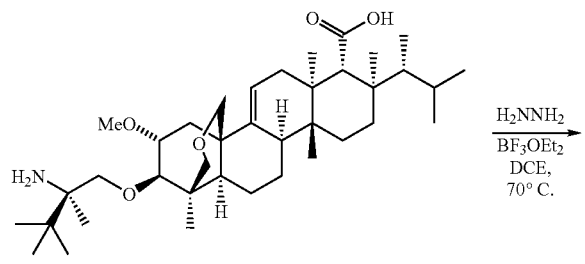

Intermediate 14

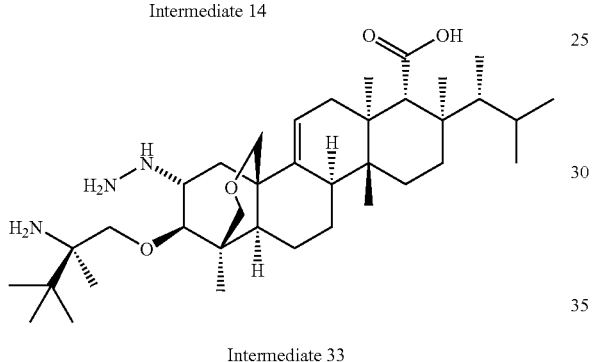

Intermediate 33

A suspension of Intermediate 14 (3.0 g, 0.048 mol), anhydrous hydrazine (0.762 mL, 0.024 mol) and boron trifluoride etherate (12.36 mL, 0.098 mol) in 1,2-dichloroethane (24.4 mL) was blanketed with nitrogen and heated in a 70° C. oil bath for 2 hours. The mixture was cooled to room temperature, methanol (30 mL) and water (20 mL) were added and the mixture was evaporated to approximately 20 mL. Ethyl acetate (125 mL) and saturated aqueous sodium bicarbonate (180 mL) were added, the aqueous layer was re-extracted with ethyl acetate (3×40 mL) and the combined ethyl acetate layers were dried with magnesium sulfate, filtered and evaporated to a solid (3.0 g).

$^1$H NMR (CD$_3$OD, 600 MHz, ppm) δ 0.76 (s, 3H, Me), 0.77 (d, 3H, Me), 0.81 (s, 3H, Me), 0.85 (d, 3H, Me), 0.90 (d, 3H, Me), 1.05 (s, 9H, Me), 1.17 (s, 3H, Me), 1.20 (s, 3H, Me), 1.25 (s, 3H, Me), 1.23-1.34 (m), 1.41-1.45 (m), 1.48-1.65 (m), 1.70-1.90 (m), 1.90-2.00 (m), 2.06-2.11 (m), 2.16-2.24 (m), 2.49 (dd, 1H, H13), 2.85 (s, 1H, H7), 2.96 (d, 1H), 3.38 (d, 1H), 3.40-3.60 (m), 3.49 (br d, 1H), 3.82 (d, 1H), 3.89 (br m, 1H, H14), 4.07 (d, 1H), 5.56 (dd, 1H, H5).

Mass spectrum: (ESI) m/z=616.40 (M+H).

Intermediate 34

(1S,4aR,6aS,7R,8R,10aR,10bR,12aR,14R,15R)-8-[(1R)-1,2-dimethylpropyl]-14-hydrazino-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

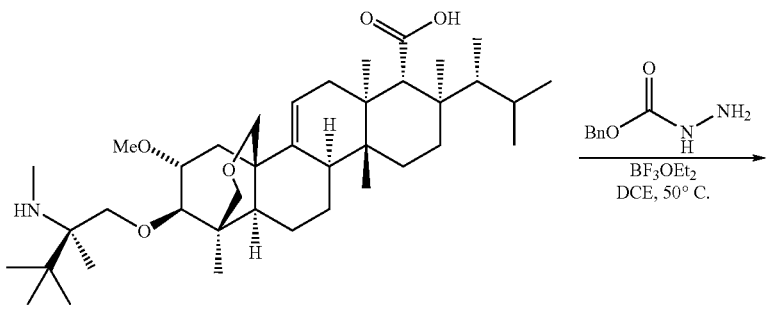

Intermediate 16

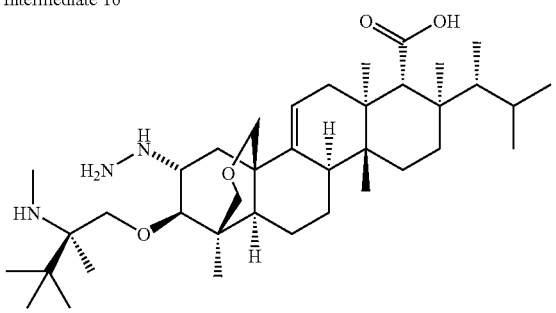

Intermediate 34

Intermediate 16 (700 mg, 1.11 mmol) and benzyl carbazate (554 mg, 3.33 mmol) were combined then diluted with dichloroethane (11 mL), then treated with BF$_3$OEt$_2$ (1.4 mL, 11 mmol) and this mixture was heated to 50° C. under nitrogen. After 1.5 hours more BF$_3$OEt$_2$ (1.4 mL, 11 mmol) was added. After 4.5 hours the reaction was cooled to room temperature then concentrated in vacuo to give a brown slurry. The crude reaction mixture was suspended in methanol (8 mL) then filtered. The filtrate was purified by multiple runs on a preparative LCMS (30×100 mm Waters Sunfire column, 5 μm, Electrospray positive detection, 0-100% MeCN/water with 0.05% TFA over 12 minutes, using Masslynx software). The product fractions from were combined and partially concentrated by rotovap then frozen and lyophilized to give Intermediate 34 (310 mg) as a white amorphous solid (TFA salt).

$^1$H NMR (CD$_3$OD, 500 MHz, ppm) δ 0.77 (s, 3H), 0.78 (d, 3H, partially obscured), 0.85 (s, 3H), 0.86 (d, 3H, partially obscured), 0.91 (d, J=6.8 Hz, 3H), 1.14 (s, 9H), 1.18 (s, 3H), 1.21 (s, 3H0, 1.23 (s, 3H), 1.23-1.67 (m), 1.73-1.90 (m), 1.98 (m, 1H), 2.10 (m, 1H), 2.19 (m, 1H), 2.61 (dd, J=13.4 Hz, 6.5 Hz, 1H), 2.80 (s, 3H), 2.86 (s, 1H), 2.90 (m, 1H), 3.44 (d, J=11.9 Hz, 1H), 3.48 (m, 2H), 3.71 (d, J=11.9 Hz, 1H), 3.83 (d, J=11.4 Hz, 1H), 3.94 (d, J=11.4 Hz, 1H), 4.04 (m, 1H), 5.57 (m, 1H).

Mass Spectrum: (ESI) m/z=630.35 (M+H).

Intermediate 35

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-hydrazino-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

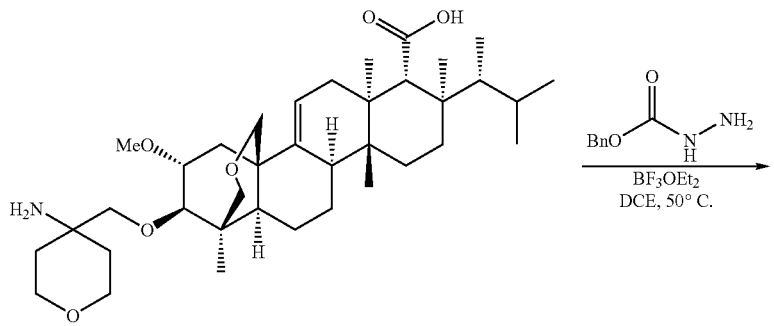

Intermediate 27

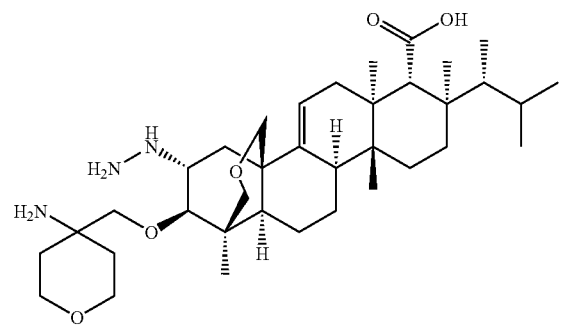

Intermediate 35

A solution of Intermediate 27 (580 mg, 0.942 mmol) in dichloroethane (9 mL) was treated with benzyl carbazate (469 mg, 2.83 mmol) then $BF_3OEt_2$ (1.19 mL, 9.42 mmol) and this mixture was heated to 55° C. under nitrogen. After 2 hours the reaction was cooled to room temperature then concentrated in vacuo. The crude product mixture was suspended in methanol (5 mL) and filtered through a sintered glass funnel. The filtrate was purified by preparative HPLC (19× 100 mm Waters Sunfire column, 5 μm, UV-detection, 30-100% MeCN/water with 0.05% TFA over 20 minutes). The product fractions were combined and partially concentrated by rotovap then frozen and lyophilized to give Intermediate 35 (580 mg) as a white amorphous solid (TFA salt).

$^1$H NMR ($CD_3OD$, 500 MHz, ppm) δ 0.78 (s, 3H), 0.79 (d, 3H, partially obscured), 0.84 (s, 3H), 0.87 (d, J=6.6 Hz, 3H), 0.92 (d, J=6.9 Hz, 3H), 1.20 (s, 3H), 1.23 (s, 3H), 1.23-2.03 (m), 2.11 (m, 1H), 2.20 (m, 1H), 2.56 (dd, J=13.2, 6.4 Hz, 1H), 2.87 (s, 1H), 3.17 (m, 1H), 3.35 (s, 1H), 3.41 (d, J=12.1 Hz, 1H), 3.49 (s, 2H), 3.64 (m, 2H), 3.79-3.88 (m, 3H), 4.02 (d, J=10.0 Hz, 1H), 4.18 (m, 1H), 5.58 (m, 1H).

Mass Spectrum: (ESI) m/z=616.78 (M+H).

Intermediate 36

(1S,4aR,6aS,7R,8R,10aR,10bR,12aR,14R,15R)-8-[(1R)-1,2-dimethylpropyl]-14-hydrazino-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

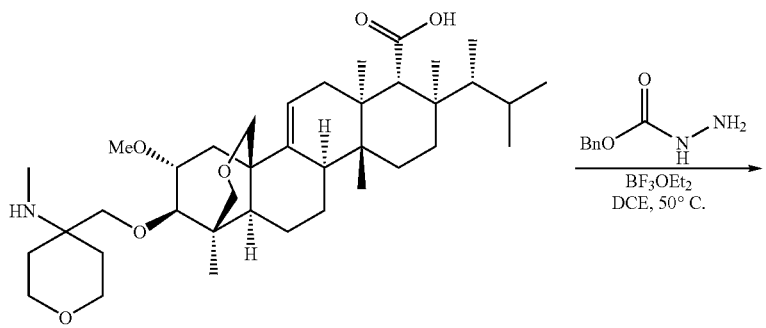

Intermediate 28

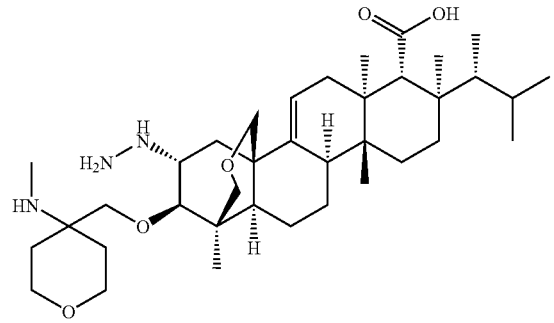

Intermediate 36

A solution of Intermediate 28 (1.58 g, 2.57 mmol) in dichloroethane (25.8 mL) was treated with benzyl carbazate (1.28 g, 7.7 mmol) then $BF_3OEt_2$ (3.25 mL, 25.7 mmol) and this mixture was heated to 55° C. under nitrogen. After 2 hours the reaction was cooled to room temperature then concentrated in vacuo. The crude product mixture was suspended in methanol (5 mL) and filtered through a sintered glass funnel. The filtrate was purified by preparative HPLC (19× 100 mm Waters Sunfire column, 5 μm, UV-detection, 30-100% MeCN/water with 0.05% TFA over 20 minutes). The product fractions were combined and partially concentrated by rotovap then frozen and lyophilized to give Intermediate 36 (800 mg) as a white amorphous solid (TFA salt).

$^1$H NMR ($CD_3OD$, 500 MHz, ppm) δ 0.79 (s, 3H), 0.80 (d, 3H, partially obscured), 0.83 (s, 3H), 0.88 (d, J=6.6 Hz, 3H), 0.92 (d, J=6.8 Hz, 3H), 1.20 (s, 3H), 1.23 (s, 3H), 1.24-2.16 (m), 2.21 (m, 1H), 2.62 (m, 1H), 2.74 (s, 3H), 2.88 (s, 1H), 3.02 (m, 1H), 3.42 (d, J=11.7 Hz, 1H), 3.44-3.67 (m, 4H), 3.76-3.85 (m, 2H), 3.76-3.85 (m, 2H), 3.86-3.96 (m, 2H), 4.00 (m, 1H), 4.04-4.14 (m, 2H), 5.60 (m, 1H).

Mass Spectrum: (ESI) m/z=630.54 (M+H).

Intermediate 37

(1S,4aR,6aS,7R,8R,10aR,10bR,12aR,14R,15R)-8-[(1R)-1,2-dimethylpropyl]-14-hydrazino-15-hydroxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

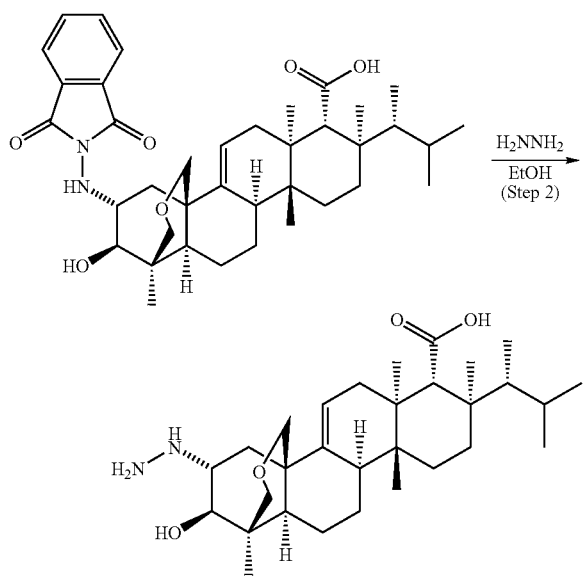

Intermediate 37

Step 1:
Boron trifluoride diethyl etherate (12.3 mL, 97.9 mmol) was added slowly to a solution of (1S,4aR,6aS,7R,8R,10aR,10bR,12aR,14R,15R)-8-[(1R)-1,2-dimethylpropyl]-15-hydroxy-14-methoxy-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (product compound from Step 2 in the synthesis of Intermediate 1; 5 g, 9.96 mmol) and N-aminophthalimide (1.94 g, 1.20 mmol) in 1,2-dichloroethane (112 mL) at room temperature. The reaction mixture was heated overnight at 50° C. and allowed to cool to room temperature. The reaction mixture was partitioned between EtOAc and water, and the layers were separated. The aqueous layer was extracted with EtOAc. The combined organic layers were dried with $Na_2SO_4$ and concentrated under reduced pressure. The residue was purified by flash chromatography, elution with 0-50% EtOAc in heptane, to give the product (4.16 g, 66%) as a pale yellow solid.

$^1$H NMR (400 MHz, $CD_3OD$) δ 0.71-0.82 (m, 9H) 0.86 (d, J=6.69 Hz, 3H) 0.91 (d, J=6.78 Hz, 3H) 1.20 (d, J=15.72 Hz, 20H) 1.94 (d, J=17.67 Hz, 1H) 2.10 (d, J=12.89 Hz, 1H) 2.20 (dt, J=13.61, 6.84 Hz, 1H) 2.29 (dd, J=13.57, 6.49 Hz, 1H) 2.85 (s, 1H) 3.26 (d, J=9.52 Hz, 1H) 3.35 (s, 2H) 3.42 (s, 2H) 3.69 (d, J=11.67 Hz, 1H) 4.05 (ddd, J=11.69, 9.49, 6.49 Hz, 1H) 5.47 (d, J=5.86 Hz, 1H) 7.58-8.08 (m, 4H).

Step 2:
Hydrazine monohydrate (13 mL, 267 mmol) was added to a solution of the product from Step 1 (4.16 g, 6.58 mmol) in EtOH (140 mL) at room temperature, and the reaction mixture was stirred overnight. The reaction mixture was poured into a mixture water (ca. 200 mL) and EtOAc (250 mL), and saturated aqueous NaCl (100 mL) was added to generate a white precipitate. The solid was collected by suction filtration, washed with water, and dried on the funnel. The remaining water was removed by evaporation with methanol under reduced pressure. Excess solvent was removed in vacuo to provide Intermediate 37 (3.24 g, 100%) as a white solid.

$^1$H NMR (400 MHz, $CD_3OD$) δ 0.70-0.81 (m, 12H) 0.84 (d, J=6.64 Hz, 3H) 0.91 (d, J=6.78 Hz, 3H) 1.24 (d, J=13.76 Hz, 19H) 1.98-2.13 (m, 2H) 2.28-2.35 (m, 1H) 2.38 (dd, J=13.40, 6.37 Hz, 1H) 2.73 (s, 1H) 3.14 (d, J=9.47 Hz, 1H) 3.35 (d, J=11.67 Hz, 1H) 3.46 (s, 2H) 3.62 (ddd, J=11.62, 9.54, 6.32 Hz, 1H) 3.70 (d, J=11.71 Hz, 1H) 5.55 (d, J=5.71 Hz, 1H).

Intermediate 38

(1S,4aR,6aS,7R,8R,10aR,10bR,12aR,14R,15R)-8-[(1R)-1,2-dimethylpropyl]-15-hydroxy-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, (4-methoxyphenyl)methyl ester

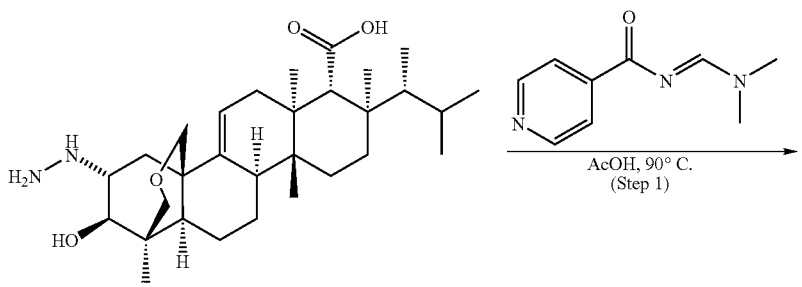

Intermediate 37

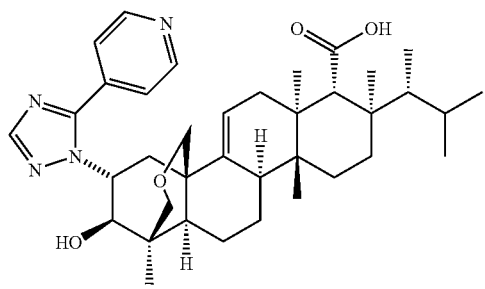 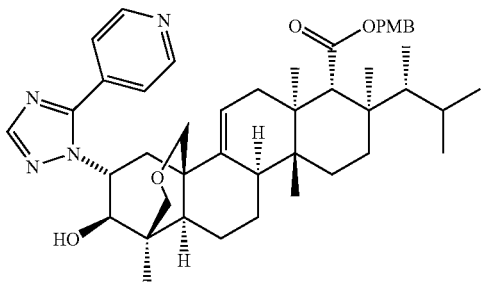

Intermediate 38

PMB = 4-methoxybenzyl

Step 1:

A solution of Intermediate 37 (3.24 g, 6.45 mmol) and N-[(1E)-(dimethylamino)methylidene]pyridine-4-carboxamide (1.26 g, 7.10 mmol) in HOAc (100 mL) was evacuated and flushed with nitrogen. The solution was heated under nitrogen at 90° C. for 1 h. The solution was allowed to cool to room temperature, and the acetic acid was removed under reduced pressure. The residue was partitioned between EtOAc and saturated aqueous NaHCO$_3$, and the layers were separated. The aqueous layer was extracted with EtOAc. The combined organic layers were washed with saturated aqueous NaCl, dried with Na$_2$SO$_4$, and concentrated under reduced pressure. The residue was purified by flash chromatography, elution with 0%-10% MeOH in CH$_2$Cl$_2$, to give the product (2.71 g, 68%) as a white solid.

$^1$H NMR (400 MHz, CD$_3$OD) δ ppm 0.74-0.83 (m, 9H) 0.87 (d, J=6.69 Hz, 3H) 0.91 (d, J=6.78 Hz, 3H) 1.08-1.72 (m, 15H) 1.71-2.00 (m, 5H) 2.06-2.26 (m, 3H) 2.26-2.42 (m, 1H) 2.85 (s, 1H) 3.41 (d, J=11.81 Hz, 1H) 3.45-3.57 (m, 2H) 3.72-3.93 (m, 2H) 5.48 (d, J=5.66 Hz, 1H) 5.62 (ddd, J=11.68, 9.82, 6.47 Hz, 1H) 7.90-7.93 (m, 2H) 8.11 (s, 1H) 8.74 (dd, J=4.61, 1.49 Hz, 2H).

Step 2:

To a solution of the product from Step 1 (2.71 g, 4.40 mmol) in DMF (30 mL) was added potassium carbonate (12.0 g, 88.0 mmol) and 4-methoxybenzyl bromide (0.64 mL, 4.40 mmol). The mixture was stirred at room temperature overnight. The reaction mixture was poured into water (ca. 300 mL) and extracted with EtOAc. The combined organic layers were washed with saturated aqueous NaCl, dried with Na$_2$SO$_4$, and concentrated under reduced pressure. The residue was purified by flash chromatography, elution with 0-10% MeOH in CH$_2$Cl$_2$, to give Intermediate 38 (2.60 g, 80%) as a white solid.

$^1$H NMR (400 MHz, CDCl$_3$) δ 0.71 (d, J=7.17 Hz, 6H) 0.78 (d, J=6.78 Hz, 3H) 0.81 (d, J=6.69 Hz, 3H) 0.87 (s, 3H) 1.04-1.57 (m, 11H) 1.68-1.92 (m, 4H) 1.97-2.28 (m, 3H) 2.59 (d, J=5.27 Hz, 1H) 2.81 (s, 1H) 3.41 (d, J=12.15 Hz, 1H) 3.44 (s, 2H) 3.79 (s, 3H) 3.89 (d, J=12.01 Hz, 1H) 4.04 (dd, J=9.37, 5.27 Hz, 1H) 4.86 (d, J=11.96 Hz, 1H) 5.03 (d, J=11.96 Hz, 1H) 5.28 (d, J=5.66 Hz, 1H) 5.73 (td, J=10.30, 7.17 Hz, 1H) 6.85 (q, J=4.82 Hz, 2H) 7.25 (d, J=8.74 Hz, 2H) 7.75 (dd, J=4.54, 1.46 Hz, 2H) 7.98 (s, 1H) 8.74 (d, J=5.86 Hz, 2H).

Intermediate 39

(1S,4aR,6aS,7R,8R,10aR,10bR,12aR,14R,15R)-8-[(1R)-1,2-dimethylpropyl]-15-hydroxy-14-(5-imidazo[1,2-a]pyridin-7-yl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, (4-methoxyphenyl)methyl ester

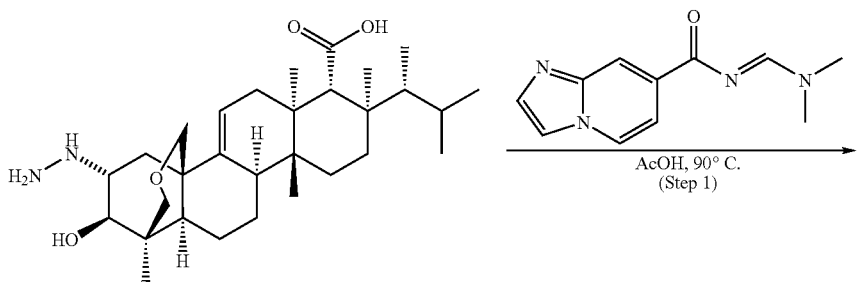

Intermediate 37

-continued

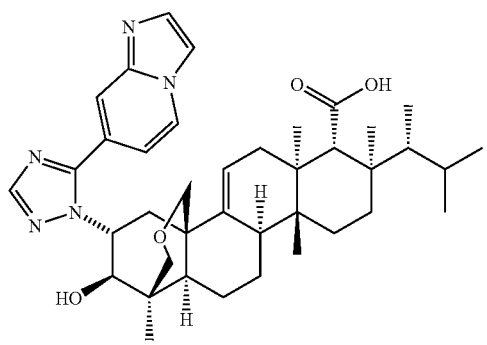

PMB = 4-methoxybenzyl

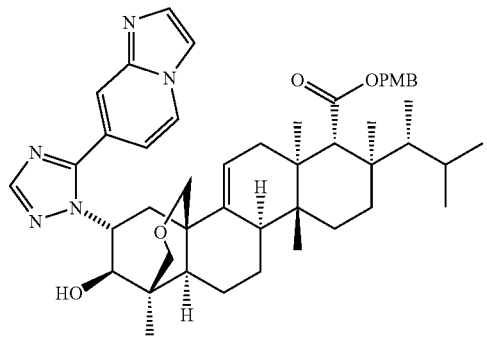

Intermediate 39

By procedures analogous to those described for Intermediate 38, the title compound was prepared starting with Intermediate 37.

¹H NMR (400 MHz, METHANOL-d₄) δ ppm 0.72 (d, J=15.67 Hz, 8H) 0.77-0.87 (m, 5H) 1.06-1.14 (m, 2H) 1.17 (s, 3H) 1.23 (s, 3H) 1.25-1.69 (m, 5H) 1.81 (d, J=13.37 Hz, 5H) 2.11 (dd, J=14.23, 7.79 Hz, 3H) 2.25-2.42 (m, 1H) 2.86 (s, 1H) 3.34-3.56 (m, 3H) 3.76 (s, 3H) 3.79-3.96 (m, 2H) 4.87-5.10 (m, 2H) 5.40 (d, J=6.64 Hz, 1H) 5.56-5.82 (m, 1H) 6.87 (d, J=8.64 Hz, 2H) 7.28 (d, J=8.64 Hz, 2H) 7.36 (d, J=7.08 Hz, 1H) 7.71 (d, J=1.17 Hz, 1H) 7.99 (s, 1H) 8.10 (s, 1H) 8.20 (s, 1H) 8.60 (s, 1H).

Intermediate 40

(1S,4aR,6aS,7R,8R,10aR,10bR,12aR,14R,15R)-8-[(1R)-1,2-dimethylpropyl]-15-hydroxy-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, (4-methoxyphenyl)methyl ester

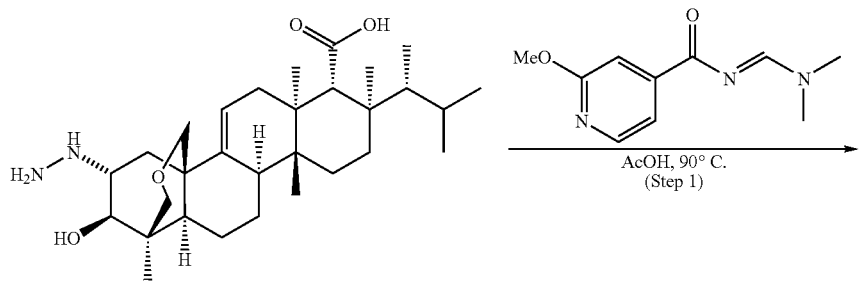

Intermediate 37

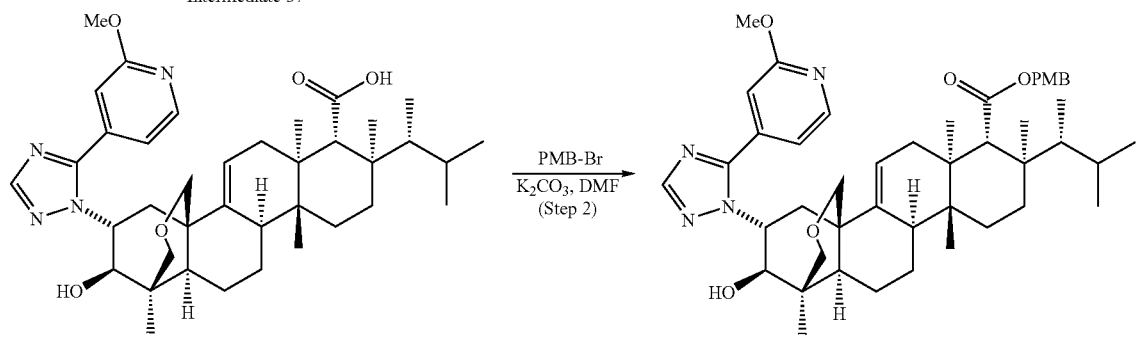

PMB = 4-methoxybenzyl

Intermediate 40

By procedures analogous to those described for Intermediate 38, the title compound was prepared starting with Intermediate 37.

Mass Spectrum: (ESI) m/z=768.0 (M+H).

Intermediate 41

(1S,4aR,6aS,7R,8R,10aR,10bR,12aR,14R,15R)-8-[(1R)-1,2-dimethylpropyl]-15-hydroxy-14-[5-(4-pyridinyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, (4-methoxyphenyl)methyl ester

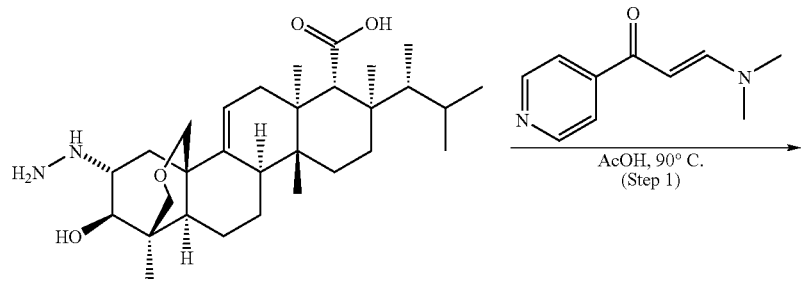

Intermediate 37

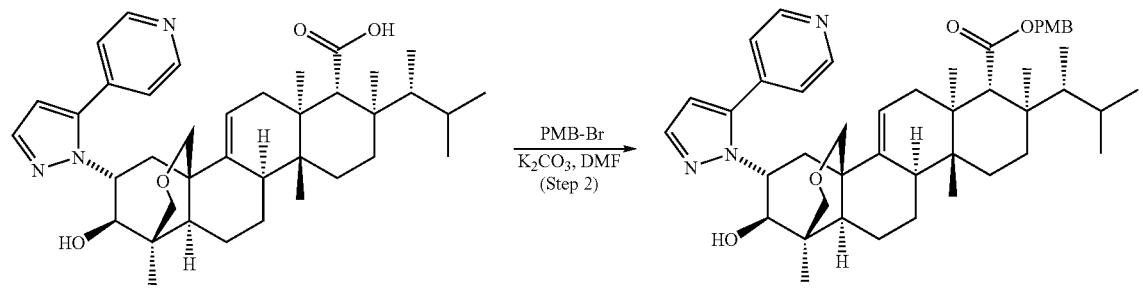

PMB = 4-methoxybenzyl

Intermediate 41

Step 1:

By a procedure analogous to that described for Intermediate 38 Step 1, but using 3-(dimethylamino)-1-(4-pyridinyl)-2-propen-1-one (cf. *J. Heterocyclic Chem.* 1977, 14, 345-347), the desired pyrazole compound was prepared starting with Intermediate 37.

$^1$H NMR (400 MHz, CDCl$_3$) δ 0.77 (d, J=7.17 Hz, 6H) 0.80-0.97 (m, 9H) 1.12 (s, 3H) 1.20 (s, 3H) 1.21-1.67 (m, 8H) 1.71-1.97 (m, 6H) 2.00-2.23 (m, 4H) 2.87 (s, 1H) 3.38 (d, J=10.98 Hz, 3H) 3.83 (d, J=11.91 Hz, 1H) 4.14 (d, J=9.18 Hz, 1H) 5.33 (d, J=6.05 Hz, 1H) 5.61 (dd, J=10.01, 4.34 Hz, 1H) 6.37 (d, J=1.85 Hz, 1H) 7.50 (d, J=6.10 Hz, 1H) 7.63 (d, J=1.85 Hz, 1H) 8.70 (d, J=6.10 Hz, 2H). LCMS: 616 (M+H).

Step 2:

By a procedure analogous to that described for Intermediate 38 Step 2, Intermediate 41 was prepared starting with the product compound from Step 1.

$^1$H NMR (400 MHz, CDCl$_3$) δ 0.70 (d, J=12.54 Hz, 6H) 0.79 (dd, J=10.47, 6.76 Hz, 6H) 0.84 (s, 3H) 1.09 (s, 3H) 1.14 (t, J=6.61 Hz, 2H) 1.21 (s, 3H) 1.23-1.63 (m, 7H) 1.69-1.88 (m, 5H) 1.97-2.20 (m, 4H) 2.82 (d, J=1.17 Hz, 1H) 2.95 (s, 1H) 3.33-3.46 (m, 3H) 3.79 (s, 3H) 3.82-3.88 (m, 1H) 4.11 (d, J=9.57 Hz, 1H) 4.48 (d, J=0.59 Hz, 1H) 4.81-5.06 (m, 2H) 5.27 (d, J=5.76 Hz, 1H) 5.60 (t, J=10.15 Hz, 1H) 6.35 (d, J=1.85 Hz, 1H) 6.86 (d, J=8.69 Hz, 2H) 7.22-7.28 (m, 2H) 7.60 (d, J=1.85 Hz, 1H).

Intermediate 42

(1S,4aR,6aS,7R,8R,10aR,10bR,12aR,14R,15R)-8-[(1R)-1,2-dimethylpropyl]-15-hydroxy-14-[5-(2-thienyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, (4-methoxyphenyl)methyl ester

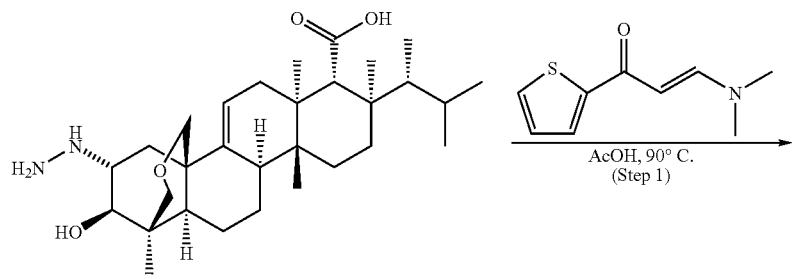

Intermediate 37

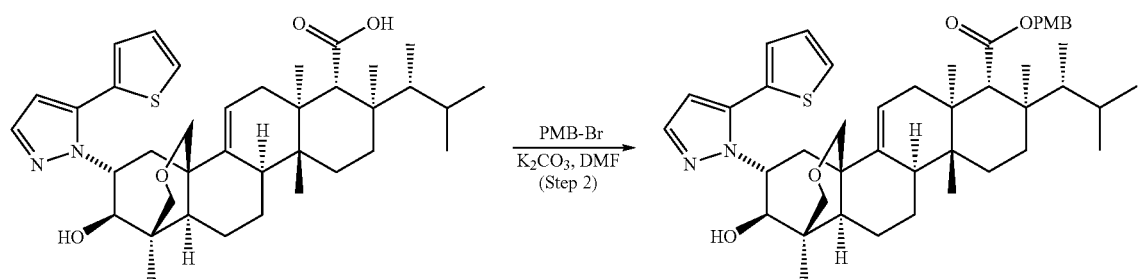

PMB = 4-methoxybenzyl

Intermediate 42

By procedures analogous to those described for Intermediate 41, Intermediate 42 was prepared starting with Intermediate 37.

$^1$H NMR (400 MHz, CDCl$_3$) δ 0.66-0.94 (m, 15H) 1.10 (s, 3H) 1.14 (dd, J=9.81, 2.34 Hz, 2H) 1.18-1.24 (m, 3H) 1.24-1.63 (m, 7H) 1.82 (d, J=14.30 Hz, 4H) 2.06 (t, J=13.50 Hz, 3H) 2.18 (s, 1H) 2.27 (dd, J=13.62, 6.25 Hz, 1H) 2.81 (s, 1H) 3.34-3.55 (m, 3H) 3.80 (s, 3H) 3.86 (d, J=11.96 Hz, 1H) 4.14 (d, J=7.61 Hz, 1H) 4.81-5.07 (m, 2H) 5.31 (dd, J=3.76, 1.90 Hz, 1H) 5.78 (ddd, J=11.95, 9.70, 6.17 Hz, 1H) 6.38 (d, J=1.81 Hz, 1H) 6.87 (d, J=8.69 Hz, 2H) 7.13 (dd, J=5.12, 3.61 Hz, 1H) 7.22-7.26 (m, 1H) 7.32 (dd, J=3.61, 1.12 Hz, 1H) 7.41 (dd, J=5.13, 1.02 Hz, 1H) 7.57 (d, J=1.56 Hz, 1H).

EXAMPLES

Unless otherwise indicated, compounds described in the following examples which contain a basic amine group were isolated as trifluoroacetic acid salts. Thus, where applicable, reference to a reaction "to give the title compound" or "to provide the title compound", "to give" a particular Example Number, "title compound was prepared", and similar language, refers the title compound as a TFA salt. Conversion to the parent free amines may be accomplished by standard methods known in the art (e.g. neutralization with an appropriate inorganic base such as NaHCO$_3$). Other desired amine salts may be prepared in a conventional manner by reacting the free base with a suitable organic or inorganic acid. Alternatively, a desired amine salt may be prepared directly from the trifluoroacetic acid salt by employing an appropriate ion exchange resin.

Example 1

(1S,4aR,6aS,7R,8R,8R,10aR,10bR,12aR,14R,15R)-15-[[(2R)-2-amino-2,3,3-trimethylbutyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 1A) and (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-(4H-1,2,4-triazol-4-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 1B)

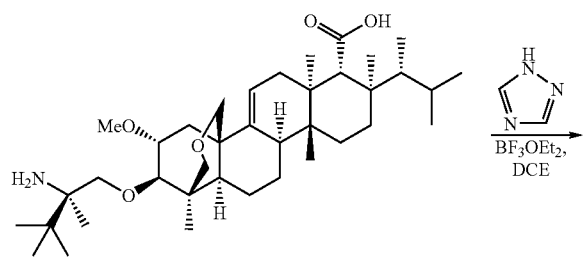

Intermediate 14

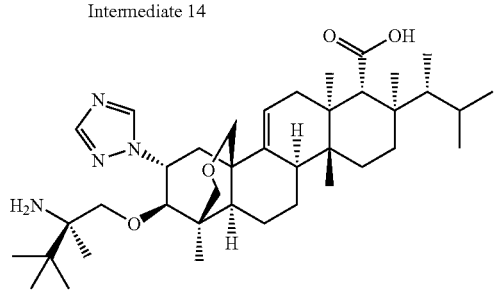

EXAMPLE 1A

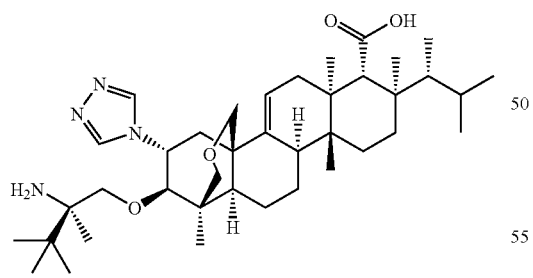

EXAMPLE 1B

A solution of Intermediate 14 (100 mg, 0.16 mmol) in dichloroethane (1.6 mL) was treated with 1H-1,2,4-triazole (56 mg, 0.8 mmol) then BF$_3$OEt$_2$ (0.21 mL, 1.6 mmol) and this mixture was heated to 50° C. under nitrogen. After 1.5 hours the reaction was cooled to room temperature then concentrated and dissolved in methanol. The reaction mixture was separated by preparative LCMS (30×100 mm Waters Sunfire column, 5 μm, Electrospray positive detection, 0-100% MeCN/water with 0.05% TFA over 12 minutes, using Masslynx software). The product fractions containing the major regioisomer were combined and partially concentrated by rotovap then frozen and lyophilized to give EXAMPLE 1A (84 mg) as a white amorphous solid. The product fractions containing the minor regioisomer were combined and partially concentrated by rotovap then frozen and lyophilized to give EXAMPLE 1B (2 mg) as a white amorphous solid.

Example 1A $^1$H NMR (CD$_3$OD, 500 MHz, ppm) δ 0.77 (d, J=7.1 Hz, 3H), 0.77 (s, 3H), 0.85 (s, 9H), 0.86 (d, 3H, partially obscured), 0.89 (s, 3H), 0.90 (d, 3H, partially obscured), 0.91 (s, 3H), 1.16 (s, 3H), 1.21 (s, 3H), 1.23-1.66 (m), 1.79-2.02 (m), 2.15 (m, 1H), 2.19 (m, 1H), 2.41 (dd, J=13.6 Hz, 6.5 Hz, 1H), 2.63 (d, J=9.8 Hz, 1H), 2.85 (s, 1H), 3.49 (d, J=11.8 Hz, 1H), 3.54 (dd, J=11.7 Hz, 1.9 Hz, 1H), 3.61 (d, 1H, partially obscured), 3.63 (d, 1H, partially obscured), 3.79 (d, J=9.8 Hz, 1H), 3.97 (d, J=11.9 Hz, 1H), 5.48 (m, 1H), 5.62 (m, 1H), 8.06 (s, 1H), 8.59 (s, 1H).

Mass Spectrum: (ESI) m/z=653.66 (M+H).

Example 1B $^1$H NMR (CD$_3$OD, 500 MHz, ppm) δ 0.77 (d, J=7.1 Hz, 3H), 0.77 (s, 3H), 0.85 (s, 9H), 0.86 (d, J=6.9 Hz, 3H), 0.88 (s, 3H), 0.91 (d, J=6.9 Hz, 3H), 1.17 (s, 3H), 1.21 (s, 3H), 1.23 (s, 3H), 1.22-1.66 (m), 1.8-2.05 (m), 2.15 (m, 1H), 2.19 (m, 1H), 2.42 (dd, J=13.5 Hz, 6.4 Hz, 1H), 2.64 (d, J=9.8 Hz, 1H), 2.85 (s, 1H), 3.27 (d, J=10.0 Hz, 1H), 3.50 (d, J=11.9 Hz, 1H), 3.54 (dd, J=11.7 Hz, 1.8 Hz, 1H), 3.62 (d, J=11.7 Hz, 1H), 3.74 (d, J=9.6 Hz, 1H), 3.90 (d, J=11.8 Hz, 1H), 5.49 (m, 1H), 5.60 (m, 1H), 8.08 (s, 1H), 8.58 (s, 1H).

Mass Spectrum: (ESI) m/z=653.66 (M+H).

Example 2

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

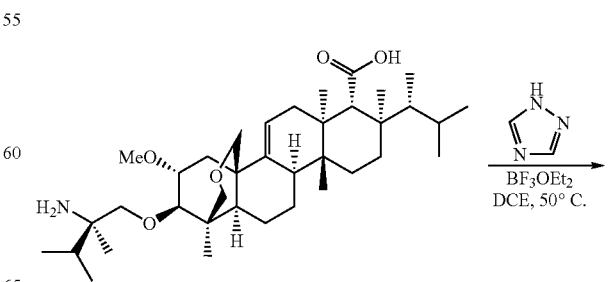

Intermediate 6

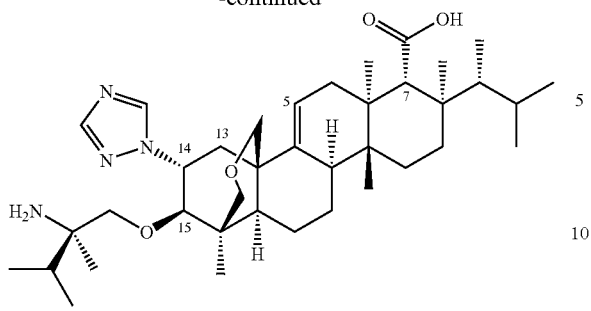

1H-1,2,4-triazole (43.7 mg, 0.633 mmol) and BF$_3$O(CH$_2$CH$_3$)$_2$ (150 μl, 1.184 mmol) were added to a stirred solution of Intermediate 6 (69.3 mg, 0.115 mmol) in 1,2-dichloroethane (1.2 ml). The reaction mixture was heated to 50° C. and was a hazy amber solution with undissolved chunks of 1,2,4-triazole. After 1.5 hours, LCMS and $^1$H NMR showed complete consumption of Intermediate 6. The reaction mixture was cooled to room temperature, the solvent was evaporated, and the resulting residue was placed under high vacuum. The residue was dissolved in methanol and purified using two HPLC runs (~35 mg/run) on a 19×150 mm Sunfire Prep C18 OBD 10 μm column by eluting with acetonitrile/water+0.1% TFA. The product HPLC fractions were combined, the solvent was evaporated under reduced pressure, and the residue was lyophilized from ethanol and benzene to give the title compound (52.1 mg) as a white solid.

$^1$H NMR (CD$_3$OD, 500 MHz, ppm) δ 0.78 (s, 3H, Me), 0.79 (d, 3H, Me), 0.81 (d, 3H, Me), 0.86 (d, 3H, Me), 0.88 (d, 3H, Me), 0.89 (s, 3H, Me), 0.92 (d, 3H, Me), 0.93 (s, 3H, Me), 1.18 (s, 3H, Me), 1.23 (s, 3H, Me), 1.24-1.37 (m), 1.41-1.47 (m), 1.49-1.68 (m), 1.78-2.04 (m), 2.12-2.25 (m), 2.42 (dd, 1H, H13), 2.62 (d, 1H), 2.86 (s, 1H, H7), 3.48 (d, 1H), 3.50 (d, 1H), 3.55 (dd, 1H), 3.62 (d, 1H), 3.78 (d, 1H), 3.96 (d, 1H), 5.50 (dd, 1H, H5), 5.58-5.66 (m, 1H, H14), 8.16 (broad s, 1H, triazole), 8.73 (broad s, 1H, triazole).

Mass Spectrum: (ESI) m/z=639.65 (M+H).

Example 3

(1S,4aR,6aS,7R,8R,10aR,10bR,12aR,14R,15R)-15-[[(2S)-2,3-dimethyl-2-(methylamino)butyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

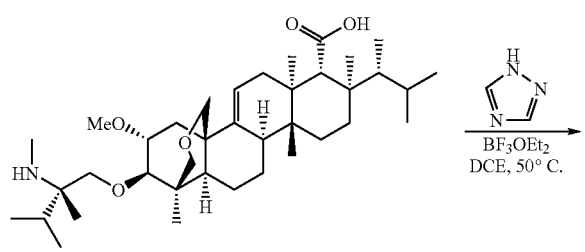

Intermediate 9

By a procedure analogous to that described in Example 2, but starting with Intermediate 9, the title compound was prepared and isolated as a white solid.

$^1$H NMR (CD$_3$OD, 600 MHz, ppm) δ 0.68 (d, 3H, Me), 0.76 (s, 3H, Me), 0.77 (d, 3H, Me), 0.84 (d, 3H, Me), 0.85 (d, 3H, Me), 0.89 (d, 3H, Me), 0.90 (s, 3H, Me), 1.11 (s, 3H, Me), 1.14 (s, 3H, Me), 1.20 (s, 3H, Me), 1.22-1.35 (m), 1.40-1.44 (m), 1.47-1.56 (m), 1.59-1.65 (m), 1.71-1.76 (m), 1.81-1.95 (m), 2.10-2.22 (m), 2.32 (s, 3H, NMe), 2.38 (dd, 1H, H13), 2.83 (s, 1H, H7), 2.96 (d, 1H), 3.51 (d, 1H), 3.52 (d, 1H), 3.53 (dd, 1H), 3.60 (d, 1H), 3.87 (d, 1H), 3.91 (d, 1H), 5.46 (dd, 1H, H5), 5.55-5.62 (m, 1H, H14), 8.07 (s, 1H, triazole), 8.57 (s, 1H, triazole).

Mass Spectrum: (ESI) m/z=653.65 (M+H).

Example 4

(1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

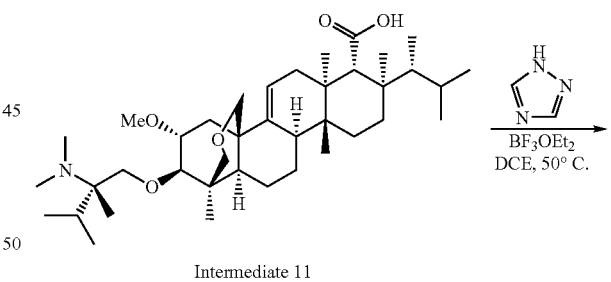

Intermediate 11

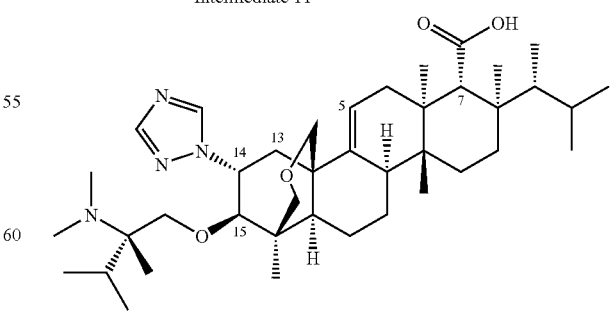

By a procedure analogous to that described in Example 2, but starting with Intermediate 11, the title compound was prepared and isolated as a white solid.

¹H NMR (CD₃OD, 600 MHz, ppm) δ 0.74 (d, 3H, Me), 0.76 (s, 3H, Me), 0.77 (d, 3H, Me), 0.85 (d, 3H, Me), 0.87 (d, 3H, Me), 0.89 (d, 3H, Me), 0.91 (s, 3H, Me), 1.14 (s, 3H, Me), 1.18 (s, 3H, Me), 1.20 (s, 3H, Me), 1.22-1.35 (m), 1.39-1.44 (m), 1.47-1.56 (m), 1.58-1.65 (m), 1.79-2.02 (m), 2.09-2.21 (m), 2.38 (dd, 1H, H13), 2.74 (s, 3H, NMe), 2.75 (s, 3H, NMe), 2.83 (s, 1H, H7), 3.08 (d, 1H), 3.52 (d, 2H), 3.60 (d, 1H), 3.61 (d, 1H), 3.81 (d, 1H), 3.91 (d, 1H), 5.46 (dd, 1H, H5), 5.57-5.64 (m, 1H, H14), 8.08 (s, 1H, triazole), 8.67 (s, 1H, triazole).

Mass Spectrum: (ESI) m/z=667.68 (M+H).

Example 5

(1S,4aR,6aS,7R,8R,10aR,10bR,12aR,14R,15R)-14-(3-amino-1H-1,2,4-triazol-1-yl)-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

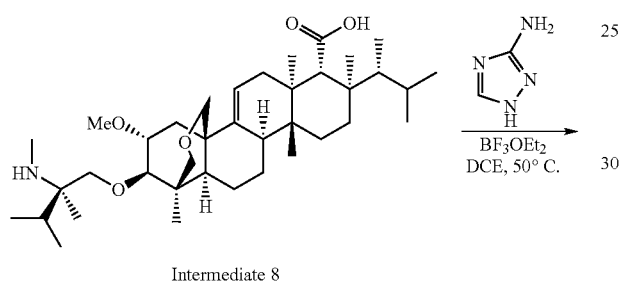

Intermediate 8

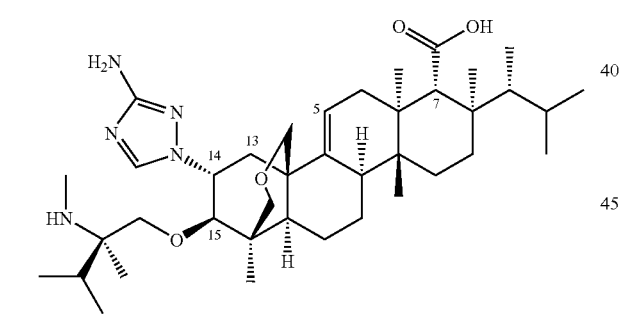

3-amino-1,2,4-triazole (13.8 mg, 0.164 mmol) and BF₃O(CH₂CH₃)₂ (41 µl, 0.324 mmol) were added to a stirred solution of Intermediate 8 (20.2 mg, 0.033 mmol) in 1,2-dichloroethane (0.33 ml). The reaction mixture was a yellow suspension that was heated to 50° C. After 3 hours, LCMS and ¹H NMR showed complete consumption of Intermediate 8. The reaction mixture was cooled to room temperature, the solvent was evaporated, and the resulting residue was placed under high vacuum. The residue was dissolved in methanol and purified using a single HPLC run on a 19×150 mm Sunfire Prep C18 OBD 10 µm column by eluting with acetonitrile/water+0.1% TFA. The product HPLC fractions were combined, the solvent was evaporated under reduced pressure, and the residue was lyophilized from ethanol and benzene to give the title compound (16.3 mg) as a white solid.

¹H NMR (CD₃OD, 600 MHz, ppm) δ 0.76 (s, 3H, Me), 0.77 (d, 3H, Me), 0.85 (d, 3H, Me), 0.86 (d, 3H, Me), 0.87 (s, 3H, Me), 0.90 (d, 3H, Me), 0.90 (d, 3H, Me), 0.94 (s, 3H, Me), 1.15 (s, 3H, Me), 1.20 (s, 3H, Me), 1.22-1.34 (m), 1.39-1.44 (m), 1.47-1.65 (m), 1.73-1.96 (m), 2.00-2.07 (m), 2.09-2.14 (m), 2.15-2.22 (m), 2.34 (dd, 1H, H13), 2.46 (s, 3H, NMe), 2.84 (s, 1H, H7), 3.01 (d, 1H), 3.47 (d, 1H), 3.51 (dd, 1H), 3.57 (d, 1H), 3.63 (d, 1H), 3.74 (d, 1H), 3.85 (d, 1H), 5.29-5.35 (m, 1H, H14), 5.48 (dd, 1H, H5), 8.22 (s, 1H, triazole).

Mass Spectrum: (ESI) m/z=668.65 (M+H).

Example 6

(1S,4aR,6aS,7R,8R,10aR,10bR,12aR,14R,15R)-15-[[(2R)-2-amino-2,3-dimethylbutyl]oxy]-14-(3-bromo-4H-1,2,4-triazol-4-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 6A) and (1S,4aR,6aS,7R,8R,10aR,10bR,12aR,14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 6B) and (1S,4aR,6aS,7R,8R,10aR,10bR,12aR,14R,15R)-15-[[(2R)-2-amino-2,3-dimethylbutyl]oxy]-14-(3-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 6C)

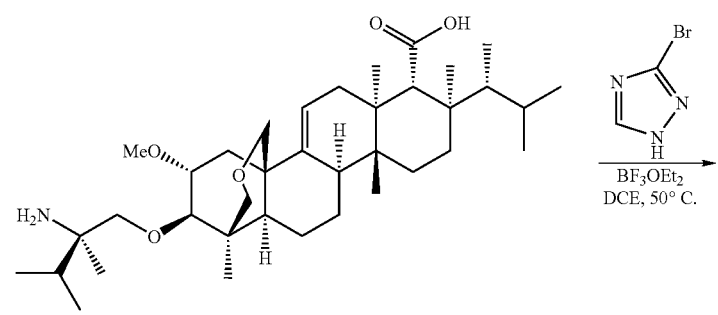

Intermediate 6

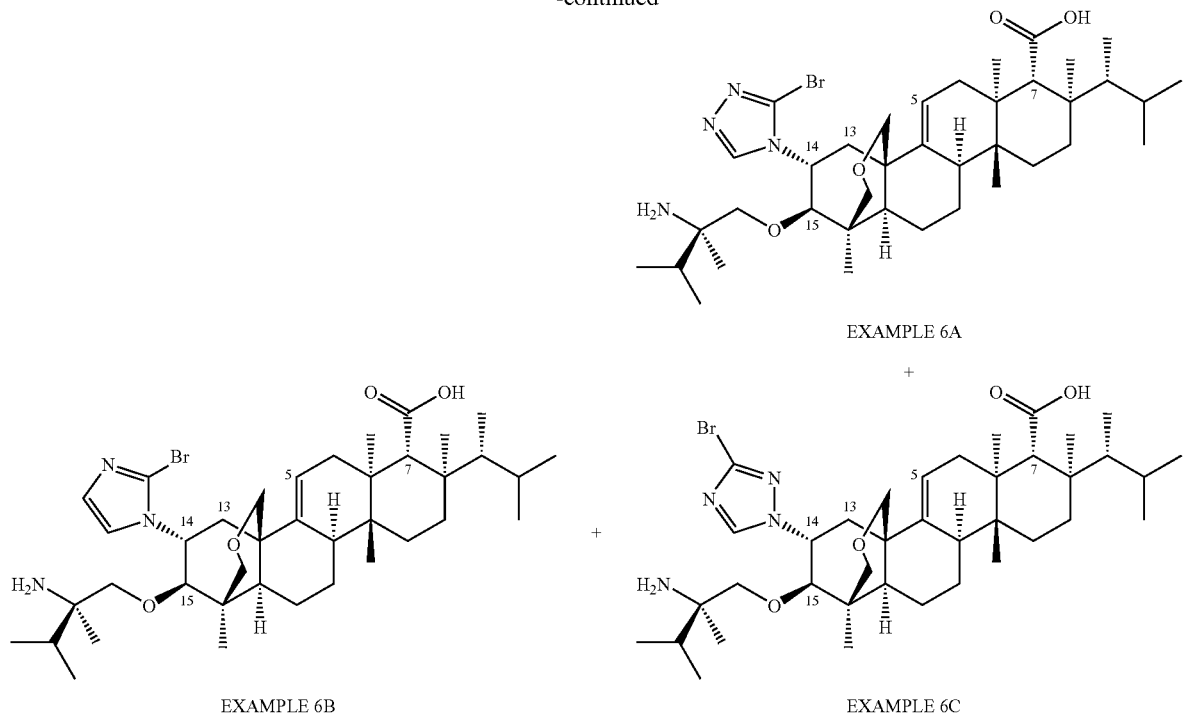

EXAMPLE 6A

EXAMPLE 6B

EXAMPLE 6C 3-bromo-1H-1,2,4-triazole (32.1 mg, 0.217 mmol) and BF$_3$OEt$_2$ (54 μl, 0.426 mmol) were added to a stirred solution of Intermediate 6 (26.0 mg, 0.043 mmol) in 1,2-dichloroethane (0.43 ml). The reaction mixture was a light yellow solution that was heated to 50° C. After 1.75 hr, LCMS and $^1$H NMR showed complete consumption of Intermediate 6. The reaction mixture was cooled to room temperature, the solvent was evaporated, and the resulting residue was placed under high vacuum. The residue was dissolved in methanol and separated using a single HPLC run on a 19×150 mm Sunfire Prep C18 OBD 10 μm column by eluting with acetonitrile/water+0.1% TFA. The HPLC fractions containing the fastest eluting regioisomer were combined, the solvent was evaporated under reduced pressure, and the residue was lyophilized from ethanol and benzene to give EXAMPLE 6A (3.6 mg) as a white solid. The HPLC fractions containing the second eluting regioisomer were combined, the solvent was evaporated under reduced pressure, and the residue was lyophilized from ethanol and benzene to give EXAMPLE 6B (13.1 mg) as a white solid. The HPLC fractions containing the slowest eluting regioisomer were combined, the solvent was evaporated under reduced pressure, and the residue was lyophilized from ethanol and benzene to give EXAMPLE 6C (5.8 mg) as a white solid.

Example 6A $^1$H NMR (CD$_3$OD, 600 MHz, ppm) δ 0.76 (s, 3H, Me), 0.76 (d, 3H, Me), 0.81 (d, 3H, Me), 0.84 (d, 3H, Me), 0.85 (d, 3H, Me), 0.88 (s, 3H, Me), 0.89 (d, 3H, Me), 0.94 (s, 3H, Me), 1.16 (s, 3H, Me), 1.20 (s, 3H, Me), 1.22-1.35 (m), 1.40-1.44 (m), 1.46-1.65 (m), 1.73-1.96 (m), 2.11-2.22 (m), 2.43 (broad dd, 1H, H13), 2.79 (broad d, 1H), 2.84 (s, 1H, H7), 3.49 (d, 1H), 3.53 (d, 2H), 3.60 (d, 1H), 3.73 (broad d, 1H), 3.94 (d, 1H), 5.50 (dd, 1H, H5), 5.72-5.80 (broad m, 1H, H14), 9.29 (broad s, 1H, triazole).

Mass Spectrum: (ESI) m/z=717.32 (719.32) (M+H).

Example 6B $^1$H NMR (CD$_3$OD, 600 MHz, ppm) δ 0.75 (s, 3H, Me), 0.76 (d, 3H, Me), 0.79 (d, 3H, Me), 0.83 (d, 3H, Me), 0.84 (d, 3H, Me), 0.88 (s, 3H, Me), 0.89 (d, 3H, Me), 0.91 (s, 3H, Me), 1.13 (s, 3H, Me), 1.19 (s, 3H, Me), 1.22-1.34 (m), 1.39-1.43 (m), 1.46-1.56 (m), 1.58-1.64 (m), 1.72-1.95 (m), 2.09-2.21 (m), 2.30 (dd, 1H, H13), 2.83 (s, 1H, H7), 2.85 (d, 1H), 3.48 (d, 1H), 3.48 (d, 1H), 3.54 (dd, 1H), 3.60 (d, 1H), 3.88 (d, 1H), 3.95 (d, 1H), 5.47 (dd, 1H, H5), 5.71-5.77 (m, 1H, H14), 8.10 (s, 1H, triazole).

Mass Spectrum: (ESI) m/z=717.32 (719.32) (M+H).

Example 6C $^1$H NMR (CD$_3$OD, 600 MHz, ppm) δ 0.76 (s, 3H, Me), 0.77 (d, 3H, Me), 0.82 (d, 3H, Me), 0.85 (d, 3H, Me), 0.86 (s, 3H, Me), 0.86 (d, 3H, Me), 0.89 (d, 3H, Me), 0.92 (s, 3H, Me), 1.16 (s, 3H, Me), 1.20 (s, 3H, Me), 1.22-1.34 (m), 1.39-1.44 (m), 1.48-1.65 (m), 1.76-1.96 (m), 2.11-2.22 (m), 2.41 (dd, 1H, H13), 2.72 (d, 1H), 2.84 (s, 1H, H7), 3.47 (d, 1H), 3.50 (d, 1H), 3.52 (dd, 1H), 3.58 (d, 1H), 3.72 (d, 1H), 3.91 (d, 1H), 5.48 (dd, 1H, H5), 5.51-5.57 (m, 1H, H14), 8.52 (s, 1H, triazole).

Mass Spectrum: (ESI) m/z=717.32 (719.32) (M+H).

Example 7

(1S,4aR,6aS,7R,8R,10aR,10bR,12aR,14R,15R)-15-[[(2R)-2-amino-2,3-dimethylbutyl]oxy]14-(3-cyano-4H-1,2,4-triazol-4-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-penanthro[1,2-c]pyran-7-carboxylic acid (EXAMPLE 7A) and (1S,4aR,6aS,7R,8R,10aR,10bR,12aR,14R,15R)-15-[[(2R)-2-amino-2,3-dimethylbutyl]oxy]14-(5-cyano-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 7B) and (1S,4aR,6aS,7R,8R,10aR,10bR,12aR,14R,15R)-15-[[(2R)-2-amino-2,3-dimethylbutyl]oxy]14-(3-cyano-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 7C)

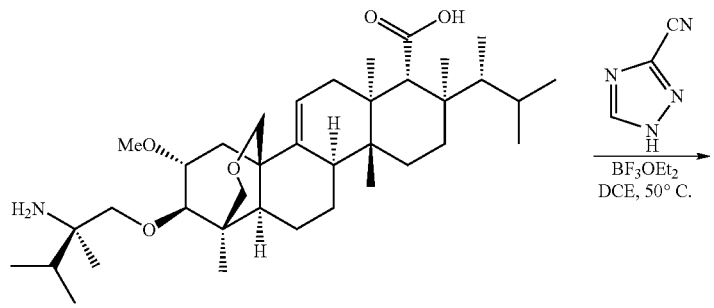

Intermediate 6

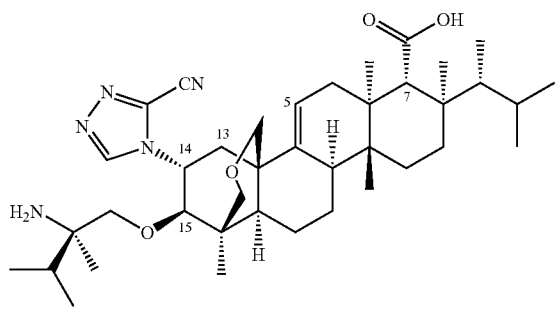

EXAMPLE 7A

+

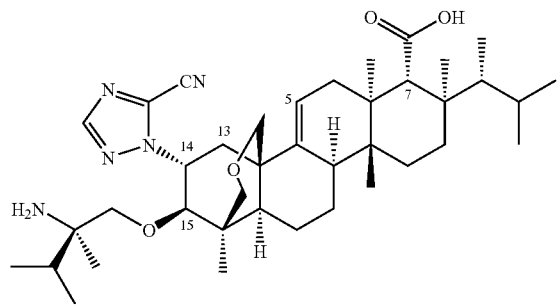

EXAMPLE 7B

+

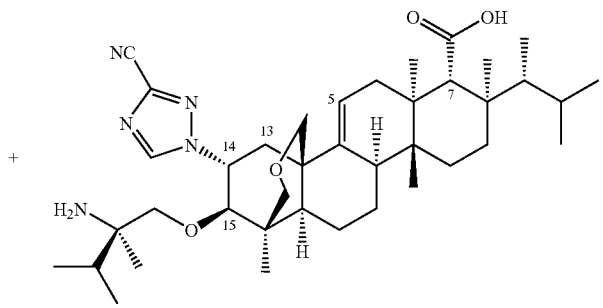

EXAMPLE 7C

A suspension of Intermediate 6 (28 mg, 0.041 mmol), 1H-1,2,4-triazole-3-carbonitrile (24 mg, 0.255 mmol) and boron trifluoride diethyl etherate (50 μL, 0.388 mmol) in dichloroethane (0.7 mL) was blanketed with nitrogen and placed in a 50° C. oil bath for 2 hours. The mixture was cooled to room temperature, evaporated and the residual oil was separated by reverse phase HPLC using a 19×150 mm Sunfire Preparative C18 OBD column. The HPLC fractions containing the fastest eluting regioisomer were combined, the solvent was evaporated under reduced pressure, and the residue was lyophilized from ethanol and benzene to give EXAMPLE 7A (3.2 mg) as a white solid. The HPLC fractions containing the second eluting regioisomer were combined, the solvent was evaporated under reduced pressure, and the residue was lyophilized from ethanol and benzene to give EXAMPLE 7B (3.9 mg) as a white solid. The HPLC fractions containing the slowest eluting regioisomer were combined, the solvent was evaporated under reduced pressure, and the residue was lyophilized from ethanol and benzene to give EXAMPLE 7C (15.5 mg) as a white solid.

Example 7A $^1$H NMR (CD$_3$OD, 600 MHz, ppm) δ 0.77 (s, 3H, Me), 0.77 (d, 3H, Me), 0.80 (d, 3H, Me), 0.84 (d, 3H, Me), 0.85 (d, 3H, Me), 0.88 (s, 3H, Me), 0.89 (d, 3H, Me), 1.00 (s, 3H, Me), 1.17 (s, 3H, Me), 1.21 (s, 3H, Me), 1.23-1.36 (m), 1.41-1.45 (m), 1.48-1.65 (m), 1.75-1.98 (m), 2.13-2.21 (m), 2.58 (d, 1H), 2.63 (dd, 1H, H13), 2.84 (s, 1H, H7), 3.51 (d, 1H), 3.54 (d, 1H), 3.55 (dd, 1H), 3.59 (d, 1H), 3.64 (d, 1H), 3.67 (d, 1H), 3.97 (d, 1H), 5.54 (dd, 1H, H5), 5.73 (m, 1H, H14), 9.21 (s, 1H, triazole).

Mass spectrum: (ESI) m/z=664.35 (M+H).

Example 7B $^1$H NMR (CD$_3$OD, 600 MHz, ppm) δ 0.78 (s, 3H, Me), 0.78 (d, 3H, Me), 0.79 (d, 3H, Me), 0.84 (d, 3H, Me), 0.85 (d, 3H, Me), 0.88 (s, 3H, Me), 0.89 (d, 3H, Me), 0.95 (s, 3H, Me), 1.14 (s, 3H, Me), 1.20 (s, 3H, Me), 1.22-1.35 (m), 1.40-1.44 (m), 1.48-1.57 (m), 1.59-1.65 (m), 1.75-2.01 (m), 1.98-2.05 (m), 2.11-2.21 (m), 2.49 (dd, 1H, H13), 2.60 (d, 1H), 2.84 (s, 1H, H7), 3.50 (d, 1H), 3.51 (d, 1H), 3.56 (dd, 1H), 3.65 (d, 1H), 3.84 (d, 1H), 3.99 (d, 1H), 4.05 (d, 1H), 5.51 (dd, 1H, H5), 5.87 (m, 1H, H14), 8.27 (s, 1H, triazole).

Mass spectrum: (ESI) m/z=664.35 (M+H).

Example 7C $^1$H NMR (CD$_3$OD, 600 MHz, ppm) δ 0.76 (s, 3H, Me), 0.77 (d, 3H, Me), 0.82 (d, 1H, Me), 0.85 (d, 3H, Me), 0.86 (d, 3H, Me), 0.88 (s, 3H, Me), 0.89 (s, 3H, Me), 0.89 (d, 3H, Me), 0.99 (d, 3H, Me), 1.15 (s, 3H, Me), 1.21 (s, 3H, Me), 1.22-1.34 (m), 1.40-1.44 (m), 1.48-1.58 (m), 1.59-1.65 (m), 1.80-1.96 (m), 2.11-2.21 (m), 2.45 (dd, 1H, H13), 2.65 (d, 1H), 2.84 (s, 1H, H7), 3.50 (d, 1H), 3.48 (d, 1H), 3.53 (dd, 1H), 3.53 (d, 1H), 3.59 (d, 1H), 3.78 (d, 1H), 3.92 (d, 1H), 4.05 (d, 1H), 5.48 (dd, 1H, H5), 5.69 (m, 1H, H14), 8.76 (s, 1H, triazole).

Mass spectrum: (ESI) m/z=664.35 (M+H).

Example 8

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[3-(methoxycarbonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 8A) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(methoxycarbonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 8B)

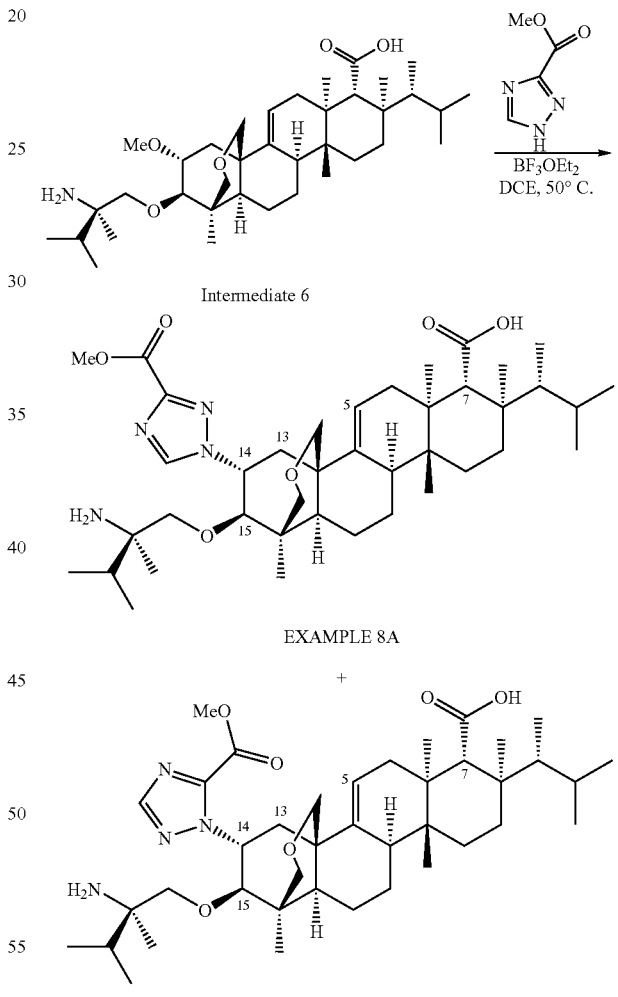

Methyl 1,2,4-triazole-3-carboxylate (27.1 mg, 0.213 mmol) and BF$_3$OEt$_2$ (54 μl, 0.426 mmol) were added to a stirred solution of Intermediate 6 (25.9 mg, 0.043 mmol) in 1,2-dichloroethane (0.43 ml). The reaction mixture was a light yellow suspension that was heated at 50° C. for 7.5 hr and then stirred at room temperature for 64 hr. The solvent was evaporated and the resulting residue was placed under high vacuum. The residue was dissolved in methanol and separated using a single HPLC run on a 19×150 mm Sunfire Prep C18 OBD 10 μm column by eluting with acetonitrile/water+0.1% TFA. The HPLC fractions of the faster eluting regioisomer were combined, the solvent was evaporated under reduced pressure, and the residue was lyophilized from ethanol and benzene to give EXAMPLE 8A (8.9 mg, 10.97 μmol) as a white solid. The HPLC fractions of the slower eluting regioisomer were combined, the solvent was evaporated under reduced pressure, and the residue was lyophilized from ethanol and benzene to give EXAMPLE 8B (1.5 mg, 1.85 μmol) as a white solid.

Example 8A $^1$H NMR (CD$_3$OD, 600 MHz, ppm) δ 0.76 (s, 3H, Me), 0.76 (d, 3H, Me), 0.79 (d, 3H, Me), 0.83 (d, 3H, Me), 0.85 (d, 3H, Me), 0.88 (s, 3H, Me), 0.88 (s, 3H, Me), 0.89 (d, 3H, Me), 1.16 (s, 3H, Me), 1.20 (s, 3H, Me), 1.22-1.35 (m), 1.39-1.44 (m), 1.47-1.65 (m), 1.78-2.02 (m), 2.10-2.22 (m), 2.46 (dd, 1H, H13), 2.66 (d, 1H), 2.83 (s, 1H, H7), 3.48 (d, 1H), 3.50 (d, 1H), 3.53 (dd, 1H), 3.60 (d, 1H), 3.77 (d, 1H), 3.92 (d, 1H), 3.95 (s, 3H, COOMe), 5.48 (dd, 1H, H5), 5.61-5.68 (m, 1H, H14), 8.77 (broad s, 1H, triazole).

Mass Spectrum: (ESI) m/z=697.42 (M+H).

Example 8B $^1$H NMR (CD$_3$OD, 600 MHz, ppm) δ 0.76 (s, 3H, Me), 0.76 (d, 3H, Me), 0.79 (s, 3H, Me), 0.79 (d, 3H, Me), 0.82 (d, 3H, Me), 0.85 (d, 3H, Me), 0.88 (s, 3H, Me), 0.89 (d, 3H, Me), 1.13 (s, 3H, Me), 1.20 (s, 3H, Me), 1.22-1.36 (m), 1.39-1.44 (m), 1.47-1.55 (m), 1.59-1.65 (m), 1.72-1.96 (m), 2.10-2.22 (m), 2.46 (dd, 1H, H13), 2.78 (d, 1H), 2.84 (s, 1H, H7), 3.48 (d, 1H), 3.50 (d, 1H), 3.55 (dd, 1H), 3.62 (d, 1H), 3.93 (d, 1H), 3.98 (d, 1H), 3.99 (s, 3H, COOMe), 5.47 (dd, 1H, H5), 6.53-6.59 (m, 1H, H14), 8.14 (s, 1H, triazole).

Mass Spectrum: (ESI) m/z=697.42 (M+H).

Example 9

(1S,4aR,6aS,7R,8R,10aR,10bR,12aR,14R,15R)-14-(3-chloro-4H-1,2,4-triazol-4-yl)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (EXAMPLE 9A) and (1S,4aR,6aS,7R,8R,10aR,10bR,12aR,14R,15R)-14-(5-chloro-1H-1,2,4-triazol-1-yl)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (EXAMPLE 9B) and (1S,4aR,6aS,7R,8R,10aR,10bR,12aR,14R,15R)-14-(3-chloro-1H-1,2,4-triazol-1-yl)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (EXAMPLE 9C)

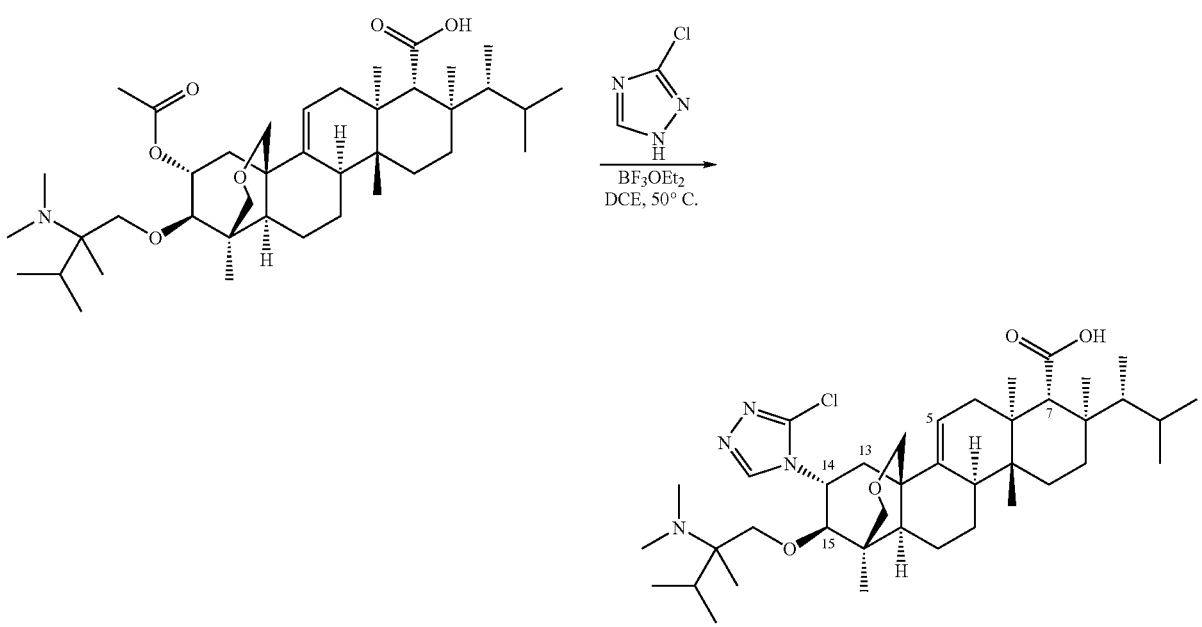

EXAMPLE 9A

+

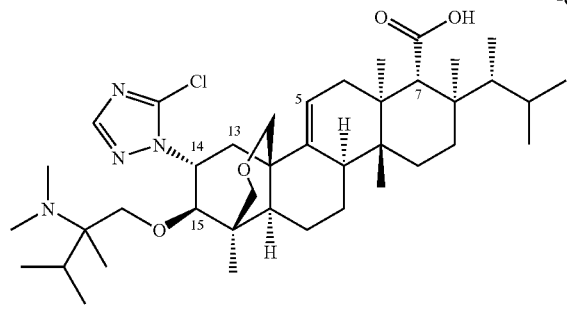

EXAMPLE 9B

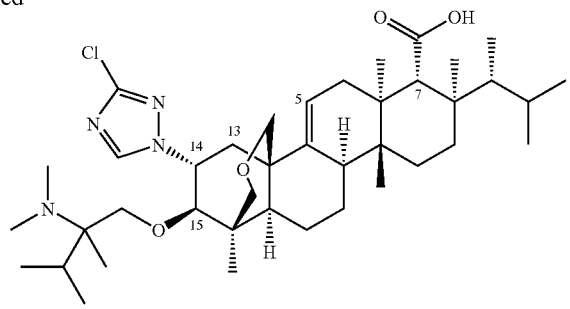

EXAMPLE 9C

A suspension of (1S,4aR,6aS,7R,8R,10aR,10bR,12aR, 14R,15R)-14-(acetyloxy)-15-[2-(dimethylamino)-2,3-dimethylbutoxy]-8-[(1R)-1,2-dimethylpropyl]-1,6,6a,7,8,9,10, 10a,10b,11,12,12a-dodecahydro-1,6a,8,10a-tetramethyl-6-oxo-4H-1,4a-propano-2H-phenanthro[1,2-c]pyran-7-carboxylic acid (the compound of Example 130 in International Patent Publication No. WO 2007/127012, herein incorporated by reference in its entirety; 20 mg, 0.03 mmol), 3-chloro-1H-1,2,4-triazole (26.8 mg, 0.259 mmol) and boron trifluoride etherate (75 μL, 0.592 mmol) in dichloroethane (0.7 mL) was blanketed with nitrogen and placed in a 50° C. oil bath for 24 hours. The mixture was cooled to room temperature, evaporated and the residual oil was separated by reverse phase HPLC using a 19×150 mm Sunfire Preparative C18 OBD column. The product containing fractions were evaporated and freeze-dried from a mixture of ethanol and benzene to give EXAMPLE 9A as a white solid (3.4 mg), EXAMPLE 9B as a white solid (2.0 mg) and EXAMPLE 9C as a white solid (2.0 mg).

Example 9A $^1$H NMR (CD$_3$OD, 600 MHz, ppm) δ 0.70 (d, 3H, Me), 0.77 (d, 3H, Me), 0.80 (s, 3H, Me), 0.86-0.98 (multiple Me signals), 1.09 (s, 3H, Me), 1.16 (s, 3H, Me), 1.18 (s, 3H, Me), 1.29-1.48 (m), 1.52-1.57 (m), 1.70 (s, 3H, Me), 1.67-1.86 (m), 1.94-1.99 (m), 2.20-2.26 (m), 2.52 (dd, 1H, H13), 2.54 (dd, 1H, H13), 2.74 (s, NMe2), 2.80 (s, NMe2), 2.82 (s, NMe2), 2.85 (s, NMe2), 3.09 (s, 1H, H7), 3.58 (d, 1H), 3.62 (dd, 1H), 3.68 (d, 1H), 3.79 (d, 1H), 3.85 (d, 1H), 5.60 (br m, 1H, H14), 5.79 (dd, 1H, H5), 5.80 (dd, 1H, H5), 9.04 (br s, 1H, triazole).

Mass spectrum: (ESI) m/z=715.38 (M+H).

Example 9B $^1$H NMR (CD$_3$OD, 600 MHz, ppm) δ 0.72 (d, 3H, Me), 0.76 (d, 3H, Me), 0.80 (s, 3H, Me), 0.88 (d, 3H, Me), 0.89 (d, 3H, Me), 0.91 (d, 3H, Me), 0.92 (d, 3H, Me), 0.95 (d, 3H, Me), 0.96 (s, 3H, Me), 1.09 (s, 3H, Me), 1.16 (s, 3H, Me), 1.29-1.48 (m), 1.52-1.57 (m), 1.67 (s, 3H, Me), 1.68-1.86 (m), 1.90-1.99 (m), 2.04-2.09 (m), 2.19-2.26 (m), 2.37 (dd, 1H, H13), 2.39 (dd, 1H, H13), 2.66-2.72 (m), 2.71 (s, NMe2), 2.79 (s, NMe2), 2.81 (d, 1H), 3.09 (s, 1H, H7), 3.17 (d, 1H), 3.57 (d, 1H), 3.60-3.64 (m), 3.68 (dd, 1H), 3.72 (d, 1H), 3.80 (d, 1H), 3.86 (d, 1H), 3.99 (d, 1H), 4.20 (d, 1H), 5.72 (m, 1H, H14), 5.77 (dd, 1H, H5), 8.07 (s, 1H, triazole).

Mass spectrum: (ESI) m/z=715.38 (M+H).

Example 9C $^1$H NMR (CD$_3$OD, 600 MHz, ppm) δ 0.72 (d, 3H, Me), 0.75 (d, 3H, Me), 0.77 (d, 3H, Me), 0.80 (s, 3H, Me), 0.86- 0.96 (multiple Me signals), (s, 3H, Me), 1.03 (s, 3H, Me), 1.05 (s, 3H, Me), 1.09 (s, 3H, Me), 1.17 (s, 3H, Me), 1.19 (s, 3H, Me), 1.28-1.48 (m), 1.50 (s, 3H, Me), 1.52-1.54 (m), 1.69 (s, 3H, Me), 1.60-1.81 (m), 1.90-1.98 (m), 2.20-2.26 (m), 2.46 (dd, 1H, H13), 2.48 (dd, 1H, H13), 2.76 (s, NMe2), 2.80 (s, NMe2), 2.81 (d, 1H), 3.09 (s, 1H, H7), 3.10 (s, 1H, H7), 3.52-3.68 (m), 3.71-3.90 (m), 5.60 (m, 1H, H14), 5.76 (dd, 1H, H5), 8.63 (s, 1H, triazole).

Mass spectrum: (ESI) m/z=715.38 (M+H).

Example 10

(1S,4aR,6aS,7R,8R,10aR,10bR,12aR,14R,15R)-15-[[(2R)-2-amino-2,3,3-trimethylbutyl]oxy]-14-(5-chloro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

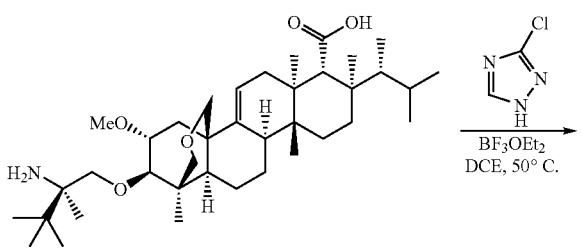

Intermediate 14

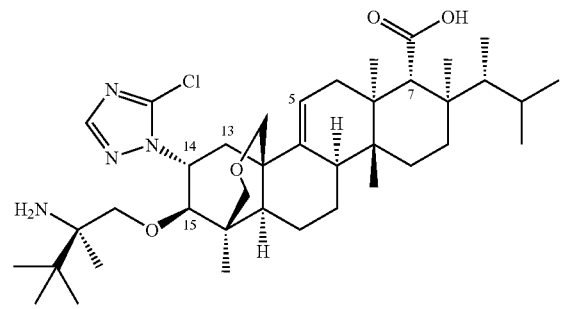

By a procedure analogous to that described in Example 9, but starting with Intermediate 14, the title compound was prepared and isolated as a white solid.

$^1$H NMR (CD$_3$OD, 500 MHz, ppm) δ 0.77 (d, J=7.4 Hz, 3H), 0.77 (s, 3H), 0.86 (d, 3H, partially obscured), 0.87 (s, 9H), 0.90 (d, J=6.6 Hz, 3H), 0.90 (s, 3H), 0.94 (s, 3H), 1.15 (s, 3H), 1.21 (s, 3H), 1.23-1.47 (m), 1.47-1.68 (m), 1.78-1.96 (m), 2.14 (m, 1H), 2.19 (m, 1H), 2.34 (dd, J=13.5 Hz, 6.4 Hz, 1H), 2.84 (s, 1H), 2.89 (d, J=9.8 Hz, 1H), 3.51 (d, J=11.9 Hz, 1H), 3.56 (dd, J=11.6 Hz, 2.0 Hz, 1H), 3.62 (d, J=11.6 Hz, 1H), 3.67 (d, J=10.1 Hz, 1H), 3.89 (d, J=9.9 Hz, 1H), 3.98 (d, J=12.1 Hz, 1H), 5.50 (m, 1H), 5.73 (m, 1H), 8.04 (s, 1H).

Mass spectrum: (ESI) m/z=687.65 (M+H).

Example 11

(1S,4aR,6aS,7R,8R,10aR,10bR,12aR,14R,15R)-15-[[(2R)-2-amino-2,3,3-trimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

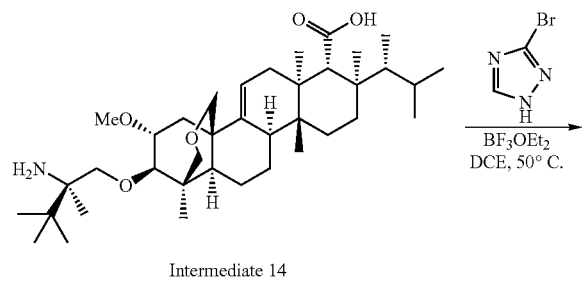

Intermediate 14

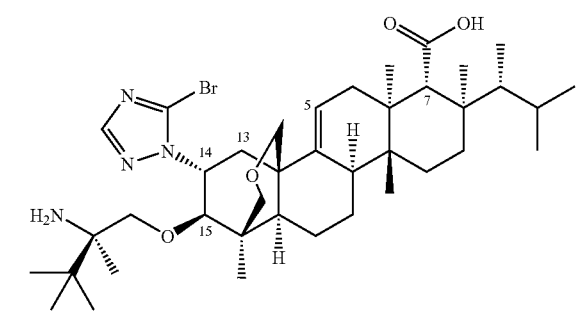

By a procedure analogous to that described in Example 6, but starting with Intermediate 14, the title compound was prepared and isolated as a white solid.

¹H NMR (CD₃OD, 500 MHz, ppm) δ 0.77 (d, 3H, partially obscured), 0.77 (s, 3H), 0.86 (d, 3H, partially obscured), 0.86 (s, 9H), 0.90 (d, 3H, partially obscured), 0.90 (s, 3H), 0.93 (s, 3H), 1.15 (s, 3H), 1.21 (s, 3H), 1.22-1.67 (m), 1.78-1.98 (m), 2.14 (m, 1H), 2.19 (m, 1H), 2.32 (dd, J=13.5 Hz, 6.4 Hz, 1H), 2.84 (s, 1H), 2.91 (d, J=10.1 Hz, 1H), 3.51 (d, J=11.8 Hz, 1H), 3.56 (dd, J=11.7 Hz, 1.9 Hz, 1H), 3.62 (d, J=11.6 Hz, 1H), 3.65 (d, J=9.8 Hz, 1H), 3.93 (d, J=9.8 Hz, 1H), 3.99 (d, J=11.9 Hz, 1H), 5.49 (m, 1H), 5.78 (m, 1H), 8.08 (s, 1H).

Mass spectrum: (ESI) m/z=733.58, 735.57 (M+H).

Example 12

(1S,4aR,6aS,7R,8R,10aR,10bR,12aR,14R,15R)-8-[(1R)-1,2-dimethylpropyl]-15-[[tetrahydro-4-(methylamino)-2H-pyran-4-yl]methoxy]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

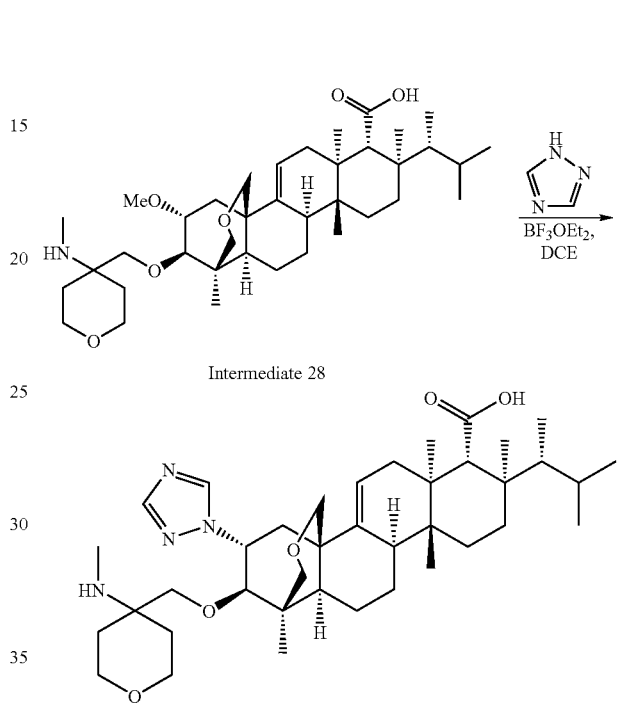

A solution of Intermediate 28 (120 mg, 0.191 mmol) in dichloroethane (1.3 mL) was treated with 1H-1,2,4-triazole (65.8 mg, 0.953 mmol) then BF₃OEt₂ (0.241 mL, 1.91 mmol) and this mixture was heated to 55° C. under nitrogen. After 1 hour the reaction was cooled to room temperature then concentrated in vacuo. The crude product mixture was suspended in methanol (3 mL) and filtered through a sintered glass funnel. The filtrate was purified by preparative HPLC (19× 100 mm Waters Sunfire column, 5 μm, UV-detection, 30-100% MeCN/water with 0.05% TFA over 20 minutes). The fractions containing the desired product (major regioisomer) were combined and partially concentrated by rotovap then frozen and lyophilized to give the title compound (65 mg) was a white amorphous solid.

¹H NMR (CD₃OD, 500 MHz, ppm) δ 0.78 (s, 3H), 0.79 (d, 3H, partially obscured), 0.87 (d, J=6.0 Hz, 3H), 0.91 (d, 3H, partially obscured), 0.92 (s, 3H), 1.16 (s, 3H), 1.22 (s, 3H), 1.23-1.98 (m), 2.15 (m, 1H, partially obscured), 2.20 (m, 1H, partially obscured), 2.38 (s, 3H), 2.40 (dd, 1H, partially obscured), 2.85 (s, 1H), 3.01 (m, 1H), 3.22 (d, J=10.8 Hz, 1H), 3.34 (m, 1H, partially obscured), 3.51 (d, partially obscured, 1H), 3.54 (d, 1H, partially obscured), 3.61 (d, 1H, partially obscured), 3.65 (m, 1H, partially obscured), 3.78-3.88 (m, 3H), 3.83 (d, 1H, partially obscured), 3.98 (d, J=9.9 Hz, 1H), 5.49 (m, 1H), 5.60 (m, 1H), 8.10 (s, 1H), 8.60 (s, 1H).

Mass spectrum: (ESI) m/z=667.54 (M+H).

Example 13

(1S,4aR,6aS,7R,8R,10aR,10bR,12aR,14R,15R)-14-(5-bromo-1H-1,2,4-triazol-1-yl)-8-[(1R)-1,2-dimethylpropyl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

Example 14

(1S,4aR,6aS,7R,8R,10aR,10bR,12aR,14R,15R)-14-(5-chloro-1H-1,2,4-triazol-1-yl)-8-[(1R)-1,2-dimethylpropyl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

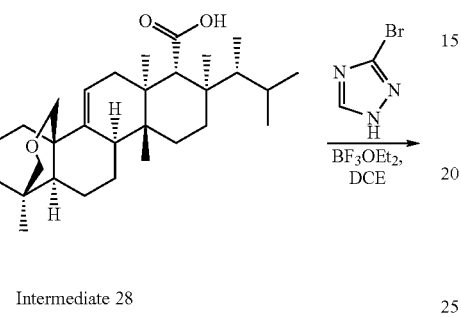

Intermediate 28

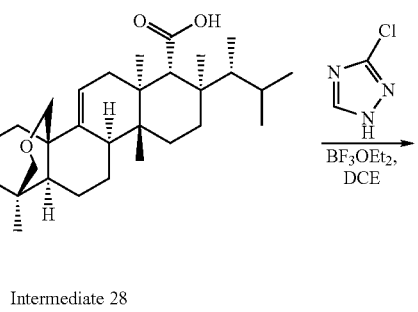

Intermediate 28

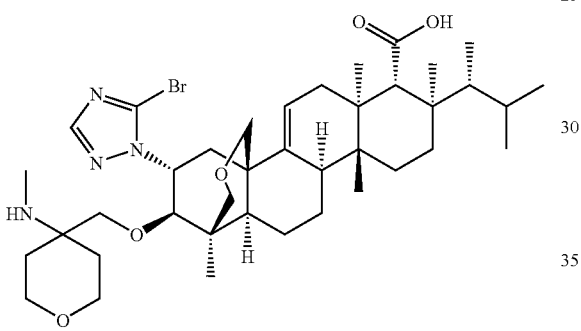

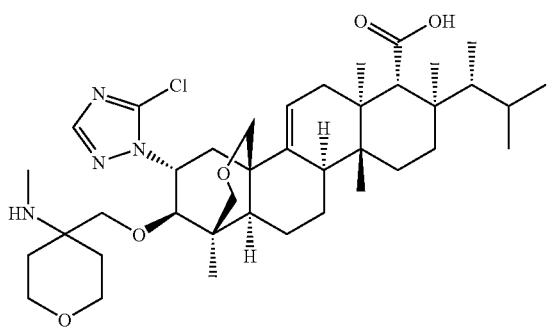

A solution of Intermediate 28 (250 mg, 0.397 mmol) in dichloroethane (4 mL) was treated with 3-bromo-1H-1,2,4-triazole (294 mg, 1.98 mmol) then $BF_3OEt_2$ (0.503 mL, 3.97 mmol) and this mixture was heated to 55° C. under nitrogen. After 1 hour the reaction was cooled to room temperature then concentrated in vacuo. The crude product mixture was suspended in methanol (3 mL) and filtered through a sintered glass funnel. The filtrate was purified by preparative HPLC (19×100 mm Waters Sunfire column, 5 μm, UV-detection, 30-100% MeCN/water with 0.05% TFA over 20 minutes). The fractions containing the desired product (major regioisomer) were combined and partially concentrated by rotovap then frozen and lyophilized to give the title compound (80 mg) was a white amorphous solid.

$^1$H NMR (CD$_3$OD, 500 MHz, ppm) δ 0.78 (s, 3H), 0.79 (d, 3H, partially obscured), 0.87 (d, J=6.6 Hz, 3H), 0.91 (d, 3H, partially obscured), 0.92 (s, 3H), 1.15 (s, 3H), 1.22 (s, 3H), 1.23-1.98 (m), 2.14 (m, 1H), 2.20 (m, 1H), 2.31 (dd, J=13.5, 6.4 Hz, 1H), 2.45 (s, 3H), 2.85 (s, 1H), 2.91 (m, 1H), 3.32-3.35 (m, 1H, partially obscured), 3.37 (d, J=11.2 Hz, 1H), 3.53 (d, 1H, partially obscured), 3.56 (dd, 1H, partially obscured), 3.60 (m, 1H, partially obscured), 3.67 (m, 1H), 3.80 (m, 1H, partially obscured), 3.82 (d, 1H, partially obscured), 3.90 (d, J=12.2 Hz, 1H), 4.09 (d, J=9.8 Hz, 1H), 5.49 (m, 1H), 5.76 (m, 1H), 8.14 (s, 1H)

Mass spectrum: (ESI) m/z=747.48 (M+H).

By a procedure analogous to that described in Example 13, but employing 3-chloro-1H-1,2,4-triazole, the title compound was prepared and isolated as a white solid.

$^1$H NMR (CD$_3$OD, 500 MHz, ppm) δ 0.78 (s, 3H), 0.79 (d, 3H, partially obscured), 0.87 (d, J=6.6 Hz, 3H), 0.91 (d, 3H, partially obscured), 0.92 (s, 3H), 1.15 (s, 3H), 1.22 (s, 3H), 1.23-1.98 (m), 2.13 (m, 1H), 2.20 (m, 1H), 2.33 (dd, J=13.5, 6.6 Hz, 1H), 2.45 (s, 3H), 2.85 (s, 1H), 2.95 (m, 1H), 3.32-3.35 (m, 1H, partially obscured), 3.37 (d, partially obscured, 1H), 3.53 (d, 1H, partially obscured), 3.56 (dd, 1H, partially obscured), 3.61 (m, 1H, partially obscured), 3.67 (m, 1H), 3.80 (m, 1H, partially obscured), 3.83 (d, 1H, partially obscured), 3.90 (d, J=11.9 Hz, 1H), 4.04 (d, J=10.1 Hz, 1H), 5.50 (m, 1H), 5.70 (m, 1H), 8.10 (s, 1H).

Mass spectrum: (ESI) m/z=701.74 (M+H).

Example 15

(1S,4aR,6aS,7R,8R,10aR,10bR,12aR,14R,15R)-15-[(4-aminotetrahydro-2H-pyran-4-yl)methoxy]-14-(5-bromo-1H-1,2,4-triazol-1-yl)-8-[(1R)-1,2-dimethyl-propyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

Example 16

(1S,4aR,6aS,7R,8R,10aR,10bR,12aR,14R,15R)-8-[(1R)-1,2-dimethylpropyl]-15-[[1-(methylamino)cyclohexyl]methoxy]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

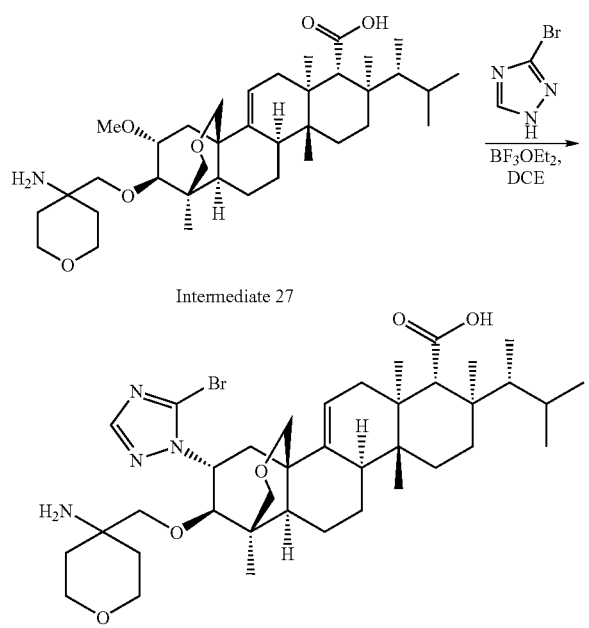

Intermediate 27

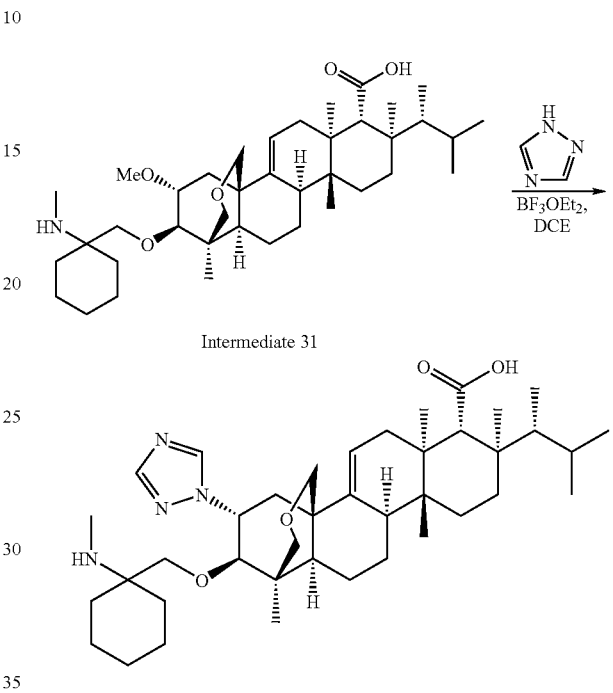

Intermediate 31

By a procedure analogous to that described in Example 13, but starting with Intermediate 27, the title compound was prepared and isolated as a white solid.
$^1$H NMR (CD$_3$OD, 500 MHz, ppm) δ 0.78 (s, 3H), 0.79 (d, 3H, partially obscured), 0.87 (d, J=6.7 Hz, 3H), 0.90 (s, 3H), 0.91 (d, 3H, partially obscured), 1.16 (s, 3H), 1.22 (s, 3H), 1.23-1.98 (m), 2.14 (m, 1H), 2.20 (m, 1H), 2.31 (dd, J=13.8, 6.7 Hz, 1H), 2.85 (s, 1H), 2.91 (m, 1H), 3.18-3.28 (m, 4H, partially obscured), 3.47-3.65 (m, 5H, partially obscured), 3.73 (m, 1H), 3.95 (m, 2H, partially obscured), 5.50 (m, 1H), 5.75 (m, 1H), 8.14 (s, 1H).
Mass spectrum: (ESI) m/z=733.78 (M+H).

By a procedure analogous to that described in Example 12, but starting with Intermediate 31, the title compound was prepared and isolated as a white solid.
$^1$H NMR (MeOH-d$_4$, 500 MHz, ppm) δ 0.80 (m, 6H), 0.85 (d, 3H), 0.92 (m, 6H), 1.18 (s, 3H), 1.22 (s, 3H), 1.22-1.70 (m, 15H), 1.80-2.00 (m, 7H), 2.18 (m, 2H), 2.35 (s, 3H), 2.40 (m, 1H), 2.83 (s, 1H), 3.05 (d, 1H), 3.50-3.70 (m, 4H), 3.90 (m, 2H), 5.48 (m, 1H), 5.60 (m, 1H), 8.10 (s, 1H), 8.60 (s, 1H).
Mass spectrum: (ESI) m/z=665 (M+H).

Examples 17-23

The following compounds were prepared using methods analogous to those described in the preceding examples:

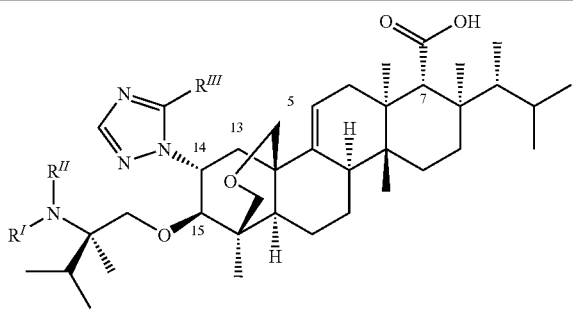

| 17 | $R^I$ = Me<br>$R^{II}$ = H | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-(1H-1,2,4-triazol-1- |

-continued

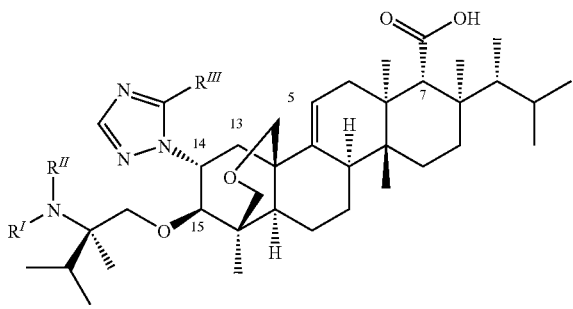

| | | |
|---|---|---|
| $R^{III}$ = H | | yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.78 (s, 3H, Me), 0.79 (d, 3H, Me), 0.84 (d, 3H, Me), 0.85 (s, 3H, Me), 0.87 (d, 3H, Me), 0.88 (d, 3H, Me), 0.92 (s, 3H, Me), 0.92 (d, 3H, Me), 1.17 (s, 3H, Me), 1.23 (s, 3H, Me), 1.24-1.37 (m), 1.42-1.47 (m), 1.49-1.60 (m), 1.60-1.68 (m), 1.82-1.99 (m), 1.99-2.08 (m), 2.12-2.24 (m), 2.42 (dd, 1H, H13), 2.43 (s, 3H, NMe), 2.79 (d, 1H), 2.86 (s, 1H, H7), 3.52 (d, 1H), 3.55 (dd, 1H), 3.62 (d, 2H), 3.90 (d, 1H), 3.91 (d, 1H), 5.49 (dd, 1H, H5), 5.59-5.66 (m, 1H, H14), 8.09 (s, 1H, triazole), 8.63 (s, 1H, triazole).

Mass Spectrum: (ESI) m/z = 653.57 (M + H).

| 18 | $R^I$ = Me | (1S,4aR,6aS,7R,8R,10aR,10bR,12aR,14R,15R)-15-[[(2R)-2- |
|---|---|---|
| | $R^{II}$ = Me | (dimethylamino)-2,3-dimethylbutyl]oxy]-8-[(1R)-1,2-dimethylpropyl]-14- |
| | $R^{III}$ = H | (1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.78 (s, 3H, Me), 0.79 (d, 3H, Me), 0.87 (d, 3H, Me), 0.92 (d, 3H, Me), 0.92 (s, 3H, Me), 0.94 (d, 3H, Me), 0.95 (s, 3H, Me), 0.95 (d, 3H, Me), 1.16 (s, 3H, Me), 1.22 (s, 3H, Me), 1.24-1.37 (m), 1.41-1.47 (m), 1.49-1.59 (m), 1.60-1.68 (m), 1.82-1.98 (m), 2.12-2.24 (m), 2.24-2.32 (m), 2.42 (dd, 1H, H13), 2.70 (s, 3H, NMe), 2.76 (s, 3H, NMe), 2.86 (s, 1H, H7), 3.00 (d, 1H), 3.55 (d, 2H), 3.63 (d, 1H), 3.72 (d, 1H), 3.78 (d, 1H), 3.92 (d, 1H), 5.49 (dd, 1H, H5), 5.61-5.68 (m, 1H, H14), 8.10 (s, 1H, triazole), 8.70 (s, 1H, triazole).

Mass Spectrum: (ESI) m/z = 667.67 (M + H).

| 19 | $R^I$ = H | (1S,4aR,6aS,7R,8R,10aR,10bR,12aR,14R,15R)-15-[[(2R)-2-amino-2,3- |
|---|---|---|
| | $R^{II}$ = H | dimethylbutyl]oxy]-14-(5-chloro-1H-1,2,4-triazol-1-yl)-8-[(1R)-1,2- |
| | $R^{III}$ = Cl | dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 3H, Me), 0.80 (d, 3H, Me), 0.84 (d, 3H, Me), 0.85 (d, 3H, Me), 0.88 (s, 3H, Me), 0.89 (d, 3H, Me), 0.92 (s, 3H, Me), 1.14 (s, 3H, Me), 1.20 (s, 3H, Me), 1.22-1.34 (m), 1.39-1.44 (m), 1.47-1.57 (m), 1.58-1.65 (m), 1.74-1.96 (m), 2.10-2.22 (m), 2.33 (dd, 1H, H13), 2.84 (s, 1H, H7), 2.85 (d, 1H), 3.49 (d, 1H), 3.50 (d, 1H), 3.54 (dd, 1H), 3.60 (d, 1H), 3.84 (d, 1H), 3.95 (d, 1H), 5.48 (dd, 1H, H5), 5.67-5.73 (m, 1H, H14), 8.03 (s, 1H, triazole).

Mass Spectrum: (ESI) m/z = 673.42 (M + H).

| 20 | $R^I$ = Me | (1S,4aR,6aS,7R,8R,10aR,10bR,12aR,14R,15R)-14-(5-chloro-1H-1,2,4- |
|---|---|---|
| | $R^{II}$ = H | triazol-1-yl)-15-[[(2R)-2,3-dimethyl-2-(methylamino)butyl]oxy]-8-[(1R)- |
| | $R^{III}$ = Cl | 1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.78 (s, 3H, Me), 0.79 (d, 3H, Me), 0.85 (d, 3H, Me), 0.87 (d, 3H, Me), 0.88 (s, 3H, Me), 0.89 (d, 3H, Me), 0.92 (d, 3H, Me), 0.92 (s, 3H, Me), 1.16 (s, 3H, Me), 1.23 (s, 3H, Me), 1.24-1.38 (m), 1.41-1.47 (m), 1.49-1.68 (m), 1.77-1.99 (m), 1.99-2.06 (m), 2.12-2.24 (m), 2.36 (dd, 1H, H13), 2.47 (s, 3H, NMe), 2.86 (s, 1H, H7), 3.00 (d, 1H), 3.53 (d, 1H), 3.57 (dd, 1H), 3.63 (d, 1H), 3.68 (d, 1H), 3.92 (d, 1H), 3.98 (d, 1H), 5.51 (dd, 1H, H5), 5.69-5.76 (m, 1H, H14), 8.08 (s, 1H, triazole).

Mass Spectrum: (ESI) m/z = 687.64 (M + H).

| 21 | $R^I$ = Me | (1S,4aR,6aS,7R,8R,10aR,10bR,12aR,14R,1SR)-14-(5-bromo-1H-1,2,4- |
|---|---|---|
| | $R^{II}$ = H | triazol-1-yl)-15-[[(2R)-2,3-dimethyl-2-(methylainino)butyl]oxy]-8-[(1R)- |
| | $R^{III}$ = Br | 1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.76 (d, 3H, Me), 0.82 (d, 3H, Me), 0.85 (s, 3H, Me), 0.85 (d, 3H, Me), 0.86 (d, 3H, Me), 0.90 (d, 3H, Me), 0.90 (s, 3H, Me), 1.13 (s, 3H, Me), 1.20 (s, 3H, Me), 1.22-1.35 (m), 1.40-1.44 (m), 1.48-1.57 (m), 1.59-1.64 (m), 1.73-2.03 (m), 2.10-2.21 (m), 2.31 (dd, 1H, H13), 2.44 (dd, 1H, H13), 2.84 (s, 1H, H7), 2.99 (d, 1H), 3.51 (d, 1H), 3.55 (dd, 1H), 3.60 (d, 1H), 3.64 (d, 1H), 3.91 (d, 1H), 4.00 (d, 1H), 5.48 (dd, 1H, H5), 5.75 (m, 1H, H14), 8.09 (s, 1H, triazole).

Mass spectrum: (ESI) m/z = 731.32 (733.30) (M + H).

| 22 | $R^I$ = H | (1S,4aR,6aS,7R,8R,10aR,10bR,12aR,14R,1SR)-15-[[(2R)-2,3-dimethyl-2- |
|---|---|---|
| | $R^{II}$ = H | (methylamino)butyl]oxy]-8-[(1R)-1,2-dimethylpropyl]-14-(5-iodo-1H-1,2,4- |
| | $R^{III}$ = I | triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.76 (d, 3H, Me), 0.79 (d, 3H, Me), 0.82 (d, 3H, Me), 0.85 (d, 3H, Me), 0.88 (s, 3H, Me), 0.89 (d, 3H, Me), 0.92 (s, 3H, Me), 1.14 (s, 3H, Me), 1.20 (s, 3H, Me), 1.22-1.35 (m), 1.39-1.44 (m), 1.47-1.57 (m), 1.58-1.65 (m), 1.71-1.96 (m), 2.10-2.22 (m), 2.26 (dd, 1H, H13), 2.84 (s, 1H, H7), 2.85 (d, 1H), 3.45 (d, 1H), 3.50 (d, 1H), 3.56

-continued

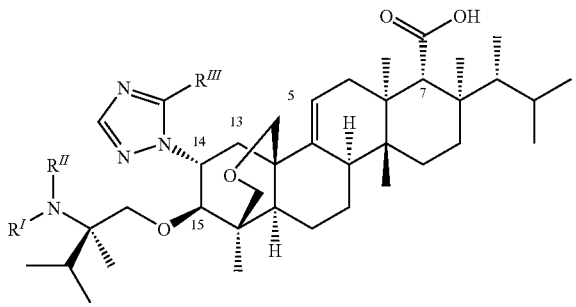

(dd, 1H), 3.61 (d, 1H), 3.94 (d, 1H), 3.96 (d, 1H), 5.47 (dd, 1H, H5), 5.74-5.80 (m, 1H, H14), 8.10 (s, 1H, triazole).
Mass Spectrum: (ESI) m/z = 765.23 (M + H).

| 23 | $R^I$ = H | (1S,4aR,6aS,7R,8R,10aR,10bR,12aR,14R,1SR)-15-[[(2R)-2,3-dimethyl- |
| | $R^{II}$ = H | 2-(methylamino)butyl]oxy]-8-[(1R)-1,2-dimethylpropyl]-14-[5- |
| | $R^{III}$ = CO$_2$Bn | [(phenylmethoxy)carbonyl]-1H-1,2,4-triazol-1-yl]- |
| | | 1,6,6a,7,8,9,10,10a,10b,11,12,12a-dodecahydro-1,6a,8,10a-tetramethyl- |
| | | 4H-1,4a-propano-2H-phenanthro[1,2-c]pyran-7-carboxylic acid |

Selected $^1$H NMR (CD$_3$OD, 600 MHz, ppm) 0.71 (s, 3H), 0.76 (s, 3H), 0.86 (d, J = 6.8 Hz, 3H), 0.87 (s, 3H), 0.90 (d, J = 7.5 Hz, 3H), 1.13 (s, 3H), 1.20 (s, 3H), 2.41 (dd, J = 6.5, 13.4 Hz, 1H, H-13), 2.84 (s, 1H, H-7), 5.37 (ABq, J = 12.1 Hz, 1H, OCH$_a$H$_b$), 5.52 (ABq, J = 12.1 Hz, 1H, OCH$_a$H$_b$), 6.53 (ddd, J = 6.5, 10.0, 11.8 Hz, 1H, H-14), 7.3-7.5 (m, 5H, ArH), 8.15 (s, 1, H-5 triazole).
Mass Spectrum: (ESI) m/z = 773.9 (M + H).

Examples 24-28

The following compounds were prepared using methods analogous to those described in the preceding examples:

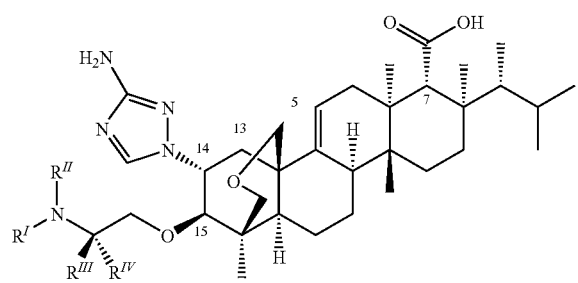

| 24 | $R^I$ = H | (1S,4aR,6aS,7R,8R,10aR,10bR,12aR,14R,15R)-15-[[(2R)-2-amino-3,3- |
| | $R^{II}$ = H | dimethylbutyl]oxy]-14-(3-amino-1H-1,2,4-triazol-1-yl)-8-[(1R)-1,2- |
| | $R^{III}$ = t-Bu | dimethylpropyl]-1,6,6a,7,8,9,10,10a,10b,11,12,12a-dodecahydro- |
| | $R^{IV}$ = H | 1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.86 (d, J = 6.4
Hz, 3H), 0.86 (s, 3H), 0.89 (s, 9H), 0.90 (d, 3H, partially obscured), 1.17 (s, 3H), 1.22 (s, 3H), 1.23-1.67 (m), 1.73-2.07 (m), 2.14 (m, 1H), 2.19 (m, 1H), 2.36 (dd,
J = 13.6 Hz, 6.3 Hz, 1H),
2.49 (dd, J = 10.3 Hz, 3.0 Hz, 1H), 2.85 (s, 1H), 3.12 (dd, J = 10.8 Hz, 3.2 Hz, 1H),
3.46 (d, J = 11.9
Hz, 1H), 3.52 (dd, J = 11.7 Hz, 1.7 Hz, 1H), 3.55-3.63 (m, 3H), 3.88 (d, J = 11.9 Hz, 1H), 5.26 (m, 1H), 5.50 (m, 1H), 8.27 (s, 1H).
Mass spectrum: (ESI) m/z = 654.55 (M + H).

| 25 | $R^I$ = Me | (1S,4aR,6aS,7R,8R,10aR,10bR,12aR,14R,15R)-14-(3-amino-1H-1,2,4- |
| | $R^{II}$ = H | triazol-1-yl)-15-[[(2S)-3,3-dimethyl-2-(methylamino)butyl]oxy]-8-[(1R)- |
| | $R^{III}$ = H | 1,2-dimethylpropyl]-1,6,6a,7,8,9,10,10a,10b,11,12,12a-dodecahydro- |
| | $R^{IV}$ = t-Bu | 1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.77 (d, 3H, partially obscured), 0.86 (d, 3H, partially obscured), 0.87 (s, 3H), 0.90 (d, J = 6.9 Hz, 3H), 0.97 (s, 9H), 1.17 (s, 3H), 1.22 (s, 3H), 1.23-1.67 (m), 1.74-2.02 (m), 2.13 (m, 1H), 2.19 (m, 1H), 2.37 (dd, J = 13.5 Hz, 6.4 Hz, 1H), -continued

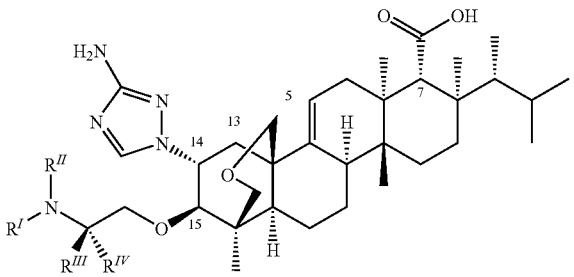

2.76 (s, 3H), 2.85 (s, 3H), 2.95 (dd, J = 7.1 Hz, 3.3 Hz, 1H), 3.14 (dd, J = 11.6 Hz, 7.6 Hz, 1H), 3.47 (d, J = 11.9 Hz, 1H), 3.52 (dd, J = 11.6 Hz, 2.2 Hz, 1H), 3.58 (d, J = 11.9 Hz, 1H), 3.62 (d, J = 9.6 Hz, 1H), 3.72 (dd, J = 11.2 Hz, 3.2 Hz, 1H), 3.76 (d, J = 11.9 Hz, 1H), 5.30 (m, 1H), 5.51 (m, 1H), 8.31 (s, 1H).
Mass spectrum: (ESI) m/z = 668.55 (M +H).

| 26 | $R^I$ = Me | (1S,4aR,6aS,7R,8R,10aR,10bR,12aR,14R,15R)-14-(3-amino-1H-1,2,4- |
| | $R^{II}$ = H | triazol-1-yl)-15-[[(2S)-2,3-dimethyl-2-(methylamino)butyl]oxy]-8-[(1R)- |
| | $R^{III}$ = Me | 1,2-dimethylpropyl]-1,6,6a,7,8,9,10,10a,10b,11,12,12a-dodecahydro- |
| | $R^{IV}$ = i-Pr | 1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 6H, 2Me), 0.85 (d, 3H, Me), 0.88 (s, 3H, Me), 0.89 (d, 3H, Me), 0.90 (d, 3H, Me), 1.14 (s, 3H, Me), 1.15 (s, 3H, Me), 1.20 (s, 3H, Me), 1.22-1.34 (m), 1.39-1.44 (m), 1.47-1.65 (m), 1.74-1.96 (m), 2.08-2.13 (m), 2.15-2.21 (m), 2.32 (dd, 1H, H13), 2.42 (s, 3H, NMe), 2.84 (s, 1H, H7), 3.18 (d, 1H), 3.48 (d, 1H), 3.51 (dd, 1H), 3.56 (d, 1H), 3.57 (d, 1H), 3.78 (d, 1H), 3.83 (d, 1H), 5.27-5.33 (m, 1H, H14), 5.47 (dd, 1H, H5), 8.17 (s, 1H, triazole).
Mass Spectrum: (ESI) m/z = 668.65 (M + H).

| 27 | $R^I$ = Me | (1S,4aR,6aS,7R,8R,10aR,10bR,12aR,14R,15R)-14-(3-amino-1H-1,2,4- |
| | $R^{II}$ = Me | triazol-1-yl)-15-[[(2S)-2-(dimethylamino)-2,3-dimethylbutyl]oxy]-8-[(1R)- |
| | $R^{III}$ = Me | 1,2-dimethylpropyl]-1,6,6a,7,8,9,10,10a,10b,11,12,12a-dodecahydro- |
| | $R^{IV}$ = i-Pr | 1,6a,8,10a-tetramethyl-4H-1,4a-propano-2H-phenanthro[1,2-c]pyran-7-carboxylic acid |

¹H NMR (CD₃OD, 600 MHz, ppm) δ 0.75 (s, 3H, Me), 0.76 (d, 3H, Me), 0.82 (d, 3H, Me), 0.85 (d, 3H, Me), 0.89 (d, 3H, Me), 0.89 (s, 3H, Me), 0.92 (d, 3H, Me), 1.14 (s, 3H, Me), 1.20 (s, 3H, Me), 1.21 (s, 3H, Me), 1.22-1.33 (m), 1.39-1.44 (m), 1.47-1.65 (m), 1.74-1.96 (m), 2.02-2.13 (m), 2.14-2.22 (m), 2.34 (dd, 1H, H13), 2.80 (s, 3H, NMe), 2.81 (s, 3H, NMe), 2.84 (s, 1H, H7), 3.32 (d, 1H), 3.50 (d, 1H), 3.51 (dd, 1H), 3.57 (d, 1H), 3.67 (d, 1H), 3.77 (d, 1H), 3.79 (d, 1H), 5.31-5.37 (m, 1H, H14), 5.47 (dd, 1H, H5), 8.38 (s, 1H, triazole).
Mass Spectrum: (ESI) m/z = 682.69 (M + H).

| 28 | $R^I$ = Me | (1S,4aR,6aS,7R,8R,10aR,10bR,12aR,14R,15R)-14-(3-amino-1H-1,2,4- |
| | $R^{II}$ = Me | triazol-1-yl)-15-[[(2R)-2-(dimethylamino)-2,3-dimethylbutyl]oxy]-8-[(1R)- |
| | $R^{III}$ = i-Pr | 1,2-dimethylpropyl]-1,6,6a,7,8,9,10,10a,10b,11,12,12a-dodecahydro- |
| | $R^{IV}$ = Me | 1,6a,8,10a-tetramethyl-4H-1,4a-propano-2H-phenanthro[1,2-c]pyran-7-carboxylic acid |

¹H NMR (CD₃OD, 500 MHz, ppm) δ 0.78 (s, 3H, Me), 0.79 (d, 3H, Me), 0.87 (d, 3H, Me), 0.92 (d, 3H, Me), 0.93 (s, 3H, Me), 0.98 (d, 3H, Me), 0.99 (d, 3H, Me), 1.02 (s, 3H, Me), 1.17 (s, 3H, Me), 1.23 (s, 3H, Me), 1.24-1.36 (m), 1.41-1.47 (m), 1.49-1.68 (m), 1.76-1.99 (m), 2.10-2.16 (m), 2.17-2.24 (m), 2.26-2.33 (m), 2.36 (dd, 1H, H13), 2.76 (s, 3H, NMe), 2.81 (s, 3H, NMe), 2.86 (s, 1H, H7), 3.26 (d, 1H), 3.52 (d, 1H), 3.53 (dd, 1H), 3.60 (d, 1H), 3.74 (d, 1H), 3.76 (d, 1H), 3.79 (d, 1H), 5.33-5.41 (m, 1H, H14), 5.50 (dd, 1H, H5), 8.32 (s, 1H, triazole).
Mass Spectrum: (ESI) m/z = 682.67 (M + H).

Example 29

(1S,4aR,6aS,7R,8R,8R,10R,10bR,12aR,14R,15R)-15-[[(2R)-2-amino-2,3-dimethylbutyl]oxy]-14-(5-bromo-3-nitro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 29A) and (1S,4aR,6aS,7R,8R,10aR,10bR,12aR,14R,15R)-15-[[(2R)-2-amino-2,3-dimethylbutyl]oxy]-14-(3-bromo-5-nitro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 29B)

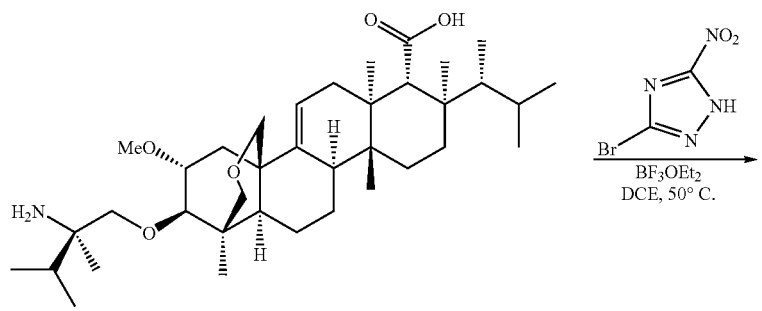

Intermediate 6

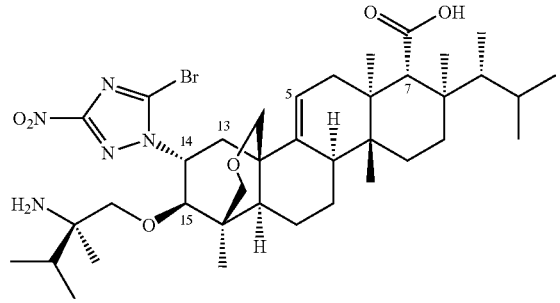

EXAMPLE 29A

+

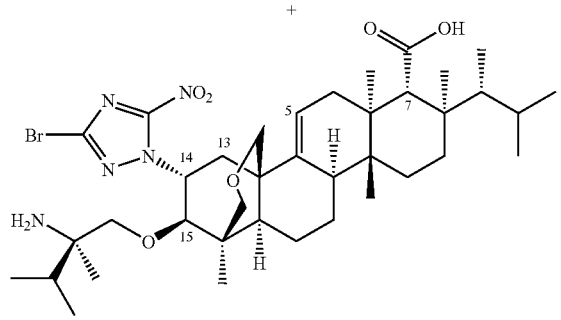

EXAMPLE 29B

A mixture of Intermediate 6 (27 mg, 0.039 mmol), 3-bromo-5-nitro-1H-1,2,4-triazole (27 mg, 0.141 mmol) and boron trifluoride etherate (100 μL, 0.775 mmol) was dissolved on dichloroethane (0.7 mL) and heated in a 50° C. oil bath for 45 minutes. The mixture was cooled to room temperature, evaporated and the residual oil was separated by reverse phase HPLC using a 19×150 mm Sunfire Preparative C18 OBD column. Fractions containing the faster eluting regioisomer were evaporated and freeze-dried from a mixture of ethanol and benzene to give EXAMPLE 29A as a white solid (8.4 mg). Fractions containing the slower eluting regioisomer were evaporated and freeze-dried from a mixture of ethanol and benzene to give EXAMPLE 29B as a white solid salt (10.2 mg).

Example 29A $^1$H NMR (CD$_3$OD, 600 MHz, ppm) 0.76 (s, 3H, Me), 0.77 (d, 3H, Me), 0.83 (d, 3H, Me), 0.84 (d, 3H, Me), 0.85 (d, 3H, Me), 0.89 (d, 3H, Me), 0.90 (s, 3H, Me), 0.91 (s, 3H, Me), 1.14 (s, 3H, Me), 1.20 (s, 3H, Me), 1.22-1.34 (m), 1.40-1.44 (m), 1.48-1.56 (m), 1.59-1.65 (m), 1.79-1.96 (m), 2.12-2.21 (m), 2.45 (dd, 1H, H13), 2.84 (s, 1H, H7), 2.99 (d, 1H), 3.52 (d, 1H), 3.56 (dd, 1H), 3.60 (d, 1H), 3.61 (d, 1H), 3.97 (m), 5.51 (dd, 1H, H5), 5.89 (m, 1H, H14).

Mass spectrum: (ESI) m/z (M+H)=762.36 (764.36).

Example 29B $^1$H NMR (CD$_3$OD, 600 MHz, ppm) 0.76 (s, 3H, Me), 0.77 (d, 3H, Me), 0.81 (s, 3H, Me), 0.86 (d, 3H, Me), 0.87 (d, 3H, Me), 0.88 (s, 3H, Me), 0.88 (d, 3H, Me), 0.89 (d, 3H, Me), 1.15 (s, 3H, Me), 1.21 (s, 3H, Me), 1.22-1.33 (m), 1.40-1.44 (m), 1.48-1.58 (m), 1.59-1.66 (m), 1.80-1.97 (m), 2.12-2.22 (m), 2.63 (dd, 1H, H13), 2.84 (s, 1H, H7), 3.00 (d, 1H), 3.49 (d, 1H), 3.55 (dd, 1H), 3.62 (d, 1H), 3.64 (d, 1H), 3.89 (d, 1H), 3.99 (d, 1H), 3.87 (d, 1H), 5.51 (dd, 1H, H5), 6.43 (m, 1H, H14).

Mass spectrum: (ESI) m/z (M+H)=762.35 (764.35).

Example 30

(1S,4aR,6aS,7R,8R,10aR,10bR,12aR,14R,15R)-15-[[(2R)-2-amino-2,3-dimethylbutyl]oxy]-14-(3-amino-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

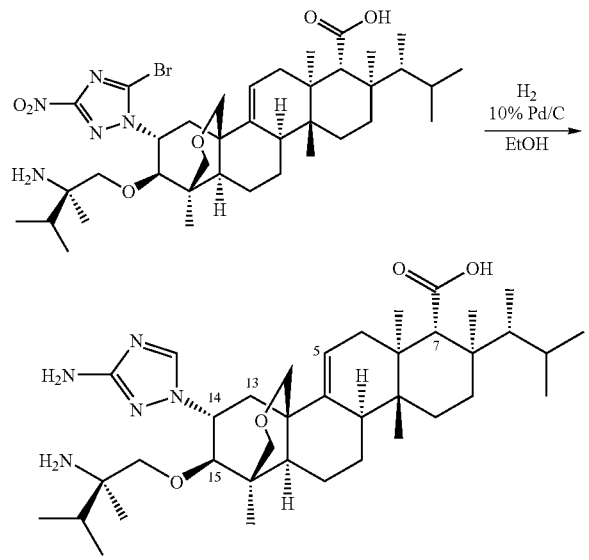

A mixture of (1S,4aR,6aS,7R,8R,10aR,10bR,12aR,14R,15R)-15-[[(2R)-2-amino-2,3-dimethylbutyl]oxy]-14-(5-bromo-3-nitro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 29A, 9.0 mg, 0.012 mmol), 10% Pd/C (18 mg) and several drops of acetic acid in ethanol (2.0 mL) was stirred under a balloon of hydrogen for 2 hours. The mixture was filtered, evaporated and the residual oil was purified by reverse phase HPLC using a 19×150 mm Sunfire Preparative C18 OBD column. Product containing fractions were evaporated and freeze-dried from a mixture of ethanol and benzene to give the title compound as a TFA salt (1.5 mg).

$^1$H NMR of the crude reduction product prior to HPLC purification showed a triazole proton at 8.07 ppm. This proton showed an NOE correlation with the H14 proton, which is consistent with the assigned structure. After HPLC purification, the TFA salt displayed essentially no triazole proton in the $^1$H NMR spectrum due to peak broadening.

$^1$H NMR (CD$_3$OD, 600 MHz, ppm) 0.75 (s, 3H, Me), 0.76 (d, 3H, Me), 0.84 (br s, 3H, Me), 0.85 (br d, 3H, Me), 0.89 (d, 3H, Me), 0.92 (br d, 3H, Me), 1.02 (br d, 3H, Me), 1.13 (br, 3H, Me), 1.19 (s, 3H, Me), 1.22-1.32 (m), 1.39-1.42 (m), 1.46-1.56 (m), 1.58-1.64 (m), 1.68-1.96 (br m), 2.06-2.11 (br m), 2.15-2.20 (m), 2.24 (br m), 2.78 (br m), 2.83 (br s, 1H, H7), 3.40-3.50 (br m), 3.52 (br m), 3.77 (br m), 3.88 (d, 1H), 5.15 (br m, 1H, H14), 5.43 (br dd, 1H, H5).

Mass spectrum: (ESI) m/z (M+H)=654.38.

Example 31

(1S,4aR,6aS,7R,8R,10aR,10bR,12aR,14R,15R)-15-[[(2R)-2-amino-2,3-dimethylbutyl]oxy]-14-(5-amino-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

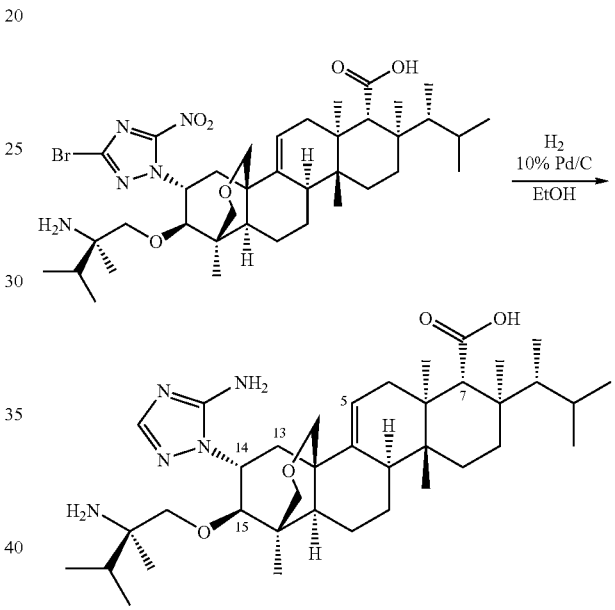

A mixture of (1S,4aR,6aS,7R,8R,10aR,10bR,12aR,14R,15R)-15-[[(2R)-2-amino-2,3-dimethylbutyl]oxy]-14-(3-bromo-5-nitro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 29B, 6.7 mg, 0.009 mmol) and 10% Pd/C (9.35 mg) in ethanol (1.0 mL) was stirred under a balloon of hydrogen for 18 hours. The mixture was filtered, evaporated and the residual oil was purified by reverse phase HPLC using a 19×150 mm Sunfire Preparative C18 OBD column. Product containing fractions were evaporated and freeze-dried from a mixture of ethanol and benzene to give the title compound as a TFA salt (1.6 mg).

$^1$H NMR (CD$_3$OD, 600 MHz, ppm) 0.75 (s, 3H, Me), 0.76 (d, 3H, Me), 0.84 (d, 3H, Me), 0.85 (s, 3H, Me), 0.89 (d, 3H, Me), 1.02 (br d, 3H, Me), 1.12 (s, 3H, Me), 1.19 (s, 3H, Me), 1.22-1.33 (m), 1.39-1.42 (m), 1.48-1.56 (m), 1.58-1.64 (m), 1.70-1.96 (m), 2.06-2.11 (m), 2.15-2.20 (br m), 2.25 (br m), 2.83 (s, 1H, H7), 2.94 (br d, 1H), 3.49 (d, 1H), 3.52 (br dd, 1H), 3.60 (d, 1H), 3.81 (br d, 1H), 3.89 (d, 1H), 3.99 (d, 1H), 3.87 (d, 1H), 5.12 (br m, 1H, H14), 5.45 (dd, 1H, H5).

Mass spectrum: (ESI) m/z (M+H)=654.38.

Example 32

(1S,4aR,6aS,7R,8R,10aR,10bR,12aR,14R,15R)-14-(3-amino-5-cyclopropyl-1H-1,2,4-triazol-1-yl)-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 32A) and (1S,4aR,6aS,7R,8R,10aR,10bR,12aR,14R,15R)-14-(5-amino-3-cyclopropyl-1H-1,2,4-triazol-1-yl)-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 32B)

then stirred at room temperature for 64 hr. The solvent was evaporated and the resulting residue was placed under high vacuum. The residue was dissolved in methanol and separated using a single HPLC run on a 19×150 mm Sunfire Prep C18 OBD 10 μm column by eluting with acetonitrile/water+ 0.1% TFA. The HPLC fractions of the faster eluting regioisomer were combined, the solvent was evaporated under reduced pressure, and the residue was lyophilized from ethanol and benzene to give EXAMPLE 32A (9.1 mg) as a white solid. The HPLC fractions of the slower eluting regioisomer were combined, the solvent was evaporated under reduced pressure, and the residue was lyophilized from ethanol and benzene to give EXAMPLE 32B (7.8 mg) as a white solid. The regiochemistry of the two isomers was assigned based on an $^1$H NMR NOE from H14 to the methine proton of the cyclopropyl which was observed for EXAMPLE 32A, but not for EXAMPLE 32B.

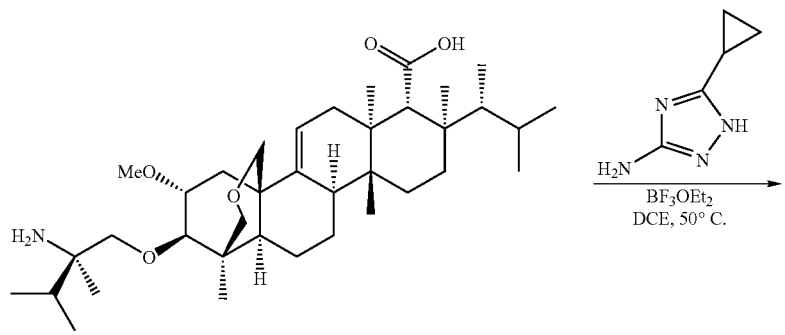

Intermediate 6

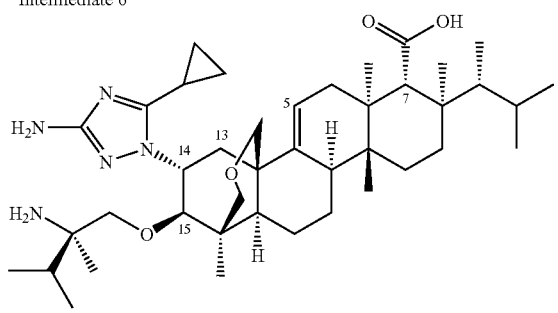

EXAMPLE 32A

+

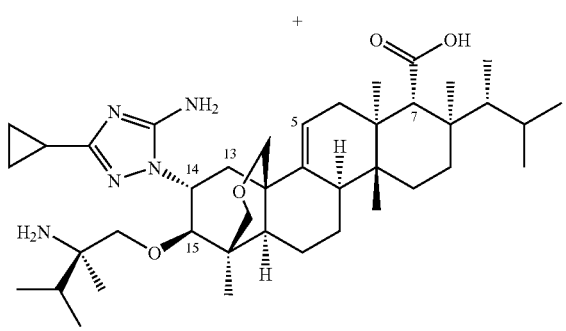

EXAMPLE 32B 5-cyclopropyl-1H-1,2,4-triazol-3-amine (27.3 mg, 0.220 mmol) and BF$_3$OEt$_2$ (53 μl, 0.418 mmol) were added to a stirred solution of Intermediate 6 (25.2 mg, 0.042 mmol) in 1,2-dichloroethane (0.42 ml). The reaction mixture was a light tan suspension that was heated at 50° C. for 5.5 hr and

Example 32A $^1$H NMR (CD$_3$OD, 600 MHz, ppm) δ 0.76 (s, 3H, Me), 0.77 (d, 3H, Me), 0.85 (d, 3H, Me), 0.87 (d, 3H, Me), 0.88 (s, 3H, Me), 0.89 (d, 3H, Me), 0.91 (d, 3H, Me), 1.03 (s, 3H, Me), 1.08-1.19 (m), 1.14 (s, 3H, Me), 1.20 (s, 3H, Me), 1.22-1.34 (m), 1.40-1.44 (m), 1.47-1.65 (m), 1.73-1.97 (m), 2.09-2.14 (m), 2.15-2.22 (m), 2.36 (dd, 1H, H13), 2.84 (s, 1H, H7), 3.19 (d, 1H), 3.49 (d, 1H), 3.54 (dd, 1H), 3.59 (d, 1H), 3.61 (d, 1H), 3.85 (d, 1H), 3.92 (d, 1H), 5.51 (dd, 1H, H5), 5.57-5.63 (m, 1H, H14).

Mass Spectrum: (ESI) m/z=694.55 (M+H).

Example 32B $^1$H NMR (CD$_3$OD, 600 MHz, ppm) δ 0.76 (s, 3H, Me), 0.77 (d, 3H, Me), 0.85 (d, 3H, Me), 0.86 (s, 3H, Me), 0.88 (d, 3H, Me), 0.90 (d, 3H, Me), 0.92 (d, 3H, Me), 0.95-1.01 (m), Example 33

(1S,4aR,6aS,7R,8R,10aR,10bR,12aR,14R,15R)-15-[[(2R)-2-amino-2,3-dimethylbutyl]oxy]-14-(3,5-dibromo-4H-1,2,4-triazol-4-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 33A) and (1S,4aR,6aS,7R,8R,10aR,10bR,12aR,14R,15R)-15-[[(2R)-2-amino-2,3-dimethylbutyl]oxy]-14-(3,5-dibromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 33B)

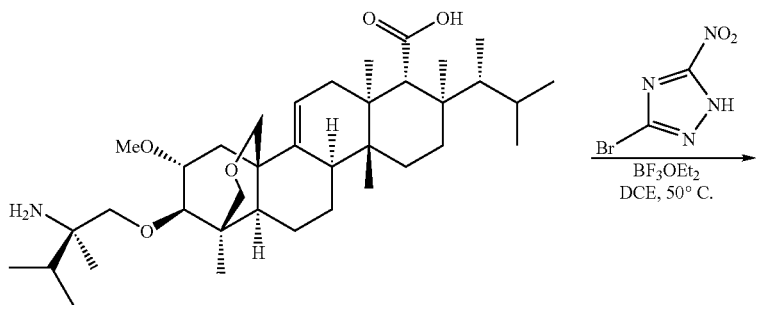

Intermediate 6

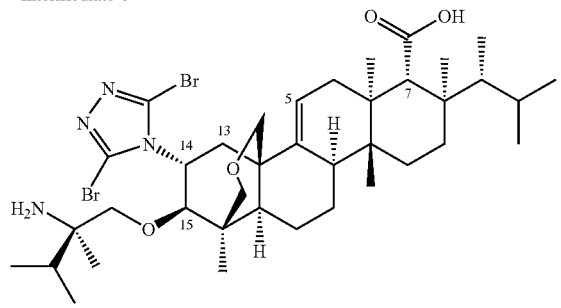

EXAMPLE 33A

+

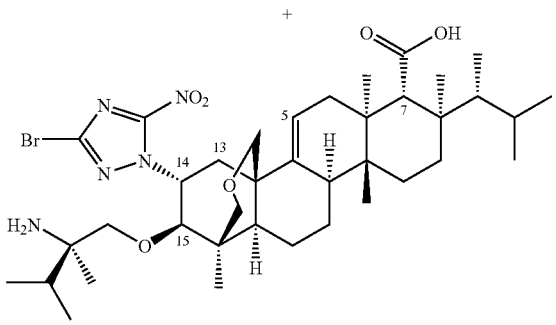

EXAMPLE 33B 1.06 (s, 3H, Me), 1.09-1.12 (m), 1.15 (s, 3H, Me), 1.20 (s, 3H, Me), 1.22-1.34 (m), 1.39-1.44 (m), 1.47-1.65 (m), 1.71-2.00 (m), 2.09-2.14 (m), 2.15-2.22 (m), 2.33 (dd, 1H, H13), 2.84 (s, 1H, H7), 3.08 (d, 1H), 3.46 (d, 1H), 3.51 (dd, 1H), 3.58 (d, 1H), 3.61 (d, 1H), 3.74 (d, 1H), 3.91 (d, 1H), 5.19-5.25 (m, 1H, H14), 5.49 (dd, 1H, H5).

Mass Spectrum: (ESI) m/z=694.56 (M+H).

3,5-dibromo-1H-1,2,4-triazole (48.1 mg, 0.212 mmol) and BF$_3$OEt$_2$ (53 µl, 0.418 mmol) were added to a stirred solution of Intermediate 6 (25.4 mg, 0.042 mmol) in 1,2-dichloroethane (0.42 ml). The reaction mixture was a yellow solution that was heated to 50° C. After 1.5 hr, the reaction mixture had become an orange suspension. LCMS and $^1$H NMR showed complete consumption of Intermediate 6. The reaction mixture was cooled to room temperature, the solvent was evaporated, and the resulting residue was placed under high vacuum. The residue was dissolved in methanol and purified using a single HPLC run on a 19×150 mm Sunfire Prep C18 OBD 10 μm column by eluting with acetonitrile/water+0.1% TFA. The HPLC fractions of the faster eluting regioisomer were combined, the solvent was evaporated under reduced pressure, and the residue was lyophilized from ethanol and benzene to give EXAMPLE 33A (2.1 mg) as a white solid. The HPLC fractions of the slower eluting regioisomer were combined, the solvent was evaporated under reduced pressure, and the residue was lyophilized from ethanol and benzene to give EXAMPLE 33B (25.9 mg) as a white solid.

Example 33A $^1$H NMR (CD$_3$OD, 600 MHz, ppm) δ 0.76 (s, 3H, Me), 0.76 (d, 3H, Me), 0.82 (d, 3H, Me), 0.84 (d, 3H, Me), 0.85 (d, 3H, Me), 0.89 (d, 3H, Me), 0.90 (s, 3H, Me), 1.03 (s, 3H, Me), 1.16 (s, 3H, Me), 1.20 (s, 3H, Me), 1.22-1.35 (m), 1.40-1.44 (m), 1.46-1.52 (m), 1.55-1.65 (m), 1.75-1.97 (m), 2.12-2.22 (m), 2.25-2.31 (m), 2.38 (dd, 1H, H13), 2.84 (s, 1H, H7), 2.85 (d, 1H), 3.49 (d, 1H), 3.56 (dd, 1H), 3.56 (d, 1H), 3.61 (d, 1H), 3.96 (d, 1H), 4.19 (d, 1H), 5.53 (dd, 1H, H5), 5.92-5.98 (m, 1H, H14).

Mass Spectrum: (ESI) m/z=795.22 (797.22) (M+H).

Example 33B $^1$H NMR (CD$_3$OD, 600 MHz, ppm) δ 0.76 (s, 3H, Me), 0.76 (d, 3H, Me), 0.84 (d, 3H, Me), 0.85 (d, 3H, Me), 0.87 (d, 3H, Me), 0.88 (s, 3H, Me), 0.89 (d, 3H, Me), 0.93 (s, 3H, Me), 1.15 (s, 3H, Me), 1.20 (s, 3H, Me), 1.22-1.34 (m), 1.39-1.43 (m), 1.47-1.65 (m), 1.75-1.96 (m), 2.10-2.22 (m), 2.34 (dd, 1H, H13), 2.84 (s, 1H, H7), 2.96 (d, 1H), 3.48 (d, 1H), 3.54 (dd, 1H), 3.54 (d, 1H), 3.58 (d, 1H), 3.84 (d, 1H), 3.93 (d, 1H), 5.49 (dd, 1H, H5), 5.71-5.77 (m, 1H, H14).

Mass Spectrum: (ESI) m/z=795.21 (797.19) (M+H).

Examples 34-36

The following compounds were prepared using methods analogous to those described in the preceding examples:

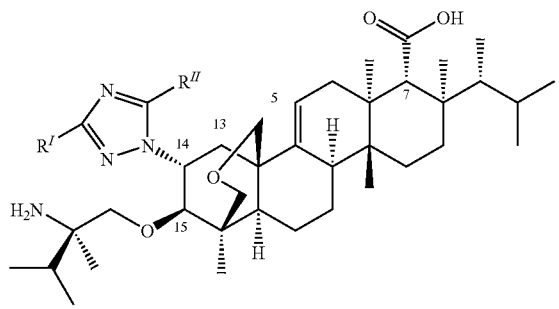

| 34 | $R^I$ = Cl<br>$R^{II}$ = Cl | (1S,4aR,6aS,7R,8R,10aR,10bR,12aR,14R,15R)-15-[[(2R)-2-amino-2,3-dimethylbutyl]oxy]-14-(3,5-dichloro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) 0.76 (s, 3H, Me), 0.77 (d, 3H, Me),
0.84 (d, 3H, Me), 0.85 (d,
3H, Me), 0.87 (s, 3H, Me), 0.87 (d, 3H, Me),
0.89 (d, 3H, Me), 0.94 (s, 3H, Me), 1.15 (s, 3H, Me),
1.20 (s, 3H, Me), 1.22-1.32 (m), 1.41-1.44
(m), 1.48-1.64 (m), 1.76-1.96 (m), 2.10-2.22 (m), 2.37
(dd, 1H, H13), 2.84 (s, 1H, H7), 2.96 (d, 1H), 3.48 (d, 1H), 3.54 (dd, 1H), 3.56 (d, 1H), 3.59 (d, 1H), 3.79 (d, 1H), 3.93 (d, 1H), 5.50 (dd, 1H, H5) and 5.68 (m, 1H, H14).
Mass spectrum: (ESI) m/z (M + H). = 707.38.

| 35 | $R^I$ = NH$_2$<br>$R^{II}$ = CH$_2$OH | (1S,4aR,6aS,7R,8R,10aR,10bR,12aR,14R,15R)-15-[[(2R)-2-amino-2,3-dimethylbutyl]oxy]-14-[3-amino-5-(hydroxymethyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) 0.76 (s, 3H, Me), 0.77 (d, 3H, Me),
0.85 (d, 3H, Me), 0.86 (s,
3H, Me), 0.87 (d, 3H, Me), 0.89 (d, 3H, Me), 0.90 (d, 3H, Me), 0.93 (s,
3H, Me), 1.15 (s, 3H, Me),
1.20 (s, 3H, Me), 1.22-1.32 (m), 1.40-1.44 (m),
1.48-1.64 (m), 1.73-1.96 (m), 2.08-2.22 (m), 2.35
(dd, 1H, H13), 2.84 (s, 1H, H7), 2.99 (d, 1H), 3.47 (d, 1H), 3.52 (dd, 1H), 3.56 (d, 1H), 3.58 (d, 1H), 3.76 (d, 1H), 3.88 (d, 1H), 5.44 (m, 1H, H14) and 5.47 (dd, 1H, H5).
Mass spectrum: (ESI) m/z (M + H). = 684.37.

| 36 | $R^I$ = NH$_2$<br>$R^{II}$ = Ph | (1S,4aR,6aS,7R,8R,10aR,10bR,12aR,14R,15R)-15-[[(2R)-2-amino-2,3-dimethylbutyl]oxy]-14-(3-amino-5-phenyl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

-continued

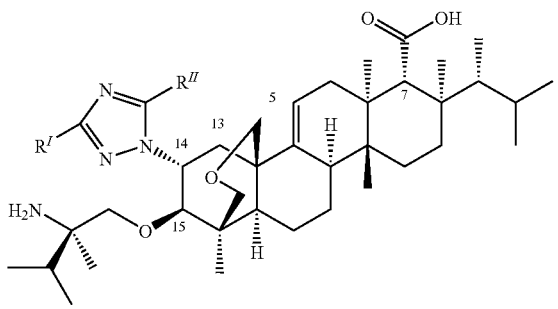

$^1$H NMR (CD$_3$OD, 600 MHz, ppm) 0.77 (s, 3H, Me), 0.77 (d, 3H, Me), 0.83 (s, 3H, Me), 0.86 (d, 3H, Me), 0.86 (d, 3H, Me), 0.89 (d, 3H, Me), 0.90 (d, 3H, Me), 0.91 (s, 3H, Me), 1.18 (s, 3H, Me), 1.22 (s, 3H, Me), 1.22-1.32 (m), 1.41-1.44 (m), 1.48-1.66 (m), 1.72-1.90 (br m), 1.94-1.98 (m), 2.04-2.09 (m), 2.25-2.22 (m), 2.47 (dd, 1H, H13), 2.85 (s, 1H, H7), 3.16 (d, 1H), 3.39 (d, 1H), 3.47 (d, 1H), 3.51 (dd, 1H), 3.57 (m), 3.76 (br m), 3.87 (d, 1H), 5.59 (dd, 1H, H5), 5.66 (m, 1H, H14), 7.54 (m) and 7.70 (m, ArH).
Mass spectrum: (ESI) m/z (M + H). = 730.50.

Example 37

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[3-[[(1-methylethyl)amino]carbonyl]-4H-1,2,4-triazol-4-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 37A) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[3-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 37B) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10 b,11,12,12a-dodecahydro-1,6a,8,10a-tetramethyl-4H-1,4a-propano-2H-phenanthro[1,2-c]pyran-7-carboxylic acid (EXAMPLE 37C)

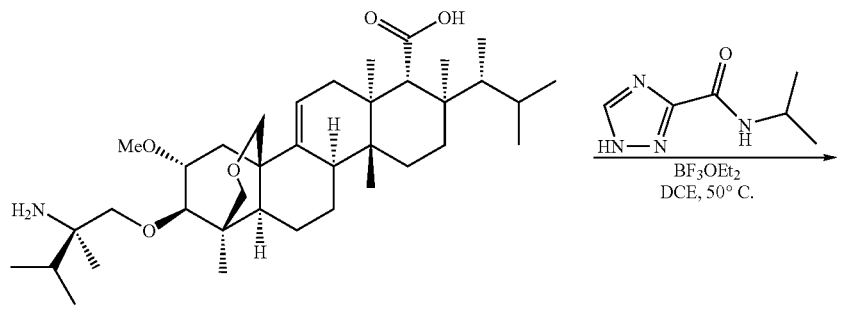

Intermediate 6

-continued

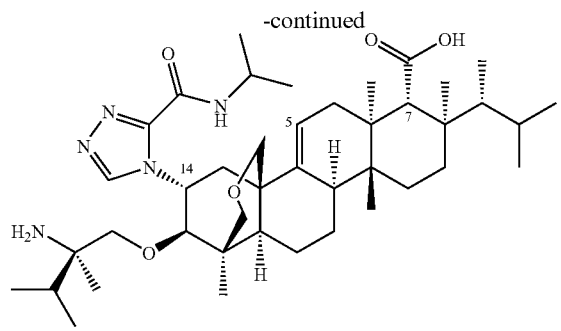

EXAMPLE 37A

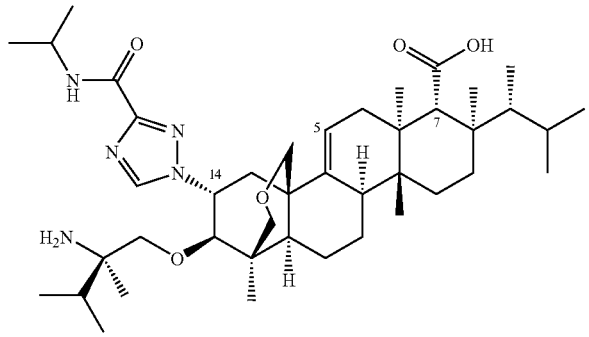

EXAMPLE 37B

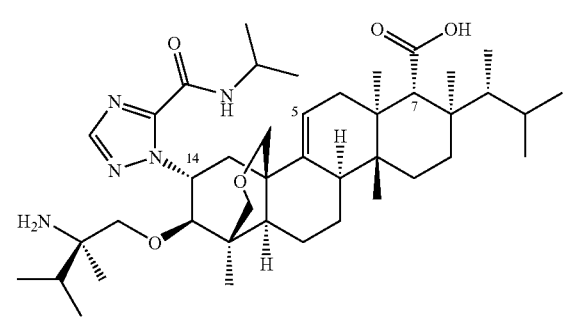

EXAMPLE 37C

N-(1-methylethyl)-1H-1,2,4-triazole-3-carboxamide (42.0 mg, 0.272 mmol) and BF$_3$OEt$_2$ (68 µl, 0.537 mmol) were added to a stirred solution of Intermediate 6 (32.6 mg, 0.054 mmol) in 1,2-dichloroethane (1.0 ml). The reaction mixture was a pale yellow solution that was heated to 50° C. After 4.5 hr, LCMS and $^1$H NMR showed about 75% conversion of Intermediate 6 to a mixture of the three triazole regioisomers at C14. After 4.75 hours, additional BF$_3$OEt$_2$ (30 µl, 0.237 mmol) was added to the reaction mixture. After 6 hr, the reaction mixture was cooled to room temperature, the solvent was evaporated, and the resulting residue was placed under high vacuum. The residue was dissolved in methanol and separated using a single HPLC run on a 19×150 mm Sunfire Prep C18 OBD 10 µm column by eluting with acetonitrile/water+0.1% TFA. The total flow rate was 20 ml/min and the HPLC method employed a 12 minute 20%-100% acetonitrile/water gradient followed by a 6 minute acetonitrile flush. The HPLC fractions of the fastest eluting regioisomer were combined, the solvent was evaporated under reduced pressure, and the residue was lyophilized from ethanol and benzene to give EXAMPLE 37A (4.3 mg) as a white solid. The HPLC fractions of the second eluting regioisomer were combined, the solvent was evaporated under reduced pressure, and the residue was lyophilized from ethanol and benzene to give EXAMPLE 37B (2.5 mg) as a white solid. The HPLC fractions of the slowest eluting regioisomer were combined, the solvent was evaporated under reduced pressure, and the residue was lyophilized from ethanol and benzene to give EXAMPLE 37C (10.5 mg) as a white solid.

Example 37A $^1$H NMR (CD$_3$OD, 500 MHz, ppm) δ 0.78 (s, 3H, Me), 0.79 (d, 3H, Me), 0.83 (d, 3H, Me), 0.87 (s, 3H, Me), 0.88 (d, 3H, Me), 0.89 (d, 3H, Me), 0.90 (s, 3H, Me), 0.92 (d, 3H, Me), 1.18 (s, 3H, Me), 1.22 (s, 3H, Me), 1.24-1.37 (m), 1.26 (d, 3H, Me), 1.29 (d, 3H, Me), 1.42-1.47 (m), 1.49-1.68 (m), 1.77-1.99 (m), 2.13-2.24 (m), 2.53 (broad dd, 1H, H13), 2.76 (d, 1H), 2.86 (s, 1H, H7), 3.48 (d, 1H), 3.54 (dd, 1H), 3.60 (broad d, 1H), 3.61 (d, 1H), 3.72 (broad d, 1H), 3.94 (d, 1H), 4.17-4.25 (m, 1H, CONCH), 5.50 (dd, 1H, H5), 6.43-6.56 (broad m, 1H, H14), 8.70 (d, 1H, CONH), 9.11 (broad s, 1H, triazole).

Mass Spectrum: (ESI) m/z=724.35 (M+H).

Example 37B $^1$H NMR (CD$_3$OD, 500 MHz, ppm) δ 0.79 (s, 3H, Me), 0.79 (d, 3H, Me), 0.83 (d, 3H, Me), 0.87 (s, 3H, Me), 0.89 (d, 6H, 2Me), 0.91 (s, 3H, Me), 0.92 (d, 3H, Me), 1.19 (s, 3H, Me), 1.23 (s, 3H, Me), 1.24-1.39 (m), 1.26 (d, 6H, 2Me), 1.42-1.47 (m), 1.49-1.68 (m), 1.79-1.99 (m), 2.02-2.08 (m), 2.13-2.24 (m), 2.50 (dd, 1H, H13), 2.70 (d, 1H), 2.86 (s, 1H, H7), 3.50 (d, 1H), 3.52 (d, 1H), 3.56 (dd, 1H), 3.63 (d, 1H), 3.77 (d, 1H), 3.94 (d, 1H), 4.17-4.26 (m, 1H, CONCH), 5.53 (dd, 1H, H5), 5.59-5.66 (m, 1H, H14), 8.60 (s, 1H, triazole).

Mass Spectrum: (ESI) m/z=724.35 (M+H).

Example 37C $^1$H NMR (CD$_3$OD, 500 MHz, ppm) δ 0.78 (s, 3H, Me), 0.79 (d, 3H, Me), 0.81 (d, 3H, Me), 0.82 (s, 3H, Me), 0.86 (d, 3H, Me), 0.88 (d, 3H, Me), 0.89 (s, 3H, Me), 0.92 (d, 3H, Me), 1.16 (s, 3H, Me), 1.22 (s, 3H, Me), 1.24-1.37 (m), 1.25 (d, 3H, Me), 1.28 (d, 3H, Me), 1.41-1.47 (m), 1.49-1.58 (m), 1.60-1.68 (m), 1.76-1.98 (m), 2.12-2.25 (m), 2.41 (dd, 1H, H13), 2.76 (d, 1H), 2.86 (s, 1H, H7), 3.48 (d, 1H), 3.52 (d, 1H), 3.54 (dd, 1H), 3.63 (d, 1H), 3.93 (d, 1H), 3.96 (d, 1H), 4.15-4.23 (m, 1H, CONCH), 5.48 (dd, 1H, H5), 6.61-6.69 (m, 1H, H14), 8.04 (s, 1H, triazole), 8.56 (d, 1H, CONH).

Mass Spectrum: (ESI) m/z=724.35 (M+H).

Example 38

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-[[(1-methylethyl)
amino]carbonyl]-1H-1,2,4-triazol-1-yl]-1,6,6a,7,8,9,
10,10a,10b,11,12,12a-dodecahydro-1,6a,8,10a-
tetramethyl-4H-1,4a-propano-2H-phenanthro[1,2-c]
pyran-7-carboxylic acid

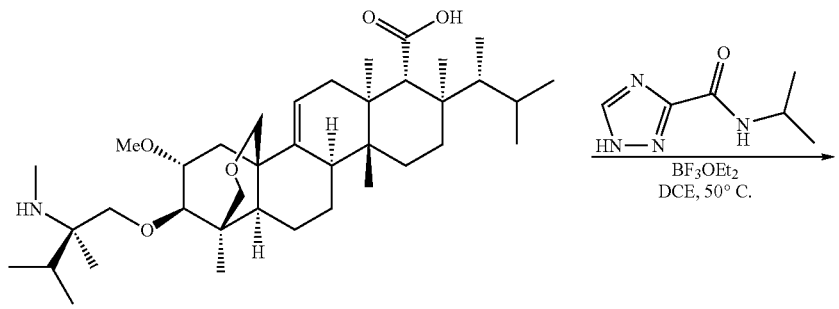

Intermediate 8

N-(1-methylethyl)-1H-1,2,4-triazole-3-carboxamide (753.1 mg, 4.88 mmol) and BF$_3$OEt$_2$ (1.3 ml, 10.26 mmol) were added to a stirred solution of Intermediate 8 (602.2 mg, 0.978 mmol) in 1,2-dichloroethane (14.0 ml). The reaction mixture was a white suspension that was heated to 50° C. After 6 hr, LCMS and $^1$H NMR showed complete consumption of. Intermediate 8. The reaction mixture was cooled to room temperature and partitioned between ethyl acetate (100 ml) and saturated NaHCO$_3$ (50 ml). The aqueous layer was extracted with ethyl acetate (1×50 ml). The organic layers were combined, dried over magnesium sulfate, and filtered. The solvent was evaporated under reduced pressure to give a light yellow residue. The residue was dissolved in methanol and purified using 15 HPLC runs (~40 mg/run) on a 19×150 mm Sunfire Prep C18 OBD 10 μm column by eluting with acetonitrile/water+0.1% TFA. The total flow rate was 15 ml/min and the HPLC method employed a 12 minute 20%-100% acetonitrile/water gradient followed by a 7 minute acetonitrile flush. The HPLC fractions containing the desired product were combined and the solvent was evaporated under reduced pressure to give the title compound (450 mg) as a colorless residue.

$^1$H NMR (CD$_3$OD, 600 MHz, ppm) δ 0.74 (s, 3H, Me), 0.76 (s, 3H, Me), 0.77 (d, 3H, Me), 0.81 (d, 3H, Me), 0.85 (d, 3H, Me), 0.86 (d, 3H, Me), 0.89 (s, 3H, Me), 0.89 (d, 3H, Me), 1.13 (s, 3H, Me), 1.20 (s, 3H, Me), 1.22-1.37 (m), 1.24 (d, 3H, Me), 1.26 (d, 3H, Me), 1.39-1.44 (m), 1.47-1.54 (m), 1.58-1.65 (m), 1.78-1.95 (m), 1.98-2.03 (m), 2.09-2.21 (m), 2.38 (dd, 1H, H13), 2.40 (s, 3H, NMe), 2.83 (s, 1H, H7), 2.92 (d, 1H), 3.47 (d, 1H), 3.52 (dd, 1H), 3.61 (d, 1H), 3.63 (d, 1H), 3.89 (d, 1H), 4.02 (d, 1H), 4.14-4.20 (m, 1H, CONCH), 5.45 (dd, 1H, H5), 6.58-6.65 (m, 1H, H14), 8.02 (s, 1H, triazole), 8.56 (d, 1H, CONH).

Mass Spectrum: (ESI) m/z=738.78 (M+H).

Example 39

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid

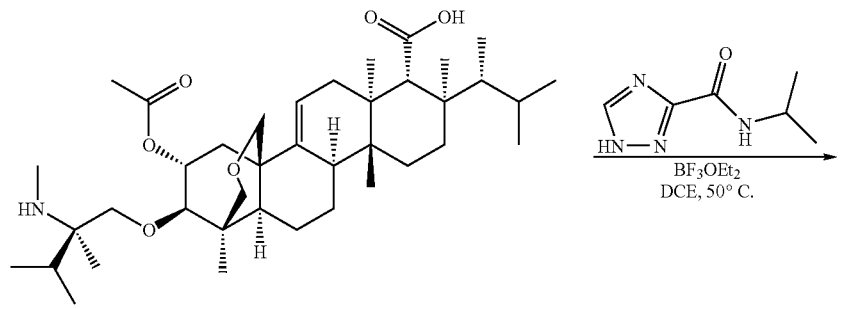

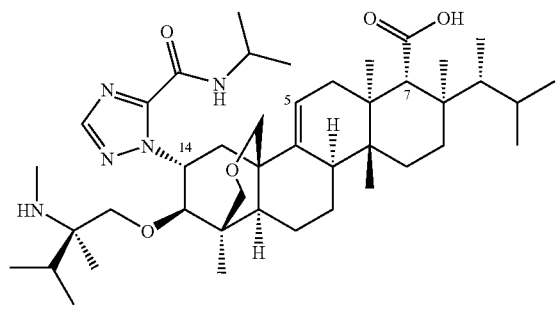

N-(1-methylethyl)-1H-1,2,4-triazole-3-carboxamide (82.3 mg, 0.534 mmol) and BF$_3$OEt$_2$ (200 μl, 1.578 mmol) were added to a stirred solution of (1S,4aR,6aS,7R,8R,10aR,10bR,12aR,14R,15R)-14-(acetyloxy)-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid (free base form of Example 152 in WO2007127012, herein incorporated by reference in its entirety, 70.2 mg, 0.107 mmol) in 1,2-dichloroethane (1.5 ml). The reaction mixture was a light amber solution that was heated to 50° C. After 50 hours, the reaction mixture was cooled to room temperature, the solvent was evaporated under reduced pressure, and the resulting residue was placed under high vacuum. The residue was dissolved in methanol and purified using two HPLC runs (~35 mg/run) on a 19×150 mm Sunfire Prep C18 OBD 10 μm column by eluting with acetonitrile/water+0.1% TFA. The total flow rate was 15 ml/min and the HPLC method employed a 12 minute 20%-100% acetonitrile/water gradient followed by a 7 minute acetonitrile flush. The product HPLC fractions were combined, the solvent was evaporated under reduced pressure, and the residue was lyophilized from ethanol and benzene to give the title compound (24.2 mg, 0.028 mmol) as a white solid.

$^1$H NMR (CD$_3$OD, 600 MHz, ppm) δ 0.75 (s, 3H, Me), 0.76 (d, 3H, Me), 0.80 (s, 3H, Me), 0.82 (d, 3H, Me), 0.86 (d, 3H, Me), 0.87 (d, 3H, Me), 0.92 (s, 3H, Me), 0.94 (d, 3H, Me), 1.08 (s, 3H, Me), 1.24 (d, 3H, Me), 1.26 (d, 3H, Me), 1.28-1.33 (m), 1.36-1.48 (m), 1.52-1.56 (m), 1.66-1.72 (m), 1.67 (s, 3H, Me), 1.74-1.81 (m), 1.87-2.04 (m), 2.18-2.25 (m), 2.41 (s, 3H, NMe), 2.43 (dd, 1H, H13), 2.68-2.73 (m), 2.92 (d, 1H), 3.09 (s, 1H, H7), 3.50 (d, 1H), 3.60 (dd, 1H), 3.64 (d, 1H), 3.67 (d, 1H), 3.94 (d, 1H), 4.06 (d, 1H), 4.14-4.22 (m, 1H, CONCH), 5.74 (d, 1H, H5), 6.64-6.72 (m, 1H, H14), 8.04 (s, 1H, triazole), 8.58 (d, 1H, CONH).

Mass Spectrum: (ESI) m/z=752.73 (M+H).

Example 40

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid

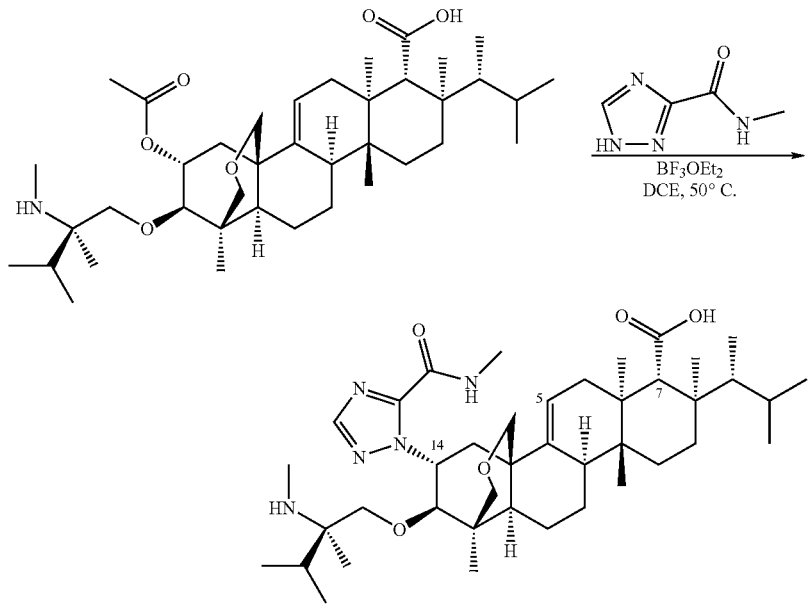

By a procedure analogous to that described for Example 39, but employing N-methyl-1H-1,2,4-triazole-3-carboxamide, the title compound was prepared and isolated as a white solid.

$^1$H NMR (CD$_3$OD, 600 MHz, ppm) δ 0.73 (s, 3H, Me), 0.76 (d, 3H, Me), 0.80 (s, 3H, Me), 0.81 (d, 3H, Me), 0.85 (d, 3H, Me), 0.87 (d, 3H, Me), 0.93 (s, 3H, Me), 0.94 (d, 3H, Me), 1.08 (s, 3H, Me), 1.30 (m), 1.40 (m), 1.46 (m), 1.52-1.56 (m), 1.67 (s, 3H, Me), 1.68-1.80 (m), 1.84-2.03 (m), 2.22 (m), 2.40 (s, 3H, NMe), 2.43 (dd, 1H, H13), 2.54 (d, 1H), 2.70 (m), 2.90 (s, 3H, CONMe), 2.95 (d, 1H), 3.08 (s, 1H, H7), 3.49 (d, 1H), 3.59 (dd, 1H), 3.64 (d, 1H), 3.68 (d, 1H), 3.94 (d, 1H), 4.08 (d, 1H), 5.74 (d, 1H, H5), 6.74 (m, 1H, H14), 8.02 (d, 1H, triazole H).

Mass spectrum: (ESI) m/z=724.70 (M+H).

Example 41

(1S,4aR,6aS,7R,8R,10aR,10bR,12aR,14R,15R)-14-[5-(aminocarbonyl)-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

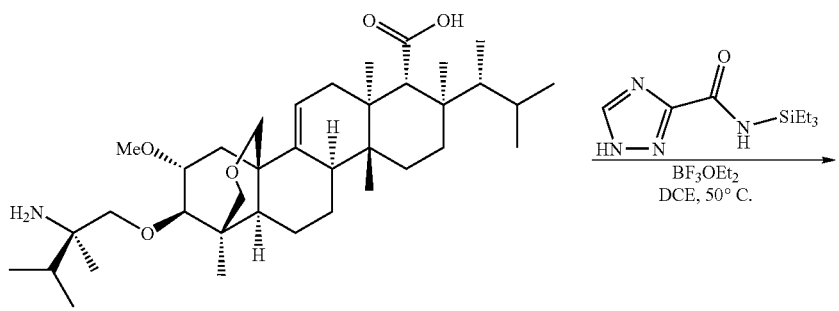

Intermediate 6

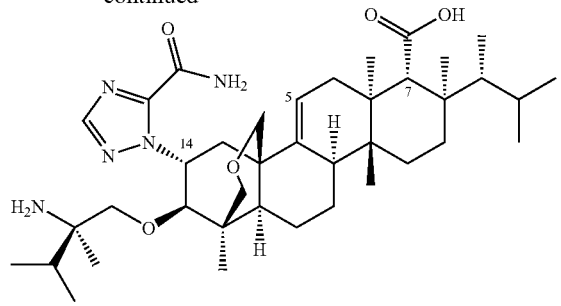

N-(triethylsilyl)-1H-1,2,4-triazole-3-carboxamide (78.6 mg, 0.347 mmol) and BF₃OEt₂ (130 µl, 1.026 mmol) were added to a stirred solution of Intermediate 6 (41.6 mg, 0.069 mmol) in 1,2-dichloroethane (1.15 ml). The reaction mixture was a tan suspension that was heated to 50° C. After 2 hr, LCMS and ¹H NMR showed complete consumption of Intermediate 6. The reaction mixture was cooled to room temperature, the solvent was evaporated, and the resulting residue was placed under high vacuum. The residue was dissolved in methanol and purified using a single HPLC run on a 19×150 mm Sunfire Prep C18 OBD 10 µm column by eluting with acetonitrile/water+0.1% TFA. The total flow rate was 15 ml/min and the HPLC method employed a 12 minute 20%-100% acetonitrile/water gradient followed by a 7 minute acetonitrile flush. The HPLC fractions containing the desired product were combined, the solvent was evaporated under reduced pressure, and the residue was lyophilized from ethanol and benzene to give the title compound (9.0 mg) as a white solid.

¹H NMR (CD₃OD, 600 MHz, ppm) δ 0.76 (s, 3H, Me), 0.77 (d, 3H, Me), 0.80 (d, 3H, Me), 0.80 (s, 3H, Me), 0.84 (d, 3H, Me), 0.85 (d, 3H, Me), 0.87 (s, 3H, Me), 0.89 (d, 3H, Me), 1.14 (s, 3H, Me), 1.20 (s, 3H, Me), 1.22-1.35 (m), 1.39-1.44 (m), 1.47-1.55 (m), 1.58-1.65 (m), 1.73-1.95 (m), 2.09-2.21 (m), 2.39 (dd, 1H, H13), 2.80 (d, 1H), 2.84 (s, 1H, H7), 3.45 (d, 1H), 3.51 (d, 1H), 3.51 (dd, 1H), 3.60 (d, 1H), 3.93 (d, 1H), 3.95 (d, 1H), 5.46 (dd, 1H, H5), 6.64-6.71 (m, 1H, H14), 8.02 (s, 1H, triazole).

Mass Spectrum: (ESI) m/z=682.71 (M+H).

Example 42

(1S,4aR,6aS,7R,8R,10aR,10bR,12aR,14R,15R)-14-[5-(aminocarbonyl)-1H-1,2,4-triazol-1-yl]-15-[[(2R)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

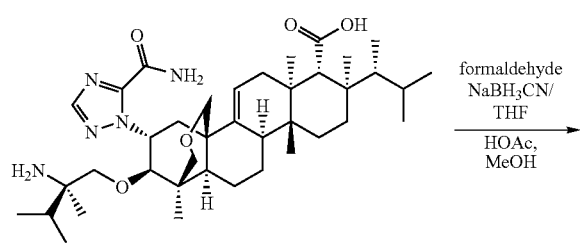

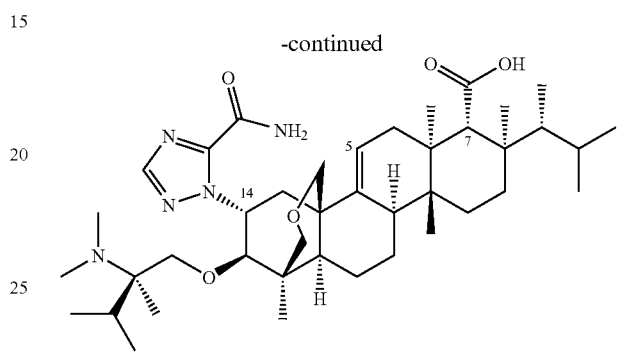

Acetic acid (2 µl, 0.035 mmol), formaldehyde 37% in water (5.4 µl, 0.073 mmol), and sodium cyanoborohydride 1.0 M in THF (67 µl, 0.067 mmol) were added to a stirred hazy solution of (1S,4aR,6aS,7R,8R,10aR,10bR,12aR,14R,15R)-14-[5-(aminocarbonyl)-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 41, 13.3 mg, 0.017 mmol) in methanol (0.33 ml). The reaction mixture was a hazy solution. After 6 hr, LCMS showed complete consumption of starting material. The reaction mixture was diluted with methanol, the solvent was evaporated under reduced pressure, and the resulting residue was placed under high vacuum. The residue was dissolved in methanol and purified using a single HPLC run on a 19×150 mm Sunfire Prep C18 OBD 10 µm column by eluting with acetonitrile/water+0.1% TFA. The total flow rate was 15 ml/min and the HPLC method employed a 12 minute 20%-100% acetonitrile/water gradient followed by a 7 minute acetonitrile flush. The product HPLC fractions were combined and the solvent was evaporated under reduced pressure to give the title compound as a colorless residue.

¹H NMR (CD₃OD, 600 MHz, ppm) δ 0.75 (s, 3H, Me), 0.76 (d, 3H, Me), 0.85 (d, 3H, Me), 0.86 (s, 3H, Me), 0.89 (d, 3H, Me), 0.92 (s, 3H, Me), 0.93 (d, 3H, Me), 0.94 (d, 3H, Me), 1.12 (s, 3H, Me), 1.19 (s, 3H, Me), 1.21-1.34 (m), 1.39-1.43 (m), 1.46-1.54 (m), 1.58-1.64 (m), 1.71-1.94 (m), 2.08-2.13 (m), 2.14-2.21 (m), 2.24-2.31 (m), 2.37 (dd, 1H, H13), 2.64 (s, 3H, NMe), 2.71 (s, 3H, NMe), 2.83 (s, 1H, H7), 3.14 (d, 1H), 3.49 (d, 1H), 3.50 (dd, 1H), 3.60 (d, 1H), 3.69 (d, 1H), 3.75 (d, 1H), 4.06 (d, 1H), 5.43 (dd, 1H, H5), 6.63-6.70 (m, 1H, H14), 8.05 (s, 1H, triazole).

Mass Spectrum: (ESI) m/z=710.66 (M+H).

Example 43

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2-(ethylamino)-2,3-dimethylbutyl]oxy]-1,6,6a,7,8,9,10,10a,10 b,11,12,12a-dodecahydro-1,6a,8,10a-tetramethyl-4H-1,4a-propano-2H-phenanthro[1,2-c]pyran-7-carboxylic acid

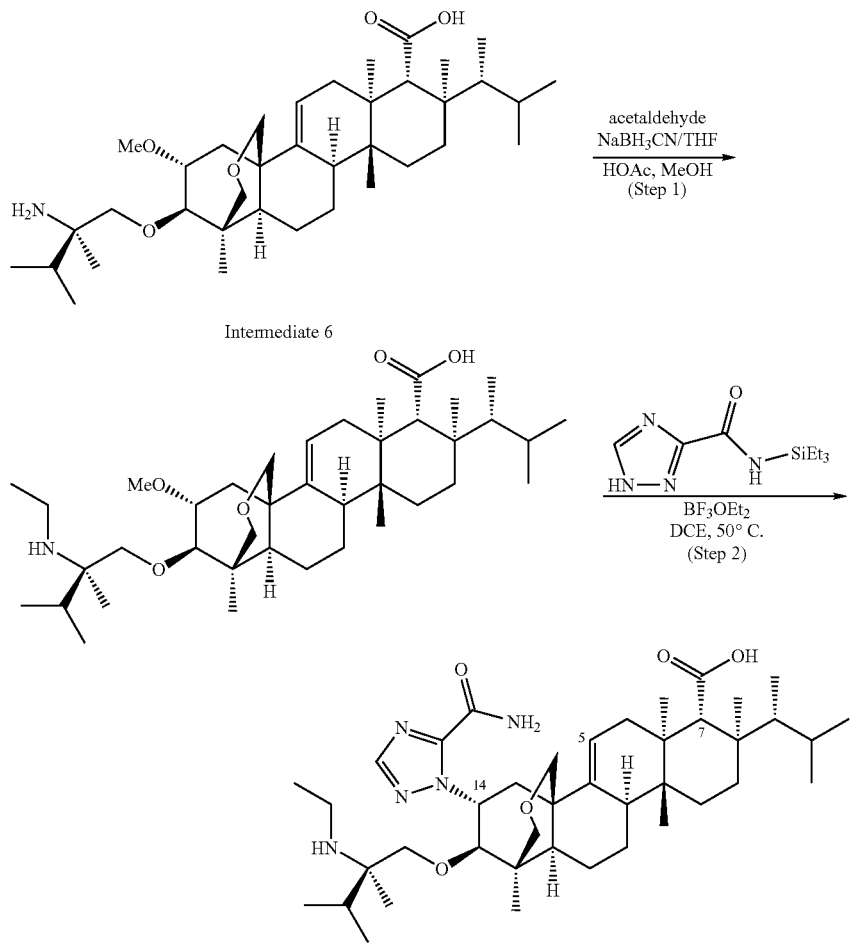

Step 1:

Acetic acid (65 µl, 1.135 mmol), acetaldehyde (0.41 ml, 7.26 mmol), and sodium cyanoborohydride 1.0 M in THF (2.3 ml, 2.30 mmol) were added to a stirred solution of Intermediate 6 (338.0 mg, 0.562 mmol) in methanol (5.6 ml). The reaction mixture was a colorless solution. After 4 hours, LCMS showed complete consumption of Intermediate 6. The reaction mixture was partitioned between ethyl acetate (100 ml) and water (100 ml). The aqueous layer was extracted with ethyl acetate (1×50 ml). The organic layers were combined, dried over magnesium sulfate, and filtered. The solvent was evaporated under reduced pressure and the residue was lyophilized from ethanol and benzene to give the product (337.5 mg) as a white solid.

$^1$H NMR (CD$_3$OD, 500 MHz, ppm) δ 0.78 (s, 3H, Me), 0.79 (d, 3H, Me), 0.82 (s, 3H, Me), 0.88 (d, 3H, Me), 0.92 (d, 3H, Me), 1.02 (d, 3H, Me), 1.04 (d, 3H, Me), 1.16 (s, 3H, Me), 1.19 (s, 3H, Me), 1.23 (s, 3H, Me), 1.24-1.35 (m), 1.38 (t, 3H), 1.40-1.46 (m), 1.48-1.55 (m), 1.58-1.68 (m), 1.72-1.88 (m), 1.95-2.02 (m), 2.08-2.14 (m), 2.18-2.25 (m), 2.27-2.35 (m), 2.60 (dd, 1H, H13), 2.87 (s, 1H, H7), 2.98 (d, 1H), 3.07-3.15 (m, 1H, NCH$_2$), 3.28-3.35 (obscured m, 1H, NCH$_2$), 3.37 (d, 1H), 3.38 (s, 3H, OMe), 3.44 (s, 2H), 3.70 (d, 1H), 3.72 (d, 1H), 3.90 (d, 1H), 4.22-4.29 (m, 1H, H14), 5.57 (dd, 1H, H14).

Mass Spectrum: (ESI) m/z=630.58 (M+H).

Step 2:

N-(triethylsilyl)-1H-1,2,4-triazole-3-carboxamide (220.0 mg, 0.972 mmol) and BF$_3$OEt$_2$ (0.37 ml, 2.92 mmol) were added to a stirred solution of the product compound from Step 1 (122.8 mg, 0.195 mmol) in 1,2-dichloroethane (3.2 ml). The reaction mixture was a light tan suspension that was heated to 50° C. After 2.5 hr, LCMS and $^1$H NMR showed complete consumption of starting material. The reaction mixture was cooled to room temperature, the solvent was evaporated, and the resulting residue was placed under high vacuum. The residue was taken up in methanol and the resulting white suspension was filtered (0.45 µm syringe filter) before being purified using three HPLC runs (~41 mg/run) on a 19×150 mm Sunfire Prep C18 OBD 10 µm column by eluting with acetonitrile/water+0.1% TFA. The total flow rate was 15 ml/min and the HPLC method employed a 12 minute 20%-100% acetonitrile/water gradient followed by a 7 minute acetonitrile flush. The product HPLC fractions were combined, the solvent was evaporated under reduced pressure, and the residue was lyophilized from ethanol and benzene to give the title compound (21.6 mg) as a white solid.

¹H NMR (CD₃OD, 600 MHz, ppm) δ 0.73 (s, 3H, Me), 0.75 (s, 3H, Me), 0.76 (d, 3H, Me), 0.79 (d, 3H, Me), 0.85 (d, 3H, Me), 0.88 (d, 3H, Me), 0.88 (s, 3H, Me), 0.89 (d, 3H, Me), 1.12 (s, 3H, Me), 1.20 (s, 3H, Me), 1.21-1.35 (m), 1.26 (t, 3H), 1.39-1.44 (m), 1.46-1.54 (m), 1.58-1.65 (m), 1.74-1.95 (m), 2.01-2.07 (m), 2.08-2.13 (m), 2.14-2.22 (m), 2.38 (dd, 1H, H13), 2.66-2.73 (m, 1H, NCH₂), 2.80-2.87 (m, 1H, NCH₂), 2.83 (s, 1H, H7), 2.96 (d, 1H), 3.48 (d, 1H), 3.51 (dd, 1H), 3.60 (d, 1H), 3.65 (d, 1H), 3.87 (d, 1H), 4.06 (d, 1H), 5.44 (dd, 1H, H5), 6.64-6.72 (m, 1H, H14), 8.03 (s, 1H, triazole).

Mass Spectrum: (ESI) m/z=710.66 (M+H).

Example 44

(1S,4aR,6aS,7R,8R,10aR,10bR,12aR,14R,15R)-14-[5-(aminocarbonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

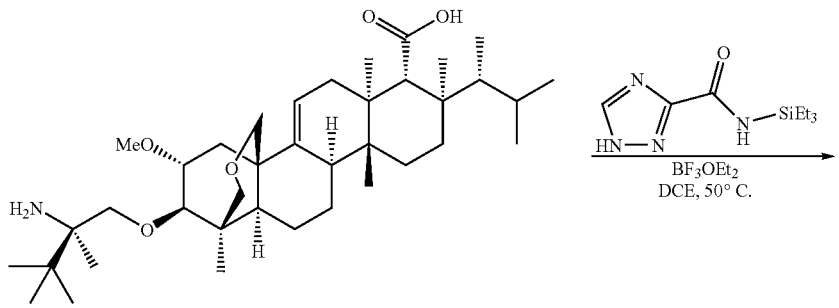

Intermediate 14

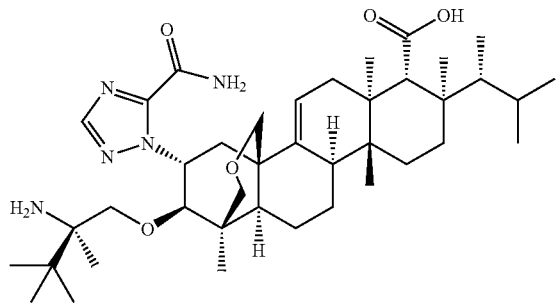

A solution of Intermediate 14 (520 mg, 0.844 mmol) in dichloroethane (5.7 mL) was treated with N-(triethylsilyl)-1H-1,2,4-triazole-3-carboxamide (669 mg, 2.95 mmol) then BF₃OEt₂ (1.07 mL, 8.44 mmol) and this mixture was heated to 50° C. under nitrogen. After 2 hours the reaction was cooled to room temperature and quenched with sat. NaHCO₃. The mixture was partitioned between ethyl acetate and sat. NaHCO₃ and the organic phase was washed with water (a small amount of methanol was added to help dissolve a precipitate). The organic phase was dried (MgSO₄) and concentrated in vacuo to give a white solid. Purification was accomplished by preparative HPLC (30×100 mm Waters Sunfire column, 5 µm, UV-detection, 10-100% MeCN/water with 0.05% TFA over 12 minutes, 5 runs). The product fractions (the desired product is the third regioisomer to elute under these conditions) were combined and partially concentrated by rotovap then frozen and lyophilized to give the title compound (255 mg) as a white amorphous solid (trifluoroacetate salt).

¹H NMR (CD₃OD, 500 MHz, ppm) δ 0.77 (s, 3H), 0.78 (d, 3H, partially obscured), 0.81 (s, 3H), 0.85 (s, 9H), 0.86 (d, 3H, partially obscured), 0.89 (s, 3H), 0.90 (d, 3H, partially obscured), 1.14 (s, 3H), 1.21 (s, 3H), 1.22-1.67 (m), 1.78-1.97 (m), 2.14 (m, 1H), 2.19 (m, 1H), 2.41 (dd, J=13.3 Hz, 6.4 Hz, 1H), 2.84 (d, J=9.8 Hz, 1H), 2.84 (s, 1H), 3.46 (d, J=11.8 Hz, 1H), 3.52 (d, J=11.4 Hz, 1.8 Hz, 1H), 3.62 (d, J=11.6 Hz, 1H), 3.70 (d, J=9.8 Hz, 1H), 3.94-4.0 (m, 2H), 5.47 (m, 1H), 6.73 (m, 1H), 8.02 (s, 1H).

Mass Spectrum: m/z=696.50 (M+H).

Conversion of Example 44 to Hydrochloride Salt

Example 44 TFA salt (255 mg, 0.315 mmol) was dissolved in methanol (1.5 mL) and the solution was diluted with 3 mL of 1:1 MeCN/H₂O. The solution was loaded onto a column of Dowex® 1×8 chloride form ion exchange resin (10 g, ~1.8 meq/g) and the column was eluted with 1:1 MeCN/H₂O (~1.5 column volumes). The eluant was concentrated in vacuo to remove most of the acetonitrile and then frozen and lyophilized to give 226 mg of the hydrochloride salt as a white solid.

Example 45

(1S,4aR,6aS,7R,8R,10aR,10bR,12aR,14R,15R)-8-[(1R)-1,2-dimethylpropyl]-14-[5-[(methylamino)carbonyl]-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

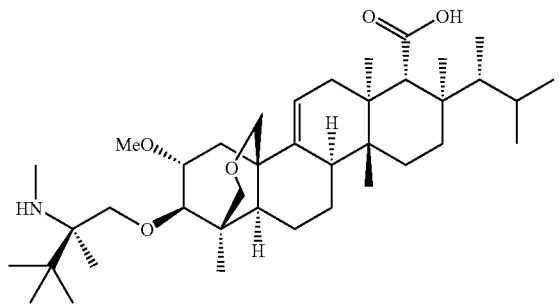

Intermediate 16

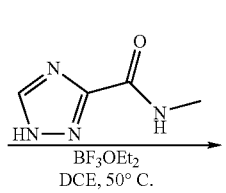

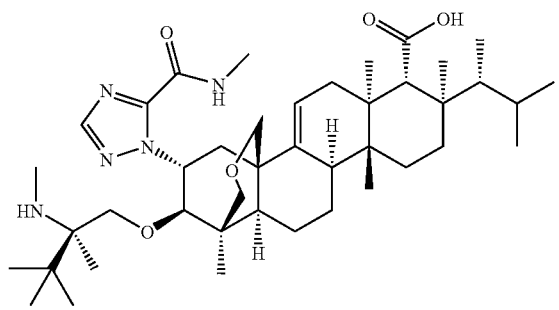

A solution of Intermediate 16 (75 mg, 0.11 mmol) in dichloroethane (1.1 mL) was treated with N-methyl-1H-1,2,4-triazole-3-carboxamide (75 mg, 0.65 mmol) then $BF_3OEt_2$ (0.15 mL, 1.1 mmol) and this mixture was heated to 50° C. under nitrogen. After 1.5 hours the reaction was cooled to room temperature then concentrated in vacuo. The crude product mixture was suspended in methanol (3 mL) and filtered through a sintered glass funnel. The filtrate was purified by preparative HPLC (19×100 mm Waters Sunfire column, 5 µm, UV-detection, 30-100% MeCN/water with 0.05% TFA over 20 minutes). The product fractions (the desired product is the third regioisomer to elute under these conditions) were combined and partially concentrated by rotovap then frozen and lyophilized to give the title compound (38 mg) as a white amorphous solid.

$^1$H NMR (CD$_3$OD, 500 MHz, ppm) δ 0.76 (s, 3H), 0.77 (d, 3H, partially obscured), 0.80 (s, 3H), 0.85 (d, J=6.8 Hz, 3H), 0.90 (d, J=7.0 Hz, 3H), 0.91 (s, 9H), 0.93 (s, 3H), 1.13 (s, 3H), 1.20 (s, 3H), 1.22-1.56 (m), 1.62 (m, 1H), 1.75-1.96 (m), 2.12 (m, 1H), 2.19 (m, 1H), 2.39 (dd, J=13.5 Hz, 6.5 Hz, 1H), 2.53 (s, 3H), 2.84 (s, 1H), 2.92 (d, J=4.3 Hz, 3H), 3.12 (d, J=11.2 Hz, 1H), 3.51 (d, J=11.8 Hz, 1H), 3.52 (dd, J=11.4 Hz, 2.1 Hz, 1H), 3.62 (d, 11.4 Hz, 1H), 3.78 (d, J=11.8 Hz, 1H), 3.84 (d, J=11.2 Hz, 1H), 4.03 (d, J=9.9 Hz, 1 Hz, 5.45 (m, 1H), 6.65 (m, 1H), 8.02 (s, 1H), 8.79 (m, 1H).

Mass Spectrum: m/z=724.79 (M+H).

Example 46

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

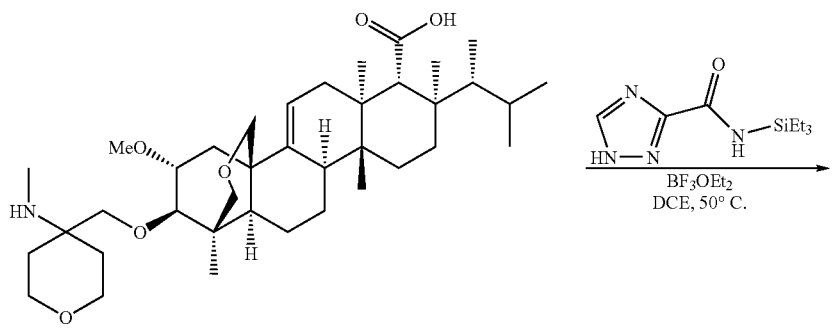

Intermediate 28

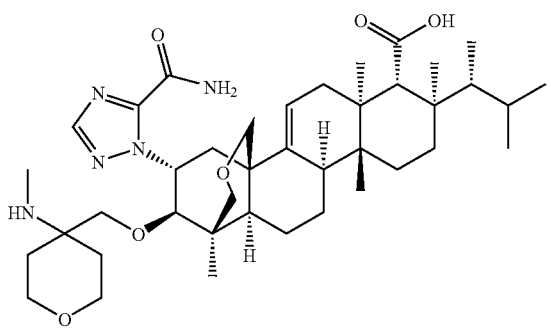

A solution of Intermediate 28 (180 mg, 0.286 mmol) in dichloroethane (1.3 mL) was treated with N-(triethylsilyl)-1H-1,2,4-triazole-3-carboxamide (323 mg, 1.43 mmol) then $BF_3OEt_2$ (0.36 mL, 2.86 mmol) and this mixture was heated to 55° C. under nitrogen. After 1 hour the reaction was cooled to room temperature then concentrated in vacuo. The crude product mixture was suspended in methanol (3 mL) and filtered through a sintered glass funnel. The filtrate was purified by preparative HPLC (19×100 mm Waters Sunfire column, 5 μm, UV-detection, 30-100% MeCN/water with 0.05% TFA over 20 minutes). The fractions containing the desired product (the desired product is the third regioisomer to elute under these conditions) were combined and partially concentrated by rotovap then frozen and lyophilized to give the title compound (80 mg) as a white amorphous solid.

$^1$H NMR (CD$_3$OD, 500 MHz, ppm) δ 0.77 (s, 3H), 0.78 (d, 3H, partially obscured), 0.87 (d, J=6.6 Hz, 3H), 0.91 (d, 3H, partially obscured), 0.92 (s, 3H), 1.14 (s, 3H), 1.22 (s, 3H), 1.23-1.58 (m), 1.64 (m, 2H), 1.74-1.98 (m), 2.13 (m, 1H), 2.20 (m, 1H), 2.38 (dd, partially obscured, 1H), 2.40 (s, 3H), 2.85 (s, 1H), 2.94 (m, 1H), 3.35 (t, 2H, partially obscured), 3.49 (d, 1H, partially obscured), 3.52 (dd, 1H, partially obscured), 3.61 (d, 1H, partially obscured), 3.62 (m, 1H, partially obscured), 3.80 (m, 1H, partially obscured), 3.85 (m, 2H, partially obscured), 4.15 (d, J=9.9 Hz, 1H), 5.46 (m, 1H), 6.65 (m, 1H), 8.08 (s, 1H).

Mass Spectrum m/z=710.67 (M+H).

Examples 47-83

The following compounds were prepared using methods analogous to those described in the preceding examples:

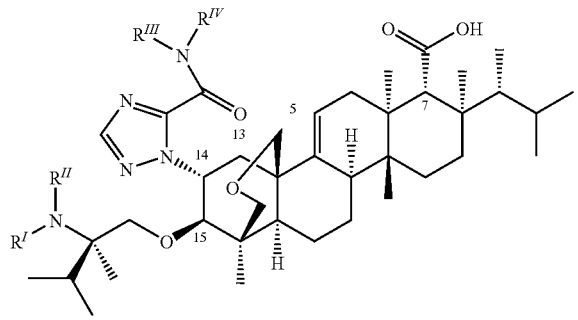

| 47 | $R^I$ = Me<br>$R^{II}$ = H<br>$R^{III}$ = H<br>$R^{IV}$ = H | (1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2,3-dimethyl-2-(methylamino)butyl]oxy]-1,6,6a,7, 8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.74 (s, 3H, Me), 0.76 (s, 3H, Me), 0.76 (d, 3H, Me), 0.82 (d, 3H, Me), 0.85 (d, 3H, Me), 0.86 (d, , 3H, Me), 0.90 (d, 3H, Me), 0.90 (s, 3H, Me), 1.12 (s, , 3H, Me), 1.20 (s, 3H, Me), 1.22-1.35 (m), 1.39-1.44 (m), 1.47-1.55 (m), 1.58-1.65 (m), 1.75-1.95 (m), 1.98-2.05 (m), 2.09-2.21 (m), 2.39 (dd, 1H, H13), 2.40 (s, 3H, NMe), 2.83 (s, 1H, H7), 2.96 (d, 1H), 3.47 (d, 1H), 3.51 (dd, 1H), 3.60 (d, 1H), 3.63 (d, 1H), 3.88 (d, 1H), 4.05 (d, 1H), 5.45 (dd, 1H, H5), 6.63-6.70 (m, 1H, H14), 8.03 (s, 1H, triazole).
Mass spectrum: (ESI) m/z = 696.64 (M + H).

| 48 | $R^I$ = n-Pr<br>$R^{II}$ = H<br>$R^{III}$ = H<br>$R^{IV}$ = H | (1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2,3-dimethyl-2-(propylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 500 MHz, ppm) δ 0.74 (s, 3H, Me), 0.78 (s, 3H, Me), 0.79 (d, 6H, 2Me), 0.87 (d, 3H, Me), 0.90 (d, 3H, Me), 0.91 (s, 3H, Me), 0.92 (d, 3H, Me), 1.02 (t, 3H), 1.15 (s, 3H, Me), 1.22 (s, 3H, Me), 1.24-1.37 (m), 1.41-1.46 (m), 1.49-1.57 (m) 1.60-1.73 (m), 1.78-1.98 (m), 2.00-2.08 (m), 2.11-2.24 (m), 2.39 (dd, 1H, H13), 2.70-2.81 (m, 2H, NCH$_2$), 2.86 (s, 1H, H7), 3.00 (d, 1H), 3.50 (d, 1H), 3.54 (dd, 1H), 3.63 (d, 1H), 3.69 (d, 1H), 3.88 (d, 1H), 4.08 (d, 1H), 5.47 (dd, 1H, H5), 6.66-6.74 (m, 1H, H14), 8.06 (s, 1H, triazole).
Mass spectrum: (ESI) m/z = 724.61 (M + H).

| 49 | $R^I$ = H<br>$R^{II}$ = H<br>$R^{III}$ = Me<br>$R^{IV}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (d, 3H, Me), 0.77 (s, 3H, Me), 0.79 (d, 3H, Me), 0.84 (d, 3H, Me), 0.85 (d, 3H, Me), 0.87 (s, 3H, Me), 0.89 (d, 3H, Me), 1.13 (s, 3H, Me), 1.20 (s, 3H, Me), 1.22-1.34 (m), 1.40-1.44 (m), 1.48-1.55 (m), 1.58-1.65 (m), 1.74-1.95 (m), 2.10-2.21 (m), 2.38 (dd, 1H, H13), 2.80 (d, 1H), 2.83 (s, 1H, H7), 2.90 (s, 3H, NMe), 3.46 (d, 1H), 3.51 (d, 1H), 3.52 (dd, 1H), 3.61 (d, 1H), 3.93 (d, 1H), 3.94 (d, 1H), 5.45 (dd, 1H, H5), 6.68 (m, 1H, H14), 7.99 (s, 1H, triazole).
Mass spectrum: (ESI) m/z = 696.33 (M + H).

| 50 | $R^I$ = H<br>$R^{II}$ = H<br>$R^{III}$ = Me<br>$R^{IV}$ = Me | (1S,4aR,6aS,7R,8R,10aR,10bR,12aR,14R,15R)-15-[[(2R)-2-amino-2,3-dimethylbutyl]oxy]-14-[5-[(dimethylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) 0.76 (s, 3H, Me), 0.77 (d, 3H, Me), 0.79 (s, 3H, Me), 0.85 (d, 3H, Me), 0.87 (d, 3H, Me), 0.88 (s, 3H, Me), 0.89 (d, 3H, Me), 0.92 (d, 3H, Me), 1.14 (s, 3H, Me), 1.20 (s, 3H, Me), 1.22-1.32 (m), 1.40-1.44 (m), 1.48-1.56 (m), 1.58-1.64 (m), 1.78-2.04 (m), 2.10-2.21 (m), 2.33 (dd, 1H, H13), 2.73 (d, 1H), 2.84 (s, 1H, H7), 2.98 (s, 3H, NMe), 3.16 (s, 3H, NMe), 3.46 (d, 1H), 3.51 (dd, 1H), 3.57 (d, 1H), 3.61 (d, 1H), 3.86 (d, 1H), 3.87 (d, 1H), 5.47 (dd, 1H, H5), 5.61 (m, 1H, H14), 8.10 (s, 1H, triazole).
Mass spectrum: (ESI) m/z = 710.48 (M + H).

| 51 | $R^I$ = Me<br>$R^{II}$ = H<br>$R^{III}$ = Me<br>$R^{IV}$ = H | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 500 MHz, ppm) δ 0.74 (s, 3H, Me), 0.78 (s, 3H, Me), 0.79 d, 3H, Me), 0.84 (d, 3H, Me), 0.87 (d, 3H, Me), 0.88 (d, 3H, Me), 0.92 (d, 3H, Me), 0.92 (s, 3H, Me), 1.14 (s, -continued

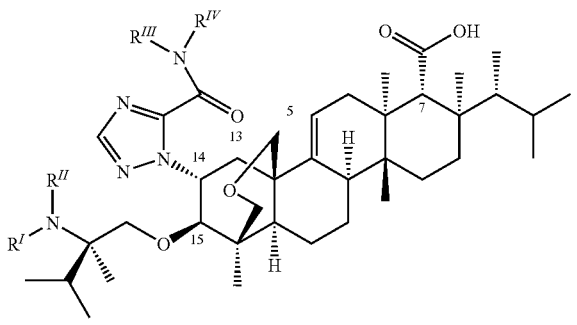

3H, Me), 1.22 (s, 3H, Me), 1.23-1.38 (m), 1.41-1.47 (m), 1.49-1.57 (m), 1.60-1.68 (m), 1.77-1.98 (m), 1.99-2.07 (m), 2.11-2.24 (m), 2.40 (dd, 1H, H13), 2.41 (s, 3H, NMe), 2.86 (s, 1H, H7), 2.93 (d, 3H, CONMe), 2.98 (d, 1H), 3.50 (d, 1H), 3.54 (dd, 1H), 3.64 (d, 1H), 3.66 (d, 1H), 3.91 (d, 1H), 4.07 (d, 1H), 5.47 (dd, 1H, H5), 6.66-6.73 (m, 1H, H14), 8.04 (s, 1H, triazole), 8.80 (q, 1H, CONH).
Mass spectrum: (ESI) m/z = 710.32 (M + H).

| 52 | $R^I$ = Me<br>$R^{II}$ = Me<br>$R^{III}$ = Me<br>$R^{IV}$ = H | (1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.75 (s, 3H, Me), 0.76 (d, 3H, Me), 0.85 (s, 3H, Me), 0.85 (d, 3H, Me), 0.89 (d, 3H, Me), 0.92 (d, 3H, Me), 0.92 (s, 3H, Me), 0.94 (d, 3H, Me), 1.11 (s, 3H, Me), 1.19 (s, 3H, Me), 1.21-1.36 (m), 1.39-1.43 (m), 1.46-1.54 (m), 1.58-1.65 (m), 1.70-1.77 (m), 1.77-1.94 (m), 2.08-2.13 (m), 2.14-2.21 (m), 2.23-2.30 (m), 2.37 (dd, 1H, H13), 2.64 (s, 3H, NMe), 2.70 (s, 3H, NMe), 2.83 (s, 1H, H7), 2.92 (d, 3H, CONMe), 3.13 (d, 1H), 3.50 (d, 1H), 3.50 (dd, 1H), 3.61 (d, 1H), 3.69 (d, 1H), 3.76 (d, 1H), 4.06 (d, 1H), 5.43 (dd, 1H, H5), 6.64-6.71 (m, 1H, H14), 8.03 (s, 1H, triazole), 8.77 (q, 1H, CONH).
Mass spectrum: (ESI) m/z = 724.47 (M + H).

| 53 | $R^I$ = n-Pr<br>$R^{II}$ = H<br>$R^{III}$ = Me<br>$R^{IV}$ = H | (1S,4aR,6aS,7R,8R,10aR,10bR,12aR,14R,15R)-8-[(1R)-1,2-dimethylpropyl]-15-[[(2R)-2,3-dimethyl-2-(propylamino)butyl]oxy]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.70 (s, 3H, Me), 0.76 (d, 3H, Me), 0.76 (s, 3H, Me), 0.76 (d, 3H, Me), 0.85 (d, 3H, Me), 0.87 (d, 3H, Me), 0.88 (s, 3H, Me), 0.89 (d, 3H, Me), 0.99 (t, 3H), 1.12 (s, 3H, Me), 1.20 (s, 3H, Me), 1.21-1.35 (m), 1.39-1.44 (m), 1.47-1.54 (m), 1.58-1.69 (m), 1.75-1.95 (m), 1.98-2.05 (m), 2.08-2.03 (m), 2.14-2.22 (m), 2.36 (dd, 1H, H13), 2.67-2.77 (m, 2H, NCH$_2$), 2.83 (s, 1H, H7), 2.91 (d, 3H, CONMe), 2.96 (d, 1H), 3.48 (d, 1H), 3.51 (dd, 1H), 3.61 (d, 1H), 3.66 (d, 1H), 3.87 (d, 1H), 4.04 (d, 1H), 5.44 (dd, 1H, H5), 6.66-6.73 (m, 1H, H14), 8.01 (s, 1H, triazole), 8.79 (q, 1H, CONH).
Mass spectrum: (ESI) m/z = 738.50 (M + H).

| 54 | $R^I$ = Me<br>$R^{II}$ = H<br>$R^{III}$ = Me<br>$R^{IV}$ = Me | (1S,4aR,6aS,7R,8R,10aR,10bR,12aR,14R,15R)-14-[5-[(dimethylamino)carbonyl]-1H-1,2,4-triazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.68 (s, 3H, Me), 0.75 (s, 3H, Me), 0.76 (d, 3H, Me), 0.85 (d, 3H, Me), 0.89 (d, 3H, Me), 0.90 (d, 3H, Me), 0.90 (d, 3H, Me), 0.92 (s, 3H, Me), 1.14 (s, 3H, Me), 1.20 (s, 3H, Me), 1.22-1.35 (m), 1.39-1.44 (m), 1.47-1.65 (m), 1.58-1.65 (m), 1.79-1.96 (m), 2.03-2.10 (m), 2.09-2.14 (m), 2.15-2.21 (m), 2.31 (dd, 1H, H13), 2.33 (s, 3H, NMe), 2.83 (s, 1H, H7), 3.11 (s, 3H, CONMe), 3.16 (s, 3H, CONMe), 3.17 (d, 1H), 3.48 (d, 1H), 3.50 (dd, 1H), 3.56 (d, 1H), 3.77 (d, 1H), 3.82 (d, 1H), 3.96 (d, 1H), 5.46 (dd, 1H, H5), 5.64-5.70 (m, 1H, H14), 8.10 (s, 1H, triazole).
Mass spectrum: (ESI) m/z = 724.55 (M + H).

| 55 | $R^I$ = Et<br>$R^{II}$ = H<br>$R^{III}$ = Me<br>$R^{IV}$ = H | (1S,4aR,6aS,7R,8R,10aR,10bR,12aR,14R,15R)-14-[5-[(dimethylamino)carbonyl]-1H-1,2,4-triazol-1-yl]-8-[(1R)-1,2-dimethylpropyl]-15-[[(2R)-2-(ethylamino)-2,3-dimethylbutyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.54 (s, 3H, Me), 0.76 (s, 3H, Me), 0.77 (d, 3H, Me), 0.81 (d, 3H, Me), 0.85 (d, 3H, Me), 0.88 (d, 3H, Me), 0.89 (d, 3H, Me), 0.91 (s, 3H, Me), 1.14 (s, 3H, Me), 1.20 (s, 3H, Me), 1.22-1.36 (m), 1.34 (t, 3H), 1.39-1.44 (m), 1.47-1.56 (m), 1.58-1.65 (m), 1.79-2.05 (m), 2.10-2.22 (m), 2.30 (dd, 1H, H13), 2.82-2.89 (m, 1H, NCH), 2.83 (s, 1H, H7), 2.91-2.97 (m, 1H, NCH), 3.12 (s, 3H, CONMe), 3.16 (s, 3H, CONMe), 3.20 (d, 1H), 3.50 (d, 1H), 3.51 (d, 1H), 3.56 (d, 1H), 3.79 (d, 1H), 3.84 (d, 1H), 3.96 (d, 1H), 5.47 (dd, 1H, H5), 5.69-5.75 (m, 1H, H14), 8.09 (s, 1H, triazole).
Mass spectrum: (ESI) m/z = 738.65 (M + H).

| 56 | $R^I$ = H<br>$R^{II}$ = H<br>$R^{III}$ = Et<br>$R^{IV}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(ethylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

-continued

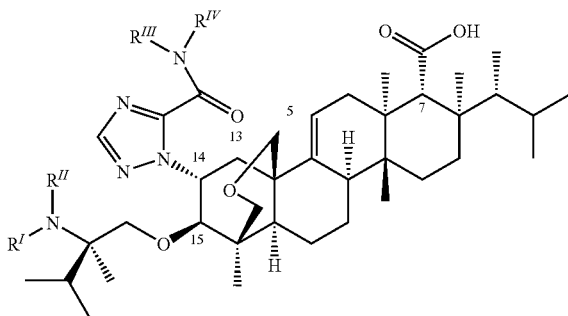

¹H NMR (CD₃OD, 600 MHz, ppm) δ 0.76 (s, 3H, Me), 0.77 (d, 3H, Me), 0.78 (d, 3H, Me), 0.79 (s, 3H, Me), 0.84 (d, 3H, Me), 0.85 (d, 3H, Me), 0.88 (d, 3H, Me), 0.89 (s, 3H, Me), 1.14 (s, 3H, Me), 1.20 (s, 3H, Me), 1.21 (t, 3H), 1.22-1.34 (m), 1.40-1.44 (m), 1.48-1.55 (m), 1.58-1.65 (m), 1.74-1.95 (m), 2.10-2.21 (m), 2.39 (dd, 1H, H13), 2.77 (d, 1H), 2.84 (s, 1H, H7), 3.34-3.45 (m), 3.46 (d, 1H), 3.50 (d, 1H), 3.52 (dd, 1H), 3.61 (d, 1H), 3.92 (d, 1H), 3.93 (d, 1H), 5.46 (dd, 1H, H5), 6.67 (m, 1H, H14), 8.00 (s, 1H, triazole).
Mass spectrum: (ESI) m/z = 710.48 (M + H).

| 57 | $R^I$ = Me<br>$R^{II}$ = H<br>$R^{III}$ = Et<br>$R^{IV}$ = H | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[(ethylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.73 (s, 3H, Me), 0.76 (s, 3H, Me), 0.76 (d, 3H, Me), 0.81 (d, 3H, Me), 0.85 (d, 6H, 2Me), 0.89 (d, 3H, Me), 0.89 (s, 3H, Me), 1.12 (s, 3H, Me), 1.20 (s, 3H, Me), 1.21 (t, 3H), 1.21-1.35 (m), 1.39-1.44 (m), 1.47-1.54 (m), 1.58-1.65 (m), 1.77-1.95 (m), 1.97-2.04 (m), 2.09-2.14 (m), 2.15-2.22 (m), 2.38 (dd, 1H, H13), 2.40 (s, 3H, NMe), 2.83 (s, 1H, H7), 2.92 (d, 1H), 3.35-3.44 (m, 2H, CONCH₂), 3.47 (d, 1H), 3.51 (dd, 1H), 3.61 (d, 1H), 3.63 (d, 1H), 3.89 (d, 1H), 4.03 (d, 1H), 5.44 (dd, 1H, H5), 6.63-6.70 (m, 1H, H14), 8.02 (s, 1H, triazole), 8.83 (t, 1H, CONH).
Mass spectrum: (ESI) m/z = 724.84 (M + H).

| 58 | $R^I$ = H<br>$R^{II}$ = H<br>$R^{III}$ = Et<br>$R^{IV}$ = Et | (1S,4aR,6aS,7R,8R,10aR,10bR,12aR,14R,15R)-15-[[(2R)-2-amino-2,3-dimethylbutyl]oxy]-14-[5-[(diethylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.78 (s, 3H, Me), 0.79 (d, 3H, Me), 0.82 (s, 3H, Me), 0.87 (d, 3H, Me), 0.90 (s, 3H, Me), 0.91 (d, 3H, Me), 0.92 (d, 3H, Me), 0.95 (d, 3H, Me), 1.17 (s, 3H, Me), 1.22-1.37 (m), 1.23 (s, 3H, Me), 1.25 (t, 3H), 1.29 (t, 3H), 1.41-1.47 (m), 1.49-1.68 (m), 1.80-1.99 (m), 2.01-2.10 (m), 2.12-2.24 (m), 2.27 (dd, 1H, H13), 2.74 (d, 1H), 2.86 (s, 1H, H7), 3.20-3.28 (m, 1H, CONCH₂), 3.42-3.59 (m, 2H, CONCH₂), 3.48 (d, 1H), 3.54 (s, 2H), 3.66 (d, 1H), 3.69-3.77 (m, 1H, CONCH₂), 3.85 (d, 1H), 3.87 (d, 1H), 5.45 (dd, 1H, H5), 5.55-5.63 (m, 1H, H14), 8.11 (s, 1H, triazole).
Mass spectrum: (ESI) m/z = 738.79 (M + H).

| 59 | $R^I$ = H<br>$R^{II}$ = H<br>$R^{III}$ = n-Pr<br>$R^{IV}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(propylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 3H, Me), 0.78 (d, 3H, Me), 0.79 (s, 3H, Me), 0.83 (d, 3H, Me), 0.85 (d, 3H, Me), 0.87 (s, 3H, Me), 0.89 (d, 3H, Me), 0.96 (t, 3H), 1.13 (s, 3H, Me), 1.20 (s, 3H, Me), 1.22-1.34 (m), 1.40-1.44 (m), 1.48-1.55 (m), 1.58-1.65 (m), 1.74-1.95 (m), 2.10-2.21 (m), 2.38 (dd, 1H, H13), 2.78 (d, 1H), 2.83 (s, 1H, H7), 3.26-3.37 (m), 3.45 (d, 1H), 3.51 (d, 1H), 3.52 (dd, 1H), 3.60 (d, 1H), 3.92 (d, 1H), 3.93 (d, 1H), 5.45 (dd, 1H, H5), 6.66 (m, 1H, H14), 8.00 (s, 1H, triazole), 8.79 (t, 1H, NH).
Mass spectrum: (ESI) m/z = 724.48 (M + H).

| 60 | $R^I$ = Me<br>$R^{II}$ = Me<br>$R^{III}$ = i-Pr<br>$R^{IV}$ = H | (1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.77 (s, 3H, Me), 0.78 (d, 3H, Me), 0.87 (d, 3H, Me), 0.89 (s, 3H, Me), 0.91 (d, 3H, Me), 0.94 (d, 3H, Me), 0.94 (s, 3H, Me), 0.96 (d, 3H, Me), 1.14 (s, 3H, Me), 1.22 (s, 3H, Me), 1.23-1.37 (m), 1.27 (d, 3H), 1.29 (d, 3H), 1.40-1.46 (m), 1.48-1.56 (m), 1.59-1.67 (m), 1.75-1.97 (m), 2.10-2.15 (m), 2.16-2.24 (m), 2.25-2.33 (m), 2.39 (dd, 1H, H13), 2.67 (s, 3H, NMe), 2.74 (s, 3H, NMe), 2.85 (s, 1H, H7), 3.13 (d, 1H), 3.52 (d, 1H), 3.53 (dd, 1H), 3.62 (d, 1H), 3.71 (d, 1H), 3.78 (d, 1H), 4.06 (d, 1H), 4.15-4.24 (m, 1H, CONCH), 5.45 (dd, 1H, H5), 6.59-6.67 (m, 1H, H14), 8.07 (s, 1H, triazole), 8.58 (d, 1H, CONH).
Mass spectrum: (ESI) m/z = 752.66 (M + H).

| 61 | $R^I$ = Et<br>$R^{II}$ = H | (1S,4aR,6aS,7R,8R,10aR,10bR,12aR,14R,15R)-8-[(1R)-1,2-dimethylpropyl]-15-[[(2R)-2-(ethylamino)-2,3-dimethylbutyl]oxy]-14- |

-continued

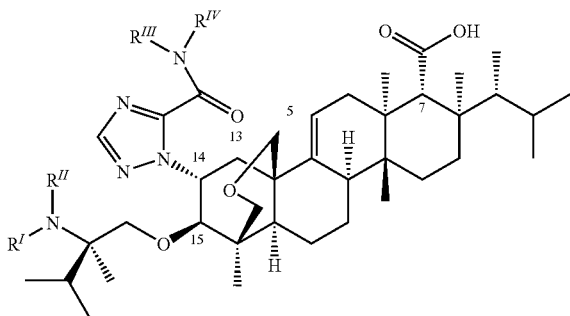

| | | |
|---|---|---|
| | $R^{III}$ = i-Pr | [5-[[(1-methylethyl)amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.73 (s, 3H, Me), 0.76 (s, 3H, Me), 0.76 (d, 3H, Me), 0.77 (d, 3H, Me), 0.85 (d, 3H, Me), 0.87 (d, 3H, Me), 0.88 (s, 3H, Me), 0.89 (d, 3H, Me), 1.12 (s, 3H, Me), 1.20 (s, 3H, Me), 1.22-1.37 (m), 1.24 (d, 3H, Me), 1.25 (t, 3H), 1.26 (d, 3H, Me), 1.39-1.44 (m), 1.47-1.55 (m), 1.58-1.65 (m), 1.76-1.95 (m), 1.99-2.06 (m), 2.08-2.13 (m), 2.14-2.22 (m), 2.38 (dd, 1H, H13), 2.65-2.72 (m, 1H, NCH$_2$), 2.80-2.87 (m, 1H, NCH$_2$), 2.83 (s, 1H, H7), 2.95 (d, 1H), 3.48 (d, 1H), 3.52 (dd, 1H), 3.61 (d, 1H), 3.66 (d, 1H), 3.88 (d, 1H), 4.04 (d, 1H), 4.14-4.21 (m, 1H, CONCH), 5.44 (dd, 1H, H5), 6.62-6.69 (m, 1H, H14), 8.02 (s, 1H, triazole), 8.55 (d, 1H, CONH).
Mass spectrum: (ESI) m/z = 752.66 (M + H).

| 62 | $R^I$ = n-Pr | (1S,4aR,6aS,7R,8R,10aR,10bR,12aR,14R,15R)-8-[(1R)-1,2- |
| | $R^{II}$ = H | dimethylpropyl]-15-[[(2R)-2,3-dimethyl-2-(propylamino)butyl]oxy]-14- |
| | $R^{III}$ = i-Pr | [5-[[(1-methylethyl)amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.72 (s, 3H, Me), 0.75 (d, 3H, Me), 0.76 (s, 3H, Me), 0.76 (d, 3H, Me), 0.85 (d, 3H, Me), 0.86 (d, 3H, Me), 0.88 (s, 3H, Me), 0.89 (d, 3H, Me), 0.99 (t, 3H), 1.12 (s, 3H, Me), 1.20 (s, 3H, Me), 1.22-1.37 (m), 1.24 (d, 3H, Me), 1.26 (d, 3H, Me), 1.39-1.44 (m), 1.47-1.55 (m), 1.58-1.70 (m), 1.78-1.95 (m), 1.96-2.03 (m), 2.09-2.14 (m), 2.15-2.22 (m), 2.36 (dd, 1H, H13), 2.68-2.78 (m, 2H, NCH$_2$), 2.83 (s, 1H, H7), 2.94 (d, 1H), 3.48 (d, 1H), 3.52 (dd, 1H), 3.60 (d, 1H), 3.68 (d, 1H), 3.87 (d, 1H), 4.02 (d, 1H), 4.14-4.22 (m, 1H, CONCH), 5.44 (dd, 1H, H5), 6.61-6.68 (m, 1H, H14), 8.02 (s, 1H, triazole), 8.56 (d, 1H, CONH).
Mass spectrum: (ESI) m/z = 766.56 (M + H).

| 63 | $R^I$ = H | (1S,4aR,6aS,7R,8R,10aR,10bR,12aR,14R,15R)-15-[[(2R)-2-amino-2,3- |
| | $R^{II}$ = H | dimethylbutyl]oxy]-14-[5-[(cyclopropylamino)carbonyl]-1H-1,2,4- |
| | $R^{III}$ = c-Pr | triazol-1-yl]-8-[(1R)-1,2-dimethylpropyl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

H NMR (CD$_3$OD, 600 MHz, ppm) δ 0.60-0.70 (m), 0.76 (s, 3H, Me), 0.77 (d, 3H, Me), 0.78 (s, 3H, Me), 0.78 (d, 3H, Me), 0.82 (m, obscured), 0.83 (d, 3H, Me), 0.85 (d, 3H, Me), 0.87 (s, 3H, Me), 0.89 (d, 3H, Me), 1.13 (s, 3H, Me), 1.20 (s, 3H, Me), 1.22-1.35 (m), 1.39-1.44 (m), 1.47-1.55 (m), 1.58-1.65 (m), 1.73-1.96 (m), 2.09-2.22 (m), 2.39 (dd, 1H, H13), 2.76 (d, 1H), 2.82-2.86 (m, 1H, CONCH), 3.83 (s, 1H, H7), 3.45 (d, 1H), 3.50 (d, 1H), 3.52 (dd, 1H), 3.61 (d, 1H), 3.92 (d, 1H), 3.94 (d, 1H), 5.46 (dd, 1H, H5), 6.63-6.69 (m, 1H, H14), 7.99 (s, 1H, triazole), 8.84 (d, 1H, CONH).
Mass spectrum: (ESI) m/z = 722.55 (M + H).

| 64 | $R^I$ = Me | (1S,4aR,6aS,7R,8R,10aR,10bR,12aR,14R,15R)-14-[5- |
| | $R^{II}$ = H | [(cyclopropylamino)carbonyl]-1H-1,2,4-triazol-1-yl]-15-[[(2R)-2,3- |
| | $R^{III}$ = c-Pr | dimethyl-2-(methylamino)butyl]oxy]-8-[(1R)-1,2-dimethylpropyl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.63-0.73 (m), 0.75 (s, 3H, Me), 0.78 (s, 3H, Me), 0.79 (d, 3H, Me), 0.83 (d, 3H, Me), 0.85 (m, obscured), 0.87 (d, 6H, 2Me), 0.92 (d, 3H, Me), 0.92 (s, 3H, Me), 1.15 (s, 3H, Me), 1.22 (s, 3H, Me), 1.24-1.37 (m), 1.41-1.47 (m), 1.49-1.67 (m), 1.60-1.68 (m), 1.78-1.98 (m), 1.99-2.07 (m), 2.11-2.25 (m), 2.42 (dd, 1H, H13), 2.42 (s, 3H, NMe), 2.84-2.90 (m, 1H, CONCH), 2.86 (s, 1H, H7), 2.95 (d, 1H), 3.50 (d, 1H), 3.54 (dd, 1H), 3.64 (d, 1H), 3.65 (d, 1H), 3.92 (d, 1H), 4.06 (d, 1H), 5.47 (dd, 1H, H5), 6.63-6.71 (m, 1H, H14), 8.03 (s, 1H, triazole), 8.89 (d, 1H, CONH).
Mass spectrum: (ESI) m/z = 736.75 (M + H).

| 65 | $R^I$ = Et | (1S,4aR,6aS,7R,8R,10aR,10bR,12aR,14R,15R)-14-[5- |
| | $R^{II}$ = H | [(cyclopropylamino)carbonyl]-1H-1,2,4-triazol-1-yl]-8-[(1R)-1,2- |
| | $R^{III}$ = c-Pr | dimethylpropyl]-15-[[(2R)-2-(ethylamino)-2,3-dimethylbutyl]oxy]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.63-0.74 (m), 0.74 (s, 3H, Me), 0.78 (s, 3H, Me), 0.79 (d, 3H, Me), 0.80 (d, 3H, Me), 0.85 (m, obscured), 0.87 (d, 3H, Me), 0.90 (d, 3H, Me), 0.91 (s, 3H, Me), 0.92 (d, 3H, Me), 1.15 (s, 3H, Me), 1.22 (s, 3H, Me), 1.23-1.38 (m), 1.27 (t, 3H), 1.41-1.47 (m), 1.49-1.57 (m), 1.60-1.68 (m), 1.75-1.98 (m), 2.01-2.10 (m), 2.10-2.17 (m), 2.17-2.25 (m), 2.41 (dd, 1H, H13), 2.67-2.75 (m, 1H, NCH$_2$), 2.82-2.92 (m, 2H, NCH$_2$ and CONCH), 2.86 (s, 1H, H7), 2.98 (d, 1H), 3.51 (d, 1H), 3.54 (dd, 1H), 3.65 (d, 1H), 3.67 (d, -continued

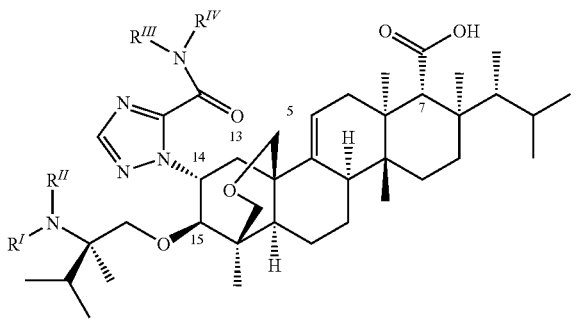

1H), 3.90 (d, 1H), 4.07 (d, 1H), 5.48 (dd, 1H, H5), 6.66-6.74 (m, 1H, H14), 8.03 (s, 1H, triazole), 8.90 (d, 1H, CONH).
Mass spectrum: (ESI) m/z = 750.85 (M + H).

| 66 | $R^I$ = H | (1S,4aR,6aS,7R,8R,10aR,10bR,12aR,14R,15R)-15-[[(2R)-2-amino-2,3- |
| | $R^{II}$ = H | dimethylbutyl]oxy]-14-[5-[(butylamino)carbonyl]-1H-1,2,4-triazol-1- |
| | $R^{III}$ = n-Bu | yl]-8-[(1R)-1,2-dimethylpropyl]-1,6,6a,7,8,9,10,10a,10b,11,12,12a- |
| | $R^{IV}$ = H | dodecahydro-1,6a,8,10a-tetramethyl-4H-1,4a-propano-2H- |
| | | phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.79 (d, 3H, Me), 0.79 (s, 3H, Me), 0.83 (d, 3H, Me), 0.85 (d, 3H, Me), 0.87 (s, 3H, Me), 0.89 (d, 3H, Me), 0.96 (t, 3H), 1.13 (s, 3H, Me), 1.20 (s, 3H, Me), 1.21-1.35 (m), 1.36-1.44 (m), 1.47-1.65 (m), 1.72-1.95 (m), 2.09-2.15 (m), 2.15-2.22 (m), 2.38 (dd, 1H, H13), 2.77 (d, 1H), 2.83 (s, 1H, H7), 3.30-3.41 (m, 2H, NCH$_2$), 3.45 (d, 1H), 3.51 (d, 1H), 3.51 (dd, 1H), 3.60 (d, 1H), 3.92 (d, 1H), 3.93 (d, 1H), 5.45 (dd, 1H, H5), 6.62-6.69 (m, 1H, H14), 8.01 (s, 1H, triazole), 8.78 (t, 1H, CONH).
Mass spectrum: (ESI) m/z = 738.64 (M + H).

| 67 | $R^I$ = H | (1S,4aR,6aS,7R,8R,10aR,10bR,12aR,14R,15R)-15-[[(2R)-2-amino-2,3- |
| | $R^{II}$ = H | dimethylbutyl]oxy]-8-[(1R)-1,2-dimethylpropyl]-14-[5-[[(2- |
| | $R^{III}$ = i-Bu | methylpropyl)amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl- |
| | | 4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.78 (s, 3H, Me), .79 (d, 3H, Me), 0.83 (d, 3H, Me), 0.85 (d, 3H, Me), 0.87 (s, 3H, Me), 0.89 (d, 3H, Me), 0.96 d, 6H, 2Me), 1.13 (s, 3H, Me), 1.20 (s, 3H, Me), 1.22-1.35 (m), 1.39-1.44 (m), 1.47-1.55 (m), 1.58-1.65 (m), 1.72-1.96 (m), 2.10-2.15 (m), 2.05-2.21 (m), 2.38 (dd, 1H, H13), 2.80 (d, 1H), 2.83 (s, 1H, H7) 3.18 (dq, 2H, CONCH$_2$), 3.45 (d, 1H), 3.51 (d, 2H), 3.60 (d, 1H), 3.93 (d, 1H), 3.94 (d, 1H), 5.45 (dd, 1H, H5), 6.61-6.68 (m, 1H, H14), 8.02 (s, 1H, triazole).
Mass spectrum: (ESI) m/z = 738.69 (M + H).

| 68 | $R^I$ = H | (1S,4aR,6aS,7R,8R,10aR,10bR,12aR,14R,15R)-15-[[(2R)-2-amino- |
| | $R^{II}$ = H | 2,3-dimethylbutyl]oxy]-8-[(1R)-1,2-dimethylpropyl]-14-[5-[[[(1R)- |
| | $R^{III}$ = (R)-2-Bu | 1-methylpropyl]amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a- |
| | | tetramethyl-4H-1,4a-propano-2H-phenanthro[1,2-c]pyran-7- |
| | | carboxylic acid |

$^1$H NMR (CD$_3$OD, 600 MHz, ppm) δ 0.76 (s, 3H, Me), 0.77 (d, 3H, Me), 0.80 (d, 3H, Me), 0.81 (s, 3H, Me), 0.84 (d, 3H, Me), 0.85 (d, 3H, Me), 0.87 (s, 3H, Me), 0.89 (d, 3H, Me), 0.96 (t, 3H), 1.14 (s, 3H, Me), 1.20 (s, 3H, Me), 1.21 (d, 3H), 1.22-1.35 (m), 1.39-1.44 (m), 1.47-1.55 (m), 1.57-1.65 (m), 1.74-1.96 (m),
2.10-2.22 (m), 2.39 (dd, 1H, H13), 2.74 (d, 1H), 2.84
(s, 1H, H7), 3.46 (d, 1H), 3.51 (d, 1H), 3.52 (dd, 1H), 3.59 (d, 1H), 3.91 (d, 1H), 3.93 (d, 1H), 3.95-4.02 (m, 1H, CONCH), 5.45 (dd, 1H, H5), 6.55-6.61 (m, 1H, H14), 8.02 (s, 1H, triazole).
Mass spectrum: (ESI) m/z = 738.68 (M + H).

| 69 | $R^I$ = H | (1S,4aR,6aS,7R,8R,10aR,10bR,12aR,14R,15R)-15-[[(2R)-2-amino- |
| | $R^{II}$ = H | 2,3-dimethylbutyl]oxy]-8-[(1R)-1,2-dimethylpropyl]-14-[5-[[[(1S)- |
| | $R^{III}$ = (S)-2-Bu | 1-methylpropyl]amino]carbonyl]-1H-1,2,4-triazol-1-yl] |
| | $R^{IV}$ = H | 1,6,6a,7,8,9,10,10a,10b,11,12,12a-dodecahydro-1,6a,8,10a- |
| | | tetramethyl-4H-1,4a-propano-2H-phenanthro[1,2-c]pyran-7- |
| | | carboxylic acid |

$^1$H NMR (CD$_3$OD, 600 MHz, ppm) δ 0.76 (s, 3H, Me), 0.77 (d, 3H, Me), 0.79 (s, 3H, Me), 1.79 (d, 3H, Me), 0.83 (d, 3H, Me), 0.85 (d, 3H, Me), 0.87 (s, 3H, Me), 0.89 (d, 3H, Me), 0.94 t, 3H), 1.14 (s, 3H, Me), 1.20 (s, 3H, Me), 1.22-1.35 (m), 1.23 (d, 3H), 1.39-1.44 (m), 1.47-1.65 (m), 1.72-1.96 (m), 2.10-2.22 (m),
2.39 (dd, 1H, H13), 2.78 (d, 1H), 2.83 (s, 1H, H7),
3.46 (d, 1H), 3.51 (d, 1H), 3.52 (dd, 1H), 3.60 (d, 1H), 3.93 (d, 2H), 3.95-4.01 (m, 1H, CONCH), 5.46 (dd, 1H, H5), 6.60-6.67 (m, 1H, H14), 8.02 (s, 1H, triazole).
Mass spectrum: (ESI) m/z = 738.71 (M + H).

| 70 | $R^I$ = H | (1S,4aR,6aS,7R,8R,10aR,10bR,12aR,14R,15R)-15-[[(2R)-2-amino-2,3- |
| | $R^{II}$ = H | dimethylbutyl]oxy]-14-[5-[[(1,1 -dimethylethyl)amino]carbonyl]-1H- |
| | $R^{III}$ = t-Bu | 1,2,4-triazol-1-yl]-8-[(1R)-1,2-dimethylpropyl]- |
| | $R^{IV}$ = H | 1,6,6a,7,8,9,10,10a,10b,11,12,12a-dodecahydro-1,6a,8,10a-tetramethyl- |
| | | 4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.80 (d, 3H, Me), 0.82 (s, 3H, Me), 0.85 (d, 3H, Me), 0.85 (d, 3H, Me), 0.87 (s, 3H, Me), 0.90 (d, 3H, Me), 1.14 (s, 3H, Me), 1.20 (s, 3H, Me), 1.22-1.35 (m), 1.40-1.45 (m), 1.45 (s, 9H, t-bu), 1.47-1.56 (m), -continued

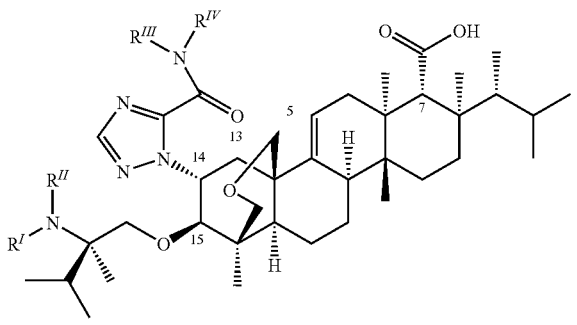

1.59-1.65 (m), 1.74-1.96 (m), 2.10-2.22 (m), 2.39 (dd, 1H, H13), 2.71 (d, 1H), 2.84 (s, 1H, H7), 3.46 (d, 1H), 3.51 (d, 1H), 3.53 (dd, 1H), 3.61 (d, 1H), 3.88 (d, 1H), 3.94 (d, 1H), 5.47 (dd, 1H, H5), 6.53-6.60 (m, 1H, H14), 8.00 (s, 1H, triazole).
Mass spectrum: (ESI) m/z = 738.63 (M + H).

| 71 | $R^I$ = H | (1S,4aR,6aS,7R,8R,10aR,10bR,12aR,14R,15R)-15-[[(2R)-2-amino-2,3- |
| | $R^{II}$ = H | dimethylbutyl]oxy]-14-[5-[(cyclobutylamino)carbonyl]-1H-1,2,4- |
| | $R^{III}$ = c-Bu | triazol-1-yl]-8-[(1R)-1,2-dimethylpropyl]- |
| | $R^{IV}$ = H | 1,6,6a,7,8,9,10,10a,10b,11,12,12a-dodecahydro-1,6a,8,10a-tetramethyl- |
| | | 4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.78 (s, 3H, Me), 89 (d, 3H, Me), 0.83 (d, 3H, Me), 0.85 (d, 3H, Me), 0.86 (s, 3H, Me), 0.89 (d, 3H, Me), 1.13 , 3H, Me), 1.20 (s, 3H, Me), 1.22-1.35 (m), 1.39-1.44 (m), 1.47-1.54 (m), 1.58-1.64 (m), 1.73-1.95 (m), 2.07-2.21 (m), 2.28-2.36 (m), 2.38 (dd, 1H, H13), 2.75 (d, 1H), 2.83 (s, 1H, H7), 3.45 (d, 1H), 3.50 (d, 1H), 3.51 (dd, 1H), 3.60 (d, 1H), 3.90 (d, 1H), 3.92 (d, 1H), 4.43-4.49 (m, 1H, CONCH), 5.45 (dd, 1H, H5), 6.60-6.66 (m, 1H, H14), 8.02 (s, 1H, triazole), 8.90 (d, 1H, CONH).
Mass spectrum: (ESI) m/z = 736.80 (M + H).

| 72 | $R^I$ = H | (1S,4aR,6aS,7R,8R,10aR,10bR,12aR,14R,15R)-15-[[(2R)-2-amino- |
| | $R^{II}$ = H | 2,3-dimethylbutyl]oxy]-8-[(1R)-1,2-dimethylpropyl]-14-[5-[[(2,2- |
| | $R^{III}$ = neopentyl | dimethylpropyl)amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H, Me), 0.79 (d, 3H, Me), 0.81 (s, 3H, Me), 0.82 (d, 3H, Me), 0.86 (d, 3H, Me), 0.88 (d, 3H, Me), 0.90 (s, 3H, Me), 0.92 (d, 3H, Me), 0.99 (s, 9H, t-bu), 1.16 (s, 3H, Me), 1.22 (s, 3H, Me), 1.24-1.37 (m), 1.41-1.47 (m), 1.49-1.57 (m), 1.60-1.68 (m), 1.75-1.98 (m), 2.12-2.24 (m), 2.40 (dd, 1H, H13), 2.86 (d, 1H), 2.86 (s, 1H, H7), 3.22 (dq, 2H, CONCH$_2$), 3.48 (d, 1H), 3.54 (dd, 1H), 3.55 (d, 1H), 3.61 (d, 1H), 3.96 (d, 1H), 3.98 (d, 1H), 5.46 (dd, 1H, H5), 6.60-6.67 (m, 1H, H14), 8.05 (s, 1H, triazole), 8.63 (t, 1H, CONH).
Mass spectrum: (ESI) m/z = 752.86 (M + H).

| 73 | $R^I$ = H | (1S,4aR,6aS,7R,8R,10aR,10bR,12aR,14R,15R)-15-[[(2R)-2-amino- |
| | $R^{II}$ = H | 2,3-dimethylbutyl]oxy]-8-[(1R)-1,2-dimethylpropyl]-14-[5- |
| | $R^{III}$ = phenyl | [(phenylamino)carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.80 (d, 3H, Me), 0.82 (s, 3H, Me), 0.84 (d, 3H, Me), 0.85 (d, 3H, Me), 0.88 (s, 3H, Me), 0.89 (d, 3H, Me), 1.14 (s, 3H, Me), 1.20 (s, 3H, Me), 1.22-1.34 (m), 1.40-1.44 (m), 1.48-1.55 (m), 1.58-1.65 (m), 1.74-1.95 (m), 2.11-2.21(m), 2.46 (dd, 1H, H13), 2.83 (d, 1H), 2.83 (s, 1H, H7), 3.48 (d, 1H), 3.53 (d, 1H), 3.54 (dd, 1H), 3.64 (d, 1H), 3.96 (d, 1H), 3.98 (d, 1H), 5.48 (dd, 1H, H5), 6.75 (m, 1H, H14), 7.18 (dd, 1H), 7.37 (dd, 1H), 7.72 (d, 1H), 8.09 (s, 1H, triazole).
Mass spectrum: (ESI) m/z = 758.50 (M + H).

| 74 | $R^I$ = H | (1S,4aR,6aS,7R,8R,10aR,10bR,12aR,14R,15R)-15-[[(2R)-2-amino- |
| | $R^{II}$ = H | 2,3-dimethylbutyl]oxy]-8-[(1R)-1,2-dimethylpropyl]-14-[5- |
| | $R^{III}$ = benzyl | [[(phenylmethyl)amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.73 (s, 3H, Me), 0.76 (s, 3H, Me), 0.76 (d, 6H, 2Me), 0.80 (d, 3H, Me), 0.85 (d, 3H, Me), 0.86 (s, 3H, Me), 0.89 (d, 3H, Me), 1.13 (s, 3H, Me), 1.20 (s, 3H, Me), 1.22-1.35 (m), 1.39-1.44 (m), 1.47-1.54 (m), 1.58-1.65 (m), 1.69-1.95 (m), 2.09-2.22 (m), 2.38 (dd, 1H, H13), 2.76 (d, 1H), 2.83 (s, 1H, H7), 3.45 (d, 1H), 3.49 (d, 1H), 3.51 (dd, 1H), 3.60 (d, 1H), 3.93 (d, 2H), 4.53 (abq, 2H), 5.43 (dd, 1H, H5), 6.64-6.70 (m, 1H, H14), 7.25 (t, 1H, ArH), 7.31 (t, 2H, ArH), 7.35 (d, 2H, ArH), 8.02 (s, 1H, triazole), 9.31 (t, 1H, CONH).
Mass spectrum: (ESI) m/z = 772.50 (M + H).

| 75 | $R^I$ = H | (1S,4aR,6aS,7R,8R,10aR,10bR,12aR,14R,15R)-15-[[(2R)-2-amino- |
| | $R^{II}$ = H | 2,3-dimethylbutyl]oxy]-8-[(1R)-1,2-dimethylpropyl]-14-[5-[[(2- |
| | $R^{III}$ = phenethyl | phenylethyl)amino]carbonyl]-1H-1,2,4-triazol-1-yl]- |
| | $R^{IV}$ = H | 1,6,6a,7,8,9,10,10a,10b,11,12,12a-dodecahydro-1,6a,8,10a- |

-continued

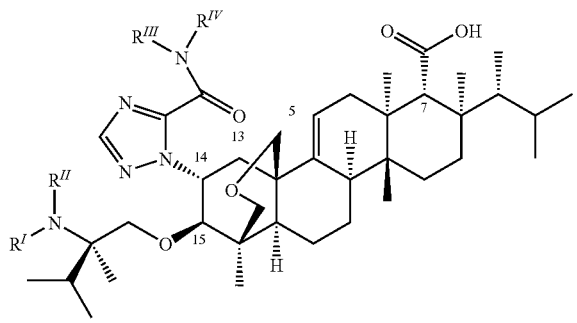

tetramethyl-4H-1,4a-propano-2H-phenanthro[1,2-c]pyran-7-carboxylic acid $^1$H NMR (CD$_3$OD, 600 MHz, ppm) δ 0.74 (s, 3H, Me), 0.76 (s, 3H, Me), 0.76 (d, 3H, Me), 0.78 (d, 3H, Me), 0.82 (d, 3H, Me), 0.85 (d, 3H, Me), 0.87 (s, 3H, Me), 0.89 (d, 3H, Me), 1.14 (s, 3H, Me), 1.20 (s, 3H, Me), 1.22-1.34 (m), 1.40-1.44 (m), 1.48-1.55 (m), 1.59-1.65 (m), 1.72-1.96 (m), 2.10-2.21 (m), 2.34 (dd, 1H, H13), 2.78 (d, 1H), 2.84 (s, 1H, H7), 2.90 (m), 3.46 (d, 1H), 3.50 (d, 1H), 3.53 (dd, 1H), 3.57-3.62 (m), 3.93 (d, 1H), 3.94 (d, 1H), 5.45 (dd, 1H, H5), 6.67 (m, 1H, H14), 7.19 (dd, 1H), 7.24-7.30 (m), 7.99 (s, 1H, triazole).
Mass spectrum: (ESI) m/z = 786.38 (M + H).

| 76 | $R^I$ = H<br>$R^{II}$ = H<br>$R^{III}$ = CH$_2$CH$_2$F<br>$R^{IV}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.78 (d, 3H, Me), 0.80 (s, 3H, Me), 0.83 (d, 3H, Me), 0.85 (d, 3H, Me), 0.87 (s, 3H, Me), 0.89 (d, 3H, Me), 1.14 (s, 3H, Me), 1.20 (s, 3H, Me), 1.22-1.35 (m), 1.39-1.44 (m), 1.48-1.54 (m), 1.58-1.65 (m), 1.72-1.95 (m), 2.10-2.21 (m), 2.40 (dd, 1H, H13), 2.76 (d, 1H), 2.83 (s, 1H, H7), 3.45 (d, 1H), 3.49 (d, 1H), 3.52 (dd, 1H), 3.56-3.64 (m, 1H, CONCH$_2$), 3.61 (d, 2H), 3.68-3.77 (m, 1H, CONCH$_2$), 3.93 (d, 1H), 3.94 (d, 1H), 4.04 (d, 1H), 4.51 (t, 1H, CH$_2$F), 4.59 (t, 1H, CH$_2$F), 5.46 (dd, 1H, H5), 6.68 (m, 1H, H14), 8.02 (s, 1H, triazole), 8.98 (t, 1H, CONH).
Mass spectrum: (ESI) m/z = 728.35 (M + H).

| 77 | $R^I$ = Me<br>$R^{II}$ = H<br>$R^{III}$ = CH$_2$CH$_2$F<br>$R^{IV}$ = H | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.75 (s, 3H, Me), 0.76 (d, 3H, Me), 0.76 (d, 3H, Me), 0.81 (d, 3H, Me), 0.85 (d, 6H, 2Me), 0.89 (s, 3H, Me), 0.89 (d, 3H, Me), 1.13 (s, 3H, Me), 1.20 (s, 3H, Me), 1.22-1.35 (m), 1.39-1.44 (m), 1.47-1.54 (m), 1.58-1.65 (m), 1.78-1.95 (m), 1.97-2.24 (m), 2.09-2.20 (m), 2.39 (s, 3H, NMe), 2.40 (dd, 1H, H13), 2.83 (s, 1H, H7), 2.90 (d, 1H), 3.47 (d, 1H), 3.52 (dd, 1H), 3.53-3.64 (m, 1H, CONCH$_2$), 3.61 (d, 2H), 3.70-3.79 (m, 1H, CONCH$_2$), 3.89 (d, 1H), 4.04 (d, 1H), 4.51 (t, 1H, CH$_2$F), 4.59 (t, 1H, CH$_2$F), 5.45 (dd, 1H, H5), 6.64-6.71 (m, 1H, H14), 8.04 (s, 1H, triazole), 9.00 (t, 1H, CONH).
Mass spectrum: (ESI) m/z = 742.76 (M + H).

| 78 | $R^I$ = Et<br>$R^{II}$ = H<br>$R^{III}$ = CH$_2$CH$_2$F<br>$R^{IV}$ = H | (1S,4aR,6aS,7R,8R,10aR,10bR,12aR,14R,15R)-8-[(1R)-1,2-dimethylpropyl]-15-[[(2R)-2-(ethylamino)-2,3-dimethylbutyl]oxy]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.74 (s, 3H, Me), 0.76 (s, 3H, Me), 0.76 (d, 3H, Me), 0.78 (d, 3H, Me), 0.85 (d, 3H, Me), 0.87 (d, 3H, Me), 0.88 (s, 3H, Me), 0.89 (d, 3H, Me), 1.12 (s, 3H, Me), 1.20 (s, 3H, Me), 1.24 (t, 3H), 1.22-1.36 (m), 1.39-1.44 (m), 1.47-1.54 (m), 1.58-1.65 (m), 1.75-1.96 (m), 2.00-2.06 (m), 2.08-2.13 (m), 2.14-2.22 (m), 2.38 (dd, 1H, H13),
2.63-2.70 (m, 1H, NCH$_2$), 2.79-2.86 (m, 1H, NCH$_2$), 2.83 (s, 1H, H7), 2.95 (d, 1H), 3.48 (d, 1H), 3.52 (dd, 1H), 3.55-3.66 (m, 1H, CONCH$_2$), 3.61 (d, 1H), 3.64 (d, 1H), 3.69-3.79 (m, 1H, CONCH$_2$), 3.88 (d, 1H), 4.05 (d, 1H), 4.52 (t, 1H, CH$_2$F), 4.60 (t, 1H, CH$_2$F), 5.44 (dd, 1H, H5), 6.66-6.73 (m, 1H, H14), 8.04 (s, 1H, triazole), 9.01 (t, 1H, CONH).
Mass spectrum: (ESI) m/z = 756.77 (M + H).

| 79 | $R^I$ = H<br>$R^{II}$ = H<br>$R^{III}$ = CH$_2$CHF$_2$<br>$R^{IV}$ = H | (1S,4aR,6aS,7R,8R,10aR,10bR,12aR,14R,15R)-15-[[(2R)-2-amino-2,3-dimethylbutyl]oxy]-14-[5-[[(2,2-difluoroethyl)amino]carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.78 (d, 3H, Me), 0.80 (s, 3H, Me), 0.82 (d, 3H, Me), 0.85 (d, 3H, Me), 0.87 (s, 3H, Me), 0.89 (d, 3H, Me), 2.14 (s, 3H, Me), 1.20 (s, 3H, Me), 1.22-1.35 (m), 1.39-1.44 (m), 1.47-1.55 (m), 1.58-1.65 (m), 1.70-1.77 (m), 1.78-1.95 (m), 2.10-2.22 (m), 2.40 (dd, 1H, 14H), 2.76 (d, 1H), 2.84 (s, 1H, H7), 3.46 (d, 1H), 3.49 (d, 1H), 3.52 (dd, 1H), 3.61 (d, 1H), 3.65 (dq, 1H, CONCH$_2$), 3.82 (dq, -continued

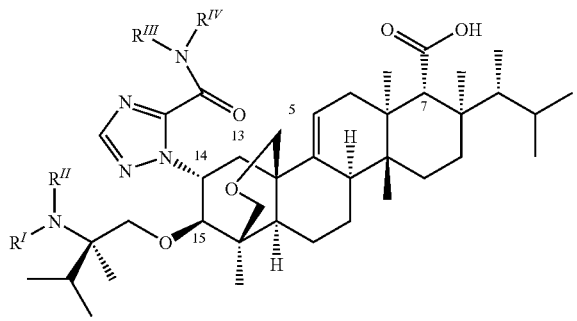

1H, CONCH₂), 3.94 (d, 2H), 5.46 (dd, 1H, H5), 6.00 (2dt, 1H, CHF₂), 6.67-6.73 (m, 1H, H14), 8.03 (s, 1H, triazole).
Mass spectrum: (ESI) m/z = 746.70 (M + H).

80  $R^I$ = H  
     $R^{II}$ = H  
     $R^{III}$ = CH₂CF₃  
     $R^{IV}$ = H (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2,2,2-trifluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid ¹H NMR (CD₃OD, 500 MHz, ppm) δ 0.78 (s, 3H, Me), 0.78 (d, 3H, Me), 0.80 (d, 3H, Me), 0.82 (s, 3H, Me), 0.84 (d, 3H, Me), 0.87 (d, 3H, Me), 0.89 (s, 3H, Me), 0.92 (d, 3H, Me), 1.16 (s, 3H, Me), 1.22 (s, 3H, Me), 1.24-1.38 (m), 1.41-1.47 (m), 1.49-1.58 (m), 1.60-1.68 (m), 1.71-1.79 (m), 1.79-1.96 (m), 2.12-2.25 (m), 2.42 (dd, 1H, H13), 2.78 (d, 1H), 2.86 (s, 1H, H7), 3.48 (d, 1H), 3.51 (d, 1H), 3.55 (dd, 1H), 3.63 (d, 1H), 3.90-4.00 (m, 1H, CONCH₂CF₃), 3.96 (d, 1H), 3.97 (d, 1H), 4.18-4.28 (m, 1H, CONCH₂CF₃), 5.47 (dd, 1H, H5), 6.70-6.77 (m, 1H, H14), 8.07 (s, 1H, triazole).
Mass spectrum: (ESI) m/z = 764.79 (M + H).

81  $R^I$ = H  
     $R^{II}$ = H  
     $R^{III}$ = CH₂CH₂OMe  
     $R^{IV}$ = H (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-methoxyethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid ¹H NMR (CD₃OD, 600 MHz, ppm) δ 0.76 (s, 3H, Me), 0.76 (d, 3H, Me), 0.79 (d, 3H, Me), 0.79 (s, 3H, Me), 0.83 (d, 3H, Me), 0.85 (d, 3H, Me), 0.87 (s, 3H, Me), 0.89 (d, 3H, Me), 1.14 (s, 3H, Me), 1.20 (s, 3H, Me), 1.22-1.35 (m), 1.39-1.44 (m), 1.47-1.55 (m), 1.58-1.65 (m), 1.73-1.95 (m), 2.09-2.22 (m), 2.38 (dd, 1H, H13), 2.76 (d, 1H), 2.83 (s, 1H, H7), 3.36 (s, 3H, OMe), 3.45 (d, 1H), 3.50 (d, 1H), 3.51 (dd, 1H) 3.53-3.56 (m, 4H), 3.60 (d, 1H), 3.92 (d, 1H), 3.93 (d, 1H), 5.45 (dd, 1H, H5), 6.64-6.70 (m, 1H, H14), 8.01 (s, 1H, triazole).
Mass spectrum: (ESI) m/z = 740.38 (M + H).

82  $R^I$ = H  
     $R^{II}$ = H  
     $R^{III}$ = CH₂CH₂OEt  
     $R^{IV}$ = H (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-ethoxyethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid ¹H NMR (CD₃OD, 600 MHz, ppm) δ 0.76 (s, 3H, Me), 0.76 (d, 3H, Me), 0.79 (d, 3H, Me), 0.79 (s, 3H, Me), 0.83 (d, 3H, Me), 0.85 (d, 3H, Me), 0.87 (s, 3H, Me), 0.89 (d, 3H, Me), 1.14 (s, 3H, Me), 1.18 (t, 3H), 1.20 (s, 3H, Me), 1.22-1.35 (m), 1.39-1.44 (m), 1.47-1.55 (m), 1.58-1.65 (m), 1.73-1.95 (m), 2.09-2.22 (m), 2.38 (dd, 1H, H13), 2.77 (d, 1H), 2.83 (s, 1H, H7), 3.45 (d, 1H), 3.48-3.62 (m, 9H), 3.93 (d, 2H), 5.45 (dd, 1H, H5), 6.65-6.71 (m, 1H, H14), 8.01 (s, 1H, triazole), 8.68 (t, 1H, CONH).
Mass spectrum: (ESI) m/z = 754.83 (M + H).

83  $R^I$ = H  
     $R^{II}$ = H  
     $R^{III}$ = CH₂CH₂NMe₂  
     $R^{IV}$ = H (1S,4aR,6aS,7R,8R,10aR,10bR,12aR,14R,15R)-15-[[(2R)-2-amino-2,3-dimethylbutyl]oxy]-14-[5-[[[2-(dimethylamino)ethyl]amino]carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid ¹H NMR (CD₃OD, 600 MHz, ppm) δ 0.76 (s, 3H, Me), 0.77 (d, 3H, Me), 0.79 (d, 3H, Me), 0.80 (s, 3H, Me), 0.83 (d, 3H, Me), 0.85 (d, 3H, Me), 0.89 (s, 3H, Me), 0.89 (d, 3H, Me), 1.13 (s, 3H, Me), 1.20 (s, 3H, Me), 1.22-1.35 (m), 1.39-1.44 (m), 1.48-1.54 (m), 1.58-1.65 (m), 1.72-1.965 (m), 2.11-2.22 (m), 2.41 (dd, 1H, H13), 2.83 (s, 1H, H7), 2.84 (d, 1H), 2.94-3.00 (br s), 3.35-3.42 (m), 3.46-3.60 (m), 3.93 (d, 1H), 3.90-3.96 (m), 3.99 (d, 2H), 5.43 (dd, 1H, H5), 6.69 (m, 1H, H14), 8.06 (s, 1H, triazole).
Mass spectrum: (ESI) m/z = 753.34 (M + H).

Examples 84-87

The following compounds were prepared using methods analogous to those described in the preceding examples:

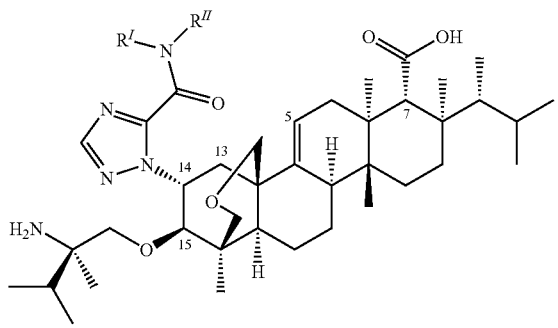

| 84 | NR$^I$R$^{II}$ =  | (1S,4aR,6aS,7R,8R,10aR,10bR,12aR,14R,15R)-15-[[(2R)-2-amino-2,3-dimethylbutyl]oxy]-14-[5-(1-azetidinylcarbonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.81 (d, 3H, Me), 0.85 (d, 3H, Me), 0.86 (d, 3H, Me), 0.87 (s, 3H, Me), 0.89 (d, 3H, Me), 1.13 (s, 3H, Me), 1.20 (s, 3H, Me), 1.22-1.32 (m), 1.40-1.44 (m), 1.48-1.55 (m), 1.59-1.64 (m), 1.77-1.95 (m), 2.10-2.20 (m), 2.38 (dd, 1H, H13), 2.84 (d, 1H), 2.84 (s, 1H, H7), 3.45 (d, 1H), 3.50 (dd, 1H), 3.54 (d, 1H), 3.59 (d, 1H), 3.91 (d, 1H), 3.96 (d, 1H), 4.08 (m), 4.15 (m), 4.23 (m), 4.58 (m), 5.46 (dd, 1H, H5), 6.54 (m, 1H, H14), 8.04 (s, 1H, triazole).
Mass spectrum: (ESI) m/z = 722.48 (M + H).

| 85 | NR$^I$R$^{II}$ = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-pyrrolidinylcarbonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.75 (s, 3H, Me), 0.76 (s, 3H, Me), 0.77 (d, 3H, Me), 0.85 (d, 3H, Me), 0.86 (d, 3H, Me), 0.88 (s, 3H, Me), 0.89 (d, 3H, Me), 0.89 (d, 3H, Me), 1.14 (s, 3H, Me), 1.20 (s, 3H, Me), 1.22-1.34 (m), 1.40-1.44 (m), 1.48-1.55 (m), 1.590-1.64 (m), 1.78-2.02 (m), 2.10-2.21 (m), 2.36 (dd, 1H, H13), 2.79 (d, 1H), 2.84 (s, 1H, H7), 3.46 (d, 1H), 3.50 (dd, 1H), 3.56 (d, 1H), 3.60 (d, 1H), 3.60-3.76 (m), 3.74-3.89 (m), 3.89 (d, 1H), 3.91 (d, 1H), 5.46 (dd, 1H, H5), 5.94 (m, 1H, H14), 8.07 (s, 1H, triazole).
Mass spectrum: (ESI) m/z = 736.52 (M + H).

| 86 | NR$^I$R$^{II}$ = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-morpholinylcarbonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H, Me), 0.79 (d, 3H, Me), 0.81 (s, 3H, Me), 0.87 (d, 3H, Me), 0.90 (d, 3H, Me), 0.91 (s, 3H, Me), 0.92 (d, 3H, Me), 0.94 (d, 3H, Me), 1.17 (s, 3H, Me), 1.23 (s, 3H, Me), 1.24-1.37 (m), 1.41-1.47 (m), 1.49-1.59 (m), 1.60-1.68 (m), 1.81-2.04 (m), 2.12-2.24 (m), 2.34 (dd, 1H, H13), 2.79 (d, 1H), 2.86 (s, 1H, H7), 3.50 (d, 1H), 3.55 (dd, 1H), 3.56-3.61 (m), 3.65 (d, 1H), 3.66-3.71 (m), 3.74-3.89 (m), 3.88 (d, 1H), 3.91 (d, 1H), 5.48 (dd, 1H, H5), 5.67-5.74 (m, 1H, H14), 8.13 (s, 1H, triazole).
Mass spectrum: (ESI) m/z = 752.41 (M + H).

| 87 | NR$^I$R$^{II}$ = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(4-methyl-1-piperazinyl)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.77 (s, 3H, Me), 0.84 (d, 3H, Me), 0.85 (d, 3H, Me), 0.98 (d, 3H, Me), 0.98 (s, 3H, Me), 0.99 (d, 3H, Me), 1.13 (s, 3H, Me), 1.20 (s, 3H, Me), 1.22-1.33 (m), 1.40-1.44 (m), 1.48-1.54 (m), 1.59-1.64 (m), 1.78-1.95 (m), 2.10-2.21 (m), 2.34 (dd, 1H, H13), 2.40 (br m), 2.84 (s, 1H, H7), 2.90 (d, 1H), 2.97 (s, NMe), 3.47 (d, 1H), 3.51 (dd, 1H), 3.56 (d, 1H), 3.60 (d, 1H), 3.74-3.89 (m), 3.90 (d,

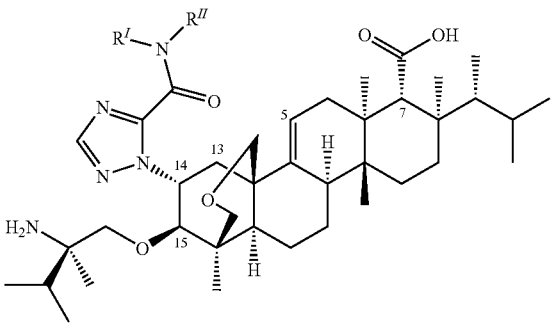

1H), 3.99 (d, 1H), 5.45 (dd, 1H, H5), 5.92 (br m, 1H, H14), 8.12 (s, 1H, triazole).
Mass spectrum: (ESI) m/z = 765.53 (M + H).

Examples 88-96

The following compounds were prepared using methods analogous to those described in the preceding examples:

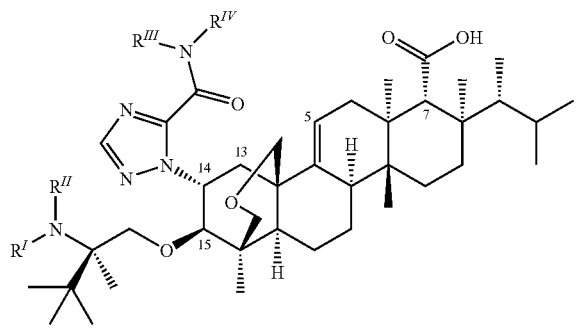

| 88 | $R^I$ = Me<br>$R^{II}$ = H<br>$R^{III}$ = H<br>$R^{IV}$ = H | (1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 500 MHz, ppm) δ 0.76 (s, 3H), 0.77 (d, J = 7.1 Hz, 3H), 0.83 (s, 3H), 0.85 (d, J = 6.6 Hz, 3H), 0.90 (d, J = 6.9 Hz, 3H), 0.92 (s, 9H), 0.93 (s, 3H), 1.13 (s, 3H), 1.20 (s, 3H), 1.22-1.56 (m), 1.63 (m, 1H), 1.74-1.96 (m), 2.12 (m, 1H), 2.19 (m, 1H), 2.39 (dd, J = 13.2 Hz, 6.4 Hz, 1H), 2.53 (s, 3H), 2.84 (s, 1H), 3.12 (d, J = 11.2 Hz, 1H), 3.51 (d, J = 11.7 Hz, 1H), 3.52 (dd, J = 11.6 Hz, 1.9 Hz, 1H), 3.61 (d, J = 11.4 Hz, 1H), 3.77 (d, J = 11.9 Hz, 1H), 3.85 (d, J = 11.0 Hz, 1H), 4.04 (d, J = 10.1 Hz, 1h), 5.45 (m, 1H), 6.64 (m, 1H), 8.04 (s, 1H).
Mass spectrum: (ESI) m/z = 710.77 (M + H).

| 89 | $R^I$ = H<br>$R^{II}$ = H<br>$R^{III}$ = Me<br>$R^{IV}$ = H | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 500 MHz, ppm) δ 0.77 (s, 3H), 0.78 (s, 3H), 0.78 (d, 3H, partially obscured), 0.85 (s, 9H), 0.86 (d, 3H, partially obscured), 0.90 (s, 3H), 0.91 (d, 3H, partially obscured), 1.14 (s, 3H), 1.21 (s, 3H), 1.22-1.67 (m), 1.77-1.97 (m), 2.13 (m, 1H), 2.19 (m, 1H), 2.40 (dd, J = 13.3 Hz, 6.4 Hz, 1H), 2.83 (d, 1H, partially obscured), 2.84 (s, 1H), 2.91 (d, J = 4.3 Hz, 3H), 3.47 (d, J = 11.9 Hz, 1H), 3.53 (dd, J = 11.7 Hz, 1.8 Hz, 1H), 3.62 (d, J = 11.7 Hz, 1H), 3.69 (d, J = 9.8 Hz, 1H), 3.94-3.97 (m, 2H), 5.46 (m, 1H), 6.75 (m, 1H), 8.00 (s, 1H), 8.77 (m, 1H).
Mass spectrum: (ESI) m/z = 710.62 (M + H).

| 90 | $R^I$ = H<br>$R^{II}$ = H<br>$R^{III}$ = Me<br>$R^{IV}$ = Me | (1S,4aR,6aS,7R,8R,10aR,10bR,12aR,14R,15R)-15-[[(2R)-2-amino-2,3,3-trimethylbutyl]oxy]-14-[5-[(dimethylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 500 MHz, ppm) δ 0.71 (s, 3H), 0.77 (s, 3H), 0.78 (d, 3H, partially obscured), 0.86 (d, J = 6.8 Hz, 3H), 0.90 (d, J = 6.8 Hz, 3H), 0.92 (s, 9H), 0.92 (s, 3H), 1.15 (s, 3H), 1.21 (s, 3H), 1.20-1.57 (m), 1.63 (m, 1H), 1.80-1.97 (m), 2.13 (m, 1H), 2.19 (m, 1H), -continued

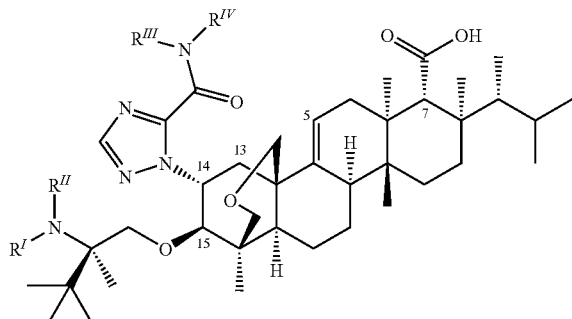

2.37 (dd, J = 13.4 Hz, 6.5 Hz, 1H), 2.84 (s, 1H), 2.98 (d, J = 9.9 Hz, 1H), 3.14 (s, 3H), 3.16 (s, 3H), 3.48 (d, J = 12.4 Hz, 1H), 3.52 (dd, J = 11.8 Hz, 2.0 Hz, 1H), 3.58 (d, J = 11.7 Hz, 1H), 3.85 (d, J = 10.1 Hz, 1H), 3.90 (d, J = 11.9 Hz, 1H), 3.98 (d, J = 10.1 Hz, 1H), 5.48 (m, 1H), 5.79 (m, 1H), 8.09 (s, 1H).
Mass spectrum (ESI) m/z = 724.69 (M + H).

| 91 | $R^I$ = H<br>$R^{II}$ = H<br>$R^{III}$ = Et<br>$R^{IV}$ = H | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[(ethylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

Mass spectrum: (ESI) m/z = 724.48 (M + H).

| 92 | $R^I$ = H<br>$R^{II}$ = H<br>$R^{III}$ = CH$_2$CH$_2$F<br>$R^{IV}$ = H | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.80 (s, 3H, Me), 0.84 (s, 9H, t-bu), 0.85 (d, 3H, Me), 0.88 (s, 3H, Me), 0.89 (d, 3H, Me), 1.13 (s, 3H, Me), 1.20 (s, 3H, Me), 1.22-1.35 (m), 1.39-1.44 (m), 1.47-1.55 (m), 1.58-1.65 (m), 1.77-1.95 (m), 2.10-2.22 (m), 2.40 (dd, 1H, H13), 2.78 (d, 1H), 2.83 (s, 1H, H7), 3.46 (d, 1H), 3.52 (dd, 1H), 3.55-3.65 (m, 1H, CONCH$_2$), 3.61 (d, 1H), 3.66 (d, 1H), 3.67-3.77 (m, 1H, CONCH$_2$), 3.95 (d, 1H), 3.96 (d, 1H), 4.50 (t, 1H, CH$_2$F), 4.58 (t, 1H, CH$_2$F), 5.46 (dd, 1H, H5), 6.70-6.77 (m, 1H, H14), 8.02 (s, 1H, triazole), 8.98 (t, 1H, CONH).
Mass Spectrum: (ESI) m/z = 742.90 (M + H).

| 93 | $R^I$ = H<br>$R^{II}$ = H<br>$R^{III}$ = i-Pr<br>$R^{IV}$ = H | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H) 0.77 (d, 3H, partially obscured), 0.80 (s, 3H), 0.85 (s, 9H), 0.86 (d, 3H, partially obscured), 0.89 (s, 3H), 0.90 (d, 3H, partially obscured), 1.14 (s, 3H), 1.21 (s, 3H), 1.24 (d, J = 6.7 Hz, 3H), 1.27 (d, J = 6.7 Hz, 3H), 1.23-1.63 (m), 1.78-1.97 (m), 2.13 (m, 1H), 2.19 (m, 1H), 2.40 (dd, J = 13.2 Hz, 6.4 Hz, 1H), 2.79 (d, J = 9.8 Hz, 1H), 2.84 (s, 1H), 3.47 (d, J = 11.9 Hz, 1H), 3.53 (dd, J = 11.4 Hz, 1.8 Hz, 1H), 3.62 (d, J = 11.5 Hz, 1H), 3.68 (d, J = 9.9 Hz, 1H), 3.94-3.97 (m, 2H), 4.18 (m, 1H), 5.47 (m, 1H), 6.72 (m, 1H), 8.01 (s, 1H), 8.52 (d, 9.3 Hz, 1H)
Mass spectrum: (ESI) m/z = 738.67 (M + H).

| 94 | $R^I$ = Me<br>$R^{II}$ = H<br>$R^{III}$ = i-Pr<br>$R^{IV}$ = H | (1S,4aR,6aS,7R,8R,10aR,10bR,12aR,14R,15R)-8-[(1R)-1,2-dimethylpropyl]-14-[5-[[(1-methylethyl)amino]carbonyl]-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.76 (s, 3H), 0.77 (d, 3H, partially obscured), 0.83 (s, 3H), 0.86 (d, J = 6.6 Hz, 3H), 0.90 (d, J = 6.8 Hz, 3H), 0.92 (s, 9H), 0.93 (s, 3H), 1.13 (s, 3H), 1.20 (s, 3H), 1.22-1.56 (m), 1.25 (d, J = 6.7 Hz, 3H), 1.27 (d, J = 6.5 Hz, 3H), 1.63 (m, 1H), 1.77-1.96 (m), 2.12 (m, 1H), 2.19 (m, 1H), 2.39 (dd, J = 13.3 Hz, 6.7 Hz, 1H), 2.51 (s, 3H), 2.84 (s, 1H), 3.08 (d, J = 11.2 Hz, 1H), 3.50 (d, J = 11.9 Hz, 1H), 3.52 (dd, J = 11.4 Hz, 2.0 Hz, 1H), 3.61 (d, J = 11.5 Hz, 1H), 3.78 (d, J = 11.8 Hz, 1H), 3.84 (d, J = 11.2 Hz, 1H), 4.00 (d, J = 9.9 Hz, 1H), 4.18 (m, 1H), 5.45 (m, 1H), 6.57 (m, 1H), 8.03 (s, 1H), 8.58 (d, J = 8.2 Hz, 1H).
Mass spectrum: (ESI) m/z = 752.82 (M + H).

| 95 | $R^I$ = CH$_2$CH$_2$OH<br>$R^{II}$ = H<br>$R^{III}$ = Me<br>$R^{IV}$ = H | (1S,4aR,6aS,7R,8R,10aR,10bR,12aR,14R,15R)-8-[(1R)-1,2-dimethylpropyl]-15-[[(2R)-2-[(2-hydroxyethyl)amino]-2,3,3-trimethylbutyl]oxy]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.76 (s, 3H), 0.77 (d, 3H, partially obscured), 0.84 (s, 3H), 0.85 (d, J = 6.9 Hz, 3H), 0.90 (d, J = 6.6 Hz, 3H), 0.92 (bs, 12H), 1.13 (s, 3H), 1.20 (s, 3H), 1.22-1.56 (m), 1.62 (m, 1H), 1.76-1.96 (m), 2.12 (m, 1H), 2.19 (m, 1H), 2.40 (dd, J = 13.3 Hz, 6.4 Hz, 1H), 2.84 (s, 1H), 2.91 (d, J = 4.8 Hz, 3H), 3.04 (d, J = 10.9 Hz, 1H), 3.2 (m, 2H), 3.49 (d, J = 11.9 Hz, 1H), 3.52 (dd, J = 11.6 Hz, 2.0 Hz, 1H), 3.75 (m, 2H), 3.82 (d, J = 12.1 Hz,

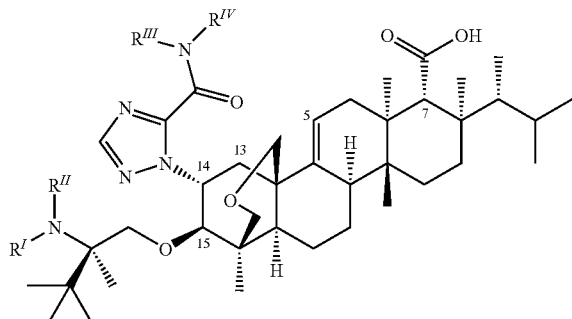

1H), 3.87 (d, J = 11.0 Hz, 1H), 4.06 (d, J = 9.9 Hz, 1H), 5.46 (m, 1H), 6.73 (m, 1H), 8.02 (s, 1H), 8.76 (m, 1H).
Mass spectrum: (ESI) m/z = 754.72 (M + H).

| 96 | $R^I$ = Me | (1S,4aR,6aS,7R,8R,10aR,10bR,12aR,14R,15R)-14-[5-[[(2- |
| | $R^{II}$ = H | aminoethyl)amino]carbonyl]-1H-1,2,4-triazol-1-yl]-8-[(1R)-1,2- |
| | $R^{III}$ = CH$_2$CH$_2$NH$_2$ | dimethylpropyl]-15-[[(2R)-2,3,3-trimethyl-2- |
| | $R^{IV}$ = H | (methylamino)butyl]oxy]-1,6,6a,7,8,9,10,10a,10b,11,12,12a- |
| | | dodecahydro-1,6a,8,10a-tetramethyl-4H-1,4a-propano-2H- |
| | | phenanthro[1,2-c]pyran-7-carboxylic acid |

$^1$H NMR (CD$_3$OD, 500 MHz, ppm) δ 0.76 (s, 3H), 0.77 (d, 3H, partially obscured), 0.80 (s, 3H), 0.86 (d, J = 6.8 Hz, 3H), 0.89 (s, 9H), 0.90 (d, 3H, partially obscured), 0.94 (s, 3H), 1.13 (s, 3H), 1.20 (s, 3H), 1.23-1.56 (m), 1.62 (m, 1H), 1.74-1.96 (m), 2.13 (m, 1H), 2.19 (m, 1H), 2.42 (dd, J = 13.3 Hz, 6.4 Hz, 1H), 2.60 (m, 3H), 2.84 (s, 1H), 3.12-3.24 (m, 3H), 3.43-3.56 (m, 3H), 3.59 (d, J = 11.7 Hz, 1H), 3.77 (d, J = 12.1 Hz, 1H), 3.79-3.87 (m, 2H), 4.06 (d, J = 9.8 Hz, 1H), 5.43 (m, 1H), 6.67 (m, 1H), 8.07 (s, 1H).
Mass spectrum: (ESI) m/z = 753.35 (M + H).

Examples 97-105

The following compounds were prepared using methods analogous to those described in the preceding examples:

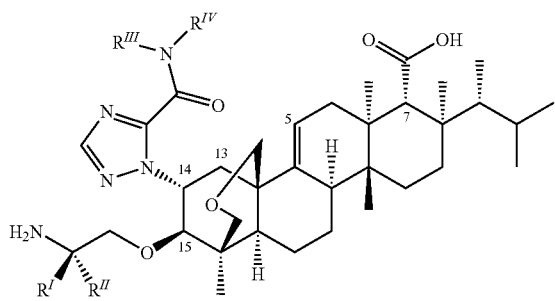

| 97 | $R^I$ = t-Bu | (1S,4aR,6aS,7R,8R,10aR,10bR,12aR,14R,15R)-14-[5-(aminocarbonyl)- |
| | $R^{II}$ = H | 1H-1,2,4-triazol-1-yl]-15-[[(2R)-2-amino-3,3-dimethylbutyl]oxy]-8- |
| | $R^{III}$ = H | [(1R)-1,2-dimethylpropyl]-1,6,6a,7,8,9,10,10a,10b,11,12,12a- |
| | $R^{IV}$ = H | dodecahydro-1,6a,8,10a-tetramethyl-4H-1,4a-propano-2H- |
| | | phenanthro[1,2-c]pyran-7-carboxylic acid |

$^1$H NMR (CD$_3$OD, 500 MHz, ppm) δ 0.77 (s, 3H), 0.77 (d, 3H, partially obscured), 0.83 (s, 9H), 0.84 (d, 3H, partially obscured), 0.87 (s, 3H), 0.90 (d, J = 6.8 Hz, 3H), 1.16 (s, 3H), 1.21 (s, 3H), 1.23-1.66 (m), 1.76-2.04 (m), 2.14 (m, 1H), 2.19 (m. 1H), 2.36 (dd, J = 10.1 Hz, 3.3 Hz, 1H), 2.41 (dd, J = 13.2 Hz, 6.4 Hz, 1H), 2.85 (s, 1H), 2.97 (dd, J = 10.5 Hz, 3.4 Hz, 1H), 3.46 (d, J = 12.1 Hz, 1H), 3.5-3.63 (m, 3H), 3.80 (d, J = 9.8 Hz, 1H), 3.91 (d, J = 11.9 Hz, 1H), 5.48 (m, 1H), 6.57 (m, 1H), 8.04 (s, 1H).
Mass spectrum: (ESI) m/z = 682.55 (M + H).

| 98 | $R^I$ = t-Bu | (1S,4aR,6aS,7R,8R,10aR,10bR,12aR,14R,15R)-15-[[(2R)-2-amino-3,3- |
| | $R^{II}$ = H | dimethylbutyl]oxy]-8-[(1R)-1,2-dimethylpropyl]-14-[5- |
| | $R^{III}$ = Me | [(methylamino)carbonyl]-1H-1,2,4-triazol-1-yl]- |
| | $R^{IV}$ = H | 1,6,6a,7,8,9,10,10a,10b,11,12,12a-dodecahydro-1,6a,8,10a-tetramethyl- |
| | | 4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.83 (s, 9H), 0.86 (d, J = 6.7 Hz, 1H), 0.87 (s, 3H), 0.90 (d, J = 6.7 Hz, 3H), 1.15 (s, 3H), 1.21 (s, 3H), 1.23-1.67 (m), 1.76-2.0 (m), 2.14 (m, 1H), 2.19 (m, 1H), 2.30 (dd, J = 10.1 Hz, 3.4 Hz, 1H), -continued

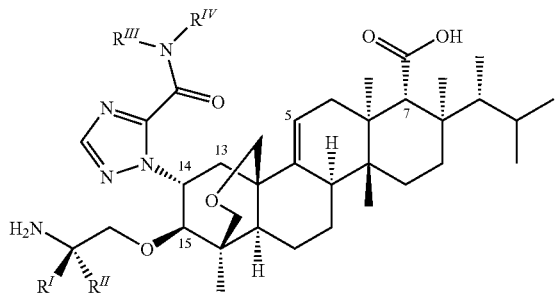

2.40 (dd, J = 13.2 Hz, 6.4 Hz, 1H), 2.85 (s, 1H), 2.93 (d, J = 4.2 Hz, 3H), 3.00 (dd, J = 11.6, 3.5 Hz, 1H), 3.46 (d, J = 11.9 Hz, 1H), 3.50-3.59 (m, 3H), 3.61 (d, J = 11.4 Hz, 1H), 3.82 (d, J = 9.9 Hz, 1H), 3.92 (d, J = 11.9 Hz, 1H), 5.47 (m, 1H), 6.57 (m, 1H), 8.03 (s, 1H), 8.4 (m, 1H).

| 99 | $R^I$ = t-Bu<br>$R^{II}$ = H<br>$R^{III}$ = i-Pr<br>$R^{IV}$ = H | (1S,4aR,6aS,7R,8R,10aR,10bR,12aR,14R,15R)-15-[[(2R)-2-amino-3,3-dimethylbutyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.77 (s, 3H), 0.78 (d, J = 7.1 Hz, 3H), 0.84 (s, 9H), 0.86 (d, 3H, partially obscured), 0.87 (s, 3H), 0.91 (d, J = 6.8 Hz, 3H), 1.16 (s, 3H), 1.21 (s, 3H), 1.23-1.67 (m), 1.27 (d, J = 6.4 Hz, 3H), 1.27 (d, J = 6.7 Hz, 3H), 1.77-2.04 (m), 2.14 (m), 2.19 (m), 2.34 (dd, J = 9.9 Hz, 3.4 Hz, 1H), 2.40 (d, J = 13.4 Hz, 6.4 Hz, 1H), 2.85 (s, 1H), 2.95 (dd, J = 10.7 Hz, 3.4 Hz, 1H), 3.46 (d, J = 11.7 Hz, 1H), 3.52-3.62 (m, 3H), 3.79 (d, J = 9.9 Hz, 1H), 3.91 (d, J = 11.9 Hz, 1H), 4.20 (m, 1H), 5.47 (m, 1H), 6.46 (m, 1H), 8.04 (s, 1H).
Mass spectrum: (ESI) m/z = 724.63 (M + H).

| 100 | $R^I$ = Et<br>$R^{II}$ = Et<br>$R^{III}$ = H<br>$R^{IV}$ = H | (1S,4aR,6aS,7R,8R,10aR,10bR,12aR,14R,15R)-14-[5-(aminocarbonyl)-1H-1,2,4-triazol-1-yl]-15-(2-amino-2-ethylbutoxy)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.64 (t, J = 7.5 Hz, 3H), 0.76 (s, 3H), 0.77 (d, 3H, partially obscured), (t, J = 7.8 Hz, 3H), 0.86 (d, J = 6.8 Hz, 3H), 0.88 (s, 3H), 0.90 (d, J = 6.6 Hz, 3H), 1.14 (s, 3H), 1.21 (s, 3H), 1.22-1.57 (m), 1.63 (m, 1H), 1.77-1.96 (m), 2.12 (m, 1H), 2.19 (m, 1H), 2.38 (dd, J = 13.3 Hz, 6.6 Hz, 1H), 2.83 (d, 1H, partially obscured), 2.84 (s, 1H), 3.45 (d, 1H, partially obscured), 3.46 (d, 1H, partially obscured), 3.51 (dd, J = 11.4 Hz, 1.8 Hz, 1H), 3.60 (d, J = 11.7 Hz, 1H), 3.91 (d, J = 11.9 Hz, 1H), 3.94 (d, J = 9.9 Hz, 1H), 5.45 (m, 1H), 6.65 (m, 1H), 8.02 (s, 1H).
Mass spectrum: (ESI) m/z = 682.59 (M + H).

| 101 | $R^I$ = Et<br>$R^{II}$ = Et<br>$R^{III}$ = Me<br>$R^{IV}$ = H | (1S,4aR,6aS,7R,8R,10aR,10bR,12aR,14R,15R)-15-(2-amino-2-ethylbutoxy)-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹NMR (CD₃OD, 500 MHz, ppm) δ 0.62 (t, J = 7.5 Hz, 3H), 0.76 (s, 3H), 0.77 (d, 3H, partially obscured), 0.78 (t, 3H, partially obscured), 0.86 (d, J = 6.9 Hz, 3H), 0.88 (s, 3H), 0.90 (d, 3H), 1.14 (s, 3H), 1.19-1.56 (m), 1.14 (s, 3H), 1.20 (s, 3H), 1.63 (m, 1H), 1.77-1.96 (m), 2.13 (m, 1H), 2.19 (m), 2.37 (dd, J = 13.2 Hz, 6.6 Hz, 1H), 2.82 (d, J = 9.9 Hz, 1H), 2.84 (s, 1H), 2.92 (d, J = 4.3 Hz, 1H), 3.44-3.47 (m, 2H), 3.52 (dd, J = 11.5 Hz, 1.7 Hz, 1H), 3.61 (d, J = 11.5 Hz, 1H), 3.90-3.96 (m, 2H), 5.45 (m, 1H), 6.65 (m, 1H), 8.00 (s, 1H), 8.78 (m, 1H)
Mass spectrum: (ESI) m/z = 696.53 (M + H).

| 102 | $R^I$ = Et<br>$R^{II}$ = Et<br>$R^{III}$ = i-Pr<br>$R^{IV}$ = H | (1S,4aR,6a8,7R,8R,10aR,10bR,12aR,14R,15R)-15-(2-amino-2-ethylbutoxy)-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.64 (t, J = 7.5 Hz, 3H), 0.77 (s, 3H), 0.78 (d, 3H, partially obscured), 0.78 (t, J = 7.5 Hz, 3H), 0.86 (d, J = 6.6 Hz, 3H), 0.88 (s, 3H), 0.90 (d, J = 6.9 Hz, 3H), 1.14 (s, 3H), 1.19-1.46 (m), 1.21 (s, 3H), 1.25 (d, J = 7.1 Hz, 3H), 1.27 (d, J = 7.1 Hz, 3H), 1.63 (m, 1H), 1.76-1.97 (m), 2.13 (m, 1H), 2.19 (m, 1H), 2.37 (dd, J = 13.3, 6.7 Hz, 1H), 2.79 (d, J = 9.8 Hz, 1H), 2.84 (s, 1H), 3.43 3.48 (m), 3.52 (dd, J = 11.5 Hz, 2.0 Hz, 1H), 3.60 (d, J = 11.4 Hz, 1H), 3.89-3.95 (m, 2H), 4.18 (m, 1H), 5.45 (m, 1H), 6.59 (m, 1H), 8.02 (s, 1H), 8.56 (d, J = 8.2 Hz, 1H).
Mass spectrum: (ESI) m/z = 724.58 (M + H).

| 103 | $R^I$ = Me<br>$R^{II}$ = i-Pr<br>$R^{III}$ = H<br>$R^{IV}$ = H | (1S,4aR,6aS,7R,8R,10aR,10bR,12aR,14R,15R)-14-[5-(aminocarbonyl)-1H-1,2,4-triazol-1-yl]-15-[[(2S)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm, selected resonances) 0.49 (d, J = 6.8 Hz, 3H), 0.76 (s, 3H), 0.77 (d, J = 7.3 Hz, 3H), 0.84 (d, J = 7.1 Hz, 3H), 0.86 (d, J = 6.6 Hz, 3H), 0.89 (s, 3H), 0.90 (d, J = 7.0 Hz, 3H), 1.00 (s, 3H), 1.13 (s, 3H), 1.20 (s, 3H), 2.35 (dd, J = 6.6, 13.3 Hz, 1H, H-13), 2.84 (s, H-7), 3.01 (d, J = 10.1 Hz, 1H, H-15), 5.44 (m, 1H, H-5), 6.63 (ddd, J = 6.6, 10.1, 12 Hz, 1H, H-14), 8.02 (s, 1H, triazole).
Mass spectrum: (ESI) m/z = 682.8 (M + H).

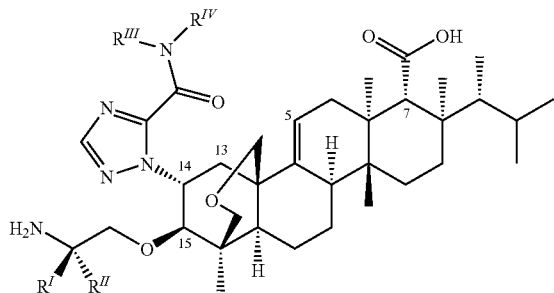

| | | |
|---|---|---|
| 104 | $R^I$ = Me<br>$R^{II}$ = i-Pr<br>$R^{III}$ = Me<br>$R^{IV}$ = H | (1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonances) 0.47 (d, J = 6.9 Hz, 3H), 0.76 (s, 3H), 0.77 (d, J = 7.7 Hz, 3H), 0.82 (d, J = 7.0 Hz, 3H), 0.86 (d, J = 6.7 Hz, 3H), 0.89 (s, 3H), 0.90 (d, J = 7.6 Hz, 3H), 0.99 (s, 3H), 1.13 (s, 3H), 1.20 (s, 3H), 2.35 (dd, J = 6.6, 13.3 Hz, 1H, H-13), 2.92 (br s, 3H, NCH$_3$), 3.98 (d, J = 9.9 Hz, 1H, H-15), 5.44 (m, 1H, H-5), 6.63 (ddd, J = 6.6, 9.9, 11.8 Hz, 1H, H-14), 8.00 (s, 1H, triazole), 8.77 (m, 1H, NH).
Mass spectrum: (ESI) m/z = 696.37 (M + H).

| | | |
|---|---|---|
| 105 | $R^I$ = Me<br>$R^{II}$ = i-Pr<br>$R^{III}$ = n-Pr<br>$R^{IV}$ = H | (1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-[5-[(propylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm, selected resonances) 0.46 (d, J = 6.8 Hz, 3H), 0.76 (s, 3H), 0.77 (d, J = 7.8 Hz, 3H), 0.82 (d, J = 7.0 Hz, 3H), 0.86 (d, J = 6.8 Hz, 3H), 0.89 (s, 3H), 0.90 (d, J = 7.5 Hz, 3H), 0.99 (s, 3H), 1.13 (s, 3H), 1.20 (s, 3H), 2.34 (dd, J = 6.6, 13.4 Hz, 1H, H-13), 2.84 (s, 1H, H-7), 3.98 (d, J = 9.9 Hz, 1H, H-15), 5.44 (m, 1H, H-5), 6.61 (ddd, J = 6.6, 9.9, 12.0 Hz, 1H, H-14), 8.01 (s, 1H, triazole), 8.81 (t, J = 6.0 Hz, 1H, NH).
Mass spectrum: (ESI) m/z = 724.47 (M + H).

Examples 106-117

The following compounds were prepared using methods analogous to those described in the preceding examples:

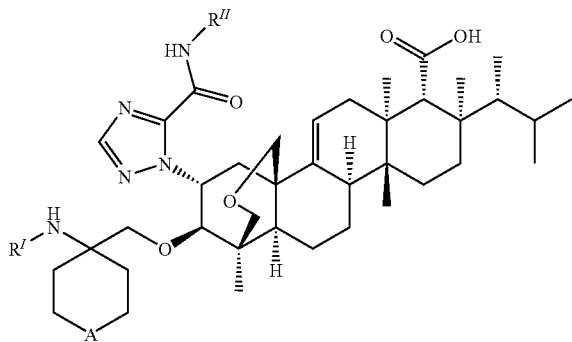

| | | |
|---|---|---|
| 106 | $R^I$ = H<br>$R^{II}$ = H<br>A = CH$_2$ | (1S,4aR,6aS,7R,8R,10aR,10bR,12aR,14R,15R)-14-[5-(aminocarbonyl)-1H-1,2,4-triazol-1-yl]-15-[(1-aminocyclohexyl)methoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$NMR (MeOH-d$_4$, 500 MHz, ppm) δ 0.78 (m, 6H), 0.84 (m, 9H), 1.12 (s, 3H), 1.20 (s, 3H), 1.20-1.62 (m, 18H), 1.80-1.95 (m, 6H), 2.10 (m, 1H), 2.20 (m, 1H), 2.35 (m, 1H), 2.84 (s, 1H), 3.03 (d, 1H), 3.40-3.60 (m, 4H), 3.90 (d, 1H), 3.92 (d, 1H), 5.43 (m, 1H), 6.63 (m, 1H).
Mass spectrum: (ESI) m/z = 694 (M + H).

| | | |
|---|---|---|
| 107 | $R^I$ = Me<br>$R^{II}$ = H<br>A = CH$_2$ | (1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[1-(methylamino)cyclohexyl]methoxy]-1,6,6a,7,8,9,10,10a,10b,11,12,12a- |

-continued

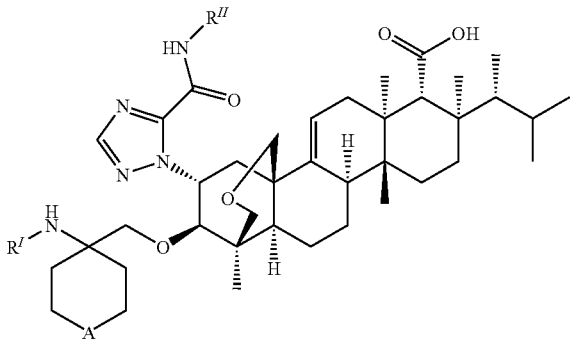

dodecahydro-1,6a,8,10a-tetramethyl-4H-1,4a-propano-2H-phenanthro[1,2-c]pyran-7-carboxylic acid $^1$H NMR (MeOH-d$_4$, 500 MHz, ppm) δ 0.80 (m, 6H), 0.84 (d, 3H), 0.91 (m, 6H), 1.14 (s, 3H), 1.22 (s, 3H), 1.22-1.70 (m, 15H), 1.80-2.00 (m, 8H), 2.13 (m, 1H), 2.20 (m, 1H), 2.38 (s, 3H), 2.40 (m, 1H), 2.83 (s, 1H), 3.19 (d, 1H), 3.42-3.70 (m, 4H), 3.90 (d, 1H), 4.10 (d, 1H), 5.43 (m, 1H), 6.63 (m, 1H), 8.05 (s, 1H).

Mass spectrum: (ESI) m/z = 708 (M + H).

| 108 | $R^I$ = H<br>$R^{II}$ = i-Pr<br>A = CH$_2$ | (1S,4aR,6aS,7R,8R,10aR,10bR,12aR,14R,15R)-15-[(1-aminocyclohexyl)methoxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl 4H-1,4a-propano-2H-phenanthro[1,2-c]pyran-7-carboxylic acid |

$^1$H NMR (MeOH-d$_4$, 500 MHz, ppm) δ 0.80 (m, 6H), 0.88 (m, 9H), 1.17 (s, 3H), 1.21-1.70 (m, 24H), 1.80-1.97 (m, 6H), 2.20 (m, 2H), 2.39 (m, 1H), 2.84 (s, 1H), 3.00 (d, 1H), 3.43 (m, 2H), 3.52 (m, 1H), 3.60 (m, 1H), 3.95 (m, 2H), 4.20 (m, 1H), 5.43 (m, 1H), 6.62 (m, 1H), 8.05 (s, 1H), 8.55 (d, 1H).

Mass spectrum: (ESI) m/z = 737 (M + H).

| 109 | $R^I$ = Et<br>$R^{II}$ = H<br>A = CH$_2$ | (1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[1-(ethylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (hydrochloride salt) |

$^1$H NMR (MeOH-d$_4$, 500 MHz, ppm) δ 0.80 (m, 6H), 0.88 (m, 9H), 1.13 (s, 3H), 1.20-1.92 (m, 28H), 2.10 (m, 1H), 2.20 (m, 1H), 2.38 (m, 1H), 2.44 (m, 1H), 2.83 (m, 3H), 3.20 (d, 1H), 3.48 (m, 2H), 3.60 (m, 1H), 3.72 (m, 1H), 3.84 (m, 1H), 4.12 (d, 1H), 5.43 (m, 1H), 6.70 (m, 1H), 8.10 (s, 1H).

Mass spectrum: (ESI) m/z = 723 (M + H).

| 110 | $R^I$ = n-Pr<br>$R^{II}$ = H<br>A = CH$_2$ | (1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[1-(propylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm) δ 0.80 (m, 6H), 0.84 (d, 3H), 0.90 (m, 6H), 1.02 (t, 3H), 1.13 (s, 3H), 1.15-1.70 (m, 14H), 1.71-1.98 (m, 7H), 2.10 (m, 1H), 2.20 (m, 1H), 2.38 (m, 1H), 2.48 (m, 1H), 2.73 (m, 1H), 2.84 (s, 1H), 3.22 (d, 1H), 3.50 (m, 2H), 3.60 (d, 1H), 3.72 (d, 1H), 3.84 (d, 1H), 4.15 (d, 1H), 5.42 (m, 1H), 6.70 (m, 1H), 8.05 (s, 1H).

Mass spectrum: (ESI) m/z = 737 (M + H).

| 111 | $R^I$ = H<br>$R^{II}$ = H<br>A = O | (1S,4aR,6aS,7R,8R,10aR,10bR,12aR,14R,15R)-14-[5-(aminocarbonyl)-1H-1,2,4-triazol-1-yl]-15-[(4-aminotetrahydro-2H-pyran-4-yl)methoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.86 (d, J = 6.6 Hz, 3H), 0.89 (s, 3H), 0.91 (d, 3H, partially obscured), 1.15 (s, 3H), 1.22 (s, 3H), 1.20-1.36 (m), 1.40-1.57 (m), 1.58-1.72 (m), 1.78-1.98 (m), 2.13 (m, 1H), 2.20 (m, 1H), 2.38 (dd, J = 13.5, 6.6 Hz, 1H), 2.85 (s, 1H), 2.90 (m, 1H), 3.21 (d, J = 10.0 Hz, 1H), 3.31 (partially obscured), 3.47 (d, J = 12.2, 1H), 3.50-3.63 (m, 4H), 3.72 (m, 1H), 3.93 (d, J = 11.9 Hz, 1H), 4.01 (d, J = 10.1 Hz, 1H), 5.46 (m, 1H), 6.67 (m, 1H), 8.08 (s, 1H).

Mass spectrum: (ESI) m/z = 696.61 (M + H).

| 112 | $R^I$ = H<br>$R^{II}$ = Me<br>A = O | (1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.79 (d, 3H, partially obscured), 0.87 (d, J = 6.6 Hz, 3H), 0.90 (s, 3H), 0.91 (d, 3H, partially obscured), 1.15 (s, 3H), 1.17 (s, 3H), 1.20-1.72 (m), 1.80-1.98 (m), 2.14 (m, 1H), 2.20 (m, 1H), 2.37 (dd, J = 13.3, 6.4 Hz, 1H), 2.85 (s, 1H), 2.86 (m, partially obscured, 1H), 2.90 (s, 3H), 3.22 (d, J = 10.1 Hz, 1H), 3.30 (partially obscured), 3.47 (d, J = 12.1, 1H), 3.50-3.63 (m, 4H), 3.72 (m, 1H), 3.93 (d, J = 11.9 Hz, 1H), 4.01 (d, J = 10.1 Hz, 1H), 5.46 (m, 1H), 6.67 (m, 1H), 8.06 (s, 1H).

Mass spectrum: (ESI) m/z = 710.75 (M + H).

| 113 | $R^I$ = Me | (1S,4aR,6aS,7R,8R,10aR,10bR,12aR,14R,15R)-8-[(1R)-1,2- |

-continued

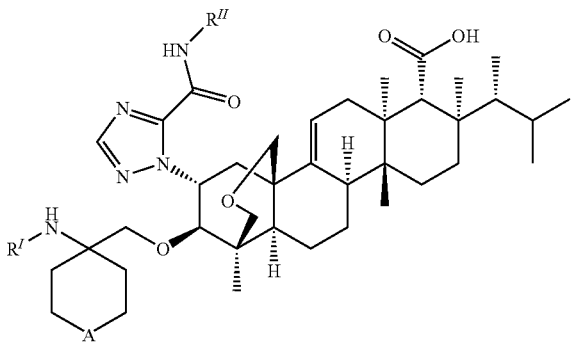

| | $R^{II}$ = Me | dimethylpropyl]-14-[5-[(methylamino)carbonyl]-1H-1,2,4-triazol-1-yl]- |
| | A = O | 15-[[tetrahydro-4-(methylamino)-2H-pyran-4-yl]methoxy]-
1,6,6a,7,8,9,10,10a,10b,11,12,12a-dodecahydro-1,6a,8,10a-tetramethyl-
4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.87 (d, J = 6.6 Hz, 3H), 0.90 (d, 3H, partially obscured), 0.92 (s, 3H), 1.14 (s, 3H), 1.22 (s, 3H), 1.23-1.72 (m), 1.77-1.98 (m), 2.13 (m, 1H), 2.20 (m, 1H), 2.38 (dd, partially obscured, 1H), 2.39 (s, 3H), 2.85 (s, 1H), 2.90 (m, partially obscured, 1H), 2.93 (s, 3H), 3.32-3.39 (m, 2H, partially obscured), 3.50 (d, 1H, partially obscured), 3.53 (dd, 1H, partially obscured), 3.60 (m, 1H, partially obscured), 3.62 (d, 1H, partially obscured), 3.80 (m, 1H, partially obscured), 3.85 (m, 2H, partially obscured), 4.15 (d, J = 10.0 Hz, 1H), 5.46 (m, 1H), 6.65 (m, 1H), 8.07 (s, 1H).
Mass spectrum: (ESI) m/z = 724.69 (M + H).

| 114 | $R^I$ = H | (1S,4aR,6aS,7R,8R,10aR,10bR,12aR,14R,15R)-15-[(4-aminotetrahydro- |
| | $R^{II}$ = i-Pr | 2H-pyran-4-yl)methoxy]-8-[(1R)-1,2-dimethylpropyl]-14-[5- |
| | A = O | [(methylamino)carbonyl]-1H-1,2,4-triazol-1-yl]-
1,6,6a,7,8,9,10,10a,10b,11,12,12a-dodecahydro-1,6a,8,10a-tetramethyl-
4H-1,4a-propano-2H-phenanthro[1,2-c]pyran-7-carboxylic acid |

$^1$H NMR (CD$_3$OD, 500 MHz, ppm) δ 0.78 (s, 3H), 0.79 (d, 3H, partially obscured), 0.87 (d, J = 6.6 Hz, 3H), 0.89 (s, 3H), 0.91 (d, J = 6.6, 3H, partially obscured), 1.16 (s, 3H), 1.22 (s, 3H), 1.25 (d, J = 6.3 Hz, 3H), 1.27 (d, J = 6.7 Hz, 3H), 1.16-1.70 (m), 1.80-1.98 (m), 2.15 (m, 1H), 2.20 (m, 1H), 2.38 (dd, J = 13.4, 6.4 Hz, 1H), 2.85 (s, 1H), 2.90 (m, 1H), 3.18 (d, J = 10.3, 1H, partially obscured), 3.22 (m, 1H, partially obscured), 3.48 (d, J = 11.7 Hz, 1H), 3.51-3.63 (m, 3H), 3.73 (m, 1H), 3.93 (d, J = 12.1 Hz, 1H), 3.99 (d, J = 10.0 Hz, 1H), 4.18 (m, 1H), 5.46 (m, 1H), 6.62 (m, 1H), 8.07 (s, 1H).
Mass spectrum: (ESI) m/z = 738.78 (M + H).

| 115 | $R^I$ = Me | (1S,4aR,6aS,7R,8R,10aR,10bR,12aR,14R,15R)-8-[(1R)-1,2- |
| | $R^{II}$ = i-Pr | dimethylpropyl]-14-[5-[[(1-methylethyl)amino]carbonyl]-1H-1,2,4- |
| | A = O | triazol-1-yl]-15-[[tetrahydro-4-(methylamino)-2H-pyran-4-yl]methoxy]-
1,6,6a,7,8,9,10,10a,10b,11,12,12a-dodecahydro-1,6a,8,10a-tetramethyl-
4H-1,4a-propano-2H-phenanthro[1,2-c]pyran-7-carboxylic acid |

$^1$H NMR (CD$_3$OD, 500 MHz, ppm) δ 0.76 (s, 3H), 0.77 (d, 3H, partially obscured), 0.85 (d, J = 6.8 Hz, 3H), 0.89 (d, 3H, partially obscured), 0.90 (s, 3H), 1.12 (s, 3H), 1.20 (s, 3H), 1.24 (d, J = 6.6 Hz, 3H), 1.25 (d, J = 6.5 Hz, 3H), 1.13 1.70 (m), 1.76-1.96 (m), 2.11 (m, 1H), 2.18 (m, 1H), 2.36 (dd, partially obscured, 1H), 2.39 (s, 3H), 2.83 (s, 1H), 2.90 (m, 1H), 3.32-3.39 (m, 2H, partially obscured), 3.48 (d, J = 11.8 Hz, 1H), 3.51 (dd, J = 11.7, 2.1 Hz 1H,), 3.59 (d, 1H, partially obscured), 3.60 (m, 1H, partially obscured), 3.78 (m, 1H, partially obscured), 3.81 (d, 1H, partially obscured), 3.86 (d, J = 12.0 Hz, 1H), 4.11 (d, J = 9.7 Hz, 1H), 4.18 (m, 1H), 5.44 (m, 1H), 6.58 (m, 1H), 8.05 (s, 1H).
Mass spectrum: (ESI) m/z = 752.80 (M + H).

| 116 | $R^I$ = Me | (1S,4aR,6aS,7R,8R,10aR,10bR,12aR,14R,15R)-8-[(1R)-1,2- |
| | $R^{II}$ = Me | dimethylpropyl]-14-[5-[(methylamino)carbonyl]-1H-1,2,4-triazol-1-yl]- |
| | A = S | 15-[[tetrahydro-4-(methylamino)-2H-thiopyran-4-yl]methoxy]-
1,6,6a,7,8,9,10,10a,10b,11,12,12a-dodecahydro-1,6a,8,10a-tetramethyl-
4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.87 (d, J = 6.6 Hz, 3H), 0.91 (d, 3H, partially obscured), 0.92 (s, 3H), 1.14 (s, 3H), 1.22 (s, 3H), 1.23-1.38 (m), 1.43 (m, 1H), 1.47-1.58 (m, 2H), 1.60-1.73 (m, 3H), 1.74-1.98 (m), 2.07-2.24 (m), 2.38 (dd, partially obscured, 1H), 2.39 (s, 3H), 2.58 (m, 2H), 2.85 (s, 1H), 2.93 (s, 3H), 2.94 (m, partially obscured, 1H), 3.23 (d, J = 11.0 Hz, 1H), 3.49 (d, 1H, partially obscured), 3.53 (dd, 1H, partially obscured), 3.62 (d, J = 11.5 Hz, 1H), 3.72 (d, J = 11.2 Hz, 1H), 3.88 (d, J = 11.9 Hz, 1H), 4.12 (d, J = 9.8 Hz, 1H), 5.45 (m, 1H), 6.65 (m, 1H), 8.07 (s, 1H).
Mass spectrum: (ESI) m/z = 740.76 (M + H).

-continued

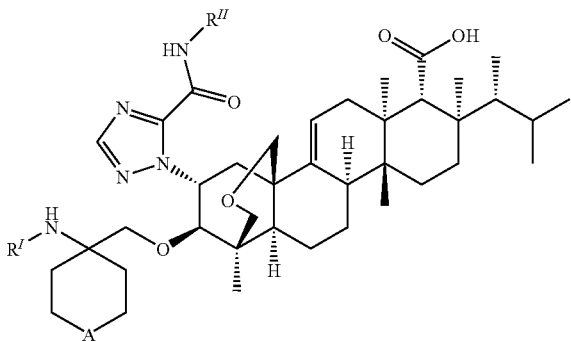

| 117 | $R^I$ = Me<br>$R^{II}$ = Me<br>A = $SO_2$ | (1S,4aR,6aS,7R,8R,10aR,10bR,12aR,14R,15R)-8-[(1R)-1,2-dimethylpropyl]-14-[5-[(methylamino)carbonyl]-1H-1,2,4-triazol-1-yl]-15-[[tetrahydro-4-(methylamino)-1,1-dioxido-2H-thiopyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.87 (d, J = 6.6 Hz, 3H), 0.91 (d, J = 6.9 Hz, 3H), 0.93 (s, 3H), 1.14 (s, 3H), 1.21 (s, 3H), 1.23-1.38 (m, 1H), 1.43 (m, 1H), 1.49-1.56 (m, 2H), 1.63 (m, 1H), 1.78 (m, 1H), 1.82-1.98 (m), 2.06 (m, 1H), 2.15 (m, 1H), 2.20 (m, 1H), 2.25 (m, partially obscured, 1H), 2.35 (m, partially obscured, 1H), 2.39 (dd, partially obscured, 1H), 2.42 (s, 3H), 2.74 (m, 1H), 2.85 (s, 1H), 2.88 (m, partially obscured, 1H), 2.94 (s, 3H), 3.08 (m, partially obscured, 2H), 3.36 (d, J = 11.5 Hz, 1H), 3.52 (m, partially obscured, 2H), 3.63 (d, J = 11.5 Hz, 1H), 3.88 (m, partially obscured, 2H), 4.20 (d, J = 10.1 Hz, 1H), 5.45 (m, 1H), 6.65 (m, 1H), 8.08 (s, 1H).
Mass spectrum: (ESI) m/z = 772.78 (M + H).

Example 118

(1S,4aR,6aS,7R,8R,10aR,10bR,12aR,14R,15R)-14-[3-(aminocarbonyl)-5-bromo-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 118A) and (1S,4aR,6aS,7R,8R,10aR,10bR,12aR,14R,15R)-14-[5-(aminocarbonyl)-3-bromo-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 118B)

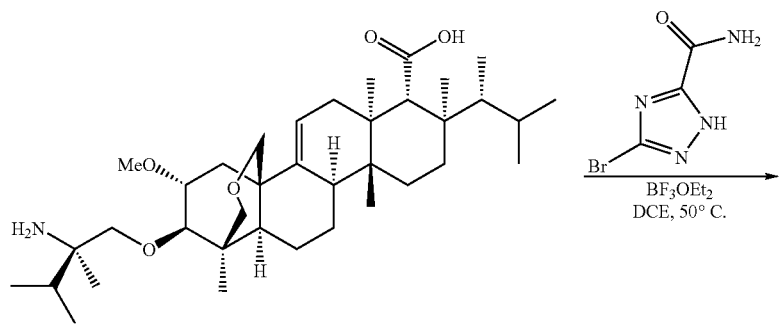

Intermediate 6

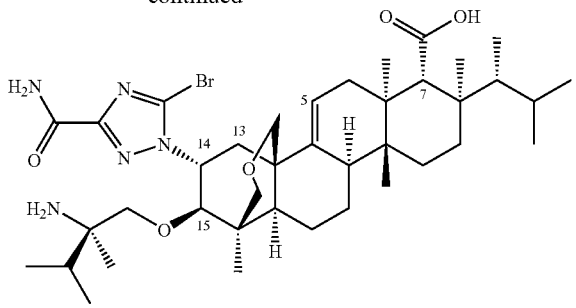

EXAMPLE 118A

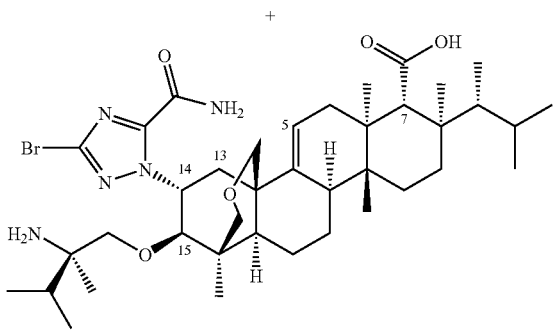

EXAMPLE 118B

A stirred mixture of Intermediate 6 (50 mg, 0.083 mmol) in 1,2-dichloroethane (1.39 mL) was treated with boron trifluoride etherate (158 µL, 1.25 mmol) and 3-bromo-1H-1,2,4-triazole-5-carboxamide (64 mg, 0.332 mmol) and heated at 50° C. After 2.5 hours the reaction was allowed to cool to room temperature and chromatographed by reverse phase HPLC (C-18, acetonitrile: 0.1% trifluoroacetic acid in water) using mass directed collection (m/z 760.4) to give two products. The fractions containing the first eluting isomer were combined and lyophilized to give EXAMPLE 118A (10.6 mg) as a white solid. The fractions containing the second eluting isomer were combined and lyophilized to give EXAMPLE 118B (8.2 mg) as a white solid.

Example 118A $^1$H NMR (CD$_3$OD, 500 MHz, ppm, selected resonances) 0.76-0.91 (m), 1.14 (s, 3H), 1.20 (s, 3H), 2.38 (dd, J=6.3, 13.4 Hz, 1H, H-13), 2.84 (s, 1H, H-7), 5.50 (m, 1H, H-5), 8.82 (ddd, J=6.3, 9.9, 12.0 Hz, 1H, H-14).

Example 118B $^1$H NMR (CD$_3$OD, 500 MHz, ppm, selected resonances) 0.77 (s, 3H), 0.77 (d, J=7.3 Hz, 3H), 0.81-0.91 (m), 1.16 (s, 3H), 1.21 (s, 3H), 2.44 (dd, 6.4, 13.2 Hz, 1H, H-13), 2.84 (s, 1H, H-7), 5.48 (m, 1H, H-5), 6.70 (m, 1H, H-14).

Example 119

(1S,4aR,6aS,7R,8R,10aR,10bR,12aR,14R,15R)-14-[3-amino-5-(aminocarbonyl)-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

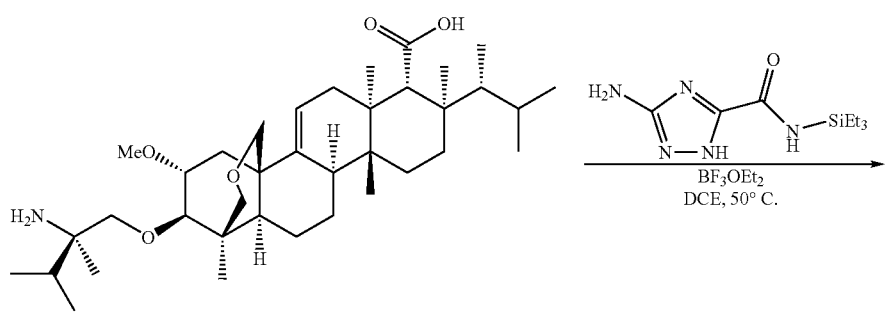

Intermediate 6

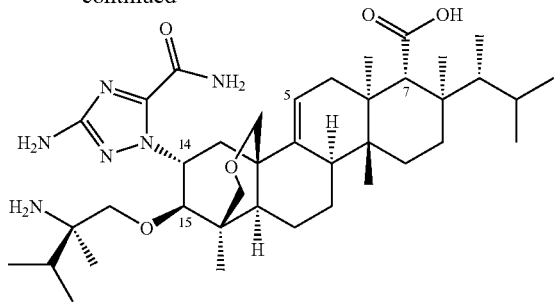

A stirred mixture of Intermediate 6 (50 mg, 0.083 mmol) in 1,2-dichloroethane (1.39 mL) was treated with boron trifluoride etherate (158 µL, 1.25 mmol) and 3-amino-N-(triethylsilyl)-1H-1,2,4-triazole-5-carboxamide (80 mg, 0.332 mmol) and heated at 50° C. After 2.5 hours the reaction was allowed to cool to room temperature and chromatographed by reverse phase HPLC (C-18, acetonitrile: 0.1% trifluoroacetic acid in water) using mass directed collection (m/z 697.5) to give the title compound as a white solid (24.2 mg).

$^1$H NMR (CD$_3$OD, 600 MHz, ppm, selected resonances) 0.76 (s, 3H), 0.77 (d, J=8.7 Hz, 3H), 0.84-0.92 (m), 1.15 (s), 1.21 (s), 2.33 (dd, J=6.5, 13.4 Hz, 1H, H-13), 2.84 (s, 1H, H-7), 3.83 (d, J=9.9 Hz, 1H, H-15), 5.47 (m, 1H, H-5), 6.47 (m, 1H, H-14).

Examples 120-122

The following compounds were prepared using methods analogous to those described in the preceding examples:

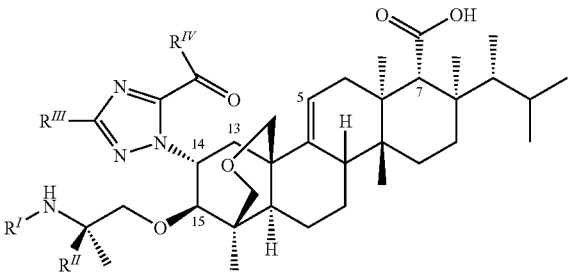

| | | |
|---|---|---|
| 120 | $R^I$ = H<br>$R^{II}$ = i-Pr<br>$R^{III}$ = Br<br>$R^{IV}$ = OMe | (1S,4aR,6aS,7R,8R,10aR,10bR,12aR,14R,15R)-15-[[(2R)-2-amino-2,3-dimethylbutyl]oxy]-14-[3-bromo-5-(methoxycarbonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | $^1$H NMR (CD$_3$OD, 500 MHz, ppm, selected resonances) 0.77 (s, 3H), 0.77 (d, J = 7.4 Hz, 3H), 0.80 (s, 3H), 0.83-0.91 (m), 1.16 (s, 3H), 1.21 (s, 3H), 2.51 (dd, 6.3, 13.2 Hz, 1H, H-13), 2.84 (s, 1H, H-7), 3.99 (s, 3H, CO$_2$Me), 5.49 (m, 1H, H-5), 6.56 (m, 1H, H-14). | |
| 121 | $R^I$ = H<br>$R^{II}$ = t-Bu<br>$R^{III}$ = Br<br>$R^{IV}$ = NH$_2$ | (1S,4aR,6aS,7R,8R,10aR,10bR,12aR,14R,15R)-14-[5-(aminocarbonyl)-3-bromo-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | $^1$H NMR (CD$_3$OD, 600 MHz, ppm, selected resonances) 0.77 (s, 3H), 0.77 (d, J = 7.1 Hz, 3H), 0.83 (s, 3H), 0.86 (d, J = 6.7 Hz, 3H), 0.89 (s, 9H, t-Bu), 0.90 (d, J = 7.8 Hz, 3H), 1.16 (s, 3H), 1.21 (s, 3H), 2.46 (dd, 6.4, 13.3 Hz, 1H, H-13), 2.85 (s, 1H, H-7), 5.48 (m, 1H, H-5), 6.73 (m, 1H, H-14). | |
| 122 | $R^I$ = Me<br>$R^{II}$ = i-Pr<br>$R^{III}$ = NH$_2$<br>$R^{IV}$ = NHMe | (1S,4aR,6aS,7R,8R,10aR,10bR,12aR,14R,15R)-15-[[(2R)-2-amino-2,3-dimethylbutyl]oxy]-14-[3-amino-5-[(methylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
| | $^1$H NMR (CD$_3$OD, 600 MHz, ppm) 0.76 (s, 3H, Me), 0.76 (d, 3H, Me), 0.84 (s, 3H, Me), 0.85 (d, 3H, Me), 0.85 (d, 3H, Me), 0.86 (s, 3H, Me), 0.89 (d, 3H, Me), 0.89 (d, 3H, Me), 1.13 (s, 3H, Me), 1.20 (s, 3H, Me), 1.22-1.32 (m), 1.40-1.44 (m), 1.48-1.64 (m), 1.72-1.95 (m), 2.00-2.22 (m), 2.32 (dd, 1H, H13), 2.43 (s, 3H, NMe), 2.84 (s, 1H, H7), 2.86 (s, 3H, NMe), 3.18 (d, 1H), 3.44 (d, 1H), 3.49 (dd, 1H), 3.58 (d, 1H), 3.64 (d, 1H), 3.86 (d, 1H), 3.91 (d, 1H), 5.45 (dd, 1H, H5) and 6.46 (m, 1H, H14).<br>Mass spectrum: (ESI) m/z (M + H). = 725.49. | |

Example 123

(1S,4aR,6aS,7R,8R,10aR,10bR,12aR,14R,15R)-14-[3-(aminosulfonyl)-4H-1,2,4-triazol-4-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 123A) and (1S,4aR,6aS,7R,8R,10aR,10bR,12aR,14R,15R)-14-[3-(aminosulfonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-penanthro[1,2-c]pyran-7-carboxylic acid (EXAMPLE 123B) and (1S,4aR,6aS,7R,8R,10aR,10bR,12aR,14R,15R)-14-[5-(aminosulfonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 123C)

A solution of Intermediate 14 (50 mg, 0.08 mmol) in dichloroethane (0.8 mL) was treated with 1H-1,2,4-triazole-5-sulfonamide (*J. Heterocycl. Chem.* 1988, 25, 1857, herein incorporate by reference in its entirety; 50 mg, 0.39 mmol) then BF$_3$OEt$_2$ (0.10 mL, 0.80 mmol) and this mixture was heated to 50° C. under nitrogen. After 1.5 hours the reaction was cooled to room temperature then concentrated in vacuo. The crude product mixture was suspended in methanol (3 mL) and filtered through a sintered glass funnel. The filtrate was separated by preparative HPLC (19×100 mm Waters Sunfire column, 5 µm, UV-detection, 30-100% MeCN/water with 0.05% TFA over 20 minutes). The product fractions for each of the regioisomeric products were combined and partially concentrated by rotovap then frozen and lyophilized to give EXAMPLE 123A (5 mg), EXAMPLE 123B (13), and EXAMPLE 123C (6 mg) each as a white amorphous solid.

Example 123A $^1$H NMR (CD$_3$OD, 500 MHz, ppm, selected resonances) δ 6.10 (m, 1H), 9.12 (s, 1H).

Mass spectrum: (ESI) m/z=732.49 (M+H).

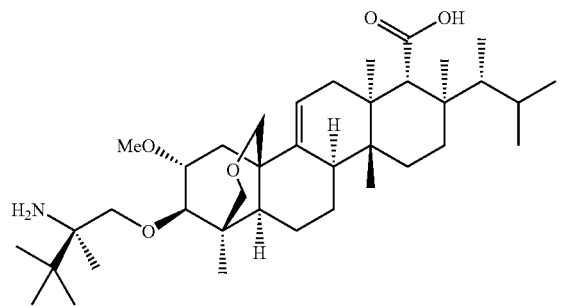

Intermediate 14

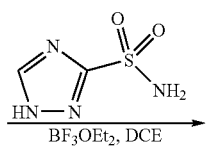

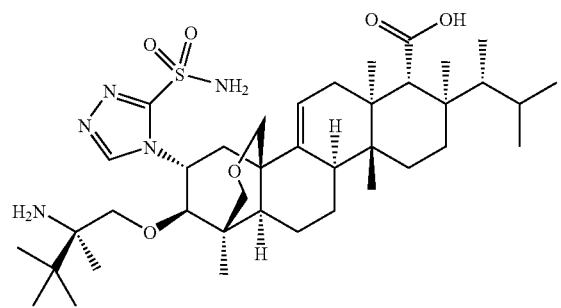

EXAMPLE 123A

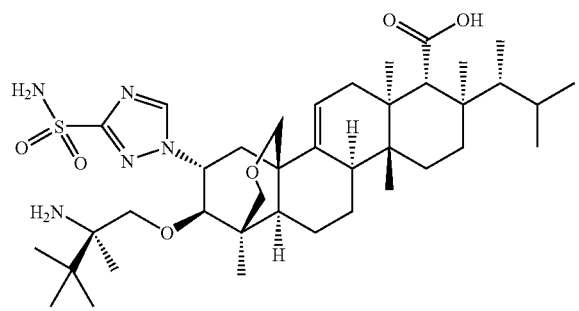

EXAMPLE 123B

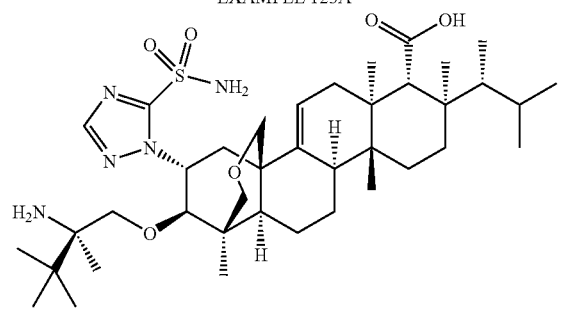

EXAMPLE 123C

Example 123B

¹H NMR (CD₃OD, 500 MHz, ppm, selected resonances) δ 5.68 (m, 1H), 8.67 (s, 1H).
Mass spectrum: (ESI) m/z=732.49 (M+H).

Example 123C

¹H NMR (CD₃OD, 500 MHz, ppm) δ 0.77 (s, 3H), 0.78 (d, 3H, partially obscured), 0.84 (s, 3H), 0.85 (d, 3H, partially obscured), 0.87 (s, 9H), 0.90 (d, J=6.9 Hz, 3H), 0.91 (s, 3H), 1.14 (s, 3H), 1.20 (s, 3H), 1.13-1.98 (m), 2.13 (m, 1H), 2.19 (m, 1H), 2.52 (dd, J=13.4 Hz, 6.4 Hz, 1H), 2.84 (s, 1H), 3.06 (d, J=9.8 Hz, 1H), 3.48 (d, J=11.9 Hz, 1H), 3.53 (dd, J=13.3 Hz, 1.8 Hz, 1H), 3.60 (d, J=11.4 Hz, 1H), 3.72 (d, J=9.9 Hz, 1H), 3.98 (d, J=11.9 Hz, 1H), 4.08 (d, J=9.8 Hz, 1H), 5.45 (m, 1H), 6.25 (m, 1H), 8.07 (s, 1H).
Mass spectrum: (ESI) m/z=732.49 (M+H).

Examples 124-127

The following compounds were prepared using methods analogous to those described in the preceding examples:

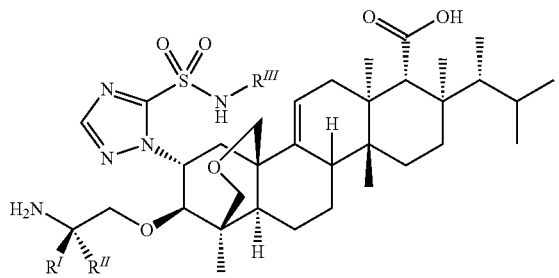

| 124 | $R^I$ = Et<br>$R^{II}$ = Et<br>$R^{III}$ = H | (1S,4aR,6aS,7R,8R,10aR,10bR,12aR,14R,15R)-15-(2-amino-2-ethylbutoxy)-14-[5-(aminosulfonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 500 MHz, ppm) δ 0.61 (t, J = 7.6 Hz, 3H), 0.76 (s, 3H), 0.77 (d, 3H, partially obscured), 0.80 (t, J = 7.6 Hz, 3H), 0.86 (d, J = 6.6 Hz, 3H), 0.90 (s, 3H), 0.90 (d, 3H, partially obscured), 1.14 (s, 3H), 1.20 (s, 3H), 1.22-1.56 (m), 1.63 (m, 1H), 1.72-1.97 (m), 2.13 (m, 1H), 2.19 (m, 1H), 2.46 (dd, J = 13.4 Hz, 6.5 Hz, 1H), 2.84 (s, 1H), 2.96 (d, J = 10.1 Hz, 1H), 3.47 (m, 2H), 3.52 (dd, J = 11.7 Hz, 1.6 Hz, 1H), 3.59 (d, J = 11.7 Hz, 1H), 3.93 (d, J = 11.8 Hz, 1H), 4.01 (d, J = 9.8 Hz, 1H), 5.43 (m, 1H), 6.20 (m, 1H), 8.07 (s, 1H).
Mass spectrum: (ESI) m/z = 718.50 (M + H).

| 125 | $R^I$ = Et<br>$R^{II}$ = Et<br>$R^{III}$ = Et | (1S,4aR,6aS,7R,8R,10aR,10bR,12aR,14R,15R)-15-(2-amino-2-ethylbutoxy)-8-[(1R)-1,2-dimethylpropyl]-14-[5-[(ethylamino)sulfonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 500 MHz, ppm) δ 0.61 (t, J = 7.6 Hz, 3H), 0.77 (s, 3H), 0.78 (d, 3H, partially obscured), 0.79 (t, J = 7.7 Hz, 3H), 0.86 (d, J = 6.8 Hz, 3H), 0.90 (s, 3H), 0.90 (d, 3H, partially obscured), 1.13 (s, 3H), 1.21 (s, 3H), 1.22 (t, J = 7.3 Hz, 3H), 1.22-1.36 (m), 1.40-1.56 (m), 1.63 (m, 1H), 1.74-1.97 (m), 2.12 (m, 1H), 2.19 (m, 1H), 2.43 (dd, J = 13.3 Hz, 6.4 Hz, 1), 2.84 (s, 1 h), 2.97 (d, J = 9.9 Hz, 1H), 3.25-3.33 (m, 2H, partially obscured), 3.47 (d, J = 12.1 Hz, 1H), 3.48 (d, J = 9.9 Hz, 1H), 3.52 (dd, J = 11.6 Hz, 2.1 Hz, 1H), 3.59 (d, J = 11.5 Hz, 1H), 3.93 (d, J = 12.0 Hz, 1H), 4.01 (d, J = 9.6 Hz, 1H), 5.43 (m, 1H), 6.20 (m, 1H), 8.08 (s, 1H). Mass spectrum: (ESI) m/z = 746.38 (M + H).

| 126 | $R^I$ = Et<br>$R^{II}$ = Et<br>$R^{III}$ = n-Pr | (1S,4aR,6aS,7R,8R,10aR,10bR,12aR,14R,15R)-15-(2-amino-2-ethylbutoxy)-8-[(1R)-1,2-dimethylpropyl]-14-[5-[(propylamino)sulfonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 500 MHz, ppm) δ 0.62 (t, J = 7.6 Hz, 1H), 0.77 (s, 3H), 0.78 (d, 3H, partially obscured), 0.80 (t, J = 7.6 H, 3H), 0.86 (d, J = 6.6 Hz, 3H), 0.90 (s, 3H), 0.91 (d, 3H, partially obscured), 0.97 (t, J = 7.4 Hz, 3H), 1.14 (s, 3H), 1.20 (s, 3H), 1.22-1.36 (m), 1.38-1.66 (m), 1.74-1.99 (m), 2.13 (m, 1H), 2.19 (m, 1H), 2.43 (dd, J = 13.5 Hz, 6.4 Hz, 1H), 2.85 (s, 1H), 2.97 (d, J = 10.1 Hz, 1H), 3.20 (m, 2H), 3.44-3.62 (m, 4H), 3.94 (d, J = 11.6 Hz, 1H), 4.02 (d, J = 9.6 Hz, 1H), 5.43 (m, 1H), 6.21 (m, 1H), 8.08 (s, 1H).
Mass spectrum: (ESI) m/z = 760.53 (M + H).

| 127 | $R^I$ = i-Pr<br>$R^{II}$ = Me<br>$R^{III}$ = H | (1S,4aR,6aS,7R,8R,10aR,10bR,12aR,14R,15R)-15-[[(2R)-2-amino-2,3-dimethylbutyl]oxy]-14-[5-(aminosulfonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 500 MHz, ppm) δ 0.77 (s, 3H), 0.78 (d, 3H, partially obscured), 0.82 (d, J = 6.8 Hz, 3H), 0.84 (s, 3H), 0.86 (d, 3H, partially obscured), 0.90 (s, 3H), 0.91 (d, 3H, partially obscured), 1.14 (s, 3H), 1.20 (s, 3H), 1.10-1.56 (m), 1.74-1.96 (m), 2.13 (m, 1H), 2.19 (m, 1H), 2.49 (dd, J = 13.3 Hz, 6.4 Hz, 1H), 2.84 (s, 1H), 2.95 (d, J = 9.8 Hz, 1H), 3.47 (d, J = 11.9 Hz, 1H), 3.50-3.56 (m, 2H), 3.60 (d, J = 11.7 Hz, 1H), 3.95 (d, J = 11.8 Hz, 1H), 4.03 (d, J = 9.6 Hz, 1H), 5.44 (m, 1H), 6.23 (m, 1H), 8.07 (s, 1H).
Mass spectrum: (ESI) m/z = 718.53 (M + H).

Example 128

(1S,4aR,6aS,7R,8R,10aR,10bR,12aR,14R,15R)-15-[[(2R)-2-amino-2,3-dimethylbutyl]oxy]-14-[5-(4,5-dihydro-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

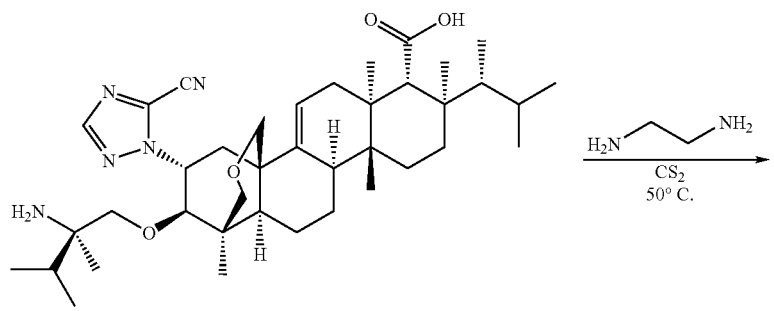

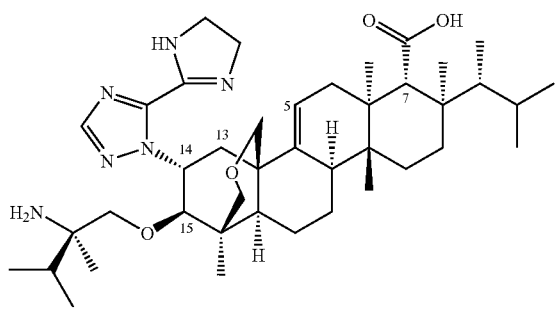

A solution of (1S,4aR,6aS,7R,8R,10aR,10bR,12aR,14R,15R)-15-[[(2R)-2-amino-2,3-dimethylbutyl]oxy]14-(5-cyano-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 5B, 18 mg, 0.027 mmol), 1,2-ethanediamine (0.7 mL, 17.0 mmol) and carbon disulfide (50 μL, 0.84 mmol) was blanketed with nitrogen and placed in a 50° C. oil bath for 18 hours. The mixture was cooled to room temperature, evaporated and the residual oil was purified by reverse phase HPLC using a 19×150 mm Sunfire Preparative C18 OBD column eluting with acetonitrile/water+0.1% TFA. Fractions were evaporated and freeze-dried from a mixture of ethanol and benzene to give the title compound as a TFA salt (8.2 mg).

$^1$H NMR (CD$_3$OD, 600 MHz, ppm) δ 0.76 (s, 3H, Me), 0.76 (d, 3H, Me), 0.80 (d, 3H, Me), 0.83 (s, 3H, Me), 0.85 (d, 3H, Me), 0.85 (d, 3H, Me), 0.87 (s, 3H, Me), 0.90 (s, 3H, Me), 1.14 (s, 3H, Me), 1.20 (s, 3H, Me), 1.22-1.34 (m), 1.40-1.44 (m), 1.48-1.56 (m), 1.59-1.65 (m), 1.74-1.99 (m), 2.11-2.21 (m), 2.64 (dd, 1H, H13), 2.68 (d, 1H), 2.84 (s, 1H, H7), 3.49 (d, 1H), 3.52 (d, 1H), 3.53 (dd, 1H), 3.69 (d, 1H), 3.92 (d, 1H), 3.95 (d, 1H), 4.20 (m), 5.53 (dd, 1H, H5), 5.78 (m, 1H, H14), 8.29 (s, 1H, triazole).

Mass spectrum: (ESI) m/z=707.76 (M+H).

Example 129

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(1,4,5,6-tetrahydro-2-pyrim-
idinyl)-1H-1,2,4-triazol-1-yl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid

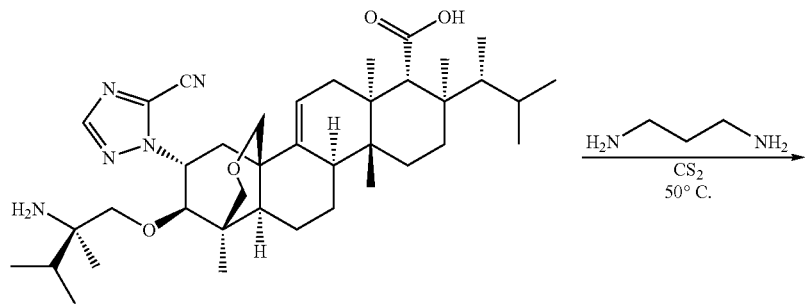

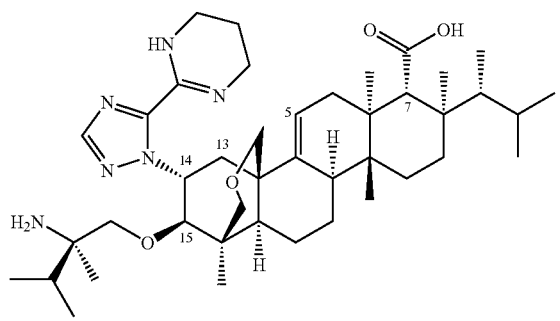

By a procedure analogous to that described in Example 128, but employing 1,3-propanediamine, the title compound was prepared and isolated as a white solid.

$^1$H NMR (CD$_3$OD, 600 MHz, ppm) δ 0.76 (s, 3H, Me), 0.77 (d, 3H, Me), 0.78 (s, 3H, Me), 0.85 (d, 3H, Me), 0.87 (s, 3H, Me), 0.88 (d, 3H, Me), 0.89 (d, 3H, Me), 0.93 (d, 3H, Me), 1.14 (br s, 3H, Me), 1.20 (br s, 3H, Me), 1.22-1.34 (m), 1.40-1.44 (m), 1.48-1.56 (m), 1.59-1.65 (m), 1.76-2.06 (m), 2.11-2.21 (m), 2.35 (dd, 1H, H13), 2.58 (d, 1H), 2.84 (br s, 1H, H7), 3.00 (m), 3.46 (m), 3.53 (m), 3.60 (d, 1H), 3.76 (d, 1H), 3.83 (d, 1H), 5.45 (dd, 1H, H5), 5.85 (m, 1H, H14), 8.03 (s, 1H, triazole).

Examples 130-136

The following compounds were prepared using methods analogous to those described in the preceding examples:

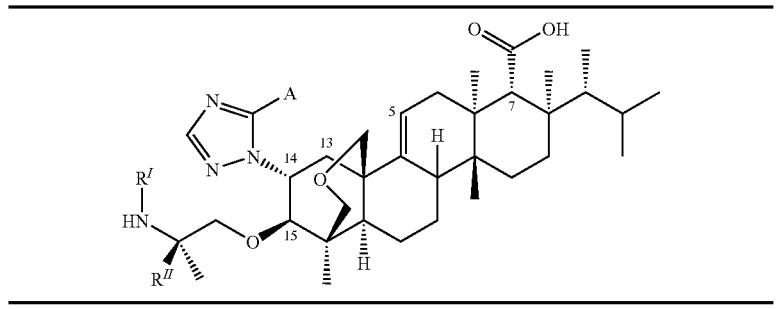

| 130 | $R^I$ = H<br>$R^{II}$ = i-Pr<br>A = ![imidazoline with N-methyl] | (1S,4aR,6aS,7R,8R,10aR,10bR,12aR,14R,15R)-15-[[(2R)-2-amino-2,3-dimethylbutyl]oxy]-14-[5-(4,5-dihydro-1-methyl-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.72 (s, 3H, Me), 0.76 (s, 3H, Me), 0.77 (d, 3H, Me), 0.85 (d, 3H, Me), 0.87 (d, 3H, Me), 0.88 (s, 3H, Me), 0.89 (d, 3H, Me), 0.92 (s, 3H, Me), 1.14 (s, 3H, Me), 1.20 (s, 3H, Me), 1.22-1.34 (m), 1.40-1.44 (m), 1.48-1.56 (m), 1.59-1.65 (m), 1.80-1.99 (m), 2.11-2.21 (m), 2.26 (dd, 1H, H13), 2.70 (d, 1H), 2.84 (s, 1H, H7), 2.88 (br s, 3H, NMe), 3.47 (d, 1H), 3.52 (dd, 1H), 3.56 (d, 1H), 3.62 (d, 1H), 3.65 (m), 3.87 (d, 1H), 3.95 (d, 1H), 5.46 (dd, 1H, H5), 5.79 (m, 1H, H14), 8.17 (s, 1H, triazole).
Mass spectrum: (ESI) m/z = 721.47 (M + H).

| 131 | $R^I$ = H<br>$R^{II}$ = i-Pr<br>A = ![imidazoline with N-ethyl] | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-ethyl-4,5-dihydro-1H-imidazol-2-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.78 (s, 3H, Me), 0.84 (d, 3H, Me), 0.85 (d, 3H, Me), 0.86 (d, 3H, Me), 0.89 (d, 3H, Me), 0.91 (s, 3H, Me), 1.13 (s, 3H, Me), 1.20 (s, 3H, Me), 1.22-1.34 (m), 1.37 (t, 3H, CH2CH3), 1.40-1.44 (m), 1.48-1.56 (m), 1.58-1.64 (m), 1.78-1.96 (m), 2.11-2.21(m), 2.50 (dd, 1H, H13), 2.83 (s, 1H, H7), 3.10 (d, 1H), 3.50 (d, 1H), 3.54 (dd, 1H), 3.58 (m), 3.62 (d, 1H), 3.63 (d, 1H), 3.65 (m), 3.69 (m), 3.90 (d, 1H), 4.11 (d, 1H), 4.18-4.30 (m), 5.52 (dd, 1H, H5), 5.79 (m, 1H, H14), 8.36 (s, 1H, triazole).
Mass spectrum: (ESI) m/z = 735.49 (M + H).

| 132 | $R^I$ = H<br>$R^{II}$ = i-Pr<br>A = ![imidazoline with N-isopropyl] | (1S,4aR,6aS,7R,8R,10aR,10bR,12aR,14R,15R)-15-[[(2R)-2-amino-2,3-dimethylbutyl]oxy]-14-[5-[4,5-dihydro-1-(1-methylethyl)-1H-imidazol-2-yl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.80 (s, 3H, Me), 0.85 (d, 3H, Me), 0.86 (d, 3H, Me), 0.86 (d, 3H, Me), 0.89 (d, 3H, Me), 0.91 (s, 3H, Me), 1.13 (s, 3H, Me), 1.20 (s, 3H, Me), 1.22-1.34 (m), 1.36 (dd, 3H, CH(CH3)2), 1.40-1.44 (m), 1.48-1.54 (m), 1.58-1.64 (m), 1.78-1.96 (m), 2.11-2.21 (m), 2.44 (dd, 1H, H13), 2.83 (s, 1H, H7), 3.23 (d, 1H), 3.50 (d, 1H), 3.55 (dd, 1H), 3.62 (d, 1H), 3.65 (d, 1H), 3.90 (d, 1H), 4.14 (d, 1H), 4.22-4.39 (m), 5.50 (dd, 1H, H5), 5.75 (m, 1H, H14), 8.36 (s, 1H, triazole).
Mass spectrum: (ESI) m/z = 749.54 (M + H).

-continued

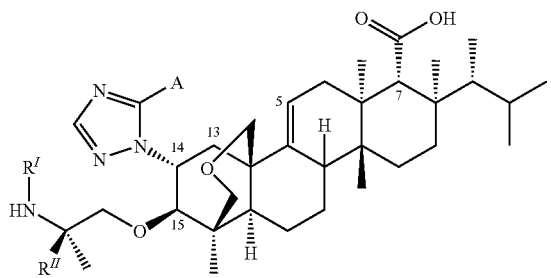

| 133 | $R^I$ = H<br>$R^{II}$ = i-Pr<br>A = | (1S,4aR,6aS,7R,8R,10aR,10bR,12aR,14R,15R)-15-[[(2R)-2-amino-2,3-dimethylbutyl]oxy]-14-[5-(4,5-dihydro-4,4-dimethyl-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (d, 3H, Me), 0.77 (d, 3H, Me), 0.80 (s, 3H, Me), 0.84 (d, 3H, Me), 0.85 (d, 3H, Me), 0.87 (s, 3H, Me), 0.88 (d, 3H, Me), 0.89 (d, 3H, Me), 1.14 (s, 3H, Me), 1.20 (s, 3H, Me), 1.22-1.34 (m), 1.40-1.44 (m), 1.41 (br m), 1.48-1.56 (m), 1.59-1.65 (m), 1.80-1.96 (m), 2.11-2.21 (m), 2.42 (dd, 1H, H13), 2.72 (br d, 1H), 2.84 (s, 1H, H7), 3.47 (d, 1H), 3.52 (d, 1H), 3.54 (d, 1H), 3.59 (d, 1H), 3.67 (br m), 3.89 (d, 1H), 3.91 (br d, 1H), 5.46 (dd, 1H, H5), 6.08 (br m, 1H, H14), 8.13 (s, 1H, triazole).
Mass spectrum: (ESI) m/z = 735.52 (M + H).

| 134 | $R^I$ = Me<br>$R^{II}$ = i-Pr<br>A = | (1S,4aR,6aS,7R,8R,10aR,10bR,12aR,14R,15R)-14-[5-(4,5-dihydro-1H-imidazol-2-yl)-1H-1,2,4-triazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.81 (d, 3H, Me), 0.85 (d, 3H, Me), 0.85 (d, 3H, Me), 0.89 (d, 3H, Me), 0.90 (s, 3H, Me), 1.14 (s, 3H, Me), 1.20 (s, 3H, Me), 1.22-1.34 (m), 1.40-1.44 (m), 1.48-1.56 (m), 1.59-1.65 (m), 1.82-1.99 (m), 2.11-2.21 (m), 2.46 (s, 3H, NMe), 2.60 (dd, 1H, H13), 2.84 (s, 1H, H7), 2.90 (d, 1H), 3.49 (d, 1H), 3.52 (dd, 1H), 3.67 (dd, 1H), 3.69 (d, 1H), 3.87 (d, 1H), 4.08 (d, 1H), 4.20 (m), 5.53 (dd, 1H, H5), 5.82 (m, 1H, H14), 8.31 (s, 1H, triazole).
Mass spectrum: (ESI) m/z = 721.47 (M + H).

| 135 | $R^I$ = H<br>$R^{II}$ = t-Bu<br>A = | (1S,4aR,6aS,7R,8R,10aR,10bR,12aR,14R,15R)-15-[[(2R)-2-amino-2,3,3-trimethylbutyl]oxy]-14-[5-(4,5-dihydro-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.78 (d, J = 6.9 Hz, 3H), 0.85 (s, 3H), 0.86 (d, 3H, partially obscured), 0.86 (s, 9H), 0.90 (s, 3H), 0.91 (d, 3H, partially obscured), 1.16 (s, 3H), 1.22 (s, 3H), 1.23-1.67 (m), 1.82-2.06 (m), 2.13-2.23 (m, 2H), 2.64 (d, J = 9.8 Hz, 1H), 2.69 (dd, J = 13.5 Hz, 6.4 Hz, 1H), 2.85 (s, 1H), 3.50-3.58 (m, 2H), 3.66 (d, J = 10.3 Hz, 1H), 3.73 (d, J = 11.2 Hz, 1H), 3.94 (d, J = 12.2 Hz, 1H), 3.97 (d, J = 9.8 Hz, 1H), 4.15-4.23 (m, 4H), 5.55 (m, 1H), 5.80 (m, 1H), 8.32 (s, 1H).
Mass spectrum: (ESI) m/z = 721.48 (M + H).

| 136 | $R^I$ = Me<br>$R^{II}$ = t-Bu<br>A = | (1S,4aR,6aS,7R,8R,10aR,10bR,12aR,14R,15R)-8-[(1R)-1,2-dimethylpropyl]-14-[5-(1,4,5,6-tetrahydro-2-pyrimidinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (d, 3H, partially obscured), 0.81 (s, 3H), 0.86 (d, J = 6.6 Hz, 3H), 0.90 (d, J = 6.8 Hz, 3H), 0.93 (s, 9H), 0.95 (s, 3H), 1.14 (s, 3H), 1.21 (s, 3H), 1.23-1.67 (m), 1.83-1.98 (m), 2.12-2.23 (m), 2.65 (dd, 1H, partially

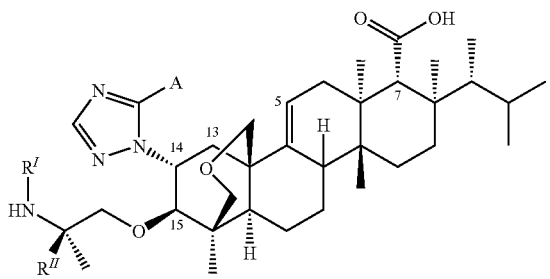

obscured), 2.66 (s, 3H), 2.85 (s, 1H), 3.23 (d, J = 11.2 Hz, 1H), 3.54-3.59 (m, 2H), 3.65 (d, J = 11.7 Hz, 1H), 3.68-3.77 (m, 5H), 3.90 (d, J = 11.2 Hz, 1H), 4.07 (d, J = 9.6 Hz, 1H), 5.55 (m, 1H), 5.75 (m, 1H), 8.26 (s, 1H).
Mass spectrum: (ESI) m/z = 749.63 (M + H).

Example 137

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-pyrrolidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

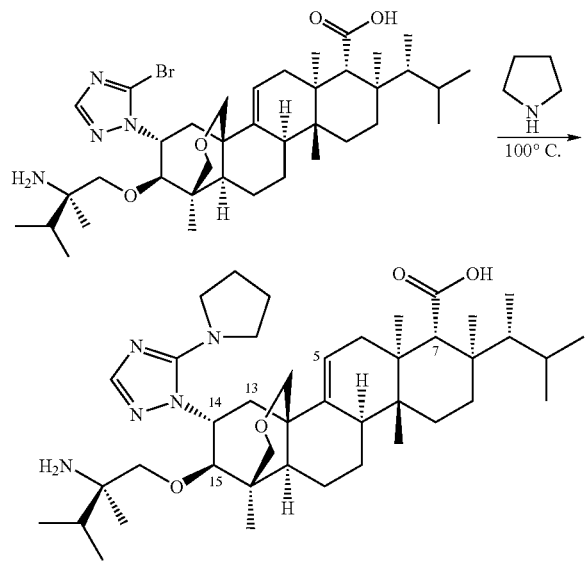

A solution of (1S,4aR,6aS,7R,8R,10aR,10bR,12aR,14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 6B, 6 mg, 0.0084 mmol) and pyrrolidine (200 mg, 1.35 mmol) was blanketed with nitrogen and placed in a 100° C. oil bath for 18 hours. The mixture was cooled to room temperature, evaporated and the residual oil was purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (3.3 mg).

$^1$H NMR (CD$_3$OD, 600 MHz, ppm) δ 0.75 (s, 3H, Me), 0.76 (d, 3H, Me), 0.85 (d, 3H, Me), 0.86 (d, 3H, Me), 0.87 (d, 3H, Me), 1.10 (s, 3H, Me), 1.15 (s, 3H, Me), 1.20 (s, 3H, Me), 1.22-1.34 (m), 1.40-1.44 (m), 1.48-1.65 (m), 1.75-1.98 (m), 2.03-2.15 (m), 2.16-2.21 (m), 2.43 (dd, 1H, H13), 2.84 (s, 1H, H7), 2.98 (d, 1H), 3.48 (d, 1H), 3.54 (dd, 1H), 3.54 (d, 1H), 3.60 (d, 1H), 3.63 (m), 3.72 (m), 3.80 (d, 1H), 3.91 (d, 1H), 5.54 (dd, 1H, H5), 5.86 (m, 1H, H14), 8.14 (s, 1H, triazole).
Mass spectrum: (ESI) m/z=708.46 (M+H).

Example 138

(1S,4aR,6aS,7R,8R,10aR,10bR,12aR,14R,15R)-15-[[(2R)-2-amino-2,3-dimethylbutyl]oxy]-14-[1,5'-bi-1H-1,2,4-triazol]-1'-yl-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

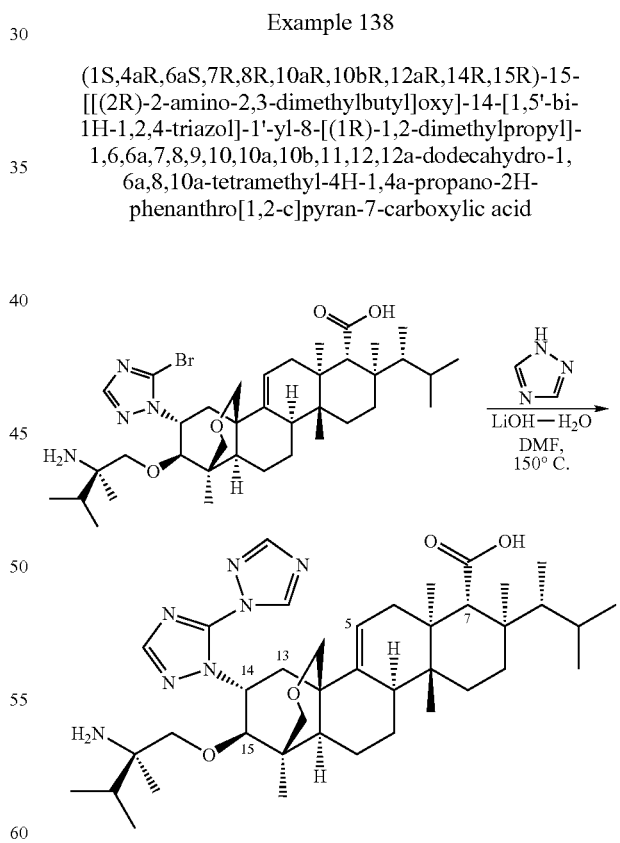

A solution of (1S,4aR,6aS,7R,8R,10aR,10bR,12aR,14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 6B, 9.4 mg, 0.013 mmol), 1H-1, 2,4-triazole (28 mg, 0.41 mmol) and lithium hydroxide hydrate (15.9 mg, 0.38 mmol) in DMF (0.2 mL) was blanketed with nitrogen and placed in a 150° C. oil bath for 12 hours. The mixture was cooled to room temperature and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (1.5 mg).

$^1$H NMR (CD$_3$OD, 600 MHz, ppm) δ 0.76 (s, 3H, Me), 0.76 (d, 3H, Me), 0.77 (s, 3H, Me), 0.82 (d, 3H, Me), 0.85 (d, 3H, Me), 0.85 (d, 3H, Me), 0.88 (s, 3H, Me), 0.89 (d, 3H, Me), 1.14 (s, 3H, Me), 1.20 (s, 3H, Me), 1.22-1.34 (m), 1.40-1.44 (m), 1.48-1.65 (m), 1.77-1.95 (m), 2.11-2.21 (m), 2.51 (dd, 1H, H13), 2.83 (s, 1H, H7), 3.03 (d, 1H), 3.46 (d, 1H), 3.52 (dd, 1H), 3.56 (d, 1H), 3.57 (d, 1H), 3.86 (d, 1H), 4.02 (d, 1H), 5.46 (dd, 1H, H5), 6.22 (m, 1H, H14), 8.07 (s, 1H, triazole), 8.36 (s, 1H, triazole) and 9.19 (s, 1H, triazole).

Example 139

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethylthio)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

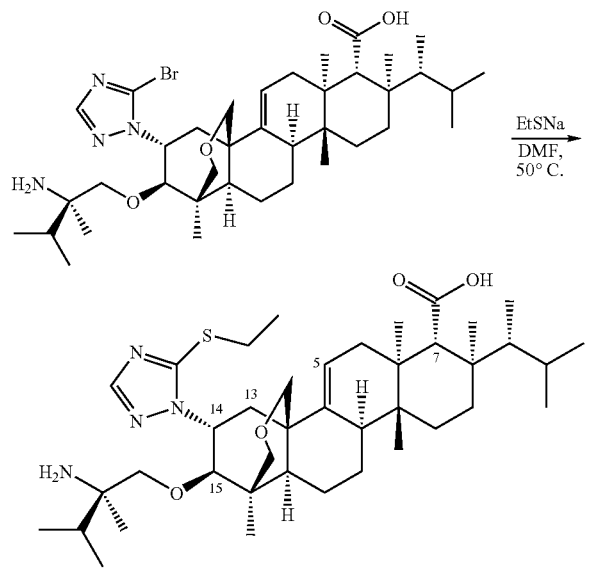

A solution of (1S,4aR,6aS,7R,8R,10aR,10bR,12aR,14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 6B, 8.5 mg, 0.012 mmol) and sodium ethane thiolate (18 mg, 0.214 mmol) in DMF (0.3 mL) was blanketed with nitrogen and placed in a 50° C. oil bath for 18 hours. The mixture was cooled to room temperature, evaporated and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (5.8 mg).

$^1$H NMR (CD$_3$OD, 600 MHz, ppm) δ 0.76 (s, 3H, Me), 0.76 (d, 3H, Me), 0.79 (d, 3H, Me), 0.84 (d, 3H, Me), 0.85 (d, 3H, Me), 0.87 (s, 3H, Me), 0.89 (d, 3H, Me), 0.92 (s, 3H, Me), 1.14 (s, 3H, Me), 1.20 (s, 3H, Me), 1.22-1.34 (m), 1.38 (t, SCH$_2$CH$_3$), 1.40-1.44 (m), 1.48-1.65 (m), 1.72-1.96 (m), 2.10-2.21 (m), 2.24 (dd, 1H, H13), 2.84 (s, 1H, H7), 2.90 (d, 1H), 3.19-3.27 (m), 3.45 (d, 1H), 3.48 (d, 1H), 3.54 (dd, 1H), 3.58 (d, 1H), 3.85 (d, 1H), 3.94 (d, 1H), 5.45 (dd, 1H, H5), 5.53 (m, 1H, H14), 7.99 (s, 1H, triazole).

Mass spectrum: (ESI) m/z=699.50 (M+H).

Example 140

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethylsulfonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

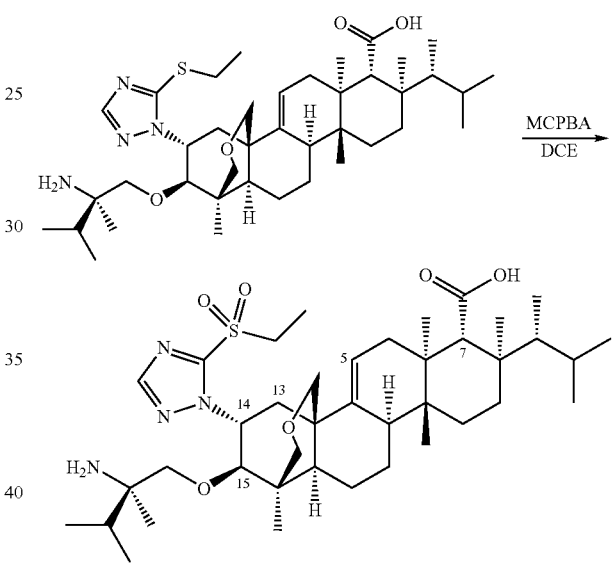

A solution of (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethylthio)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 139, 9.9 mg, 0.014 mmol) and approx. 90% pure meta chloroperbenzoic acid (9.5 mg, 0.05 mmol) was blanketed with nitrogen and stirred at room temperature for 1.5 hours. The mixture was evaporated and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (6.4 mg).

$^1$H NMR (CD$_3$OD, 600 MHz, ppm) δ 0.76 (s, 3H, Me), 0.76 (d, 3H, Me), 0.81 (d, 3H, Me), 0.84 (s, 3H, Me), 0.84 (d, 3H, Me), 0.85 (d, 3H, Me), 0.89 (s, 3H, Me), 0.89 (d, 3H, Me), 1.13 (s, 3H, Me), 1.20 (s, 3H, Me), 1.22-1.34 (m), 1.41 (t, SCH2CH3), 1.40-1.44 (m), 1.48-1.65 (m), 1.77-1.96 (m), 2.10-2.21 (m), 2.45 (dd, 1H, H13), 2.84 (s, 1H, H7), 2.95 (d, 1H), 3.48 (d, 1H), 3.53 (dd, 1H), 3.56 (d, 1H), 3.63 (m), 3.70 (m), 3.94 (d, 1H), 4.04 (d, 1H), 5.44 (dd, 1H, H5), 6.33 (m, 1H, H14), 8.17 (s, 1H, triazole).

Mass spectrum: (ESI) m/z=731.41 (M+H).

Example 141

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-phenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

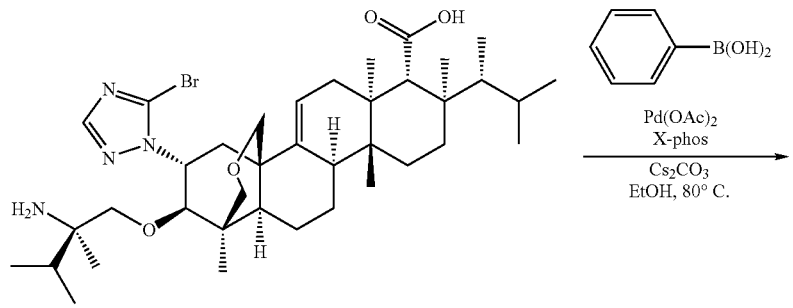

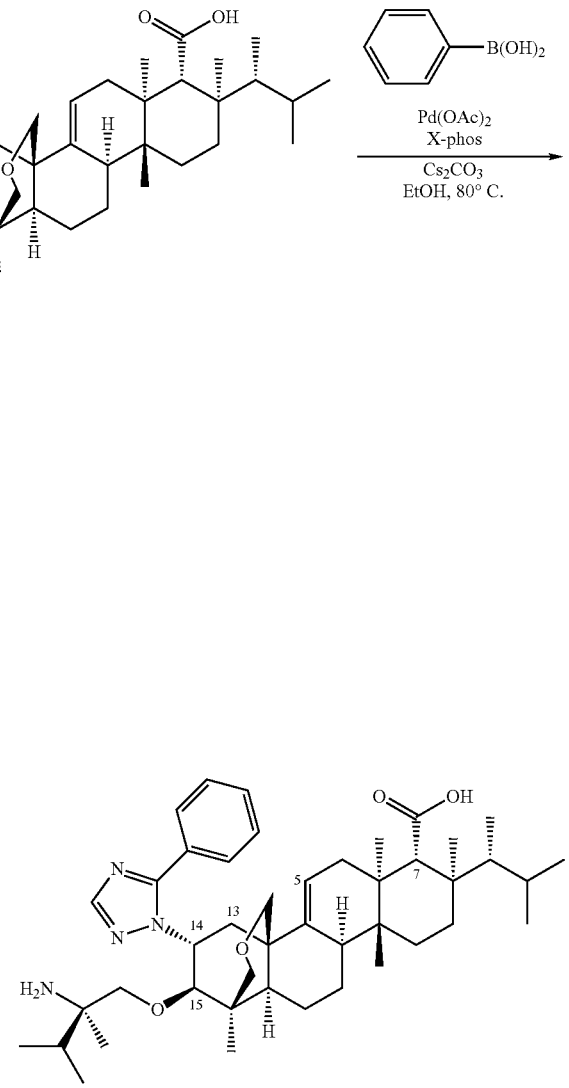

A suspension of (1S,4aR,6aS,7R,8R,10aR,10bR,12aR,14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 6B, 64 mg, 0.089 mmol), cesium carbonate (680 mg, 2.09 mmol), phenyl boronic acid (139.7 mg, 1.15 mmol), palladium (II) acetate (11 mg, 0.05 mmol) and 2-dicyclohexylphosphino-2',4',6'-triisopropylbiphenyl (11.3 mg, 0.024 mmol) in ethanol (2.3 mL) was blanketed with nitrogen and placed in a 80° C. oil bath for 2 hours. The mixture was cooled to room temperature, filtered and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (22.6 mg).

$^1$H NMR (CD$_3$OD, 600 MHz, ppm) δ 0.77 (s, 3H, Me), 0.77 (d, 3H, Me), 0.80 (s, 3H, Me), 0.80 (d, 3H, Me), 0.83 (d, 3H, Me), 0.85 (s, 3H, Me), 0.85 (d, 3H, Me), 0.90 (d, 3H, Me), 1.17 (s, 3H, Me), 1.21 (s, 3H, Me), 1.23-1.34 (m), 1.40-1.44 (m), 1.48-1.65 (m), 1.71 (m), 1.82-1.98 (m), 2.04-2.09 (m), 2.13-2.21 (m), 2.52 (dd, 1H, H13), 2.85 (s, 1H, H7), 2.90 (d, 1H), 3.42 (d, 1H), 3.46 (d, 1H), 3.53 (dd, 1H), 3.59 (d, 1H), 3.79 (d, 1H), 3.98 (d, 1H), 5.58 (dd, 1H, H5), 5.89 (m, 1H, H14), 7.58 (br d, ArH), 7.74 (br d, ArH) and 8.14 (br s, 1H, triazole).

Mass spectrum: (ESI) m/z=715.48 (M+H).

Example 142

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-(5-phenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

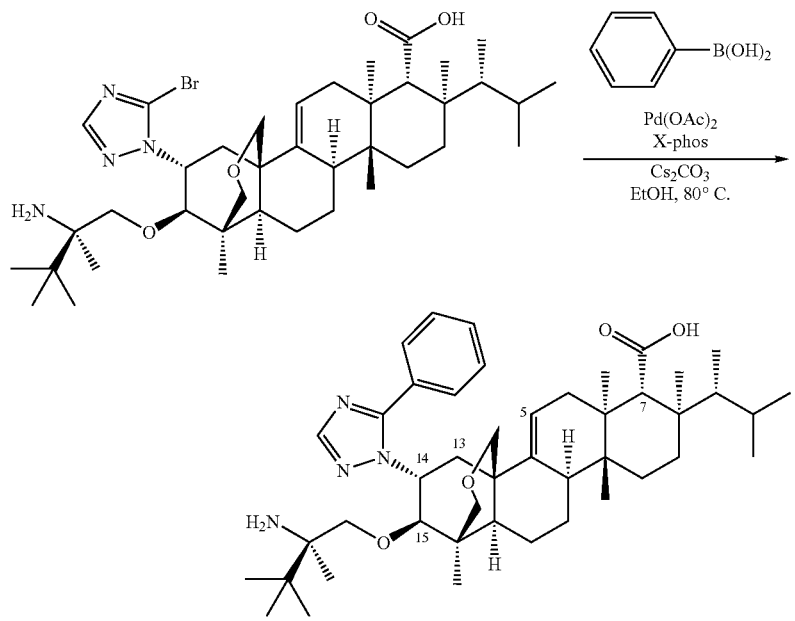

By a procedure analogous to that described for Example 141, but starting with (1S,4aR,6aS,7R,8R,10aR,10bR,12aR,14R,15R)-15-[[(2R)-2-amino-2,3,3-trimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 11), the title compound was prepared and isolated as a white solid.

$^1$H NMR (CD$_3$OD, 500 MHz, ppm) δ 0.78 (d, 3H, partially obscured), 0.78 (s, 3H), 0.80 (s, 3H), 0.86 (s, 9H), 0.87 (d, 3H, partially obscured), 0.87 (s, 3H), 0.91 (d, J=6.9 Hz, 3H), 1.19 (s, 3H), 1.22 (s, 3H), 1.23-1.67 (m), 1.82-2.0 (m), 2.09 (m, 1H), 2.15-2.24 (m, 2H), 2.57 (dd, J=13.8 Hz, 6.0 Hz, 1H), 2.86 (s, 1H), 2.91 (d, J=9.9 Hz, 1H), 3.43 (d, J=11.9 Hz, 1H), 3.55 (dd, J=11.6 Hz, 1.8 Hz, 1H), 3.63 (d, 1H, partially obscured), 3.64 (d, 1H, partially obscured), 3.81 (d, J=12.2 Hz, 1H), 4.01 (d, J=9.9 Hz, 1H), 5.61 (m, 1H), 5.90 (m, 1H), 7.58 (m, 3H), 7.74 (m, 2H), 8.11 (s, 1H).

Mass spectrum: (ESI) m/z=729.66 (M+H).

Example 143

(1S,4aR,6aS,7R,8R,10aR,10bR,12aR,14R,15R)-8-[(1R)-1,2-dimethylpropyl]-14-(5-phenyl-1H-1,2,4-triazol-1-yl)-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

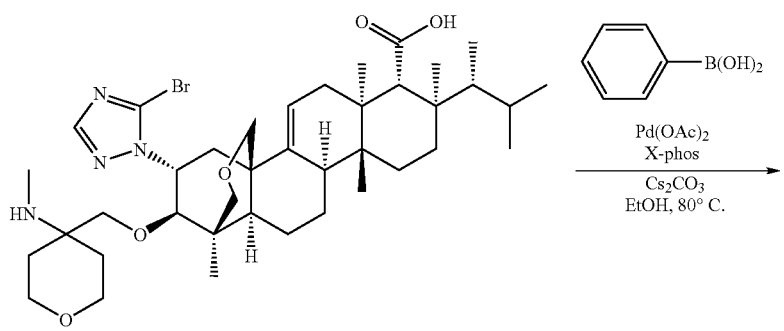

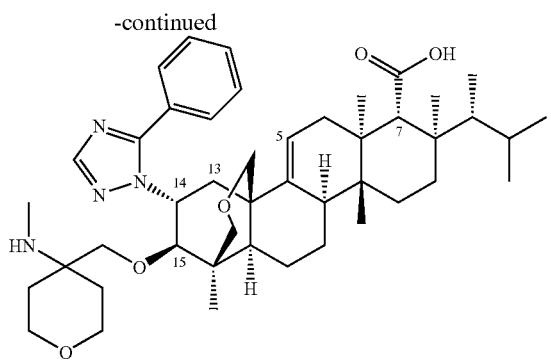

By a procedure analogous to that described for Example 141, but starting with (1S,4aR,6aS,7R,8R,10aR,10bR,12aR,14R,15R)-14-(5-bromo-1H-1,2,4-triazol-1-yl)-8-[(1R)-1,2-dimethylpropyl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 13), the title compound was prepared and isolated as a white solid.

$^1$H NMR (CD$_3$OD, 500 MHz, ppm) δ 0.78 (s, 3H), 0.79 (d, 3H, partially obscured), 0.87 (d, J=6.7 Hz, 3H), 0.90 (s, 3H), 0.91 (d, 3H, partially obscured), 1.19 (s, 3H), 1.23 (s, 3H), 1.24-1.78 (m), 1.82-2.06 (m), 2.14-2.24 (m, 2H), 2.39 (s, 3H), 2.51 (dd, J=13.5, 6.0 Hz, 1H), 2.86 (s, 1H), 2.91 (m, 1H), 3.30-3.36 (m, partially obscured), 3.43 (d, J=11.2 Hz, 1H), 3.47 (d, J=12.4 Hz, 1H), 3.55 (m, 1H), 3.61 (d, J=11.7 Hz, 1H), 3.66 (m, 1H), 3.75-3.82 (m, 3H), 4.18 (d, J=9.6 Hz, 1H), 5.58 (m, 1H), 5.91 (m, 1H), 7.58-7.65 (m, 3H), 7.75 (m, 2H), 8.18 (s, 1H).

Mass spectrum: (ESI) m/z=743.62 (M+H).

Example 144

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-furanyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

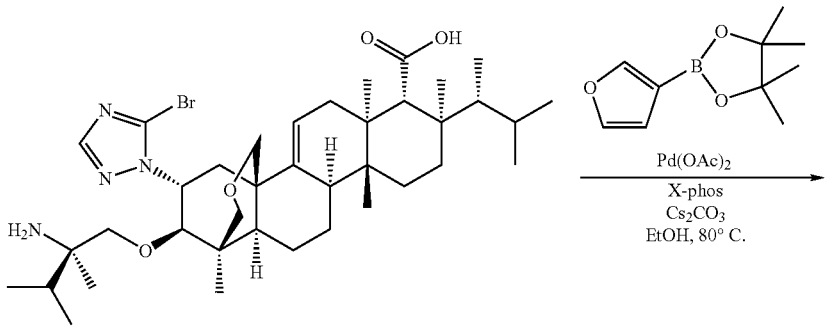

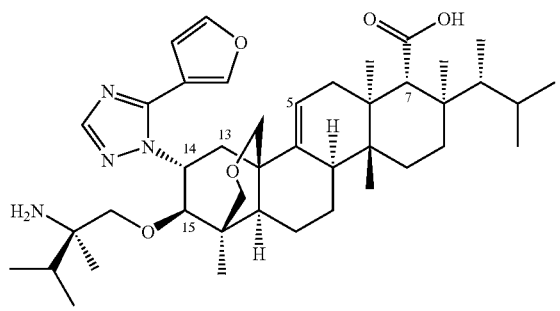

A suspension of (1S,4aR,6aS,7R,8R,10aR,10bR,12aR, 14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a, 8,10a-tetramethyl-4H-1,4a-propano-2H-phenanthro[1,2-c]pyran-7-carboxylic acid (Example 6B, 7.8 mg, 0.011 mmol), cesium carbonate (139 mg, 0.427 mmol), 3-(4,4,5,5-tetramethyl-1,3,2-dioxaborolan-2-yl)furan (24 mg, 0.124 mmol), palladium (II) acetate (3.5 mg, 0.016 mmol) and 2-dicyclohexylphosphino-2',4',6'-triisopropylbiphenyl (2.2 mg, 0.005 mmol) in ethanol (0.2 mL) and water (0.1 mL) was blanketed with nitrogen and placed in a 80° C. oil bath for 2.5 hours. The mixture was cooled to room temperature, filtered and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (2.0 mg)

$^1$H NMR (CD$_3$OD, 600 MHz, ppm) δ 0.76 (s, 3H, Me), 0.77 (d, 3H, Me), 0.77 (s, 3H, Me), 0.78 (d, 3H, Me), 0.80 (d, 3H, Me), 0.86 (d, 3H, Me), 0.87 (s, 3H, Me), 0.89 (d, 3H, Me), 1.16 (s, 3H, Me), 1.21 (s, 3H, Me), 1.23-1.34 (m), 1.40-1.44 (m), 1.48-1.72 (m), 1.82-2.02 (m), 2.12-2.21 (m), 2.41 (dd, 1H, H13), 2.84 (s, 1H, H7), 2.86 (d, 1H), 3.46 (d, 1H), 3.50 (d, 1H), 3.57 (dd, 1H), 3.68 (d, 1H), 3.91 (d, 1H), 3.93 (d, 1H), 5.53 (dd, 1H, H5), 5.90 (m, 1H, H14), 6.91 (d, furan), 7.74 (dd, furan), 8.07 (br s) and 8.13 (br s, 1H).

Mass spectrum: (ESI) m/z=705.42 (M+H).

Example 145

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-ethenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

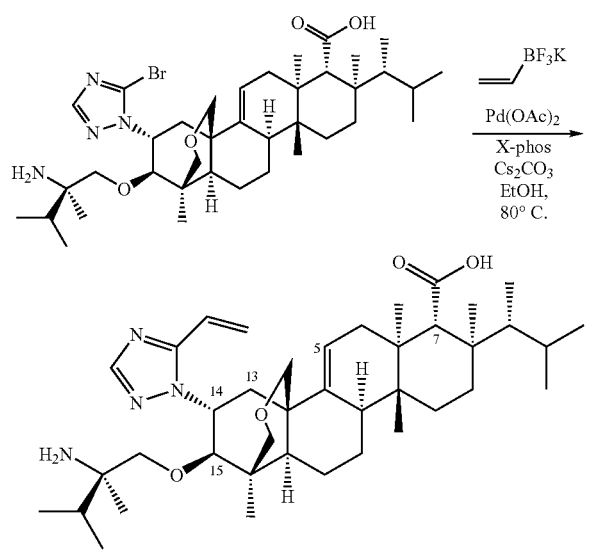

A suspension of (1S,4aR,6aS,7R,8R,10aR,10bR,12aR, 14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a, 8,10a-tetramethyl-4H-1,4a-propano-2H-phenanthro[1,2-c]pyran-7-carboxylic acid (Example 6B, 9.4 mg, 0.013 mmol), cesium carbonate (134 mg, 0.411 mmol), potassium vinyltrifluoroborate (23.5 mg, 0.175 mmol), palladium (II) acetate (3.0 mg, 0.013 mmol) and 2-dicyclohexylphosphino-2',4',6'-triisopropylbiphenyl (2.2 mg, 0.005 mmol) in ethanol (0.2 mL) and water (0.1 mL) was blanketed with nitrogen and placed in a 80° C. oil bath for 6 hours. The mixture was cooled to room temperature, filtered and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (5.2 mg).

$^1$H NMR (CD$_3$OD, 600 MHz, ppm) δ 0.78 (s, 3H, Me), 0.78 (d, 3H, Me), 0.79 (d, 3H, Me), 0.83 (d, 3H, Me), 0.87 (s, 3H, Me), 0.87 (d, 3H, Me), 0.89 (s, 3H, Me), 0.92 (d, 3H, Me), 1.17 (s, 3H, Me), 1.22 (s, 3H, Me), 1.24-1.36 (m), 1.42-1.46 (m), 1.48-1.67 (m), 1.74 (m), 1.80-1.98 (m), 2.12-2.24 (m), 2.34 (dd, 1H, H13), 2.77 (d, 1H), 2.86 (s, 1H, H7), 2.90 (d, 1H), 3.47 (d, 1H), 3.52 (d, 1H), 3.57 (dd, 1H), 3.65 (d, 1H), 3.88 (d, 1H), 3.96 (d, 1H), 5.50 (dd, 1H, H5), 5.64 (m, 1H, H14), 5.80 (d, 1H, vinyl), 6.37 (d, 1H, vinyl), 6.90 (dd, 1H, vinyl) and 8.03 (br s, 1H, triazole).

Mass spectrum: (ESI) m/z=665.61 (M+H).

Example 146

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-ethyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

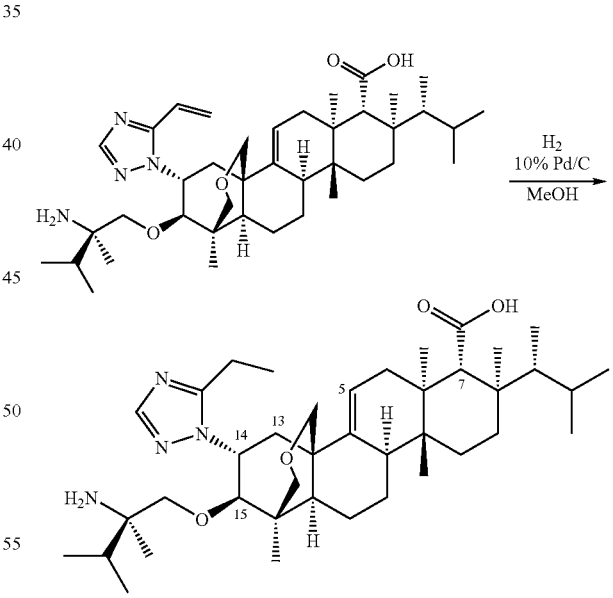

A suspension of (1S,4aR,6aS,7R,8R,10aR,10bR,12aR, 14R,15R)-15-[[(2R)-2-amino-2,3-dimethylbutyl]oxy]-8-[(1R)-1,2-dimethylpropyl]-14-(5-ethenyl-1H-1,2,4-triazol-1-yl)-1,6,6a,7,8,9,10,10a,10b,11,12,12a-dodecahydro-1,6a, 8,10a-tetramethyl-4H-1,4a-propano-2H-phenanthro[1,2-c]pyran-7-carboxylic acid (Example 145, 5.0 mg, 0.008 mmol) and 10% Pd/C (5 mg) in methanol (1.0 mL) was stirred rapidly under a balloon of hydrogen for 5 hours. The mixture was filtered and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound as a TFA salt (4.6 mg).

$^1$H NMR (CD$_3$OD, 600 MHz, ppm) δ 0.76 (s, 3H, Me), 0.76 (d, 3H, Me), 0.79 (d, 3H, Me), 0.82 (d, 3H, Me), 0.85 (d, 3H, Me), 0.85 (s, 3H, Me), 0.87 (s, 3H, Me), 0.89 (d, 3H, Me), 1.14 (s, 3H, Me), 1.20 (s, 3H, Me), 1.22-1.35 (m), 1.35 (t, 3H, Me), 1.40-1.44 (m), 1.48-1.65 (m), 1.70-1.96 (m), 2.12-2.21 (m), 2.29 (dd, 1H, H13), 2.81 (d, 1H), 2.84 (s, 1H, H7), 2.87 (m), 3.44 (d, 1H), 3.50 (d, 1H), 3.56 (dd, 1H), 3.61 (d, 1H), 3.86 (d, 1H), 3.92 (d, 1H), 5.48 (dd, 1H, H5), 5.48 (m, 1H, H14) and 7.92 (br s, 1H, triazole).

Mass spectrum: (ESI) m/z=667.42 (M+H).

Examples 147-172

The following compounds were prepared using methods analogous to those described in the preceding examples:

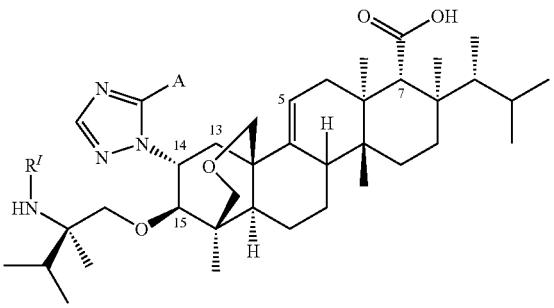

| 147 | $R^1$ = H<br>A = 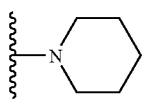 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.80 (d, 3H, Me), 0.85 (s, 3H, Me), 0.85 (d, 3H, Me), 0.86 (d, 3H, Me), 0.89 (d, 3H, Me), 0.98 (s, 3H, Me), 1.15 (s, 3H, Me), 1.20 (s, 3H, Me), 1.22-1.34 (m), 1.40-1.44 (m), 1.48-1.96 (m), 2.12-2.21 (m), 2.32 (dd, 1H, H13), 2.83 (d, 1H), 2.84 (s, 1H, H7), 3.13 (m), 3.24 (m), 3.40 (d, 1H), 3.48 (d, 1H), 3.56 (m), 3.95 (d, 1H), 5.47 (m, 1H, H14), 5.51 (dd, 1H, H5), 7.82 (s, 1H, triazole).
Mass spectrum: (ESI) m/z = 722.51 (M + H).

| 148 | $R^1$ = H<br>A = 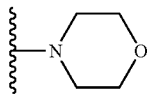 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-morpholinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.80 (d, 3H, Me), 0.84 (d, 3H, Me), 0.85 (s, 3H, Me), 0.85 (d, 3H, Me), 0.89 (d, 3H, Me), 0.95 (s, 3H, Me), 1.15 (s, 3H, Me), 1.20 (s, 3H, Me), 1.22-1.34 (m), 1.40-1.44 (m), 1.48-1.96 (m), 2.12-2.21 (m), 2.31 (dd, 1H, H13), 2.82 (d, 1H), 2.84 (s, 1H, H7), 3.10 (m), 3.40 (d, 1H), 3.48 (d, 1H), 3.55 (dd, 1H), 3.59 (d, 1H), 3.78 (m), 3.83 (m), 3.94 (d, 1H), 5.46 (m, 1H, H14), 5.53 (dd, 1H, H5), 7.76 (s, 1H, triazole).
Mass spectrum: (ESI) m/z = 724.55 (M + H).

| 149 | $R^1$ = Me<br>A = 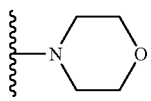 | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(1-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.81 (d, 3H, Me), 0.85 (d, 3H, Me), 0.86 (d, 3H, Me), 0.87 (s, 3H, Me), 0.89 (s, 3H, Me), 0.89 (d, 3H, Me), 1.15 (s, 3H, Me), 1.20 (s, 3H, Me), 1.22-1.34 (m), 1.40-1.44 (m), 1.48-1.65 (m), 1.78-2.01 (m), 2.12-2.21 (m), 2.32 (dd, 1H, H13), 2.84 (s, 1H, H7), 2.85 (d, 1H), 3.09 (m), 3.49 (d, 1H), 3.53 (d, 1H), 3.48 (d, 1H), 3.55 (dd, 1H), 3.59 (d, 1H), 3.77 (m), 3.84 (m), 3.86 (d, 1H), 3.91 (d, 1H), 5.46 (m, 1H, H14), 5.52 (dd, 1H, H5), 7.78 (s, 1H, triazole).
Mass spectrum: (ESI) m/z = 738.48 (M + H).

-continued

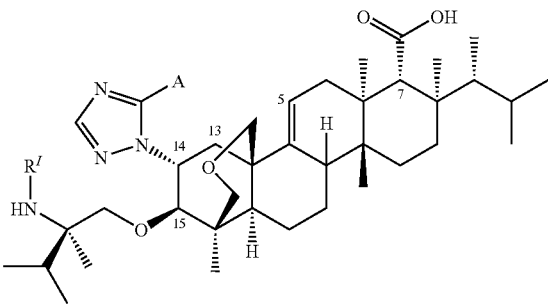

| 150 | $R^I$ = Me<br>A = 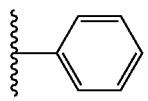 | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-(5-phenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.77 (s, 3H, Me), 0.81 (d, 3H, Me), 0.84 (d, 3H, Me), 0.85 (d, 3H, Me), 0.86 (s, 3H, Me), 0.90 (d, 3H, Me), 1.18 (s, 3H, Me), 1.21 (s, 3H, Me), 1.23-1.34 (m), 1.40-1.44 (m), 1.48-1.65 (m), 1.71 (m), 1.82-1.98 (m), 2.02-2.08 (m), 2.14-2.22 (m), 2.34 (s, 3H, NMe), 2.56 (dd, 1H, H13), 2.85 (s, 1H, H7), 2.97 (d, 1H), 3.43 (d, 1H), 3.54 (dd, 1H), 3.62 (d, 1H), 3.75 (d, 1H), 4.06 (d, 1H), 5.60 (dd, 1H, H5), 5.88 (m, 1H, H14), 7.59 (br d, ArH), 7.74 (m, ArH) and 8.12 (br s, 1H, triazole).

| 151 | $R^I$ = H<br>A = 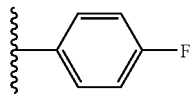 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H, Me), 0.77 (d, 3H, Me), 0.80 (s, 3H, Me), 0.80 (d, 3H, Me), 0.83 (d, 3H, Me), 0.85 (s, 3H, Me), 0.85 (d, 3H, Me), 0.90 (d, 3H, Me), 1.17 (s, 3H, Me), 1.21 (s, 3H, Me), 1.23-1.34 (m), 1.40-1.44 (m), 1.48-1.65 (m), 1.71 (m), 1.82-1.97 (m), 2.03-2.08 (m), 2.13-2.21 (m), 2.51 (dd, 1H, H13), 2.85 (s, 1H, H7), 2.89 (d, 1H), 3.43 (d, 1H), 3.46 (d, 1H), 3.53 (dd, 1H), 3.61 (d, 1H), 3.80 (d, 1H), 3.97 (d, 1H), 5.58 (dd, 1H, H5), 5.83 (m, 1H, H14), 7.34 (dd, ArH), 7.78 (dd, ArH) and 8.11 (br s, 1H, triazole).
Mass spectrum: (ESI) m/z = 733.50 (M + H).

| 152 | $R^I$ = H<br>A = 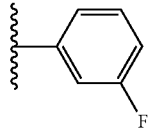 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H, Me), 0.77 (d, 3H, Me), 0.80 (s, 3H, Me), 0.80 (d, 3H, Me), 0.83 (d, 3H, Me), 0.85 (s, 3H, Me), 0.85 (d, 3H, Me), 0.90 (d, 3H, Me), 1.17 (s, 3H, Me), 1.21 (s, 3H, Me), 1.23-1.34 (m), 1.40-1.44 (m), 1.48-1.65 (m), 1.71 (m), 1.82-1.97 (m), 2.03-2.08 (m), 2.13-2.21 (m), 2.52 (dd, 1H, H13), 2.85 (s, 1H, H7), 2.89 (d, 1H), 3.44 (d, 1H), 3.47 (d, 1H), 3.54 (dd, 1H), 3.59 (d, 1H), 3.81 (d, 1H), 3.98 (d, 1H), 5.58 (dd, 1H, H5), 5.88 (m, 1H, H14), 7.33 (m, ArH), 7.49 (m, ArH), 7.57 (m, ArH), 7.62 (m, ArH) and 8.11 (s, 1H, triazole).
Mass spectrum: (ESI) m/z = 733.50 (M + H).

| 153 | $R^I$ = H<br>A = 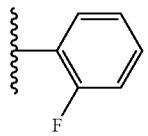 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.82 (s, 3H, Me), 0.84 (d, 3H, Me), 0.84 (d, 3H, Me), 0.86 (s, 3H, Me), 0.86 (d, 3H, Me), 0.90 (d, 3H, Me), 1.17 (s, 3H, Me), 1.21 (s, 3H, Me), 1.20-1.34 (m), 1.40-1.44 (m), 1.48-1.65 (m), 1.73 (m), 1.80-2.01 (m), 2.12-2.21 (m), 2.50 (dd, 1H, H13), 2.84 (s, 1H, H7), 2.92 (d, 1H), 3.40 (d, 1H), 3.45 (d, -continued

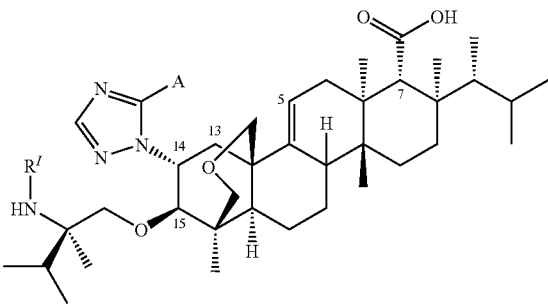

1H), 3.50 (s, 3H, OMe), 3.51 (d, 1H), 3.76 (d, 1H), 3.96 (d, 1H), 5.49 (dd, 1H, H5), 5.56 (m, 1H, H14), 7.37 (m, ArH), 7.41 (m, ArH), 7.64 (m, ArH) and 8.18 (s, 1H, triazole).
Mass spectrum: (ESI) m/z = 733.50 (M + H).

| 154 | $R^I$ = H<br>A = 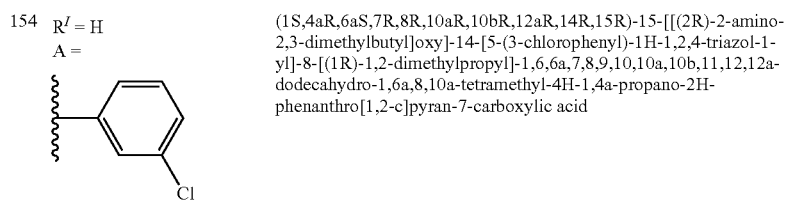 | (1S,4aR,6aS,7R,8R,10aR,10bR,12aR,14R,15R)-15-[[(2R)-2-amino-2,3-dimethylbutyl]oxy]-14-[5-(3-chlorophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H, Me), 0.77 (d, 3H, Me), 0.80 (s, 3H, Me), 0.80 (d, 3H, Me), 0.83 (d, 3H, Me), 0.85 (s, 3H, Me), 0.85 (d, 3H, Me), 0.90 (d, 3H, Me), 1.18 (s, 3H, Me), 1.21 (s, 3H, Me), 1.23-1.34 (m), 1.40-1.44 (m), 1.48-1.65 (m), 1.71 (m), 1.82-1.98 (m), 2.04-2.10 (m), 2.14-2.21 (m), 2.54 (dd, 1H, H13), 2.84 (s, 1H, H7), 2.89 (d, 1H), 3.44 (d, 1H), 3.46 (d, 1H), 3.54 (dd, 1H), 3.60 (d, 1H), 3.80 (d, 1H), 3.98 (d, 1H), 5.59 (dd, 1H, H5), 5.87 (m, 1H, H14), 7.59 (m, ArH), 7.68 (m, ArH), 7.75 (m, ArH) and 8.12 (s, 1H, triazole).

| 155 | $R^I$ = H<br>A = 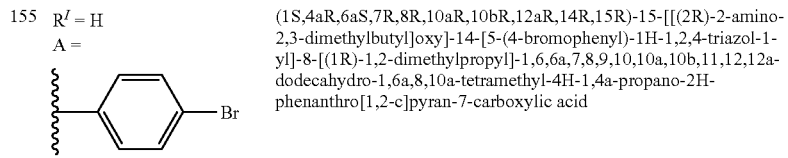 | (1S,4aR,6aS,7R,8R,10aR,10bR,12aR,14R,15R)-15-[[(2R)-2-amino-2,3-dimethylbutyl]oxy]-14-[5-(4-bromophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.76 (d, 3H, Me), 0.77 (s, 3H, Me), 0.80 (d, 3H, Me), 0.83 (d, 3H, Me), 0.85 (s, 3H, Me), 0.85 (d, 3H, Me), 0.90 (d, 3H, Me), 1.17 (s, 3H, Me), 1.21 (s, 3H, Me), 1.23-1.34 (m), 1.40-1.44 (m), 1.48-1.65 (m), 1.70 (m), 1.82-1.98 (m), 2.04-2.09 (m), 2.13-2.23 (m), 2.52 (dd, 1H, H13), 2.85 (s, 1H, H7), 2.86 (d, 1H), 3.43 (d, 1H), 3.46 (d, 1H), 3.54 (dd, 1H), 3.64 (d, 1H), 3.79 (d, 1H), 3.96 (d, 1H), 5.59 (dd, 1H, H5), 5.82 (m, 1H, H14), 7.65 (d, ArH), 7.76 (d, ArH) and 8.12 (br s, 1H, triazole).
Mass spectrum: (ESI) m/z = 793.39 (M + H).

| 156 | $R^I$ = H<br>A = 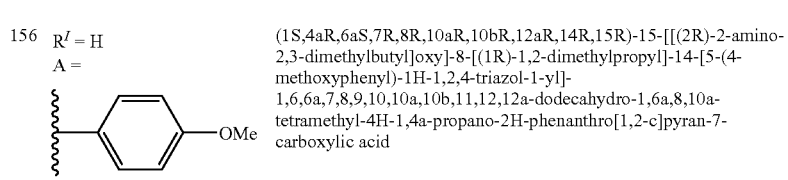 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-methoxyphenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H, Me), 0.77 (d, 3H, Me), 0.80 (s, 3H, Me), 0.80 (d, 3H, Me), 0.83 (d, 3H, Me), 0.85 (s, 3H, Me), 0.85 (d, 3H, Me), 0.90 (d, 3H, Me), 1.17 (s, 3H, Me), 1.21 (s, 3H, Me), 1.23-1.34 (m), 1.40-1.44 (m), 1.48-1.66 (m), 1.71 (m), 1.82-1.98 (m), 2.03-2.08 (m), 2.13-2.21 (m), 2.50 (dd, 1H, H13), 2.85 (s, 1H, H7), 2.88 (d, 1H), 3.43 (d, 1H), 3.45 (d, 1H), 3.54 (dd, 1H), 3.61 (d, 1H), 3.81 (d, 1H), 3.96 (d, 1H), 5.58 (dd, 1H, H5), 5.87 (m, 1H, H14), 7.13 (br d, ArH), 7.69 (br d, ArH) and 8.15 (br s, 1H, triazole).
Mass spectrum: (ESI) m/z = 745.52 (M + H).

| 157 | $R^I$ = H<br>A = 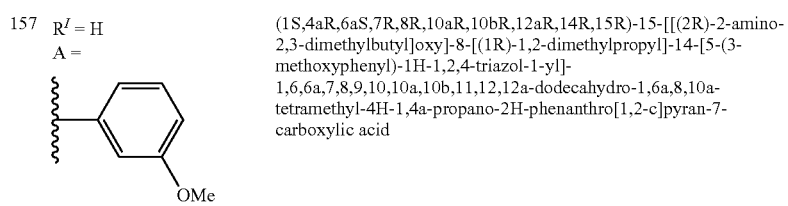 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-methoxyphenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

-continued

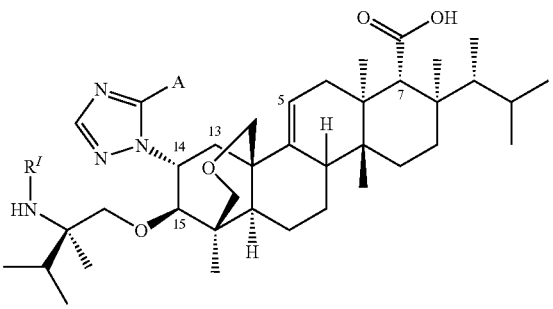

¹H NMR (CD₃OD, 600 MHz, ppm) δ 0.77 (s, 3H, Me), 0.77 (d, 3H, Me), 0.79 (d, 3H, Me), 0.80 (s, 3H, Me), 0.81 (d, 3H, Me), 0.85 (s, 3H, Me), 0.85 (d, 3H, Me), 0.90 (d, 3H, Me), 1.18 (s, 3H, Me), 1.22 (s, 3H, Me), 1.23-1.34 (m), 1.40-1.44 (m), 1.48-1.64 (m), 1.68 (m), 1.82-1.98 (m), 2.05-2.10 (m), 2.13-2.21 (m), 2.53 (dd, 1H, H13), 2.84 (s, 1H, H7), 2.87 (d, 1H), 3.43 (d, 1H), 3.55 (m), 3.80 (d, 1H), 3.96 (d, 1H), 5.57 (dd, 1H, H5), 5.94 (m, 1H, H14), 7.12 (dd, ArH), 7.25 (dd, ArH), 7.31 (dd, ArH), 7.48 (dd, ArH) and 8.09 (s, 1H, triazole).
Mass spectrum: (ESI) m/z = 745.53 (M + H).

| 158 | R¹ = H<br>A = 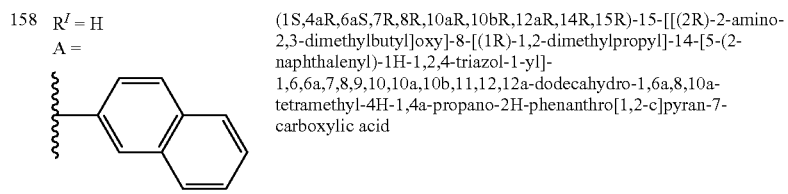 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-naphthalenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.80 (d, 3H, Me), 0.81 (s, 3H, Me), 0.83 (d, 3H, Me), 0.83 (s, 1H, Me), 0.84 (d, 3H, Me), 0.85 (d, 3H, Me), 0.86 (s, 3H, Me), 0.88 (d, 3H, Me), 0.92 (d, 1H, Me), 1.22 (s, 3H, Me), 1.24 (s, 3H, Me), 1.23-1.37 (m), 1.44-1.48 (m), 1.48-1.67 (m), 1.73 (m), 1.84-1.93 (m), 1.98-2.03 (m), 2.14-2.24 (m), 2.69 (dd, 1H, H13), 2.88 (s, 1H, H7), 2.94 (d, 1H), 3.42 (d, 1H), 3.48 (d, 1H), 3.58 (d, 1H), 3.68 (d, 1H), 3.78 (d, 1H), 4.02 (d, 1H), 5.69 (dd, 1H, H5), 6.05 (m, 1H, H14), 7.64 (m, ArH), 7.84 (br d, ArH), 7.996 (br dd, ArH), 8.04 (br d, ArH), 8.10 (d, ArH), 8.22 (br d, ArH) and 8.30 (br s, 1H, triazole).
Mass spectrum: (ESI) m/z = 765.44 (M + H).

| 159 | R¹ = H<br>A = 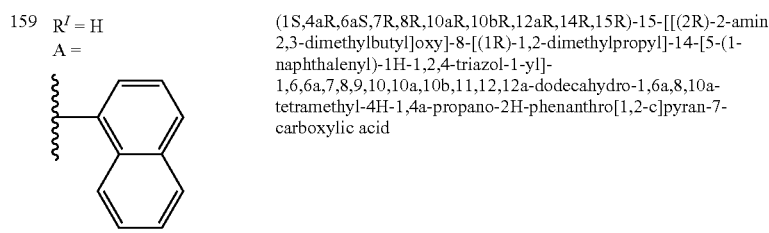 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-naphthalenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.73 (s, 3H, Me), 0.79 (d, 3H, Me), 0.86 (d, 3H, Me), 0.86 (s, 3H, Me), 0.88 (d, 3H, Me), 0.90-0.92 (m, Me), 1.17 (s, 3H, Me), 1.23 (s, 3H, Me), 1.23-1.30 (m), 1.40-1.44 (m), 1.48-1.65 (m), 1.78-1.94 (m), 2.04-2.09 (m), 2.09-2.23 (m), 2.31 (dd, 1H, H13), 2.84 (s, 1H, H7), 3.05 (dd, 1H), 3.14 (d, 1H), 3.27 (d, 1H), 3.36 (d, 1H), 3.56 (d, 1H), 3.61 (d, 1H), 3.71 (d, 1H), 4.12 (d, 1H), 5.27 (dd, 1H, H5), 5.58 (m, 1H, H14), 7.59 (br d, ArH), 7.63 (dd, ArH), 7.69 (dd, ArH), 7.76 (br d, ArH), 7.84 (br d, ArH), 8.04 (d, ArH), 8.15 (d, ArH) and 8.32 (br s, 1H, triazole).
Mass spectrum: (ESI) m/z = 765.44 (M + H).

| 160 | R¹ = H<br>A = 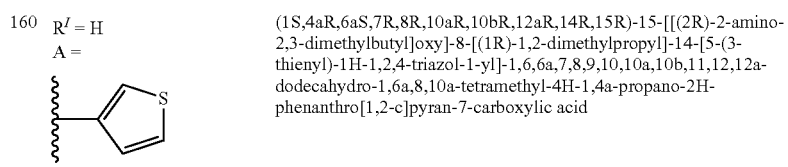 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-thienyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 3H, Me), 0.77 (s, 3H, Me), 0.78 (d, 3H, Me), 0.81 (d, 3H, Me), 0.85 (d, 3H, Me), 0.86 (s, 3H, Me), 0.89 (d, 3H, Me), 1.17 (s, 3H, Me), 1.21 (s, 3H, Me), 1.23-1.34 (m), 1.40-1.44 (m), 1.48-1.72 (m), 1.82-2.06 (m), 2.13-2.21 (m), 2.49 (dd, 1H, H13), 2.84 (s, 1H, H7), 2.87 (d, 1H), 3.45 (d, 1H), 3.47 (d, 1H), 3.55 (dd, 1H), 3.66 (d, 1H), 3.86 (d, 1H), 3.96 (d, 1H), 5.57 (dd, 1H, H5), 5.99 (m, 1H, H14), 7.52 (br d, ArH), 7.67 (br dd, ArH), 7.98 (br d, ArH) and 8.07 (br s, 1H, triazole)

-continued

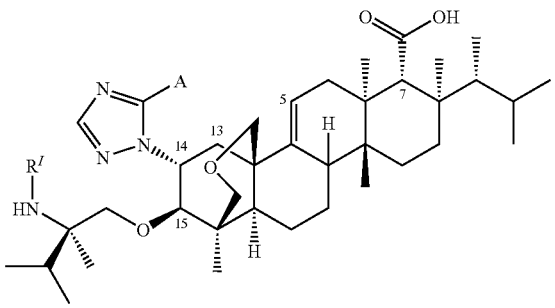

Mass spectrum: (ESI) m/z = 721.45 (M + H).

| 161 | $R^I$ = Me<br>A =<br> | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(3-thienyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.73 (s, 3H, Me), 0.76 (d, 3H, Me), 0.77 (s, 3H, Me), 0.80 (d, 3H, Me), 0.82 (d, 3H, Me), 0.85 (d, 3H, Me), 0.87 (s, 3H, Me), 0.90 (d, 3H, Me), 1.16 (s, 3H, Me), 1.21 (s, 3H, Me), 1.23-1.34 (m), 1.40-1.44 (m), 1.48-1.65 (m), 1.82-2.03 (m), 2.13-2.21 (m), 2.33 (s, 3H, NMe), 2.52 (dd, 1H, H13), 2.84 (s, 1H, H7), 2.95 (d, 1H), 3.42 (d, 1H), 3.47 (d, 1H), 3.56 (dd, 1H), 3.69 (d, 1H), 3.82 (d, 1H), 4.04 (d, 1H), 5.58 (dd, 1H, H5), 5.97 (m, 1H, H14), 7.52 (br d, ArH), 7.68 (br d, ArH), 7.99 (br d, ArH) and 8.09 (br s, 1H, triazole).
Mass spectrum: (ESI) m/z = 735.47 (M + H).

| 162 | $R^I$ = H<br>A =<br> | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-thienyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 3H, Me), 0.77 (s, 3H, Me), 0.78 (d, 3H, Me), 0.80 (d, 3H, Me), 0.85 (d, 3H, Me), 0.87 (s, 3H, Me), 0.89 (d, 3H, Me), 1.16 (s, 3H, Me), 1.21 (s, 3H, Me), 1.23-1.34 (m), 1.40-1.44 (m), 1.48-1.72 (m), 1.82-2.03 (m), 2.13-2.21 (m), 2.47 (dd, 1H, H13), 2.84 (s, 1H, H7), 2.93 (d, 1H), 3.47 (d, 1H), 3.48 (d, 1H), 3.57 (dd, 1H), 3.66 (d, 1H), 3.90 (d, 1H), 3.99 (d, 1H), 5.54 (dd, 1H, H5), 6.10 (m, 1H, H14), 7.24 (dd, thiophene), 7.67 (br dd, thiophene), 7.72 (d, thiophene) and 8.06 (br s, 1H, triazole).
Mass spectrum: (ESI) m/z = 721.41 (M + H).

| 163 | $R^I$ = Me<br>A =<br> | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-thienyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.73 (s, 3H, Me), 0.76 (d, 3H, Me), 0.77 (s, 3H, Me), 0.81 (d, 3H, Me), 0.82 (d, 3H, Me), 0.85 (d, 3H, Me), 0.89 (s, 3H, Me), 0.89 (d, 3H, Me), 1.15 (s, 3H, Me), 1.21 (s, 3H, Me), 1.23-1.34 (m), 1.40-1.44 (m), 1.48-1.65 (m), 1.83-1.98 (m), 2.13-2.21 (m), 2.32 (s, 3H, NMe), 2.49 (dd, 1H, H13), 2.84 (s, 1H, H7), 3.03 (d, 1H), 3.49 (d, 1H), 3.58 (dd, 1H), 3.62 (d, 1H), 3.69 (d, 1H), 3.85 (d, 1H), 4.08 (d, 1H), 5.54 (dd, 1H, H5), 6.08 (m, 1H, H14), 7.26 (dd, thiophene), 7.68 (br dd, thiophene), 7.75 (d, thiophene) and 8.07 (br s, 1H, triazole).
Mass spectrum: (ESI) m/z = 735.47 (M + H).

| 164 | $R^I$ = Me<br>A =<br> | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(1H-pyrazol-4-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.74 (s, 3H, Me), 0.79 (s, 3H, Me), 0.79 (d, 3H, Me), 0.83 (d, 3H, Me), 0.84 (d, 3H, Me), 0.88 (d, 3H, Me), 0.91 (s, 3H, Me), 0.92 (d, 3H, Me), 1.18 (s, 3H, Me), 1.23 (s, 3H, Me), 1.23-1.34 (m), 1.42-1.46 (m), 1.48-1.68 (m), 1.84-2.01 (m), 2.15-2.24 (m), 2.35 (s, 3H, NMe), 2.48 (dd, 1H, H13), 2.86 (s, 1H, H7), 3.02 (d, 1H), 3.53 (d, -continued

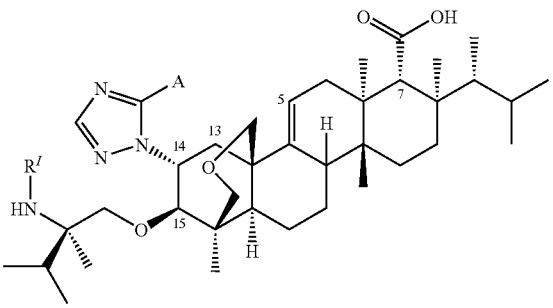

1H), 3.61 (dd, 1H), 3.63 (d, 1H), 3.72 (d, 1H), 3.88 (d, 1H), 4.06 (d, 1H), 5.57 (dd, 1H, H5), 5.94 (m, 1H, H14), 7.99 (d, 1H, triazole H) and 8.16 (s, 1H, pyrazole H).

| 165 | $R^I$ = Me<br>A = vinyl | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-(5-ethenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (s, 3H, Me), 0.76 (d, 3H, Me), 0.78 (s, 3H, Me), 0.80 (d, 3H, Me), 0.84 (d, 3H, Me), 0.85 (d, 3H, Me), 0.89 (s, 3H, Me), 0.89 (d, 3H, Me), 1.13 (s, 3H, Me), 1.20 (s, 3H, Me), 1.23-1.34 (m), 1.40-1.44 (m), 1.48-1.64 (m), 1.80-2.00 (m), 2.10-2.21 (m), 2.31 (dd, 1H, H13), 2.39 (s, 3H, NMe), 2.83 (s, 1H, H7), 2.90 (d, 1H), 3.51 (d, 1H), 3.55 (dd, 1H), 3.61 (d, 1H), 3.63 (d, 1H), 3.89 (d, 1H), 3.98 (d, 1H), 5.47 (dd, 1H, H5), 5.62 (m, 1H, H14), 5.79 (dd, 1H, vinyl), 6.35 (d, 1H, vinyl), 6.89 (dd, 1H, vinyl) and 8.01 (s, 1H, triazole).
Mass spectrum: (ESI) m/z = 679.43 (M + H).

| 166 | $R^I$ = H<br>A = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(1E)-1-propenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.78 (s, 3H, Me), 0.78 (d, 3H, Me), 0.77 (d, 3H, Me), 0.81 (d, 3H, Me), 0.85 (s, 3H, Me), 0.85 (d, 3H, Me), 0.87 (s, 3H, Me), 0.89 (d, 3H, Me), 1.14 (s, 3H, Me), 1.20 (s, 3H, Me), 1.23-1.34 (m), 1.40-1.44 (m), 1.48-1.64 (m), 1.73 (m), 1.78-1.96 (m), 1.98 (dd, 3H, vinylMe), 2.10-2.22 (m), 2.31 (dd, 1H, H13), 2.75 (d, 1H), 2.84 (s, 1H, H7), 3.44 (d, 1H), 3.51 (d, 1H), 3.56 (dd, 1H), 3.64 (d, 1H), 3.84 (d, 1H), 3.94 (d, 1H), 5.48 (dd, 1H, H5), 5.57 (m, 1H, H14), 6.56 (dd, 1H, vinyl), 6.91 (m, 1H, vinyl) and 7.98 (br s, 1H, triazole).
Mass spectrum: (ESI) m/z = 679.45 (M + H).

| 167 | $R^I$ = H<br>A = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(1Z)-1-propenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (s, 3H, Me), 0. (d, 3H, Me), 0.77 (d, 3H, Me), 0.80 (d, 3H, Me), 0.83 (s, 3H, Me), 0.85 (d, 3H, Me), 0.87 (s, 3H, Me), 0.89 (d, 3H, Me), 1.15 (s, 3H, Me), 1.21 (s, 3H, Me), 1.23-1.34 (m), 1.40-1.44 (m), 1.48-1.72 (m), 1.78-1.96 (m), 2.10 (dd, 3H, vinylMe), 2.10-2.21 (m), 2.27 (dd, 1H, H13), 2.77 (d, 1H), 2.83 (s, 1H, H7), 3.49 (d, 1H), 3.54 (dd, 1H), 3.60 (d, 1H), 3.85 (d, 1H), 3.92 (d, 1H), 5.46 (dd, 1H, H5), 5.55 (m, 1H, H14), 6.30 (m, 1H, vinyl), 6.44 (m, 1H, vinyl) and 8.01 (br s, 1H, triazole)
Mass spectrum: (ESI) m/z = 679.61 (M + H).

| 168 | $R^I$ = H<br>A = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-methylethenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (s, 3H, Me), 0.76 (d, 3H, Me), 0.80 (d, 3H, Me), 0.82 (d, 3H, Me), 0.85 (s, 3H, Me), 0.85 (d, 3H, Me), 0.87 (s, 3H, Me), 0.89 (d, 3H, Me), 1.15 (s, 3H, Me), 1.20 (s, 3H, Me), 1.22-1.34 (m), 1.40-1.44 (m), 1.48-1.65 (m), 1.73 (m), 1.80-1.96 (m), 2.12-2.22 (m), 2.21 (br s, 3H, vinylMe), 2.33 (dd, 1H, H13), 2.84 (s, 1H, H7), 2.92 (d, -continued

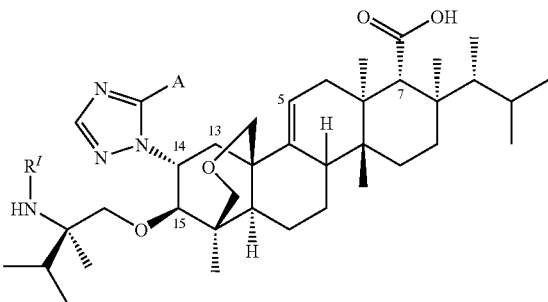

1H), 3.46 (d, 1H), 3.48 (dd, 1H), 3.55 (m), 3.89 (d, 1H), 3.97 (d, 1H), 5.49 (dd, 1H, H5), 5.58 (d, 1H, vinyl), 5.68 (br d, 1H, vinyl), 5.87 (m, 1H, H14) and 7.99 (br s, 1H, triazole).
Mass spectrum: (ESI) m/z = 679.40 (M + H).

| 169 | $R^I$ = H<br>A = n-Propyl | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-propyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (s, 3H, Me), 0.77 (d, 3H, Me), 0.79 (d, 3H, Me), 0.82 (d, 3H, Me), 0.86 (d, 3H, Me), 0.87 (s, 3H, Me), 0.88 (s, 3H, Me), 0.89 (d, 3H, Me), 1.03 (t, 3H, Me), 1.15 (s, 3H, Me), 1.20 (s, 3H, Me), 1.22-1.34 (m), 1.40-1.44 (m), 1.48-1.65 (m), 1.70-1.95 (m), 2.12-2.22 (m), 2.27 (dd, 1H, H13), 2.78 (d, 1H), 2.78 (m), 2.84 (s, 1H, H7), 3.44 (d, 1H), 3.51 (d, 1H), 3.56 (dd, 1H), 3.61 (d, 1H), 3.86 (d, 1H), 3.93 (d, 1H), 5.47 (dd, 1H, H5), 5.49 (m, 1H, H14) and 7.92 (br s, 1H, triazole).
Mass spectrum: (ESI) m/z = 681.46 (M + H).

| 170 | $R^I$ = Me<br>A = 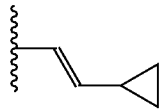 | (1S,4aR,6aS,7R,8R,10aR,10bR,12aR,14R,15R)-14-[5-[(E)-2-cyclopropylethenyl]-1H-1,2,4-triazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.65 (m), 0.76 (s, 3H, Me), 0.76 (d, 3H, Me), 0.80 (d, 3H, Me), 0.81 (s, 3H, Me), 0.84 (d, 3H, Me), 0.85 (d, 3H, Me), 0.89 (s, 3H, Me), 0.89 (d, 3H, Me), 0.96 (m), 1.14 (s, 3H, Me), 1.20 (s, 3H, Me), 1.23-1.34 (m), 1.40-1.44 (m), 1.48-1.64 (m), 1.71 (m), 1.80-2.00 (m), 2.10-2.21 (m), 2.31 (dd, 1H, H13), 2.39 (s, 3H, NMe), 2.84 (s, 1H, H7), 2.90 (d, 1H), 3.52 (d, 1H), 3.56 (dd, 1H), 3.58 (d, 1H), 3.66 (d, 1H), 3.90 (d, 1H), 3.95 (d, 1H), 5.49 (dd, 1H, H5), 5.56 (m, 1H, H14), 6.33 (d, 1H, vinyl), 6.60 (d, 1H, vinyl) and 7.92 (s, 1H, triazole).
Mass spectrum: (ESI) m/z = 719.51 (M + H).

| 171 | $R^I$ = H<br>A = 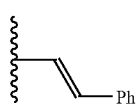 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(E)-2-phenylethenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (d, 3H, Me), 0.76 (d, 3H, Me), 0.77 (s, 3H, Me), 0.80 (d, 3H, Me), 0.85 (s, 3H, Me), 0.85 (d, 3H, Me), 0.89 (s, 3H, Me), 0.89 (d, 3H, Me), 1.15 (s, 3H, Me), 1.21 (s, 3H, Me), 1.22-1.35 (m), 1.40-1.44 (m), 1.48-1.65 (m), 1.71 (m), 1.82-2.02 (m), 2.12-2.21 (m), 2.41 (dd, 1H, H13), 2.74 (d, 1H), 2.83 (s, 1H, H7), 3.44 (d, 1H), 3.54 (d, 1H), 3.60 (dd, 1H), 3.72 (d, 1H), 3.87 (d, 1H), 3.98 (d, 1H), 5.52 (dd, 1H, H5), 5.66 (m, 1H, H14), 5.79 (s, 1H, vinyl), 7.21 (d, 1H, vinyl), 7.38 (m, 1H, ArH), 7.42 (m, 1H, ArH), 7.66 (m, 1H, ArH), 7.71 (d, 1H, vinyl) and 8.05 (s, 1H, triazole).
Mass spectrum: (ESI) m/z = 741.44 (M + H).

| 172 | $R^I$ = H<br>A = 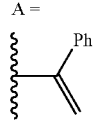 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-phenylethenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.70 (s, 3H, Me), 0.78 (d, 3H, Me), 0.82 (s, 3H, Me), 0.84 (d, 3H, Me), 0.86 (d, 3H, Me), 0.87 (d, 3H, Me), 0.90 (s, 3H, Me), 0.92 (d, 3H, Me), 1.11 (s, 3H, Me), 1.21 (s, 3H, Me), 1.20-1.31 (m), 1.36-1.41 (m), 1.44-1.82 (m), 2.03 (m), 2.21 (m), 2.72 (d, 1H), 2.82 (s, 1H, H7), 2.96 (d, 1H), 3.22 (d, 1H), 3.43 (d, 1H), 3.76 (d, 1H), 3.85 (d, 1H), 3.85 (d, 1H), 4.90 (dd, 1H, H5), 5.25 (m, 1H, H14), 5.79 (s, 1H, vinyl), 5.98 (s, 1H, -continued

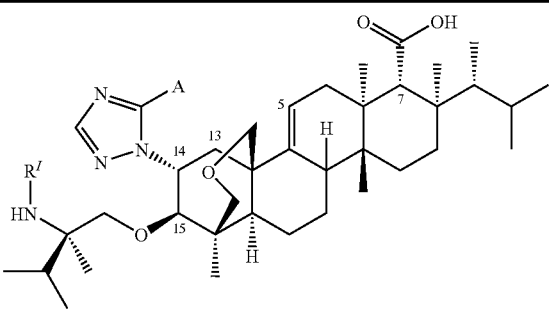

vinyl), 7.30 (m, ArH), 7.47 (m, ArH) and 8.11 (br s, 1H, triazole).
Mass spectrum: (ESI) m/z = 741.49 (M + H).

Example 173

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid A suspension of (1S,4aR,6aS,7R,8R,10aR,10bR,12aR,14R,15R)-15-[[(2R)-2-amino-2,3,3-trimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 11, 37.2 mg, 0.044 mmol), cesium carbonate (255 mg, 0.78 mmol), 4-(4,4,5,5-tetramethyl-1,3,2-dioxaborolan-2-yl)pyridine (129 mg, 0.63 mmol), palladium (II) acetate (14.4 mg, 0.06 mmol) and 2-dicyclohexylphosphino-2',4',6'-triisopropylbiphenyl (24 mg, 0.05 mmol) in dioxane (1.2 mL) was blanketed with nitrogen and heated in a microwave at 150° C. for 45 minutes. The mixture was cooled to room temperature, filtered and purified by reverse phase HPLC using a 19×150 mm Sunfire Preparative C18 OBD column eluting with acetonitrile/water+0.1% TFA. Product fractions were evaporated and freeze-dried from a mixture of ethanol and benzene to give the title compound (5.9 mg) as a white solid (trifluoroacetic acid salt).

$^1$H NMR (CD$_3$OD, 600 MHz, ppm) δ 0.74 (s, 3H, Me), 0.76 (d, 3H, Me), 0.77 (s, 3H, Me), 0.85 (s, 9H, Me), 0.86 (d,

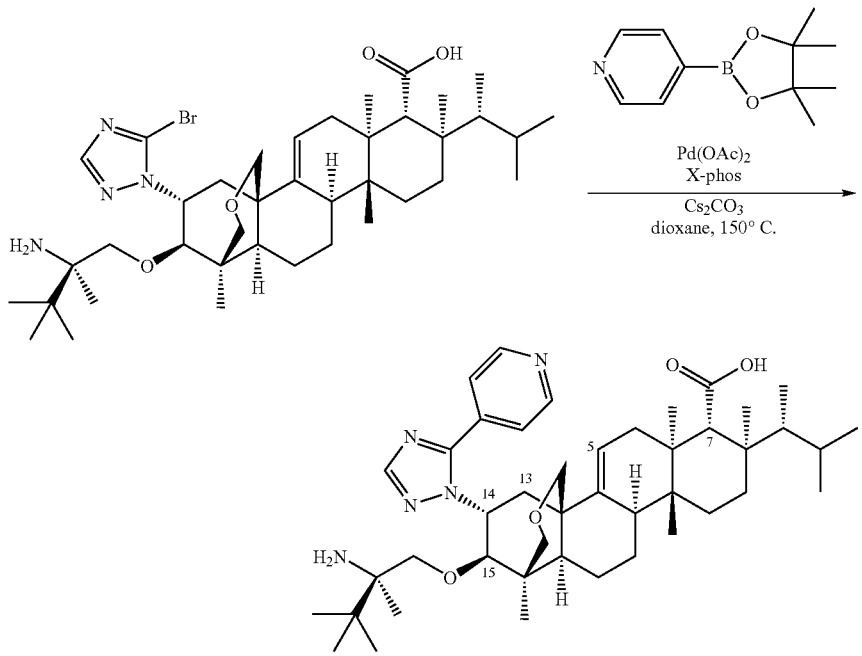

3H, Me), 0.87 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.82-1.98 (m), 2.06-2.11 (m), 2.13-2.21 (m), 2.62 (dd, 1H, H13), 2.85 (s, 1H, H7), 2.87 (d, 1H), 3.46 (d, 1H), 3.56 (dd, 1H), 3.65 (d, 1H), 3.68 (d, 1H), 3.82 (d, 1H), 4.03 (d, 1H), 5.62 (dd, 1H, H5), 5.88 (m, 1H, H14), 7.96 (br d, 2H, pyridyl H), 8.21 (s, 1H, triazole) and 8.90 (br d, 2H, pyridyl H).

Mass spectrum: (ESI) m/z=730.71 (M+H).

Example 173

Alternative Synthesis (1S,4aR,6aS,7R,8R,10aR,10bR,12aR,14R,15R)-15-
[[(2R)-2-amino-2,3,3-trimethylbutyl]oxy]-8-[(1R)-1,
2-dimethylpropyl]-14-[5-(4-pyridinyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid

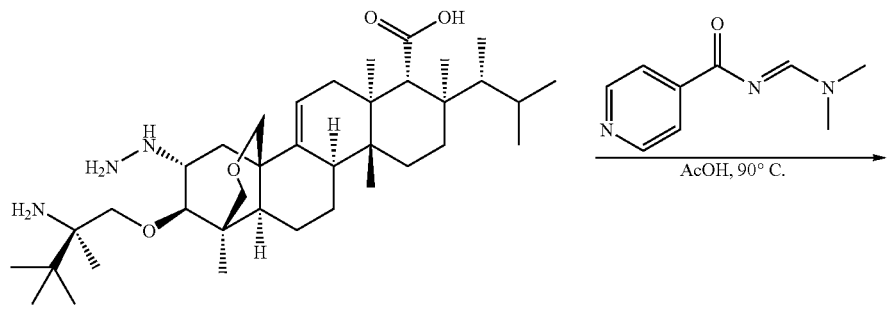

Intermediate 33

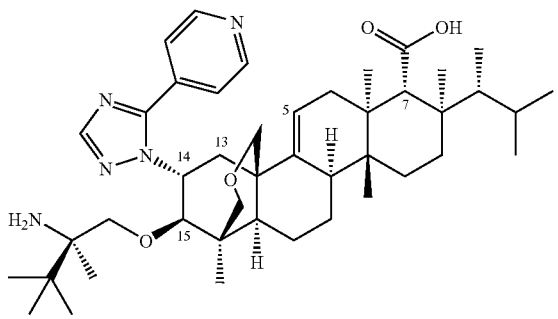

A suspension of Intermediate 33 (2.83 g, 0.046 mol) and N-[(1E)-(dimethylamino)methylidene]pyridine-4-carboxamide (0.93 g, 0.052 mol) in acetic acid (44.4 mL) was blanketed with nitrogen and heated in a 90° C. oil bath for 1 hour. The mixture was cooled to room temperature, evaporated and purified by reverse phase HPLC using a 19×150 mm Sunfire Preparative C18 OBD column eluting with acetonitrile/water+0.1% TFA. The product fractions were combined, concentrated under vacuum and freeze-dried to give the title compound (2.21 g) as a white solid (trifluoroacetic acid salt).

Conversion of Example 173 to Hydrochloride Salt

A portion of the trifluoroacetic acid salt from above (0.90 g, 1.07 mmol) was dissolved in methanol (9 mL) and the solution was diluted with 9 mL of 1:1 MeCN/H₂O. The solution was loaded onto a column of Dowex® 1×8 chloride form ion exchange resin (48 mL, ~34 g, ~1.8 meq/g) and the column was eluted with 1:1 MeCN/H₂O (120 mL). The eluant was concentrated in vacuo to remove most of the acetonitrile and then frozen and lyophilized to give 0.72 g of the hydrochloride salt as a white solid.

Conversion of Example 173 to Free Base

A portion of the trifluoroacetic acid salt from above (35.2 mg, 0.042 mmol) was dissolved in ethyl acetate (10 mL) and the solution was washed with sat. NaHCO₃ (3 mL) followed by brine (3 mL). The separated organic layer was dried over Na₂SO₄ and evaporated in vacuo to give a glassy solid. The solid was dissolved in benzene and a small amount of methanol and the solution was frozen and lyophilized to give 24.2 mg of the free base as a white solid.

$^1$H NMR (CD$_3$OD, 500 MHz, ppm) δ 0.73 (s, 3H, Me), 0.86 (d, 3H, Me), 0.79 (s, 3H, Me), 0.81 (s, 9H, Me), 0.87 (d, 3H, Me), 0.89 (s, 3H, Me), 0.92 (d, 3H, Me), 1.23 (s, 3H, Me), 1.25 (s, 3H, Me), 1.29-1.38 (m), 1.38-1.45 (m), 1.53 (t, 1H), 1.59-1.67 (m), 1.81-1.94 (m), 2.01 (d, 1H), 2.11 (d, 1H), 2.13-2.21 (m), 2.23-2.31 (m, 1H), 2.58 (dd, 1H, H13), 2.78 (s, 1H, H7), 2.79 (d, 1H), 3.44-3.49 (m, 2H), 3.56 (d, 1H), 3.67 (d, 1H), 3.80 (d, 1H), 3.94 (d, 1H), 5.63 (d, 1H, H5), 5.83-5.92 (m, 1H, H14), 7.81 (d, 2H, pyridyl H), 8.18 (s, 1H, triazole), 8.79 (d, 2H, pyridyl H).

Mass spectrum: (ESI) m/z=730.70 (M+H).

Example 174

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

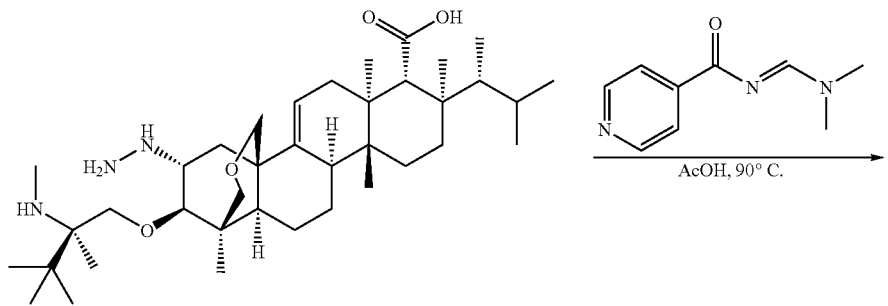

Intermediate 34

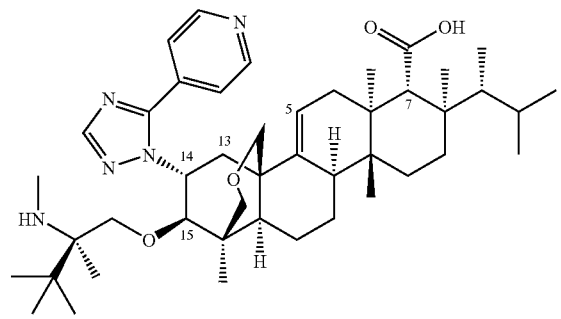

Intermediate 34 (166 mg, 0.22 mmol) was dissolved in acetic acid (7.5 mL) under nitrogen. To this solution was added N-[(1E)-(dimethylamino)methylidene]pyridine-4-carboxamide (47 mg, 0.27 mmol) and the resulting solution heated at 90° C. After two hours the reaction was allowed to cool to room temperature then concentrated in vacuo. The crude reaction mixture was dissolved in methanol then purified by HPLC (30×100 mm Waters Sunfire column, 5 μm, UV detection, 30-100% MeCN/water with 0.05% TFA over 20 minutes). The product fractions were partially concentrated by rotovap then frozen and lyophilized overnight to provide the title compound (128 mg) as an amorphous white solid.

$^1$H NMR (CD$_3$OD, 500 MHz, ppm) δ 0.73 (s, 3H), 0.77 (d, J=6.9 Hz, 3H), 0.78 (s, 3H), 0.86 (d, J=6.6 Hz, 3H), 0.89 (s, 9H), 0.89 (d, 3H, partially obscured), 0.91 (s, 3H), 1.17 (s, 3H), 1.22 (s, 3H), 1.24-1.68 (m), 1.83-2.08 (m), 2.15-2.24 (m, 2H), 2.56 (s, 3H), 2.57 (dd, 1H, partially obscured), 2.85 (s, 1H), 3.15 (d, J=11.0 Hz, 1H), 3.50 (d, J=12.1 Hz, 1H), 3.56 (dd, J=11.7 Hz, 2.0 Hz, 1H), 3.64 (d, J=8.7 Hz, 1H), 3.67 (d, J=8.5 Hz, 1H), 3.84 (d, J=11.2 Hz, 1H), 4.07 (d, J=9.9 Hz, 1H), 5.61 (m, 1H), 5.87 (m, 1H), 7.81 (m, 2H), 8.20 (s, 1H), 8.82 (m, 2H).

Mass Spectrum: (ESI) m/z=744.32 (M+H).

Example 175

(1S,4aR,6aS,7R,8R,10aR,10bR,12aR,14R,15R)-15-[[(2R)-2-amino-2,3-dimethylbutyl]oxy]-14-[5-(2-bromo-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

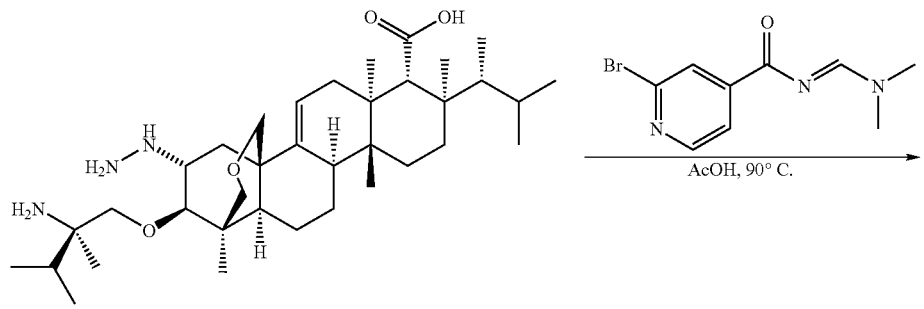

Intermediate 32

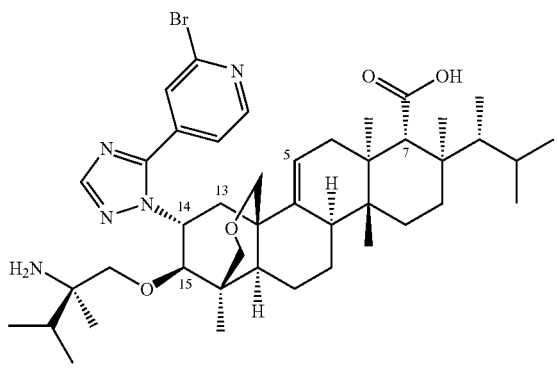

2-bromo-N-[(1E)-(dimethylamino)methylidene]pyridine-4-carboxamide (19.7 mg, 0.077 mmol) was added to a stirred solution of Intermediate 32 (50.3 mg, 0.070 mmol) in acetic acid (1.0 ml, 17.47 mmol). The reaction mixture was a light yellow solution that was degassed (2×) and placed under nitrogen before being heated to 90° C. After 30 minutes, LCMS and $^1$H NMR showed complete conversion of to product. The reaction mixture was cooled to room temperature and evaporated under reduced pressure to give a light yellow residue. The residue was dissolved in methanol and purified using two HPLC runs (~25 mg/run) on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give the title compound (42.2 mg, 0.046 mmol) as a white solid.

$^1$H NMR (CD$_3$OD, 500 MHz, ppm) δ 0.79 (s, 3H, Me), 0.80 (d, 3H, Me), 0.80 (s, 3H, Me), 0.82 (d, 3H, Me), 0.84 (d, 3H, Me), 0.88 (d, 3H, Me), 0.89 (s, 3H, Me), 0.92 (d, 3H, Me), 1.20 (s, 3H, Me), 1.24 (s, 3H, Me), 1.25-1.39 (m), 1.43-1.47 (m), 1.51-1.77 (m), 1.83-2.01 (m), 2.06-2.13 (m), 2.15-2.25 (m), 2.61 (dd, 1H, H13), 2.88 (s, 1H, H7), 2.88 (d, 1H), 3.49 (d, 1H), 3.50 (d, 1H), 3.59 (dd, 1H), 3.67 (d, 1H), 3.84 (d, 1H), 4.00 (d, 1H), 5.63 (dd, 1H, H5), 5.85-5.93 (m, 1H, H14), 7.78 (dd, 1H, ArH), 7.98 (d, 1H, ArH), 8.21 (s, 1H, triazole), 8.60 (d, 1H, ArH).

Mass Spectrum: (ESI) m/z=794.61 (796.61) (M+H).

Example 176

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(5-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

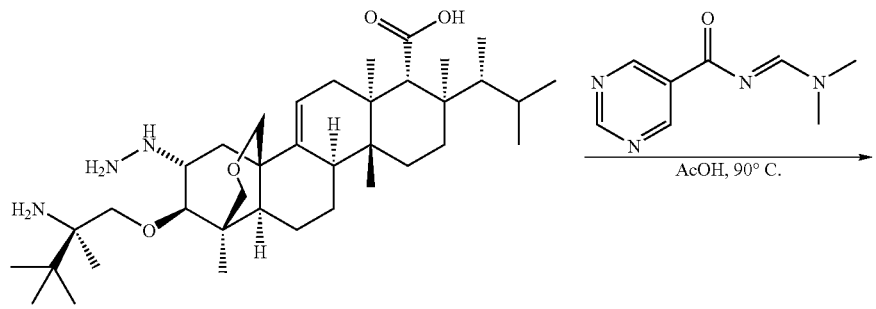

Intermediate 33

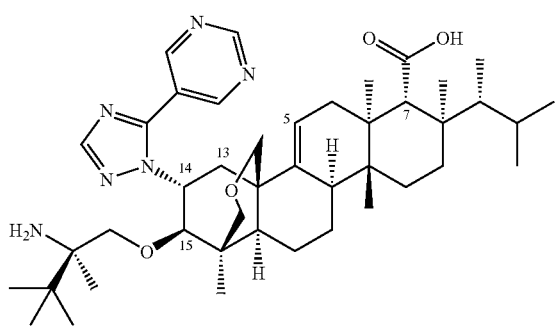

N-[(1E)-(dimethylamino)methylidene]pyrimidine-5-carboxamide (13.8 mg, 0.077 mmol) was added to a stirred solution of Intermediate 33 (50.7 mg, 0.069 mmol) in acetic acid (1.0 ml, 17.47 mmol). The reaction mixture was a light yellow solution that was degassed (2×) and placed under nitrogen before being heated to 90° C. After 30 minutes, LCMS and $^1$H NMR showed complete conversion to product. The reaction mixture was cooled to room temperature, diluted with methanol, and evaporated under reduced pressure to give a light yellow residue. The residue was dissolved in methanol and purified using two HPLC runs (~25 mg/run) on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give the title compound (29.0 mg) as a white solid.

$^1$H NMR (CD$_3$OD, 500 MHz, ppm) δ 0.78 (s, 3H, Me), 0.79 (d, 3H, Me), 0.80 (s, 3H, Me), 0.88 (d, 3H, Me), 0.88 (s, 9H, t-bu), 0.91 (s, 3H, Me), 0.92 (d, 3H, Me), 1.18 (s, 3H, Me), 1.22 (s, 3H, Me), 1.24-1.38 (m), 1.42-1.47 (m), 1.50-1.68 (m), 1.83-2.01 (m), 2.07-2.14 (m), 2.15-2.25 (m), 2.64 (dd, 1H, H13), 2.87 (s, 1H, H7), 2.94 (d, 1H), 3.48 (d, 1H), 3.58 (dd, 1H), 3.66 (d, 1H), 3.70 (d, 1H), 3.85 (d, 1H), 4.05 (d, 1H), 5.62 (dd, 1H, H5), 5.79-5.86 (m, 1H, H14), 8.24 (s, 1H, triazole), 9.21 (s, 2H, ArH), 9.36 (s, 1H, ArH).

Mass Spectrum: (ESI) m/z=731.71 (M+H).

Example 177

(1S,4aR,6aS,7R,8R,10aR,10bR,12aR,14R,15R)-15-[[(2R)-2-amino-2,3,3-trimethylbutyl]oxy]-14-[5-(4-cyanophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

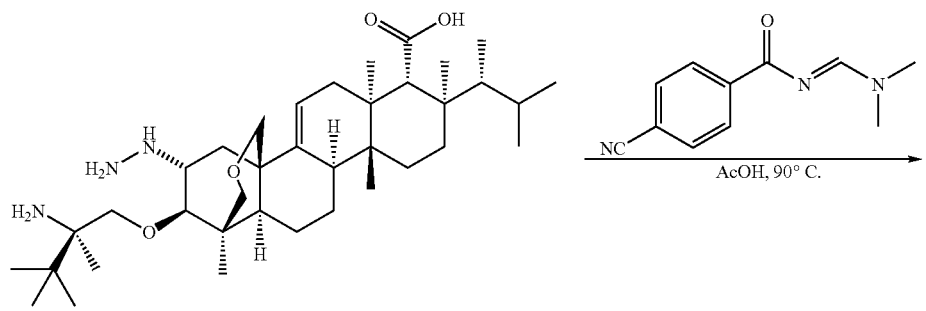

Intermediate 33

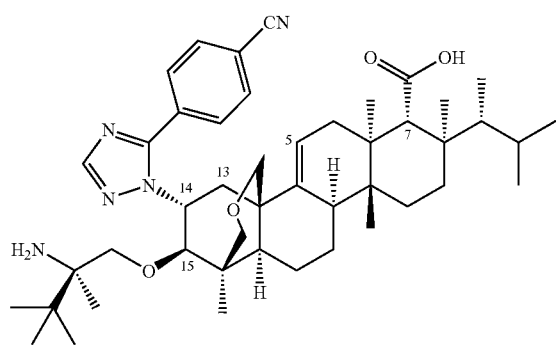

4-cyano-N-[(1E)-(dimethylamino)methylidene]benzamide (15.3 mg, 0.076 mmol) was added to a stirred solution of Intermediate 33 (50.5 mg, 0.069 mmol) in acetic acid (1.0 ml, 17.47 mmol). The reaction mixture was a light yellow solution that was degassed (2×) and placed under nitrogen before being heated to 90° C. After 30 minutes, LCMS and $^1$H NMR showed the reaction to be complete. The reaction mixture was cooled to room temperature, diluted with methanol, and evaporated under reduced pressure to give a tan residue. The residue was dissolved in methanol and purified using two HPLC runs (~25 mg/run) on a 30×150 mm Sunfire Prep C18 OBD 10 µm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give the title compound (33.8 mg) as a white solid.

$^1$H NMR (CD$_3$OD, 600 MHz, ppm) δ 0.76 (s, 3H, Me), 0.77 (d, 3H, Me), 0.78 (s, 3H, Me), 0.85 (s, 9H, t-bu), 0.86 (d, 3H, Me), 0.86 (s, 3H, Me), 0.90 (d, 3H, Me), 1.18 (s, 3H, Me), 1.21 (s, 3H, Me), 1.23-1.35 (m), 1.41-1.45 (m), 1.49-1.66 (m), 1.80-1.99 (m), 2.05-2.11 (m), 2.14-2.23 (m), 2.59 (dd, 1H, H13), 2.85 (s, 1H, H7), 2.87 (d, 1H), 3.44 (d, 1H), 3.55 (dd, 1H), 3.63 (d, 1H), 3.66 (d, 1H), 3.80 (d, 1H), 4.01 (d, 1H), 5.62 (dd, 1H, H5), 5.79-5.85 (m, 1H, H14), 7.92 (d, 2H, ArH), 7.96 (d, 2H, ArH), 8.16 (s, 1H, triazole).

Mass Spectrum: (ESI) m/z=754.55 (M+H).

Example 178

(1S,4aR,6aS,7R,8R,10aR,10bR,12aR,14R,15R)-14-[5-[4-(aminomethyl)phenyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

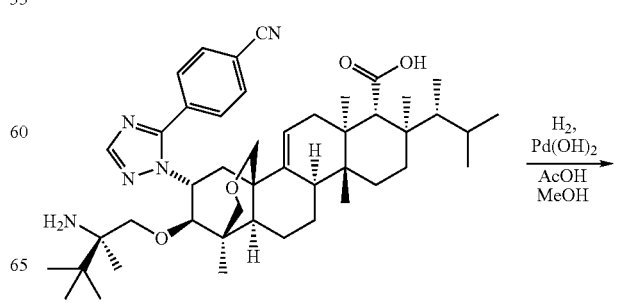

-continued

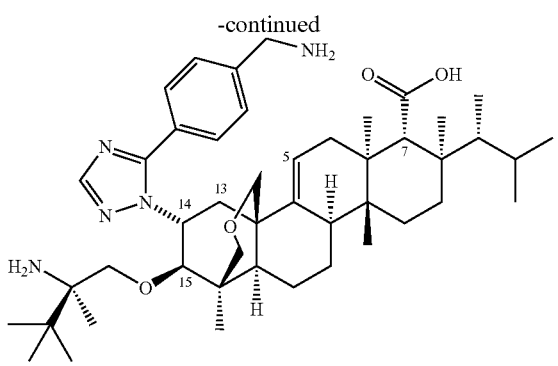

Palladium hydroxide on carbon (10.6 mg, 0.015 mmol) and acetic acid (17 µl, 0.297 mmol) were added to a stirred solution of (1S,4aR,6aS,7R,8R,10aR,10bR,12aR,14R,15R)-15-[[(2R)-2-amino-2,3,3-trimethylbutyl]oxy]-14-[5-(4-cyanophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 168, 52.5 mg, 0.060 mmol) in methanol (3.0 ml). The reaction mixture was degassed (3×) and purged with hydrogen before being placed under a hydrogen balloon. After 6 hours, the hydrogen balloon was removed. The reaction mixture was degassed (2×), diluted with methanol, and filtered through a pad of Celite. The filtrate was evaporated under reduced pressure to give a colorless residue. The residue was dissolved in methanol and purified using a single HPLC run on a 30×150 mm Sunfire Prep C18 OBD 10 µm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give the title compound (35.4 mg) as a white solid $^1$H NMR (CD$_3$OD, 600 MHz, ppm) δ 0.77 (s, 3H, Me), 0.77 (d, 3H, Me), 0.83 (s, 3H, Me), 0.85 (s, 9H, t-bu), 0.86 (d, 3H, Me), 0.87 (s, 3H, Me), 0.90 (d, 3H, Me), 1.18 (s, 3H, Me), 1.21 (s, 3H, Me), 1.23-1.35 (m), 1.41-1.46 (m), 1.49-1.66 (m), 1.80-1.98 (m), 2.04-2.10 (m), 2.14-2.23 (m), 2.53 (dd, 1H, H13), 2.85 (s, 1H, H7), 2.92 (d, 1H), 3.44 (d, 1H), 3.54 (dd, 1H), 3.55 (d, 1H), 3.59 (d, 1H), 3.78 (d, 1H), 4.02 (d, 1H), 4.22 (s, 2H, CH$_2$NH$_2$), 5.57 (dd, 1H, H5), 5.83-5.89 (m, 1H, H14), 7.68 (d, 2H, ArH), 7.83 (d, 2H, ArH), 8.16 (s, 1H, triazole).

Mass Spectrum: (ESI) m/z=758.60 (M+H).

Example 179

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[2-(ethoxycarbonyl)-4-pyridinyl]-1H-1,2,4-triazol-1-yl]-1,6,6a,7,8,9,10,10a,10 b,11,12,12a-dodecahydro-1,6a,8,10a-tetramethyl-4H-1,4a-propano-2H-phenanthro[1,2-c]pyran-7-carboxylic acid

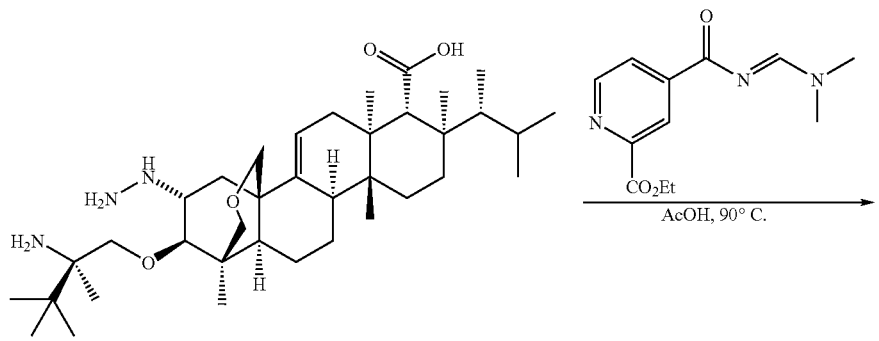

Intermediate 33

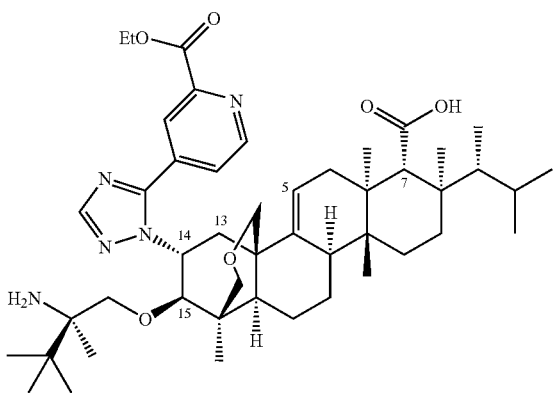

Ethyl 4-({[(1E)-(dimethylamino)methylidene]amino}carbonyl)pyridine-2-carboxylate (40.6 mg, 0.163 mmol) was added to a stirred solution of Intermediate 33 (91.1 mg, 0.148 mmol) in acetic acid (1.8 ml, 31.4 mmol). The reaction mixture was an orange solution that was degassed (2×) and placed under nitrogen before being heated to 90° C. After 30 minutes, LCMS and $^1$H NMR showed the reaction to be complete. The reaction mixture was cooled to room temperature, diluted with methanol, and evaporated under reduced pressure to give an amber residue. The residue was dissolved in methanol and purified using two HPLC runs (~45 mg/run) on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give the title compound (41.0 mg) as a white solid.

$^1$H NMR (CD$_3$OD, 600 MHz, ppm) δ 0.72 (s, 3H, Me), 0.77 (d, 3H, Me), 0.79 (s, 3H, Me), 0.85 (s, 9H, t-bu), 0.86 (d, 3H, Me), 0.87 (s, 3H, Me), 0.90 (d, 3H, Me), 1.19 (s, 3H, Me), 1.22 (s, 3H, Me), 1.23-1.37 (m), 1.42-1.46 (m), 1.44 (t, 3H), 1.50-1.67 (m), 1.82-1.94 (m), 1.95-2.00 (m), 2.09-2.15 (m), 2.15-2.23 (m), 2.69 (dd, 1H, H13), 2.86 (s, 1H, H7), 2.90 (d, 1H), 3.46 (d, 1H), 3.58 (dd, 1H), 3.64 (d, 1H), 3.73 (d, 1H), 3.79 (d, 1H), 4.04 (d, 1H), 4.49 (q, 2H, COOCH$_2$), 5.64 (dd, 1H, H5), 5.85-5.91 (m, 1H, H14), 7.99 (dd, 1H, ArH), 8.21 (s, 1H, triazole), 8.49 (d, 1H, ArH), 8.91 (d, 1H, ArH).

Mass Spectrum: (ESI) m/z=802.70 (M+H).

Example 180

(1S,4aR,6aS,7R,8R,10aR,10bR,12aR,14R,15R)-14-[5-[2-(aminocarbonyl)-4-pyridinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

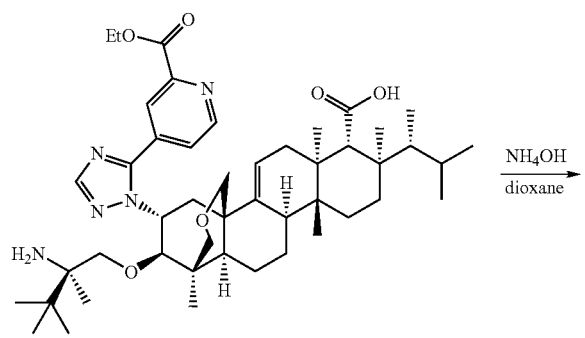

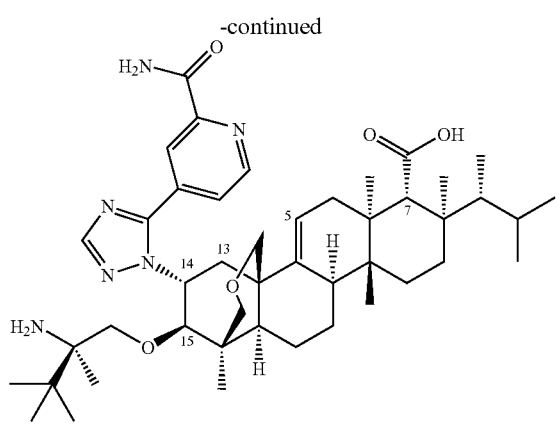

Concentrated ammonium hydroxide (0.15 ml, 1.079 mmol) was added to a stirred solution of (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[2-(ethoxycarbonyl)-4-pyridinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 171, 38.1, 0.042 mmol) in 1,4-dioxane (0.42 ml). A white precipitate formed about a minute or two after the addition of ammonium hydroxide. The reaction mixture was stirred at room temperature. After 20 hours, additional 1,4-dioxane (0.15 ml) and concentrated ammonium hydroxide (0.05 ml, 0.360 mmol) were added to the reaction mixture. After 26 hours, the reaction mixture had become a colorless solution. After 44 hours, LCMS and $^1$H NMR showed the reaction to be complete. The reaction mixture was evaporated under reduced pressure to give a colorless residue. The residue was dissolved in methanol and purified using a single HPLC run on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from acetonitrile and water to give the title compound (29.9 mg) as a white solid.

$^1$H NMR (CD$_3$OD, 600 MHz, ppm) δ 0.74 (s, 3H, Me), 0.77 (d, 3H, Me), 0.78 (s, 3H, Me), 0.85 (s, 9H, t-bu), 0.86 (d, 3H, Me), 0.88 (s, 3H, Me), 0.90 (d, 3H, Me), 1.18 (s, 3H, Me), 1.21 (s, 3H, Me), 1.23-1.36 (m), 1.41-1.45 (m), 1.49-1.66 (m), 1.81-1.99 (m), 2.07-2.13 (m), 2.14-2.23 (m), 2.61 (dd, 1H, H13), 2.85 (s, 1H, H7), 2.92 (d, 1H), 3.45 (d, 1H), 3.54 (dd, 1H), 3.66 (d, 1H), 3.71 (d, 1H), 3.83 (d, 1H), 4.03 (d, 1H), 5.63 (dd, 1H, H5), 5.89-5.95 (m, 1H, H14), 7.90 (dd, 1H, ArH), 8.19 (s, 1H, triazole), 8.52 (d, 1H, ArH), 8.86 (d, 1H, ArH).

Mass Spectrum: (ESI) m/z=773.67 (M+H).

Example 181

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

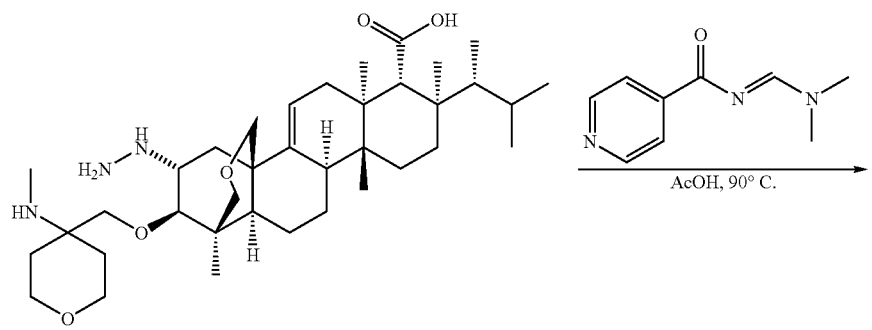

Intermediate 36

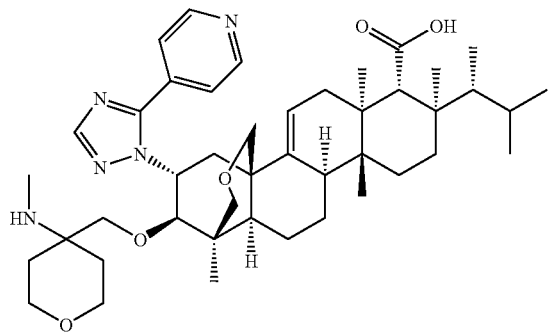

A solution of Intermediate 36 (710 mg, 0.95 mmol) in acetic acid (29 mL) was treated with N-[(1E)-(dimethylamino)methylidene]pyridine-4-carboxamide (186 mg, 1.05 mmol) and this mixture was heated to 90° C. under nitrogen. After 0.5 hours the reaction was cooled to room temperature then concentrated in vacuo. The crude product mixture was suspended in methanol (3 mL) and filtered through a sintered glass funnel. The filtrate was purified by preparative HPLC (19×100 mm Waters Sunfire column, 5 μm, UV-detection, 30-100% MeCN/water with 0.05% TFA over 20 minutes). The product fractions were combined and partially concentrated by rotovap then frozen and lyophilized to give the title compound (500 mg) as a white amorphous solid.

$^1$H NMR (CD$_3$OD, 500 MHz, ppm) δ 0.78 (s, 3H), 0.79 (d, 3H, partially obscured), 0.87 (d, J=6.6 Hz, 3H), 0.91 (d, 3H, partially obscured), 0.92 (s, 3H), 1.17 (s, 3H), 1.21 (s, 3H), 1.23-1.78 (m), 1.84-2.05 (m), 2.12-2.23 (m, 2H), 2.40 (s, 3H), 2.54 (dd, J=13.8, 6.2 Hz, 1H), 2.85 (s, 1H), 2.88 (m, 1H, partially obscured), 3.28-3.36 (m, 2H, partially obscured), 3.43 (d, J=11.2 Hz, 1H), 3.50 (d, J=12.1 Hz, 1H), 3.56 (dd, J=11.6, 1.6 Hz, 1H), 3.63 (m, 1H, partially obscured), 3.67 (d, 1H, partially obscured), 3.76-3.86 (m, 3H), 4.20 (d, J=9.6 Hz, 1H), 5.58 (m, 1H), 5.93 (m, 1H), 8.00 (br, 2H), 8.27 (s, 1H), 8.92 (br, 2H).

Mass Spectrum: (ESI) m/z=744.66 (M+H).

Examples 182-200

The following compounds were prepared using methods analogous to those described in the preceding examples:

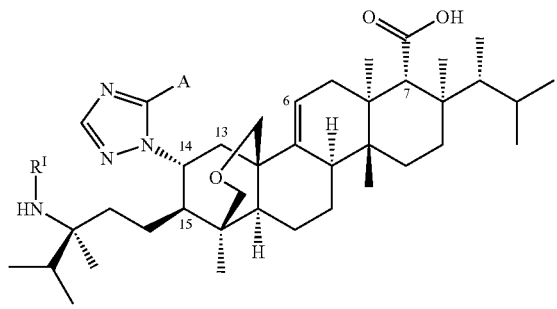

| 182 | $R^I$ = H<br>A = <br>(3-pyridinyl) | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-pridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.77 (s, 3H, Me), 0.77 (d, 3H, Me), 0.78 (s, 3H, Me), 0.80 (d, 3H, Me), 0.83 (d, 3H, Me), 0.86 (d, 3H, Me), 0.86 (s, 3H, Me), 0.90 (d, 3H, Me), 1.17 (s, 3H, Me), 1.21 (s, 3H, Me), 1.22-1.35 (m), 1.40-1.45 (m), 1.49-1.66 (m), 1.68-1.75 (m), 1.81-1.98 (m), 2.05-2.11 (m), 2.13-2.22 (m), 2.55 (dd, 1H, H13), 2.85 (s, 1H, H7), 2.89 (d, 1H), 3.44 (d, 1H), 3.48 (d, 1H), 3.53 (dd, 1H), 3.61 (d, 1H), 3.80 (d, 1H), 4.00 (d, 1H), 5.59 (dd, 1H, H5), 5.80-5.86 (m, 1H, H14), 7.67 (dd, 1H, ArH), 8.17 (s, 1H, triazole), 8.22 (d, 1H, ArH), 8.74 (broad, 1H, ArH), 8.94 (broad, 1H, ArH).
Mass Spectrum: (ESI) m/z = 716.74 (M + H).

| 183 | $R^I$ = Me<br>A = <br>(3-pyridinyl) | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(3-pyridinyl)-1H-1,2,4-triazol-1-yl] 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.74 (s, 3H, Me), 0.77 (s, 3H, Me), 0.77 (d, 3H, Me), 0.81 (d, 3H, Me), 0.83 (d, 3H, Me), 0.85 (d, 3H, Me), 0.88 (s, 3H, Me), 0.90 (d, 3H, Me), 1.17 (s, 3H, Me), 1.21 (s, 3H, Me), 1.23-1.34 (m), 1.40-1.45 (m), 1.49-1.66 (m), 1.81-1.98 (m), 2.02-2.08 (m), 2.13-2.22 (m), 2.37 (s, 3H, NMe), 2.58 (dd, 1H, H13), 2.85 (s, 1H, H7), 2.99 (d, 1H), 3.45 (d, 1H), 3.54 (dd, 1H), 3.63 (d, 1H), 3.64 (d, 1H), 3.76 (d, 1H), 4.08 (d, 1H), 5.60 (dd, 1H, H5), 5.79-5.85 (m, 1H, H14), 7.72 (broad, 1H, ArH), 8.19 (s, 1H, triazole), 8.27 (d, 1H, ArH), 8.79 (broad, 1H, ArH), 8.99 (broad, 1H, ArH).
Mass Spectrum: (ESI) m/z = 730.76 (M + H).

| 184 | $R^I$ = H<br>A = <br>(4-pyridinyl) | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.76 (s, 3H, Me), 0.77 (d, 3H, Me), 0.77 (s, 3H, Me), 0.80 (d, 3H, Me), 0.82 (d, 3H, Me), 0.86 (d, 3H, Me), 0.86 (s, 3H, Me), 0.90 (d, 3H, Me), 1.17 (s, 3H, Me), 1.21 (s, 3H, Me), 1.23-1.35 (m), 1.41-1.45 (m), 1.49-1.66 (m), 1.68-1.75 (m), 1.81-1.98 (m), 2.05-2.11(m), 2.13-2.22 (m), 2.57 (dd, 1H, H13), 2.85 (s, 1H, H7), 2.86 (d, 1H), 3.46 (d, 1H), 3.49 (d, 1H), 3.55 (dd, 1H), 3.66 (d, 1H), 3.82 (d, 1H), 4.00 (d, 1H), 5.60 (dd, 1H, H5), 5.86-5.92 (m, 1H, H14), 7.88 (d, 2H, ArH), 8.20 (s, 1H, triazole), 8.83 (broad d, 2H, ArH).
Mass Spectrum: (ESI) m/z = 716.74 (M + H).

| 185 | $R^I$ = Me<br>A = <br>(4-pyridinyl) | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.72 (s, 3H, Me), 0.77 (d, 3H, Me), 0.77 (s, 3H, Me), 0.81 (d, 3H, Me), 0.83 (d, 3H, Me), 0.86 (d, 3H, Me), 0.88 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.84-1.98 (m), 2.03-2.08 (m), 2.16-2.21 (m), 2.37 (s, 3H, NMe), 2.60 (dd, 1H, H13), 2.85 (s, 1H, H7), 2.95 (d, 1H), 3.47 (d, 1H), 3.56 (dd, 1H), 3.64 (d, 1H), 3.68 (d, 1H), 3.77 (d, 1H), 4.08 (d, 1H), 5.62

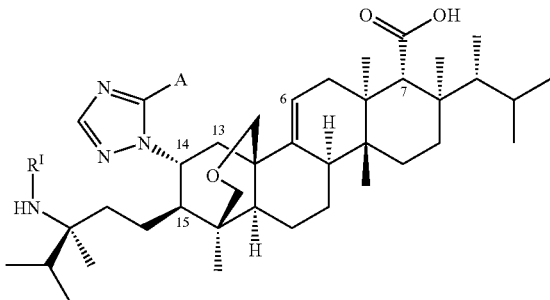

(dd, 1H, H5), 5.88 (m, 1H, H14), 7.90 (br d, 1H, pyridyl H), 8.21 (s, 1H, triazole) and 8.83 (br d, 1H, pyridyl H).
Mass spectrum: (ESI) m/z = 730.76 (M + H).

| 186 | $R^I$ = Me<br>A = <br>*(2-pyridinyl group)* | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.68 (s, 3H, Me), 0.76 (s, 3H, Me), 0.76 (d, 3H, Me), 0.85 (d, 3H, Me), 0.85 (s, 3H, Me), 0.86 (s, 3H, Me), 0.89 (s, 3H, Me), 0.90 (d, 3H, Me), 1.14 (s, 3H, Me), 1.21 (s, 3H, Me), 1.23-1.34 (m), 1.41-1.45 (m), 1.48-1.65 (m), 1.80-1.94 (m), 2.01 (m), 2.12-2.21 (m), 2.29 (s, 3H, NMe), 2.56 (dd, 1H, H13), 2.83 (s, 1H, H7), 3.14 (d, 1H), 3.47 (d, 1H), 3.54 (dd, 1H), 3.60 (d, 1H), 3.65 (d, 1H), 3.82 (d, 1H), 4.16 (d, 1H), 5.44 (dd, 1H, H5), 6.72 (m, 1H, H14), 8.21 (s, 1H, triazole), 7.53 (br d, 1H, pyridyl 14), 8.00 (br d, 1H, pyridyl H), 8.06 (br d, 1H, pyridyl H), 8.12 (br d, 1H, pyridyl H) and 8.86 (br d, 1H, pyridyl H).
Mass spectrum: (ESI) m/z = 730.51 (M + H).

| 187 | $R^I$ = H<br>A = <br>*(pyrazinyl group)* | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-pyrazinyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.67 (s, 3H, Me), 0.76 (d, 3H, Me), 0.77 (s, 3H, Me), 0.79 (d, 3H, Me), 0.80 (d, 3H, Me), 0.85 (d, 3H, Me), 0.88 (s, 3H, Me), 0.89 (d, 3H, Me), 1.14 (s, 3H, Me), 1.20 (s, 3H, Me), 1.22-1.37 (m), 1.40-1.45 (m), 1.48-1.55 (m), 1.58-1.65 (m), 1.69-1.76 (m), 1.81-1.95 (m), 2.12-2.22 (m), 2.58 (dd, 1H, H13), 2.83 (s, 1H, H7), 2.98 (d, 1H), 3.47 (d, 1H), 3.52 (d, 1H), 3.56 (dd, 1H), 3.64 (d, 1H), 3.86 (d, 1H), 4.08 (d, 1H), 5.46 (dd, 1H, H5), 6.68-6.74 (m, 1H, H14), 8.16 (s, 1H, triazole), 8.72 (d, 1H, ArH), 8.78 (dd, 1H, ArH), 9.28 (d, 1H, ArH).
Mass Spectrum: (ESI) m/z = 717.72 (M + H).

| 188 | $R^I$ = H<br>A = <br>*(4-pyridazinyl group)* | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridazinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.74 (s, 3H, Me), 0.79 (d, 3H, Me), 0.80 (s, 3H, Me), 0.82 (d, 3H, Me), 0.85 (d, 3H, Me), 0.88 (d, 3H, Me), 0.90 (s, 3H, Me), 0.92 (d, 3H, Me), 1.19 (s, 3H, Me), 1.23 (s, 3H, Me), 1.24-1.38 (m), 1.43-1.48 (m), 1.50-1.69 (m), 1.70-1.79 (m), 1.83-2.01 (m), 2.07-2.14 (m), 2.16-2.25 (m), 2.64 (dd, 1H, H13), 2.87 (s, 1H, H7), 2.87 (d, 1H), 3.50 (d, 1H), 3.53 (d, 1H), 3.58 (dd, 1H), 3.70 (d, 1H), 3.85 (d, 1H), 4.04 (d, 1H), 5.62 (dd, 1H, H5), 5.85-5.92 (m, 1H, H14), 8.11 (dd, 1H, ArH), 8.27 (s, 1H, triazole), 9.47 (d, 1H, ArH), 9.62 (broad d, 1H, ArH).
Mass Spectrum: (ESI) m/z = 717.73 (M + H).

| 189 | $R^I$ = H<br>A = <br>*(3-pyridazinyl group)* | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-pyridazinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.68 (s, 3H, Me), 0.76 (s, 3H, Me), 0.77 (d, 3H, Me), 0.81 (d, 3H, Me), 0.83 (d, 3H, Me), 0.85 (d, 3H, Me), 0.89 (d, 3H, Me), 0.89 (s, 3H, Me), 1.14 (s, 3H, Me), 1.20 (s, 3H, Me), 1.22-1.35 (m), 1.40-1.44 (m), 1.48-1.54 (m), 1.58-1.65 (m), 1.75-1.95 (m), 2.12-2.22 (m), 2.58 (dd, 1H, H13), 2.83 (s, 1H, H7), 3.01 (d, 1H), 3.44 (d, 1H), 3.50 (dd, 1H), 3.57 (d, 1H), 3.63 (d, 1H), 3.87 (d, 1H), 4.12 (d, 1H), 5.46 (dd, 1H, H5), 6.55-

-continued

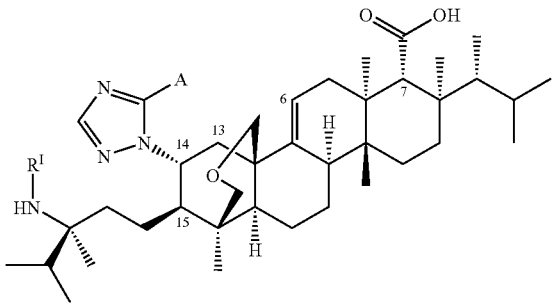

6.61 (m, 1H, H14), 7.94 (dd, 1H, ArH), 8.19 (s, 1H, triazole), 8.30 (dd, 1H, ArH), 9.33 (dd, 1H, ArH).
Mass Spectrum: (ESI) m/z = 717.72 (M + H).

| | | |
|---|---|---|
| 190 | $R^I$ = H<br>A = 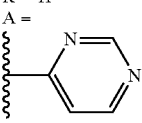 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.67 (s, 3H, Me), 0.79 (d, 3H, Me), 0.80 (s, 3H, Me), 0.81 (d, 3H, Me), 0.82 (d, 3H, Me), 0.88 (d, 3H, Me), 0.91 (s, 3H, Me), 0.92 (d, 3H, Me), 1.17 (s, 3H, Me), 1.22 (s, 3H, Me), 1.24-1.39 (m), 1.42-1.48 (m), 1.50-1.58 (m), 1.61-1.69 (m), 1.70-1.78 (m), 1.83-1.98 (m), 2.14-2.25 (m), 2.62 (dd, 1H, H13), 2.86 (s, 1H, H7), 2.98 (d, 1H), 3.52 (d, 1H), 3.54 (d, 1H), 3.60 (dd, 1H), 3.70 (d, 1H), 3.92 (d, 1H), 4.11 (d, 1H), 5.50 (dd, 1H, H5), 6.94-7.01 (m, 1H, H14), 8.17 (dd, 1H, ArH), 8.19 (s, 1H, triazole), 9.01 (d, 1H, ArH), 9.36 (d, 1H, ArH).
Mass Spectrum: (ESI) m/z = 717.74 (M + H).

| | | |
|---|---|---|
| 191 | $R^I$ = H<br>A = 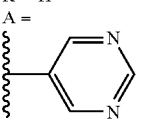 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(5-pyrimdinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 6H, 2Me), 0.77 (d, 3H, Me), 0.81 (d, 3H, Me), 0.83 (d, 3H, Me), 0.86 (d, 3H, Me), 0.87 (s, 3H, Me), 0.90 (d, 3H, Me), 1.17 (s, 3H, Me), 1.21 (s, 3H, Me), 1.22-1.35 (m), 1.40-1.45 (m), 1.48-1.66 (m), 1.69-1.76 (m), 1.81-1.97 (m), 2.04-2.11 (m), 2.13-2.22 (m), 2.57 (dd, 1H, H13), 2.84 (s, 1H, H7), 2.88 (d, 1H), 3.46 (d, 1H), 3.50 (d, 1H), 3.54 (dd, 1H), 3.61 (d, 1H), 3.82 (d, 1H), 4.01 (d, 1H), 5.58 (dd, 1H, H5), 5.77-5.83 (m, 1H, H14), 8.21 (s, 1H, triazole), 9.19 (s, 2H, ArH), 9.34 (s, 1H, ArH).
Mass Spectrum: (ESI) m/z = 717.79 (M + H).

| | | |
|---|---|---|
| 192 | $R^I$ = H<br>A = 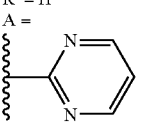 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.68 (s, 3H, Me), 0.76 (d, 3H, Me), 0.77 (s, 3H, Me), 0.78 (d, 3H, Me), 0.81 (d, 3H, Me), 0.85 (d, 3H, Me), 0.87 (s, 3H, Me), 0.89 (d, 3H, Me), 1.15 (s, 3H, Me), 1.20 (s, 3H, Me), 1.22-1.36 (m), 1.40-1.45 (m), 1.48-1.56 (m), 1.58-1.65 (m), 1.68-1.75 (m), 1.81-1.97 (m), 2.12-2.22 (m), 2.63 (dd, 1H, H13), 2.84 (s, 1H, H7), 2.88 (d, 1H), 3.46 (d, 1H), 3.49 (d, 1H), 3.56 (dd, 1H), 3.66 (d, 1H), 3.84 (d, 1H), 4.03 (d, 1H), 5.49 (dd, 1H, H5), 6.68-6.74 (m, 1H, H14), 7.58 (t, 1H, ArH), 8.17 (s, 1H, triazole), 9.00 (d, 2H, ArH).
Mass Spectrum: (ESI) m/z = 717.76 (M + H).

| | | |
|---|---|---|
| 193 | $R^I$ = H<br>A = 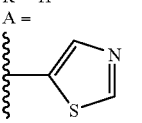 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(5-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

1H NMR (CD$_3$OD, 600 MHz, ppm) δ 0.74 (s, 3H, Me), 0.77 (d, 3H, Me), 0.77 (s, 3H, Me), 0.78 (d, 3H, Me), 0.80 (d, 3H, Me), 0.85 (d, 3H, Me), 0.88 (s, 3H, Me), 0.90 (d, 3H, Me), 1.16 (s, 3H, Me), 1.21 (s, 3H, Me), 1.22-1.36 (m), 1.40-1.45 (m), 1.48-1.66 (m), 1.66-1.73 (m), 1.82-1.97 (m), 1.97-2.04 (m), 2.13-2.22 (m), 2.49 (dd, 1H, H13), 2.84 (s, 1H, H7), 2.92 (d, 1H), 3.49 (d, 1H), 3.50 (d, 1H), 3.58 (dd, 1H), 3.67 (d, 1H), 3.90 (d, 1H), 4.00 (d, 1H), 5.54 (dd, 1H, H5), 6.00-6.06 (m, 1H, H14), 8.11 (s, 1H, triazole), 8.42 (s, 1H, thiazole), 9.24 (s, 1H, thiazole).

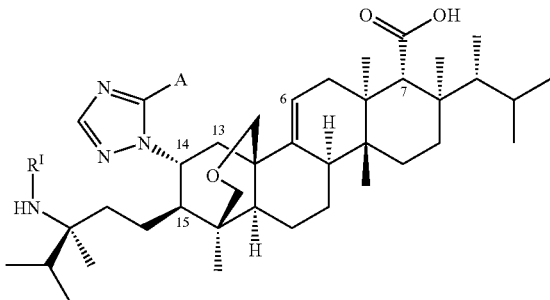

Mass Spectrum: (ESI) m/z = 722.74 (M + H).

| 194 | R¹ = H  A = 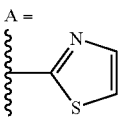 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.68 (s, 3H, Me), 0.79 (d, 3H, Me), 0.79 (s, 3H, Me), 0.80 (d, 3H, Me), 0.82 (d, 3H, Me), 0.87 (d, 3H, Me), 0.91 (s, 3H, Me), 0.92 (d, 3H, Me), 1.17 (s, 3H, Me), 1.22 (s, 3H, Me), 1.24-1.39 (m), 1.42-1.47 (m), 1.50-1.57 (m), 1.61-1.68 (m), 1.69-1.77 (m), 1.83-1.97 (m), 2.14-2.25 (m), 2.52 (dd, 1H, H13), 2.86 (m, 1H, H7), 2.97 (d, 1H), 3.51 (d, 1H), 3.54 (d, 1H), 3.58 (dd, 1H), 3.67 (d, 1H), 3.96 (d, 1H), 4.07 (d, 1H), 5.47 (dd, 1H, H5), 6.93-7.00 (m, 1H, H14), 7.86 (d, 1H, thiazole), 8.06 (d, 1H, thiazole), 8.10 (s, 1H, triazole).
Mass Spectrum: (ESI) m/z = 722.74 (M + H).

| 195 | R¹ = H  A = 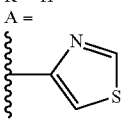 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14- [5-(4-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.71 (s, 3H, Me), 0.79 (s, 3H, Me), 0.79 (d, 3H, Me), 0.81 (d, 3H, Me), 0.83 (d, 3H, Me), 0.88 (d, 3H, Me), 0.90 (s, 3H, Me), 0.92 (d, 3H, Me), 1.17 (s, 3H, Me), 1.22 (s, 3H, Me), 1.24-1.38 (m), 1.42-1.47 (m), 1.50-1.58 (m), 1.60-1.68 (m), 1.70-1.79 (m), 1.82-1.98 (m), 2.13-2.25 (m), 2.52 (dd, 1H, H13), 2.86 (s, 1H, H7), 2.96 (d, 1H), 3.49 (d, 1H), 3.53 (d, 1H), 3.56 (dd, 1H), 3.64 (d, 1H), 3.91 (d, 1H), 4.04 (d, 1H), 5.48 (dd, 1H, H5), 6.65-6.72 (m, 1H, H14), 8.11 (s, 1H, triazole), 8.29 (s, 1H, thiazole), 9.20 (s, 1H, thiazole).
Mass Spectrum: (ESI) m/z = 722.59 (M + H).

| 196 | R¹ = H  A = 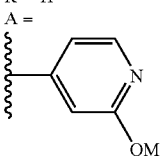 | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.77 (d, 3H, Me), 0.77 (s, 3H, Me), 0.78 (s, 3H, Me), 0.80 (d, 3H, Me), 0.82 (d, 3H, Me), 0.86 (d, 3H, Me), 0.86 (s, 3H, Me), 0.90 (d, 3H, Me), 1.17 (s, 3H, Me), 1.21 (s, 3H, Me), 1.23-1.35 (m), 1.41-1.45 (m), 1.49-1.66 (m), 1.67-1.73 (m), 1.80-1.98 (m), 2.03-2.09 (m), 2.13-2.22 (m), 2.53 (dd, 1H, H13), 2.85 (s, 1H, H7), 2.86 (d, 1H), 3.45 (d, 1H), 3.46 (d, 1H), 3.55 (dd, 1H), 3.60 (d, 1H), 3.81 (d, 1H), 3.97 (s, 3H, OMe), 3.98 (d, 1H), 5.58 (dd, 1H, H5), 5.86-5.92 (m, 1H, H14), 7.11 (d, 1H, ArH), 7.28 (dd, 1H, ArH), 8.15 (s, 1H, triazole), 8.34 (d, 1H, ArH).
Mass Spectrum: (ESI m/z = 746.90 (M + H).

| 197 | R¹ = H  A = 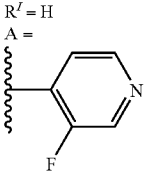 | (1S,4aR,6aS,7R,8R,10aR,10bR,12aR,14R,15R)-15-[[(2R)-2-amino-2,3-dimethylbutyl]oxy]-14-[5-(3-fluoro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.77 (s, 3H, Me), 0.77 (d, 3H, Me), 0.82 (d, 3H, Me), 0.82 (s, 3H, Me), 0.85 (d, 3H, Me), 0.85 (d, 3H, Me), 0.85 (d, 3H, Me), 0.90 (d, 3H, Me), 1.17 (s, 3H, Me), 1.21 (s, 3H, Me), 1.23-1.34 (m), 1.40-1.45 (m), 1.49-1.66 (m), 1.69-1.76 (m), 1.79-1.91 (m), 1.93-1.98 (m), 2.00-2.06 (m), 2.13-2.22 (m), 2.54 (dd, 1H, H13), 2.85 (s, 1H, H7), 2.88 (d, 1H), 3.43 (d, 1H), 3.47 (d, 1H), 3.52 (dd, 1H), 3.56 (d, 1H), 3.76 (d, 1H), 3.98 (d, -continued

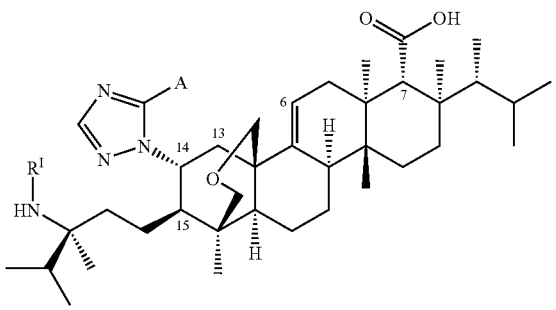

1H), 5.53 (dd, 1H, H5), 5.53-5.59 (m, 1H, H14), 7.72 (t, 1H, ArH), 8.24 (s, 1H, triazole), 8.65 (broad, 1H, ArH), 8.78 (broad, 1H, ArH).

Mass Spectrum: (ESI) m/z = 734.61 (M + H).

198  $R^I$ = H
A = 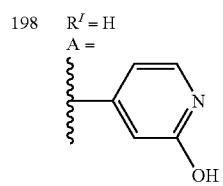

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-hydroxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid $^1$H NMR (CD$_3$OD, 500 MHz, ppm) δ 0.78 (s, 3H, Me), 0.79 (d, 3H, Me), 0.82 (d, 3H, Me), 0.83 (s, 3H, Me), 0.86 (d, 3H, Me), 0.88 (d, 3H, Me), 0.90 (s, 3H, Me), 0.92 (d, 3H, Me), 1.18 (s, 3H, Me), 1.23 (s, 3H, Me), 1.24-1.38 (m), 1.42-1.47 (m), 1.50-1.68 (m), 1.72-1.80 (m), 1.82-2.00 (m), 2.02-2.10 (m), 2.14-2.25 (m), 2.48 (dd, 1H, H13), 2.86 (s, 1H, H7), 2.88 (d, 1H), 3.49 (d, 1H), 3.52 (d, 1H), 3.54 (dd, 1H), 3.67 (d, 1H), 3.91 (d, 1H), 4.00 (d, 1H), 5.58 (dd, 1H, H5), 5.88-5.95 (m, 1H, H14), 6.70 (dd, 1H, ArH), 6.92 (d, 1H, ArH), 7.66 (d, 1H, ArH), 8.17 (s, 1H, triazole).

Mass Spectrum: (ESI) m/z = 732.51 (M + H).

199  $R^I$ = H
A = 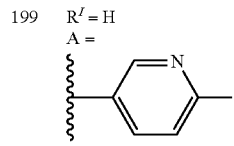

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(6-hydroxy-3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid $^1$H NMR (CD$_3$OD, 500 MHz, ppm) δ 0.78 (s, 3H, Me), 0.79 (d, 3H, Me), 0.82 (d, 3H, Me), 0.83 (s, 3H, Me), 0.86 (d, 3H, Me), 0.88 (d, 3H, Me), 0.90 (s, 3H, Me), 0.92 (d, 3H, Me), 1.18 (s, 3H, Me), 1.23 (s, 3H, Me), 1.24-1.38 (m), 1.42-1.47 (m), 1.50-1.68 (m), 1.72-1.80 (m), 1.82-2.00 (m), 2.02-2.10 (m), 2.14-2.25 (m), 2.48 (dd, 1H, H13), 2.86 (s, 1H, H7), 2.88 (d, 1H), 3.49 (d, 1H), 3.52 (d, 1H), 3.54 (dd, 1H), 3.67 (d, 1H), 3.91 (d, 1H), 4.00 (d, 1H), 5.58 (dd, 1H, H5), 5.88-5.95 (m, 1H, H14), 6.70 (dd, 1H, ArH), 6.92 (d, 1H, ArH), 7.66 (d, 1H, ArH), 8.17 (s, 1H, triazole).

Mass Spectrum: (ESI) m/z = 732.51 (M + H).

200  $R^I$ = H
A = 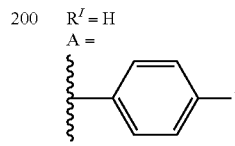

(1S,4aR,6aS,7R,8R,10aR,10bR,12aR,14R,15R)-15-[[(2R)-2-amino-2,3-dimethylbutyl]oxy]-14-[5-(4-aminophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid $^1$H NMR (MeOH-d$_4$, 500 MHz, ppm, selected resonances) δ 2.83 (s, 1H), 5.50 (m, 1H), 5.90 (m, 1H), 6.80 (d, 2H), 7.42 (d, 2H), 8.02 (s, 1H).

Mass Spectrum: (ESI) m/z = 731 (M + H).

Examples 201-239

The following compounds were prepared using methods analogous to those described in the preceding examples:

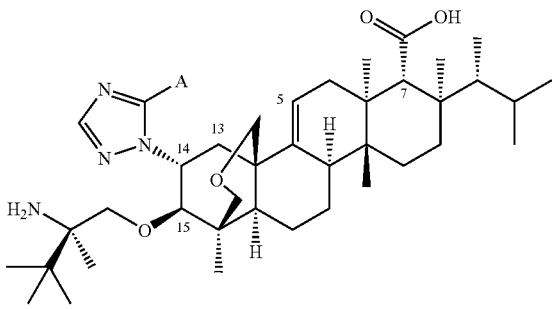

| 201 | A= 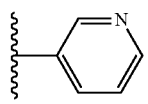 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.77 (s, 3H, Me), 0.77 (d, 3H, Me), 0.77 (s, 3H, Me), 0.86 (s, 9H, Me), 0.86 (d, 3H, Me), 0.87 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.82-1.98 (m), 2.06-2.11 (m), 2.14-2.21 (m), 2.59 (dd, 1H, H13), 2.85 (s, 1H, H7), 2.91 (d, 1H), 3.44 (d, 1H), 3.54 (dd, 1H), 3.63 (d, 1H), 3.65 (d, 1H), 3.81 (d, 1H), 4.02 (d, 1H), 5.61 (dd, 1H, H5), 5.82 (m, 1H, H14), 7.74 (br d, 1H, pyridyl H), 8.18 (s, 1H, triazole), 8.28 (d, 1H, pyridyl H), 8.82 (br d, 1H, pyridyl H) and 9.02 (br d, 1H, pyridyl H).
Mass spectrum: (ESI) m/z = 730.71 (M + H).

| 202 | A = 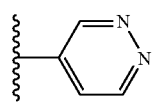 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridazinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.71 (s, 3H, Me), 0.77 (d, 3H, Me), 0.77 (s, 3H, Me), 0.85 (s, 9H, Me), 0.85 (d, 3H, Me), 0.88 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.82-1.98 (m), 2.06-2.11(m), 2.14-2.21 (m), 2.56 (dd, 1H, H13), 2.85 (s, 1H, H7), 2.87 (d, 1H), 3.48 (d, 1H), 3.57 (dd, 1H), 3.66 (d, 1H), 3.70 (d, 1H), 3.82 (d, 1H), 4.03 (d, 1H), 5.63 (dd, 1H, H5), 5.85 (m, 1H, H14), 8.08 (dd, 1H, pyridazinyl H), 8.24 (s, 1H, triazole), 9.46 (br d, 1H, pyridazinyl H) and 9.60 (br d, 1H, pyridazinyl H).
Mass spectrum: (ESI) m/z = 731.50 (M + H).

| 203 | A = 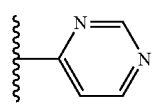 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.64 (s, 3H, Me), 0.76 (d, 3H, Me), 0.77 (s, 3H, Me), 0.82 (s, 9H, t-bu), 0.85 (d, 3H, Me), 0.89 (d, 3H, Me), 0.90 (s, 3H, Me), 1.14 (s, 3H, Me), 1.20 (s, 3H, Me), 1.22-1.37 (m), 1.40-1.45 (m), 1.48-1.55 (m), 1.58-1.65 (m), 1.81-1.96 (m), 2.12-2.22 (m), 2.62 (dd, 1H, H13), 2.83 (s, 1H, H7), 2.99 (d, 1H), 3.49 (d, 1H), 3.58 (dd, 1H), 3.68 (d, 1H), 3.69 (d, 1H), 3.90 (d, 1H), 4.10 (d, 1H), 5.48 (dd, 1H, H5), 6.93-6.99 (m, 1H, H14), 8.15 (dd, 1H, ArH), 8.17 (s, 1H, triazole), 8.99 (d, 1H, ArH), 9.34 (d, 1H, ArH).
Mass Spectrum: (ESI) m/z = 731.59 (M + H).

| 204 | A = 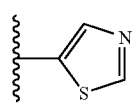 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(5-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.73 (s, 3H, Me), 0.76 (d, 3H, Me), 0.77 (s, 3H, Me), 0.84 (s, 9H, Me), 0.85 (d, 3H, Me), 0.89 (s, 3H, Me), 0.89 (d, 3H, Me), 1.16 (s, 3H, Me), 1.21 (s, 3H, Me), 1.23-1.34 (m), 1.41-1.45 (m), 1.48-1.65 (m), 1.84-2.03 (m), 2.14-2.21 (m), 2.51 (dd, 1H, H13), 2.84 (s, 1H, H7), 2.95 (d, 1H), 3.50 (d, 1H), 3.59 (dd, 1H), 3.64 (d, 1H), 3.69 (d, 1H), 3.91 (d, 1H), 4.02 (d, 1H), 5.56 (dd, 1H, H5), 6.03 (m, 1H, H14), 8.11 (s, 1H, triazole), 8.42 (br d, 1H, thiazolyl H) and 9.23 (br d, 1H, thiazolyl H).
Mass spectrum: (ESI) m/z = 736.64 (M + H).

-continued

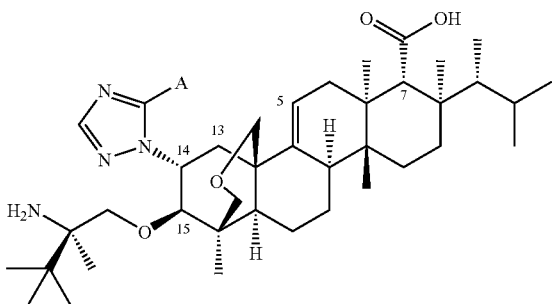

| 205 | A = 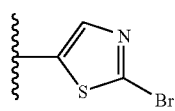 | (1S,4aR,6aS,7R,8R,10aR,10bR,12aR,14R,15R)-15-[[(2R)-2-amino-2,3,3-trimethylbutyl]oxy]-14-[5-(2-bromo-5-thiazolyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

Mass spectrum: (ESI) m/z = 815 (M + H).

| 206 | A = 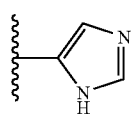 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1H-imidazol-4-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.72 (s, 3H, Me), 0.78 (s, 3H, Me), 0.79 (d, 3H, Me), 0.87 (d, 3H, Me), 0.88 (s, 9H, Me), 0.92 (d, 3H, Me), 0.93 (s, 3H, Me), 1.16 (s, 3H, Me), 1.22 (s, 3H, Me), 1.23-1.34 (m), 1.42-1.46 (m), 1.48-1.68 (m), 1.82-1.97 (m), 2.12-2.24 (m), 2.39 (dd, 1H, H13), 2.85 (s, 1H, H7), 3.00 (d, 1H), 3.50 (d, 1H), 3.54 (dd, 1H), 3.61 (d, 1H), 3.77 (d, 1H), 3.98 (d, 1H), 4.03 (d, 1H), 5.47 (dd, 1H, H5), 6.51 (m, 1H, H14), 7.74 (d, 1H, imidazolyl H), 8.03 (d, 1H, imidazolyl H) and 8.06 (br d, 1H, triazole H).
Mass spectrum: (ESI) m/z = 719.51 (M + H).

| 207 | A = 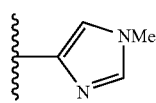 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-1H-imidazol-4-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.71 (s, 3H, Me), 0.78 (s, 3H, Me), 0.79 (d, 3H, Me), 0.87 (d, 3H, Me), 0.88 (s, 9H, Me), 0.92 (d, 3H, Me), 0.93 (s, 3H, Me), 1.16 (s, 3H, Me), 1.22 (s, 3H, Me), 1.23-1.34 (m), 1.41-1.46 (m), 1.48-1.68 (m), 1.82-1.97 (m), 2.12-2.24 (m), 2.35 (dd, 1H, H13), 2.85 (s, 1H, H7), 3.01 (d, 1H), 3.49 (d, 1H), 3.53 (dd, 1H), 3.58 (d, 1H), 3.76 (d, 1H), 3.84 (s, 3H, NMe), 3.98 (d, 1H), 4.03 (d, 1H), 5.45 (dd, 1H, H5), 6.56 (m, 1H, H14), 7.67 (dd, 1H, imidazolyl H), 7.85 (d, 1H, imidazolyl H) and 8.03 (br d, 1H, triazole H).
Mass spectrum: (ESI) m/z = 733.54 (M + H).

| 208 | 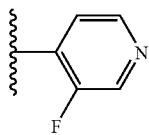 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (s, 3H, Me), 0.77 (d, 3H, Me), 0.82 (s, 3H, Me), 0.86 (s, 9H, Me), 0.86 (d, 3H, Me), 0.87 (s, 3H, Me), 0.90 (d, 3H, Me), 1.18 (s, 3H, Me), 1.22 (s, 3H, Me), 1.25-1.36 (m), 1.41-1.45 (m), 1.50-1.66 (m), 1.82-2.00 (m), 2.02-2.07 (m), 2.16-2.22 (m), 2.58 (dd, 1H, H13), 2.85 (s, 1H, H7), 2.88 (d, 1H), 3.43 (d, 1H), 3.54 (dd, 1H), 3.59 (d, 1H), 3.63 (d, 1H), 3.77 (d, 1H), 4.00 (d, 1H), 5.56 (dd, 1H, H5), 5.57 (m, 1H, H14), 7.72 (dd, 1H, pyridyl H), 8.25 (s, 1H, triazole), 8.66 (d, 1H, pyridyl H) and 8.76 (d, 1H, pyridyl H).
Mass spectrum: (ESI) m/z = 748.55 (M + H).

| 209 | A = 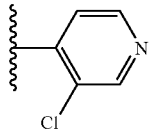 | (1S,4aR,6aS,7R,8R,10aR,10bR,12aR,14R,15R)-15-[[(2R)-2-amino-2,3,3-trimethylbutyl]oxy]-14-[5-(3-chloro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

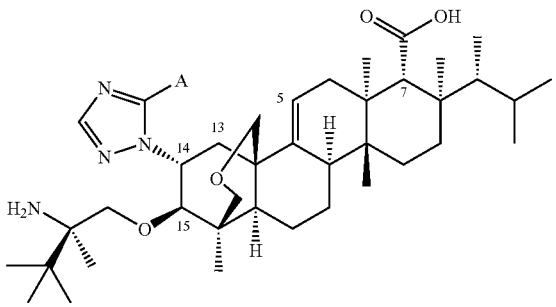

¹H NMR (CD₃OD, 600 MHz, ppm) δ 0.75 (s, 3H, Me), 0.76 (d, 3H, Me), 0.85 (d, 3H, Me), 0.89 (d, 3H, Me), 0.89 (s, 3H, Me), 0.90 (s, 9H, Me), 0.93 (s, 3H, Me), 1.15 (s, 3H, Me), 1.21 (s, 3H, Me), 1.22-1.31 (m), 1.39-1.44 (m), 1.50-1.64 (m), 1.80-1.96 (m), 2.10-2.21 (m), 2.48 (dd, 1H, H13), 2.84 (s, 1H, H7), 3.18 (d, 1H), 3.42 (d, 1H), 3.48 (dd, 1H), 3.70 (d, 1H), 3.78 (d, 1H), 4.09 (d, 1H), 5.47 (dd, 1H, H5), 5.50 (m, 1H, H14), 7.62 (dd, 1H, pyridyl H), 8.23 (s, 1H, triazole), 8.71 (d, 1H, pyridyl H) and 8.86 (s, 1H, pyridyl H).

| 210 | A = 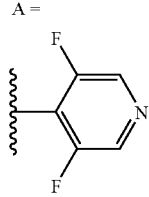 | (1S,4aR,6aS,7R,8R,10aR,10bR,12aR,14R,15R)-15-[[(2R)-2-amino-2,3,3-trimethylbutyl]oxy]-14-[5-(3,5-difluoro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 3H, Me), 0.86 (d, 3H, Me), 0.87 (s, 3H, Me), 0.87 (s, 9H, Me), 0.87 (s, 3H, Me), 0.90 (d, 3H, Me), 1.16 (s, 3H, Me), 1.21 (s, 3H, Me), 1.23-1.34 (m), 1.40-1.45 (m), 1.48-1.65 (m), 1.80-1.98 (m), 2.14-2.21 (m), 2.49 (dd, 1H, H13), 2.84 (d, 1H), 2.99 (s, 1H, H7), 3.42 (d, 1H), 3.55 (dd, 1H), 3.55 (d, 1H), 3.64 (d, 1H), 3.78 (d, 1H), 4.05 (d, 1H), 5.43 (m, 1H, H14), 5.45 (dd, 1H, H5), 8.31 (s, 1H, triazole) and 8.71 (br d, 2H, pyridyl H).
Mass spectrum: (ESI) m/z = 766.43 (M + H).

| 211 | A = 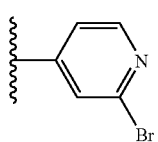 | (1S,4aR,6aS,7R,8R,10aR,10bR,12aR,14R,15R)-15-[[(2R)-2-amino-2,3,3-trimethylbutyl]oxy]-14-[5-(2-bromo-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.75 (s, 3H, Me), 0.76 (d, 3H, Me), 0.85 (d, 3H, Me), 0.89 (d, 3H, Me), 0.89 (s, 3H, Me), 0.90 (s, 9H, Me), 0.93 (s, 3H, Me), 1.15 (s, 3H, Me), 1.21 (s, 3H, Me), 1.22-1.31 (m), 1.39-1.44 (m), 1.50-1.64 (m), 1.80-1.96 (m), 2.10-2.21 (m), 2.48 (dd, 1H, H13), 2.84 (s, 1H, H7), 3.18 (d, 1H), 3.42 (d, 1H), 3.48 (dd, 1H), 3.70 (d, 1H), 3.78 (d, 1H), 4.09 (d, 1H), 5.47 (dd, 1H, H5), 5.50 (m, 1H, H14), 7.62 (dd, 1H, pyridyl H), 8.23 (s, 1H, triazole), 8.71 (d, 1H, pyridyl H) and 8.86 (s, 1H, pyridyl H).

| 212 | A = 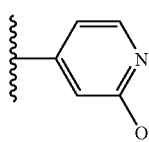 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.76 (d, 3H, Me), 0.77 (s, 3H, Me), 0.85 (s, 9H, Me), 0.86 (d, 3H, Me), 0.87 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.82-1.98 (m), 2.06-2.10 (m), 2.14-2.21 (m), 2.56 (dd, 1H, H13), 2.85 (s, 1H, H7), 2.87 (d, 1H), 3.45 (d, 1H), 3.58 (dd, 1H), 3.62 (d, 1H), 3.63 (d, 1H), 3.82 (d, 1H), 3.97 (s, 3H, OMe), 4.00 (d, 1H), 5.60 (dd, 1H, H5), 5.89 (m, 1H, H14), 7.10 (d, 1H, pyridyl H), 7.28 (dd, 1H, pyridyl H), 8.15 (s, 1H, triazole) and 8.34 (d, 1H, pyridyl H).
Mass spectrum: (ESI) m/z = 760.53 (M + H).

| 213 | A = 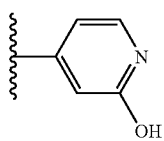 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2-hydroxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

-continued

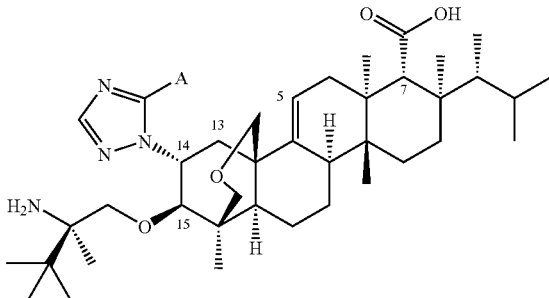

¹H NMR (CD₃OD, 600 MHz, ppm) δ 0.79 (s, 3H, Me), 0.79 (d, 3H, Me), 0.82 (s, 3H, Me), 0.88 (s, 9H, Me), 0.88 (d, 3H, Me), 0.91 (s, 3H, Me), 0.92 (d, 3H, Me), 1.19 (s, 3H, Me), 1.23 (s, 3H, Me), 1.23-1.36 (m), 1.42-1.46 (m), 1.48-1.68 (m), 1.84-2.00 (m), 2.04-2.10 (m), 2.14-2.24 (m), 2.53 (dd, 1H, H13), 2.87 (s, 1H, H7), 2.89 (d, 1H), 3.49 (d, 1H), 3.56 (dd, 1H), 3.68 (d, 1H), 3.70 (d, 1H), 3.91 (d, 1H), 4.03 (d, 1H), 5.61 (dd, 1H, H5), 5.91 (m, 1H, H14), 6.70 (d, 1H, pyridyl H), 6.91 (d, 1H, pyridyl H), 7.65 (dd, 1H, pyridyl H) and 8.17 (s, 1H, triazole).

| 214 | A = 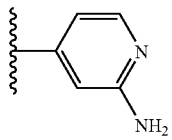 | (1S,4aR,6aS,7R,8R,10aR,10bR,12aR,14R,15R)-14-[5-(2-amino-4-pyridinyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 600 MHz, ppm) δ 0.79 (s, 3H, Me), 0.79 (d, 3H, Me), 0.80 (s, 3H, Me), 0.88 (s, 9H, Me), 0.88 (d, 3H, Me), 0.91 (s, 3H, Me), 0.92 (d, 3H, Me), 1.19 (s, 3H, Me), 1.23 (s, 3H, Me), 1.23-1.34 (m), 1.43-1.48 (m), 1.48-1.69 (m), 1.84-2.01 (m), 2.03-2.10 (m), 2.15-2.24 (m), 2.54 (dd, 1H, H13), 2.87 (s, 1H, H7), 2.93 (d, 1H), 3.50 (d, 1H), 3.58 (dd, 1H), 3.66 (d, 1H), 3.69 (d, 1H), 3.89 (d, 1H), 4.02 (d, 1H), 5.61 (dd, 1H, H5), 5.75 (m, 1H, H14), 7.18 (d, 1H, pyridyl H), 8.16 (s, 1H, triazole), 8.18 (dd, 1H, pyridyl H) and 8.31 (d, 1H, pyridyl H).
Mass spectrum: (ESI) m/z = 745.55 (M + H).

| 215 | A = 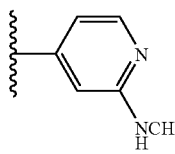 | (1S,4aR,6aS,7R,8R,10aR,10bR,12aR,14R,15R)-15-[[(2R)-2-amino-2,3,3-trimethylbutyl]oxy] -8-[(1R)-1,2-dimethylpropyl]-14-[5-[2-(formylamino)-4-pyridinyl]-1H-1,2,4-triazol-1-yl]1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 600 MHz, ppm) δ 0.79 (s, 3H, Me), 0.79 (d, 3H, Me), 0.80 (s, 3H, Me), 0.88 (s, 9H, Me), 0.88 (d, 3H, Me), 0.89 (s, 3H, Me), 0.92 (d, 3H, Me), 1.20 (s, 3H, Me), 1.23 (s, 3H, Me), 1.23-1.34 (m), 1.43-1.48 (m), 1.48-1.69 (m), 1.84-2.01 (m), 2.07-2.13 (m), 2.15-2.24 (m), 2.58 (dd, 1H, H13), 2.87 (s, 1H, H7), 2.91 (d, 1H), 3.47 (d, 1H), 3.58 (dd, 1H), 3.66 (d, 1H), 3.68 (d, 1H), 3.85 (d, 1H), 4.02 (d, 1H), 5.63 (dd, 1H, H5), 5.83 (m, 1H, H14), 7.12 (br d, 1H, pyridyl H), 8.16 (s, 1H, triazole), 8.36 (br d, 1H, pyridyl H), 8.68 (br d, 1H, pyridyl H) and 9.48 (br s, 1H, formyl H).
Mass spectrum: (ESI) m/z = 773.55 (M = H).

| 216 | A = 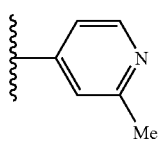 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2-methyl-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 600 MHz, ppm) δ 0.77 (s, 3H, Me), 0.79 (d, 3H, Me), 0.80 (s, 3H, Me), 0.88 (s, 9H, Me), 0.89 (d, 3H, Me), 0.90 (s, 3H, Me), 0.92 (d, 3H, Me), 1.20 (s, 3H, Me), 1.24 (s, 3H, Me), 1.25-1.36 (m), 1.44-1.48 (m), 1.50-1.69 (m), 1.84-2.02 (m), 2.08-2.14 (m), 2.16-2.24 (m), 2.65 (dd, 1H, H13), 2.70 (s, 3H, Me), 2.88 (s, 1H, H7), 2.90 (d, 1H), 3.49 (d, 1H), 3.61 (dd, 1H), 3.66 (d, 1H), 3.69 (d, 1H), 3.84 (d, 1H), 4.04 (d, 1H), 5.66 (dd, 1H, H5), 5.92 (m, 1H, H14), 7.71 (dd, 1H, pyridyl H), 7.76 (br s, 1H, pyridyl H), 8.22 (s, 1H, triazole) and 8.71 (d, 1H, pyridyl H).
Mass spectrum: (ESI) m/z = 744.51 (M + H).

-continued

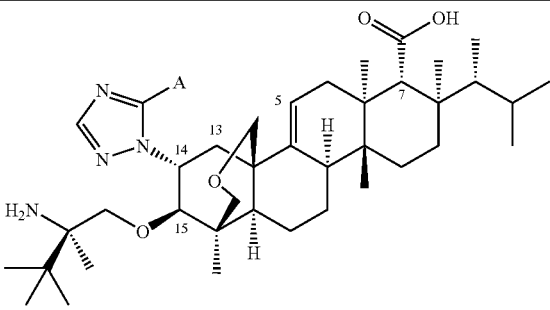

| 217 | A = 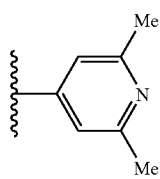 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2,6-dimethyl-4-pyridinyl)-1H-1,2,4-triazol-1-yl] 1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.78 (s, 3H, Me), 0.79 (d, 3H, Me), 0.80 (s, 3H, Me), 0.88 (s, 9H, Me), 0.88 (d, 3H, Me), 0.90 (s, 3H, Me), 0.92 (d, 3H, Me), 1.20 (s, 3H, Me), 1.24 (s, 3H, Me), 1.25-1.34 (m), 1.44-1.46 (m), 1.50-1.69 (m), 1.84-2.02 (m), 2.08-2.14 (m), 2.16-2.24 (m), 2.66 (dd, 1H, H13), 2.74 (s, 6H, Me), 2.88 (s, 1H, H7), 2.91 (d, 1H), 3.50 (d, 1H), 3.62 (dd, 1H), 3.65 (d, 1H), 3.67 (d, 1H), 3.84 (d, 1H), 4.04 (d, 1H), 5.67 (dd, 1H, H5), 5.93 (m, 1H, H14), 7.74 (s, 2H, pyridyl H) and 8.24 (s, 1H, triazole).
Mass spectrum: (ESI) m/z = 758.57 (M + H).

| 218 | A = 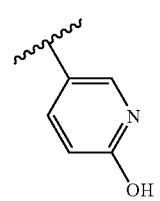 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(6-hydroxy-3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.79 (s, 3H, Me), 0.79 (d, 3H, Me), 0.80 (s, 3H, Me), 0.88 (s, 9H, Me), 0.88 (d, 3H, Me), 0.90 (s, 3H, Me), 0.92 (d, 3H, Me), 1.19 (s, 3H, Me), 1.23 (s, 3H, Me), 1.23-1.34 (m), 1.43-1.48 (m), 1.48-1.69 (m), 1.84-2.01 (m), 2.03-2.10 (m), 2.15-2.24 (m), 2.55 (dd, 1H, H13), 2.87 (s, 1H, H7), 2.90 (d, 1H), 3.50 (d, 1H), 3.59 (dd, 1H), 3.65 (d, 1H), 3.69 (d, 1H), 3.88 (d, 1H), 4.00 (d, 1H), 5.63 (dd, 1H, H5), 5.75 (m, 1H, H14), 6.71 (d, 1H, pyridyl H), 7.85 (d, 1H, pyridyl H), 7.90 (dd, 1H, pyridyl H) and 8.10 (s, 1H, triazole)
Mass spectrum: (ESI) m/z = 746.60 (M + H).

| 219 | A = 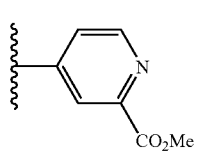 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[2-(methoxycarbonyl)-4-pyridinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

$^1$H NMR (CD$_3$OD, 600 MHz, ppm) δ 0.72 (s, 3H, Me), 0.77 (d, 3H, Me), 0.79 (s, 3H, Me), 0.85 (s, 9H, t-bu), 0.86 (d, 3H, Me), 0.88 (s, 3H, Me), 0.90 (d, 3H, Me), 1.18 (s, 3H, Me), 1.22 (s, 3H, Me), 1.23-1.37 (m), 1.41-1.46 (m), 1.49-1.66 (m), 1.82-1.93 (m), 1.95-2.01 (m), 2.08-2.14 (m), 2.15-2.23 (m), 2.68 (dd, 1H, H13), 2.86 (s, 1H, H7), 2.90 (d, 1H), 3.46 (d, 1H), 3.58 (dd, 1H), 3.64 (d, 1H), 3.72 (d, 1H), 3.79 (d, 1H), 4.02 (s, 3H, COOMe), 4.04 (d, 1H), 5.64 (dd, 1H, H5), 5.85-5.92 (m, 1H, H14), 8.00 (dd, 1H, ArH), 8.21 (s, 1H, triazole), 8.50 (d, 1H, ArH), 8.91 (d, 1H, ArH).
Mass Spectrum: (ESI) m/z = 788.65 (M + H).

| 220 | A = 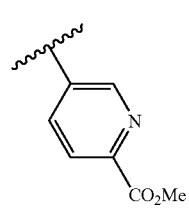 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[6-(methoxycarbonyl)-3-pyridinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

-continued

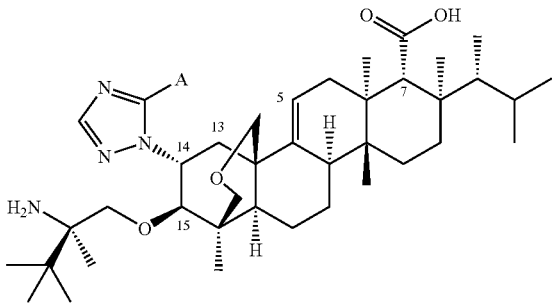

¹H NMR (CD₃OD, 600 MHz, ppm) δ 0.75 (s, 3H, Me), 0.77 (d, 3H, Me), 0.78 (s, 3H, Me), 0.85 (s, 9H, t-bu), 0.86 (d, 3H, Me), 0.87 (s, 3H, Me), 0.90 (d, 3H, Me), 1.18 (s, 3H, Me), 1.21 (s, 3H, Me), 1.23-1.35 (m), 1.41-1.45 (m), 1.49-1.66 (m), 1.81-1.99 (m), 2.07-2.13 (m), 2.14-2.23 (m), 2.62 (dd, 1H, H13), 2.85 (s, 1H, H7), 2.89 (d, 1H), 3.45 (d, 1H), 3.55 (dd, 1H), 3.64 (d, 1H), 3.66 (d, 1H), 3.80 (d, 1H), 4.02 (s, 3H, COOMe), 4.03 (d, 1H), 5.62 (dd, 1H, H5), 5.79-5.85 (m, 1H, H14), 8.21 (s, 1H, triazole), 8.35 (d, 1H, ArH), 8.38 (dd, 1H, ArH), 9.05 (d, 1H, ArH).
Mass Spectrum: (ESI) m/z = 788.68 (M + H).

| 221 | A = 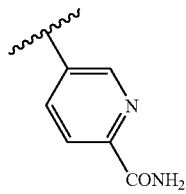 | (1S,4aR,6aS,7R,8R,10aR,10bR,12aR,14R,15R)-14-[5-[6-(aminocarbonyl)-3-pyridinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.75 (s, 3H, Me), 0.77 (d, 3H, Me), 0.78 (s, 3H, Me), 0.85 (s, 9H, t-bu), 0.86 (d, 3H, Me), 0.87 (s, 3H, Me), 0.90 (d, 3H, Me), 1.18 (s, 3H, Me), 1.22 (s, 3H, Me), 1.23-1.36 (m), 1.41-1.46 (m), 1.49-1.66 (m), 1.81-1.99 (m), 2.07-2.23 (m), 2.63 (dd, 1H, H13), 2.85 (s, 1H, H7), 2.89 (d, 1H), 3.45 (d, 1H), 3.56 (dd, 1H), 3.64 (d, 1H), 3.66 (d, 1H), 3.80 (d, 1H), 4.02 (d, 1H), 5.63 (dd, 1H, H5), 5.80-5.86 (m, 1H, H14), 8.20 (s, 1H, triazole), 8.31 (d, 1H, ArH), 8.34 (dd, 1H, ArH), 9.00 (d, 1H, ArH).
Mass Spectrum: (ESI) m/z = 773.60 (M + H).

| 222 | A = 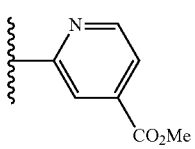 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[4-(methoxycarbonyl)-2-pyridinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.65 (s, 3H, Me), 0.76 (d, 3H, Me), 0.76 (s, 3H, Me), 0.83 (s, 9H, t-bu), 0.85 (d, 3H, Me), 0.89 (d, 3H, Me), 0.90 (s, 3H, Me), 1.14 (s, 3H, Me), 1.20 (s, 3H, Me), 1.22-1.36 (m), 1.40-1.44 (m), 1.47-1.55 (m), 1.58-1.65 (m), 1.80-1.95 (m), 2.11-2.22 (m), 2.62 (dd, 1H, H13), 2.83 (s, 1H, H7), 3.03 (d, 1H), 3.46 (d, 1H), 3.56 (dd, 1H), 3.66 (d, 1H), 3.68 (d, 1H), 3.87 (d, 1H), 3.99 (s, 3H, COOMe), 4.09 (d, 1H), 5.47 (dd, 1H, H5), 6.79-6.85 (m, 1H, H14), 8.00 (broad, 1H, ArH), 8.13 (s, 1H, triazole), 8.57 (broad, 1H, ArH), 8.92 (broad, 1H, ArH).
Mass Spectrum: (ESI) m/z = 788.67 (M + H).

| 223 | A = 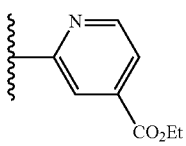 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[4-(ethoxycarbonyl)-2-pyridinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.66 (s, 3H, Me), 0.76 (d, 3H, Me), 0.76 (s, 3H, Me), 0.83 (s, 9H, t-bu), 0.85 (d, 3H, Me), 0.89 (d, 3H, Me), 0.90 (s, 3H, Me), 1.14 (s, 3H, Me), 1.20 (s, 3H, Me), 1.21-1.36 (m), 1.39-1.44 (m), 1.42 (t, 3H), 1.47-1.55 (m), 1.58-1.65 (m), 1.80-1.95 (m), 2.11-2.22 (m), 2.61 (dd, 1H, H13), 2.83 (s, 1H, H7), 3.04 (d, 1H), 3.47 (d, 1H), 3.56 (dd, 1H), 3.66 (d, 1H), 3.68 (d, 1H), 3.87 (d, 1H), 4.09 (d, 1H), 4.45 (q, 2H, COOCH₂), 5.47 (dd, 1H, H5), 6.79-6.85 (m, 1H, H14), 8.00 (broad, 1H, ArH), 8.13 (s, 1H, triazole), 8.58 (broad, 1H, ArH), 8.92 (broad, 1H, ArH).
Mass Spectrum: (ESI) m/z = 802.70 (M + H).

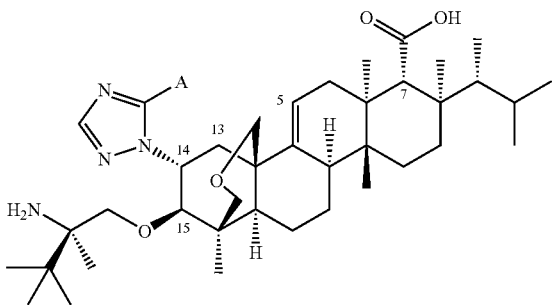

| | | |
|---|---|---|
| 224 | A = 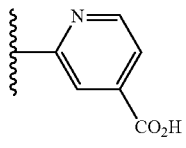 | (1S,4aR,6aS,7R,8R,10aR,10bR,12aR,14R,15R)-15-[[(2R)-2-amino-2,3,3-trimethylbutyl]oxy]-14-[5-(4-carboxy-2-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.67 (s, 3H, Me), 0.77 (d, 3H, Me), 0.77 (s, 3H, Me), 0.85 (s, 9H, t-bu), 0.85 (d, 3H, Me), 0.88 (s, 3H, Me), 0.89 (d, 3H, Me), 1.16 (s, 3H, Me), 1.21 (s, 3H, Me), 1.22-1.36 (m), 1.40-1.45 (m), 1.48-1.66 (m), 1.80-1.97 (m), 2.12-2.22 (m), 2.66 (dd, 1H, H13), 2.84 (s, 1H, H7), 3.00 (d, 1H), 3.43 (d, 1H), 3.54 (dd, 1H), 3.64 (d, 1H), 3.68 (d, 1H), 3.83 (d, 1H), 4.05 (d, 1H), 5.51 (dd, 1H, H5), 6.56-6.64 (m, 1H, H14), 7.89 (broad, 1H, ArH), 8.07 (broad s, 1H, triazole), 8.46 (broad, 1H, ArH), 8.75 (broad, 1H, ArH).
Mass Spectrum: (ESI) m/z = 774.65 (M + H).

| | | |
|---|---|---|
| 225 | A = 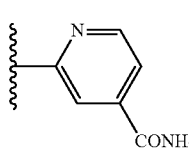 | (1S,4aR,6aS,7R,8R,10aR,10bR,12aR,14R,15R)-14-[5-[4-(aminocarbonyl)-2-pyridinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.67 (s, 3H, Me), 0.77 (d, 3H, Me), 0.77 (s, 3H, Me), 0.83 (s, 9H, t-bu), 0.85 (d, 3H, Me), 0.89 (d, 3H, Me), 0.89 (s, 3H, Me), 1.15 (s, 3H, Me), 1.21 (s, 3H, Me), 1.22-1.36 (m), 1.40-1.45 (m), 1.48-1.56 (m), 1.59-1.66 (m), 1.80-1.97 (m), 2.12-2.22 (m), 2.62 (dd, 1H, H13), 2.84 (s, 1H, H7), 3.03 (d, 1H), 3.47 (d, 1H), 3.57 (dd, 1H), 3.65 (d, 1H), 3.67 (d, 1H), 3.87 (d, 1H), 4.09 (d, 1H), 5.48 (dd, 1H, H5), 6.74-6.80 (m, 1H, H14), 7.87 (dd, 1H, ArH), 8.12 (s, 1H, triazole), 8.45 (d, 1H, ArH), 8.87 (d, 1H, ArH).
Mass Spectrum: (ESI) m/z = 773.66 (M + H).

| | | |
|---|---|---|
| 226 | A = 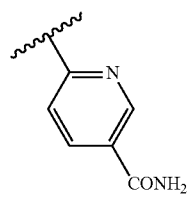 | (1S,4aR,6aS,7R,8R,10aR,10bR,12aR,14R,15R)-14-[5-[5-(aminocarbonyl)-2-pyridinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.65 (s, 3H, Me), 0.76 (d, 3H, Me), 0.77 (s, 3H, Me), 0.82 (s, 9H, t-bu), 0.85 (d, 3H, Me), 0.89 (d, 3H, Me), 0.89 (s, 3H, Me), 1.16 (s, 3H, Me), 1.21 (s, 3H, Me), 1.22-1.37 (m), 1.40-1.45 (m), 1.48-1.67 (m), 1.59-1.66 (m), 1.80-1.97 (m), 2.12-2.23 (m), 2.63 (dd, 1H, H13), 2.83 (s, 1H, H7), 3.01 (d, 1H), 3.47 (d, 1H), 3.58 (dd, 1H), 3.65 (d, 1H), 3.67 (d, 1H), 3.87 (d, 1H), 4.09 (d, 1H), 5.48 (dd, 1H, H5), 6.81-6.87 (m, 1H, H14), 8.13 (s, 1H, triazole), 8.16 (d, 1H, ArH), 8.40 (dd, 1H, ArH), 9.19 (d, 1H, ArH).
Mass Spectrum: (ESI) m/z = 773.60 (M + H).

| | | |
|---|---|---|
| 227 | A = 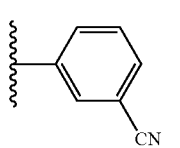 | (1S,4aR,6aS,7R,8R,10aR,10bR,12aR,14R,15R)-15-[[(2R)-2-amino-2,3,3-trimethylbutyl]oxy]-14-[5-(3-cyanophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

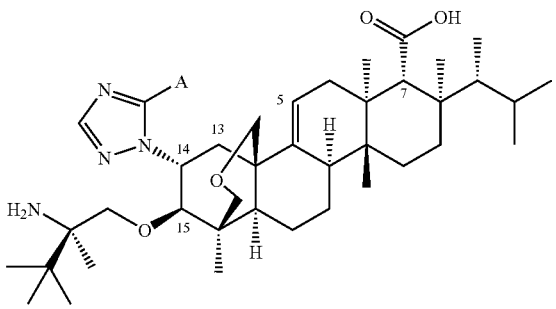

¹H NMR (CD₃OD, 600 MHz, ppm) δ 0.77 (d, 3H, Me), 0.77 (s, 3H, Me), 0.78 (s, 3H, Me), 0.86 (d, 3H, Me), 0.86 (s, 9H, t-bu), 0.87 (s, 3H, Me), 0.90 (d, 3H, Me), 1.18 (s, 3H, Me), 1.21 (s, 3H, Me), 1.23-1.36 (m), 1.41-1.46 (m), 1.49-1.66 (m), 1.80-1.99 (m), 2.04-2.11 (m), 2.14-2.23 (m), 2.61 (dd, 1H, H13), 2.85 (s, 1H, H7), 2.92 (d, 1H), 3.44 (d, 1H), 3.56 (dd, 1H), 3.62 (d, 1H), 3.64 (d, 1H), 3.80 (d, 1H), 4.01 (d, 1H), 5.63 (dd, 1H, H5), 5.80-5.86 (m, 1H, H14), 7.79 (t, 1H, ArH), 7.95 (dt, 1H, ArH), 8.05 (dt, 1H, ArH), 8.09 (t, 1H, ArH), 8.15 (s, 1H, triazole).
Mass Spectrum: (ESI) m/z = 754.57 (M + H).

| 228 | A = 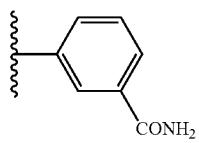 | (1S,4aR,6aS,7R,8R,10aR,10bR,12aR,14R,15R)-14-[5-[3-(aminocarbonyl)phenyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.77 (s, 6H, 2Me), 0.77 (d, 3H, Me), 0.86 (s, 9H, t-bu), 0.86 (d, 3H, Me), 0.87 (s, 3H, Me), 0.90 (d, 3H, Me), 1.18 (s, 3H, Me), 1.22 (s, 3H, Me), 1.23-1.35 (m), 1.41-1.45 (m), 1.49-1.66 (m), 1.80-1.98 (m), 2.06-2.12 (m), 2.13-2.22 (m), 2.60 (dd, 1H, H13), 2.85 (s, 1H, H7), 2.94 (d, 1H), 3.42 (d, 1H), 3.52 (dd, 1H), 3.65 (d, 1H), 3.65 (d, 1H), 3.81 (d, 1H), 4.01 (d, 1H), 5.63 (dd, 1H, H5), 5.89-5.95 (m, 1H, H14), 7.69 (t, 1H, ArH), 7.92 (dt, 1H, ArH), 8.05 (dt, 1H, ArH), 8.13 (s, 1H, triazole), 8.34 (t, 1H, ArH).
Mass Spectrum: (ESI) m/z = 772.77 (M + H).

| 229 | A = 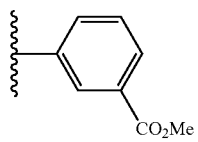 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[3-(methoxycarbonyl)phenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.78 (d, 3H, Me), 0.79 (s, 3H, Me), 0.85 (s, 9H, t-bu), 0.86 (d, 3H, Me), 0.87 (s, 3H, Me), 0.90 (d, 3H, Me), 1.19 (s, 3H, Me), 1.22 (s, 3H, Me), 1.23-1.37 (m), 1.41-1.46 (m), 1.50-1.56 (m), 1.57-1.67 (m), 1.80-1.94 (m), 1.95-2.01 (m), 2.08-2.14 (m), 2.15-2.24 (m), 2.64 (dd, 1H, H13), 2.86 (s, 1H, H7), 2.93 (d, 1H), 3.42 (d, 1H), 3.55 (dd, 1H), 3.63 (d, 1H), 3.69 (d, 1H), 3.78 (d, 1H), 3.96 (s, 3H, COOMe), 4.02 (d, 1H), 5.63 (dd, 1H, H5), 5.85-5.91 (m, 1H, H14), 7.72 (t, 1H, ArH), 7.98 (dt, 1H, ArH), 8.14 (s, 1H, triazole), 8.20 (dt, 1H, ArH), 8.42 (t, 1H, ArH).
Mass Spectrum: (ESI) m/z = 787.62 (M + H).

| 230 | A = 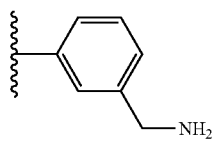 | (1S,4aR,6aS,7R,8R,10aR,10bR,12aR,14R,15R)-14-[5-[3-(aminomethyl)phenyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.80 (s, 3H, Me), 0.80 (d, 3H, Me), 0.83 (s, 3H, Me), 0.88 (d, 3H, Me), 0.88 (s, 9H, t-bu), 0.90 (s, 3H, Me), 0.92 (d, 3H, Me), 1.20 (s, 3H, Me), 1.24 (s, 3H, Me), 1.24-1.38 (m), 1.43-1.48 (m), 1.51-1.69 (m), 1.82-2.01 (m), 2.06-2.13 (m), 2.16-2.25 (m), 2.54 (dd, 1H, H13), 2.87 (s, 1H, H7), 2.96 (d, 1H), 3.48 (d, 1H), 3.58 (dd, 1H), 3.62 (d, 1H), 3.65 (d, 1H), 3.84 (d, 1H), 4.04 (d, 1H), 4.25 (s, 2H, CH₂NH₂), 5.61 (dd, 1H, H5), 5.88-5.95 (m, 1H, H14), 7.70-7.72 (m, ArH), 7.78 (broad t, 1H, ArH), 7.83-7.87 (m, ArH), 8.18 (s, 1H, triazole).
Mass Spectrum: (ESI) m/z = 758.67 (M + H).

-continued

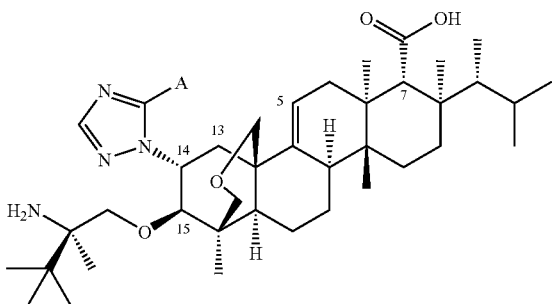

| 231 | A = 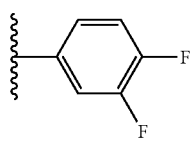 | (1S,4aR,6aS,7R,8R,10aR,10bR,12aR,14R,15R)-15-[[(2R)-2-amino-2,3,3-trimethylbutyl]oxy]-14-[5-(3,4-difluorophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.78 (d, 3H, Me), 0.79 (s, 3H, Me), 0.85 (s, 9H, t-bu), 0.86 (d, 3H, Me), 0.87 (s, 3H, Me), 0.90 (d, 3H, Me), 1.19 (s, 3H, Me), 1.22 (s, 3H, Me), 1.23-1.37 (m), 1.41-1.46 (m), 1.50-1.56 (m), 1.57-1.67 (m), 1.80-1.94 (m), 1.95-2.01 (m), 2.08-2.14 (m), 2.15-2.24 (m), 2.64 (dd, 1H, H13), 2.86 (s, 1H, H7), 2.93 (d, 1H), 3.42 (d, 1H), 3.55 (dd, 1H), 3.63 (d, 1H), 3.69 (d, 1H), 3.78 (d, 1H), 3.96 (s, 3H, COOMe), 4.02 (d, 1H), 5.63 (dd, 1H, H5), 5.85-5.91 (m, 1H, H14), 7.72 (t, 1H, ArH), 7.98 (dt, 1H, ArH), 8.14 (s, 1H, triazole), 8.20 (dt, 1H, ArH), 8.42 (t, 1H, ArH).
Mass Spectrum: (ESI) m/z = 787.62 (M + H).

| 232 | A = 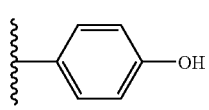 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-hydroxyphenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (d, 3H, Me), 0.78 (s, 3H, Me), 0.80 (s, 3H, Me), 0.85 (s, 9H, t-bu), 0.86 (d, 3H, Me), 0.86 (s, 3H, Me), 0.90 (d, 3H, Me), 1.18 (s, 3H, Me), 1.21 (s, 3H, Me), 1.23-1.35 (m), 1.41-1.46 (m), 1.49-1.66 (m), 1.80-1.99 (m), 2.02-2.09 (m), 2.13-2.23 (m), 2.54 (dd, 1H, H13), 2.85 (s, 1H, H7), 2.88 (d, 1H), 3.43 (d, 1H), 3.55 (dd, 1H), 3.61 (d, 1H), 3.64 (d, 1H), 3.82 (d, 1H), 3.98 (d, 1H), 5.60 (dd, 1H, H5), 5.84-5.90 (m, 1H, H14), 6.95 (d, 2H, ArH), 7.56 (d, 2H, ArH), 8.10 (s, 1H, triazole).
Mass Spectrum: (ESI) m/z = 745.55 (M + H).

| 233 | A = 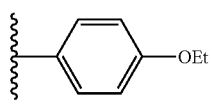 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-ethoxyphenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (d, 3H, Me), 0.78 (s, 3H, Me), 0.80 (s, 3H, Me), 0.85 (s, 9H, t-bu), 0.86 (s, 3H, Me), 0.86 (d, 3H, Me), 0.90 (d, 3H, Me), 1.18 (s, 3H, Me), 1.21 (s, 3H, Me), 1.23-1.36 (m), 1.41 (t, 3H), 1.41-1.45 (m), 1.49-1.66 (m), 1.80-1.99 (m), 2.03-2.10 (m), 2.14-2.23 (m), 2.54 (dd, 1H, H13), 2.85 (s, 1H, H7), 2.88 (d, 1H), 3.43 (d, 1H), 3.55 (dd, 1H), 3.60 (d, 1H), 3.64 (d, 1H), 3.81 (d, 1H), 3.98 (d, 1H), 4.11 (q, 2H, OCH$_2$), 5.60 (dd, 1H, H5), 5.83-5.90 (m, 1H, H14), 7.09 (d, 2H, ArH), 7.65 (d, 2H, ArH), 8.08 (s, 1H, triazole).
Mass Spectrum: (ESI) m/z = 773.68 (M + H).

| 234 | A = 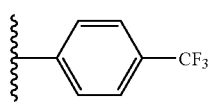 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[4-(trifluoromethyl)phenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^{i1}$H NMR (CD$_3$OD, 600 MHz, ppm) δ 0.77 (s, 3H, Me), 0.77 (d, 3H, Me), 0.78 (s, 3H, Me), 0.86 (s, 9H, t-bu), 0.86 (d, 3H, Me), 0.86 (s, 3H, Me), 0.90 (d, 3H, Me), 1.18 (s, 3H, Me), 1.21 (s, 3H, Me), 1.23-1.36 (m), 1.41-1.46 (m), 1.49-1.66 (m), 1.80-1.99 (m), 2.07-2.13 (m), 2.14-2.23 (m), 2.62 (dd, 1H, H13), 2.85 (s, 1H, H7), 2.88 (d, 1H), 3.43 (d, 1H), 3.55 (dd, 1H), 3.64 (d, 1H), 3.68 (d, 1H), 3.79 (d, 1H), 4.01 (d, 1H), 5.64 (dd, 1H, H5), 5.82-5.88 (m, 1H, H14), 7.91 (d, 2H, ArH), 7.94 (d, 2H, ArH), 8.16 (s, 1H, triazole).
Mass Spectrum: (ESI) m/z = 797.59 (M + H).

-continued

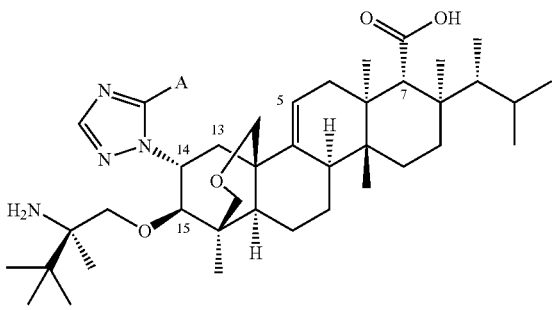

| 235 | A = 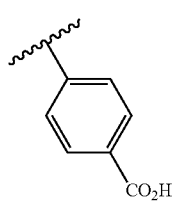 CO₂H | (1S,4aR,6aS,7R,8R,10aR,10bR,12aR,14R,15R)-15-[[(2R)-2-amino-2,3,3-trimethylbutyl]oxy]-14-[5-(4-carboxyphenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (d, 3H, Me), 0.78 (s, 6H, 2Me), 0.86 (s, 9H, t-bu), 0.86 (d, 3H, Me), 0.86 (s, 3H, Me), 0.90 (d, 3H, Me), 1.18 (s, 3H, Me), 1.22 (s, 3H, Me), 1.23-1.36 (m), 1.40-1.46 (m), 1.49-1.66 (m), 1.81-1.99 (m), 2.06-2.12 (m), 2.14-2.23 (m), 2.60 (dd, 1H, H13), 2.86 (s, 1H, H7), 2.89 (d, 1H), 3.43 (d, 1H), 3.55 (dd, 1H), 3.62 (d, 1H), 3.66 (d, 1H), 3.80 (d, 1H), 4.01 (d, 1H), 5.64 (dd, 1H, H5), 5.84-5.91 (m, 1H, H14), 7.85 (d, 2H, ArH), 8.14 (s, 1H, triazole), 8.21 (d, 2H, ArH).
Mass Spectrum: (ESI) m/z = 773.53 (M + H).

| 236 | A = 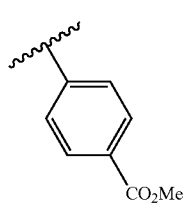 CO₂Me | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[4-(methoxycarbonyl)phenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.77 (d, 3H, Me), 0.78 (s, 3H, Me), 0.78 (s, 3H, Me), 0.85 (s, 9H, t-bu), 0.86 (d, 3H, Me), 0.86 (s, 3H, Me), 0.90 (d, 3H, Me), 1.18 (s, 3H, Me), 1.22 (s, 3H, Me), 1.23-1.35 (m), 1.41-1.45 (m), 1.49-1.66 (m), 1.80-1.93 (m), 1.93-1.99 (m), 2.06-2.12 (m), 2.14-2.23 (m), 2.59 (dd, 1H, H13), 2.85 (s, 1H, H7), 2.88 (d, 1H), 3.43 (d, 1H), 3.55 (dd, 1H), 3.62 (d, 1H), 3.65 (d, 1H), 3.79 (d, 1H), 3.95 (s, 3H, COOMe), 4.01 (d, 1H), 5.63 (dd, 1H, H5), 5.83-5.90 (m, 1H, H14), 7.86 (d, 2H, ArH), 8.15 (s, 1H, triazole), 8.21 (d, 2H, ArH).
Mass Spectrum: (ESI) m/z = 787.62 (M + H).

| 237 | A = 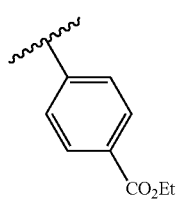 CO₂Et | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[4-(ethoxycarbonyl)phenyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

-continued

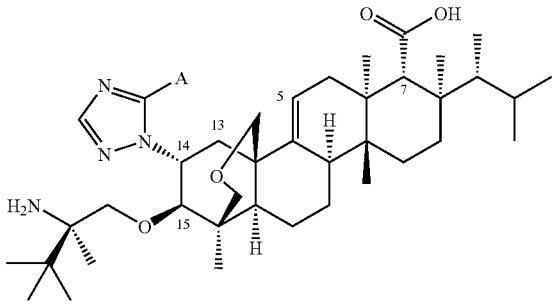

¹H NMR (CD₃OD, 600 MHz, ppm) δ 0.77 (d, 3H, Me), 0.78 (s, 6H, 2Me), 0.86 (s, 9H, t-bu), 0.86 (d, 3H, Me), 0.86 (s, 3H, Me), 0.90 (d, 3H, Me), 1.18 (s, 3H, Me), 1.22 (s, 3H, Me), 1.23-1.38 (m), 1.40 (t, 3H), 1.41-1.46 (m), 1.49-1.66 (m), 1.80-1.93 (m), 1.94-1.99 (m), 2.06-2.12 (m), 2.14-2.23 (m), 2.60 (dd, 1H, H13), 2.86 (s, 1H, H7), 2.88 (d, 1H), 3.43 (d, 1H), 3.55 (dd, 1H), 3.62 (d, 1H), 3.66 (d, 1H), 3.79 (d, 1H), 4.00 (d, 1H), 4.41 (dq, 2H, COOCH₂), 5.63 (dd, 1H, H5), 5.84-5.90 (m, 1H, H14), 7.86 (d, 2H, ArH), 8.15 (s, 1H, triazole), 8.21 (d, 2H, ArH). Mass Spectrum: (ESI) m/z = 801.60 (M + H).

| 238 | A = 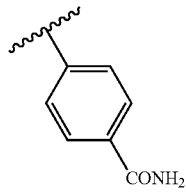 | (1S,4aR,6aS,7R,8R,10aR,10bR,12aR,14R,15R)-14-[5-[4-(aminocarbonyl)phenyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 600 MHz, ppm) δ 0.77 (d, 3H, Me), 0.78 (s, 6H, 2Me), 0.86 (s, 9H, t-bu), 0.86 (d, 3H, Me), 0.86 (s, 3H, Me), 0.90 (d, 3H, Me), 1.18 (s, 3H, Me), 1.22 (s, 3H, Me), 1.23-1.36 (m), 1.41-1.46 (m), 1.49-1.66 (m), 1.80-1.99 (m), 2.06-2.12 (m), 2.14-2.23 (m), 2.60 (dd, 1H, H13), 2.86 (s, 1H, H7), 2.89 (d, 1H), 3.43 (d, 1H), 3.55 (dd, 1H), 3.62 (d, 1H), 3.64 (d, 1H), 3.80 (d, 1H), 4.01 (d, 1H), 5.62 (dd, 1H, H5), 5.85-5.91 (m, 1H, H14), 7.84 (d, 2H, ArH), 8.07 (d, 2H, ArH), 8.14 (s, 1H, triazole). Mass Spectrum: (ESI) m/z = 772.78 (M + H).

| 239 | A = 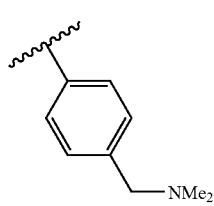 | (1S,4aR,6aS,7R,8R,10aR,10bR,12aR,14R,15R)-15-[[(2R)-2-amino-2,3,3-trimethylbutyl]oxy]-14-[5-[4-[(dimethylamino)methyl]phenyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|

¹H NMR (CD₃OD, 600 MHz, ppm) δ 0.77 (d, 3H, Me), 0.77 (s, 3H, Me), 0.81 (s, 3H, Me), 0.85 (s, 9H, t-bu), 0.86 (d, 3H, Me), 0.87 (s, 3H, Me), 0.90 (d, 3H, Me), 1.18 (s, 3H, Me), 1.21 (s, 3H, Me), 1.23-1.36 (m), 1.41-1.46 (m), 1.49-1.66 (m), 1.81-1.98 (m), 2.05-2.11 (m), 2.14-2.23 (m), 2.55 (dd, 1H, H13), 2.85 (s, 1H, H7), 2.90 (broad s, 6H, 2NMe), 2.93 (d, 1H), 3.44 (d, 1H), 3.55 (dd, 1H), 3.59 (d, 1H), 3.60 (d, 1H), 3.79 (d, 1H), 4.03 (d, 1H), 4.41 (abq, 2H, CH₂N), 5.59 (dd, 1H, H5), 5.83-5.89 (m, 1H, H14), 7.73 (d, 2H, ArH), 7.87 (d, 2H, ArH), 8.16 (s, 1H, triazole). Mass Spectrum: (ESI) m/z = 786.67 (M + H).

Examples 240-249

The following compounds were prepared using methods analogous to those described in the preceding examples:

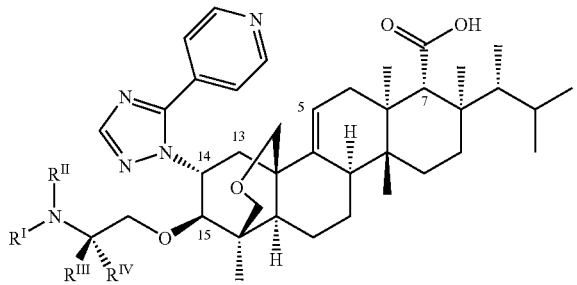

240    $R^I$ = H    (1S,4aR,6aS,7R,8R,10aR,10bR,12aR,14R,15R)-15-(2-amino-2-
       $R^{II}$ = H    methylpropoxy)-8-[(1R)-1,2-dimethylpropyl]-14-[5-(4-pyridinyl)-1H-
       $R^{III}$ = Me    1,2,4-triazol-1-yl]-1,6,6a,7,8,9,10,10a,10b,11,12,12a-dodecahydro-
       $R^{IV}$ = Me    1,6a,8,10a-tetramethyl-4H-1,4a-propano-2H-phenanthro[1,2-c]pyran-7-
                carboxylic acid $^1$H NMR (CD$_3$OD, 500 MHz, ppm) δ 0.79 (s, 3H, Me), 0.79 (d, 3H, Me), 0.88 (d, 3H, Me), 0.88 (s, 3H, Me), 0.92 (d, 3H, Me), 0.93 (s, 3H, Me), 1.09 (s, 3H, Me), 1.19 (s, 3H, Me), 1.23 (s, 3H, Me), 1.25-1.39 (m), 1.42-1.48 (m), 1.50-1.68 (m), 1.83-2.00 (m), 2.07-2.14 (m), 2.15-2.25 (m), 2.57 (dd, 1H, H13), 2.75 (d, 1H), 2.87 (s, 1H, H7), 3.49 (d, 1H), 3.49 (d, 1H), 3.56 (dd, 1H), 3.66 (d, 1H), 3.82 (d, 1H), 4.00 (d, 1H), 5.60 (dd, 1H, H5), 5.88-5.95 (m, 1H, H14), 7.98 (d, 2H, ArH), 8.22 (s, 1H, triazole), 8.88 (d, 2H, ArH).
Mass Spectrum: (ESI) m/z = 688.65 (M + H).

241    $R^I$ = H    (1S,4aR,6aS,7R,8R,10aR,10bR,12aR,14R,15R)-15-(2-amino-2-
       $R^{II}$ = H    ethylbutoxy)-8-[(1R)-1,2-dimethylpropyl]-14-[5-(4-pyridinyl)-1H-1,2,4-
       $R^{III}$ = Et    triazol-1-yl]-1,6,6a,7,8,9,10,10a,10b,11,12,12a-dodecahydro-1,6a,8,10a-
       $R^{IV}$ = Et    tetramethyl-4H-1,4a-propano-2H-phenanthro[1,2-c]pyran-7-carboxylic
               acid $^1$H NMR (CD$_3$OD, 500 MHz, ppm) δ 0.62 (t, J = 7.6 Hz, 3H), 0.74-0.80 (m, 9H), 0.86 (d, J = 6.6 Hz, 1H), 0.88 (s, 3H), 0.90 (d, J = 6.8 Hz, 3H), 1.14-1.67 (m), 1.17 (s, 3H), 1.22 (s, 3H), 1.80-2.0 (m), 2.06 (m, 1H), 2.13-2.23 (m, 2H), 2.53 (dd, J = 13.7 Hz, 6.2 Hz, 1H), 2.85 (s, 1H), 2.91 (d, J = 10.1 Hz, 1H), 3.43-3.49 (m, 2H), 3.54 (dd, J = 11.7 Hz, 1.8 Hz, 1H), 3.64 (d, J = 11.6 Hz, 1H), 3.80 (d, J = 12.1 Hz, 1H), 4.01 (d, J = 9.8 Hz, 1H), 5.59 (5.59 (m, 1H), 5.88 (m, 1H), 7.82 (m, 2H), 8.19 (s, 1H), 8.81 (m, 1H).
Mass Spectrum: (ESI) m/z = 716.64 (M + H).

242    $R^I$ = Me    (1S,4aR,6aS,7R,8R,10aR,10bR,12aR,14R,15R)-8-[(1R)-1,2-
       $R^{II}$ = H    dimethylpropyl]-15-[2-ethyl-2-(methylamino)butoxy]-14-[5-(4-
       $R^{III}$ = Et    pyridinyl)-1H-1,2,4-triazol-1-yl]-1,6,6a,7,8,9,10,10a,10b,11,12,12a-
       $R^{IV}$ = Et    dodecahydro-1,6a,8,10a-tetramethyl-4H-1,4a-propano-2H-
               phenanthro[1,2-c]pyran-7-carboxylic acid $^1$H NMR (CD$_3$OD, 500 MHz, ppm) δ 0.63 (t, J = 7.6 Hz, 3H), 0.76-0.81 (m, 9H), 0.86 (d, J = 6.6 Hz, 3H), 0.90 (s, 9H), 0.90 (d, 3H, partially obscured), 1.15-1.67 (m), 1.17 (s, 3H), 1.21 (s, 3H), 1.82-2.06 (m), 2.13-2.23 (m, 2H), 2.37 (s, 3H), 2.54 (dd, J = 13.7 Hz, 6.2 Hz, 1H), 2.85 (s, 1H), 3.01 (d, J = 10.7 Hz, 1H), 3.48 (d, J = 11.9 Hz, 1H), 3.56 (dd, J = 11.7 Hz, 2.1 Hz, 1H), 3.60 (d, J = 11.0 Hz, 1H), 3.66 (d, J= 11.7 Hz, 1H), 3.76 (d, J = 12.1 Hz, 1H), 4.01 (d, J = 9.6 Hz, 1H), 5.59 (m, 1H), 5.87 (m, 1H), 7.84 (m, 2H), 8.21 (s, 1H), 8.83 (m, 2H).
Mass Spectrum: (ESI) m/z = 730.71 (M +H).

243    $R^I$ = H    (1S,4aR,6aS,7R,8R,10aR,10bR,12aR,14R,15R)-15-[[(2R)-2-amino-3,3-
       $R^{II}$ = H    dimethylbutyl]oxy]-8-[(1R)-1,2-dimethylpropyl]-14-[5-(4-pyridinyl)-
       $R^{III}$ = t-Bu    1H-1,2,4-triazol-1-yl]-1,6,6a,7,8,9,10,10a,10b,11,12,12a-
       $R^{IV}$ = H    dodecahydro-1,6a,8,10a-tetramethyl-4H-1,4a-propano-2H-
               phenanthro[1,2-c]pyran-7-carboxylic acid $^1$H NMR (CD$_3$OD, 500 MHz, ppm) δ 0.77 (s, 3H), 0.78 (d, J = 6.9 Hz, 1H), 0.83 (s, 9H), 0.86 (s, 3H), 0.86 (d, J = 6.6 Hz, 1H), 0.91 (d, J = 6.7 Hz, 1H), 1.19 (s, 3H), 1.22 (s, 3H), 1.23-1.68 (m), 1.80-1.98 (m), 2.15-2.24 (m), 2.41 (dd, J = 10.2 Hz, 2.7 Hz, 1H), 2.54 (dd, J = 13.6 Hz, 6.3 Hz, 1H), 2.85 (s, 1H), 2.91 (dd, J = 10.6 Hz, 1H), 3.42-3.50 (m, 2H), 3.53 (dd, J = 11.9 Hz, 1.9 Hz, 1H), 3.62 (d, J = 11.6 Hz, 1H), 3.84 (d, 1H, partially obscured), 3.84 (d, 1H, partially obscured), 5.58 (m, 1H), 5.84 (m, 1H), 7.85 (m, 2H), 8.21 (s, 1H), 8.81 (m, 2H).
Mass Spectrum: (ESI) m/z = 716.64 (M + H).

-continued

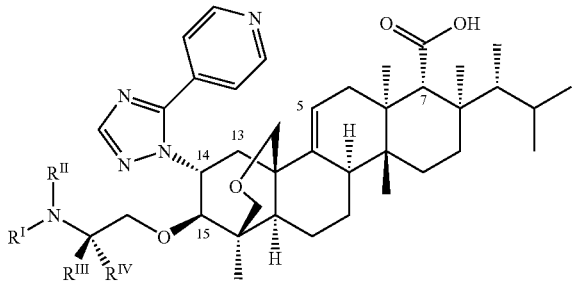

| 244 | $R^I$ = H<br>$R^{II}$ = H<br>$R^{III}$ = Me<br>$R^{IV}$ = i-Pr | (1S,4aR,6aS,7R,8R,10aR,10bR,12aR,14R,15R)-15-[[(2S)-2-amino-2,3-dimethylbutyl]oxy]-8-[(1R)-1,2-dimethylpropyl] -14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

Mass Spectrum: (ESI) m/z = 717 (M + H).

| 245 | $R^I$ = H<br>$R^{II}$ = H<br>$R^{III}$ = Ph<br>$R^{IV}$ = Me | (1S,4aR,6aS,7R,8R,10aR,10bR,12aR,14R,15R)-15-[[(2R)-2-amino-2-phenylpropyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm) δ 0.80 (m, 9H), 0.85 (d, 3H), 0.90 (d, 3H), 1.20 (s, 3H), 1.23 (s, 3H), 1.23-1.40 (m, 3H), 1.42 (s, 3H), 1.43-1.70 (m, 4H), 1.80-2.10 (m, 10H), 2.43 (m, 1H), 2.83 (m, 1H), 3.15 (m, 1H), 3.50 (m, 3H), 3.75 (d, 1H), 3.80 (m, 1H), 4.03 (d, 1H), 5.53 (m, 1H), 5.88 (m, 1H), 7.22-7.40 (m, 5H), 7.70 (d, 2H), 8.23 (s, 1H), 8.78 (d, 2H)
Mass Spectrum: (ESI) m/z = 751 (M + H).

| 246 | $R^I$ = H<br>$R^{II}$ = H<br>$R^{III}$ = 1-Me-cPr<br>$R^{IV}$ = Me | (1S,4aR,6aS,7R,8R,10aR,10bR,12aR,14R,15R)-15-[[(2R)-2-amino-2-(1-methylcyclopropyl)propyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm, selected resonances) δ 0.30 (m, 2H), 0.42 (m, 1H), 0.62 (m, 1H), 3.84 (s, 1H), 5.62 (m, 1H), 5.90 (m, 1H), 7.83 (m, 2H), 8.22 (s, 1H), 8.84 (m, 2H)
Mass Spectrum: (ESI) m/z = 729 (M + H).

| 247 | $R^I$ = Me<br>$R^{II}$ = Me<br>$R^{III}$ = t-Bu<br>$R^{IV}$ = Me | (1S,4aR,6aS,7R,8R,10aR,10bR,12aR,14R,15R)-15-[[(2R)-2-(dimethylamino)-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm, selected resonances) δ 0.80 (m, 9H), 0.90 (m, 9H), 1.00 (s, 9H), 1.20 (s, 3H), 1.22 (s, 3H), 2.77 (s, 3H), 2.84 (s, 1H), 2.92 (s, 3H), 5.62 (m, 1H), 5.90 (m, 1H), 7.82 (d, 2H), 8.22 (s, 1H), 8.82 (d, 2H).
Mass Spectrum: (ESI) m/z = 759 (M + H).

| 248 | $R^I$ = Et<br>$R^{II}$ = H<br>$R^{III}$ = t-Bu<br>$R^{IV}$ = Me | (1S,4aR,6aS,7R,8R,10aR,10bR,12aR,14R,15R)-8-[(1R)-1,2-dimethylpropyl]-15-[[(2R)-2-(ethylamino)-2,3,3-trimethylbutyl]oxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm, selected resonances) δ0.72 (s, 3H), 0.75 (m, 6H), 0.90 (m, 18H), 1.18 (s, 3H), 1.23 (s, 3H), 2.83 (s, 1H), 5.60 (m, 1H), 5.83 (m, 1H), 7.80 (d, 2H), 8.20 (s, 1H), 8.80 (d, 2H).
Mass Spectrum: (ESI) m/z = 759 (M + H).

| 249 | $R^I$ = n-Pr<br>$R^{II}$ = H<br>$R^{III}$ = t-Bu<br>$R^{IV}$ = Me | (1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl] -15-[ [(2R)-2,3,3-trimethyl-2-(propylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm, selected resonances) $^1$H NMR (MeOH-d$_4$, 500 MHz, ppm) δ 0.80 (m, 9H), 0.90 (m, 21H), 1.20 (s, 3H), 1.23 (s, 3H), 2.84 (2, 1H), 5.62 (m, 1H), 5.90 (m, 1H) 7.82 (d, 2H), 8.22 (s, 1H), 8.83 (d, 2H).
Mass Spectrum: (ESI) m/z = 773 (M + H).

Examples 250-251

The following compounds were prepared using methods analogous to those described in the preceding examples:

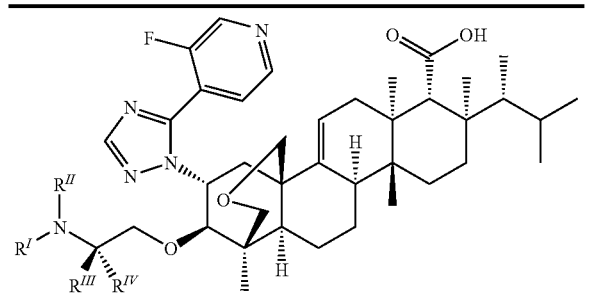

| 250 | $R^I$ = Me<br>$R^{II}$ = H<br>$R^{III}$ = t-Bu<br>$R^{IV}$ = Me | (1S,4aR,6aS,7R,8R,10aR,10bR,12aR,14R,15R)-8-[(1R)-1,2-dimethylpropyl]-14-[5-(3-fluoro-4-pyridinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.77 (s, 3H), 0.78 (s, 3H), 0.78 (d, 3H, partially obscured), 0.86 (d, J = 6.7 Hz, 3H), 0.91 (d, 3H, partially obscured), 0.91 (s, 3H), 0.91 (s, 9H), 1.17 (s, 3H), 1.21 (s, 3H), 1.23-1.67 (m), 1.82-2.00 (m), 2.13-2.23 (m, 2H), 2.50 (dd, J = 13.6 Hz, 5.8 Hz, 1H), 2.60 (s, 3H), 2.85 (s, 1H), 3.22 (d, J = 11.2 Hz, 1H), 3.48 (d, J = 11.9 Hz, 1H), 3.53 (AB, 2H), 3.61 (d, J = 12.3 Hz, 1H), 3.87 (d, J = 11.1 Hz, 1H),

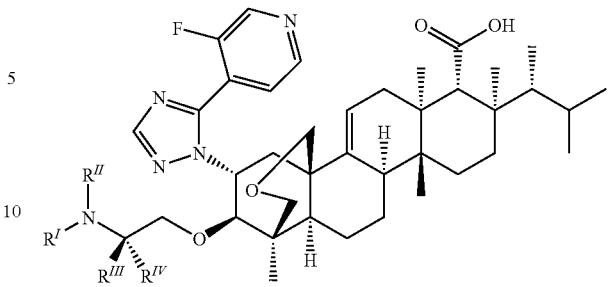

4.05 (d, J = 9.8 Hz, 1H), 5.51 (m, 1H), 5.59 (m, 1H), 7.72 (m, 1H), 8.25 (m, 1H), 8.66 (m, 1H), 8.79 (m, 1H).
Mass Spectrum: (ESI) m/z = 762.96 (M + H).

| 251 | $R^I$ = H<br>$R^{II}$ = H<br>$R^{III}$ = c-Pr<br>$R^{IV}$ = Me | (1S,4aR,6aS,7R,8R,10aR,10bR,12aR,14R,15R)-15-[[(2R)-2-amino-2-cyclopropylpropyl]oxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (MeOH-d$_4$, 500 MHz, ppm, selected resonances) δ 0.28 (m, 1H), 0.50 (m, 3H), 2.83 (s, 1H), 5.58 (m, 2H), 7.72 (m, 1H), 8.23 (s, 1H), 8.62 (m, 1H), 8.79 (m, 1H).
Mass Spectrum: (ESI) m/z = 732 (M + H).

Examples 252-259

The following compounds were prepared using methods analogous to those described in the preceding examples:

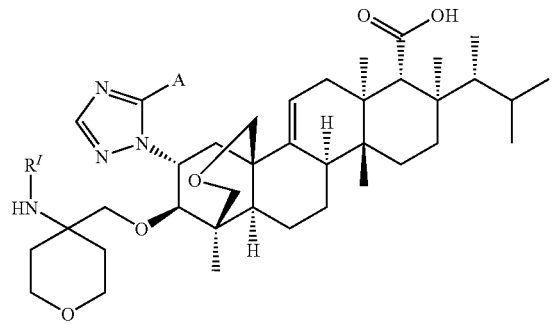

| 252 | $R^I$ = H<br>A = <br>*pyridin-4-yl* | (1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.79 (s, 3H), 0.80 (d, 3H, partially obscured), 0.88 (d, J = 6.6 Hz, 3H), 0.90 (s, 3H), 0.91 (d, J = 6.6 Hz, 3H), 1.19 (s, 3H), 1.23 (s, 3H), 1.23-1.68 (m), 1.82-2.00 (m), 2.07 (m, 1H), 2.14-2.23 (m, 2H), 2.55 (dd, J = 13.8, 6.5 Hz, 1H), 2.86 (s, 1H), 2.82 (m, 1H), 3.30-3.36 (m), 3.49 (d, J = 11.9 Hz, 1H), 3.53-3.61 (m, 3H), 3.65 (d, J = 11.7 Hz, 1H), 3.72 (m, 1H), 3.83 (d, J = 12.1 Hz, 1H), 4.08 (d, J = 9.8 Hz, 1H), 5.59 (m, 1H), 5.90 (m, 1H), 7.83 (dd, J = 4.8, 1.6 Hz, 2H), 8.25 (s, 1H), 8.83 (d, J = 6.1 Hz, 2H).
Mass spectrum: (ESI) m/z = 730.81 (M + H).

| 253 | $R^I$ = Me<br>A = <br>*pyridin-3-yl* | (1S,4aR,6aS,7R,8R,10aR,10bR,12aR,14R,15R)-8-[(1R)-1,2-dimethylpropyl]-14-[5-(3-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.79 (d, 3H, partially obscured), 0.87 (d, J = 6.7 Hz, 3H), 0.91 (d, 3H, partially obscured), 0.92 (s, 3H), 1.18 (s, 3H), 1.23 (s, 3H), 1.24-1.78 (m), 1.82-2.06 (m), 2.12-2.23 (m, 2H), 2.40 (s, 3H), 2.54 (dd, J = 13.5, 6.0 Hz, 1H), 2.86 (s, 1H), 2.91 (m, 1H), 3.30-3.37 (m, partially obscured), 3.46 (d, J = 11.2 Hz, 1H), 3.50

-continued

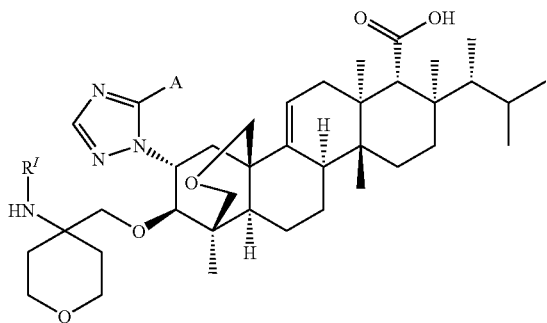

(d, J = 11.9 Hz, 1H), 3.55 (m, 1H), 3.59-3.67 (m, 2H), 3.76-3.85 (m, 3H), 4.20 (d, J = 9.6 Hz, 1H), 5.58 (m, 1H), 5.85 (m, 1H), 7.83 (br, 1H), 8.26 (s, 1H), 8.31 (d, J = 7.8 Hz, 1H), 8.90 (br, 2H).

Mass spectrum: (ESI) m/z = 744.87 (M + H).

| 254 | R$^I$ = H<br>A = 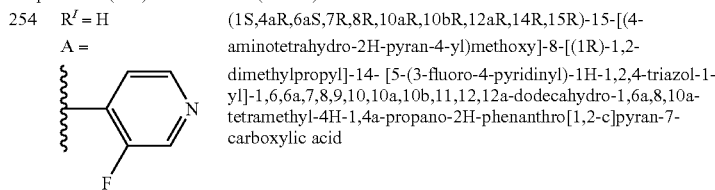 | (1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14- [5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.79 (d, 3H, partially obscured), 0.87 (d, 3H, partially obscured), 0.88 (s, 3H), 0.91 (d, J = 6.7 Hz, 3H), 1.18 (s, 3H), 1.23 (s, 3H), 1.23-1.68 (m), 1.82-2.04 (m), 2.12-2.23 (m, 2H), 2.50 (dd, J = 13.7, 5.9 Hz, 1H), 2.86 (s, 1H), 3.00 (m), 3.36-3.42 (m, 2H), 3.45 (d, J = 11.9 Hz, 1H), 3.54 (s, 1H), 3.58 (d, J = 10.3 Hz, 1H), 3.63 (m, 1H), 3.70-3.78 (m, 2H), 4.09 (d, J = 9.8 Hz, 1H), 5.50-5.60 (m, 2H), 7.70 (t, J = 5.7 Hz, 1H), 8.30 (s, 1H), 8.66 (d, J = 4.8 Hz, 1H), 8.78 (s, 1H).

Mass spectrum: (ESI) m/z = 748.75 (M + H).

| 255 | R$^I$ = Me<br>A = 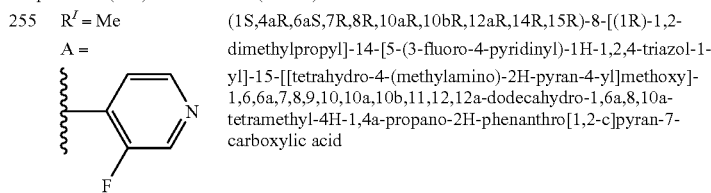 | (1S,4aR,6aS,7R,8R,10aR,10bR,12aR,14R,15R)-8-[(1R)-1,2-dimethylpropyl]-14-[5-(3-fluoro-4-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.79 (d, 3H, partially obscured), 0.88 (d, J = 6.6 Hz, 3H), 0.92 (d, 3H, partially obscured), 0.92 (s, 3H), 1.18 (s, 3H), 1.23 (s, 3H), 1.23-2.00 (m), 2.12-2.23 (m, 2H), 2.43 (s, 3H), 2.50 (dd, J = 13.7, 6.0 Hz, 1H), 2.86 (s, 1H), 2.92 (m, 1H,), 3.30-3.38 (m, partially obscured), 3.47 (d, J = 11.9 Hz, 1H), 3.50 (d, 1H, partially obscured),, 3.54 (s, 1H, partially obscured), 3.65-3.74 (m, 2H), 3.77-3.86 (m, 2H), 4.20 (d, J = 9.9 Hz, 1H), 5.53 (m, 1H), 5.58 (m, 1H), 7.72 (t, J = 5.5 Hz, 1H), 8.31 (s, 1H), 8.67 (d, J = 4.8 Hz, 1H), 8.79 (s, 1H).

Mass spectrum: (ESI) m/z = 762.81 (M + H).

| 256 | R$^I$ = H<br>A = 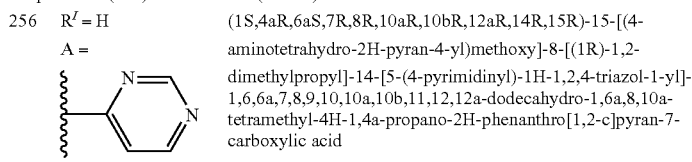 | (1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(4-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.79 (s, 3H), 0.79 (d, 3H, partially obscured), 0.87 (d, J = 6.7 Hz, 3H), 0.89 (d, 3H, partially obscured), 0.92 (s, 3H), 1.16 (s, 3H), 1.22 (s, 3H), 1.23-1.68 (m), 1.83-1.97 (m), 2.13-2.23 (m, 2H), 2.57 (dd, J = 13.3, 6.4 Hz, 1H), 2.82-2.89 (m, 2H), 3.27-3.35 (m), 3.38 (d, J = 10.3 Hz, 1H), 3.46 (m, 1H), 3.52 (d, J = 11.9 Hz, 1H), 3.60 (m, 1H), 3.66-3.74 (m, 2H), 3.91 (d, J = 11.9Hz, 1H), 4.19 (d, J = 9.8 Hz, 1H), 5.50 (m, 1H), 6.95 (m, 1H), 8.17 (d, J = 5.3 Hz, 1H), 8.23 (s, 1H), 9.01 (d, J = 5.3 Hz, 1H), 9.35 (s, 1H).

Mass spectrum: (ESI) m/z = 731.82 (M + H).

-continued

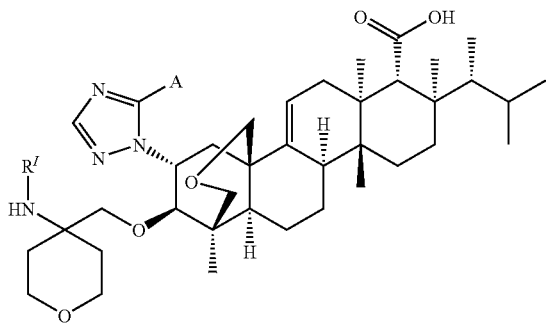

| 257 | $R^I$ = H<br>A = 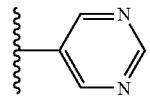 | (1S,4aR,6aS,7R,8R,10aR,10bR,12aR,14R,15R)-15-[(4-aminotetrahydro-2H-pyran-4-yl)methoxy]-8-[(1R)- 1,2-dimethylpropyl]-14-[5-(5-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.79 (d, 3H, partially obscured), 0.87 (d, J = 6.6 Hz, 3H), 0.91 (s, 3H), 0.92 (d, 3H, partially obscured), 1.18 (s, 3H), 1.23 (s, 3H), 1.23-1.68 (m), 1.83-1.98 (m), 2.07 (m, 1H), 2.13-2.23 (m, 2H), 2.55 (dd, J = 13.7, 6.0 Hz, 1H), 2.86 (s, 1H), 2.96 (m, 1H), 3.32-3.39 (m), 3.50 (d, J = 12.3 Hz, 1H), 3.53-3.63 (m, 3H), 3.73 (m, 1H), 3.85 (d, J = 12.1 Hz, 1H), 4.10 (d, J = 9.8 Hz, 1H), 5.56 (m, 1H), 5.83 (m, 1H), 8.27 (s, 1H), 9.20 (s, 2H), 9.36 (s, 1H).

Mass spectrum: (ESI) m/z = 731.84 (M + H).

| 258 | $R^I$ = Me<br>A = 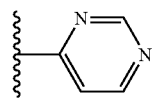 | (1S,4aR,6aS,7R,8R,10aR,10bR,12aR,14R,15R)-8-[(1R)-1,2-dimethylpropyl]-14-[5-(4-pyrimidinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.78 (s, 3H), 0.78 (d, 3H, partially obscured), 0.87 (d, J = 6.7 Hz, 3H), 0.91 d, J = 6.8 Hz, 3H), 0.94 (s, 3H), 1.15 (s, 3H), 1.22 (s, 3H), 1.23-1.68 (m), 1.77-1.97 (m), 2.02-2.23 (m, 2H), 2.31 (s, 3H), 2.57 (dd, J = 13.3, 6.4 Hz, 1H), 2.85 (s, 1H), 2.93 (m, 1H), 3.30-3.35 (m), 3.50 (d, J = 11.0 Hz, 1H), 3.52-3.62 (m, 3H), 3.69 (d, J = 11.4 Hz, 1H), 3.80 (m, 1H), 3.83-3.89 (m, 2H), 4.31 (d, J = 9.8 Hz, 1H), 5.46 (m, 1H), 6.92 (m, 1H), 8.17 (dd, J = 5.3, 1.4 Hz, 1H), 8.23 (s, 1H), 9.01 (d, J = 5.2 Hz, 1H), 9.35 (d, J = 1.2 Hz, 1H)

Mass spectrum: (ESI) m/z = 745.87 (M + H).

| 259 | $R^I$ =Me<br>A = 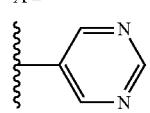 | (1S,4aR,6aS,7R,8R,10aR,10bR,12aR,14R,15R)-8-[(1R)-1,2-dimethylpropyl]-14-[5-(5-pyrimidinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro [1,2-c]pyran-7-carboxylic acid |

$^1$H NMR (CD$_3$OD, 500 MHz, ppm) δ 0.78 (s, 3H), 0.79 (d, 3H, partially obscured), 0.87 (d, J = 6.6 Hz, 3H), 0.91 (d, 3H, partially obscured), 0.93 (s, 3H), 1.17 (s, 3H), 1.22 (s, 3H), 1.23-1.37 (m), 1.44 (m, 1H), 1.50-1.71 (m), 1.77 (m, 1H), 1.82-2.05 (m), 2.13-2.25 (m, 2H), 2.34 (s, 3H), 2.56 (dd, J = 13.8, 7.8 Hz, 1H), 2.86 (s, 1H), 2.93 (m, 1H), 3.32-3.37 (m), 3.47 (d, J = 11.2 Hz, 1H), 3.51 (d, J = 12.4 Hz, 1H), 3.57 (m, 1H), 3.60-3.67 (m, 2H), 3.76-3.83 (m, 2H), 3.86 (d, J = 12.5 Hz, 1H), 4.22 (d, J = 9.6 Hz, 1H), 5.58 (m, 1H), 5.83 (m, 1H), 8.27 (s, 1H), 9.21 (s, 2H), 9.37 (s, 1H).

Mass spectrum: (ESI) m/z = 745.87 (M + H).

Example 260

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-oxido-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

Example 261

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-oxido-3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

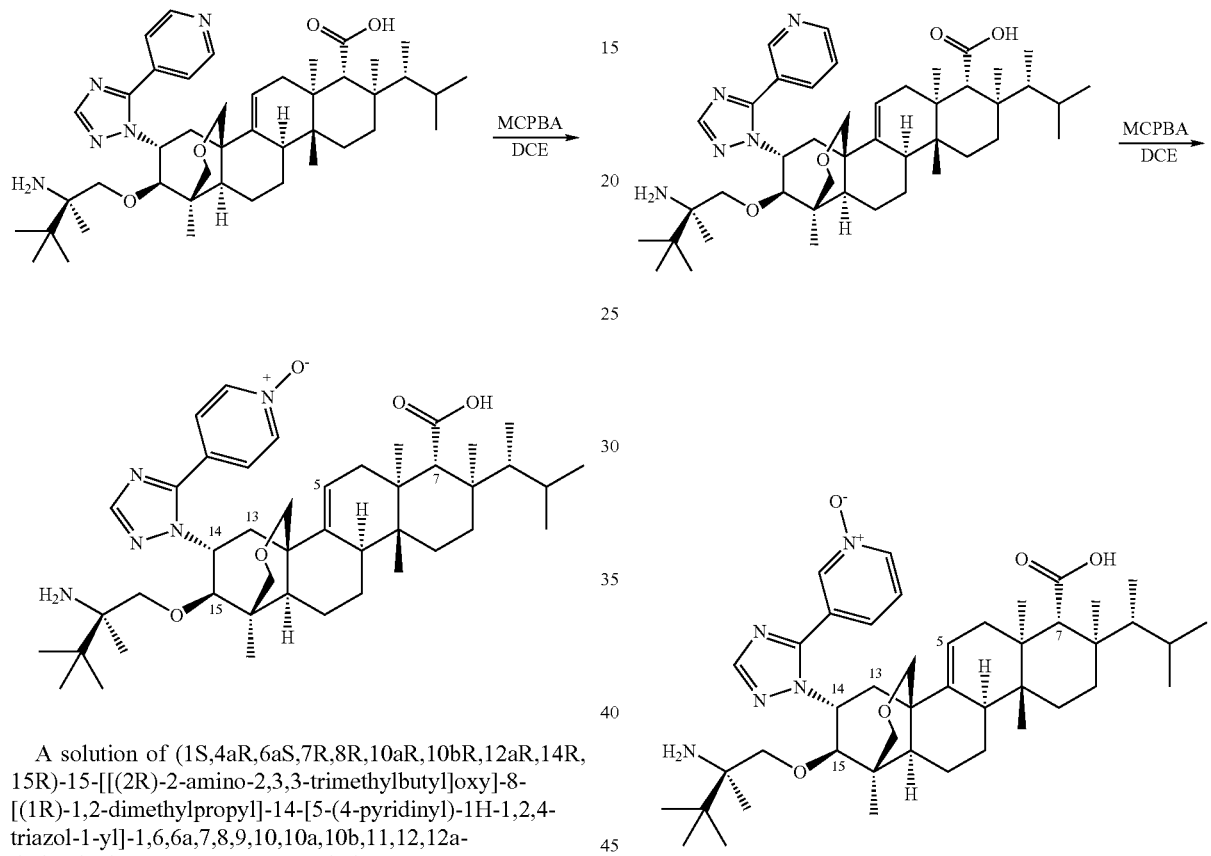

A solution of (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 173, 42.2 mg, 0.05 mmol) and 90% meta-chloroperbenzoic acid (42.2 mg, 0.22 mmol) in dichloroethane (2.0 mL) was blanketed with nitrogen and stirred at room temperature for 5 hours. The mixture was evaporated and purified by reverse phase HPLC using a 19×150 mm Sunfire Preparative C18 OBD column (elution with MeCN/water+0.05% TFA). Product fractions were evaporated and freeze-dried from a mixture of ethanol and benzene to give the title compound as a TFA salt (21 mg).

$^1$H NMR (CD$_3$OD, 600 MHz, ppm) δ 0.74 (s, 3H, Me), 0.77 (d, 3H, Me), 0.78 (s, 3H, Me), 0.85 (s, 9H, Me), 0.86 (d, 3H, Me), 0.88 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.82-1.98 (m), 2.06-2.10 (m), 2.14-2.21 (m), 2.61 (dd, 1H, H13), 2.84 (s, 1H, H7), 2.84 (d, 1H), 3.47 (d, 1H), 3.56 (dd, 1H), 3.64 (d, 1H), 3.71 (d, 1H), 3.83 (d, 1H), 4.01 (d, 1H), 5.63 (dd, 1H, H5), 5.80 (m, 1H, H14), 7.87 (br d, 2H, pyridyl H), 8.17 (s, 1H, triazole) and 8.49 (d, 2H, pyridyl H).

Mass spectrum: (ESI) m/z=746.46 (M+H).

By a procedure analogous to that described for Example 260, but starting with (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 201), the title compound was prepared and isolated as a white solid.

$^1$H NMR (CD$_3$OD, 600 MHz, ppm) δ 0.77 (s, 3H, Me), 0.77 (d, 3H, Me), 0.77 (s, 3H, Me), 0.86 (s, 9H, Me), 0.86 (d, 3H, Me), 0.89 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.82-1.98 (m), 2.04-2.09 (m), 2.14-2.21 (m), 2.58 (dd, 1H, H13), 2.85 (s, 1H, H7), 2.91 (d, 1H), 3.47 (d, 1H), 3.55 (dd, 1H), 3.67 (d, 1H), 3.67 (d, 1H), 3.84 (d, 1H), 4.02 (d, 1H), 5.62 (dd, 1H, H5), 5.79 (m, 1H, H14), 7.76 (dd, 1H, pyridyl H), 7.92 (dd, 1H, pyridyl H), 8.18 (s, 1H, triazole), 8.49 (br dd, 1H, pyridyl H) and 8.66 (br dd, 1H, pyridyl H).

Mass spectrum: (ESI) m/z=746.46 (M+H).

Example 262

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-oxido-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

Example 263

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-4-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid trifluoroacetate

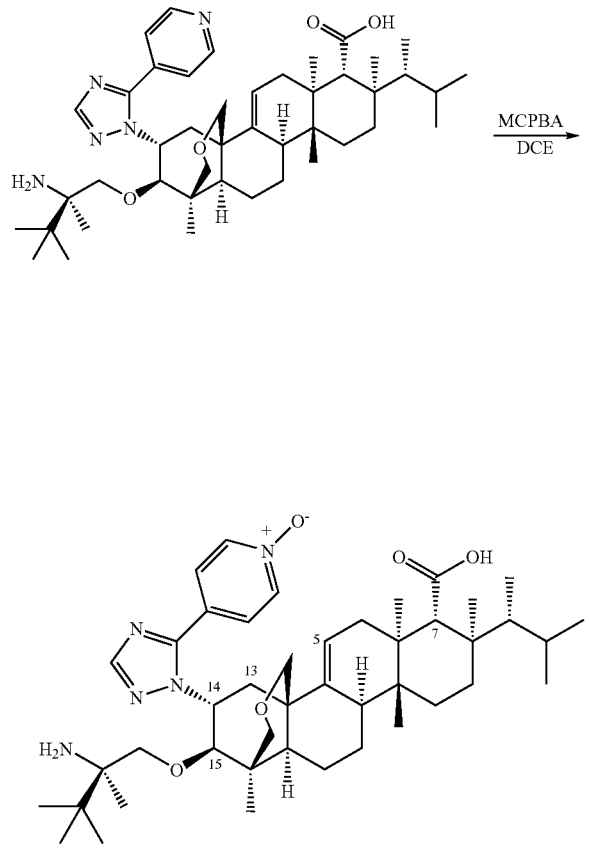

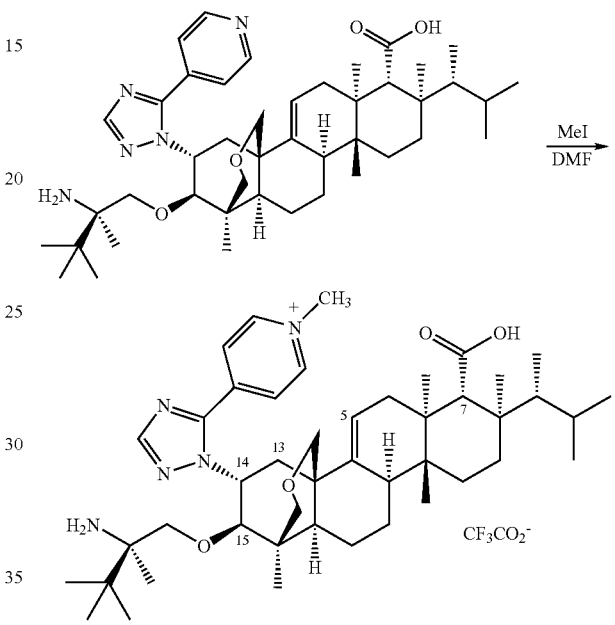

By a procedure analogous to that described for Example 260, but starting with (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 184), the title compound was prepared and isolated as a white solid.

$^1$H NMR (CD$_3$OD, 500 MHz, ppm) δ 0.78 (s, 3H, Me), 0.79 (d, 3H, Me), 0.80 (s, 3H, Me), 0.82 (d, 3H, Me), 0.85 (d, 3H, Me), 0.88 (d, 3H, Me), 0.89 (s, 3H, Me), 0.92 (d, 3H, Me), 1.19 (s, 3H, Me), 1.23 (s, 3H, Me), 1.25-1.39 (m), 1.43-1.48 (m), 1.51-1.69 (m), 1.70-1.78 (m), 1.83-2.01 (m), 2.05-2.12 (m), 2.15-2.25 (m), 2.59 (dd, 1H, H13), 2.86 (d, 1H), 2.87 (s, 1H, H7), 3.50 (d, 1H), 3.52 (d, 1H), 3.58 (dd, 1H), 3.71 (d, 1H), 3.86 (d, 1H), 4.01 (d, 1H), 5.62 (dd, 1H, H5), 5.81-5.88 (m, 1H, H14), 7.90 (d, 2H, ArH), 8.19 (s, 1H, triazole), 8.51 (d, 2H, ArH).

Mass Spectrum: (ESI) m/z=732.61 (M+H).

A solution of (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid-TFA salt (Example 173, 50 mg, 0.059 mmol) and methyl iodide (0.1 mL, 1.6 mmol) in dimethylformamide (0.2 mL) was blanketed with nitrogen and stirred at room temperature for 2.5 hours. The mixture was evaporated and purified by reverse phase HPLC using a 19×150 mm Sunfire Preparative C18 OBD column (elution with MeCN/water+0.05% TFA). Fractions were evaporated and freeze-dried from a mixture of ethanol and benzene to give the title compound as a TFA salt (40.9 mg).

$^1$H NMR (CD$_3$OD, 600 MHz, ppm) δ 0.75 (s, 3H, Me), 0.77 (d, 3H, Me), 0.77 (s, 3H, Me), 0.85 (s, 9H, Me), 0.85 (d, 3H, Me), 0.89 (s, 3H, Me), 0.90 (d, 3H, Me), 1.17 (s, 3H, Me), 1.21 (s, 3H, Me), 1.23-1.34 (m), 1.41-1.45 (m), 1.48-1.65 (m), 1.84-1.98 (m), 2.06-2.12 (m), 2.14-2.21 (m), 2.64 (dd, 1H, H13), 2.85 (s, 1H, H7), 2.89 (d, 1H), 3.51 (d, 1H), 3.58 (dd, 1H), 3.65 (d, 1H), 3.68 (d, 1H), 3.84 (d, 1H), 4.08 (d, 1H), 4.51 (s, 3H, quaternary NMe), 5.60 (dd, 1H, H5), 5.89 (m, 1H, H14), 8.31 (s, 1H, triazole), 8.44 (br d, 2H, pyridyl H) and 9.14 (d, 2H, pyridyl H).

Mass spectrum: (ESI) m/z=744.48 (M+).

Example 264

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-3-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid trifluoroacetate

Example 265

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-methyl-4-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid trifluoroacetate

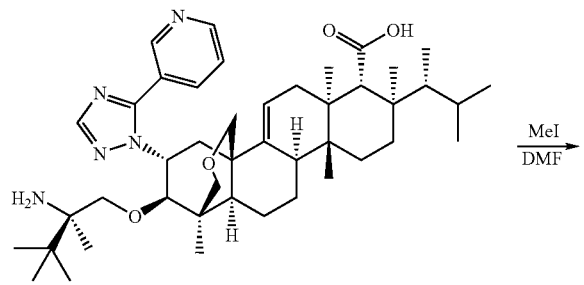

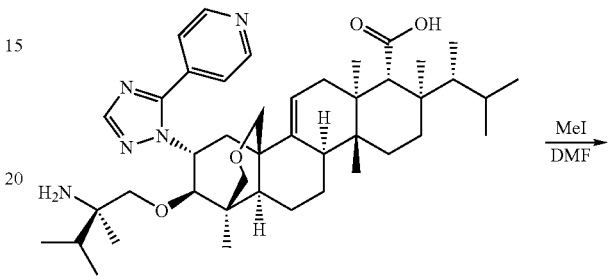

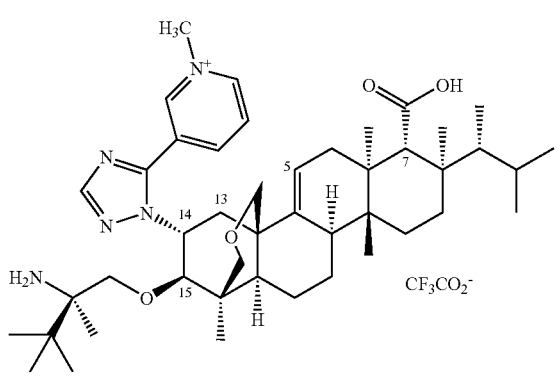

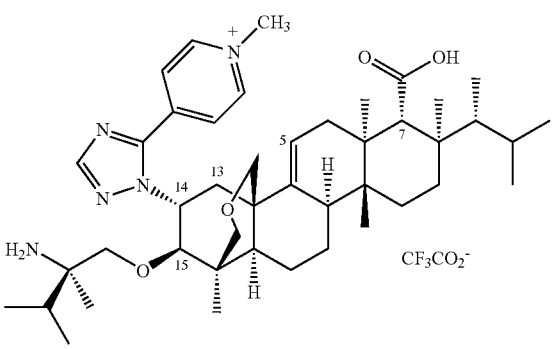

By a procedure analogous to that described for Example 263, but starting with (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 201), the title compound was prepared and isolated as a white solid.

$^1$H NMR (CD$_3$OD, 600 MHz, ppm) δ 0.75 (s, 3H, Me), 0.76 (s, 3H, Me), 0.77 (d, 3H, Me), 0.85 (d, 3H, Me), 0.86 (s, 9H, Me), 0.90 (d, 3H, Me), 0.91 (s, 3H, Me), 1.16 (s, 3H, Me), 1.21 (s, 3H, Me), 1.23-1.34 (m), 1.41-1.45 (m), 1.48-1.65 (m), 1.82-1.98 (m), 2.01-2.06 (m), 2.14-2.21 (m), 2.56 (dd, 1H, H13), 2.84 (s, 1H, H7), 2.98 (d, 1H), 3.50 (d, 1H), 3.56 (dd, 1H), 3.62 (d, 1H), 3.71 (d, 1H), 3.87 (d, 1H), 4.08 (d, 1H), 4.58 (s, 3H, quaternary NMe), 5.57 (dd, 1H, H5), 5.80 (m, 1H, H14), 8.26 (s, 1H, triazole), 8.35 (dd, 1H, pyridyl H), 8.92 (d, 1H, pyridyl H), 9.13 (br dd, 1H, pyridyl H) and 9.37 (br d, 1H, pyridyl H).

Mass spectrum: (ESI) m/z=744.47 (M+).

By a procedure analogous to that described for Example 263, but starting with (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 184), the title compound was prepared and isolated as a white solid.

$^1$H NMR (CD$_3$OD, 500 MHz, ppm) δ 0.79 (s, 3H, Me), 0.80 (d, 3H, Me), 0.81 (s, 3H, Me), 0.83 (d, 6H, 2Me), 0.88 (d, 3H, Me), 0.91 (s, 3H, Me), 0.92 (d, 3H, Me), 1.19 (s, 3H, Me), 1.24 (s, 3H, Me), 1.24-1.38 (m), 1.43-1.48 (m), 1.50-1.69 (m), 1.71-1.79 (m), 1.84-2.00 (m), 2.06-2.13 (m), 2.16-2.25 (m), 2.61 (dd, 1H, H13), 2.87 (s, 1H, H7), 2.90 (d, 1H), 3.53 (d, 2H), 3.58 (dd, 1H), 3.67 (d, 1H), 3.86 (d, 1H), 4.08 (d, 1H), 4.53 (s, 3H, ArNMe), 5.59 (dd, 1H, H5), 5.90-5.97 (m, 1H, H14), 8.33 (s, 1H, triazole), 8.46 (d, 2H, ArH), 9.16 (d, 2H, ArH).

Mass Spectrum: (ESI) m/z=730.64 (M+).

Example 266

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-ethyl-4-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid trifluoroacetate

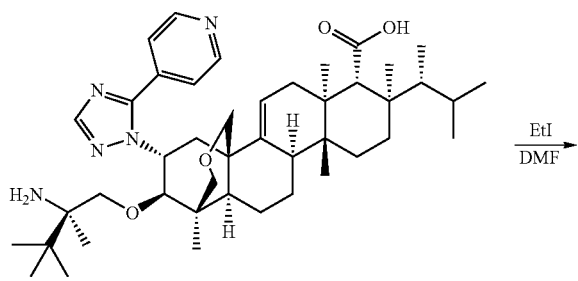

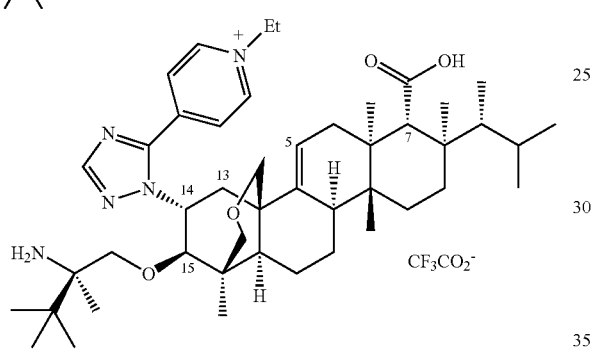

By a procedure analogous to that described in Example 263, but employing iodoethane, the title compound was prepared and isolated as a white solid.

$^1$H NMR (CD$_3$OD, 600 MHz, ppm) δ 0.75 (s, 3H, Me), 0.79 (d, 3H, Me), 0.79 (s, 3H, Me), 0.88 (s, 9H, Me), 0.88 (d, 3H, Me), 0.92 (d, 3H, Me), 0.93 (s, 3H, Me), 1.19 (s, 3H, Me), 1.23 (s, 3H, Me), 1.23-1.36 (m), 1.44-1.48 (m), 1.51-1.68 (m), 1.74 (t, 3H, quaternary NCH$_2$CH$_3$), 1.84-1.99 (m), 2.08-2.14 (m), 2.08-2.24 (m), 2.64 (dd, 1H, H13), 2.87 (s, 1H, H7), 2.92 (d, 1H), 3.52 (d, 1H), 3.60 (dd, 1H), 3.71 (d, 1H), 3.71 (d, 1H), 3.89 (d, 1H), 4.10 (d, 1H), 4.60 (q, 2H, quaternary NCH$_2$CH$_3$), 5.62 (dd, 1H, H5), 5.94 (m, 1H, H14), 8.33 (s, 1H, triazole), 8.49 (br d, 2H, pyridyl H) and 9.26 (d, 2H, pyridyl H).

Mass spectrum: (ESI) m/z=758.49 (M+).

Example 267

(1S,4aR,6aS,7R,8R,10aR,10bR,12aR,14R,15R)-15-[[(2R)-2-[(aminocarbonyl)amino]-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

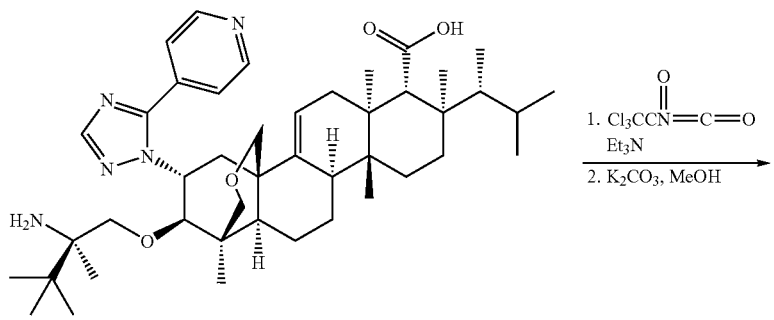

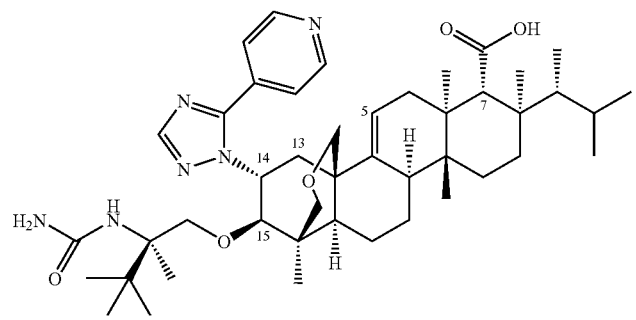

To a solution of (1S,4aR,6aS,7R,8R,10aR,10bR,12aR, 14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 173, 20 mg, 0.027 mmol) and triethylamine (0.015 mL, 0.11 mmol) in dichloroethane (0.27 mL) was added trichloroacetyl isocyanate (0.004 mL, 0.032 mmoL). The solution was stirred at room temperature for 70 min and then evaporated to dryness. Methanol (0.5 mL) was added to the residue followed by solid potassium carbonate (14.6 mg, 0.11 mmol and the mixture was stirred at room temperature. After 55 min, water (0.1 mL) was added giving a clear solution. The solution was stirred at room temperature for 1 hour and then stored at 5° C. for 64 hours. The solution was evaporated and the residue purified by reverse phase HPLC using a 19×150 mm Sunfire Preparative C18 OBD column (elution with MeCN/water+0.05% TFA). Fractions containing the product were evaporated and freeze-dried from a mixture of ethanol and benzene to give the title compound (not a salt form) as a white solid.

$^1$H NMR (CD$_3$OD, 600 MHz, ppm) δ 0.75 (s, 3H, Me), 0.75 (s, 9H, Me), 0.76 (d, 3H, Me), 0.85 (d, 3H, Me), 0.89 (d, 3H, Me), 0.90 (s, 3H, Me), 0.91 (d, 3H, Me), 1.16 (s, 3H, Me), 1.21 (s, 3H, Me), 1.23-1.34 (m), 1.40-1.45 (m), 1.48-1.65 (m), 1.80-1.95 (m), 2.16-2.21 (m), 2.43 (dd, 1H, H13), 2.81 (d, 1H), 2.83 (s, 1H, H7), 3.44 (d, 1H), 3.55 (dd, 1H), 3.56 (d, 1H), 3.78 (d, 1H), 3.84 (d, 1H), 3.94 (d, 1H), 5.51 (dd, 1H, H5), 5.87 (m, 1H, H14), 8.20 (s, 1H, triazole), 8.24 (br d, 2H, pyridyl H) and 8.99 (br d, 2H, pyridyl H).

Mass spectrum: (ESI) m/z=773.55 (M+H).

Example 268

(1S,4aR,6aS,7R,8R,8R,10aR,10bR,12aR,14R,15R)-15-[[(2R)-2-amino-2,3,3-trimethylbutyl]oxy]-14-[5-[4-(4,5-dihydro-1H-imidazol-2-yl)phenyl]-1H-1,2,4-triazol-1-yl]-8-[(1R)-1,2-dimethylpropyl]-1,6,6a,7,8, 9,10,10a,10b,11,12,12a-dodecahydro-1,6a,8,10a-tetramethyl-4H-1,4a-propano-2H-phenanthro[1,2-c]pyran-7-carboxylic acid

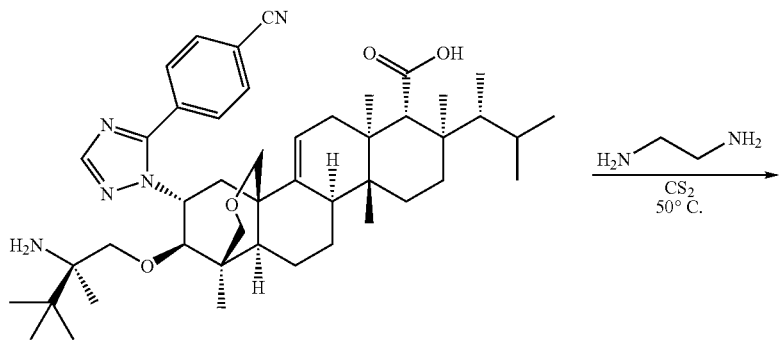

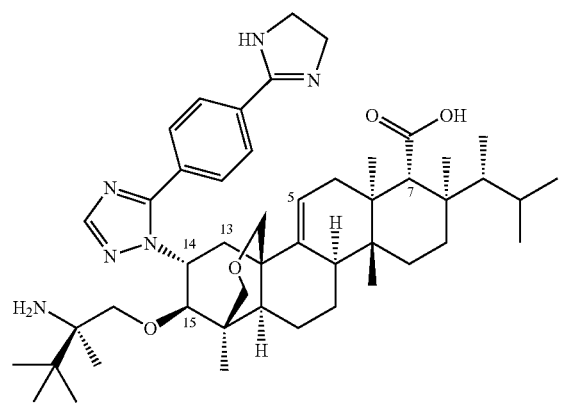

(1S,4aR,6aS,7R,8R,10aR,10bR,12aR,14R,15R)-15-[[(2R)-2-amino-2,3,3-trimethylbutyl]oxy]-14-[5-(4-cyanophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 177, 32.2 mg, 0.037 mmol), ethylenediamine (0.5 ml, 7.40 mmol), and carbon disulfide (3 μl, 0.050 mmol) were combined to give a stirred, colorless solution that was heated to 50° C. After 27.5 hours, additional carbon disulfide (3 μl, 0.050 mmol) was added to the reaction mixture. After 50 hours, LCMS showed the reaction to be complete. The reaction mixture was cooled to room temperature, diluted with methanol, and evaporated under reduced pressure to give a light yellow residue. The residue was taken up in methanol, filtered (0.45 μm syringe filter), and purified using a single HPLC run on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product HPLC fractions were combined, the solvent was removed under reduced pressure, and the residue was lyophilized from ethanol and benzene to give the title compound (28.5 mg) as a white solid.

$^1$H NMR (CD$_3$OD, 600 MHz, ppm) δ 0.78 (d, 3H, Me), 0.78 (s, 3H, Me), 0.80 (s, 3H, Me), 0.85 (s, 9H, t-bu), 0.86 (d, 3H, Me), 0.87 (s, 3H, Me), 0.90 (d, 3H, Me), 1.18 (s, 3H, Me), 1.22 (s, 3H, Me), 1.23-1.35 (m), 1.41-1.46 (m), 1.49-1.66 (m), 1.81-1.98 (m), 2.06-2.13 (m), 2.14-2.23 (m), 2.59 (dd, 1H, H13), 2.85 (s, 1H, H7), 2.91 (d, 1H), 3.44 (d, 1H), 3.55 (dd, 1H), 3.61 (d, 2H), 3.79 (d, 1H), 4.03 (d, 1H), 4.14 (s, 4H, dihydroimidazole), 5.61 (dd, 1H, H5), 5.84-5.90 (m, 1H, H14), 8.01 (d, 2H, ArH), 8.06 (d, 2H, ArH), 8.20 (s, 1H, triazole)

Mass Spectrum: (ESI) m/z=797.63 (M+H).

Example 269

(1S,4aR,6aS,7R,8R,10aR,10bR,12aR,14R,15R)-15-[[(2R)-2-amino-2,3,3-trimethylbutyl]oxy]-14-[5-[3-(4,5-dihydro-1H-imidazol-2-yl)phenyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

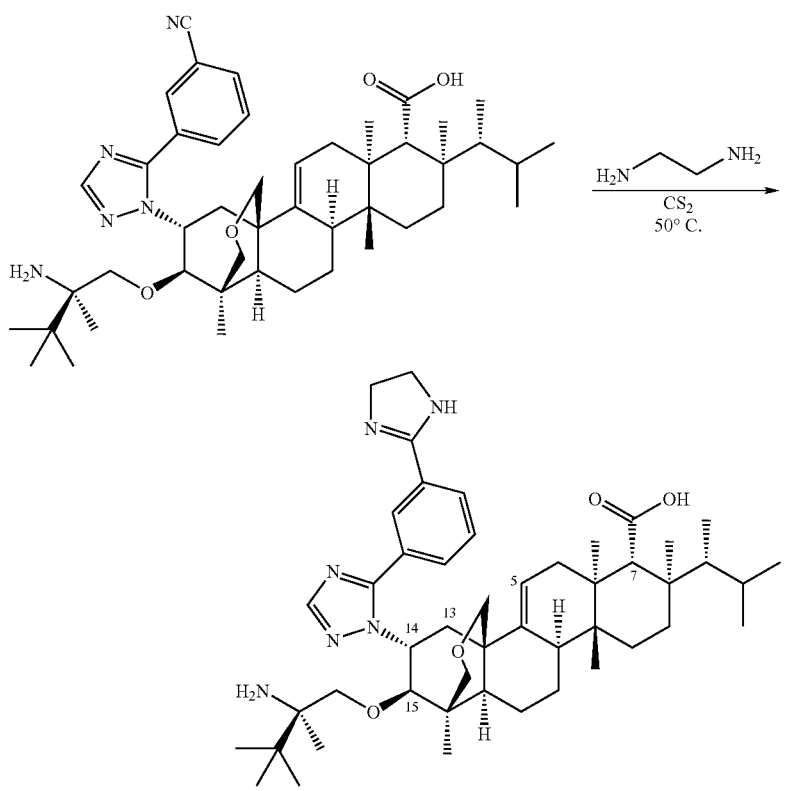

By a procedure analogous to that described in Example 268, but starting with (1S,4aR,6aS,7R,8R,10aR,10bR,12aR,14R,15R)-15-[[(2R)-2-amino-2,3,3-trimethylbutyl]oxy]-14-[5-(3-cyanophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 227), the title compound was prepared and isolated as a white solid.

$^1$H NMR (CD$_3$OD, 600 MHz, ppm) δ 0.77 (s, 3H, Me), 0.77 (d, 3H, Me), 0.78 (s, 3H, Me), 0.86 (s, 9H, t-bu), 0.86 (d, 3H, Me), 0.89 (s, 3H, Me), 0.90 (d, 3H, Me), 1.18 (s, 3H, Me), 1.21 (s, 3H, Me), 1.23-1.35 (m), 1.41-1.46 (m), 1.49-1.66 (m), 1.82-1.99 (m), 2.04-2.10 (m), 2.14-2.22 (m), 2.52 (dd, 1H, H13), 2.85 (s, 1H, H7), 2.97 (d, 1H), 3.48 (d, 1H), 3.57 (abq, 2H), 3.65 (d, 1H), 3.82 (d, 1H), 4.05 (d, 1H), 4.16 (s, 4H, dihydroimidazole), 5.58 (dd, 1H, H5), 5.86-5.92 (m, 1H, H14), 7.89 (t, 1H, ArH), 8.04 (dt, 1H, ArH), 8.14 (t, 1H, ArH), 8.18 (dt, 1H, ArH), 8.19 (s, 1H, triazole).

Mass Spectrum: (ESI) m/z=797.61 (M+H).

Example 270

(1S,4aR,6aS,7R,8R,10aR,10bR,12aR,14R,15R)-15-[[(2R)-2-amino-2,3-dimethylbutyl]oxy]-14-(5-[2,4'-bipyridin]-4-yl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

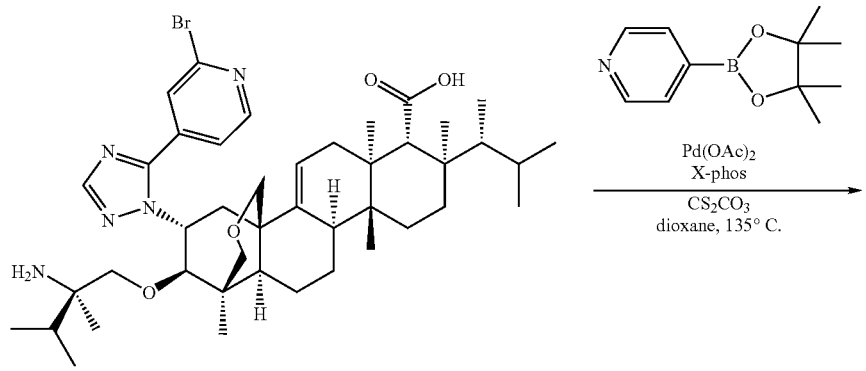

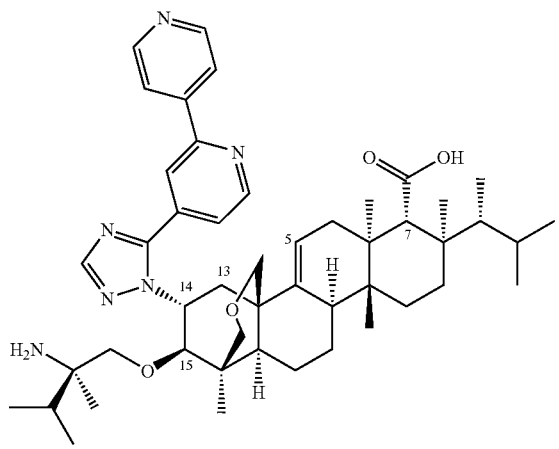

(1S,4aR,6aS,7R,8R,10aR,10bR,12aR,14R,15R)-15-[[(2R)-2-amino-2,3-dimethylbutyl]oxy]-14-[5-(2-bromo-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 175, 10.1 mg, 0.011 mmol), 4-(4,4,5,5-tetramethyl-1,3,2-dioxaborolan-2-yl)pyridine (29.2 mg, 0.142 mmol), palladium(II) acetate (1.8 mg, 8.02 mmol), 2-dicyclohexylphosphino-2',4',6'-triisopropyl-1,1'biphenyl (4.3 mg, 9.02 μmol), cesium carbonate (46.1 mg, 0.141 mmol), and 1,4-dioxane (0.5 ml) were combined in a 0.5-2 ml microwave vial. The reaction mixture was purged with nitrogen before the vial was sealed. The reaction mixture was heated at 135° C. in a microwave reactor for 30 minutes. The reaction mixture was filtered (0.45 μm syringe filter), diluted with methanol, and evaporated under reduced pressure to give a light brown residue. The residue was dissolved in methanol and purified using a single HPLC run on a 30×150 mm Sunfire Prep C18 OBD 10 μm column by eluting with acetonitrile/water+0.1% TFA. The total flow rate was 20 ml/min and the HPLC method employed a 17 minute 20%-100% acetonitrile/water gradient followed by a 2 minute acetonitrile flush. The product fractions were combined, the solvent was evaporated under reduced pressure, and the residue was lyophilized from ethanol and benzene to give the title compound (7.2 mg) as a white solid.

$^1$H NMR (CD$_3$OD, 500 MHz, ppm) δ 0.79 (s, 3H, Me), 0.80 (d, 3H, Me), 0.80 (s, 3H, Me), 0.82 (d, 3H, Me), 0.84 (d, 3H, Me), 0.88 (d, 3H, Me), 0.90 (s, 3H, Me), 0.92 (d, 3H, Me), 1.21 (s, 3H, Me), 1.24 (s, 3H, Me), 1.25-1.39 (m), 1.43-1.49 (m), 1.52-1.78 (m), 1.85-2.01 (m), 2.12-2.25 (m), 2.69 (dd, 1H, H13), 2.87 (s, 1H, H7), 2.91 (d, 1H), 3.52 (d, 1H), 3.52 (d, 1H), 3.63 (dd, 1H), 3.69 (d, 1H), 3.87 (d, 1H), 4.04 (d, 1H), 5.64 (dd, 1H, H5), 6.03-6.11 (m, 1H, H14), 8.01 (dd, 1H, ArH), 8.27 (s, 1H, triazole), 8.53 (d, 1H, ArH), 8.68 (d, 2H, ArH), 8.99 (d, 2H, ArH), 9.08 (d, 1H, ArH).

Mass Spectrum: (ESI) m/z=793.73 (M+H).

Examples 271-273

The following compounds were prepared using methods analogous to those described in the preceding examples:

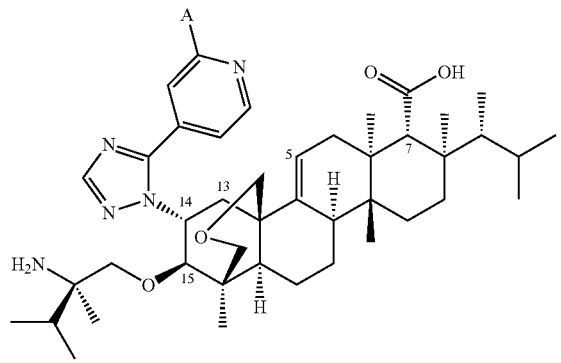

| 271 | A = | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-phenyl-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.79 (s, 3H, Me), 0.80 (d, 3H, Me), 0.81 (s, 3H, Me), 0.81 (d, 3H, Me), 0.83 (d, 3H, Me), 0.88 (d, 3H, Me), 0.89 (s, 3H, Me), 0.92 (d, 3H, Me), 1.21 (s, 3H, Me), 1.24 (s, 3H, Me), 1.25-1.40 (m), 1.43-1.49 (m), 1.51-1.76 (m), 1.84-2.01 (m), 2.11-2.26 (m), 2.70 (dd, 1H, H13), 2.88 (s, 1H, H7), 2.90 (d, 1H), 3.51 (d, 2H), 3.63 (dd, 1H), 3.70 (d, 1H), 3.88 (d, 1H), 4.03 (d, 1H), 5.63 (dd, 1H, H5), 6.05-6.13 (m, 1H, H14), 7.50-7.58 (m, 3H, ArH), 7.78 (dd, 1H, ArH), 8.06 (d, 2H, ArH), 8.17 (d, 1H, ArH), 8.24 (s, 1H, triazole), 8.87 (d, 1H, ArH).
Mass Spectrum: (ESI) m/z = 792.70 (M + H).

| 272 | A = | (1S,4aR,6aS,7R,8R,10aR,10bR,12aR,14R,15R)-15-[[(2R)-2-amino-2,3-dimethylbutyl]oxy]-14-(5-[2,3'-bipyridin]-4-yl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.79 (s, 3H, Me), 0.79 (d, 3H, Me), 0.80 (s, 3H, Me), 0.82 (d, 3H, Me), 0.84 (d, 3H, Me), 0.88 (d, 3H, Me), 0.90 (s, 3H, Me), 0.92 (d, 3H, Me), 1.20 (s, 3H, Me), 1.23 (s, 3H, Me), 1.24-1.40 (m), 1.43-1.49 (m), 1.51-1.77 (m), 1.85-2.01 (m), 2.12-2.25 (m), 2.70 (dd, 1H, H13), 2.87 (s, 1H, H7), 2.90 (d, 1H), 3.52 (d, 1H), 3.52 (d, 1H), 3.64 (dd, 1H), 3.70 (d, 1H), 3.88 (d, 1H), 4.04 (d, 1H), 5.65 (dd, 1H, H5), 6.07-6.15 (m, 1H, H14), 7.89 (d, 1H, ArH), 7.90 (d, 1H, ArH), 8.26 (s, 1H, triazole), 8.33 (d, 1H, ArH), 8.80 (dd, 1H, ArH), 8.86 (dt, 1H, ArH), 8.98 (d, 1H, ArH), 9.38 (d, 1H, ArH).
Mass Spectrum: (ESI) m/z = 793.76 (M + H).

| 273 | A = | (1S,4aR,6aS,7R,8R,10aR,10bR,12aR,14R,15R)-15-[[(2R)-2-amino-2,3-dimethylbutyl]oxy]-14-(5-[2,2'-bipyridin]-4-yl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 500 MHz, ppm) δ 0.80 (d, 3H, Me), 0.81 (s, 3H, Me), 0.82 (s, 3H, Me), 0.84 (d, 3H, Me), 0.85 (d, 3H, Me), 0.89 (d, 3H, Me), 0.89 (s, 3H, Me), 0.93 (d, 3H, Me), 1.22 (s, 3H, Me), 1.24 (s, 3H, Me), 1.25-1.40 (m), 1.43-1.49 (m), 1.51-2.26 (m), 2.72 (dd, 1H, H13), 2.89 (s, 1H, H7), 2.96 (d, 1H), 3.44 (d, 1H), 3.54 (d, 1H), 3.56 (dd, 1H), 3.78 (d, 1H), 3.79 (d, 1H), 4.06 (d, 1H), 5.70 (dd, 1H, H5), 5.97-6.05 (m, 1H, H14), 7.58 (dd, 1H, ArH), 7.84 (dd, 1H, ArH), 8.10 (dt, 1H, ArH), 8.24 (s, 1H, triazole), 8.53 (d, 1H, ArH), 8.74 (dd, 1H, ArH), 8.87 (d, 1H, ArH), 8.93 (d, 1H, ArH).
Mass Spectrum: (ESI) m/z = 793.61 (M + H).

Example 274

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

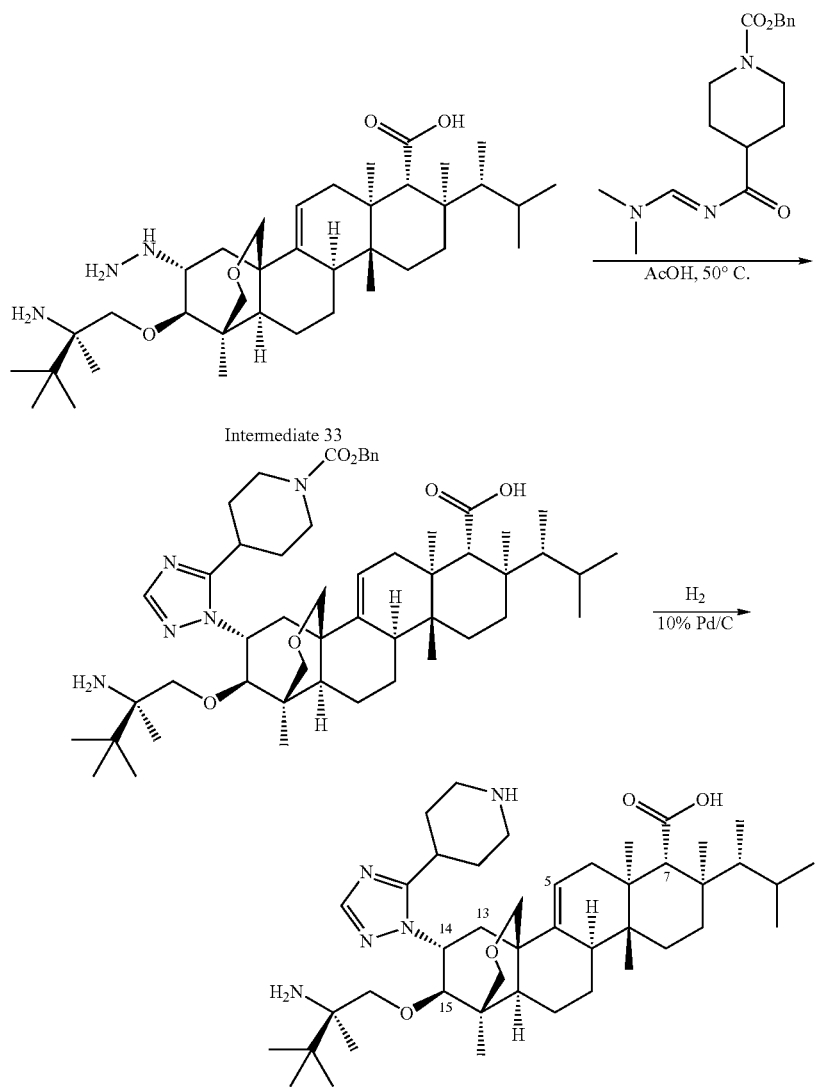

A suspension of Intermediate 33 (60.0 mg, 0.097 mol) and phenylmethyl 4-({[(1E)-(dimethylamino)methylidene]amino}carbonyl)piperidine-1-carboxylate (31 mg, 0.098 mol) in acetic acid (1.5 mL) was blanketed with nitrogen and heated in a 50° C. oil bath for 0.5 hours. After cooling to room temperature, 10% Pd/C was added and the mixture was placed under a balloon of hydrogen and stirred rapidly overnight at room temperature. The dark suspension was filtered, evaporated and purified by reverse phase HPLC using a 19×150 mm Sunfire Preparative C18 OBD column eluting with acetonitrile/water+0.1% TFA. Fractions containing the product were combined, evaporated and freeze-dried to give the title compound as a TFA salt (32.3 mg).

$^1$H NMR (CD$_3$OD, 600 MHz, ppm) δ 0.77 (s, 3H, Me), 0.77 (d, 3H, Me), 0.85 (s, 3H, Me), 0.85 (s, 9H, Me), 0.85 (d, 3H, Me), 0.90 (d, 3H, Me), 0.91 (s, 3H, Me), 1.14 (s, 3H, Me), 1.20 (s, 3H, Me), 1.23-1.34 (m), 1.41-1.44 (m), 1.48-1.65 (m), 1.81-2.01 (m), 2.09-2.22 (m), 2.29 (dd, 1H, H13), 2.84 (s, 1H, H7), 2.99 (d, 1H), 3.12-3.38 (m), 3.48 (m), 3.55 (d, 1H), 3.59 (dd, 1H), 3.62 (m), 3.63 (d, 1H), 3.66 (d, 1H), 3.94 (d, 1H), 4.02 (d, 1H), 5.47 (m, 1H, H14), 5.51 (dd, 1H, H5) and 7.98 (s, 1H, triazole).

Mass spectrum: (ESI) m/z=736.56 (M+H).

Examples 275-287

The following compounds were prepared using methods analogous to those described in the preceding examples:

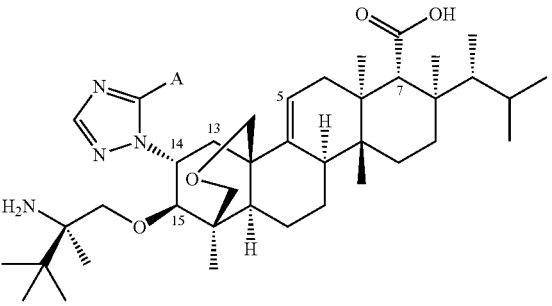

| 275 | A = | (1S,4aR,6aS,7R,8R,10aR,10bR,12aR,14R,15R)-14-[5-(1-acetyl-4-piperidinyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|
| | 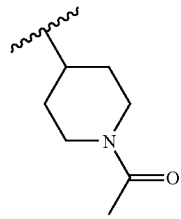 | |

$^1$H NMR (CD$_3$OD, 600 MHz, ppm) (spectra shows rotamers) δ 0.76 (s, 3H, Me), 0.76 (d, 3H, Me), 0.81 and 0.84 (s, 3H, Me), 0.85 (s, 9H, Me), 0.85 (d, 3H, Me), 0.89 (d, 3H, Me), 0.91 and 0.90 (s, 3H, Me), 1.14 (s, 3H, Me), 1.20 (s, 3H, Me), 1.23-1.34 (m), 1.40-1.44 (m), 1.48-1.65 (m), 1.74-2.01 (m), 2.12 and 2.13 (s, 3H, NAc), 2.13 and 2.29 (m), 2.29 and 2.30 (dd, 1H, H13), 2.84 (s, 1H, H7), 2.78-2.90 (m), 2.94 and 3.00 (d, 1H), 3.53 (d, 1H), 3.58 (dd, 1H), 3.63 (d, 1H), 3.65 (d, 1H), 3.94 (d, 1H), 3.88 and 4.00 (d, 1H), 4.02 and 4.08 (br m), 4.58 and 4.62 (br m), 5.51 (dd, 1H, H5), 5.54 (m, 1H, H14), 7.93 and 7.94 (s, 1H, triazole).
Mass spectrum: (ESI) m/z = 778.78 (M + H).

| 276 | A = | (1S,4aR,6aS,7R,8R,10aR,10bR,12aR,14R,1SR)-15-[[(2R)-2-amino-2,3,3-trimethylbutyl]oxy]-8-[(1R)-1,2-dimethylpropyl]-14-[5-[1-(methoxycarbonyl)-4-piperidinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|
| | 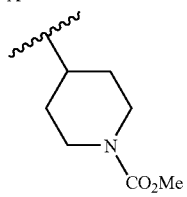 | |

$^1$H NMR (CD$_3$OD, 600 MHz, ppm) δ 0.76 (s, 3H, Me), 0.77 (d, 3H, Me), 0.82 (s, 3H, Me), 0.85 (s, 9H, Me), 0.85 (d, 3H, Me), 0.89 (d, 3H, Me), 0.90 (s, 3H, Me), 1.14 (s, 3H, Me), 1.20 (s, 3H, Me), 1.23-1.34 (m), 1.40-1.44 (m), 1.48-1.72 (m), 1.80-1.96 (m), 2.12-2.22 (m), 2.29 (dd, 1H, H13), 2.84 (s, 1H, H7), 2.97 (d, 1H), 3.00-3.22 (m), 3.53 (d, 1H), 3.58 (dd, 1H), 3.64 (d, 1H), 3.65 (d, 1H), 3.70 (s, 3H, OMe), 3.94 (d, 1H), 3.99 (d, 1H), 4.02 and 4.08 (br m), 4.18-4.27 (br m), 5.52 (dd, 1H, H5), 5.53 (m, 1H, H14), 7.93 (s, 1H, triazole).
Mass spectrum: (ESI) m/z = 794.53 (M + H).

| 277 | A = | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-4-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |
|---|---|---|
| | 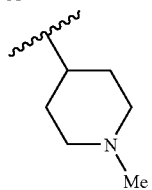 | |

$^1$H NMR (CD$_3$OD, 600 MHz, ppm) δ 0.76 (s, 3H, Me), 0.76 (d, 3H, Me), 0.82 (s, 3H, Me), 0.85 (s, 9H, t-bu), 0.85 (d, 3H, Me), 0.89 (d, 3H, Me), 0.91 (s, 3H, Me), 1.14 (s, 3H, Me), 1.20 (s, 3H, Me), 1.22-1.35 (m), 1.40-1.45 (m), 1.47-1.56 (m), 1.58-1.65 (m), 1.79-1.96 (m), 1.99-2.28 (m), 2.30 (dd, 1H, H13), 2.84 (s, 1H, H7), 2.93 (s, 3H, NMe), 3.01 (d, 1H), 3.14-3.26 (m), 3.47-3.57 (m), 3.53 (d, 1H), 3.57 (dd, 1H), 3.60-3.70 (m), 3.64 (d, 1H), 3.66 (d, 1H), 3.95 (d, 1H), 4.02 (d, 1H), 5.44-5.53 (m, 2H, H5 and H14), 7.97 (s, 1H, triazole).
Mass Spectrum: (ESI) m/z = 750.64 (M + H).

-continued

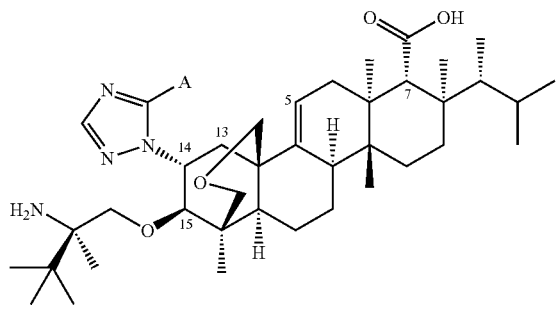

| | | |
|---|---|---|
| 278 | A = 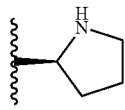 | (1S,4aR,6a5,7R,8R,10aR,10bR,12aR,14R,15R)-15-[[(2R)-2-amino-2,3,3-trimethylbutyl]oxy]-8-[(1R)-1,2-dimethylpropyl]-14-[5-[(2S)-2-pyrrolidinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.79 (s, 3H, Me), 0.85 (d, 3H, Me), 0.86 (s, 9H, Me), 0.89 (d, 3H, Me), 0.92 (s, 3H, Me), 1.12 (s, 3H, Me), 1.19 (s, 3H, Me), 1.23-1.34 (m), 1.40-1.44 (m), 1.48-1.54 (m), 1.59-1.65 (m), 1.74-1.96 (m), 2.10-2.27 (m), 2.29-2.36 (m), 2.44 (dd, 1H, H13), 2.54 (m), 2.84 (s, 1H, H7), 3.11 (d, 1H), 3.46-3.58 (m), 3.68 (d, 1H), 3.71 (d, 1H), 3.94 (d, 1H), 4.10 (d, 1H), 5.50 (dd, 1H, H5), 5.53 (m, 1H, H14), and 8.06 (s, 1H, triazole).
Mass spectrum: (ESI) m/z = 722.53 (M + H).

| | | |
|---|---|---|
| 279 | A = 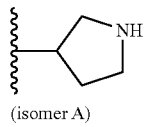<br>(isomer A) | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14--[5-[(3R or S)-3-pyrrolidinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.82 (s, 3H, Me), 0.85 (d, 3H, Me), 0.86 (s, 9H, Me), 0.89 (d, 3H, Me), 0.91 (s, 3H, Me), 1.13 (s, 3H, Me), 1.20 (s, 3H, Me), 1.23-1.34 (m), 1.40-1.44 (m), 1.48-1.56 (m), 1.59-1.65 (m), 1.78-1.96 (m), 2.10-2.22 (m), 2.32 (dd, 1H, H13), 2.36 (m), 2.49 (m), 2.84 (s, 1H, H7), 3.06 (d, 1H), 3.47 (d, 1H), 3.52 (d, 1H), 3.57 (dd, 1H), 3.62 (m), 3.64 (d, 1H), 3.68 (d, 1H), 3.75 (dd, 1H), 3.96 (d, 1H), 3.98 (m), 4.20 (d, 1H), 5.51 (dd, 1H, H5), 5.53 (m, 1H, H14), and 7.97 (s, 1H, triazole).
Mass spectrum: (ESI) m/z = 722.53 (M + H).

| | | |
|---|---|---|
| 280 | A = 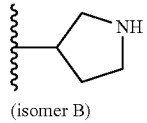<br>(isomer B) | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[(3R or S)-3-pyrrolidinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.85 (s, 9H, Me), 0.85 (d, 3H, Me), 0.89 (d, 3H, Me), 0.90 (s, 3H, Me), 1.14 (s, 3H, Me), 1.20 (s, 3H, Me), 1.23-1.34 (m), 1.40-1.44 (m), 1.48-1.56 (m), 1.59-1.65 (m), 1.80-1.96 (m), 2.06-2.22 (m), 2.29 (dd, 1H, H13), 2.57 (m), 2.84 (s, 1H, H7), 2.85 (d, 1H), 3.47 (t), 3.52 (d, 1H), 3.57 (dd, 1H), 3.62 (d, 1H), 3.65 (d, 1H), 3.67 (dd, 1H), 3.80 (dd, 1H), 3.93 (d, 1H), 3.96 (d, 1H), 3.99 (m), 5.50 (dd, 1H, H5), 5.53 (m, 1H, H14), and 7.96 (s, 1H, triazole).
Mass spectrum: (ESI) m/z = 722.53 (M + H).

| | | |
|---|---|---|
| 281 | A = 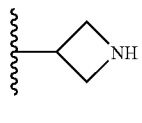 | (1S,4aR,6aS,7R,8R,10aR,10bR,12aR,14R,15R)-15-[[(2R)-2-amino-2,3,3-trimethylbutyl]oxy]-14-[5-(3-azetidinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD with K$_2$CO$_3$, 600 MHz, ppm) δ 0.75 (s, 3H, Me), 0.75 (d, 3H, Me), 0.75 (s, 9H, Me), 0.82 (d, 3H, Me), 0.86 (s, 3H, Me), 0.89 (d, 3H, Me), 1.18 (s, 3H, Me), 1.20 (s, 3H, Me), 1.26-1.40 (m), 1.45-1.51 (m), 1.55-1.63 (m), 1.74-1.92 (m), 1.98 (m), 2.10 (m), 2.19 (dd, 1H, H13), 2.29 (m), 2.65 (d, 1H), 2.72 (br s, 1H, H7), 3.48 (d, 1H), 3.53 (dd, 1H), 3.57 (d, 1H), 3.71 (br d, 1H), 3.81 (br m), 3.84 (d, 1H), 3.91 (br d, 1H), 4.00 (m), 4.28 (m), 5.31 (m, 1H, H14), 5.46 (dd, 1H, H5) and 7.95 (s, 1H, triazole).
Mass spectrum: (ESI) m/z = 708.45 (M + H).

| | | |
|---|---|---|
| 282 | A = 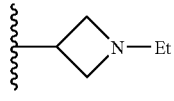 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-ethyl-3-azetidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

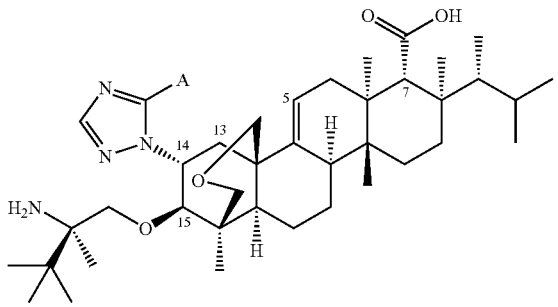

¹H NMR (CD₃OD, 600 MHz, ppm) δ 0.75 (s, 3H, Me), 0.76 (d, 3H, Me), 0.84 (s, 9H, Me), 0.85 (d, 3H, Me), 0.89 (s, 3H, Me), 0.89 (d, 3H, Me), 1.13 (s, 3H, Me), 1.20 (s, 3H, Me), 1.23-1.34 (m), 1.48-1.55 (m), 1.58-1.65 (m), 1.76-1.96 (m), 2.10-2.20 (m), 2.28 (dd, 1H, H13), 2.84 (br s, 1H, H7), 2.90 (br d, 1H), 3.39 (m), 3.50 (d, 1H), 3.55 (dd, 1H), 3.60-3.70 (br m), 3.94 (d, 1H), 3.95 (br d, 1H), 4.40-4.51 (m), 4.63-4.75 (m), 5.37 (br m, 1H, H14), 5.49 (dd, 1H, H5) and 8.06 (s, 1H, triazole).
Mass spectrum: (ESI) m/z = 736.56 (M + H).

| 283 | A = 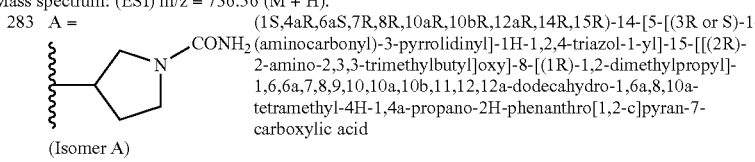 (Isomer A) | (1S,4aR,6aS,7R,8R,10aR,10bR,12aR,14R,15R)-14-[5-[(3R or S)-1-(aminocarbonyl)-3-pyrrolidinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.77 (s, 3H, Me), 0.77 (d, 3H, Me), 0.83 (s, 3H, Me), 0.85 (s, 9H, Me), 0.85 (d, 3H, Me), 0.89 (d, 3H, Me), 0.90 (s, 3H, Me), 1.14 (s, 3H, Me), 1.20 (s, 3H, Me), 1.23-1.34 (m), 1.40-1.44 (m), 1.48-1.56 (m), 1.59-1.65 (m), 1.80-1.96 (m), 2.10-2.22 (m), 2.30 (dd, 1H, H13), 2.48 and 2.32 (m), 2.84 (s, 1H, H7), 2.91 (d, 1H), 3.45 (m), 3.53 (d, 1H), 3.58 (dd, 1H), 3.66 (d, 1H), 3.68 (d, 1H), 3.79 and 3.89 (m), 3.94 (d, 1H), 3.96 (d, 1H), 5.54 (m, 1H, H14), 5.57 (dd, 1H, H5) and 7.96 (s, 1H, triazole).
Mass spectrum: (ESI) m/z = 765.49 (M + H).

| 284 | A = 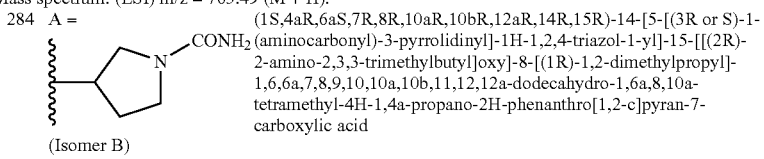 (Isomer B) | (1S,4aR,6aS,7R,8R,10aR,10bR,12aR,14R,15R)-14-[5-[(3R or S)-1-(aminocarbonyl)-3-pyrrolidinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.77 (d, 3H, Me), 0.77 (s, 3H, Me), 0.85 (s, 9H, Me), 0.85 (d, 3H, Me), 0.89 (d, 3H, Me), 0.90 (s, 3H, Me), 1.14 (s, 3H, Me), 1.20 (s, 3H, Me), 1.23-1.34 (m), 1.40-1.44 (m), 1.48-1.56 (m), 1.59-1.65 (m), 1.80-1.96 (m), 2.10-2.22 (m), 2.31 (dd, 1H, H13), 2.44 (m), 2.84 (s, 1H, H7), 2.96 (br d, 1H), 3.49 (m), 3.53 (d, 1H), 3.58 (m), 3.58 (dd, 1H), 3.65 (d, 1H), 3.69 (d, 1H), 3.70-3.82 (m), 3.96 (d, 1H), 3.97 (d, 1H), 5.51 (m, 1H, H14), 5.57 (dd, 1H, H5) and 7.94 (s, 1H, triazole).
Mass spectrum: (ESI) m/z = 765.49 (M + H).

| 285 | A = 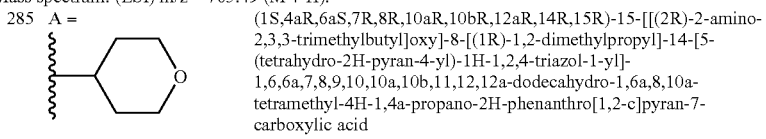 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(tetrahydro-2H-pyran-4-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 500 MHz, ppm) δ 0.78 (s, 3H, Me), 0.79 (d, 3H, Me), 0.85 (s, 3H, Me), 0.87 (s, 9H, t-bu), 0.88 (d, 3H, Me), 0.92 (d, 3H, Me), 0.93 (s, 3H, Me), 1.16 (s, 3H, Me), 1.22 (s, 3H, Me), 1.24-1.38 (m), 1.42-1.47 (m), 1.49-1.68 (m), 1.79-1.99 (m), 2.08-2.25 (m), 2.29 (dd, 1H, H13), 2.86 (s, 1H, H7), 2.96 (d, 1H), 3.21-3.29 (m), 3.54-3.65 (m), 3.55 (d, 1H), 3.59 (dd, 1H), 3.65 (d, 1H), 3.67 (d, 1H), 3.98 (d, 1H), 4.00 (d, 1H), 4.02-4.11 (m), 5.51 (dd, 1H, H5), 5.52-5.60 (m, 1H, H14), 7.98 (s, 1H, triazole).
Mass Spectrum: (ESI) m/z = 737.60 (M + H).

| 286 | A = 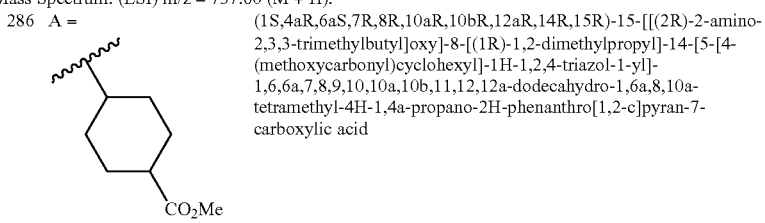 | (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[4-(methoxycarbonyl)cyclohexyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.76 (d, 3H, Me), 0.85 (s, 9H, Me), 0.85 (d, 3H, Me), 0.89 (d, 3H, Me), 0.90 (s, 3H, Me), 1.14 (s, 3H, Me), 1.20 (s, 3H, Me), 1.23-1.34 (m), 1.41-1.44 (m), 1.48-1.76 (m), 1.80-2.04 (m), 2.10-2.22 (m), 2.25 (dd, 1H, H13),

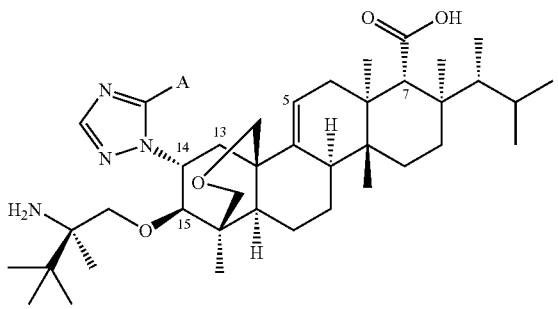

2.29-2.34 (m), 2.40-2.46 (m), 2.67 (d, 1H), 2.74 (m), 2.84 (s, 1H, H7), 2.93 (m), 3.53 (dd, 1H), 3.56-3.65 (m), 3.67 and 3.70 (s, 3H, OMe), 3.94 and 3.95 (d, 1H), 5.48 (dd, 1H, H5), 5.52 (m, 1H, H14), 7.88 and 7.92 (s, 1H, triazole).
Mass spectrum: (ESI) m/z = 793.51 (M + H).

| | | |
|---|---|---|
| 287 | A = 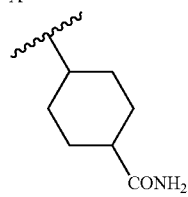 | (1S,4aR,6aS,7R,8R,10aR,10bR,12aR,14R,15R)-14-[5-[4-(aminocarbonyl)cyclohexyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (CD$_3$OD, 600 MHz, ppm) δ 0.76 (s, 3H, Me), 0.77 (d, 3H, Me), 0.85 (s, 9H, Me), 0.85 (s, 3H, Me), 0.89 (d, 3H, Me), 0.90 (s, 3H, Me), 1.14 (s, 3H, Me), 1.20 (s, 3H, Me), 1.23-1.34 (m), 1.41-1.44 (m), 1.48-1.78 (m), 1.80-2.04 (m), 2.08-2.22 (m), 2.26 (dd, 1H H13), 2.52 (m), 2.84 (s, 1H, H7), 2.86 and 2.92 (d, 1H), 3.10 (m), 3.53 (dd, 1H), 3.56-3.65 (m), 3.92 (d, 1H), 3.94 and 3.95 (d, 1H), 5.48 (dd, 1H, H5), 5.53 (m, 1H, H14), 7.89 and 7.92 (s, 1H, triazole).
Mass spectrum: (ESI) m/z = 778.53 (M + H).

Example 288

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(1H-1,2,3-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 288A) and
(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(2H-1,2,3-triazol-2-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 288B)

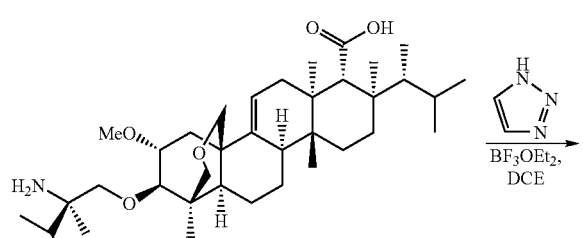

Intermediate 6

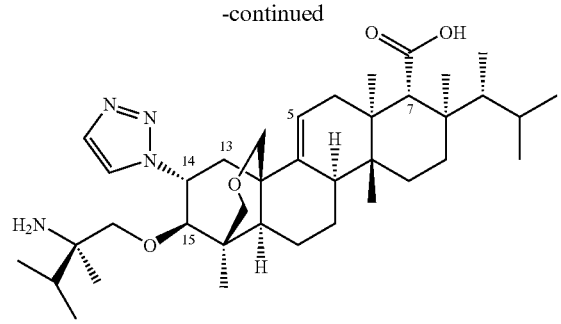

EXAMPLE 288A

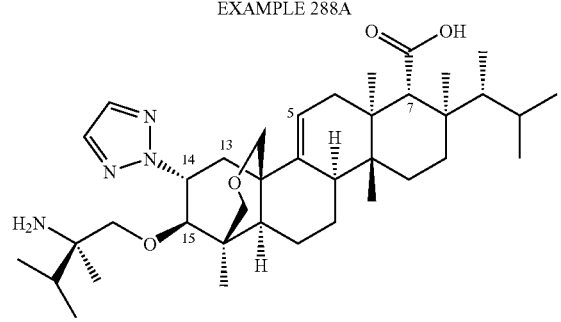

EXAMPLE 288B 1H-1,2,3-triazole (12.5 µl, 0.216 mmol) and BF$_3$O(CH$_2$CH$_3$)$_2$ (54 µl, 0.426 mmol) were added to a stirred solution of Intermediate 6 (25.5 mg, 0.042 mmol) in 1,2-dichloroethane (0.42 ml). The reaction mixture was a light yellow solution that was heated to 50° C. After 1.6 hours, LCMS and ¹H NMR showed the reaction to be complete. The reaction mixture was cooled to room temperature, the solvent was evaporated under reduced pressure, and the resulting residue was placed under high vacuum. The residue was dissolved in methanol and separated using a single HPLC run on a 19×150 mm Sunfire Prep C18 OBD 10 μm column by eluting with acetonitrile/water+0.1% TFA. The total flow rate was 20 ml/min and the HPLC method employed a 12 minute 20%-100% acetonitrile/water gradient followed by a 6 minute acetonitrile flush. The HPLC fractions of the faster eluting regioisomer were combined, the solvent was evaporated under reduced pressure, and the residue was lyophilized from ethanol and benzene to give EXAMPLE 288A (15.3 mg, 0.020 mmol) as a white solid. The HPLC fractions of the slower eluting regioisomer were combined, the solvent was evaporated under reduced pressure, and the residue was lyophilized from ethanol and benzene to give EXAMPLE 288B (8.4 mg, 0.011 mmol) as a white solid. The regiochemistry of the two isomers was assigned based on an ¹H NMR NOE from H14 to the triazole proton that was observed for EXAMPLE 288A but not for EXAMPLE 288B.

Example 288A

¹H NMR (CD₃OD, 600 MHz, ppm) [The free base was prepared by neutralizing the TFA salt with potassium carbonate to sharpen the broad triazole signals] δ 0.69 (d, 3H, Me), 0.71 (d, 3H, Me), 0.73 (s, 3H, Me), 0.75 (d, 3H, Me), 0.76 (s, 3H, Me), 0.82 (d, 3H, Me), 0.87 (s, 3H, Me), 0.89 (d, 3H, Me), 1.15-1.20 (m), 1.21 (s, 3H, Me), 1.24 (s, 3H, Me), 1.25-1.38 (m), 1.40-1.44 (m), 1.45-1.53 (m), 1.55-1.65 (m), 1.78-1.92 (m), 1.96-2.03 (m), 2.11-2.16 (m), 2.28-2.34 (m), 2.34 (d, 1H), 2.44 (dd, 1H, H13), 2.70 (s, 1H, H7), 3.15 (d, 1H), 3.48 (d, 1H), 3.52 (dd, 1H), 3.60 (d, 1H), 3.67 (d, 1H), 3.83 (d, 1H), 5.47 (dd, 1H, H5), 5.69-5.75 (m, 1H, H14), 7.72 (d, 1H, triazole), 8.14 (d, 1H, triazole)

Mass Spectrum: (ESI) m/z=639.35 (M+H)..

Example 288B

¹H NMR (CD₃OD, 600 MHz, ppm) δ 0.76 (s, 3H, Me), 0.76 (d, 3H, Me), 0.78 (d, 3H, Me), 0.83 (s, 3H, Me), 0.83 (d, 3H, Me), 0.85 (d, 3H, Me), 0.88 (s, 3H, Me), 0.89 (d, 3H, Me), 1.14 (s, 3H, Me), 1.20 (s, 3H, Me), 1.22-1.35 (m), 1.40-1.45 (m), 1.47-1.56 (m), 1.58-1.65 (m), 1.76-1.98 (m), 2.11-2.22 (m), 2.42 (dd, 1H, H13), 2.48 (d, 1H), 2.84 (s, 1H, H7), 3.38 (d, 1H), 3.48 (d, 1H), 3.53 (dd, 1H), 3.60 (d, 1H), 3.84 (d, 1H), 3.95 (d, 1H), 5.46 (dd, 1H, H5), 5.78-5.84 (m, 1H, H14), 7.72 (s, 2H, triazole).

Mass Spectrum: (ESI) m/z=639.35 (M+H).

Example 289

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[4-(methoxycarbonyl)-1H-1,2,3-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 289A) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(methoxycarbonyl)-1H-1,2,3-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 289B) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[4-(methoxycarbonyl)-2H-1,2,3-triazol-2-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 289C)

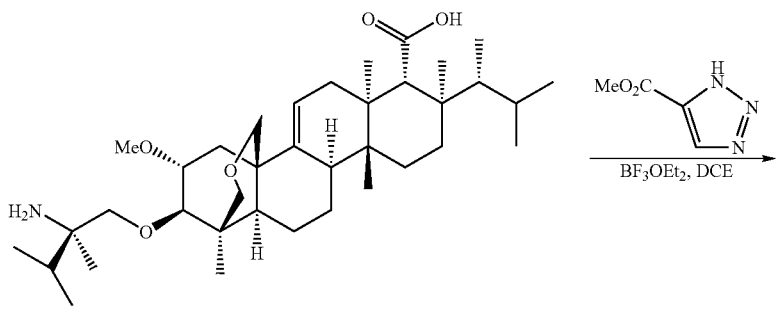

Intermediate 6

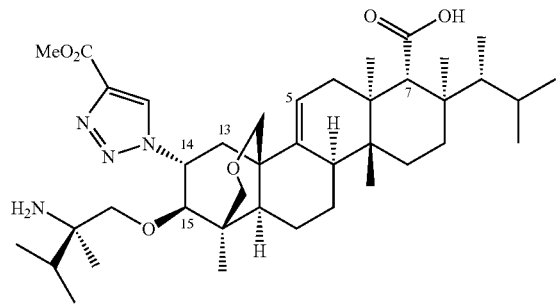

EXAMPLE 289A

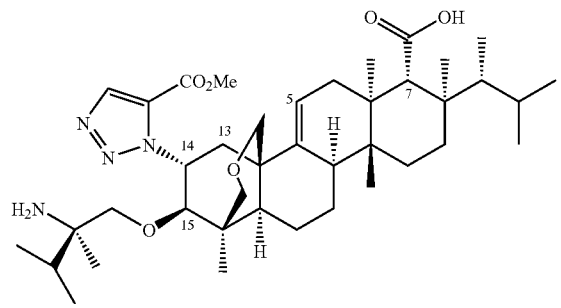

EXAMPLE 289B

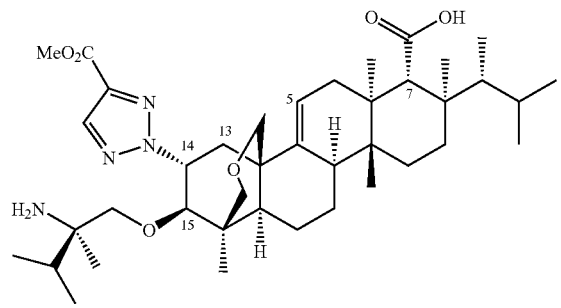

EXAMPLE 289C

Methyl 1H-1,2,3-triazole-4-carboxylate (25.1 mg, 0.197 mmol) and BF$_3$OEt$_2$ (51 µl, 0.402 mmol) were added to a stirred solution of Intermediate 6 (24.4 mg, 0.041 mmol) in 1,2-dichloroethane (0.5 ml). The reaction mixture was a light yellow solution that was heated to 50° C. After 1.75 hr, LCMS and $^1$H NMR showed the reaction to be complete. The reaction mixture was cooled to room temperature, the solvent was evaporated, and the resulting residue was placed under high vacuum. The residue was dissolved in methanol and purified using a single HPLC run on a 19×150 mm Sunfire Prep C18 OBD 10 µm column by eluting with acetonitrile/water+0.1% TFA. The total flow rate was 20 ml/min and the HPLC method employed a 12 minute 20%-100% acetonitrile/water gradient followed by a 6 minute acetonitrile flush. The HPLC fractions of the fastest eluting regioisomer were combined, the solvent was evaporated under reduced pressure, and the residue was lyophilized from ethanol and benzene to give EXAMPLE 289A (1.5 mg, 1.85 µmol) as a white solid. The HPLC fractions of the second eluting regioisomer were combined, the solvent was evaporated under reduced pressure, and the residue was lyophilized from ethanol and benzene to give EXAMPLE 289B (17.6 mg, 0.022 mmol) as a white solid. The HPLC fractions of the slowest eluting regioisomer were combined, the solvent was evaporated under reduced pressure, and the residue was lyophilized from ethanol and benzene to give EXAMPLE 289C (2.6 mg, 3.21 µmol) as a white solid. The regiochemistry of EXAMPLE 289A was assigned on the basis of an $^1$H NMR NOE observed from H14 to the triazole proton. The regiochemistry of EXAMPLE 289B was assigned by the characteristic downfield $^1$H NMR shift of its H14 proton.

Example 289A $^1$H NMR (CD$_3$OD, 600 MHz, ppm) δ 0.76 (s, 3H, Me), 0.77 (d, 3H, Me), 0.78 (d, 3H, Me), 0.82 (d, 3H, Me), 0.85 (d, 3H, Me), 0.86 (s, 3H, Me), 0.89 (s, 3H, Me), 0.90 (d, 3H, Me), 1.16 (s, 3H, Me), 1.20 (s, 3H, Me), 1.22-1.36 (m), 1.40-1.45 (m), 1.48-1.57 (m), 1.59-1.65 (m), 1.77-2.01 (m), 2.12-2.22 (m), 2.54 (dd, 1H, H13), 2.60 (d, 1H), 2.84 (s, 1H, H7), 3.50 (d, 2H), 3.54 (dd, 1H), 3.62 (d, 1H), 3.85 (d, 1H), 3.90 (s, 3H, COOMe), 3.94 (d, 1H), 5.50 (dd, 1H, H5), 5.81-5.87 (m, 1H, H14), 8.78 (s, 1H, triazole).

Mass Spectrum: (ESI) m/z=697.35 (M+H).

Example 289B $^1$H NMR (CD$_3$OD, 600 MHz, ppm) δ 0.72 (s, 3H, Me), 0.76 (s, 3H, Me), 0.76 (d, 3H, Me), 0.79 (d, 3H, Me), 0.82 (d, 3H, Me), 0.85 (d, 3H, Me), 0.89 (d, 3H, Me), 0.91 (s, 3H, Me), 1.12 (s, 3H, Me), 1.20 (s, 3H, Me), 1.22-1.36 (m), 1.39-1.44 (m), 1.47-1.55 (m), 1.58-1.65 (m), 1.71-1.79 (m), 1.81-1.96 (m), 2.11-2.22 (m), 2.54 (dd, 1H, H13), 2.83 (s, 1H, H7), 2.86 (d, 1H), 3.50 (d, 1H), 3.56 (d, 1H), 3.56 (dd, 1H), 3.63 (d, 1H), 3.94 (s, 3H, COOMe), 3.95 (d, 1H), 4.22 (d, 1H), 5.46 (dd, 1H, H5), 6.56-6.63 (m, 1H, H14), 8.24 (s, 1H, triazole).

Mass Spectrum: (ESI) m/z=697.40 (M+H).

Example 289C $^1$H NMR (CD$_3$OD, 600 MHz, ppm) δ 0.76 (s, 3H, Me), 0.76 (d, 3H, Me), 0.80 (d, 3H, Me), 0.83 (s, 3H, Me), 0.84 (d, 3H, Me), 0.85 (d, 3H, Me), 0.89 (s, 3H, Me), 0.89 (d, 3H, Me), 1.15 (s, 3H, Me), 1.20 (s, 3H, Me), 1.22-1.36 (m), 1.40-1.44 (m), 1.48-1.56 (m), 1.58-1.65 (m), 1.79-2.02 (m), 2.12-2.22 (m), 2.50 (dd, 1H, H13), 2.60 (d, 1H), 2.84 (s, 1H, H7), 3.47 (d, 1H), 3.48 (d, 1H), 3.54 (dd, 1H), 3.61 (d, 1H), 3.85 (d, 1H), 3.91 (s, 3H, COOMe), 3.94 (d, 1H), 5.48 (dd, 1H, H5), 5.83-5.89 (m, 1H, H14), 8.17 (s, 1H, triazole).

Mass Spectrum: (ESI) m/z=697.40 (M+H).

Example 290

(1S,4aR,6aS,7R,8R,10aR,10bR,12aR,14R,15R)-14-[4-amino-5-(aminocarbonyl)-2H-1,2,3-triazol-2-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

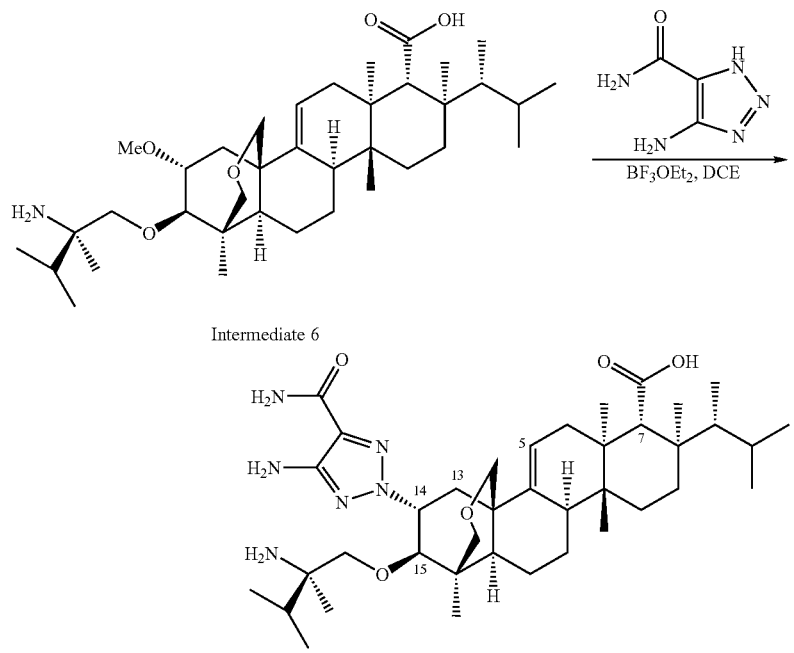

Intermediate 6

4-amino-1H-1,2,3-triazole-5-carboxamide (26.0 mg, 0.205 mmol) and $BF_3OEt_2$ (53 µl, 0.418 mmol) were added to a stirred solution of Intermediate 6 (25.0 mg, 0.042 mmol) in 1,2-dichloroethane (0.6 ml). The reaction mixture was a light yellow suspension that was heated to 50° C. After 1.75 hours, LCMS and $^1H$ NMR showed the reaction to be complete. The reaction mixture was cooled to room temperature, the solvent was evaporated under reduced pressure, and the resulting residue was placed under high vacuum. The residue was dissolved in methanol and purified using a single HPLC run on a 19×150 mm Sunfire Prep C18 OBD 10 µm column by eluting with acetonitrile/water+0.1% TFA. The total flow rate was 20 ml/min and the HPLC method employed a 12 minute 20%-100% acetonitrile/water gradient followed by a 6 minute acetonitrile flush. The product HPLC fractions were combined, the solvent was evaporated under reduced pressure, and the residue was lyophilized from ethanol and benzene to give the title compound (20.0 mg, 0.025 mmol) as a white solid. The triazole regiochemistry was assigned by analogy with previous compounds.

$^1H$ NMR (CD$_3$OD, 600 MHz, ppm) δ 0.76 (s, 3H, Me), 0.77 (d, 3H, Me), 0.82 (d, 3H, Me), 0.85 (d, 3H, Me), 0.86 (d, 3H, Me), 0.87 (s, 3H, Me), 0.89 (d, 3H, Me), 0.95 (s, 3H, Me), 1.14 (s, 3H, Me), 1.20 (s, 3H, Me), 1.22-1.34 (m), 1.39-1.44 (m), 1.47-1.65 (m), 1.74-1.96 (m), 2.08-2.22 (m), 2.43 (dd, 1H, H13), 2.74 (d, 1H), 2.84 (s, 1H, H7), 3.45 (d, 1H), 3.46 (d, 1H), 3.52 (dd, 1H), 3.57 (d, 1H), 3.75 (d, 1H), 3.92 (d, 1H), 5.48 (dd, 1H, H5), 5.52-5.58 (m, 1H, H14)

Mass Spectrum: (ESI) m/z=697.77 (M+H).

Example 291

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

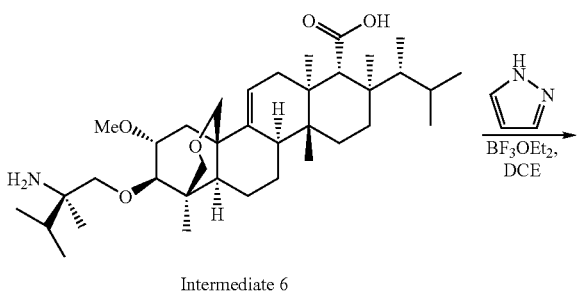

Intermediate 6

361

-continued

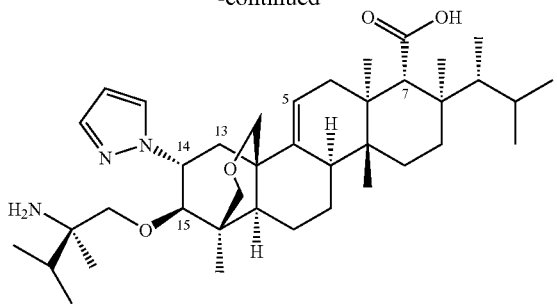

A suspension of Intermediate 6 (40 mg, 0.052 mmol), 1H-pyrazole (50 mg, 0.74 mmol) and boron trifluoride etherate (134 µL, 1.04 mmol) in dichloroethane (0.5 mL) was blanketed with nitrogen and placed in an 80° C. oil bath for 30 minutes. The mixture was cooled to room temperature, evaporated and the residual oil was purified by reverse phase HPLC using a 19×150 mm Sunfire Preparative C18 OBD column eluting with acetonitrile/water+0.1% TFA. Fractions containing the product were evaporated and freeze-dried from a mixture of ethanol and benzene to give the title compound as a TFA salt (18.5 mg).

$^1$H NMR (CD$_3$OD, 600 MHz, ppm) δ 0.76 (s, 3H, Me), 0.77 (d, 3H, Me), 0.83 (d, 3H, Me), 0.85 (s, 3H, Me), 0.85 (d, 3H, Me), 0.89 (d, 3H, Me), 0.92 (s, 3H, Me), 1.16 (s, 3H, Me), 1.20 (s, 3H, Me), 1.23-1.34 (m), 1.41-1.45 (m), 1.48-1.65 (m), 1.75-1.85 (m), 1.89-2.02 (m), 2.12-2.21 (m), 2.37 (dd, 1H, H13), 2.40 (d, 1H), 2.84 (s, 1H, H7), 3.46 (d, 1H), 3.53 (dd, 1H), 3.59 (d, 1H), 3.66 (d, 1H), 3.93 (d, 1H), 5.39 (m, 1H, H14), 5.47 (dd, 1H, H5), 6.31 (dd, 1H, pyrazole), 7.54 (d, 1H, pyrazole) and 7.74 (d, 1H, pyrazole).

Mass spectrum: (ESI) m/z=638.63 (M+H).

Example 292

(1S,4aR,6aS,7R,8R,10aR,10bR,12aR,14R,15R)-14-[3-(aminocarbonyl)-1H-pyrazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 292A) and (1S,4aR,6aS,7R,8R,10aR,10bR,12aR,14R,15R)-14-[5-(aminocarbonyl)-1H-pyrazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 292B)

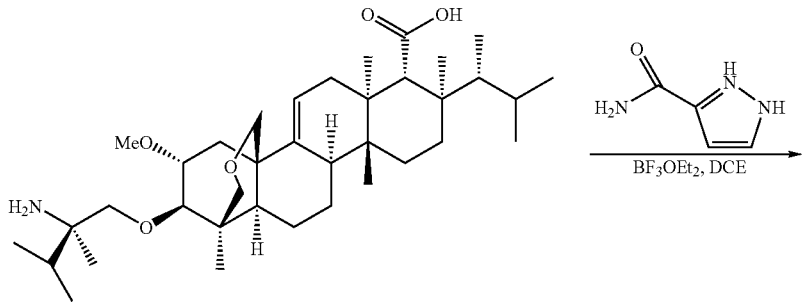

Intermediate 6

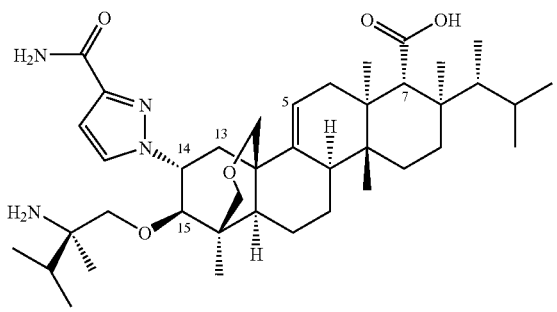

EXAMPLE 292A

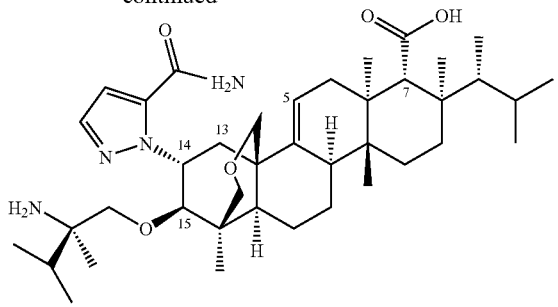

EXAMPLE 292B

A suspension of Intermediate 6 (45 mg, 0.075 mmol), 1H-pyrazole-3-carboxamide (30 mg, 0.27 mmol) and boron trifluoride etherate (100 μL, 0.79 mmol) in dichloroethane (1.0 mL) was blanketed with nitrogen and placed in a 50° C. oil bath for 90 minutes. The mixture was cooled to room temperature, evaporated and the residual oil was separated by reverse phase HPLC using a 19×150 mm Sunfire Preparative C18 OBD column eluting with acetonitrile/water+0.1% TFA. Fractions containing the slower eluting regioisomer were evaporated and freeze-dried from a mixture of ethanol and benzene to give EXAMPLE 292A as a TFA salt (7.2 mg). Fractions containing the faster eluting regioisomer were evaporated and freeze-dried from a mixture of ethanol and benzene to give EXAMPLE 292B as a TFA salt (26 mg).

Example 292A $^1$H NMR (CD$_3$OD, 600 MHz, ppm) δ 0.77 (s, 3H, Me), 0.77 (d, 3H, Me), 0.79 (d, 3H, Me), 0.85 (s, 3H, Me), 0.85 (d, 3H, Me), 0.87 (d, 3H, Me), 0.88 (s, 3H, Me), 0.90 (d, 3H, Me), 1.16 (s, 3H, Me), 1.21 (s, 3H, Me), 1.23-1.34 (m), 1.41-1.45 (m), 1.48-1.65 (m), 1.78-2.02 (m), 2.12-2.22 (m), 2.43 (dd, 1H, H13), 2.56 (d, 1H), 2.84 (s, 1H, H7), 3.40 (d, 1H), 3.47 (d, 1H), 3.54 (dd, 1H), 3.60 (d, 1H), 3.76 (d, 1H), 3.92 (d, 1H), 5.45 (m, 1H, H14), 5.49 (dd, 1H, H5), 6.75 (d, 1H, pyrazole) and 7.80 (d, 1H, pyrazole).

Mass spectrum: (ESI) m/z=681.41 (M+H).

Example 292B $^1$H NMR (CD$_3$OD, 600 MHz, ppm) δ 0.78 (s, 3H, Me), 0.79 (d, 3H, Me), 0.81 (d, 3H, Me), 0.85 (s, 3H, Me), 0.87 (d, 3H, Me), 0.87 (d, 3H, Me), 0.88 (s, 3H, Me), 0.92 (d, 3H, Me), 1.16 (s, 3H, Me), 1.22 (s, 3H, Me), 1.23-1.34 (m), 1.41-1.46 (m), 1.48-1.68 (m), 1.78-1.98 (m), 2.12-2.22 (m), 2.38 (dd, 1H, H13), 2.70 (d, 1H), 2.86 (s, 1H, H7), 3.45 (m), 3.52 (dd, 1H), 3.61 (d, 1H), 3.94 (d, 1H), 3.96 (d, 1H), 5.46 (dd, 1H, H5), 6.42 (m, 1H, H14), 6.77 (d, 1H, pyrazole) and 7.58 (d, 1H, pyrazole).

Mass spectrum: (ESI) m/z=681.35 (M+H).

Example 293

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(3-nitro-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 293A) and (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-nitro-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (EXAMPLE 293B)

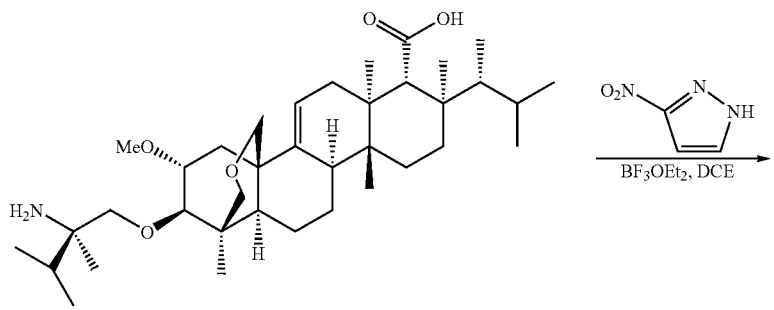

Intermediate 6

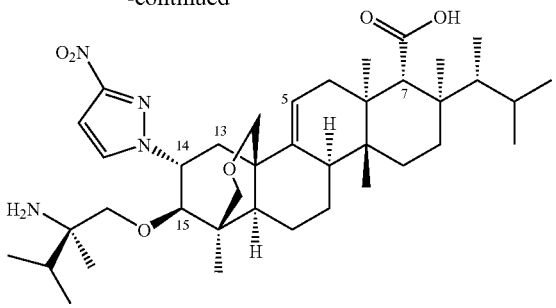

EXAMPLE 293A

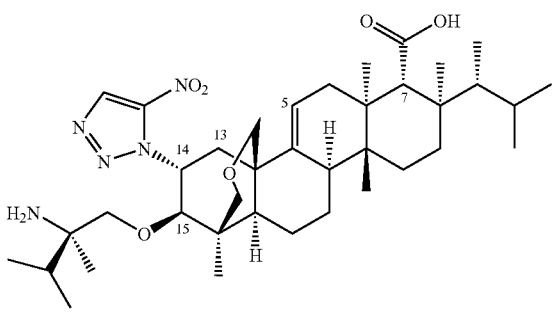

EXAMPLE 293B 3-nitro-1H-pyrazole (23.3 mg, 0.206 mmol) and $BF_3O(CH_2CH_3)_2$ (52 µl, 0.410 mmol) were added to a stirred solution of Intermediate 6 (24.8 mg, 0.041 mmol) in 1,2-dichloroethane (0.41 ml). The reaction mixture was a light yellow solution that was heated to 50° C. After 2 hours, LCMS and $^1$H NMR showed the reaction to be complete. The reaction mixture was cooled to room temperature, the solvent was evaporated under reduced pressure, and the resulting residue was placed under high vacuum. The residue was dissolved in methanol and separated using a single HPLC run on a 19×150 mm Sunfire Prep C18 OBD 10 µm column by eluting with acetonitrile/water+0.1% TFA. The total flow rate was 20 ml/min and the HPLC method employed a 12 minute 20%-100% acetonitrile/water gradient followed by a 6 minute acetonitrile flush. The HPLC fractions of the faster eluting regioisomer were combined, the solvent was evaporated under reduced pressure, and the residue was lyophilized from ethanol and benzene to give EXAMPLE 293A (14.8 mg, 0.019 mmol) as a white solid. The HPLC fractions of the slower eluting regioisomer were combined, the solvent was evaporated under reduced pressure, and the residue was lyophilized from ethanol and benzene to give EXAMPLE 293B (4.8 mg, 6.02 µmol) as a white solid. The regiochemistry of the two isomers was assigned based on an $^1$H NMR NOE from H14 to the pyrazole proton that was observed for EXAMPLE 293A but not for EXAMPLE 293B.

Example 293A $^1$H NMR (CD$_3$OD, 600 MHz, ppm) δ 0.76 (s, 3H, Me), 0.76 (d, 3H, Me), 0.79 (d, 3H, Me), 0.84 (d, 3H, Me), 0.85 (d, 3H, Me), 0.88 (s, 3H, Me), 0.89 (d, 3H, Me), 0.91 (s, 3H, Me), 1.15 (s, 3H, Me), 1.20 (s, 3H, Me), 1.22-1.35 (m), 1.39-1.44 (m), 1.47-1.57 (m), 1.58-1.65 (m), 1.79-1.97 (m), 2.11-2.22 (m), 2.45 (dd, 1H, H13), 2.70 (d, 1H), 2.83 (s, 1H, H7), 3.47 (d, 1H), 3.49 (d, 1H), 3.52 (dd, 1H), 3.60 (d, 1H), 3.79 (d, 1H), 3.92 (d, 1H), 5.46-5.54 (m, 2H, H5 and H14), 6.96 (d, 1H, pyrazole), 7.96 (d, 1H, pyrazole).

Mass Spectrum: (ESI) m/z=683.54 (M+H).

Example 293B $^1$H NMR (CD$_3$OD, 600 MHz, ppm) δ 0.76 (s, 3H, Me), 0.76 (d, 3H, Me), 0.80 (d, 3H, Me), 0.83 (s, 3H, Me), 0.84 (d, 3H, Me), 0.85 (d, 3H, Me), 0.88 (s, 3H, Me), 0.89 (d, 3H, Me), 1.14 (s, 3H, Me), 1.20 (s, 3H, Me), 1.22-1.35 (m), 1.39-1.44 (m), 1.47-1.56 (m), 1.59-1.65 (m), 1.74-1.96 (m), 2.10-2.22 (m), 2.50 (dd, 1H, H13), 2.78 (d, 1H), 2.84 (s, 1H, H7), 3.47 (d, 1H), 3.47 (d, 1H), 3.55 (dd, 1H), 3.62 (d, 1H), 3.93 (d, 1H), 4.00 (d, 1H), 5.48 (dd, 1H, H5), 6.42-6.48 (m, 1H, H14), 7.14 (d, 1H, pyrazole), 7.67 (d, 1H, pyrazole).

Mass Spectrum: (ESI) m/z=683.56 (M+H).

Example 294

(1S,4aR,6aS,7R,8R,10aR,10bR,12aR,14R,15R)-15-[[(2R)-2-amino-3,3-dimethylbutyl]oxy]-8-[(1R)-1,2-dimethylpropyl]-14-(4-nitro-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

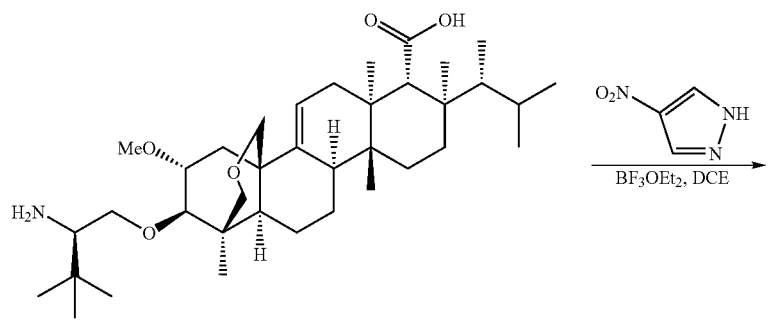

Intermediate 24

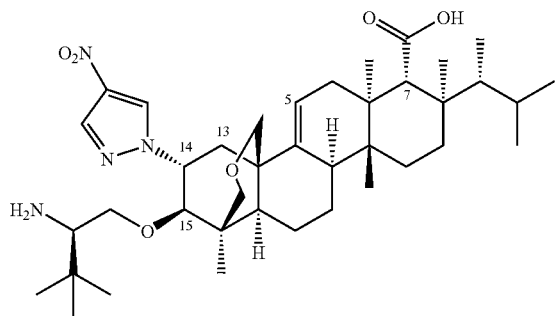

By a procedure analogous to that described for Example 190, but starting with Intermediate 24 and employing 4-nitro-1H-pyrazole, the title compound was prepared and isolated as a white solid.

$^1$H NMR (CD$_3$OD, 500 MHz, ppm) δ 0.77 (s, 3H), 0.78 (d, J=6.9 Hz, 3H), 0.82 (s, 9H), 0.86 (d, 3H, partially obscured), 0.87 (s, 3H), 0.90 (d, J=6.8 Hz, 3H), 1.17 (s, 3H), 1.22 (s, 3H), 1.23-1.66 (m), 1.78-1.96 (m), 2.06-2.23 (m), 2.44 (dd, J=13.5 Hz, 6.4 Hz, 1H), 2.48 (dd, J=10.1 Hz, 3.0 Hz, 1H), 2.85 (s, 1H), 2.87 (dd, J=10.5 Hz, 3.2 Hz, 1H), 3.47 (d, J=11.9 Hz, 1H), 3.52-3.62 (m, 3H), 3.65 (dd, J=9.9 Hz, 1H), 3.91 (d, J=11.8 Hz, 1H), 5.41 (m, 1H), 5.50 (m, 1H), 8.22 (s, 1H), 8.71 (s, 1H).

Mass Spectrum: (ESI) m/z=683.47 (M+H).

Examples 295-299

The following compounds were prepared using methods analogous to those described in the preceding examples:

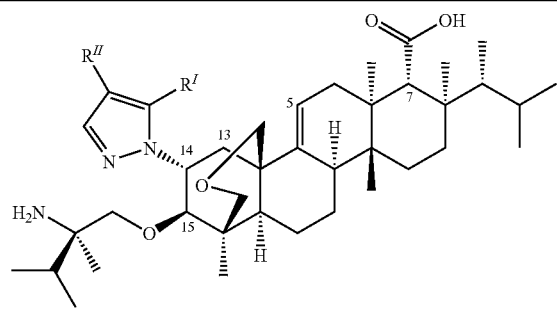

| | | | |
|---|---|---|---|
| 295 | R$^I$ = H | R$^{II}$ = Cl | (1S,4aR,6aS,7R,8R,10aR,10bR,12aR,14R,15R)-15-[[(2R)-2-amino-2,3-dimethylbutyl]oxy]-14-(4-chloro-1H-pyrazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

-continued

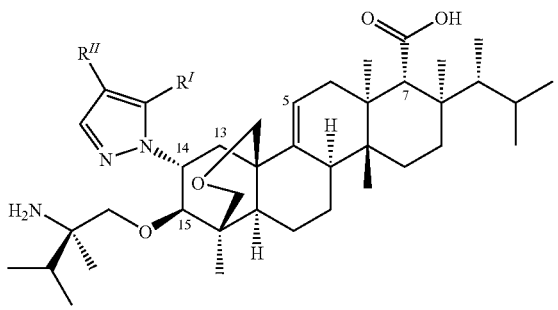

¹H NMR (CD₃OD, 600 MHz, ppm) δ 0.76 (s, 3H, Me), 0.77 (d, 3H, Me), 0.79 (d, 3H, Me), 0.85 (s, 3H, Me), 0.85 (d, 3H, Me), 0.86 (d, 3H, Me), 0.89 (d, 3H, Me), 0.98 (s, 3H, Me), 1.16 (s, 3H, Me), 1.20 (s, 3H, Me), 1.23-1.34 (m), 1.41-1.44 (m), 1.48-1.65 (m), 1.76-1.98 (m), 2.10-2.21 (m), 2.37 (dd, 1H, H13), 2.50 (d, 1H), 2.84 (s, 1H, H7), 3.35 (d, 1H), 3.46 (d, 1H), 3.52 (dd, 1H), 3.58 (d, 1H), 3.64 (d, 1H), 3.91 (d, 1H), 5.33 (m, 1H, H14), 5.48 (dd, 1H, H5), 7.51 (d, 1H, pyrazole) and 7.87 (s, 1H, pyrazole).
Mass spectrum: (ESI) m/z = 672.37 (M + H)

| 296 | $R^I$ = CF₃<br>$R^{II}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(trifluoromethyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.76 (d, 3H, Me), 0.77 (d, 3H, Me), 0.80 (d, 3H, Me), 0.85 (d, 3H, Me), 0.86 (s, 3H, Me), 0.88 (s, 3H, Me), 0.89 (d, 3H, Me), 1.13 (s, 3H, Me), 1.20 (s, 3H, Me), 1.22-1.35 (m), 1.39-1.44 (m), 1.47-1.56 (m), 1.58-1.65 (m), 1.70-1.96 (m), 2.09-2.22 (m), 2.30 (dd, 1H, H13), 2.83 (s, 1H, H7), 2.84 (d, 1H), 3.40 (d, 1H), 3.48 (d, 1H), 3.54 (s, 2H), 3.94 (d, 1H), 4.06 (d, 1H), 5.41 (dd, 1H, H5), 5.63-5.69 (m, 1H, H14), 6.75 (d, 1H, pyrazole), 7.65 (d, 1H, pyrazole).
Mass Spectrum: (ESI) m/z = 706.47 (M + H).

| 297 | $R^I$ = CO₂Et<br>$R^{II}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethoxycarbonyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.74 (d, 3H, Me), 0.75 (s, 3H, Me), 0.76 (d, 3H, Me), 0.81 (d, 3H, Me), 0.84 (s, 3H, Me), 0.85 (d, 3H, Me), 0.86 (s, 3H, Me), 0.89 (d, 3H, Me), 1.14 (s, 3H, Me), 1.20 (s, 3H, Me), 1.23-1.34 (m), 1.36 (t, 3H, OCH₂CH₃), 1.41-1.44 (m), 1.48-1.65 (m), 1.71 (m), 1.78-1.96 (m), 2.10-2.21 (m), 2.38 (dd, 1H, H13), 2.61 (d, 1H), 2.84 (s, 1H, H7), 3.35 (d, 1H), 3.46 (d, 1H), 3.54 (dd, 1H), 3.60 (d, 1H), 3.94 (d, 1H), 4.32 (m, 2H, OCH₂CH₃), 5.45 (dd, 1H, H5), 6.53 (br m, 1H, H14), 6.89 (d, 1H, pyrazole) and 7.59 (s, 1H, pyrazole).
Mass spectrum: (ESI) m/z = 710.32 (M + H).

| 298 | $R^I$ = CONHEt<br>$R^{II}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(ethylamino)carbonyl]-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

¹H NMR (CD₃OD, 600 MHz, ppm) δ 0.76 (s, 3H, Me), 0.76 (d, 3H, Me), 0.79 (d, 3H, Me), 0.81 (s, 3H, Me), 0.85 (d, 3H, Me), 0.85 (s, 3H, Me), 0.90 (d, 3H, Me), 1.14 (s, 3H, Me), 1.20 (s, 3H, Me), 1.23-1.34 (m), 1.40-1.44 (m), 1.48-1.65 (m), 1.78-1.96 (m), 2.10-2.21 (m), 2.36 (dd, 1H, H13), 2.64 (d, 1H), 2.84 (s, 1H, H7), 3.36 (q, 2H, CONCH₂CH₃), 3.43 (m, 1H), 3.50 (dd, 1H), 3.58 (d, 1H), 3.91 (d, 1H), 3.92 (d, 1H), 5.44 (dd, 1H, H5), 6.28 (m, 1H, H14), 6.66 (d, 1H, pyrazole) and 7.54 (d, 1H, pyrazole).
Mass spectrum: (ESI) m/z = 709.48 (M + H).

| 299 | $R^I$ = Ph<br>$R^{II}$ = H | (1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-phenyl-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (free base) |

¹H NMR (CD₃OD, 600 MHz, ppm) δ 0.76 (s, 3H, Me), 0.77 (d, 3H, Me), 0.78 (d, 3H, Me), 0.83 (d, 3H, Me), 0.85 (s, 3H, Me), 0.86 (d, 3H, Me), 0.89 (d, 3H, Me), 0.92 (s, 3H, Me), 1.17 (s, 3H, Me), 1.21 (s, 3H, Me), 1.23-1.34 (m), 1.41-1.44 (m), 1.48-1.72 (m), 1.80-1.98 (m), 2.10-2.21 (m), 2.20 (dd, 1H, H13), 2.75 (d, 1H), 2.84 (d, 1H), 2.85 (s, 1H, H7), 3.39 (d, 1H), 3.41 (d, 1H), 3.52 (dd, 1H), 3.54 (dd, 1H), 3.58 (d, 1H), 3.65 (d, 1H), 3.77 (d, 1H), 3.92 (d, 1H), 5.54 (dd, 1H, H5), 5.74 (m, 1H, H14), 6.40 (d, 1H, pyrazole), 7.40 (1H, dd, ArH), 7.49 (dd, 2H, ArH), 7.52 (d, 2H, ArH) and 7.59 (d, 1H, pyrazole).

Example 300

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[2-(ethoxycarbonyl)-1H-imida-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid

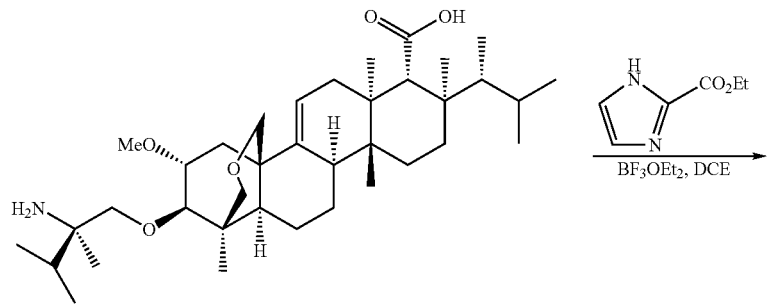

Intermediate 6

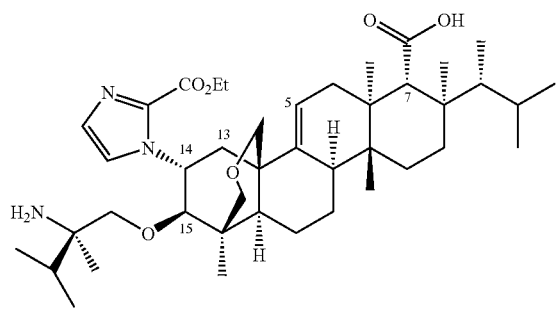

A suspension of Intermediate 6 (40 mg, 0.052 mmol), ethyl 1H-imidazole-2-carboxylate (50 mg, 0.74 mmol) and boron trifluoride etherate (134 μl, 1.04 mmol) in dichloroethane (0.5 mL) was blanketed with nitrogen and placed in a 80° C. oil bath for 30 minutes. The mixture was cooled to room temperature, evaporated and the residual oil was purified by reverse phase HPLC using a 19×150 mm Sunfire Preparative C18 OBD column eluting with acetonitrile/water+0.1% TFA. Fractions containing the product were evaporated and freeze-dried from a mixture of ethanol and benzene to give the title compound as a TFA salt (18.5 mg).

$^1$H NMR (CD$_3$OD, 600 MHz, ppm) δ 0.77 (s, 3H, Me), 0.77 (d, 3H, Me), 0.81 (d, 3H, Me), 0.86 (d, 3H, Me), 0.86 (s, 3H, Me), 0.90 (d, 3H, Me), 1.16 (s, 3H, Me), 1.20 (s, 3H, Me), 1.23-1.34 (m), 1.39 (t, OCH$_2$CH$_3$), 1.41-1.45 (m), 1.48-1.65 (m), 1.69-1.98 (m), 2.12-2.21 (m), 2.50 (dd, 1H, H13), 2.62 (d, 1H), 2.84 (s, 1H, H7), 3.42 (d, 1H), 3.45 (d, 1H), 3.55 (dd, 1H), 3.61 (d, 1H), 3.63 (d, 1H), 3.93 (d, 1H), 4.40 (q, OCH$_2$CH$_3$), 5.49 (dd, 1H, H5), 6.66 (m, 1H, H14), 7.21 (d, 1H, imidazole) and 7.85 (d, 1H, imidazole).

Mass spectrum: (ESI) m/z=710.35 (M+H).

Example 301

(1S,4aR,6aS,7R,8R,10aR,10bR,12aR,14R,15R)-14-[2-(aminocarbonyl)-1H-imidazol-1-yl]-15-[[(2S)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

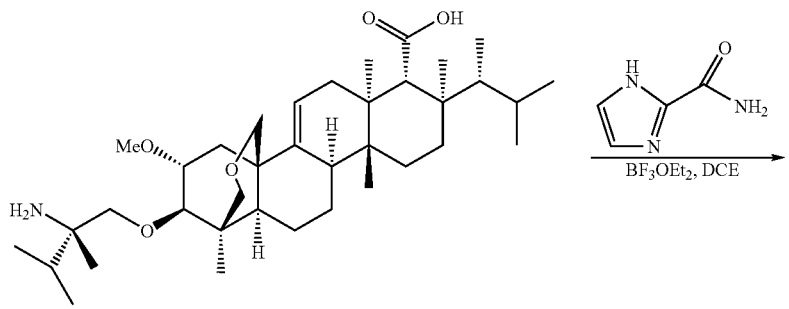

Intermediate 7

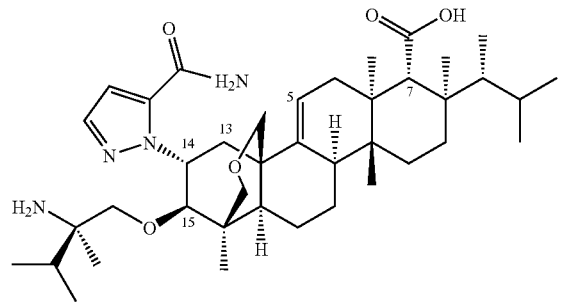

To a solution of Intermediate 7 (80 mg, 0.133 mmol) in DCE (2 mL) under a nitrogen atmosphere was added 1H-imidazole-2-carboxamide (59 mg, 0.532 mmol). Boron trifluoride etherate solution (0.1 mL, 1.33 mmol) was added and the mixture was heated to 50° C. for 16 hours. The volatiles were evaporated and the residue was dissolved in $CH_3CN$ (2 mL). The mixture was filtered and purified by reverse phase HPLC using 30-100% $CH_3CN/H_2O$ as gradient. The combined product fractions were freeze dried to afford a white solid (32 mg).

$^1$H NMR (MeOH-$d_4$, 500 MHz, ppm) δ 0.50 (d, 3H), 0.80 (m, 6H), 0.90 (m, 12H), 1.03 (s, 3H), 1.18 (s, 3H), 1.23 (s, 3H), 1.24-1.80 (m, 10H), 1.80-2.00 (m, 7H), 2.20 (m, 2H), 2.43 (m, 1H), 2.84 (s, 1H), 3.00 (d, 1H), 3.40-3.70 (m, 5H), 3.92 (d, 1H), 5.43 (m, 1H), 6.70 (m, 1H), 7.08 (s, 1H), 7.77 (s, 1H).

Mass spectrum: (ESI) m/z=681 (M+H).

Example 302

(1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxamide

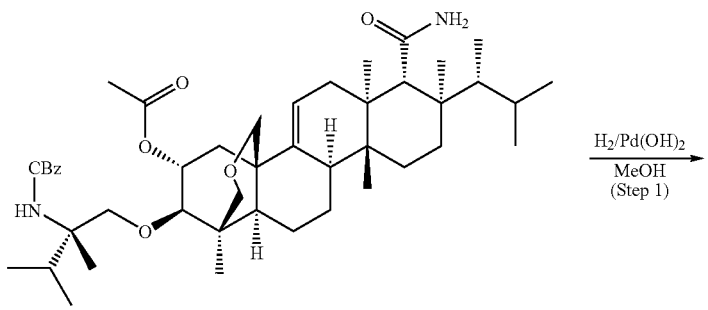

CBz = Benzyloxycarbonyl

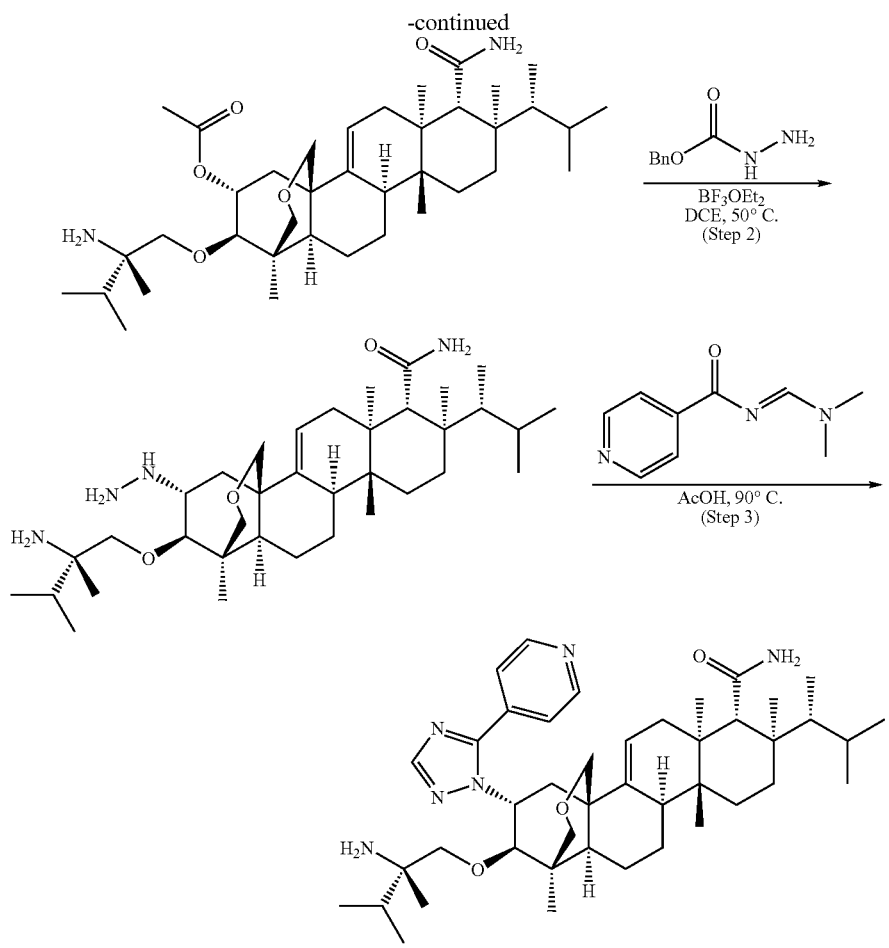

Step 1:

To a solution of (1S,2R,3R,4aR,6aS,7R,8R,10aR,10bR,12aR)-3-acetoxy-2-[[(2S)-2-[(benzyloxy)carbonyl]amino-2,3-dimethylbutyl]oxy]-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxamide [the product compound of Example 148, Step 6, in International Patent Publication No. WO 2007/127012, herein incorporated by reference in its entirety] (236 mg, 0.31 mmol) in MeOH/CH$_2$Cl$_2$ (8 ml, 1/1) was added Pd(OH)$_2$ (20% weight %, 160 mg). The mixture was purged with hydrogen then stirred under H$_2$ (1 atm, balloon) for 1 h. The reaction mixture was filtered through a pad of Celite, and the filter cake was washed with MeOH. The filtrate was concentrated under reduced pressure to afford the product (190 mg, 97% yield) as a white solid Steps 2 and 3:

Starting with the product from Step 1, and employing in Step 2 a procedure analogous to that described for the synthesis of Intermediate 32 and in Step 3 a procedure analogous to that described in Example 173 (Alternative Synthesis), the title compound (as an acetate salt) was prepared.

$^1$H NMR (400 MHz, METHANOL-d$_4$) δ ppm 0.44 (d, J=7.03 Hz, 3H) 0.76 (s, 3H) 0.79 (br. s., 3H) 0.80 (d, J=7.03 Hz, 3H) 0.86 (d, J=6.44 Hz, 3H) 0.90 (s, 3H) 0.91 (br. s., 3H) 0.92 (d, J=7.03 Hz, 3H) 1.20 (s, 3H) 1.24 (s, 3H) 1.26-1.30 (m, 2H) 1.30-1.36 (m, 2H) 1.38-1.45 (m, 1H) 1.46-1.52 (m, 1H) 1.54-1.65 (m, 2H) 1.66-1.76 (m, 2H) 1.81-1.89 (m, 3H) 2.00 (d, J=11.32 Hz, 1H) 2.18 (dd, J=14.45, 6.44 Hz, 1H) 2.45 (dd, J=13.86, 6.25 Hz, 1H) 2.67 (s, 1H) 3.06 (d, J=9.96 Hz, 1H) 3.41 (d, J=10.15 Hz, 1H) 3.46 (d, J=11.91 Hz, 1H) 3.51-3.55 (m, 1H) 3.58 (s, 1H) 3.61-3.64 (m, 1H) 3.81 (d, J=12.11 Hz, 1H) 4.02 (d, J=9.57 Hz, 1H) 5.55 (d, J=5.66 Hz, 1H) 5.87 (td, J=10.93, 6.25 Hz, 1H) 7.79 (d, J=5.38 Hz, 2H) 8.17 (s, 1H) 8.79 (d, J=5.38 Hz, 2H).

Mass spectrum: (ESI) m/z=715 (M+H).

General Procedures for Examples 303-312

General Procedure A (Alkylation)

To a ca. 0.1 M solution of an alcohol starting material [(e.g. Intermediate 38), 1.0 eq] and an electrophile [(e.g. the compound of Preparation 18), 1.2 eq] in DMF was added NaH (60 wt % in mineral oil, 20 eq). The reaction mixture was heated at 50° C. until TLC indicated that all starting alcohol was consumed. The reaction mixture was quenched with water and partitioned between EtOAc and water, and the layers were separated. The aqueous layer was extracted with EtOAc. The combined organic layers were dried with Na$_2$SO$_4$, and concentrated under reduced pressure. The residue was purified by flash chromatography, elution with 0%-10% MeOH in CH$_2$Cl$_2$, to provide the desired products.

General Procedure B (Alkylation)

To a ca. 0.1 M solution of an alcohol starting material [(e.g. Intermediate 38, 1.0 eq] and 18-crown-6 (1.8 eq) in DME at 0° C. was added KH (30 wt % in mineral oil, ca. 20 eq). The reaction mixture was stirred 10 min, a solution of an electrophile (e.g. the compound of Preparation 17) a minimum amount of DME was added heated, and the reaction mixture stirred (0° C. to RT) over 2 h. The reaction mixture was concentrated under reduced pressure, diluted with EtOAc, cooled to 0° C., treated with 5N aqueous HCl and water, and stirred 20 min. The mixture was treated subsequently with 5N aqueous NaOH until pH ~11 and partitioned with EtOAc. The layers were separated, and the aqueous phase was extracted with EtOAc. The combined organic layers were dried with Na₂SO₄, and concentrated under reduced pressure. The residue was purified by flash chromatography, elution with 0%-10% MeOH in CH₂Cl₂, to provide the desired products.

Example 303

(1S,4aR,6aS,7R,8R,10aR,10bR,12aR,14R,15R)-8-[(1R)-1,2-dimethylpropyl]-15-(3-morpholinyl-methoxy)-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

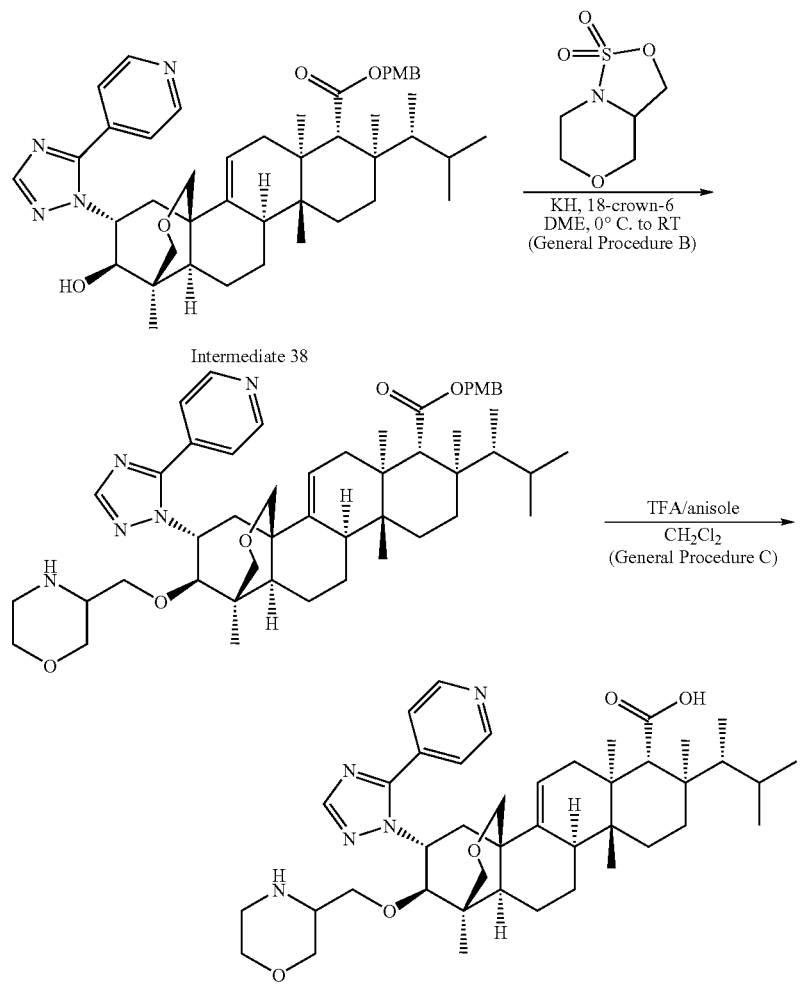

General Procedure C (Deprotection)

To a ca. 0.1 M solution of a 4-methoxybenzyl ester (from general alkylation procedure A or B, 1.0 eq) in CH₂Cl₂ was added anisole (6.0 eq) at room temperature, followed by TFA (same volume as CH₂Cl₂). The reaction mixture was stirred for 1 h and was concentrated under reduced pressure. The residue was purified by flash chromatography, elution with 0%-10% MeOH in CH₂Cl₂, to give the product.

General Procedure D (Deprotection)

To a ca. 0.1 M solution of a 4-methoxybenzyl ester (from general alkylation procedure A or B, 1.0 eq) in CH₂Cl₂ was added triethylsilane anisole (3.0 eq) at room temperature, followed by TFA (same volume as CH₂Cl₂). The reaction mixture was stirred overnight and was concentrated under reduced pressure. The residue was purified by RP HPLC to give the product.

According to General Procedures B and C, the title compound was prepared starting with Intermediate 38. Chromatographic separation of the two diastereomers gave EXAMPLE 303A (21 mg) and EXAMPLE 303B (19 mg).

Example 303A $^1$H NMR (400 MHz, CD₃OD) δ ppm 0.78 (s, 6H) 0.81 (d, J=9.22 Hz, 3H) 0.86 (d, J=0.93 Hz, 3H) 0.86 (s, 3H) 0.91 (d, J=6.78 Hz, 3H) 1.21 (d, J=15.62 Hz, 14H) 1.18 (s, 3H) 1.23 (s, 3H) 2.55 (td, J=13.57, 5.27 Hz, 1H) 2.81 (dd, J=10.30, 5.32 Hz, 1H) 2.86 (s, 1H) 3.04 (d, J=3.37 Hz, 1H) 3.09-3.24 (m, 4H) 3.37-4.03 (m, 8H) 5.60 (d, J=5.42 Hz, 1H) 5.83 (dd, J=11.91, 9.27 Hz, 1H) 7.76-7.92 (m, 2H) 8.20 (s, 1H) 8.66-9.01 (m, 2H). LC/MS 716 (M+H).

Example 303B

¹H NMR (400 MHz, CD₃OD) δ ppm 0.78 (d, J=10.49 Hz, 3H) 0.78 (s, 3H) 0.81 (d, 3H) 0.86 (s, 3H) 0.87 (d, J=6.64 Hz, 3H) 0.91 (d, J=6.74 Hz, 3H) 1.21 (d, J=15.52 Hz, 4H) 1.19 (s, 3H) 1.23 (s, 3H) 1.76-2.05 (m, 5H) 2.06-2.33 (m, 3H) 2.53 (dd, J=13.64, 6.56 Hz, 1H) 2.81 (dd, J=10.27, 5.25 Hz, 1H) 2.86 (s, 1H) 3.05-3.23 (m, 4H) 3.36-4.11 (m, 11H) 5.58 (d, J=6.05 Hz, 1H) 5.82 (dd, J=5.13, 1.32 Hz, 1H) 7.84-7.90 (m, 2H) 8.20 (s, 1H) 8.83 (d, J=6.05 Hz, 2H) LC/MS 716 (M+H).

Example 304

(1S,4aR,6aS,7R,8R,10aR,10bR,12aR,14R,15R)-8-[(1R)-1,2-dimethylpropyl]-15-[[1-(ethylamino)cyclobutyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

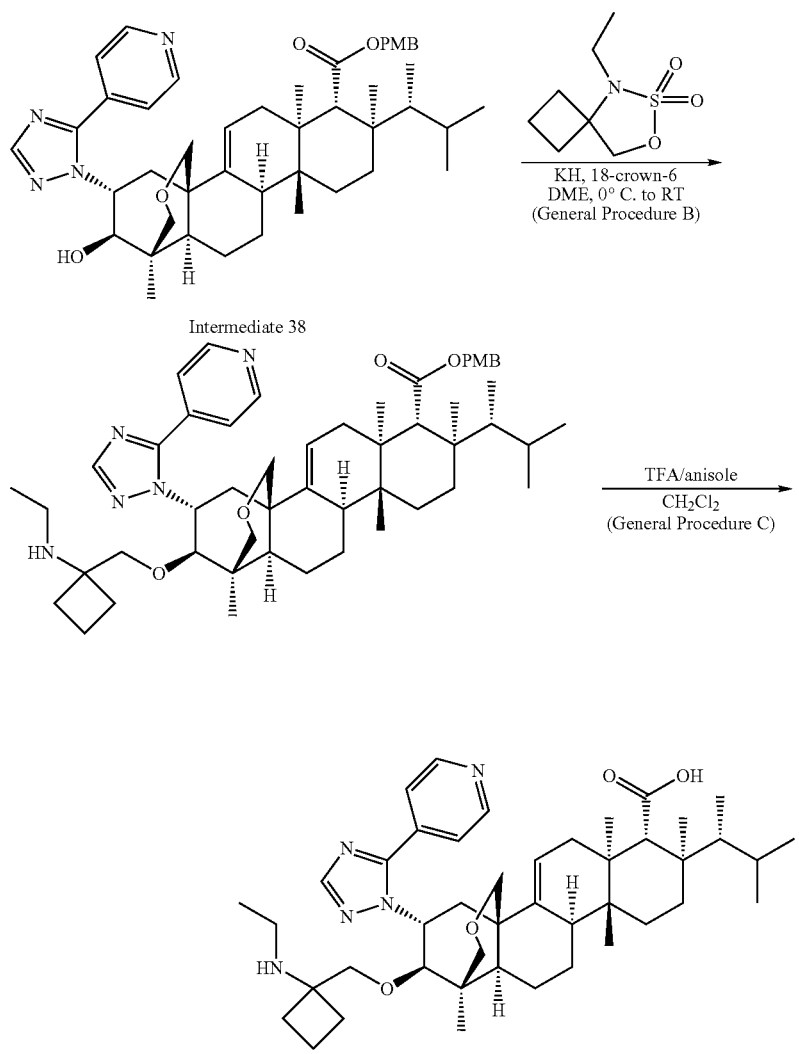

According to General Procedures B and C, the title compound was prepared and isolated as a white solid starting with Intermediate 38.

¹H NMR (400 MHz, METHANOL-d₄) δ 0.77 (t, J=3.51 Hz, 6H) 0.85 (d, J=6.64 Hz, 3H) 0.88-0.92 (m, 6H) 1.10 (t, J=7.32 Hz, 3H) 1.19 (s, 3H) 1.23 (s, 3H) 1.29 (d, J=5.86 Hz, 3H) 1.39 (br. s., 2H) 1.59 (br. s., 4H) 1.76-2.01 (m, 8H) 2.07 (s, 3H) 2.20 (br. s., 2H) 2.53 (dd, J=6.74, 3.81 Hz, 1H) 2.65 (dd, J=12.01, 7.32 Hz, 1H) 2.82 (s, 1H) 3.08 (d, J=10.74 Hz, 1H) 3.47 (d, J=11.71 Hz, 1H) 3.55 (t, J=12.30 Hz, 1H) 3.60-3.66 (m, 1H) 3.72 (dd, J=14.74, 11.42 Hz, 2H) 4.05 (d, J=9.57 Hz, 1H) 5.58 (d, J=5.66 Hz, 1H) 5.90 (br. s., 1H) 7.66-7.83 (m, 2H) 8.21 (s, 1H) 8.71-8.83 (m, 2H); MS: 728, MH+.

Example 305

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[(2S)-2-pyrrolidinylmethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

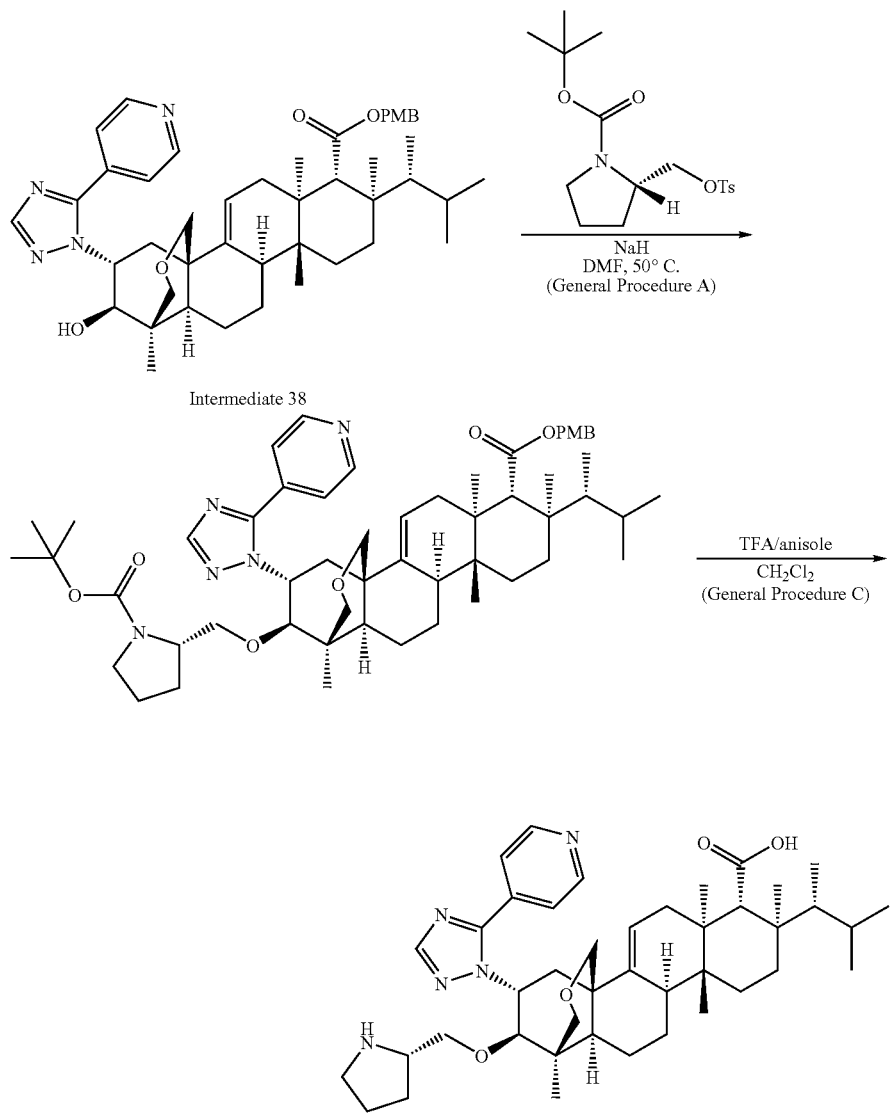

According to General Procedures A and C, the title compound was prepared and isolated as a white solid starting with Intermediate 38.

$^1$H NMR (400 MHz, METHANOL-$d_4$) δ 0.70-0.82 (m, 6H) 0.89 (dd, J=17.25, 6.76 Hz, 10H) 1.18 (s, 3H) 1.22 (s, 3H) 1.24-1.40 (m, 5H) 1.40-1.75 (m, 4H) 1.76-2.01 (m, 8H) 2.03-2.30 (m, 3H) 2.47 (dd, J=13.59, 6.22 Hz, 1H) 2.85 (s, 1H) 3.09 (dd, J=10.62, 5.83 Hz, 1H) 3.18 (t, J=6.61 Hz, 2H) 3.41-3.66 (m, 4H) 3.77 (d, J=12.01 Hz, 1H) 3.94 (d, J=9.62 Hz, 1H) 5.55 (d, J=5.76 Hz, 1H) 5.85 (dd, J=15.74, 6.03 Hz, 1H) 7.78-7.92 (m, 2H) 8.18 (s, 1H) 8.80 (d, J=5.91 Hz, 2H) MS (ESI) m/z 700.4 [M+H$^+$].

Example 306

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[(2R)-2-pyrrolidinylmethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid 3H) 1.23-1.73 (m, 13H) 1.85 (br. s., 4H) 1.94 (d, J=11.13 Hz, 4H) 2.15 (t, J=12.57 Hz, 3H) 2.33-2.53 (m, 1H) 2.87 (d, J=4.59 Hz, 2H) 3.06-3.27 (m, 3H) 3.39-3.64 (m, 4H) 3.75 (d, J=12.01 Hz, 1H) 3.85 (d, J=9.47 Hz, 1H) 5.51 (d, J=3.95 Hz, 1H) 5.73-6.02 (m, 1H) 7.79 (d, J=4.88 Hz, 2H) 8.15 (s, 1H) 8.78 (d, J=5.52 Hz, 2H) MS (ESI) m/z 700.4 [M+H$^+$].

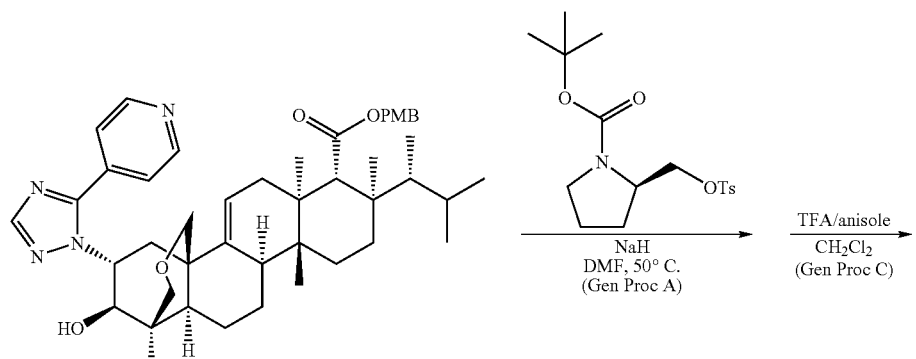

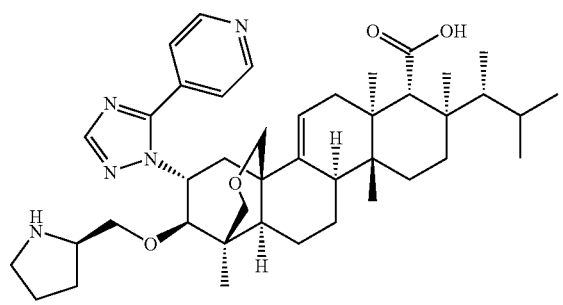

According to General Procedures A and C, the title compound (as a free base) was prepared and isolated as a white solid (142 mg) starting with Intermediate 38.

$^1$H NMR (400 MHz, METHANOL-d$_4$) δ ppm 0.67-0.80 (m, 3H) 0.87 (dd, J=17.96, 6.74 Hz, 11H) 1.17 (s, 3H) 1.21 (s,

Example 307

(1S,4aR,6aS,7R,8R,10aR,10bR,12aR,14R,15R)-8-[(1R)-1,2-dimethylpropyl]-15-[[(2R)-2-methyl-2-pyrrolidinyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

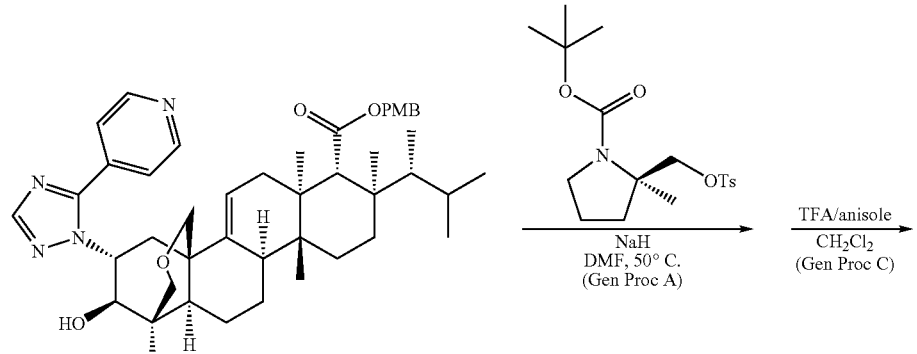

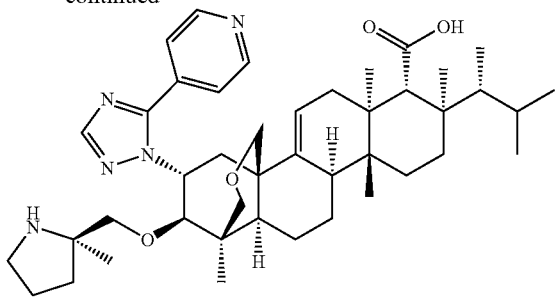

According to General Procedures A and C, the title compound was prepared and isolated as a white solid (38 mg) starting with Intermediate 38.

$^1$H NMR (400 MHz, METHANOL-$d_4$) δ 0.78 (t, J=3.49 Hz, 5H) 0.89 (dd, J=17.57, 6.88 Hz, 10H) 0.95 (s, 3H) 1.19 (s, 3H) 1.23 (s, 3H) 1.26-1.35 (m, 4H) 1.38-1.72 (m, 7H) 1.77-1.97 (m, 6H) 1.97-2.31 (m, 4H) 2.54 (dd, J=13.67, 6.20 Hz, 1H) 2.84 (s, 1H) 2.91 (d, J=9.91 Hz, 1H) 3.23 (t, J=7.54 Hz, 2H) 3.41-3.69 (m, 4H) 3.75 (d, J=12.10 Hz, 1H) 4.00 (d, J=9.76 Hz, 1H) 5.60 (d, J=5.52 Hz, 1H) 5.91 (dd, J=11.79, 5.98 Hz, 1H) 7.70-7.90 (m, 2H) 8.18 (s, 1H) 8.80 (dd, J=4.64, 1.46 Hz, 2H) MS (ESI) m/z 714.4 [M+H$^+$].

Example 308

(1S,4aR,6aS,7R,8R,10aR,10bR,12aR,14R,15R)-8-[(1R)-1,2-dimethylpropyl]-15-[[(2S)-1-methyl-2-pyrrolidinyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

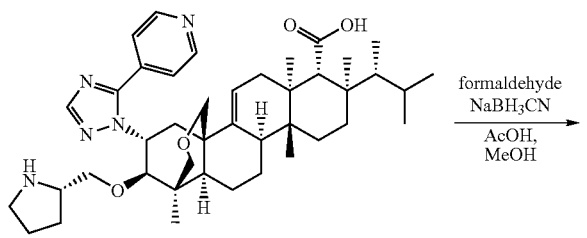

To a solution of (1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[(2S)-2-pyrrolidinylmethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 304; 98 mg, 0.14 mmol) in MeOH (6.0 mL) were added sequentially 30% (wt/wt) aqueous formaldehyde (126 mg, 4.21 mmol), HOAc (200 µL) and sodium cyanoborohydride in (448 µL of a 1.0 M solution in THF, 0.45 mmol). The reaction mixture was stirred at room temperature for 5 hours and then concentrated under reduced pressure. The residue was partitioned between CH$_2$Cl$_2$ and water and this mixture was extracted with 10% i-PrOH in CH$_2$Cl$_2$. The combined organic extracts were then dried with Na$_2$SO$_4$ and concentrated under reduced pressure. The residue was purified by RP HPLC (0.1% TFA water/methanol gradient) to provide the title compound (38 mg, 38%) as a white powder.

$^1$H NMR (400 MHz, METHANOL-$d_4$) δ ppm 0.70-0.81 (m, 3H) 0.88 (dd, J=17.91, 6.69 Hz, 9H) 1.19 (s, 3H) 1.23 (s, 3H) 1.37 (d, J=6.83 Hz, 10H) 1.41-1.75 (m, 8H) 1.73-2.04 (m, 4H) 2.19 (d, J=2.93 Hz, 9H) 2.48 (d, J=7.42 Hz, 1H) 2.73-2.92 (m, 3H) 2.98 (br. s., 1H) 3.41-3.66 (m, 3H) 3.69-3.88 (m, 2H) 5.53 (d, J=4.83 Hz, 1H) 5.74-6.00 (m, 1H) 8.24 (s, 1H) 8.29 (d, J=6.78 Hz, 2H) 8.91 (d, J=6.74 Hz, 2H) MS (ESI) m/z 714.4 [M+H$^+$].

Example 309

(1S,4aR,6aS,7R,8R,10aR,10bR,12aR,14R,15R)-8-[(1R)-1,2-dimethylpropyl]-15-[[(2R)-1-methyl-2-pyrrolidinyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

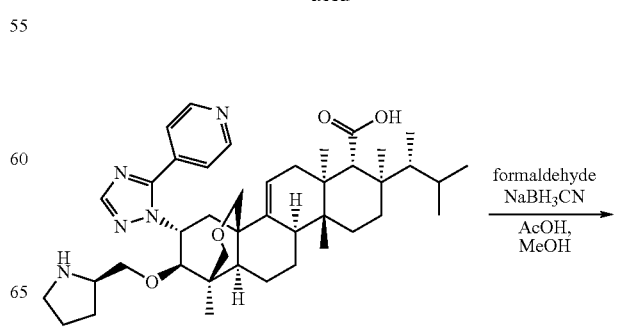

387
-continued

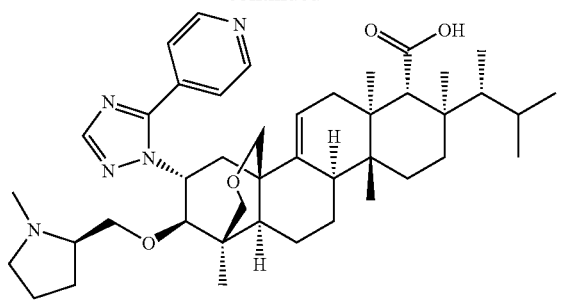

By a procedure analogous to that of Example 308, but starting with (1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[(2R)-2-pyrrolidinylmethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid (Example 306), the title compound was prepared and isolated as a white solid.

$^1$H NMR (400 MHz, METHANOL-d$_4$) δ ppm 0.78 (d, J=1.61 Hz, 6H) 0.89 (dd, J=17.03, 6.83 Hz, 10H) 1.19 (s, 3H) 1.23 (s, 3H) 1.37-1.77 (m, 6H) 1.78-2.02 (m, 7H) 2.00-2.32 (m, 5H) 2.52 (d, J=6.15 Hz, 1H) 2.71 (s, 3H) 2.86 (s, 1H) 2.95-3.24 (m, 4H) 3.42-3.83 (m, 7H) 3.94 (d, J=9.81 Hz, 1H) 5.58 (d, J=5.71 Hz, 1H) 5.85 (d, J=15.72 Hz, 1H) 7.89 (d, J=6.15 Hz, 2H) 8.21 (s, 1H) 8.84 (d, J=5.61 Hz, 2H) MS (ESI) m/z 714.4 [M+H$^+$].

Example 310

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-(5-imidazo[1,2-a]pyridin-7-yl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

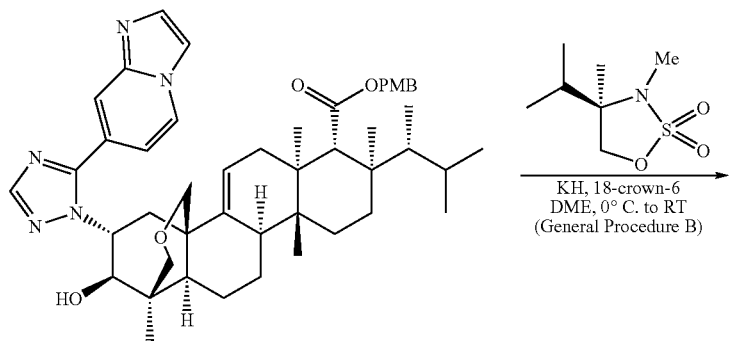

Intermediate 39

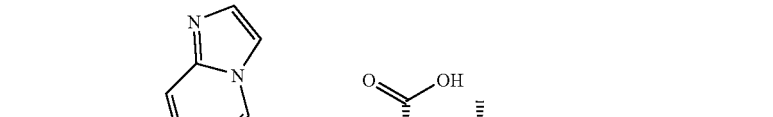

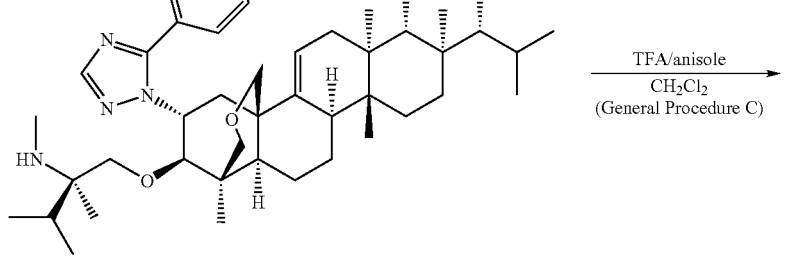

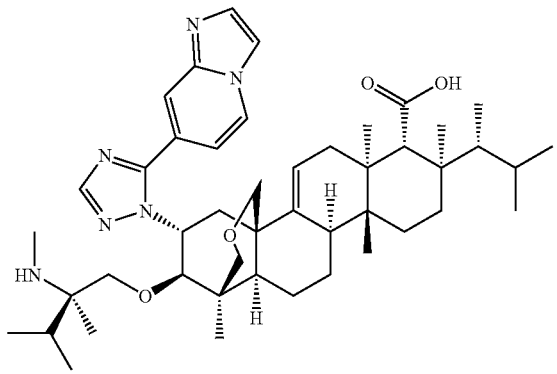

According to General Procedures B and C, the title compound was prepared and isolated as a white solid starting with Intermediate 39.

$^1$H NMR (400 MHz, METHANOL-$d_4$) δ ppm 0.67-1.00 (m, 25H) 1.14 (s, 3H) 1.19 (s, 3H) 1.25 (d, J=11.67 Hz, 4H) 1.35-1.70 (m, 4H) 1.76-2.05 (m, 7H) 2.12 (d, J=17.96 Hz, 2H) 2.31 (dd, J=13.45, 5.93 Hz, 1H) 2.46 (s, 3H) 2.81 (s, 1H) 3.11 (d, J=10.64 Hz, 1H) 3.48 (d, J=10.88 Hz, 3H) 3.73 (d, J=10.59 Hz, 1H) 3.94 (d, J=12.15 Hz, 1H) 4.09 (d, J=10.01 Hz, 1H) 5.42 (d, J=5.52 Hz, 1H) 6.02-6.29 (m, 1H) 7.72 (s, 1H) 7.77 (d, J=8.40 Hz, 1H) 8.11 (d, J=1.86 Hz, 1H) 8.21 (s, 1H) 8.32 (s, 1H) 8.67 (s, 1H) 8.96 (d, J=7.13 Hz, 1H) MS (ESI) m/z 770.4 [M+H$^+$].

Example 311

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

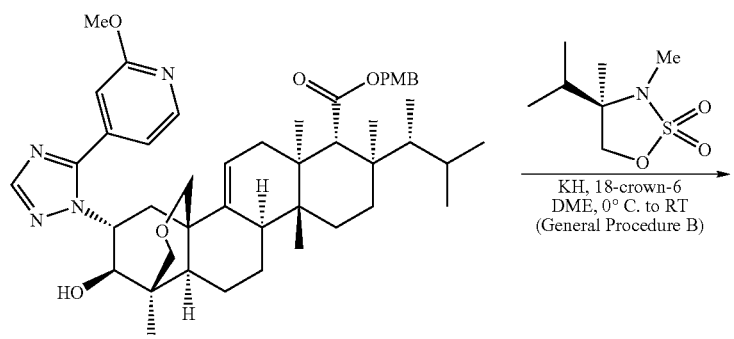

Intermediate 40

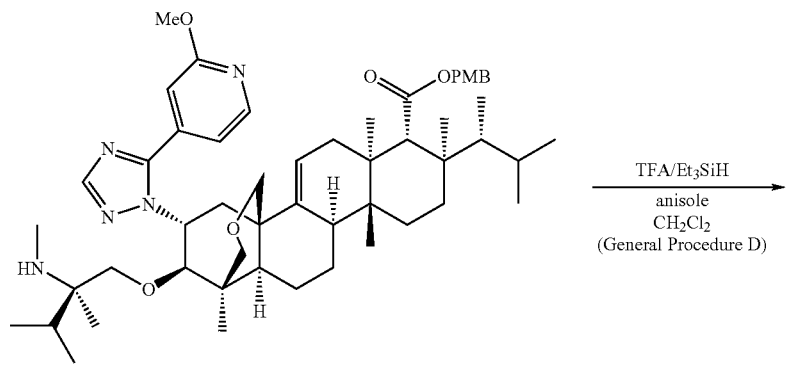

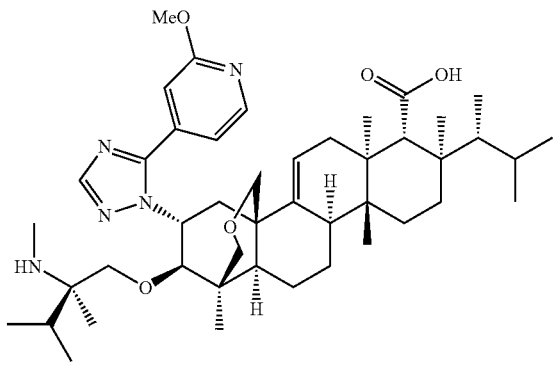

According to General Procedures B and D, the title compound was prepared and isolated as a white solid starting with Intermediate 40.

¹H NMR (400 MHz, DMSO-$d_6$) δ 0.60 (s, 3H) 0.65-0.75 (m, 12H) 0.77 (s, 3H) 0.81 (d, J=6.64 Hz, 3H) 0.85 (d, J=6.74 Hz, 3H) 1.09 (s, 3H) 1.14 (s, 3H) 1.18 (d, J=7.61 Hz, 3H) 1.30-1.59 (m, 3H) 1.65-1.96 (m, 6H) 1.97-2.19 (m, 2H) 2.23 (s, 3H) 2.61 (dd, J=13.64, 6.08 Hz, 1H) 2.68 (d, J=10.40 Hz, 2H) 3.32 (d, J=11.57 Hz, 1H) 3.38-3.52 (m, 2H) 3.55 (d, J=11.37 Hz, 1H) 3.77 (d, J=11.86 Hz, 1H) 3.89 (d, J=9.66 Hz, 1H) 3.94 (s, 3H) 5.66 (d, J=5.95 Hz, 2H) 7.12 (s, 1H) 7.35 (dd, J=5.32, 1.27 Hz, 1H) 8.22 (s, 1H) 8.40 (d, J=5.32 Hz, 1H) MS (ESI) m/z 761.5 [M+H⁺]

Example 312

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(4-pyridinyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid

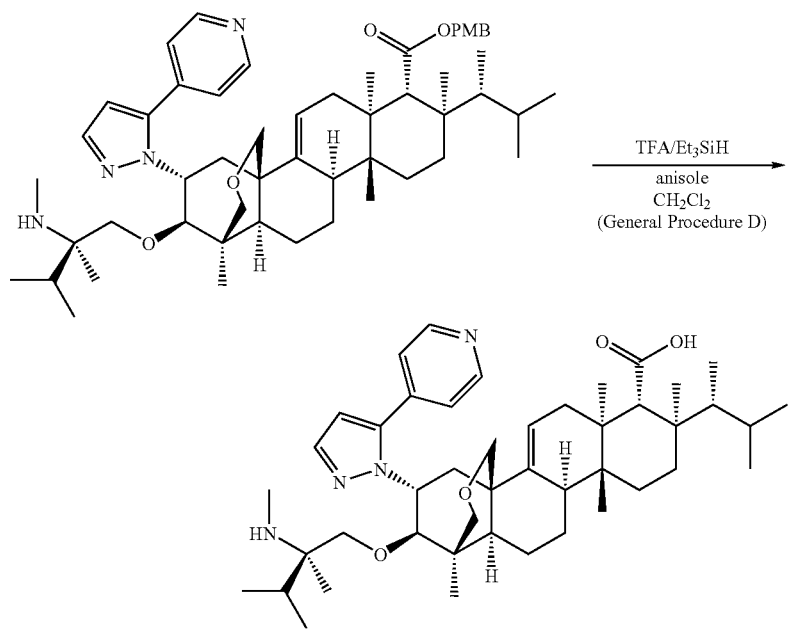

According to General Procedures B and D, the title compound was prepared and isolated as a white solid starting with Intermediate 41.

¹H NMR (400 MHz, $CDCl_3$) δ 0.74-0.97 (m, 25H) 1.18 (s, 3H) 1.22 (s, 3H) 1.23-1.39 (m, 3H) 1.40-1.73 (m, 4H) 1.79-2.04 (m, 6H) 2.04-2.28 (m, 3H) 2.40 (s, 3H) 2.54 (dd, J=13.76, 6.10 Hz, 1H) 2.83 (d, J=10.74 Hz, 2H) 3.46 (d, J=11.86 Hz, 1H) 3.55 (d, J=10.74 Hz, 2H) 3.62-3.69 (m, 1H) 3.80 (d, J=12.10 Hz, 1H) 4.08 (d, J=9.66 Hz, 1H) 5.59 (d, J=5.81 Hz, 1H) 5.75 (dd, J=9.74, 6.13 Hz, 1H) 6.83 (d, J=1.95 Hz, 1H) 7.76 (d, J=1.95 Hz, 1H) 8.02 (d, J=6.54 Hz, 2H) 8.88 (d, J=6.15 Hz, 2H).

Examples 313-318

The following compounds were prepared using methods analogous to those described in the preceding examples:

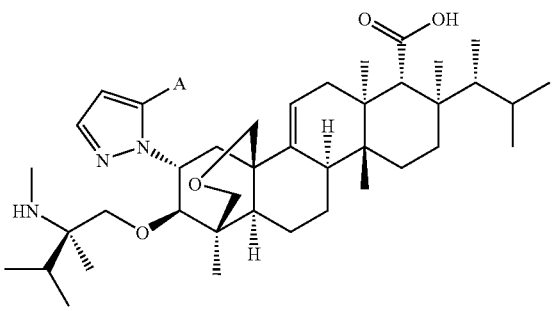

| 313 | A = 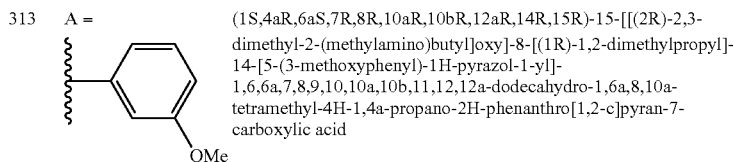 | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(3-methoxyphenyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (400 MHz, METHANOL-d$_4$) δ 0.74-0.96 (m, 26 H) 1.19 (s, 4 H) 1.23 (s, 3 H) 1.24-1.70 (m, 5 H) 1.79-2.03 (m, 5 H) 2.03-2.29 (m, 3 H) 2.36 (s, 3 H) 2.46-2.58 (m, 1 H) 2.86 (d, J = 2.83 Hz, 2 H) 3.13 (t, J = 2.17 Hz, 1 H) 3.35-3.52 (m, 2 H) 3.55 (s, 2 H) 3.76 (d, J = 12.01 Hz, 1 H) 3.87 (s, 3 H) 4.03 (d, J = 9.22 Hz, 1 H) 5.55 (d, J = 4.25 Hz, 1 H) 5.80 (ddd, J = 11.67, 10.27, 6.27 Hz, 1 H) 6.45 (d, J = 1.95 Hz, 1 H) 6.96-7.17 (m, 3 H) 7.42 (t, J = 8.00 Hz, 1 H) 7.62 (d, J = 1.81 Hz, 1 H).

| 314 | A = 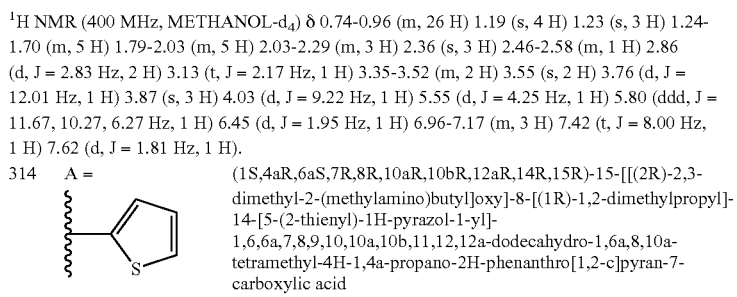 | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-thienyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (400 MHz, METHANOL-d$_4$) δ 0.71-0.97 (m, 26 H) 1.17 (s, 3 H) 1.22 (s, 3 H) 1.23-1.73 (m, 7 H) 1.78-2.06 (m, 7 H) 2.18 (dd, J = 19.52, 13.28 Hz, 2 H) 2.34 (s, 3 H) 2.45 (dd, J = 13.72, 6.35 Hz, 1 H) 2.86 (s, 1 H) 2.97 (d, J = 10.74 Hz, 1 H) 3.39-3.68 (m, 4 H) 3.83 (d, J = 12.15 Hz, 1 H) 4.09 (d, J = 9.66 Hz, 1 H) 5.52 (dd, J = 3.98, 1.83 Hz, 1 H) 5.94 (ddd, J = 11.99, 9.80, 6.32 Hz, 1 H) 6.49 (d, J = 1.90 Hz, 1 H) 7.19 (dd, J = 5.15, 3.64 Hz, 1 H) 7.35 (dd, J = 3.64, 1.05 Hz, 1 H) 7.59 (dd, J = 5.17, 1.07 Hz, 2 H).

| 315 | A = 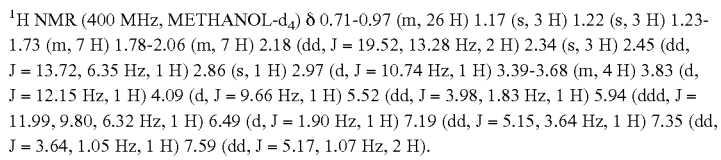 | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-thiazolyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (500 MHz, METHANOL-d$_4$) δ 0.75 (d, J = 18.24 Hz, 8 H) 0.81-0.95 (m, 16 H) 1.15 (s, 3 H) 1.21 (s, 3 H) 1.23-1.35 (m, 3 H) 1.39-1.47 (m, 1 H) 1.47-1.57 (m, 2 H) 1.58-1.68 (m, 1 H) 1.78-1.98 (m, 6 H) 2.03 (quin, J = 6.80 Hz, 1 H) 2.09-2.23 (m, 3 H) 2.31 (s, 3 H) 2.44 (dd, J = 13.73, 6.53 Hz, 1 H) 2.84 (s, 1 H) 3.08 (d, J = 10.80 Hz, 1 H) 3.45-3.63 (m, 4 H) 3.75 (d, J = 6.89 Hz, 1 H) 3.87 (d, J = 11.90 Hz, 1 H) 4.17 (d, J = 9.94 Hz, 1 H) 5.42 (dd, J = 4.00, 1.80 Hz, 1 H) 6.49 (dd, J = 11.96, 7.14 Hz, 1 H) 6.78 (d, J = 1.95 Hz, 1 H) 7.65 (d, J = 1.83 Hz, 1 H) 7.74 (d, J = 3.29 Hz, 1 H) 7.98 (d, J = 3.29 Hz, 1 H).

| 316 | A = 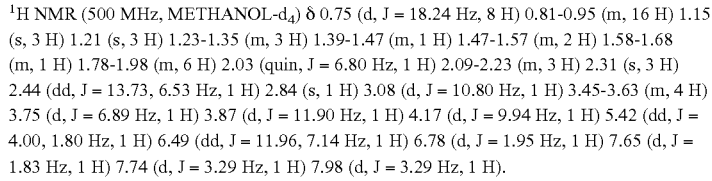 | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-pyridinyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

$^1$H NMR (400 MHz, METHANOL-d$_4$) δ 0.74-0.96 (m, 21 H) 1.16-1.20 (m, 3 H) 1.23 (s, 3 H) 1.24-1.72 (m, 8 H) 1.77-2.28 (m, 10 H) 2.38 (s, 3 H) 2.43-2.55 (m, 1 H) 2.83-2.95 (m, 2 H) 3.39-3.63 (m, 4 H) 3.76 (d, J = 12.06 Hz, 1 H) 4.06 (d, J = 0.63 Hz, 1 H) 5.57 (dd, J =

-continued

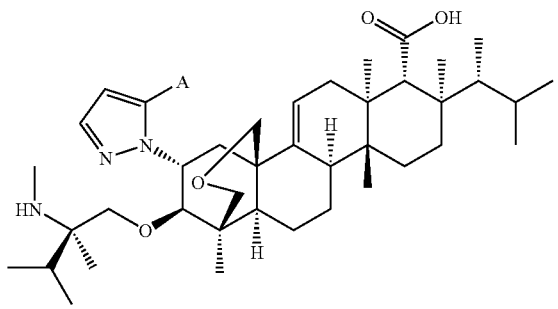

2.10, 0.39 Hz, 1 H) 5.61-5.73 (m, 1 H) 6.59 (d, J = 1.95 Hz, 1 H) 7.62-7.69 (m, 1 H) 7.70 (d, J = 1.90 Hz, 1 H) 8.09 (dt, 1 H) 8.66 (d, J = 0.98 Hz, 1 H) 8.73-8.80 (m, 1 H).

| 317 | A = | (1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(3-fluorophenyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

(3-fluorophenyl structure)

$^1$H NMR (400 MHz, METHANOL-d$_4$) δ ppm 0.75-0.95 (m, 23 H) 1.17 (d, J = 1.37 Hz, 1 H) 1.23 (s, 3 H) 1.24-1.72 (m, 7 H) 1.78-2.11 (m, 7 H) 2.11-2.29 (m, 2 H) 2.37 (s, 3 H) 2.41-2.52 (m, 1 H) 2.82-2.94 (m, 2 H) 3.38-3.60 (m, 4 H) 3.76 (d, J = 12.30 Hz, 1 H) 4.05 (d, J = 9.52 Hz, 1 H) 5.52-5.60 (m, 1 H) 5.68-5.81 (m, 1 H) 6.48 (d, J = 1.90 Hz, 1 H) 7.15-7.26 (m, 1 H) 7.25-7.35 (m, 1 H) 7.38 (d, J = 7.76 Hz, 1 H) 7.55 (td, J = 8.05, 5.95 Hz, 1 H) 7.64 (d, J =1.85 Hz, 1 H).

| 318 | A = | (1S,4aR,6a8,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[4-(trifluoromethyl)phenyl]-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid |

(4-CF$_3$-phenyl structure)

$^1$H NMR (400 MHz, METHANOL-d$_4$) δ ppm 0.74-0.94 (m, 24 H) 1.16-1.19 (m, 3 H) 1.19-1.23 (m, 3 H) 1.23-1.38 (m, 3 H) 1.38-1.71 (m, 4 H) 1.75-2.27 (m, 9 H) 2.35 (s, 3 H) 2.45-2.59 (m, 1 H) 2.83-2.90 (m, 2 H) 3.36-3.66 (m, 5 H) 3.68-3.78 (m, 2 H) 3.98-4.08 (m, 1 H) 5.53-5.64 (m, 1 H) 5.64-5.79 (m, 1 H) 6.54 (d, J = 1.90 Hz, 1 H) 7.62-7.71 (m, 1 H) 7.70-7.88 (m, 4 H).

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:
1. A compound of Formula (I):

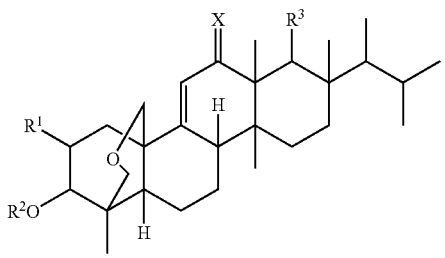

or a pharmaceutically acceptable salt thereof, wherein:

$R^1$ is a group of the following structure:

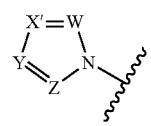

wherein W, X', Y, and Z are independently selected from N and $CR^e$ provided that two or three of W, X', Y and Z is $CR^e$;

$R^e$ is independently selected from the group consisting of:
a) H;
b) Halogen;
c) $NR^fR^g$;
d) $NHC(O)R^o$;
e) $NHC(O)NR^fR^g$;
f) $NHC(O)OR^o$;
g) $NO_2$
h) $OR^o$;
i) $SR^o$;
j) $SO_2R^o$;
k) $SO_2N(R^o)_2$;

l) CN;
m) C(O)R$^o$;
n) C(O)OR$^o$;
o) C(O)NR$^f$R$^g$;
p) C(=NR$^o$)N(R$^o$)$_2$;
q) C$_1$-C$_6$-alkyl optionally substituted with 1 to 3 substituents independently selected from phenyl, pyridyl, OR$^o$, N(R$^o$)$_2$, CO$_2$R$^o$, C(O)N(R$^o$)$_2$ or halogen;
r) C$_2$-C$_6$-alkenyl optionally substituted with 1 to 3 substituents independently selected from phenyl, OR$^o$, N(R$^o$)$_2$, CO$_2$R$^o$, C(O)N(R$^o$)$_2$ or halogen;
s) C$_3$-C$_6$-cycloalkyl, optionally substituted with oxo, OR$^o$, N(R$^o$)$_2$, CO$_2$R$^o$ or C(O)N(R$^o$)$_2$;
t) heterocyclyl, wherein the heterocyclyl is a 4- to 6-membered saturated or unsaturated non-aromatic ring having 1, 2 or 3 heteroatoms selected from N, O or S, attached through a carbon or nitrogen on the ring, and optionally substituted on a ring carbon with 1 to 2 substituents independently selected from N(R$^o$)$_2$, imino, oxo, OR$^o$, CO$_2$R$^o$, C(O)N(R$^o$)$_2$ and C$_1$-C$_6$-alkyl unsubstituted or substituted with 1 to 3 substituents independently selected from N(R$^o$)$_2$, OR$^o$, CO$_2$R$^o$, C(O)N(R$^o$)$_2$ and halogen; the heterocyclyl may also be optionally substituted on a ring nitrogen atom that is not the point of attachment with C(O)R$^o$, CO$_2$R$^o$, C(O)N(R$^o$)$_2$, SO$_2$R$^o$ or C$_1$-C$_6$ alkyl unsubstituted or substituted with 1 to 3 substituents independently selected from N(R$^o$)$_2$, OR$^o$, CO$_2$R$^o$, C(O)N(R$^o$)$_2$ and halogen; the heterocyclyl may also be optionally substituted on a sulfur atom with 1 or 2 oxo groups;
u) aryl, wherein aryl is phenyl or napthyl and aryl is unsubstituted or substituted with 1 or 2 substituents independently selected from halogen, N(R$^o$)$_2$, OR$^o$, CO$_2$R$^o$, CN, C(O)N(R$^o$)$_2$, C(=NR$^o$)N(R$^o$)$_2$, heterocyclyl as defined above, phenyl, pyridyl, and C$_1$-C$_6$-alkyl wherein said alkyl is optionally substituted with 1 to 3 substituents independently selected from N(R$^o$)$_2$, OR$^o$, or halogen;
v) heteroaryl, wherein heteroaryl is a 5- or 6-membered monocyclic aromatic ring or 9- or 10-membered bicyclic aromatic ring having 1, 2 or 3 heteroatoms selected from N, O or S, attached through a ring carbon or nitrogen, and optionally substituted on a ring carbon that is not the point of attachment, with 1 or 2 substituents independently selected from halogen, CF$_3$, NR$^f$R$^g$, NHC(O)R$^o$, OR$^o$, CO$_2$R$^o$, CON(R$^o$)$_2$, C(=NR$^o$)N(R$^o$)$_2$, CN, heterocyclyl as defined above, phenyl, pyridyl, and C$_1$-C$_6$ alkyl unsubstituted or substituted with 1 or 2 substituents independently selected from N(R$^o$)$_2$ and OR$^o$; the heteroaryl may also be optionally substituted on a ring nitrogen atom that is not the point of attachment with O or C$_1$-C$_6$ alkyl;
R$^f$ is H, C$_1$-C$_6$-alkyl, C$_3$-C$_6$-cycloalkyl or phenyl;
R$^g$ is H or C$_1$-C$_6$-alkyl optionally substituted with 1 to 3 substituents independently selected from phenyl, OR$^o$, N(R$^o$)$_2$ or halogen;
R$^f$ and R$^g$ are optionally taken together with the attached nitrogen atom to form a 3- to 7-membered ring having 0-1 additional heteroatoms independently selected from N, O and S wherein said ring may be optionally substituted on a ring nitrogen atom that is not the point of attachment with C(O)R$^o$, CO$_2$R$^o$, C(O)N(R$^o$)$_2$, SO$_2$R$^o$ or C$_1$-C$_6$ alkyl unsubstituted or substituted with 1 or 2 substituents independently selected from N(R$^o$)$_2$, OR$^o$, CO$_2$R$^o$, C(O)N(R$^o$)$_2$ or halogen; said ring may also be optionally substituted on a sulfur atom with 1 or 2 oxo groups;

R$^2$ is a group of the following structure:

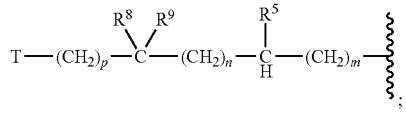

m is 0 or 1;
n is 0 or 1;
p is 0 or 1;
T is NR$^6$R$^7$ or OR$^{10}$;
R$^5$ is H or C$_1$-C$_6$-alkyl, unsubstituted or substituted with 1 or 2 substituents independently selected from N(R$^o$)$_2$ and OR$^o$;
R$^6$ is H, C$_1$-C$_6$-alkyl or C$_3$-C$_6$ cycloalkyl;
R$^7$ is
a) H;
b) C$_1$-C$_6$-alkyl, unsubstituted or substituted with 1 or 2 substituents independently selected from N(R$^o$)$_2$, OR$^o$, CO$_2$R$^o$, OC(O)R$^o$, NHC(O)R$^o$, C(O)N(R$^o$)$_2$, phenyl, heteroaryl, and heterocyclyl, wherein heteroaryl and heterocyclyl are as defined above in the definition of R$^e$;
c) C$_3$-C$_6$-cycloalkyl;
d) C(O)R$^o$;
e) C(O)OC$_1$-C$_6$-alkyl;
f) C(O)NHR$^o$;
g) C(=NH)R$^o$;
h) C(=NR$^o$)NHR$^o$;
R$^6$ and R$^7$ are optionally taken together with the attached nitrogen atom to form a 4- to 7-membered saturated, unsaturated or aromatic ring having 0 or 1 additional heteroatoms independently selected from N, O and S, wherein said ring is optionally substituted on a ring carbon with 1 to 2 substituents independently selected from halogen, CF$_3$, N(R$^o$)$_2$, OR$^o$, CO$_2$R$^o$, C(O)N(R$^o$)$_2$, and C$_1$-C$_6$ alkyl unsubstituted or substituted with 1 or 2 substituents independently selected from OR$^o$ and N(R$^o$)$_2$; said ring may also be optionally substituted on a ring nitrogen atom that is not the point of attachment with C(O)R$^o$, CO$_2$R$^o$, C(O)N(R$^o$)$_2$, SO$_2$R$^o$ or C$_1$-C$_6$ alkyl unsubstituted or substituted with 1 to 3 substituents independently selected from N(R$^o$)$_2$, OR$^o$, CO$_2$R$^o$, C(O)N(R$^o$)$_2$ and halogen; said ring may also be optionally substituted on a sulfur atom with 1 or 2 oxo groups;
R$^6$ and R$^8$ are optionally taken together to form, with the intervening atoms, a 4- to 7-membered saturated ring having 0 or 1 additional heteroatoms independently selected from N, O and S wherein said ring is optionally substituted as defined above for R$^6$ and R$^7$ when joined together to form a ring;
R$^6$ and R$^5$ are optionally taken together to form, with the intervening atoms, a 4- to 7-membered saturated ring having 0 or 1 additional heteroatoms independently selected from N, O and S wherein said ring is optionally substituted as defined above for R$^6$ and R$^7$ when joined together to form a ring;
R$^8$ is selected from the group consisting of
a) hydrogen,
b) C$_1$-C$_6$-alkyl, unsubstituted or substituted with F, OR$^o$, N(R$^o$)$_2$ or SO$_2$R$^o$, c) $C_3$-$C_6$-cycloalkyl, d) $C_4$-$C_7$-cycloalkyl-alkyl, e) aryl, wherein aryl is phenyl or naphthyl and said aryl is unsubstituted or substituted with 1 to 3 substituents selected from $C_1$-$C_6$-alkyl, halogen, $OCF_3$, $CF_3$, $N(R^0)_2$ and $OR^0$, and f) heteroaryl, wherein heteroaryl is as defined above in the definition of $R^e$;

$R^9$ is $C_1$-$C_6$-alkyl, unsubstituted or substituted with $OR^0$ or $SO_2R^0$;

$R^8$ and $R^9$ are optionally taken together to form a 3- to 7-membered saturated ring having 0 or 1 additional heteroatoms independently selected from N, O, and S, wherein said ring is optionally substituted as defined above for $R^6$ and $R^7$ when joined to form a ring;

$R^{10}$ is selected from the group consisting of a) H, b) $C_1$-$C_6$-alkyl, unsubstituted or substituted with 1 or 2 substituents selected from $N(R^0)_2$, $OR^0$, $CO_2R^0$, $OC(O)R^0$, $NHC(O)R^0$, $C(O)N(R^0)_2$, phenyl, heteroaryl, and heterocyclyl, wherein heteroaryl and heterocyclyl are as defined above in the definition of $R^e$, c) $C_3$-$C_6$-cycloalkyl, d) $C(O)R^0$, e) $C(O)NHR^0$, $R^3$ is $C(O)R^{14}$;

$R^{14}$ is OH, $OR^{15}$ or $N(R^0)_2$;

$R^{15}$ is $C_1$-$C_6$-alkyl, unsubstituted or substituted with 1 or 2 substituents independently selected from phenyl and $OC(O)R^0$, wherein said phenyl is optionally substituted with 1 to 3 $OR^0$ groups;

X is O or H, H;

each $R^0$ is independently H, $C_1$-$C_6$ alkyl, $C_3$-$C_6$ cycloalkyl or benzyl.

2. The compound according to claim 1, wherein $R^3$ is C(O)OH.

3. The compound according to claim 2, wherein the compound is of Formula Ia, or a pharmaceutically acceptable salt thereof:

Ia

4. The compound according to claim 1, wherein X is H, H.

5. The compound according to claim 1, wherein X is O.

6. The compound according to claim 1, wherein T is $OR^{10}$.

7. The compound according to claim 1, wherein T is $NR^6R^7$.

8. The compound according to claim 7, wherein $R^2$ is

9. The compound according to claim 7, wherein $R^2$ is

10. The compound according to claim 9, wherein $R^2$ is

11. The compound according to claim 7, wherein $R^2$ is

12. The compound according to claim 7, wherein $R^2$ is

13. The compound according to claim 12, wherein $R^2$ is

14. The compound according to claim 7, wherein $R^2$ is and wherein
$R^6$ is H or $C_1$-$C_3$-alkyl;
$R^7$ is H or methyl;
$R^8$ is $C_1$-$C_5$-alkyl, $C_3$-$C_5$ cycloalkyl or $C_4$-$C_6$ cycloalkyl-alkyl;

$R^9$ is H or $C_1$-$C_3$-alkyl;

or $R^8$ and $R^9$ are optionally taken together to form a 5- to 6-membered saturated ring having 0-1 heteroatom selected from O or S.

15. The compound according to claim 7, wherein $R^2$ is

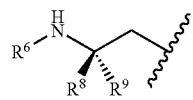

wherein
$R^6$ is H, methyl, ethyl or n-propyl;
$R^8$ is ethyl, i-propyl, t-butyl or 1-methylcyclopropyl;
$R^9$ is methyl or ethyl;
or $R^8$ and $R^9$ are optionally taken together to form a 6-membered saturated ring containing 0 or 1 oxygen atoms.

16. The compound according to claim 1, wherein $R^2$ is selected from the group consisting of:

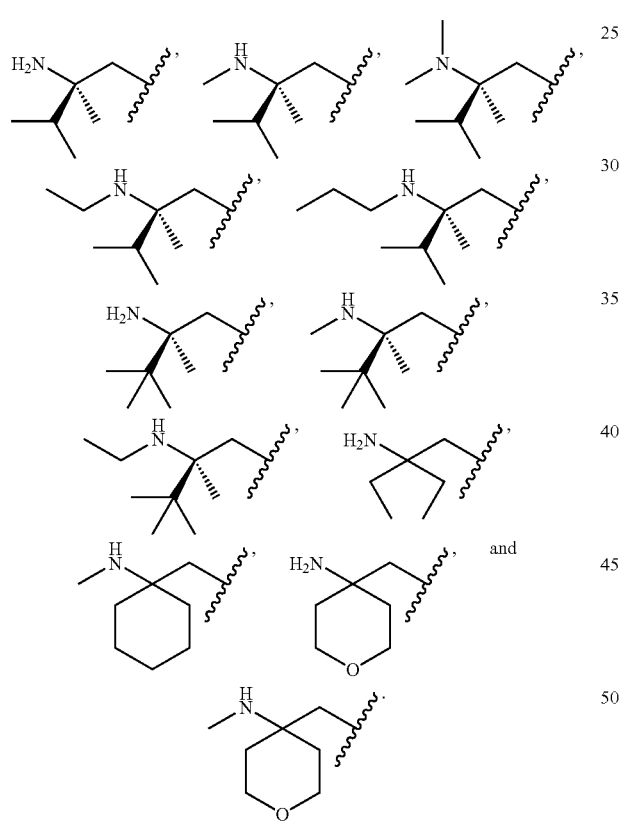

17. The compound of according to claim 1, wherein $R^1$ is

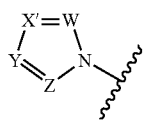

wherein W, X', Y, and Z are independently selected from N and $CR^e$ provided that two of W, X', Y and Z are $CR^e$.

18. The compound according to claim 17, wherein $R^1$ is

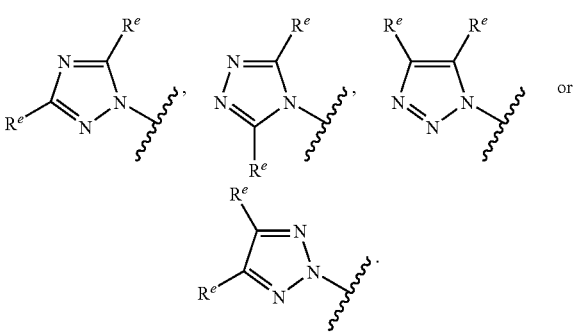

19. The compound according to claim 17, wherein $R^1$ is

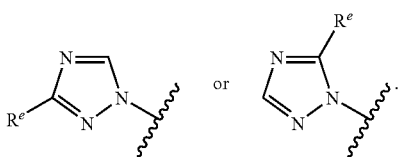

20. The compound according to claim 17, wherein $R^1$ is

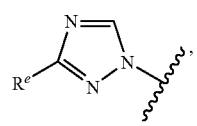

wherein $R^e$ is $NR^f R^g$.

21. The compound according to claim 17, wherein $R^1$ is

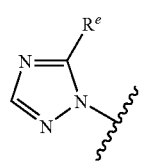

wherein $R^e$ is selected from the following:
a) H,
b) Halogen,
c) $C(O)NR^f R^g$,
d) heterocyclyl, wherein the heterocyclyl is a 4- to 6-membered saturated or unsaturated non-aromatic ring having 1 or 2 heteroatoms selected from N, O or S, attached through a carbon or nitrogen on the ring and optionally substituted on a ring carbon with $N(R^o)_2$, $OR^o$, imino or oxo; the heterocyclyl may also be optionally substituted on a ring nitrogen atom that is not the point of attachment with $C(O)R^o$, $CO_2R^o$, $C(O)N(R^o)_2$ or $C_1$-$C_4$ alkyl,
e) aryl, wherein aryl is phenyl or napthyl and aryl is unsubstituted or substituted with 1 or 2 substituents independently selected from halogen, $CF_3$, $N(R^o)_2$, $OR^o$, $CO_2R^o$, CN, $C(O)N(R^o)_2$, $C(=NR^o)N(R^o)_2$, and $C_1$-$C_3$-alkyl wherein said alkyl is optionally substituted with $N(R^o)_2$ or $OR^o$; and f) heteroaryl, wherein heteroaryl is a 5- or 6-membered aromatic ring having 1, 2 or 3 heteroatoms selected from N, O or S, attached through a ring carbon or nitrogen, and optionally substituted on a ring carbon that is not the point of attachment, with 1 or 2 substituents independently selected from halogen, $CF_3$, $NR^fR^g$, $NHC(O)R^o$, $OR^o$, $CO_2R^o$, $C(O)N(R^o)_2$, $C(=NR^o)N(R^o)_2$, CN and $C_1$-$C_3$ alkyl, wherein said alkyl is optionally substituted with $N(R^o)_2$ or $OR^o$; the heteroaryl may also be optionally substituted on a nitrogen atom that is not the point of attachment with O or $C_1$-$C_3$ alkyl.

22. The compound according to claim 17, wherein $R^1$ is

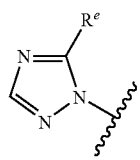

wherein $R^e$ is $C(O)NR^fR^g$.

23. The compound according to claim 22, wherein $R^1$ is selected from the group consisting of:

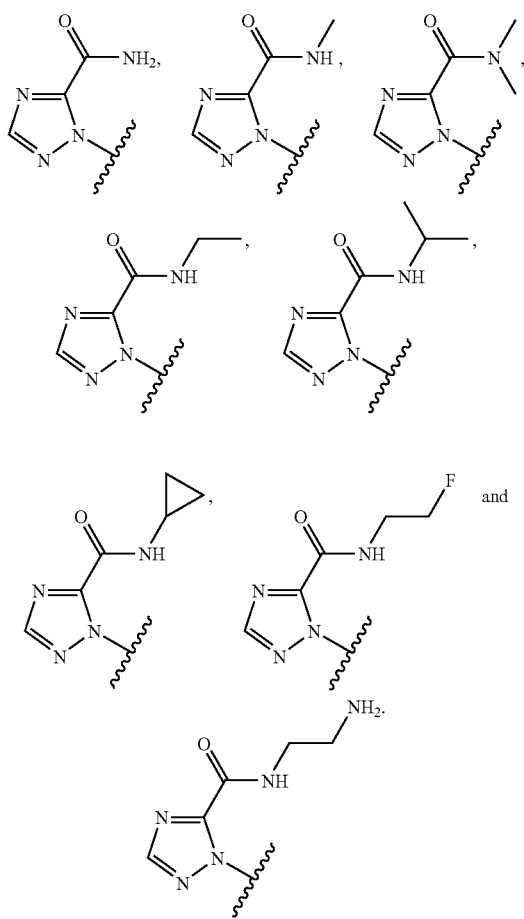

24. The compound according to claim 17, wherein $R^1$ is

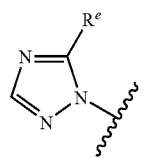

wherein $R^e$ is heterocyclyl, wherein the heterocyclyl is a 4- to 6-membered saturated or unsaturated non-aromatic ring having 1 or 2 heteroatoms selected from N, O or S, attached through a carbon or nitrogen on the ring and optionally substituted on a ring carbon with $N(R^o)_2$, $OR^o$, imino or oxo; the heterocyclyl may also be optionally substituted on a ring nitrogen atom that is not the point of attachment with $C(O)R^o$, $CO_2R^o$, $C(O)N(R^o)_2$ or $C_1$-$C_4$ alkyl.

25. The compound according to claim 24, wherein $R^1$ is selected from the group consisting of:

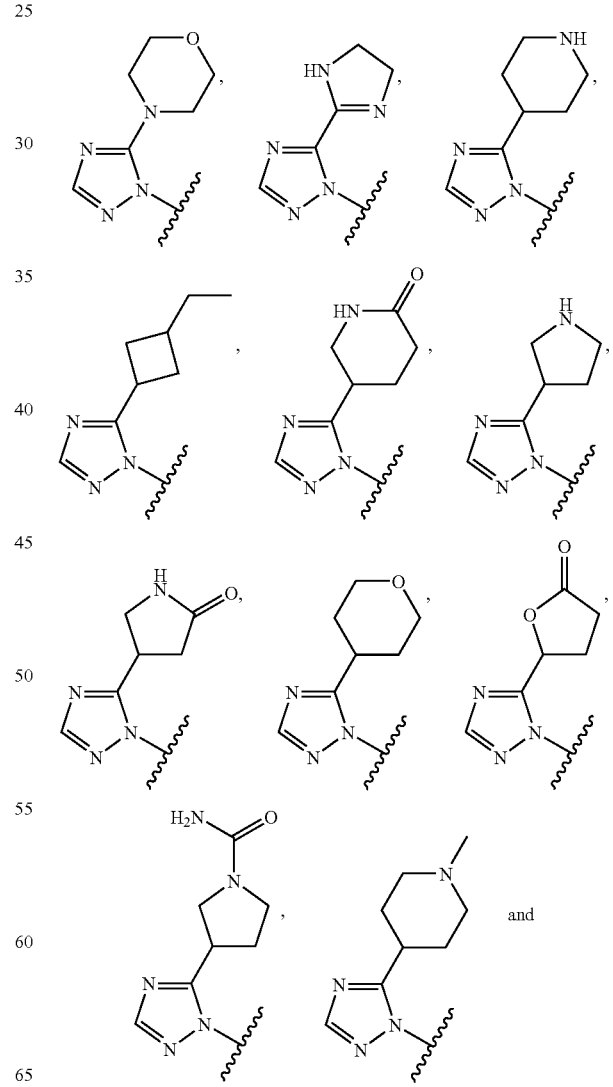

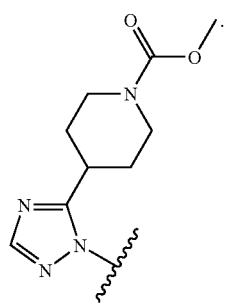

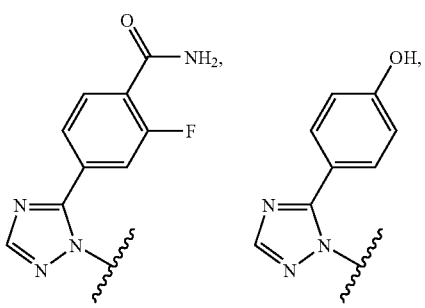

26. The compound according to claim 17, wherein R¹ is

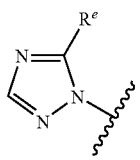

wherein $R^e$ is aryl, wherein aryl is phenyl or napthyl and aryl is unsubstituted or substituted with 1 or 2 substituents independently selected from halogen, $CF_3$, $N(R^o)_2$, $OR^o$, $CO_2R^o$, CN, $C(O)N(R^o)_2$, $C(=NR^o)N(R^o)_2$, and $C_1$-$C_3$-alkyl wherein said alkyl is optionally substituted with $N(R^o)_2$ or $OR^o$.

27. The compound according to claim 26, wherein R¹ is selected from the group consisting of:

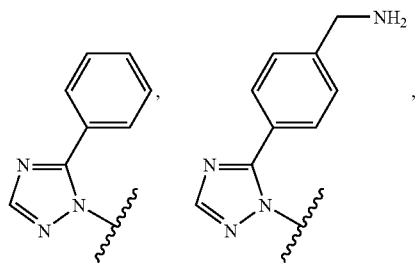

28. The compound according to claim 17, wherein R¹ is

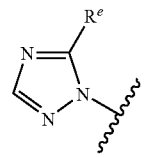

wherein $R^e$ is heteroaryl, wherein heteroaryl is a 5- or 6-membered aromatic ring having 1, 2 or 3 heteroatoms selected from N, O or S, attached through a ring carbon or nitrogen, and optionally substituted on a ring carbon that is not the point of attachment, with halogen, $NR^fR^g$, $NHC(O)R^o$, $OR^o$, $CO_2R^o$, $C(O)N(R^o)_2$, $C(=NR^o)N(R^o)_2$, CN or $C_1$-$C_3$ alkyl, wherein said alkyl is optionally substituted with $N(R^o)_2$ or $OR^o$; the heteroaryl may also be optionally substituted on a nitrogen atom that is not the point of attachment with O or $C_1$-$C_3$ alkyl.

29. The compound according to claim 28, wherein R¹ is selected from the group consisting of:

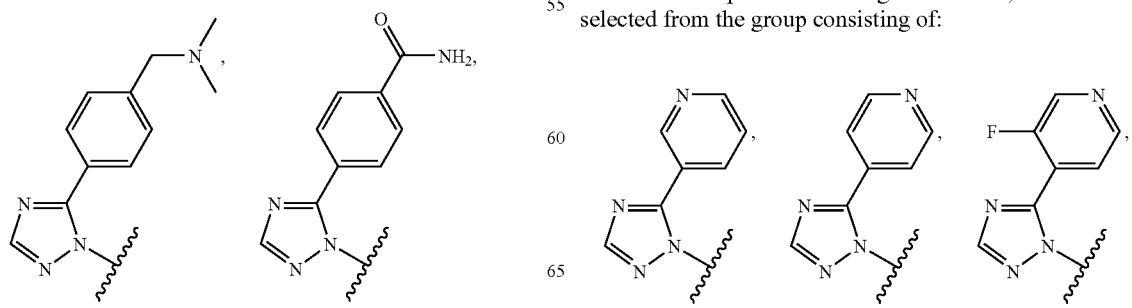

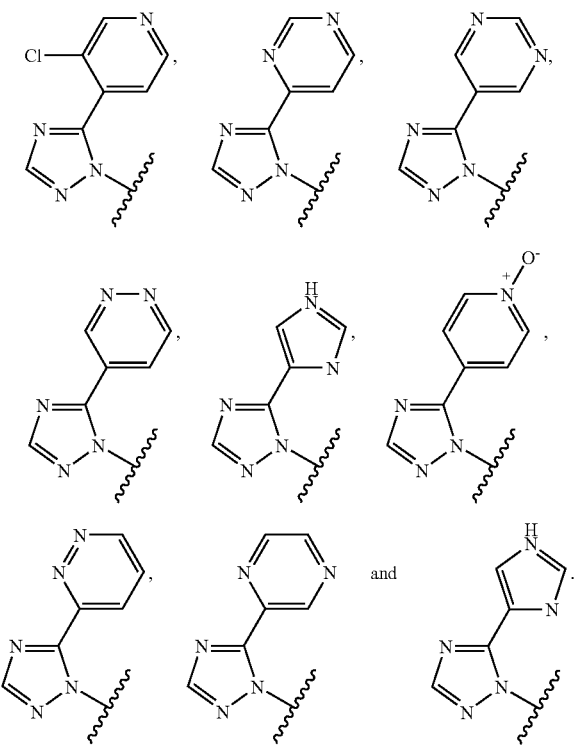

30. The compound of according to claim 1, wherein $R^1$ is

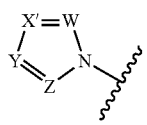

wherein W, X', Y, and Z are independently selected from N and $CR^e$ provided that three of W, X', Y and Z are $CR^e$.

31. The compound according to claim 30, wherein $R^1$ is

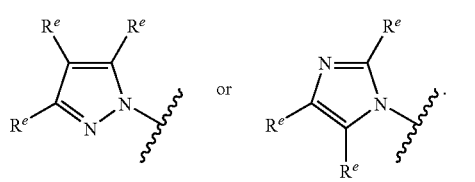

32. The compound according to claim 30, wherein $R^1$ is

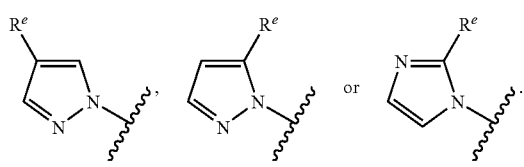

33. The compound according to claim 30, wherein $R^1$ is

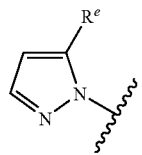

wherein $R^e$ is selected from the group consisting of:
a) H;
b) $C(O)NR^fR^g$;
c) aryl, wherein aryl is phenyl or napthyl and aryl is unsubstituted or substituted with 1 or 2 substituents independently selected from halogen, $CF_3$, $N(R^0)_2$, $OR^0$, $CO_2R^0$, CN, $C(O)N(R^0)_2$, $C(=NR^0)N(R^0)_2$, and $C_1$-$C_3$-alkyl wherein said alkyl is optionally substituted with $N(R^0)_2$ or $OR^0$; and
d) heteroaryl, wherein heteroaryl is a 5- or 6-membered aromatic ring having 1, 2 or 3 heteroatoms selected from N, O or S, attached through a ring carbon or nitrogen, and optionally substituted on a ring carbon that is not the point of attachment, with halogen, $NR^fR^g$, $NHC(O)R^0$, $OR^0$, $CO_2R^0$, $C(O)N(R^0)_2$, $C(=NR^0)N(R^0)_2$, CN or $C_1$-$C_3$ alkyl, wherein said alkyl is optionally substituted with $N(R^0)_2$ or $OR^0$; the heteroaryl may also be optionally substituted on a nitrogen atom that is not the point of attachment with O or $C_1$-$C_3$ alkyl.

34. The compound according to claim 1 having Formula (II):

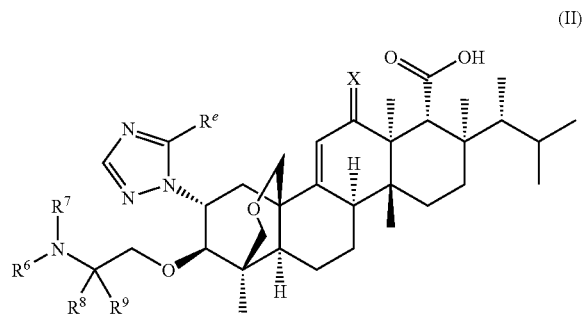

or a pharmaceutically acceptable salt thereof, wherein:
X is O or H, H;
$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;
$R^f R^g$, $R^6$ and $R^7$ are each independently hydrogen or $C_1$-$C_3$ alkyl;
$R^8$ is $C_1$-$C_4$ alkyl, $C_3$-$C_4$ cycloalkyl or $C_4$-$C_5$ cycloalkylalkyl;
$R^9$ is methyl or ethyl;
$R^8$ and $R^9$ are optionally taken together to form a 6-membered saturated ring containing 1 oxygen atom.

35. The compound according to claim 34, wherein X is H, H.

36. The compound according to claim 34 wherein $R^e$ is pyridyl or pyrimidinyl optionally mono-substituted on a ring carbon with fluoro or chloro or on a ring nitrogen with oxygen.

37. The compound according to claim 34, wherein $R^e$ is 4-pyridyl.

38. The compound according to claim 34, wherein $R^e$ is $C(O)NH_2$ or $C(O)NH(C_1-C_3$ alkyl).

39. The compound according to claim 34, wherein $R^8$ is $C_1-C_4$ alkyl and $R^9$ is methyl.

40. The compound according to claim 34, wherein $R^8$ is isopropyl or t-butyl, and $R^9$ is methyl.

41. The compound according to claim 34, wherein $R^6$ and $R^7$ are independently hydrogen or methyl.

42. The compound according to claim 1, wherein the compound is selected from the group consisting of:

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-(4H-1,2,4-triazol-4-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2,3-dimethyl-2-(methylamino)butyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2-(dimethylamino)-2,3-dimethylbutyl]oxy]-8-[(1R)-1,2-dimethylpropyl]-14-(1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(3-amino-1H-1,2,4-triazol-1-yl)-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(3-bromo-4H-1,2,4-triazol-4-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(3-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]14-(3-cyano-4H-1,2,4-triazol-4-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]14-(5-cyano-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]14-(3-cyano-1H-1,2,4-triazol-1-yl)-8-[(1R)-1,2-dimethylpropyl]1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[3-(methoxycarbonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(methoxycarbonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(3-chloro-4H-1,2,4-triazol-4-yl)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid;

(1S,4aR,6aS,7R,8R,10aR,10bR,12aR,14R,15R)-14-(5-chloro-1H-1,2,4-triazol-1-yl)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid;

(1S,4aR,6aS,7R,8R,10aR,10bR,12aR,14R,15R)-14-(3-chloro-1H-1,2,4-triazol-1-yl)-15-[2-(dimethylamino)-2,3-dimethylbutoxy]-8-[(1R)-1,2-dimethylpropyl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-(5-chloro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-(5-bromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[tetrahydro-4-(methylamino)-2H-pyran-4-yl]methoxy]-14-(1H-1,2,4-triazol-1-yl)-1, 6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;
(1S,4aR,6aS,7R,8R,10aR,10bR,12aR,14R,15R)-14-(5-
bromo-1H-1,2,4-triazol-1-yl)-8-[(1R)-1,2-dimethyl-
propyl]-15-[[tetrahydro-4-(methylamino)-2H-pyran-4-
yl]methoxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-14-(5-
chloro-1H-1,2,4-triazol-1-yl)-8-[(1R)-1,2-dimethyl-
propyl]-15-[[tetrahydro-4-(methylamino)-2H-pyran-4-
yl]methoxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-15-[(4-
aminotetrahydro-2H-pyran-4-yl)methoxy]-14-(5-
bromo-1H-1,2,4-triazol-1-yl)-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-8-[(1R)-
1,2-dimethylpropyl]-15-[[1-(methylamino)cyclohexyl]
methoxy]-14-(1H-1,2,4-triazol-1-yl)-1,6,6a,7,8,9,10,
10a,10b,11,12,12a-dodecahydro-1,6a,8,10a-
tetramethyl-4H-1,4a-propano-2H-phenanthro[1,2-c]
pyran-7-carboxylic acid;
(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-(1H-1,2,4-triazol-1-yl)-
1,6,6a,7,8,9,10,10a,10b,11,12,12a-dodecahydro-1,6a,
8,10a-tetramethyl-4H-1,4a-propano-2H-phenanthro[1,
2-c]pyran-7-carboxylic acid;
(1S,4aR,6aS,7R,8R,10aR,10bR,12aR,14R,15R)-15-
[[(2R)-2-(dimethylamino)-2,3-dimethylbutyl]oxy]-8-
[(1R)-1,2-dimethylpropyl]-14-(1H-1,2,4-triazol-1-yl)-
1,6,6a,7,8,9,10,10a,10b,11,12,12a-dodecahydro-1,6a,
8,10a-tetramethyl-4H-1,4a-propano-2H-phenanthro[1,
2-c]pyran-7-carboxylic acid;
(1S,4aR,6aS,7R,8R,10aR,10bR,12aR,14R,15R)-15-
[[(2R)-2-amino-2,3-dimethylbutyl]oxy]-14-(5-chloro-
1H-1,2,4-triazol-1-yl)-8-[(1R)-1,2-dimethylpropyl]-1,
6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;
(1S,4aR,6aS,7R,8R,10aR,10bR,12aR,14R,15R)-14-(5-
chloro-1H-1,2,4-triazol-1-yl)-15-[[(2R)-2,3-dimethyl-
2-(methylamino)butyl]oxy]-8-[(1R)-1,2-dimethylpro-
pyl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;
(1S,4aR,6aS,7R,8R,10aR,10bR,12aR,14R,15R)-14-(5-
bromo-1H-1,2,4-triazol-1-yl)-15-[[(2R)-2,3-dimethyl-
2-(methylamino)butyl]oxy]-8-[(1R)-1,2-dimethylpro-
pyl]-1,6,6a,7,8,9,10,10a,10b,11,12,12a-dodecahydro-
1,6a,8,10a-tetramethyl-4H-1,4-a-propano-2H-
phenanthro[1,2-c]pyran-7-carboxylic acid;
(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-(5-iodo-1H-1,2,4-tria-
zol-1-yl)-1,6,6a,7,8,9,10,10a,10b,11,12,12a-
dodecahydro-1,6a,8,10a-tetramethyl-4H-1,4-a-
propano-2H-phenanthro[1,2-c]pyran-7-carboxylic
acid;
(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-[(phenylmethoxy)
carbonyl]-1H-1,2,4-triazol-1-yl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;
(1S,4aR,6aS,7R,8R,10aR,10bR,12aR,14R,15R)-15-
[[(2R)-2-amino-3,3-dimethylbutyl]oxy]-14-(3-amino-
1H-1,2,4-triazol-1-yl)-8-[(1R)-1,2-dimethylpropyl]-1,
6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;
(1S,4aR,6aS,7R,8R,10aR,10bR,12aR,14R,15R)-14-(3-
amino-1H-1,2,4-triazol-1-yl)-15-[[(2S)-2,3-dimethyl-
2-(methylamino)butyl]oxy]-8-[(1R)-1,2-dimethylpro-
pyl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;
(1S,4aR,6aS,7R,8R,10aR,10bR,12aR,14R,15R)-14-(3-
amino-1H-1,2,4-triazol-1-yl)-15-[[(2S)-3,3-dimethyl-
2-(methylamino)butyl]oxy]-8-[(1R)-1,2-dimethylpro-
pyl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;
(1S,4aR,6aS,7R,8R,10aR,10bR,12aR,14R,15R)-14-(3-
amino-1H-1,2,4-triazol-1-yl)-15-[[(2S)-2-(dimethy-
lamino)-2,3-dimethylbutyl]oxy]-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-14-(3-
amino-1H-1,2,4-triazol-1-yl)-15-[[(2R)-2-(dimethy-
lamino)-2,3-dimethylbutyl]oxy]-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-15-
[[(2R)-2-amino-2,3-dimethylbutyl]oxy]-14-(5-bromo-
3-nitro-1H-1,2,4-triazol-1-yl)-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-15-
[[(2R)-2-amino-2,3-dimethylbutyl]oxy]-14-(3-bromo-
5-nitro-1H-1,2,4-triazol-1-yl)-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;
(1S,4aR,6aS,7R,8R,10aR,10bR,12aR,14R,15R)-15-
[[(2R)-2-amino-2,3-dimethylbutyl]oxy]-14-(3-amino-
1H-1,2,4-triazol-1-yl)-8-[(1R)-1,2-dimethylpropyl]-1,
6,6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;
(1S,4aR,6aS,7R,8R,10aR,10bR,12aR,14R,15)-15-[[(2R)-
2-amino-2,3-dimethylbutyl]oxy]-14-(5-amino-1H-1,2,
4-triazol-1-yl)-8-[(1R)-1,2-dimethylpropyl]-1,6,6a,7,8,
9,10,10a,10b,11,12,12a-dodecahydro-1,6a,8,10a-
tetramethyl-4H-1,4a-propano-2H-phenanthro[1,2-c]
pyran-7-carboxylic acid;
(1S,4aR,6aS,7R,8R,10aR,10bR,12aR,14R,15R)-14-(3-
amino-5-cyclopropyl-1H-1,2,4-triazol-1-yl)-15-[[(2R)-

2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-(5-amino-3-cyclopropyl-1H-1,2,4-triazol-1-yl)-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(3,5-dibromo-4H-1,2,4-triazol-4-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(3,5-dibromo-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(3,5-dichloro-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[3-amino-5-(hydroxymethyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(3-amino-5-phenyl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[3-[[(1-methylethyl)amino]carbonyl]-4H-1,2,4-triazol-4-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[3-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-6-oxo-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-15-[[(2R)-2-(dimethylamino)-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2-(ethylamino)-2,3-dimethylbutyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-[(methylamino)carbonyl]-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2,3-dimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[(2R)-2,3-dimethyl-2-(propylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[(dimethylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2,3-dimethyl-2-(propylamino)butyl]oxy]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-[(dimethylamino)carbonyl]-1H-1,2,4-triazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-[(dimethylamino)carbonyl]-1H-1,2,4-triazol-1-yl]-8-[(1R)-1,2-dimethylpropyl]-15-[[(2R)-2-(ethylamino)-2,3-dimethylbutyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(ethylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[(ethylamino)carbonyl]1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[(diethylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(propylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-(dimethylamino)-2,3-dimethylbutyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2-(ethylamino)-2,3-dimethylbutyl]oxy]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2,3-dimethyl-2-(propylamino)butyl]oxy]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[(cyclopropylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-[(cyclopropylamino)carbonyl]-1H-1,2,4-triazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-[(cyclopropylamino)carbonyl]-1H-1,2,4-triazol-1-yl]-8-[(1R)-1,2-dimethylpropyl]-15-[[(2R)-2-(ethylamino)-2,3-dimethylbutyl]oxy]-1,6,6a,7,8,9,10,10a,10b,11,12,12a-dodecahydro-1,6a,8,10a-tetramethyl-4H-1,4-a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[(butylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-methylpropyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[[(1S)-1-methylpropyl]amino]carbonyl]-1H-1,2,4-triazol-1-yl]-1,6,6a,7,8,9,10,10a,10b,11,12,12a-dodecahydro-1,6a,8,10a-tetramethyl-4H-1,4-a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[[(1R)-1-methylpropyl]amino]carbonyl]-1H-1,2,4-triazol-1-yl]-1,6,6a,7,8,9,10,10a,10b,11,12,12a-dodecahydro-1,6a,8,10a-tetramethyl-4H-1,4-a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[[(1,1-dimethylethyl)amino]carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[(cyclobutylamino)carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2,2-dimethylpropyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(phenylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(phenylmethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-phenylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2-(ethylamino)-2,3-dimethylbutyl]oxy]-14-[5-[[(2-fluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[[(2,2-difluoroethyl)amino]carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2,2,2-trifluoroethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-methoxyethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[[(2-ethoxyethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[[[2-(dimethylamino)ethyl]amino]carbonyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(1-azetidinylcarbonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(1-pyrrolidinylcarbonyl)-1H-1,
2,4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(4-morpholinylcarbonyl)-1H-1,
2,4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-[(4-methyl-1-piperazinyl)car-
bonyl]-1H-1,2,4-triazol-1-yl]-1,6,6a,7,8,9,10,10a,10b,
11,12,12a-dodecahydro-1,6a,8,10a-tetramethyl-4H-1,
4a-propano-2H-phenanthro[1,2-c]pyran-7-carboxylic
acid;

(1S,4aR,6aS,7R,8R,10aR,10bR,12aR,14R,15R)-14-[5-
(aminocarbonyl)-1H-1,2,4-triazol-1-yl]-8-[(1R)-1,2-
dimethylpropyl]-15-[[(2R)-2,3,3-trimethyl-2-(methy-
lamino)butyl]oxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[(methylamino)carbonyl]-1,6,
6a,7,8,9,10,10a,10b,11,12,12a-dodecahydro-1,6a,8,
10a-tetramethyl-4H-1,4a-propano-2H-phenanthro[1,2-
c]pyran-7-carboxylic acid;

(1S,4aR,6aS,7R,8R,10aR,10bR,12aR,14R,15R)-15-
[[(2R)-2-amino-2,3,3-trimethylbutyl]oxy]-14-[5-
[(dimethylamino)carbonyl]-1H-1,2,4-triazol-1-yl]-8-
[(1R)-1,2-dimethylpropyl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[(ethylamino)carbonyl]-1H-1,
2,4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[[(2-fluoroethyl)amino]carbo-
nyl]-1H-1,2,4-triazol-1-yl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[[(1-methylethyl)amino]carbo-
nyl]-1H-1,2,4-triazol-1-yl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-8-[(1R)-
1,2-dimethylpropyl]-14-[5-[[(1-methylethyl)amino]
carbonyl]-1H-1,2,4-triazol-1-yl]-15-[[(2R)-2,3,3-trim-
ethyl-2-(methylamino)butyl]oxy]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-8-[(1R)-
1,2-dimethylpropyl]-15-[[(2R)-2-[(2-hydroxyethyl)
amino]-2,3,3-trimethylbutyl]oxy]-14-[5-[(methy-
lamino)carbonyl]-1H-1,2,4-triazol-1-yl]-1,6,6a,7,8,9,
10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-14-[5-
[[(2-aminoethyl)amino]carbonyl]-1H-1,2,4-triazol-1-
yl]-8-[(1R)-1,2-dimethylpropyl]-15-[[(2R)-2,3,3-trim-
ethyl-2-(methylamino)butyl]oxy]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-14-[5-
(aminocarbonyl)-1H-1,2,4-triazol-1-yl]-15-[[(2R)-2-
amino-3,3-dimethylbutyl]oxy]-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-3,3-dimethylbutyl]oxy]-8-[(1R)-1,2-
dimethylpropyl]-14-[5-[(methylamino)carbonyl]-1H-
1,2,4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-3,3-dimethylbutyl]oxy]-8-[(1R)-1,2-
dimethylpropyl]-14-[5-[[(1-methylethyl)amino]carbo-
nyl]-1H-1,2,4-triazol-1-yl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
(aminocarbonyl)-1H-1,2,4-triazol-1-yl]-15-(2-amino-
2-ethylbutoxy)-8-[(1R)-1,2-dimethylpropyl]-1,6,6a,7,
8,9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-15-(2-
amino-2-ethylbutoxy)-8-[(1R)-1,2-dimethylpropyl]-
14-[5-[(methylamino)carbonyl]-1H-1,2,4-triazol-1-yl]-
1,6,6a,7,8,9,10,10a,10b,11,12,12a-dodecahydro-1,6a,
8,10a-tetramethyl-4H-1,4a-propano-2H-phenanthro[1,
2-c]pyran-7-carboxylic acid;

(1S,4aR,6aS,7R,8R,10aR,10bR,12aR,14R,15R)-15-(2-
amino-2-ethylbutoxy)-8-[(1R)-1,2-dimethylpropyl]-
14-[5-[[(1-methylethyl)amino]carbonyl]-1H-1,2,4-tria-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
(aminocarbonyl)-1H-1,2,4-triazol-1-yl]-15-[[(2S)-2-
amino-2,3-dimethylbutyl]oxy]-8-[(1R)-1,2-dimethyl-
propyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2S)-2-amino-2,3-dimethylbutyl]oxy]-8-[(1R)-1,2-
dimethylpropyl]-14-[5-[(methylamino)carbonyl]-1H-

1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-[5-[(propylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-15-[(1-aminocyclohexyl)methoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[1-(methylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(1-aminocyclohexyl)methoxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[1-(ethylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-8-[(1R)-1,2-dimethylpropyl]-15-[[1-(propylamino)cyclohexyl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-15-[(4-aminotetrahydro-2H-pyran-4-yl)methoxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-[(methylamino)carbonyl]-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-[(methylamino)carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-[[(1-methylethyl)amino]carbonyl]-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-[(methylamino)carbonyl]-1H-1,2,4-triazol-1-yl]-15-[[tetrahydro-4-(methylamino)-2H-thiopyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-[(methylamino)carbonyl]-1H-1,2,4-triazol-1-yl]-15-[[tetrahydro-4-(methylamino)-1,1-dioxido-2H-thiopyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[3-(aminocarbonyl)-5-bromo-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-3-bromo-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[3-amino-5-(aminocarbonyl)-1H-1,2,4-triazol-1-yl]-15-[[(2R)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4R,6aS,7R,8R,10aR,10bR,12aR,14R,15R)-15-[[(2R)-2-amino-2,3-dimethylbutyl]oxy]-14-[3-bromo-5-(methoxycarbonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-3-bromo-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[3-amino-5-[(methylamino)carbonyl]-1H-1,2,4-triazol-1-yl]-8-[(1R)-1,2-dimethylpropyl]-1,6,6a,7,8,9,10,10a,10b,11, 12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[3-(aminosulfonyl)-4H-1,2,4-triazol-4-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[3-(aminosulfonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminosulfonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-ethylbutoxy)-14-[5-(aminosulfonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-ethylbutoxy)-8-[(1R)-1,2-dimethylpropyl]-14-[5-[(ethylamino)sulfonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-ethylbutoxy)-8-[(1R)-1,2-dimethylpropyl]-14-[5-[(propylamino)sulfonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(aminosulfonyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(4,5-dihydro-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1,4,5,6-tetrahydro-2-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(4,5-dihydro-1-methyl-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-ethyl-4,5-dihydro-1H-imidazol-2-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-[4,5-dihydro-1-(1-methylethyl)-1H-imidazol-2-yl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(4,5-dihydro-4,4-dimethyl-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(4,5-dihydro-1H-imidazol-2-yl)-1H-1,2,4-triazol-1-yl]-15-[[(2R)-2,3-dimethyl-2-(methylamino)butyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-(4,5-dihydro-1H-imidazol-2-yl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(1,4,5,6-tetrahydro-2-pyrimidinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-pyrrolidinyl)-1H-1,2,4-triazol-1-yl]-1,6,6a,7,8,9,10,10a,10b,11,12,12a-dodecahydro-1,6a,8,10a-tetramethyl-4H-1,4-a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[1,5'-bi-1H-1,2,4-triazol]-1'-yl-8-[(1R)-1,2-dimethylpropyl]-1,6,6a,7,8,9,10,10a,10b,11,12,12a-dodecahydro-1,6a,8,10a-tetramethyl-4H-1,4-a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethylthio)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethylsulfonyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-phenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-(5-phenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-(5-phenyl-1H-1,2,4-triazol-1-yl)-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-furanyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-ethenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-ethyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-morpholinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(1-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-(5-phenyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(3-chlorophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(4-bromophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-methoxyphenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-methoxyphenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-naphthalenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-naphthalenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(3-thienyl)-1H-1,2,4-triazol-1-
yl]-1,6,6a,7,8,9,10,10a,10b,11,12,12a-dodecahydro-1,
6a,8,10a-tetramethyl-4H-1,4a-propano-2H-phenanthro
[1,2-c]pyran-7-carboxylic acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(3-thienyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(2-thienyl)-1H-1,2,4-triazol-1-
yl]-1,6,6a,7,8,9,10,10a,10b,11,12,12a-dodecahydro-1,
6a,8,10a-tetramethyl-4H-1,4a-propano-2H-phenanthro
[1,2-c]pyran-7-carboxylic acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(2-thienyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(1H-pyrazol-4-yl)-
1H-1,2,4-triazol-1-yl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-(5-ethenyl-1H-1,2,4-
triazol-1-yl)-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-[(1E)-1-propenyl]-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-[(1Z)-1-propenyl]-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(1-methylethenyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-(5-propyl-1H-1,2,4-triazol-1-yl)-
1,6,6a,7,8,9,10,10a,10b,11,12,12a-dodecahydro-1,6a,
8,10a-tetramethyl-4H-1,4a-propano-2H-phenanthro[1,
2-c]pyran-7-carboxylic acid;

(1S,4aR,6aS,7R,8R,10aR,10bR,12aR,14R,15R)-14-[5-
[(E)-2-cyclopropylethenyl]-1H-1,2,4-triazol-1-yl]-15-
[[(2R)-2,3-dimethyl-2-(methylamino)butyl]oxy]-8-
[(1R)-1,2-dimethylpropyl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-[(E)-2-phenylethenyl]-1H-1,2,
4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(1-phenylethenyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(4-pyridinyl)-1H-1,2,4-triazol-
1-yl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;

(1S,4aR,6aS,7R,8R,10aR,10bR,12aR,14R,15R)-8-[(1R)-
1,2-dimethylpropyl]-14-[5-(4-pyridinyl)-1H-1,2,4-tria-
zol-1-yl]-15-[[(2R)-2,3,3-trimethyl-2-(methylamino)
butyl]oxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-14-[5-(2-
bromo-4-pyridinyl)-1H-1,2,4-triazol-1-yl]-8-[(1R)-1,
2-dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(5-pyrimidinyl)-1H-1,2,4-tria-
zol-1-yl]1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-14-[5-(4-cy-
anophenyl)-1H-1,2,4-triazol-1-yl]-8-[(1R)-1,2-dimeth-
ylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
[4-(aminomethyl)phenyl]-1H-1,2,4-triazol-1-yl]-15-
[[(2R)-2-amino-2,3,3-trimethylbutyl]oxy]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[2-(ethoxycarbonyl)-4-pyridi-
nyl]-1H-1,2,4-triazol-1-yl]-1,6,6a,7,8,9,10,10a,10b,11, 12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-[2-(aminocarbonyl)-4-pyridinyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-pyrazinyl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridazinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-pyridazinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(5-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(5-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(3-fluoro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-hydroxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(6-hydroxy-3-pyridinyl)-1H-1,2,4-triazol-1-yl]-1,6,6a,7,8,9,10,10a,10b,11,12,12a- dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-[5-(4-aminophenyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridazinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(5-thiazolyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-(2-bromo-5-thiazolyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1H-imidazol-4-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-1H-imidazol-4-yl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-(3-chloro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-(3,5-difluoro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-(2-bromo-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2-hydroxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(2-amino-4-pyridinyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[2-(formylamino)-4-pyridinyl]-1H-1,2,4-triazol-1-yl]1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2-methyl-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(2,6-dimethyl-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(6-hydroxy-3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[2-(methoxycarbonyl)-4-py-
ridinyl]-1H-1,2,4-triazol-1-yl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[6-(methoxycarbonyl)-3-py-
ridinyl]-1H-1,2,4-triazol-1-yl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-14-[5-
[6-(aminocarbonyl)-3-pyridinyl]-1H-1,2,4-triazol-1-
yl]-15-[[(2R)-2-amino-2,3,3-trimethylbutyl]oxy]-8-
[(1R)-1,2-dimethylpropyl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[4-(methoxycarbonyl)-2-py-
ridinyl]-1H-1,2,4-triazol-1-yl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[4-(ethoxycarbonyl)-2-pyridi-
nyl]-1H-1,2,4-triazol-1-yl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-14-[5-(4-
carboxy-2-pyridinyl)-1H-1,2,4-triazol-1-yl]-8-[(1R)-1,
2-dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
[4-(aminocarbonyl)-2-pyridinyl]-1H-1,2,4-triazol-1-
yl]-15-[[(2R)-2-amino-2,3,3-trimethylbutyl]oxy]-8-
[(1R)-1,2-dimethylpropyl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
[5-(aminocarbonyl)-2-pyridinyl]-1H-1,2,4-triazol-1-
yl]-15-[[(2R)-2-amino-2,3,3-trimethylbutyl]oxy]-8-
[(1R)-1,2-dimethylpropyl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-14-[5-(3-cy-
anophenyl)-1H-1,2,4-triazol-1-yl]-8-[(1R)-1,2-dimeth-
ylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
[3-(aminocarbonyl)phenyl]-1H-1,2,4-triazol-1-yl]-15-
[[(2R)-2-amino-2,3,3-trimethylbutyl]oxy]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[3-(methoxycarbonyl)phenyl]-
1H-1,2,4-triazol-1-yl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
[3-(aminomethyl)phenyl]-1H-1,2,4-triazol-1-yl]-15-
[[(2R)-2-amino-2,3,3-trimethylbutyl]oxy]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-14-[5-(3,4-
difluorophenyl)-1H-1,2,4-triazol-1-yl]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(4-hydroxyphenyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(4-ethoxyphenyl)-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[4-(trifluoromethyl)phenyl]-
1H-1,2,4-triazol-1-yl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-14-[5-(4-
carboxyphenyl)-1H-1,2,4-triazol-1-yl]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[4-(methoxycarbonyl)phenyl]-
1H-1,2,4-triazol-1-yl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[4-(ethoxycarbonyl)phenyl]-
1H-1,2,4-triazol-1-yl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-[4-(aminocarbonyl)phenyl]-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-[4-[(dimethylamino)methyl]phenyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-methylpropoxy)-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-ethylbutoxy)-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[2-ethyl-2-(methylamino)butoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-3,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2-phenylpropyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2-(1-methylcyclopropyl)propyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-(dimethylamino)-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2-(ethylamino)-2,3,3-trimethylbutyl]oxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[(2R)-2,3,3-trimethyl-2-(propylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(3-fluoro-4-pyridinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2-cyclopropylpropyl]oxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(3-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(3-fluoro-4-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(4-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(5-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyrimidinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(5-pyrimidinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-oxido-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-oxido-3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-oxido-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-4-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-methyl-3-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-methyl-4-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-ethyl-4-pyridiniumyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-[(aminocarbonyl)amino]-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-[4-(4,5-dihydro-1H-imidazol-2-yl)phenyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-[3-(4,5-dihydro-1H-imidazol-2-yl)phenyl]-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(5-[2,4'-bipyridin]-4-yl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(2-phenyl-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(5-[2,3'-bipyridin]-4-yl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(5-[2,2'-bipyridin]-4-yl-1H-1,2,4-triazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-piperidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(1-acetyl-4-piperidinyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-[1-(methoxycarbonyl)-4-piperidinyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(1-methyl-4-piperidinyl)-1H-1,
2,4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[(2S)-2-pyrrolidinyl]-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[(3R)-3-pyrrolidinyl]-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[(3S)-3-pyrrolidinyl]-1H-1,2,4-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-14-[5-(3-
azetidinyl)-1H-1,2,4-triazol-1-yl]-8-[(1R)-1,2-dimeth-
ylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(1-ethyl-3-azetidinyl)-1H-1,2,
4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[5-
[(3R)-1-(aminocarbonyl)-3-pyrrolidinyl]-1H-1,2,4-
triazol-1-yl]15-[[(2R)-2-amino-2,3,3-trimethylbutyl]
oxy]-8-[(1R)-1,2-dimethylpropyl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-14-[5-
[(3S)-1-(aminocarbonyl)-3-pyrrolidinyl]-1H-1,2,4-
triazol-1-yl]-15-[[(2R)-2-amino-2,3,3-trimethylbutyl]
oxy]-8-[(1R)-1,2-dimethylpropyl]-1,6,6a,7,8,9,10,10a,
10b,11,12,12a-dodecahydro-1,6a,8,10a-tetramethyl-
4H-1,4a-propano-2H-phenanthro[1,2-c]pyran-7-
carboxylic acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(tetrahydro-2H-pyran-4-yl)-
1H-1,2,4-triazol-1-yl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-[4-(methoxycarbonyl)cyclo-
hexyl]-1H-1,2,4-triazol-1-yl]-1,6,6a,7,8,9,10,10a,10b,
11,12,12a-dodecahydro-1,6a,8,10a-tetramethyl-4H-1,
4a-propano-2H-phenanthro[1,2-c]pyran-7-carboxylic
acid;

(1S,4aR,6aS,7R,8R,10aR,10bR,12aR,14R,15R)-14-[5-
[4-(aminocarbonyl)cyclohexyl]-1H-1,2,4-triazol-1-yl]-
15-[[(2R)-2-amino-2,3,3-trimethylbutyl]oxy]-8-[(1R)-
1,2-dimethylpropyl]-1,6,6a,7,8,9,10,10a,10b,11,12,
12a-dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-(1H-1,2,3-triazol-1-yl)-1,6,6a,7,8,
9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-(2H-1,2,3-triazol-2-yl)-1,6,6a,7,8,
9,10,10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[4-(methoxycarbonyl)-1H-1,2,3-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(methoxycarbonyl)-1H-1,2,3-
triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[4-(methoxycarbonyl)-2H-1,2,3-
triazol-2-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-14-[4-
amino-5-(aminocarbonyl)-2H-1,2,3-triazol-2-yl]-15-
[[(2R)-2-amino-2,3-dimethylbutyl]oxy]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-(1H-pyrazol-1-yl)-1,6,6a,7,8,9,10,
10a,10b,11,12,12a-dodecahydro-1,6a,8,10a-
tetramethyl-4H-1,4a-propano-2H-phenanthro[1,2-c]
pyran-7-carboxylic acid;

(1S,4aR,6aS,7R,8R,10aR,10bR,12aR,14R,15R)-14-[3-
(aminocarbonyl)-1H-pyrazol-1-yl]-15-[[(2R)-2-amino-
2,3-dimethylbutyl]oxy]-8-[(1R)-1,2-dimethylpropyl]-
1,6,6a,7,8,9,10,10a,10b,11,12,12a-dodecahydro-1,6a,
8,10a-tetramethyl-4H-1,4a-propano-2H-phenanthro[1,
2-c]pyran-7-carboxylic acid;

(1S,4aR,6aS,7R,8R,10aR,10bR,12aR,14R,15R)-14-[5-
(aminocarbonyl)-1H-pyrazol-1-yl]-15-[[(2R)-2-amino-
2,3-dimethylbutyl]oxy]-8-[(1R)-1,2-dimethylpropyl]-
1,6,6a,7,8,9,10,10a,10b,11,12,12a-dodecahydro-1,6a, 8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(3-nitro-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-nitro-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-3,3-dimethylbutyl]oxy]-8-[(1R)-1,2-dimethylpropyl]-14-(4-nitro-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-14-(4-chloro-1H-pyrazol-1-yl)-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(trifluoromethyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(ethoxycarbonyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-[(ethylamino)carbonyl]-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-(5-phenyl-1H-pyrazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[2-(ethoxycarbonyl)-1H-imidazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[2-(aminocarbonyl)-1H-imidazol-1-yl]-15-[[(2S)-2-amino-2,3-dimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2S)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxamide;

(1S,4aR,6aS,7R,8R,10aR,10bR,12aR,14R,15R)-8-[(1R)-1,2-dimethylpropyl]-15-(3-morpholinylmethoxy)-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[1-(ethylamino)cyclobutyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[(2S)-2-pyrrolidinylmethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[(2R)-2-pyrrolidinylmethoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2-methyl-2-pyrrolidinyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2S)-1-methyl-2-pyrrolidinyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-1-methyl-2-pyrrolidinyl]methoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-(5-imidazo[1,2-a]pyridin-7-yl-1H-1,2,4-triazol-1-yl)-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(2-methoxy-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(4-pyridinyl)-1H-pyrazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(3-methoxyphenyl)-
1H-pyrazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(2-thienyl)-1H-pyra-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(2-thiazolyl)-1H-
pyrazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(2-pyridinyl)-1H-
pyrazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(3-fluorophenyl)-1H-
pyrazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-[4-(trifluoromethyl)
phenyl]-1H-pyrazol-1-yl]-1,6,6a,7,8,9,10,10a,10b,11,
12,12a-dodecahydro-1,6a,8,10a-tetramethyl-4H-1,4a-
propano-2H-phenanthro[1,2-c]pyran-7-carboxylic
acid; and pharmaceutically acceptable salts thereof.

43. The compound according to claim 1, wherein the compound is selected from the group consisting of:

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(4-pyridinyl)-1H-1,2,4-triazol-
1-yl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;

(1S,4aR,6aS,7R,8R,10aR,10bR,12aR,14R,15R)-8-[(1R)-
1,2-dimethylpropyl]-14-[5-(4-pyridinyl)-1H-1,2,4-tria-
zol-1-yl]-15-[[(2R)-2,3,3-trimethyl-2-(methylamino)
butyl]oxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(5-pyrimidinyl)-1H-1,2,4-tria-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-8-[(1R)-
1,2-dimethylpropyl]-14-[5-(4-pyridinyl)-1H-1,2,4-tria-
zol-1-yl]-15-[[tetrahydro-4-(methylamino)-2H-pyran-
4-yl]methoxy]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(3-pyridinyl)-1H-1,2,4-triazol-
1-yl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(3-pyridinyl)-1H-1,2,
4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(4-pyridinyl)-1H-1,2,4-triazol-
1-yl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;

(1S,4aR,6aS,7R,8R,10aR,10bR,12aR,14R,15R)-15-
[[(2R)-2,3-dimethyl-2-(methylamino)butyl]oxy]-8-
[(1R)-1,2-dimethylpropyl]-14-[5-(4-pyridinyl)-1H-1,2,
4-triazol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(4-pyrimidinyl)-1H-1,2,4-tria-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-8-[(1R)-1,2-
dimethylpropyl]-14-[5-(5-pyrimidinyl)-1H-1,2,4-tria-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-dimethylbutyl]oxy]-14-[5-(3-
fluoro-4-pyridinyl)-1H-1,2,4-triazol-1-yl]-8-[(1R)-1,2-
dimethylpropyl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(3-pyridinyl)-1H-1,2,4-triazol-
1-yl]-1,6,6a,7,8,9,10,10a,10b,11,12,12a-dodecahydro-
1,6a,8,10a-tetramethyl-4H-1,4a-propano-2H-
phenanthro[1,2-c]pyran-7-carboxylic acid;

(1S,4aR,6aS,7R,8R,10aR,10bR,12aR,14R,15R)-15-
[[(2R)-2-amino-2,3,3-trimethylbutyl]oxy]-8-[(1R)-1,2-
dimethylpropyl]-14-[5-(4-pyrimidinyl)-1H-1,2,4-tria-
zol-1-yl]-1,6,6a,7,8,9,10,10a,10b,11,12,12a-
dodecahydro-1,6a,8,10a-tetramethyl-4H-1,4a-
propano-2H-phenanthro[1,2-c]pyran-7-carboxylic
acid;

(1S,4aR,6aS,7R,8R,10aR,10bR,12aR,14R,15R)-15-
[[(2R)-2-amino-2,3-trimethylbutyl]oxy]-8-[(1R)-1,2- dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-14-[5-(3-chloro-4-pyridinyl)-1H-1,2,4-triazol-1-yl]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-methylpropoxy)-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-(2-amino-2-ethylbutoxy)-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[2-ethyl-2-(methylamino)butoxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2-(1-methylcyclopropyl)propyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-(dimethylamino)-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-15-[[(2R)-2-(ethylamino)-2,3,3-trimethylbutyl]oxy]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[(2R)-2,3,3-trimethyl-2-(propylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(3-fluoro-4-pyridinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2-cyclopropylpropyl]oxy]-8-[(1R)-1,2-dimethylpropyl]-14-[5-(2-fluorophenyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(3-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(3-fluoro-4-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(5-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[(4-aminotetrahydro-2H-pyran-4-yl)methoxy]-8-[(1R)-1,2-dimethylpropyl]-14-[5-(4-pyrimidinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyrimidinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(5-pyrimidinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-oxido-4-pyridinyl)-1H-1,2,4-triazol-1-yl]-1,6,6a,7,8,9,10,10a,10b,11,12,12a- dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(1-oxido-3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(1-oxido-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid; and pharmaceutically acceptable salts thereof.

44. The compound according to claim 1, wherein the compound is selected from the group consisting of:

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-[[(1-methylethyl)amino]carbonyl]-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-14-[5-(aminocarbonyl)-1H-1,2,4-triazol-1-yl]-15-[[(2R)-2-amino-2,3,3-trimethylbutyl]oxy]-8-[(1R)-1,2-dimethylpropyl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[(2R)-2,3,3-trimethyl-2-(methylamino)butyl]oxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-8-[(1R)-1,2-dimethylpropyl]-14-[5-(4-pyridinyl)-1H-1,2,4-triazol-1-yl]-15-[[tetrahydro-4-(methylamino)-2H-pyran-4-yl]methoxy]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(3-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3-dimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2,3-dimethyl-2-(methylamino)butyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(3-fluoro-4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid;

(1S,4aR,6aS,7R,8R,10aR,10bR,12aR,14R,15R)-15-[[(2R)-2-amino-2-(1-methylcyclopropyl)propyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid; and pharmaceutically acceptable salts thereof.

45. A composition comprising the compound according to claim 1 and a pharmaceutically acceptable carrier, adjuvant or vehicle.

46. The composition according to claim 45, further comprising a second therapeutic agent.

47. A method of treating a fungal infection in a patient in need thereof, comprising administering to said patient an effective amount of the compound according to claim 1.

48. The method according to claim 47, wherein said fungal infection is caused by *Cryptococcus* spp., *Candida* spp. or *Aspergillus* spp. fungi.

49. The compound according to claim 1, wherein the compound is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid or a pharmaceutically acceptable salt thereof.

50. A composition comprising the compound according to claim 49 and a pharmaceutically acceptable carrier, adjuvant or vehicle.

51. A method of treating a fungal infection in a patient in need thereof, comprising administering to said patient an effective amount of the compound according to claim 49.

* * * * *

UNITED STATES PATENT AND TRADEMARK OFFICE
CERTIFICATE OF CORRECTION

PATENT NO. : 8,188,085 B2
APPLICATION NO. : 12/461318
DATED : May 29, 2012
INVENTOR(S) : Mark L. Greenlee et al.

Page 1 of 1

It is certified that error appears in the above-identified patent and that said Letters Patent is hereby corrected as shown below:

On the Title Page, under Item (73), Assignees:

"Rahway, NC" should read --Rahway, NJ--; and

"Seynexis, Inc." should read --Scynexis, Inc.--.

Signed and Sealed this
Seventh Day of August, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,188,085 B2 |
| APPLICATION NO. | : 12/461318 |
| DATED | : May 29, 2012 |
| INVENTOR(S) | : Mark L. Greenlee et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 380 days.

Signed and Sealed this
Second Day of October, 2012

David J. Kappos
*Director of the United States Patent and Trademark Office*

UNITED STATES PATENT AND TRADEMARK OFFICE
CERTIFICATE OF CORRECTION

PATENT NO.       : 8,188,085 B2  
APPLICATION NO.  : 12/461318  
DATED            : May 29, 2012  
INVENTOR(S)      : Mark L. Greenlee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 386 days.

Signed and Sealed this
Eighteenth Day of June, 2013

Teresa Stanek Rea
*Acting Director of the United States Patent and Trademark Office*